(12) United States Patent
Voskoboynikov et al.

(10) Patent No.: US 7,763,562 B2
(45) Date of Patent: Jul. 27, 2010

(54) HETEROATOM BRIDGED METALLOCENE COMPOUNDS FOR OLEFIN POLYMERIZATION

(75) Inventors: Alexander Z. Voskoboynikov, Moscow (RU); Vyatcheslav V. Izmer, Moscow (RU); Andrey F. Asachenko, Chelyabinsk (RU); Mikhail V. Nikulin, Moscow (RU); Alexey N. Ryabov, Moscow (RU); Artyom Y. Lebedev, Moscow (RU); Catalina L. Coker, Baytown, TX (US); Jo Ann M. Canich, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 943 days.

(21) Appl. No.: 11/302,998

(22) Filed: Dec. 14, 2005

(65) Prior Publication Data

US 2007/0135597 A1  Jun. 14, 2007

(51) Int. Cl.
*C08F 4/64* (2006.01)
*C08F 4/6392* (2006.01)
*C08F 4/6592* (2006.01)
*B01J 31/22* (2006.01)
*C07F 17/00* (2006.01)

(52) U.S. Cl. ........................ 502/155; 502/103; 502/152; 526/160; 526/161; 526/165; 526/172; 526/943; 556/1; 556/53

(58) Field of Classification Search .............. 556/53, 556/1; 502/103, 152, 155; 526/160, 161, 526/165, 172, 943
See application file for complete search history.

(56) References Cited

U.S. PATENT DOCUMENTS

| | | | |
|---|---|---|---|
| 3,678,088 A | 7/1972 | Hedberg et al. | |
| 4,769,510 A | 9/1988 | Kaminsky et al. | |
| 4,794,096 A | 12/1988 | Ewen | |
| 5,434,116 A | 7/1995 | Sone et al. | |
| 5,466,766 A | 11/1995 | Patsidis et al. | |
| 5,489,659 A | 2/1996 | Sugano et al. | |
| 5,504,232 A | 4/1996 | Winter et al. | |
| 5,571,880 A | 11/1996 | Alt et al. | |
| 5,594,081 A | 1/1997 | Uchino et al. | |
| 5,763,542 A | 6/1998 | Winter et al. | |
| 5,840,644 A | 11/1998 | Küber et al. | |
| 5,936,053 A | 8/1999 | Fukuoka et al. | |
| 6,075,171 A | 6/2000 | Sullivan et al. | |
| 6,087,292 A | 7/2000 | Winter et al. | |
| 6,291,699 B1 | 9/2001 | Birmingham et al. | |
| 6,369,254 B1 | 4/2002 | Resconi et al. | |
| 6,399,723 B1 | 6/2002 | Burkhardt et al. | |
| 6,451,938 B1 | 9/2002 | Fisher et al. | |
| 6,465,700 B1 | 10/2002 | Sullivan et al. | |
| 6,492,539 B1 | 12/2002 | Bingel et al. | |
| 6,737,487 B2 | 5/2004 | Meverden | |
| 7,214,746 B2 * | 5/2007 | Voskoboynikov et al. | ... 526/161 |
| 2001/0021755 A1 * | 9/2001 | Kuber et al. | ................. 526/127 |

FOREIGN PATENT DOCUMENTS

| | | |
|---|---|---|
| EP | 0 416 815 | 3/1991 |
| EP | 0 577 581 | 1/1994 |
| EP | 0 628 566 | 12/1994 |
| EP | 0 666 267 | 8/1995 |
| EP | 693502 B1 | 1/1996 |
| EP | 846122 B1 | 10/1998 |
| EP | 0 882 078 | 12/1998 |
| EP | 1034190 B1 | 9/2000 |
| JP | 07-216011 | 8/1995 |
| JP | 08-127612 | 5/1996 |
| JP | 08-301914 | 11/1996 |
| JP | 08301914 | 11/1996 |
| JP | 11-001508 | 1/1999 |
| JP | 11001508 | 1/1999 |
| JP | 11-060588 | 3/1999 |
| JP | 11-080183 | 3/1999 |
| JP | 11060588 | 3/1999 |
| JP | 11-171925 | 6/1999 |
| JP | 11171925 | 6/1999 |
| WO | WO 91/04257 | 4/1991 |

Molecular structure of 4,4'-phenylazandiyl-*bis*(η⁵-2-methylindenyl)zirconium dichloride (N2).

| WO | WO 95/04087 | 2/1995 |
| WO | 96/04317 | 2/1996 |
| WO | WO 96/04317 | 2/1996 |
| WO | 96/38458 | 12/1996 |
| WO | WO 96/38458 | 12/1996 |
| WO | 99/26985 | 3/1999 |
| WO | WO 99/26985 | 6/1999 |
| WO | 03/000744 A1 | 3/2003 |
| WO | WO 2004/060941 | 7/2004 |

OTHER PUBLICATIONS

Wild et al., "*Synthesis and Molecular Structures of Chiral ansa-Titanocene Derivatives with Bridged Tetrahydroindenyl Ligands,*" Dec. 14, 1981, Journal of Organometallic Chemistry, 232 (1982), 233-247.

OTHER PUBLICATIONS

Kato, Taku, et al., "*Synthesis of Novel ansa-Metallocene Complex with Bridged Bis(indenyl)Ligand and Its Application for Olefin Polymerization,*" Science and Technology in Catalysis 1998, Studies in Surface Science and Catalysis 1999, 121, 473-476.

Schaverien, Colin J., et al., "*A New Class of Chiral Bridged Metallocene: Synthesis, Structure, and Olefin (Co)polymerization Behavior of rac- and meso-1,2-$CH_2CH_2${4-(7-Me-indenyl)}$_2ZrCl_2$,*"J. Am. Chem. Soc. 1998, 120 (38), 9945-9946.

Halterman, Ronald L., et al., "*Synthesis of C7, C7'-Ethylene- and C7,C7'-Methylene-Bridged $C_2$-Symmetric Bis(indenyl)zirconium and -titanium Dichlorides,*" Organometallics 1998, 17, 3900-3907.

Schulze, U., et al., "*Structure and Properties of Ethene Copolymers Synthesized by Metallocene Catalysts,*" Journal of Macromolecular Science, Pure and Applied Chemistry 1998, A35(7&8), 1037-1044.

Kravchenko et al., "Propylene Polymerization with Chiral and Achiral Unbridged 2-Arylindene Metallocenes," Organometallics, 1997, vol. 16, No. 16., pp. 3635-3639.

Johnston et al., Investigation of the Electrochemical Properties of Substituted Titanocene Dichlorides, Electrochemica Acta, 1995, vol. 40, pp. 473-477.

Waldbaum et al., Novel Organoiron Compounds Resulting from the Attempted Syntheses of Dibenzofulvalene Complexes, Inorganica Chimica Acta, 1999, vol. 291, No. 1-2, pp. 109-126.

Finch et al., Substituent Effects on the Cleavage Rates of Titanocene Metallacyclobutanes, Journal of the American Chemical Society, Washington, DC, 1988, vol. 110, No. 8, pp. 2406-2413.

Siedle et al., Synthesis of Unsymmetrical Ansa-Fluorenyl Metallocenes, Journal of Molecular Catalysis, 2004, vol. 214, No. 2, pp. 187-198.

Rausch et al., The Formation of Ring-Substituted Titanocene Derivatives Containing Chloro and Carbomethoxy Substituents, Journal of Organometallic Chemistry, Elsevier-Sequoia S.A. Lausanne, CH, 1988, vol. 358, No. 1-3, pp. 161-168.

Schmid et al., Unabridged Cyclopentadienyl-fluorenyl Complexes of Zirconium as Catalysts for Homogeneous Olefin Polymerization, Journal of Organometallic Chemistry, 1995, vol. 501, pp. 101-106.

Alt et al., Syndiospezifische Polymerisation von Propylen: 2- und 2,7-substituierte Metallocenkomplex des Typs ($C_{13}H_8$-$nRn$CR'$_2C_5H_4$) MCl$_2$($n$= 1,2; R = Alkoxy, Alkyl, Aryl, Hal; R' = Me, Ph; M = Zr, Hf)[1], Journal of Organometallic Chemistry, 1996, vol. 522, pp. 39-54.

Alt et al., Syndiospecific Polymerization of Propylene: Synthesis of $CH_2$- and CHR-Bridged Fluorenyl-Containing Ligand Precursors for Metallocene Complexes of Type ($C_{13}H_8$-$nR'n$CHR-$C_5H_4$)ZrCl$_2$ (n = 0, 2; R = H, Alkyl; R' = H, Hal), Journal of Organometallic Chemistry, 1996, vol. 526, pp. 295-301.

Kamigaito et al., Olefin polymerization with Me4Cp-amido complexes with electron-withdrawing groups, Journal of Polymer Science, Part A: Polymer Chemistry, 2000, vol. 38, No. S1, pp. 4649-4660.

Yano et al., Ethylene/1-Hexene Copolymerization with Ph$_2$C(Cp)(Flu)ZrCl$_2$ Derivatives: Correlation Between Ligand Structure and Copolymerization Behavior at High Temperature, Macromolecular Chemistry and Physics, 1999, vol. 200, No. 6, pp. 1542-1553.

Linnolahti, et al., Theoretical Study on the Factors Controlling the Accessibility of Cationic Metal Centers in Zirconocene Polymerization Catalysts, Macromolecules, 2000, vol. 33, No. 25, pp. 9205-9214.

Han et al., Permercuration of Ferrocenes and Ruthenocenes. New Approaches to Complexes Bearing Perhalogenated Cyclopentadienyl Ligands, Organometallics, 1994, vol. 13, No. 8, pp. 3009-3019.

Conway et al., Formation and Reactivity of Halogen Derivatives of (η5-Cyclopentadienyl) thallium, Organometallics, 1985, vol. 4, No. 4, pp. 688-693.

Piccolrovazzi et al., Electronic Effects in Homogeneous Indenylzirconium Ziegler-Natta Catalysts, Organometallics, 1990, vol. 9, No. 12, pp. 3098-3105.

Ryabov et al., Zirconium Complexes with Cyclopentadienyl Ligands Involving Fused a Thiophene Fragment, Organometallics, 2002, vol. 21, No. 14, pp. 2842-2855.

Coates et al., Oscillating Stereocontrol: A Strategy for the Synthesis of Thermoplastic Elastomeric Polypropylene, Science, Jan. 13, 1995, vol. 267, pp. 217-219.

Erker et al., Hydroboration of Bis(alkenylcyclopentadienyl)zirconium Dichlorides[1], Chemische Berichte, 1991, vol. 124, No. 5, pp. 1301-1310.

Hassan et al., Aryl-Aryl Bond Formation One Century after the Discovery of the Ullmann Reaction, Chem. Rev., 2002, vol. 102, No. 5, pp. 1359-1469.

Erker et al., Cp-Substituent Additivity Effects Controlling the Stereochemistry of the Propene Polymerization Reaction at Conformationally Unrestricted (Cp-CHR$^1$R$^2$)$_2$ZrCl$_2$/Methylalumoxane Catalysts, J. Am. Chem. Soc., 1991, vol. 113, No. 20, pp. 7594-7602.

Ogasawara et al., Metathesis Route to Bridged Metallocenes, J. Am. Chem. Soc., 2002, vol. 124, No. 31, pp. 9068-9069.

Bandy et al., Polymerisation of ethylene and propene using new chiral zirconium derivatives. Crystal structure of [ZrL$^1$Cl$_2$][H$_2$L$^1$=(4$S$,5$S$)-*trans*-4,5-bis(1$H$-inden-1-ylmethyl)-2,2-dimethyl-1,3-dioxolane], J. Chem. Soc., Dalton Trans., 1991, pp. 2207-2216.

Schäfer et al., ansa-Metallocene Derivatives, XII. Diastereomeric Derivatisation and Enantiomer Separation of Ethylenebis (Tetrahydroindenyl)-Titanium and -Zirconium Dichlorides, Journal of Organometallic Chemistry, 1987, vol. 328, pp. 87-99.

Rheingold et al., Preparation and Properties of Chiral Titanocene and Zirconocene Dichloride Complexes of a Chiral Ligand, Organometallics, 1992, vol. 11, No. 5, pp. 1869-1876.

Hollis et al., Preparation and Properties of (S,S)-[Ti((R,R)-cyclacene)C12], a Chiral Strapped Bent Metallocene, Organometallics, 1992, vol. 11, No. 8, pp. 2812-2816.

Erker et al., Synthesis of ansa-Metallocenes by Intramolecular Photochemical [2+2] Cycloaddition of Bis(alkenylcyclopentadienyl)zirconium Complexes, Organometallics, 1993, vol. 12, No. 6, pp. 2140-2151.

Larsonneur et al., Synthesis, Characterization, and Chemical Reactivity of Zirconium Dihydride [($C_5H_4$R)$_2$Zr(μ-H)H$_2$ (R = SiMe$_3$, CMe$_3$). H/D Exchange Reactions of Anionic Species [($C_5H_4$R)$_2$ZrH$_2$]$^-$. X-ray Crystal Structure of [($C_5H_4$SiMe$_3$)$_2$Zr(μ-H)H]$_2$, Organometallics, 1993, vol. 12, No. 8, pp. 3216-3224.

\* cited by examiner

*Primary Examiner*—Caixia Lu
(74) *Attorney, Agent, or Firm*—Catherine L. Bell

(57) ABSTRACT

This invention relates to a transition metal compound represented by the formula:

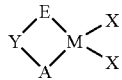

wherein

M is a group 3, 4, 5 or 6 transition metal atom, or a lanthanide metal atom, or actinide metal atom;

E is: 1) a substituted or unsubstituted indenyl ligand that is bonded to Y through the four, five, six or seven position of the indenyl ring, or 2) a substituted or unsubstituted heteroindenyl ligand that is bonded to Y through the four, five or six position of the heteroindenyl ring, provided that the bonding position is not the same as the position of the ring heteroatom, or 3) a substituted or unsubstituted fluorenyl ligand that is bonded to Y through the one, two, three, four, five, six, seven or eight position of the fluorenyl ring, or 4) a substituted or unsubstituted heterofluorenyl ligand that is bonded to Y through the one, two, three, four, five or six position of the heteroindenyl ring, provided that the bonding position is not the same as the position of the ring heteroatom;

A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, a substituted or unsubstituted heterofluorenyl ligand, or other mono-anionic ligand;

Y is a Group 15 or 16 bridging heteroatom substituent that is bonded via the heteroatom to E and A; and X are, independently, univalent anionic ligands, or both X are joined and bound to the metal atom to form a metallocycle ring, or both X join to form a chelating ligand, a diene ligand, or an alkylidene ligand.

290 Claims, 4 Drawing Sheets

Molecular structure of 4,4'-phenylazandiyl-bis($\eta^5$-2-methylindenyl)zirconium dichloride (N2).

Molecular structure of 4,4'-phenylphosphindiyl-*bis*(η⁵-2-methylindenyl)zirconium dichloride Molecular structure of 4,4'-sulfandiyl-bis($\eta^5$-2,7-dimethylindenyl)zirconium dichloride (10a).

Molecular structure of 4,4'-sulfandiyl-bis($\eta^5$-7-bromo-2-methylindenyl)zirconium dichloride (10).

Molecular structure of 4,4'-sulfandiyl-*bis*($\eta^5$-2-methyl-7-*p*-tolylindenyl)zirconium dichloride (10c).

HETEROATOM BRIDGED METALLOCENE COMPOUNDS FOR OLEFIN POLYMERIZATION

FIELD

A series of novel heteroatom bridged metallocene compounds have been synthesized, and when activated, have been shown to be useful as olefin polymerization catalysts. These transition metal catalysts demonstrate high activity for olefin polymerization, and many are capable of producing isotactic poly-alpha-olefins.

BACKGROUND

Various processes and catalysts exist for the homopolymerization or copolymerization of olefins. For many applications, it is desirable for a polyolefin to have a high weight average molecular weight while having a relatively narrow molecular weight distribution. A high weight average molecular weight, when accompanied by a narrow molecular weight distribution, provides a polyolefin with high strength properties.

Traditional Ziegler-Natta catalysts systems—a transition metal compound co-catalyzed by an aluminum alkyl—are typically capable of producing polyolefins having a high molecular weight, but with a broad molecular weight distribution. Many of these systems are also capable of producing high melting isotactic polypropylene.

More recently a catalyst system has been developed wherein the transition metal compound has two or more cyclopentadienyl ring ligands—such transition metal compound being referred to herein as a "metallocene—which catalyzes the production of olefin monomers to polyolefins. Accordingly, titanocenes, zirconocenes and haffocenes, have been utilized as the transition metal component in such "metallocene" containing catalyst system for the production of polyolefins and ethylene-alpha-olefin copolymers.

Catalysts that produce isotactic polyolefins are disclosed in U.S. Pat. No. 4,794,096. This patent discloses a chiral, stereorigid metallocene catalyst which is activated by an alumoxane cocatalyst which is reported to polymerize olefins to isotactic polyolefin forms. Alumoxane co-catalyzed metallocene structures which have been reported to polymerize alpha-olefins stereoregularly include the ethylene bridged bis-indenyl and bis-tetrahydroindenyl titanium and zirconium (IV) catalyst. Such catalyst systems were synthesized and studied in Wild et al., J. Organomet. Chem. 232, 233-47 (1982), and were later reported by Ewen and Kaminsky to polymerize alpha-olefins stereoregularly. Further reported in West German Off DE 3443087A1 (1986), but without giving experimental verification, is that the bridge length of such stereorigid metallocenes can vary from a $C_1$ to $C_4$ hydrocarbon and the metallocene rings can be simple or bi-cyclic but must be asymmetric. When substituted or unsubstituted indenyl or tetrahydroindenyl based, these metallocenes are bridged in the "1-position" of the (hydro)indenyl ring, and are of C2 symmetry. It is thought that it is the C2 symmetric structure (also referred to as the d/l-enantiomers or racemic complexes) that produces isotactic poly-alpha-olefins. An alternate form is the Cs symmetric or meso form that is thought to produce atactic poly-alpha-olefins.

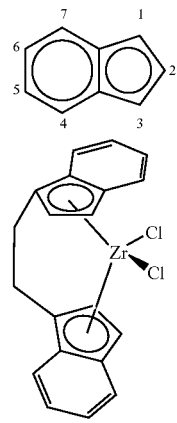

C2 symmetric; racemic form

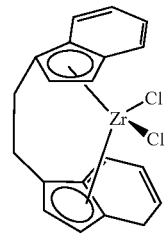

Cs symmetric; meso form

The use of metallocene compositions in olefin polymerization is known. Some metallocenes containing substituted, bridged indenyl derivatives are noted for their ability to produce isotactic propylene polymers having high isotacticity and narrow molecular weight distribution. Considerable effort has been made toward obtaining metallocene produced propylene polymers having ever—higher molecular weight and melting point, while maintaining suitable catalyst activity. Researchers are exploring the relationship between the way in which a metallocene is substituted, and the molecular structure of the resulting polymer. For the substituted, bridged indenyl type metallocenes, it is thought that the type and arrangement of substituents on the indenyl groups, as well as the type of bridge connecting the indenyl groups, determines such polymer attributes as molecular weight and melting point. Unfortunately, it is impossible at this time to accurately correlate specific substitution patterns with specific polymer attributes.

For example, U.S. Pat. No. 5,840,644 describes certain metallocenes containing aryl-substituted indenyl derivatives as ligands, which are said to provide propylene polymers having high isotacticity, narrow molecular weight distribution and very high molecular weight.

Likewise, U.S. Pat. No. 5,936,053 describes certain metallocene compounds said to be useful for producing high molecular weight propylene polymers. These metallocenes have a specific hydrocarbon substituent at the 2 position and an unsubstituted aryl substituent at the 4 position, on each indenyl group of the metallocene compound.

While metallocenes of this type have their benefits, one of the disadvantages is found in the synthesis of such materials. While the rac isomer is considered more desirable, most common synthetic schemes produce a mixture of rac and meso isomers that can be difficult to separate.

More recently, substituted and unsubstituted indenyl based metallocenes with a bridge in the 4-position have been reported. Some of these catalyst systems have been shown to produce isotactic polypropylene. EP 693502 and U.S. Pat. No. 5,594,081 discloses metallocenes with a 1,2-ethylene bridge or dimethylsilylene bridge bridging the 4-positions of substituted indenyl rings. Some catalyst systems based on the dimethylsilylene bridged complexes were shown to produce isotactic polypropylene.

WO 96/38458, EP 846122, and U.S. Pat. No. 6,369,254 disclose metallocenes with a 1,2-ethylene bridge bridging the 4-positions of substituted indenyl rings. Both rac and meso metallocene isomers are produced. A catalyst system based on the rac isomer was shown to produce isotactic polypropylene, and ethylene propylene copolymers containing propylene crystallinity.

WO 99/26985 and EP 1034190 disclose metallocenes with a 1,2-ethylene bridge bridging the 4-positions of substituted indenyl rings. Only ethylene alone or in combination with norbornene were polymerized.

Additional references of interest include: WO 96/04317; JP 11171925 (JP1999171925); JP 11060588 (JP1999060588); JP 11001508 (JP1999001508); and JP 08301914 (JP1996301914).

The following papers report metallocenes with a dimethylsilylene bridge, methylene bridge, 1,2-ethylene bridge, or 1,3-propylene bridge bridging the 4-position of substituted indenyl rings: 1) Studies in Surface Science and Catalysis 1999, 121 (Science and Technology in Catalysis 1998), 473-476; 2) J. Am. Chem. Soc. 1998, 120(38), 9945; and 3) Organometallics 1998, 17, 3900. In these papers, only the racemic 1,2-ethylene and dimethylsilylene bridged metallocenes were reported to produce isotactic polypropylene. The 1,3-propylene bridged metallocene based catalyst system (a mixture of rac and meso isomers) showed no polymerization activity towards propylene. The methylene bridged complex was reported to form only a racemic complex, however, was also reported to have poor solubility and poor stability in solution. No polymerization data was reported using this complex.

Other references of interest include WO 03/00744 and JP 11 171925 (published Jun. 29, 1999).

In view of the difficulty and practical limitations in the synthesis of bridged metallocene complexes necessary for the production of an activated metallocene catalyst system capable of producing crystalline or non-crystalline poly-alpha-olefins, it would be desirable to develop new catalytic processes which produce poly-olefins of high molecular weight and relatively narrow molecular weight distributions, and/or produce poly-alpha-olefins of high crystallinity, high molecular weight distribution and relatively narrow molecular weight distributions. Additionally, it would be beneficial to be able to form the pre-catalyst complexes exclusively as the racemic versions when desired, or exclusively as the meso version when desired while maintaining good pre-catalyst solubility and stability.

SUMMARY OF THE INVENTION

This invention relates to a transition metal compound comprising a transition metal bound to at least one substituted or unsubstituted indenyl ligand that is bridged by a heteroatom substituent in the four, five, six or seven position of the indenyl ligand, to a monoanionic ligand that is also bound to the transition metal.

This invention relates to new metallocene compounds which have at least one substituted or unsubstituted indenyl ligand that is bridged by a heteroatom substituent in the four, five, six or seven position of the indenyl ligand, to a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, a substituted or unsubstituted heterofluorenyl ligand, or other mono-anionic ligand.

This invention also relates to metallocene compounds which have at least one substituted or unsubstituted heteroindenyl ligand that is bridged by a heteroatom substituent in the four, five, or six position of the heteroindenyl ligand, provided that the bridging position is not the same as the position of the ring heteroatom, to a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, a substituted or unsubstituted heterofluorenyl ligand, or other mono-anionic ligand.

This invention also relates to metallocene compounds which have at least one substituted or unsubstituted fluorenyl ligand that is bridged by a heteroatom substituent in the one, two, three, four, five, six, seven or eight position of the fluorenyl ligand, to a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, a substituted or unsubstituted heterofluorenyl ligand, or other mono-anionic ligand.

This invention also relates to metallocene compounds which have at least one substituted or unsubstituted heterofluorenyl ligand that is bridged by a heteroatom substituent in the one, two, three, four, five, or six position of the heterofluorenyl ligand, provided that the bridging position is not the same as the position of the ring heteroatom, to a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, a substituted or unsubstituted heterofluorenyl ligand, or other mono-anionic ligand.

These new metallocene compounds can be used advantageously as catalyst components for the polymerization of olefins.

Therefore, in accordance with an aspect of the present invention, there are provided metallocene compounds represented by formula (1):

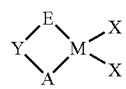

wherein

M is a group 3, 4, 5 or 6 transition metal atom, or a lanthanide metal atom, or actinide metal atom;

E is: 1) a substituted or unsubstituted indenyl ligand that is bonded to Y through the four, five, six or seven position of the indenyl ring, or 2) a substituted or unsubstituted heteroindenyl ligand that is bonded to Y through the four, five or six position of the heteroindenyl ring, provided that the bonding position is not the same as the position of the ring heteroatom, or 3) a substituted or unsubstituted fluorenyl ligand that is bonded to Y through the one, two, three, four, five, six, seven or eight position of the fluorenyl ring, or 4) a substituted or unsubstituted heterofluorenyl ligand that is bonded to Y through the one, two, three, four, five or six position of the heterofluorenyl ring, provided that the bonding position is not the same as the position of the ring heteroatom;

A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, a substituted or unsubstituted heterofluorenyl ligand, or other mono-anionic ligand.

Y is a Group 15 or 16 bridging heteroatom substituent that is bonded via the heteroatom to E and A; and X are, independently, univalent anionic ligands, or both X are joined and bound to the metal atom to form a metallocycle ring, or both X join to form a chelating ligand, a diene ligand, or an alkylidene ligand.

This invention further relates to a catalyst system comprised of the above metallocenes combined with an activator and to a process to polymerize unsaturated monomers using such catalyst system. This invention further relates to one or more methods of synthesizing the above metallocenes.

DEFINITIONS

Figure 1:
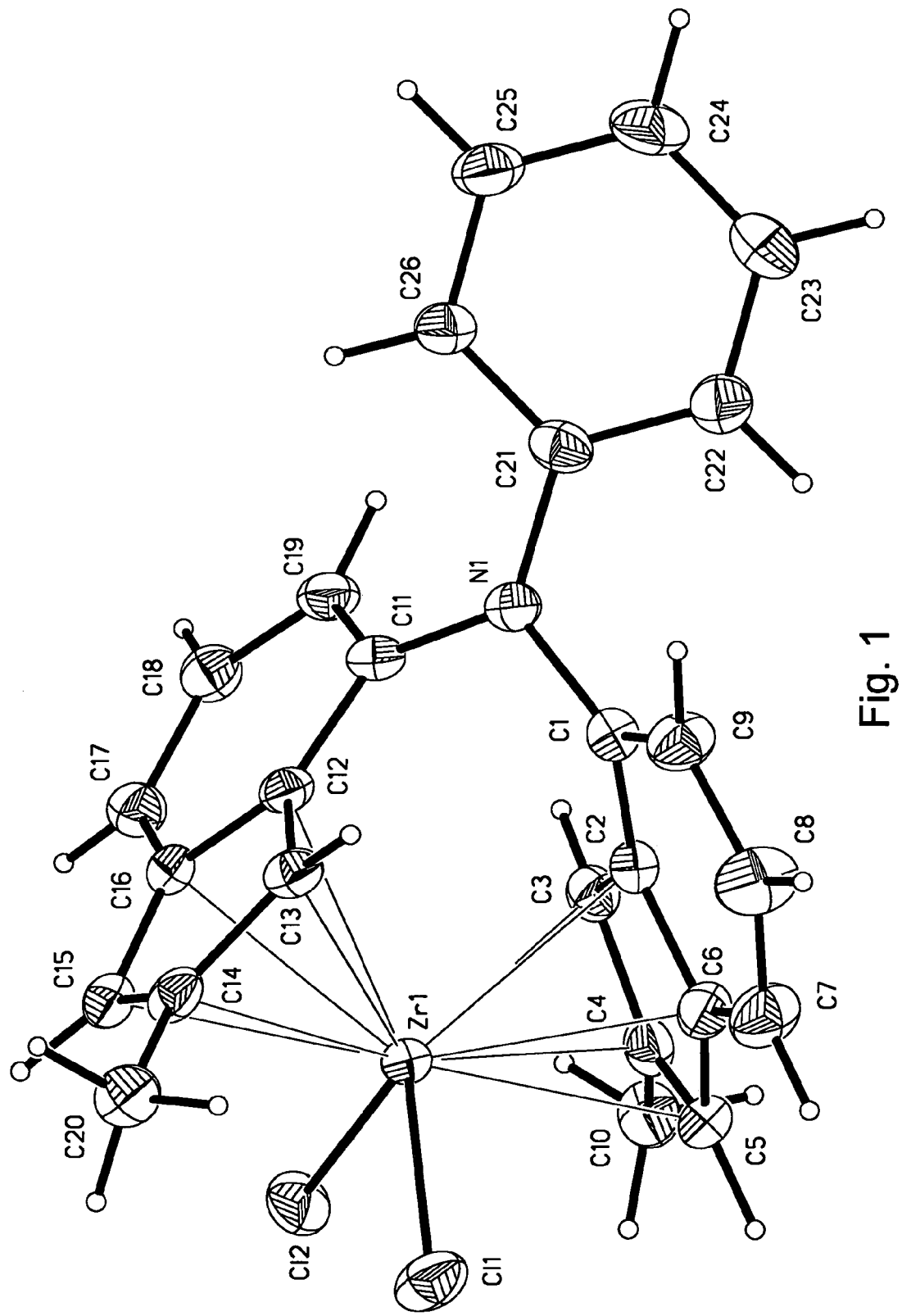
FIG. 1 is a drawing of 4,4'-phenylazandiyl-bis($\eta^5$-2-methylindenyl)zirconium dichloride (N2).

As used herein, the numbering scheme for the Periodic Table Groups is the new notation as set out in CHEMICAL AND ENGINEERING NEWS, 63(5), 27 (1985).

As used herein, Me is methyl, t-Bu and $^t$Bu are tertiary butyl, iPr and $^i$Pr are isopropyl, and Ph is phenyl.

The terms "hydrocarbyl radical," "hydrocarbyl" and hydrocarbyl group" are used interchangeably throughout this document. Likewise the terms "group" and "substituent" are also used interchangeably in this document. For purposes of this disclosure, "hydrocarbyl radical" is defined to be $C_1$-$C_{100}$ radicals, that may be linear, branched, or cyclic, and when cyclic, aromatic or non-aromatic, and include substituted hydrocarbyl radicals, halocarbyl radicals, and substituted halocarbyl radicals, silylcarbyl radicals, and germylcarbyl radicals as these terms are defined below.

Substituted hydrocarbyl radicals are radicals in which at least one hydrogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$ and the like or where at least one non-hydrocarbon atom or group has been inserted within the hydrocarbyl radical, such as —O—, —S—, —Se—, —Te—, —N(R*)—, =N—, —P(R*)—, =P—, —As(R*)—, =As—, —Sb(R*)—, =Sb—, —B(R*)—, =B—, —Si(R*)$_2$—, —Ge(R*)$_2$—, —Sn(R*)$_2$—, —Pb(R*)$_2$— and the like, where R* is independently a hydrocarbyl or halocarbyl radical, and two or more R* may join together to form a substituted or unsubstituted saturated, partially unsaturated or aromatic cyclic or polycyclic ring structure.

Halocarbyl radicals are radicals in which one or more hydrocarbyl hydrogen atoms have been substituted with at least one halogen (e.g. F, Cl, Br, I) or halogen-containing group (e.g. $CF_3$).

Substituted halocarbyl radicals are radicals in which at least one halocarbyl hydrogen or halogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$ and the like or where at least one non-carbon atom or group has been inserted within the halocarbyl radical such as —O—, —S—, —Se—, —Te—, —N(R*)—, =N—, —P(R*)—, =P—, —As(R*)—, =As—, —Sb(R*)—, =Sb—, —B(R*)—, =B—, —Si(R*)$_2$—, —Ge(R*)$_2$—, —Sn(R*)$_2$—, —Pb(R*)$_2$— and the like, where R* is independently a hydrocarbyl or halocarbyl radical provided that at least one halogen atom remains on the original halocarbyl radical. Additionally, two or more R* may join together to form a substituted or unsubstituted saturated, partially unsaturated or aromatic cyclic or polycyclic ring structure.

Silylcarbyl radicals (also called silylcarbyls) are groups in which the silyl functionality is bonded directly to the indicated atom or atoms. Examples include $SiH_3$, $SiH_2R^*$, $SiHR^*_2$, $SiR^*_3$, $SiH_2(OR^*)$, $SiH(OR^*)_2$, $Si(OR^*)_3$, $SiH_2(NR^*_2)$, $SiH(NR^*_2)_2$, $Si(NR^*_2)_3$, and the like where R* is independently a hydrocarbyl or halocarbyl radical and two or more R* may join together to form a substituted or unsubstituted saturated, partially unsaturated or aromatic cyclic or polycyclic ring structure.

Germylcarbyl radicals (also called germylcarbyls) are groups in which the germyl functionality is bonded directly to the indicated atom or atoms. Examples include $GeH_3$, $GeH_2R^*$, $GeHR^*_2$, $GeR^5_3$, $GeH_2(OR^*)$, $GeH(OR^*)_2$, $Ge(OR^*)_3$, $GeH_2(NR^*_2)$, $GeH(NR^*_2)_2$, $Ge(NR^*_2)_3$, and the like where R* is independently a hydrocarbyl or halocarbyl radical and two or more R* may join together to form a substituted or unsubstituted saturated, partially unsaturated or aromatic cyclic or polycyclic ring structure.

Polar radicals or polar groups are groups in which the heteroatom functionality is bonded directly to the indicated atom or atoms. They include heteroatoms of groups 1-17 of the periodic table either alone or connected to other elements by covalent or other interactions such as ionic, van der Waals forces, or hydrogen bonding. Examples of functional groups include carboxylic acid, acid halide, carboxylic ester, carboxylic salt, carboxylic anhydride, aldehyde and their chalcogen (Group 14) analogues, alcohol and phenol, ether, peroxide and hydroperoxide, carboxylic amide, hydrazide and imide, amidine and other nitrogen analogues of amides, nitrile, amine and imine, azo, nitro, other nitrogen compounds, sulfur acids, selenium acids, thiols, sulfides, sulfoxides, sulfones, phosphines, phosphates, other phosphorus compounds, silanes, boranes, borates, alanes, aluminates. Functional groups may also be taken broadly to include organic polymer supports or inorganic support material such as alumina, and silica. Preferred examples of polar groups include $NR^*_2$, $OR^*$, $SeR^*$, $TeR^*$, $PR^*_2$, $AsR^*_2$, $SbR^*_2$, $SR^*$, $BR^*_2$, $SnR^*_3$, $PbR^*_3$ and the like where R* is independently a hydrocarbyl, substituted hydrocarbyl, halocarbyl or substituted halocarbyl radical as defined above and two R* may join together to form a substituted or unsubstituted saturated, partially unsaturated or aromatic cyclic or polycyclic ring structure.

In some embodiments, the hydrocarbyl radical is independently selected from methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, triacontynyl, butadienyl, pentadienyl, hexadienyl, heptadienyl, octadienyl, nonadienyl, and decadienyl. Also included are isomers of saturated, partially unsaturated and aromatic cyclic and polycyclic structures wherein the radical may additionally be subjected to the types of substitutions described above. Examples include phenyl, methylphenyl, dimethylphenyl, ethylphenyl, diethylphenyl, propylphenyl, dipropylphenyl, benzyl, methylbenzyl, naphthyl, anthracenyl, cyclopentyl, cyclopentenyl, cyclohexyl, cyclohexenyl, methylcyclohexyl, cycloheptyl, cycloheptenyl, norbornyl, norbornenyl, adamantyl and the like. For this disclosure, when a radical is listed, it indicates that radical type and all other radicals formed when that radical type is subjected to the substitutions defined above. Alkyl, alkenyl and alkynyl radicals listed include all isomers including where appropriate cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl and 2-methyl-2-propenyl (and cyclobutenyls and cyclopropenyls). Cyclic compound having substitutions include all isomer forms, for example, methylphenyl would include ortho-methylphenyl, meta-methylphenyl and para-methylphenyl; dimethylphenyl would include 2,3-dimethylphenyl, 2,4-dimethylphenyl, 2,5-dimethylphenyl, 2,6-diphenylmethyl, 3,4-dimethylphenyl, and 3,5-dimethylphenyl.

For nomenclature purposes, the following numbering schemes are used for cyclopentadienyl, indenyl and fluorenyl rings. For cyclopentadienyl drawn below as an anionic ligand, all five numbered positions are equivalent. For indenyl also drawn below as an anionic ligand, positions 1 and 3 are equivalent, 4 and 7 are equivalent, and 5 and 6 are equivalent. For fluorenyl drawn below as an anionic ligand, positions 1 and 8 are equivalent, 2 and 7 are equivalent, 3 and 6 are equivalent, and 4 and 5 are equivalent.

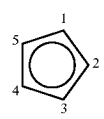
Cyclopentadienyl

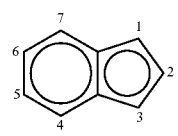
Indenyl

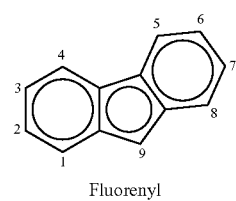
Fluorenyl

A similar numbering and nomenclature scheme is used for heteroindenyl and heterofluorenyl rings as illustrated below where Z and Q independently represent the heteroatoms O, S, Se, or Te, or heteroatom groups, NR', PR', AsR', or SbR' where R' is hydrogen, or a hydrocarbyl, substituted hydrocarbyl, halocarbyl, substituted halocarbyl, silylcarbyl, or germylcarbyl substituent.

Examples include:

Cyclopenta[b]thienyl (Z = S)
Cyclopenta[b]furanyl (Z = O)
Cyclopenta[b]selenophenyl (Z = Se)
Cyclopenta[b]tellurophenyl (Z = Te)
6-Methyl-cyclopenta[b]pyrrolyl (Z = N-Me)
6-Methyl-cyclopenta[b]phospholyl (Z = P-Me)
6-Methyl-cyclopenta[b]arsolyl (Z = As-Me)
6-Methyl-cyclopenta[b]stibolyl (Z = Sb-Me)

Examples include:

Cyclopenta[c]thienyl (Z = S)
Cyclopenta[c]furanyl (Z = O)
Cyclopenta[c]selenophenyl (Z = Se)
Cyclopenta[c]tellurophenyl (Z = Te)
5-Methyl-cyclopenta[c]pyrrolyl (Z = N-Me)
5-Methyl-cyclopenta[c]phospholyl (Z = P-Me)
5-Methyl-cyclopenta[c]arsolyl (Z = As-Me)
5-Methyl-cyclopenta[c]stibolyl (Z = Sb-Me)

heterofluorenyl ligands

-continued

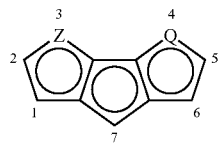

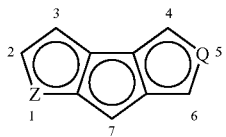

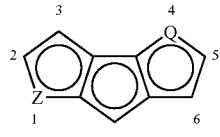

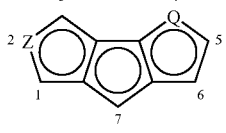

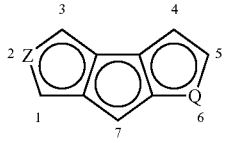

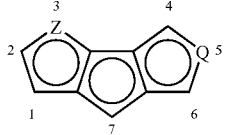

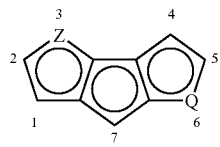

A similar numbering and nomenclature scheme is used for heterocyclopentadienyl rings as illustrated below where G and J independently represent the heteroatoms N, P, As, Sb or B. For these ligands, the one position is usually chosen to be the ring carbon position where the ligand is bonded to the bridging group, hence a numbering scheme is not illustrated below.

Examples include:
Azacyclopentadiene (G = N)
Phosphacyclopentadiene (G = P)
Stibacyclopentadiene (G = Sb)
Arsacyclopentadiene (G = As)
Boracyclopentadiene (G = B)

Depending on the position of the bridging ligand, the numbering for the following ligands will change; 1,3 and 1,2 are only used in this case to illustrate the position of the heteroatoms relative to one another.

Examples include:

1,3-Diazacyclopentadiene (G = J = N)
1,3-Diphosphacyclopentadiene (G = J = P)
1,3-Distibacyclopentadiene (G = J = Sb)
1,3-Diarsacyclopentadiene (G = J = As)
1,3-Diboracyclopentadiene (G = J = B)
1,3-Azaphosphacyclopentadiene (G = N; J = P)
1,3-Azastibacyclopentadiene (G = N; J = Sb)
1,3-Azarsacyclopentadiene (G = N; J = As)
1,3-Azaboracyclopentadiene (G = N; J = B)
1,3-Arsaphosphacyclopentadiene (G = As; J = P)
1,3-Arsastibacyclopentadiene (G = As; J = Sb)
1,3-Arsaboracyclopentadiene (G = As; J = B)
1,3-Boraphosphacyclopentadiene (G = B; J = P)
1,3-Borastibacyclopentadiene (G = B; J = Sb)
1,3-Phosphastibacyclopentadiene (G = P; J = Sb)

Examples include:

1,2-Diazacyclopentadiene (G = J = N)
1,2-Diphosphacyclopentadiene (G = J = P)
1,2-Distibacyclopentadiene (G = J = Sb)
1,2-Diarsacyclopentadiene (G = J = As)
1,2-Diboracyclopentadiene (G = J = B)
1,2-Azaphosphacyclopentadiene (G = N; J = P)
1,2-Azastibacyclopentadiene (G = N; J = Sb)
1,2-Azarsacyclopentadiene (G = N; J = As)
1,2-Azaboracyclopentadiene (G = N; J = B)
1,2-Arsaphosphacyclopentadiene (G = As; J = P)
1,2-Arsastibacyclopentadiene (G = As; J = Sb)
1,2-Arsaboracyclopentadiene (G = As; J = B)
1,2-Boraphosphacyclopentadiene (G = B; J = P)
1,2-Borastibacyclopentadiene (G = B; J = Sb)
1,2-Phosphastibacyclopentadiene (G = P; J = Sb)

Furthermore, the terms "ring heteroatom", "heteroatom substituent", and "bridging heteroatom substituent" are illustrated below where Z represents the heteroatoms O, S, Se, or Te, or heteroatom groups, NR', PR', AsR', or SbR' where R' is hydrogen, or a hydrocarbyl, substituted hydrocarbyl, halocarbyl, substituted halocarbyl, silylcarbyl, or germylcarbyl substituent. It should be noted that a "heteroatom substituent" can be a "bridging heteroatom substituent" when R' is additionally defined as the ligand "A".

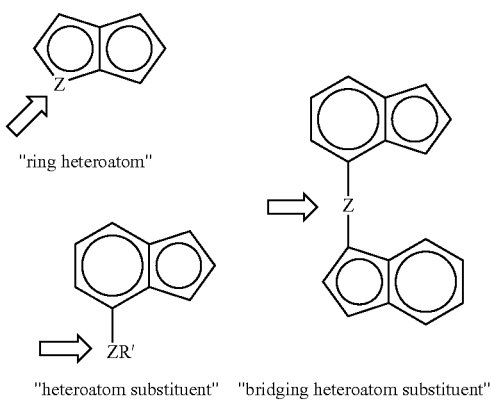

"ring heteroatom"

"heteroatom substituent"   "bridging heteroatom substituent"

A "ring carbon atom" is a carbon atom that is part of a cyclic ring structure. By this definition, an indenyl ligand has nine ring carbon atoms.

A "bondable ring position" is a ring position that is capable of bearing a substituent or bridging substituent. For example, cyclopenta[b]thienyl has five bondable ring positions (at the carbon atoms) and one non-bondable ring position (the sulfur atom); cyclopenta[b]pyrrolyl has six bondable ring positions (at the carbon atoms and at the nitrogen atom).

In the context of this document, "homopolymerization" would produce a polymer made from one monomer. For example, homopolymerization of propylene would produce homopolypropylene. Homopolymerization of ethylene would produce homopolyethylene. It should be noted, however, that some of the catalysts of this invention homopolymerize ethylene or propylene to non-traditional "polyethylene" and "polypropylene" structures, respectively. Likewise, "copolymerization" would produce polymers with more than one monomer type. For example, ethylene copolymers include polymers of ethylene with α-olefins, cyclic olefins and diolefins, vinylaromatic olefins, α-olefinic diolefins, substituted α-olefins, and/or acetylenically unsaturated monomers. Non-limiting examples of α-olefins include propylene, 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, vinylcyclohexane, and vinylnorbornane. Non-limiting examples of cyclic olefins and diolefins include cyclobutene, cyclopentene, cyclohexene, cycloheptene, cyclooctene, cyclononene, cyclodecene, norbornene, 4-methylnorbornene, 2-methylcyclopentene, 4-methylcyclopentene, vinylcyclohexane, norbornadiene, dicyclopentadiene, 5-ethylidene-2-norbornene, vinylcyclohexene, 5-vinyl-2-norbornene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, and 1,5-diallylcyclooctane. Non-limiting examples of vinylaromatic olefins include styrene, para-methylstyrene, para-t-butylstyrene, vinylnaphthylene, vinyltoluene, and divinylbenzene. Non-limiting examples of α-olefinic dienes include 1,4-hexadiene, 1,5-hexadiene, 1,5-heptadiene, 1,6-heptadiene, 6-methyl-1,6-heptadiene, 1,7-octadiene, 7-methyl-1,7-octadiene, 1,9-decadiene, 1,11-dodecene, 1,13-tetradecene and 9-methyl-1,9-decadiene. Substituted α-olefins (also called functional group containing α-olefins) include those containing at least one non-carbon Group 13 to 17 atom bound to a carbon atom of the substituted α-olefin where such substitution if silicon may be adjacent to the double bond or terminal to the double bond, or anywhere in between, and where inclusion of non-carbon and non-silicon atoms such as for example B, O, S, Se, Te, N, P, Ge, Sn, Pb, As, F, Cl, Br, or I, are contemplated, where such non-carbon or non-silicon moieties are sufficiently far removed from the double bond so as not to interfere with the coordination polymerization reaction with the catalyst and so to retain the generally hydrocarbyl characteristic. By sufficiently far removed from the double bond we intend that the number of carbon atoms, or the number of carbon and silicon atoms, separating the double bond and the non-carbon or non-silicon moiety may be 6 or greater, e.g. 7, or 8, or 9, or 10, or 11, or 12, or 13, or 14 or more. The number of such carbon atoms, or carbon and silicon atoms, is counted from immediately adjacent to the double bond to immediately adjacent to the non-carbon or non-silicon moiety. Examples include allyltrimethylsilane, divinylsilane, 8,8,8-trifluoro-1-octene, 8-methoxyoct-1-ene, 8-methylsulfanyloct-1-ene, 8-dimethylaminooct-1-ene, or combinations thereof. The use of functional group-containing α-olefins where the functional group is closer to the double bond is also within the scope of embodiments of the invention when such olefins may be incorporated in the same manner as are their α-olefin analogs. See, "Metallocene Catalysts and Borane Reagents in The Block/Graft Reactions of Polyolefins", T. C. Chung, et al, *Polym. Mater. Sci. Eng.*, v. 73, p. 463 (1995), and the masked α-olefin monomers of U.S. Pat. No. 5,153,282. Such monomers permit the preparation of both functional-group containing copolymers capable of subsequent derivatization, and of functional macromers which may be used as graft and block type polymeric segments. Copolymerization can also incorporate α-olefinic macromonomers of up to 2000 mer units.

For purposes of this disclosure, the term oligomer refers to compositions having 2-75 mer units and the term polymer refers to compositions having 76 or more mer units. A mer is defined as a unit of an oligomer or polymer that originally corresponded to the olefin(s) used in the oligomerization or polymerization reaction. For example, the mer of polyethylene would be ethylene.

The term "catalyst system" is defined to mean a catalyst precursor/activator pair. When "catalyst system" is used to describe such a pair before activation, it means the unactivated catalyst (precatalyst) together with an activator and, optionally, a co-activator. When it is used to describe such a pair after activation, it means the activated catalyst and the activator or other charge-balancing moiety.

The transition metal compound may be neutral as in a precatalyst, or a charged species with a counter ion as in an activated catalyst system.

Catalyst precursor is also often referred to as precatalyst, catalyst, catalyst precursor and transition metal compound or complex. These words are used interchangeably. Activator and cocatalyst are also used interchangeably. A scavenger is a compound that is typically added to facilitate oligomerization or polymerization by scavenging impurities. Some scavengers may also act as activators and may be referred to as co-activators. A co-activator, that is not a scavenger, may also be used in conjunction with an activator in order to form an active catalyst. In some embodiments a co-activator can be pre-mixed with the transition metal compound to form an alkylated transition metal compound, also referred to as an alkylated invention compound.

Noncoordinating anion (NCA) is defined to mean an anion either that does not coordinate to the catalyst metal cation or that does coordinate to the metal cation, but only weakly. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the noncoordinating anion. Suitable metals include, but are not limited to, aluminum, gold, and platinum. Suitable metalloids include, but are not limited to, boron, aluminum, phosphorus, and silicon.

A stoichiometric activator can be either neutral or ionic. The terms ionic activator, and stoichiometric ionic activator can be used interchangeably. Likewise, the terms neutral stoichiometric activator, and Lewis acid activator can be used interchangeably.

DETAILED DESCRIPTION OF THE INVENTION

The metallocene compounds according to the invention can exist in the racemic (d/l enantiomers) or meso form. The racemic form is preferred for use as a catalyst component for the production of crystalline poly-alpha-olefins. The meso form is preferred for use as a catalyst component for the production of amorphous poly-alpha-olefins. Both forms can be used as a catalyst component for the production of homopolymers, such as homopolyethylene or homopolypropylene, and for copolymers of ethylene with other olefins including alpha-olefins or copolymers of propylene with other olefins including alpha-olefins.

In a preferred embodiment this invention relates to transition metal compounds represented by formula (2):

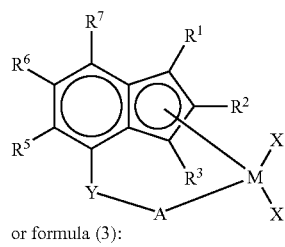

or formula (3):

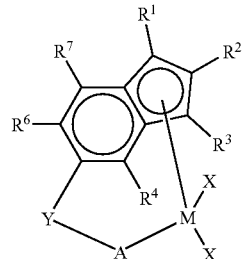

or formula (4):

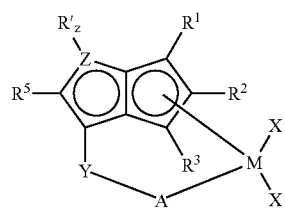

or formula (5):

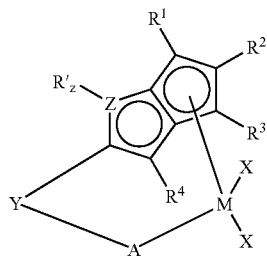

or formula (6):

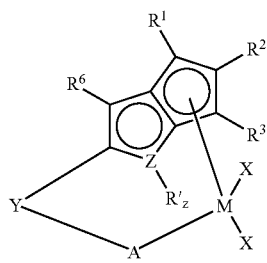

or formula (7):

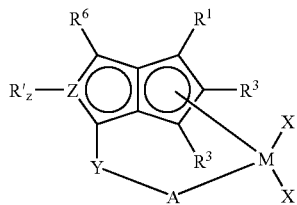

or formula (8):

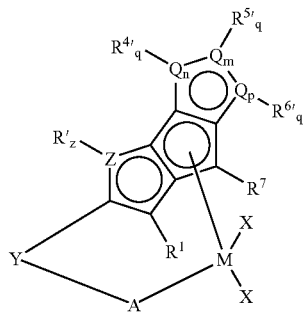

or formula (9):

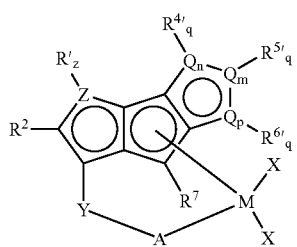

-continued or formula (10):

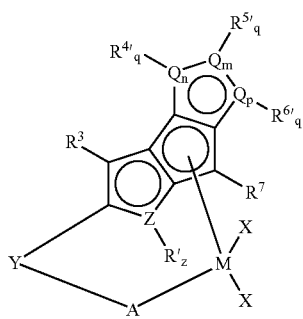

or formula (11):

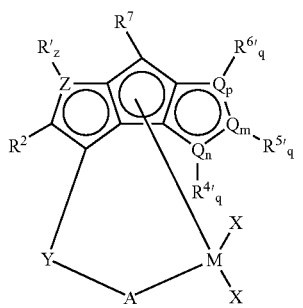

or formula (12):

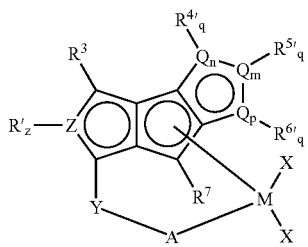

or formula (13):

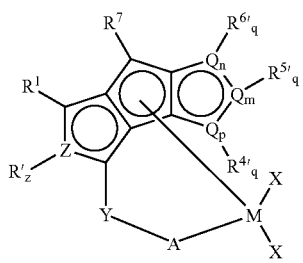

or formula (14):

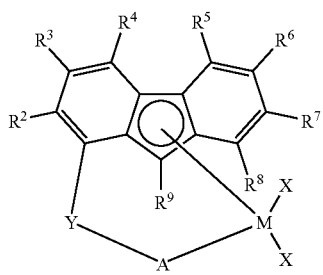

or formula (15):

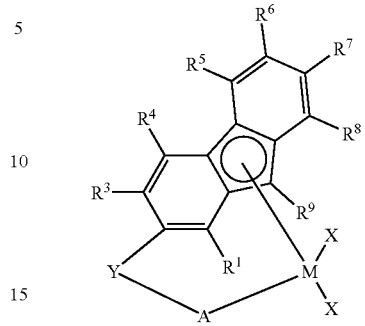

or formula (16):

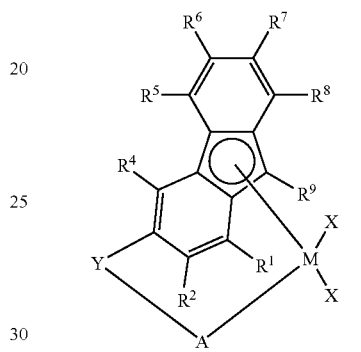

or formula (17):

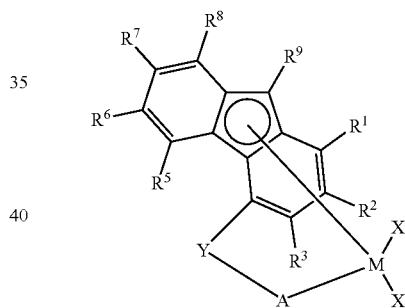

wherein

M is a group 3, 4, 5 or 6 transition metal atom, or a lanthanide metal atom, or actinide metal atom, preferably a Group 4 transition metal atom selected from titanium, zirconium or hafnium;

$R^1, R^2, R^3, R^4, R^5, R^6, R^7, R^8, R^9, R', R'', R^{4'}, R^{5'}$, and $R^{6'}$ are, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent $R^1, R^2, R^3, R^4, R^5, R^6, R^7, R^8, R^9, R', R'', R^{4'}, R^{5'}$, and $R^{6'}$ may join together to form a substituted or unsubstituted, saturated, partially unsaturated, or aromatic cyclic or polycyclic substituent;

Z is a Group 16 atom or a Group 15 atom, and preferably S, O, N, or P; when Z is a Group 15 atom, "z" is one, indicating the presence of R' bonded to Z, and when Z is a Group 16 atom, "z" is zero, indicating the absence of R';

each Q, if present, is, independently, a Group 16 atom or a Group 15 atom, and preferably S, O, N, or P; when a Q is a Group 15 atom, "q" is one, indicating the presence of $R^{4'}, R^{5'}$, or $R^{6'}$ bonded to Q, and when a Q is a Group 16 atom, "q" is zero, indicating the absence of $R^{4'}$, $R^{5'}$, or $R^{6'}$; m, n, and p are independently zero or one, and m+n+p=1; when m or n or p is one, Q is present in the ring as a Group 16 or a Group 15 atom; when m or n or p is zero, Q is absent and is replaced by a ring carbon atom having a substituent R";

Y is a Group 15 or 16 bridging heteroatom substituent that is bonded via the heteroatom to the indicated ring system, and to A; Y is preferably S, O, NR' or PR'; in another embodiment, Y may consist of two Group 15 or 16 heteroatoms bonded in series with one heteroatom bonded to the indicated ring system, and the other heteroatom bonded to A (i.e. Y is O—O, S—S, R'N—NR', R'P—PR', O—S, O—NR', O—PR', S—NR', S—PR', or R'N—PR';

A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand where A is bonded to Y through any bondable ring position; or A is a mono-anionic ligand such as a substituted or unsubstituted pentadienyl ligand, a substituted or unsubstituted allyl ligand, or a substituted or unsubstituted boratabenzene; and X are, independently, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from about 3 to about 20 carbon atoms; or both together can be an olefin, diolefin or aryne ligand; or when Lewis-acid activators, such as methylalumoxane, which are capable of donating an X ligand as described above to the transition metal component are used, both X may, independently, be a halogen, alkoxide, aryloxide, amide, phosphide or other univalent anionic ligand or both X can also be joined to form a anionic chelating ligand.

In an embodiment of the invention, in formulae 2-6, $R^1$, $R^2$ and $R^3$ are, independently, hydrogen, or a C1-C6 hydrocarbyl group, and preferably hydrogen, methyl, ethyl, propyl, butyl, pentyl, hexyl, or phenyl.

In another embodiment of the invention, in formula 2, $R^7$ is preferably hydrogen, bromine, methyl, ethyl, propyl, butyl, pentyl, hexyl, phenyl, tolyl, ethylphenyl, propylphenyl, butylphenyl, 5-methylfuryl or 5-methylthienyl.

In another embodiment of the invention, in all of the above formulae 1-17, Y is preferably oxadiyl, sulfandiyl, phenylazandiyl, phenylphosphindiyl, methylazandiyl or methylphosphindiyl.

Examples of specific invention catalyst precursors of formulae 2 through 17 are tabulated below in Table 1, where some representative components are listed. Not listed, is M which is defined above; M is, preferably, titanium, zirconium, or hafnium. When alkyl, alkenyl and alkynyl radicals are disclosed in this application the term includes all isomers and all substitution types, as previously described, unless otherwise stated. Listings for the ligand "A" include all bondable ring positions and all possible isomers. For example, a listing under "A" of indenyl would include 1-indenyl, 2-indenyl, 4-indenyl and 5-indenyl where the number indicates the bridging position; a listing of methylindenyl would include 2-(1-methylindenyl), 3-(1-methylindenyl), 4-(1-methylindenyl), 5-(1-methylindenyl), 6-(1-methylindenyl), 7-(1-methylindenyl), 1-(2-methylindenyl), 4-(2-methylindenyl), 5-(2-methylindenyl), 1-(4-methylindenyl), 2-(4-methylindenyl), 3-(4-methylindenyl), 5-(4-methylindenyl), 6-(4-methylindenyl), 7-(4-methylindenyl), 1-(5-methylindenyl), 2-(5-methylindenyl), 3-(5-methylindenyl), 4-(5-methylindenyl), 6-(5-methylindenyl), and 7-(5-methylindenyl) where the number outside the parenthesis indicates the bridging position. When more than one substituent is listed, for example, propylphenylindenyl, propyl and phenyl are each substituents on the indenyl ring, as compared to (propylphenyl)indenyl where propyl is a substituent on the phenyl ring which in turn is a substituent on the indenyl ring. The column labeled $R^1$, $R^2$, $R^3$, $R^4$, $R^5$, $R^6$, $R^7$, $R^8$, $R^9$, R', R", $R^{4'}$, $R^{5'}$, and $R^{6'}$ shows some examples of substituents that can serve as $R^1$, $R^2$, $R^3$, $R^4$, $R^5$, $R^6$, $R^7$, $R^8$, $R^9$, R', R", $R^{4'}$, $R^{5'}$, and $R^{6'}$. The selection of one substituent is independent of the selection any other substituent. In other words, the invention allows $R^1=R^2=R^3=R^4=R^5=R^6=R^7=R^8=R^9=R'=R''=R^{4'}=R^{5'}=R^{6'}$, but does not demand it. To illustrate members of the transition metal component, select a transition metal, and select any combination of the species listed in Table 1 for a given formula illustrated above. For example, using formula 2, zirconium as the transition metal, and the substituents/ligands in the first row of Table 1, the compound 4,4'-oxadiyl(indenyl)(cyclopenta[b]thienyl)zirconium dihydride (which is the same as oxadiyl-4-(indenyl)-4'-(cyclopenta[b]thienyl)zirconium dihydride) is illustrated. Any combination of components may be selected using formulae 2 through 17, and any Group 3, 4, 5 or 6 transition metal atom. Additional examples illustrated would include:

sulfandiyl-5-(2-methyl-7-phenylindenyl)-4-(indenyl) hafnium dichloride;

4,4'-phenylazandiyl-bis(2-propylindenyl)zirconium dimethyl;

4,4'-selandiyl-bis(cyclopenta[b]furanyl)titanium dibenzyl;

4,2'-oxadiyl-bis(indenyl) hafnium dibromide;

methylazandiyl-4-(2-methylindenyl)-9-(dibutylfluorenyl) zirconium methyl chloride, and the like.

TABLE 1

| Y |
| --- |
| Oxadiyl |
| Sulfandiyl |
| Selandiyl |
| Tellandiyl |
| Methylazandiyl |
| Ethylazandiyl |
| Propylazandiyl |
| Butylazandiyl |
| Pentylazandiyl |
| Hexylazandiyl |
| Heptylazandiyl |
| Octylazandiyl |
| Nonylazandiyl |
| Decylazandiyl |
| Undecylazandiyl |
| Dodecylazandiyl |
| Tridecylazandiyl |
| Tetradecylazandiyl |
| Pentadecylazandiyl |
| Hexadecylazandiyl |
| Heptdecylazandiyl |
| Octadecylazandiyl |
| Nonadecylazandiyl |
| Eicosylazandiyl |
| Heneicosylazandiyl |
| Docosylazandiyl |
| Tricosylazandiyl |
| Tetracosylazandiyl |
| Pentacosylazandiyl |
| Hexacosylazandiyl |

TABLE 1-continued

Heptacosylazandiyl
Octacosylazandiyl
Nonacosylazandiyl
Triacontylazandiyl
Vinylazandiyl
Propenylazandiyl
Butenylazandiyl
Pentenylazandiyl
Hexenylazandiyl
Heptenylazandiyl
Octenylazandiyl
Nonenylazandiyl
Decenylazandiyl
Undecenylazandiyl
Dodecenylazandiyl
Tridecenylazandiyl
Tetradecenylazandiyl
Pentadecenylazandiyl
Hexadecenylazandiyl
Heptadecenylazandiyl
Octadecenylazandiyl
Nonadecenylazandiyl
Eicosenylazandiyl
Heneicosenylazandiyl
Docosenylazandiyl
Tricosenylazandiyl
Tetracosenylazandiyl
Pentacosenylazandiyl
Hexacosenylazandiyl
Heptacosenylazandiyl
Octacosenylazandiyl
Nonacosenylazandiyl
Triacontenylazandiyl
Propynylazandiyl
Butynylazandiyl
Pentynylazandiyl
Hexynylazandiyl
Heptynylazandiyl
Octynylazandiyl
Nonynylazandiyl
Decynylazandiyl
Undecynylazandiyl
Dodecynylazandiyl
Tridecynylazandiyl
Tetradecynylazandiyl
Pentadecynylazandiyl
Hexadecynylazandiyl
Heptadecynylazandiyl
Octadecynylazandiyl
Nonadecynylazandiyl
Eicosynylazandiyl
Heneicosynylazandiyl
Docosynylazandiyl
Tricosynylazandiyl
Tetracosynylazandiyl
Pentacosynylazandiyl
Hexacosynylazandiyl
Heptacosynylazandiyl
Octacosynylazandiyl
Nonacosynylazandiyl
Triacontynylazandiyl
Cyclopropylazandiyl
Cyclobutylazandiyl
Cyclopentylazandiyl
Cyclohexylazandiyl
Cycloheptylazandiyl
Cyclooctylazandiyl
Cyclononylazandiyl
Cyclodecylazandiyl
Cycloundecylazandiyl
Cyclododecylazandiyl
Cyclotetradecylazandiyl
Cyclohexadecylazandiyl
Cyclooctadecylazandiyl
(methylcyclohexyl)azandiyl
(ethylcyclohexyl)azandiyl
(propylcyclohexyl)azandiyl
(dimethylcyclohexyl)azandiyl
(diethylcyclohexyl)azandiyl TABLE 1-continued (dipropylcyclohexyl)azandiyl
Phenylazandiyl
Tolylazandiyl
Mesitylazandiyl
(ethylphenyl)azandiyl
(propylphenyl)azandiyl
(butylphenyl)azandiyl
(pentylphenyl)azandiyl
(hexylphenyl)azandiyl
(dimethylphenyl)azandiyl
(trimethylphenyl)azandiyl
(diethylphenyl)azandiyl
(diethylmethylphenyl)azandiyl
(dipropylphenyl)azandiyl
(dipropylmethylphenyl)azandiyl
Biphenylazandiyl
Phenethylazandiyl
Napthylazandiyl
Norbornylazandiyl
Adamantylazandiyl
Fluoromethylazandiyl
Fluoroethylazandiyl
Fluoropropylazandiyl
Fluorobutylazandiyl
Fluoropentylazandiyl
Fluorohexylazandiyl
Fluoroheptylazandiyl
Fluorooctylazandiyl
Fluorononylazandiyl
Fluorodecylazandiyl
Fluoroundecylazandiyl
Fluorododecylazandiyl
Thienylazandiyl
Furanylazandiyl
Pyrrolylazandiyl
Phospholylazandiyl
(methylthienyl)azandiyl
(methylfuranyl)azandiyl
(methylpyrrolyl)azandiyl
(methylphospholyl)azandiyl
(propylthienyl)azandiyl
(propylfuranyl)azandiyl
(propylpyrrolyl)azandiyl
(propylphospholyl)azandiyl
(butylthienyl)azandiyl
(butylfuranyl)azandiyl
(butylpyrrolyl)azandiyl
(butylphospholyl)azandiyl
(pentylthienyl)azandiyl
(pentylfuranyl)azandiyl
(pentylpyrrolyl)azandiyl
(penylphospholyl)azandiyl
(hexylthienyl)azandiyl
(hexylfuranyl)azandiyl
(hexylpyrrolyl)azandiyl
(hexylphospholyl)azandiyl
(heptylthienyl)azandiyl
(heptylfuranyl)azandiyl
(heptylpyrrolyl)azandiyl
(heptylphospholyl)azandiyl
(octylthienyl)azandiyl
(octylfuranyl)azandiyl
(octylpyrrolyl)azandiyl
(octylphospholyl)azandiyl
(nonylthienyl)azandiyl
(nonylfuranyl)azandiyl
(nonylpyrrolyl)azandiyl
(nonylphospholyl)azandiyl
(decylthienyl)azandiyl
(decylfuranyl)azandiyl
(decylpyrrolyl)azandiyl
(decylphospholyl)azandiyl
(undecylthienyl)azandiyl
(undecylfuranyl)azandiyl
(undecylpyrrolyl)azandiyl
(undecylphospholyl)azandiyl
(dodecylthienyl)azandiyl
(dodecylfuranyl)azandiyl
(dodecylpyrrolyl)azandiyl

TABLE 1-continued (dodecylphospholyl)azandiyl
(dimethylthienyl)azandiyl
(dimethylfuranyl)azandiyl
(dimethylpyrrolyl)azandiyl
(dimethylphospholyl)azandiyl
(diethylthienyl)azandiyl
(diethylfuranyl)azandiyl
(diethylpyrrolyl)azandiyl
(diethylphospholyl)azandiyl
(dipropylthienyl)azandiyl
(dipropylfuranyl)azandiyl
(dipropylpyrrolyl)azandiyl
(dipropylphospholyl)azandiyl
(dibutylthienyl)azandiyl
(dibutylfuranyl)azandiyl
(dibutylpyrrolyl)azandiyl
(dibutylphospholyl)azandiyl
Fluorophenylazandiyl
Difluorophenylazandiyl
Trifluorophenylazandiyl
Tetrafluorophenylazandiyl
Pentafluorophenylazandiyl
Benzylazandiyl
Trimethylsilylmethylazandiyl
Trifluoromethylazandiyl
Trifluoromethylmethylazandiyl
Perfluoroethylazandiyl
Perfluoropropylazandiyl
Perfluorobutylazandiyl
Perfluoropentylazandiyl
Perfluorohexylazandiyl
Perfluoroheptylazandiyl
Perfluorooctylazandiyl
Perfluorononylazandiyl
Perfluorodecylazandiyl
Perfluoroundecylazandiyl
Perfluorododecylazandiyl
Trimethylsilylazandiyl
Trimethylgermylazandiyl
Trimethylsilylmethylazandiyl
Trimethylgermylmethylazandiyl
Methoxymethylazandiyl
Ethoxymethylazandiyl
Propoxymethylazandiyl
Butoxymethylazandiyl
Phenoxymethylazandiyl
Dimethylaminomethylazandiyl
Diphenylaminomethylazandiyl
Diphenylphosphinomethylazandiyl
Fluorobenzylazandiyl
Difluorobenzylazandiyl
Trifluorobenzylazandiyl
Tetrafluorobenzylazandiyl
Pentafluorobenzylazandiyl
Trifluoromethylbenzylazandiyl
Methylphosphindiyl
Ethylphosphindiyl
Propylphosphindiyl
Butylphosphindiyl
Pentylphosphindiyl
Hexylphosphindiyl
Heptylphosphindiyl
Octylphosphindiyl
Nonylphosphindiyl
Decylphosphindiyl
Undecylphosphindiyl
Dodecylphosphindiyl
Tridecylphosphindiyl
Tetradecylphosphindiyl
Pentadecylphosphindiyl
Hexadecylphosphindiyl
Heptadecylphosphindiyl
Octadecylphosphindiyl
Nonadecylphosphindiyl
Eicosylphosphindiyl
Heneicosylphosphindiyl
Docosylphosphindiyl
Tricosylphosphindiyl
Tetracosylphosphindiyl

TABLE 1-continued

Pentacosylphosphindiyl
Hexacosylphosphindiyl
Heptacosylphosphindiyl
Octacosylphosphindiyl
Nonacosylphosphindiyl
Triacontylphosphindiyl
Vinylphosphindiyl
Propenylphosphindiyl
Butenylphosphindiyl
Pentenylphosphindiyl
Hexenylphosphindiyl
Heptenylphosphindiyl
Octenylphosphindiyl
Nonenylphosphindiyl
Decenylphosphindiyl
Undecenylphosphindiyl
Dodecenylphosphindiyl
Tridecenylphosphindiyl
Tetradecenylphosphindiyl
Pentadecenylphosphindiyl
Hexadecenylphosphindiyl
Heptadecenylphosphindiyl
Octadecenylphosphindiyl
Nonadecenylphosphindiyl
Eicosenylphosphindiyl
Heneicosenylphosphindiyl
Docosenylphosphindiyl
Tricosenylphosphindiyl
Tetracosenylphosphindiyl
Pentacosenylphosphindiyl
Hexacosenylphosphindiyl
Heptacosenylphosphindiyl
Octacosenylphosphindiyl
Nonacosenylphosphindiyl
Triacontenylphosphindiyl
Propynylphosphindiyl
Butynylphosphindiyl
Pentynylphosphindiyl
Hexynylphosphindiyl
Heptynylphosphindiyl
Octynylphosphindiyl
Nonynylphosphindiyl
Decynylphosphindiyl
Undecynylphosphindiyl
Dodecynylphosphindiyl
Tridecynylphosphindiyl
Tetradecynylphosphindiyl
Pentadecynylphosphindiyl
Hexadecynylphosphindiyl
Heptadecynylphosphindiyl
Octadecynylphosphindiyl
Nonadecynylphosphindiyl
Eicosynylphosphindiyl
Heneicosynylphosphindiyl
Docosynylphosphindiyl
Tridecynylphosphindiyl
Tetradecynylphosphindiyl
Pentadecynylphosphindiyl
Hexadecynylphosphindiyl
Heptadecynylphosphindiyl
Octadecynylphosphindiyl
Nonadecynylphosphindiyl
Eicosynylphosphindiyl
Heneicosynylphosphindiyl
Docosynylphosphindiyl
Tricosynylphosphindiyl
Tetracosynylphosphindiyl
Pentacosynylphosphindiyl
Hexacosynylphosphindiyl
Heptacosynylphosphindiyl
Octacosynylphosphindiyl
Nonacosynylphosphindiyl
Triacontynylphosphindiyl
Cyclopropylphosphindiyl
Cyclobutylphosphindiyl
Cyclopentylphosphindiyl
Cyclohexylphosphindiyl
Cycloheptylphosphindiyl
Cyclooctylphosphindiyl TABLE 1-continued Cyclononylphosphindiyl
Cyclodecylphosphindiyl
Cycloundecylphosphindiyl
Cyclododecylphosphindiyl
Cyclotetradecylphosphindiyl
Cyclohexadecylphosphindiyl
Cyclooctadecylphosphindiyl
(methylcyclohexyl)phosphindiyl
(ethylcyclohexyl)phosphindiyl
(propylcyclohexyl)phosphindiyl
(dimethylcyclohexyl)phosphindiyl
(diethylcyclohexyl)phosphindiyl
(dipropylcyclohexyl)phosphindiyl
Phenylphosphindiyl
Tolylphosphindiyl
Mesitylphosphindiyl
(ethylphenyl)phosphindiyl
(propylphenyl)phosphindiyl
(butylphenyl)phosphindiyl
(pentylphenyl)phosphindiyl
(hexylphenyl)phosphindiyl
(dimethylphenyl)phosphindiyl
(trimethylphenyl)phosphindiyl
(diethylphenyl)phosphindiyl
(diethylmethylphenyl)phosphindiyl
(dipropylphenyl)phosphindiyl
(dipropylmethylphenyl)phosphindiyl
Biphenylphosphindiyl
Phenethylphosphindiyl
Napthylphosphindiyl
Norbornylphosphindiyl
Adamantylphosphindiyl
Fluoromethylphosphindiyl
Fluoroethylphosphindiyl
Fluoropropylphosphindiyl
Fluorobutylphosphindiyl
Fluoropentylphosphindiyl
Fluorohexylphosphindiyl
Fluoroheptylphosphindiyl
Fluorooctylphosphindiyl
Fluorononylphosphindiyl
Fluorodecylphosphindiyl
Fluoroundecylphosphindiyl
Fluorododecylphosphindiyl
Thienylphosphindiyl
Furanylphosphindiyl
Pyrrolylphosphindiyl
Phospholylphosphindiyl
(methylthienyl)phosphindiyl
(methylfuranyl)phosphindiyl
(methylpyrrolyl)phosphindiyl
(methylphospholyl)phosphindiyl
(propylthienyl)phosphindiyl
(propylfuranyl)phosphindiyl
(propylpyrrolyl)phosphindiyl
(propylphospholyl)phosphindiyl
(butylthienyl)phosphindiyl
(butylfuranyl)phosphindiyl
(butylpyrrolyl)phosphindiyl
(butylphospholyl)phosphindiyl
(pentylthienyl)phosphindiyl
(pentylfuranyl)phosphindiyl
(pentylpyrrolyl)phosphindiyl
(penylphospholyl)phosphindiyl
(hexylthienyl)phosphindiyl
(hexylfuranyl)phosphindiyl
(hexylpyrrolyl)phosphindiyl
(hexylphospholyl)phosphindiyl
(heptylthienyl)phosphindiyl
(heptylfuranyl)phosphindiyl
(heptylpyrrolyl)phosphindiyl
(heptylphospholyl)phosphindiyl
(octylthienyl)phosphindiyl
(octylfuranyl)phosphindiyl
(octylpyrrolyl)phosphindiyl
(octylphospholyl)phosphindiyl
(nonylthienyl)phosphindiyl
(nonylfuranyl)phosphindiyl
(nonylpyrrolyl)phosphindiyl
(nonylphospholyl)phosphindiyl
(decylthienyl)phosphindiyl
(decylfuranyl)phosphindiyl
(decylpyrrolyl)phosphindiyl
(decylphospholyl)phosphindiyl
(undecylthienyl)phosphindiyl
(undecylfuranyl)phosphindiyl
(undecylpyrrolyl)phosphindiyl
(undecylphospholyl)phosphindiyl
(dodecylthienyl)phosphindiyl
(dodecylfuranyl)phosphindiyl
(dodecylpyrrolyl)phosphindiyl
(dodecylphospholyl)phosphindiyl
(dimethylthienyl)phosphindiyl
(dimethylfuranyl)phosphindiyl
(dimethylpyrrolyl)phosphindiyl
(dimethylphospholyl)phosphindiyl
(diethylthienyl)phosphindiyl
(diethylfuranyl)phosphindiyl
(diethylpyrrolyl)phosphindiyl
(diethylphospholyl)phosphindiyl
(dipropylthienyl)phosphindiyl
(dipropylfuranyl)phosphindiyl
(dipropylpyrrolyl)phosphindiyl
(dipropylphospholyl)phosphindiyl
(dibutylthienyl)phosphindiyl
(dibutylfuranyl)phosphindiyl
(dibutylpyrrolyl)phosphindiyl
(dibutylphospholyl)phosphindiyl
Fluorophenylphosphindiyl
Difluorophenylphosphindiyl
Trifluorophenylphosphindiyl
Tetrafluorophenylphosphindiyl
Pentafluorophenylphosphindiyl
Benzylphosphindiyl
Trimethylsilylmethylphosphindiyl
Trifluoromethylphosphindiyl
Trifluoromethylmethylphosphindiyl
Perfluoroethylphosphindiyl
Perfluoropropylphosphindiyl
Perfluorobutylphosphindiyl
Perfluoropentylphosphindiyl
Perfluorohexylphosphindiyl
Perfluoroheptylphosphindiyl
Perfluorooctylphosphindiyl
Perfluorononylphosphindiyl
Perfluorodecylphosphindiyl
Perfluoroundecylphosphindiyl
Perfluorododecylphosphindiyl
Trimethylsilylphosphindiyl
Trimethylgermylphosphindiyl
Trimethylsilylmethylphosphindiyl
Trimethylgermylmethylphosphindiyl
Methoxymethylphosphindiyl
Ethoxymethylphosphindiyl
Propoxymethylphosphindiyl
Butoxymethylphosphindiyl
Phenoxymethylphosphindiyl
Dimethylaminomethylphosphindiyl
Diphenylaminomethylphosphindiyl
Diphenylphosphinomethylphosphindiyl
Fluorobenzylphosphindiyl
Difluorobenzylphosphindiyl
Trifluorobenzylphosphindiyl
Tetrafluorobenzylphosphindiyl
Pentafluorobenzylphosphindiyl
Trifluoromethylbenzylphosphindiyl
Phenylarsandiyl
Methylarsandiyl
Ethylarsandiyl
Propylarsandiyl
Butylarsandiyl
Pentylarsandiyl
Hexylarsandiyl
Heptylarsandiyl
Octylarsandiyl
Nonylarsandiyl
Decylarsandiyl
Undecylarsandiyl TABLE 1-continued Dodecylarsandiyl
Tridecylarsandiyl
Tetradecylarsandiyl
Pentadecylarsandiyl
Hexadecylarsandiyl
Heptadecylarsandiyl
Octadecylarsandiyl
Nonadecylarsandiyl
Eicosylarsandiyl
Heneicosylarsandiyl
Docosylarsandiyl
Tricosylarsandiyl
Tetracosylarsandiyl
Pentacosylarsandiyl
Hexacosylarsandiyl
Heptacosylarsandiyl
Octacosylarsandiyl
Nonacosylarsandiyl
Triacontylarsandiyl
Vinylarsandiyl
Propenylarsandiyl
Butenylarsandiyl
Pentenylarsandiyl
Hexenylarsandiyl
Heptenylarsandiyl
Octenylarsandiyl
Nonenylarsandiyl
Decenylarsandiyl
Undecenylarsandiyl
Dodecenylarsandiyl
Propynylarsandiyl
Butynylarsandiyl
Hexynylarsandiyl
Octynylarsandiyl
Decynylarsandiyl
Dodecynylarsandiyl
Cyclopropylarsandiyl
Cyclobutylarsandiyl
Cyclopentylarsandiyl
Cyclohexylarsandiyl
Cycloheptylarsandiyl
Cyclooctylarsandiyl
Cyclononylarsandiyl
Cyclodecylarsandiyl
Cycloundecylarsandiyl
Cyclododecylarsandiyl
Cyclotetradecylarsandiyl
Cyclohexadecylarsandiyl
Cyclooctadecylarsandiyl
(methylcyclohexyl)arsandiyl
(ethylcyclohexyl)arsandiyl
(propylcyclohexyl)arsandiyl
(dimethylcyclohexy)larsandiyl
(diethylcyclohexyl)arsandiyl
(dipropylcyclohexyl)arsandiyl
Phenylarsandiyl
Tolylarsandiyl
Mesitylarsandiyl
(ethylphenyl)arsandiyl
(propylphenyl)arsandiyl
(butylphenyl)arsandiyl
(pentylphenyl)arsandiyl
(hexylphenyl)arsandiyl
(dimethylphenyl)arsandiyl
(trimethylphenyl)arsandiyl
(diethylphenyl)arsandiyl
(diethylmethylphenyl)-arsandiyl
(dipropylphenyl)arsandiyl
(dipropylmethylphenyl)arsandiyl
Biphenylarsandiyl
Phenethylarsandiyl
Napthylarsandiyl
Norbornylarsandiyl
Adamantylarsandiyl
Fluoromethylarsandiyl
Fluoroethylarsandiyl
Fluoropropylarsandiyl
Fluorobutylarsandiyl
Fluorohexylarsandiyl
Fluorooctylarsandiyl
Fluorodecylarsandiyl
Thienylarsandiyl
Furanylarsandiyl
Pyrrolylarsandiyl
Phospholylarsandiyl
Methylthienylarsandiyl
Methylfuranylarsandiyl
Methylpyrrolylarsandiyl
Methylphospholylarsandiyl
Fluorophenylarsandiyl
Difluorophenylarsandiyl
Trifluorophenylarsandiyl
Tetrafluorophenylarsandiyl
Pentafluorophenylarsandiyl
Benzylarsandiyl
Trimethylsilylmethylarsandiyl
Trifluoromethylarsandiyl
Trifluoromethylmethylarsandiyl
Perfluoroethylarsandiyl
Perfluoropropylarsandiyl
Perfluorobutylarsandiyl
Perfluorohexylarsandiyl
Perfluorooctylarsandiyl
Perfluorodecylarsandiyl
Perfluorododecylarsandiyl
Trimethylsilylarsandiyl
Trimethylgermylarsandiyl
Trimethylsilylmethylarsandiyl
Trimethylgermylmethylarsandiyl
Methoxymethylarsandiyl
Ethoxymethylarsandiyl
Propoxymethylarsandiyl
Butoxymethylarsandiyl
Phenoxymethylarsandiyl
Dimethylaminomethylarsandiyl
Diphenylaminomethylarsandiyl
Diphenylphosphinomethylarsandiyl
Phenylstibandiyl
Methylstibandiyl
Ethylstibandiyl
Propylstibandiyl
Butylstibandiyl
Pentylstibandiyl
Hexylstibandiyl
Heptylstibandiyl
Octylstibandiyl
Nonylstibandiyl
Decylstibandiyl
Undecylstibandiyl
Dodecylstibandiyl
Tridecylstibandiyl
Tetradecylstibandiyl
Pentadecylstibandiyl
Hexadecylstibandiyl
Heptadecylstibandiyl
Octadecylstibandiyl
Nonadecylstibandiyl
Eicosylstibandiyl
Heneicosylstibandiyl
Docosylstibandiyl
Tricosylstibandiyl
Tetracosylstibandiyl
Pentacosylstibandiyl
Hexacosylstibandiyl
Heptacosylstibandiyl
Octacosylstibandiyl
Nonacosylstibandiyl
Triacontylstibandiyl
Vinylstibandiyl
Propenylstibandiyl
Butenylstibandiyl
Pentenylstibandiyl
Hexenylstibandiyl
Heptenylstibandiyl
Octenylstibandiyl
Nonenylstibandiyl
Decenylstibandiyl
Undecenylstibandiyl TABLE 1-continued Dodecenylstibandiyl
Propynylstibandiyl
Butynylstibandiyl
Pentynylstibandiyl
Hexynylstibandiyl
Heptynylstibandiyl
Octynylstibandiyl
Nonynylstibandiyl
Decynylstibandiyl
Undecynylstibandiyl
Dodecynylstibandiyl
Cyclopropylstibandiyl
Cyclobutylstibandiyl
Cyclopentylstibandiyl
Cyclohexylstibandiyl
Cycloheptylstibandiyl
Cyclooctylstibandiyl
Cyclononylstibandiyl
Cyclodecylstibandiyl
Cycloundecylstibandiyl
Cyclododecylstibandiyl
Cyclotetradecylstibandiyl
Cyclohexadecylstibandiyl
Cyclooctadecylstibandiyl
(methylcyclohexyl)stibandiyl
(ethylcyclohexyl)stibandiyl
(propylcyclohexyl)stibandiyl
(dimethylcyclohexyl)stibandiyl
(diethylcyclohexyl)stibandiyl
(dipropylcyclohexyl)stibandiyl
Phenylstibandiyl
Tolylstibandiyl
Mesitylstibandiyl
(ethylphenyl)stibandiyl
(propylphenyl)stibandiyl
(butylphenyl)stibandiyl
(pentylphenyl)stibandiyl
(hexylphenyl)stibandiyl
(dimethylphenyl)stibandiyl
(trimethylphenyl)stibandiyl
(diethylphenyl)stibandiyl
(diethylmethylphenyl)stibandiyl
(dipropylphenyl)stibandiyl
(dipropylmethylphenyl)stibandiyl
Biphenylstibandiyl
Phenethylstibandiyl
Napthylstibandiyl
Norbornylstibandiyl
Adamantylstibandiyl
Fluoromethylstibandiyl
Fluoroethylstibandiyl
Fluoropropylstibandiyl
Fluorobutylstibandiyl
Fluoropentylstibandiyl
Fluorohexylstibandiyl
Fluoroheptylstibandiyl
Fluorooctylstibandiyl
Fluorononylstibandiyl
Fluorodecylstibandiyl
Fluoroundecylstibandiyl
Fluorododecylstibandiyl
Thienylstibandiyl
Furanylstibandiyl
Pyrrolylstibandiyl
Phospholylstibandiyl
Methylthienylstibandiyl
Methylfuranylstibandiyl
Methylpyrrolylstibandiyl
Methylphospholylstibandiyl
Fluorophenylstibandiyl
Difluorophenylstibandiyl
Trifluorophenylstibandiyl
Tetrafluorophenylstibandiyl
Pentafluorophenylstibandiyl
Benzylstibandiyl
Trimethylsilylmethylstibandiyl
Trifluoromethylstibandiyl
Trifluoromethylmethylstibandiyl
Perfluoroethylstibandiyl
Perfluoropropylstibandiyl
Perfluorobutylstibandiyl
Perfluoropentylstibandiyl
Perfluorohexylstibandiyl
Perfluoroheptylstibandiyl
Perfluorooctylstibandiyl
Perfluorononylstibandiyl
Perfluorodecylstibandiyl
Perfluoroundecylstibandiyl
Perfluorododecylstibandiyl
Trimethylsilylstibandiyl
Trimethylgermylstibandiyl
Trimethylsilylmethylstibandiyl
Trimethylgermylmethylstibandiyl
Methoxymethylstibandiyl
Ethoxymethylstibandiyl
Propoxymethylstibandiyl
Butoxymethylstibandiyl
Phenoxymethylstibandiyl
Dimethylaminomethylstibandiyl
Diphenylaminomethylstibandiyl
Diphenylphosphinomethylstibandiyl

A cyclopenta[b]thienyl
cyclopenta[b]furanyl
cyclopenta[b]selenophenyl
cyclopenta[b]tellurophenyl
cyclopenta[b]pyrrolyl
cyclopenta[b]phospholyl
cyclopenta[b]arsolyl
cyclopenta[b]stibolyl
methylcyclopenta[b]thienyl
methylcyclopenta[b]furanyl
methylcyclopenta[b]selenophenyl
methylcyclopenta[b]tellurophenyl
methylcyclopenta[b]pyrrolyl
methylcyclopenta[b]phospholyl
methylcyclopenta[b]arsolyl
methylcyclopenta[b]stibolyl
dimethylcyclopenta[b]thienyl
dimethylcyclopenta[b]furanyl
dimethylcyclopenta[b]pyrrolyl
dimethylcyclopenta[b]phospholyl
trimethylcyclopenta[b]thienyl
trimethylcyclopenta[b]furanyl
trimethylcyclopenta[b]pyrrolyl
trimethylcyclopenta[b]phospholyl
tetramethylcyclopenta[b]thienyl
tetramethylcyclopenta[b]furanyl
tetramethylcyclopenta[b]pyrrolyl
tetramethylcyclopenta[b]phospholyl
pentamethylcyclopenta[b]pyrrolyl
pentamethylcyclopenta[b]phospholyl
ethylcyclopenta[b]thienyl
ethylcyclopenta[b]furanyl
ethylcyclopenta[b]pyrrolyl
ethylcyclopenta[b]phospholyl
diethylcyclopenta[b]thienyl
diethylcyclopenta[b]furanyl
diethylcyclopenta[b]pyrrolyl
diethylcyclopenta[b]phospholyl
triethylcyclopenta[b]thienyl
triethylcyclopenta[b]furanyl
triethylcyclopenta[b]pyrrolyl
triethylcyclopenta[b]phospholyl
propylcyclopenta[b]thienyl
propylcyclopenta[b]furanyl
propylcyclopenta[b]pyrrolyl
propylcyclopenta[b]phospholyl
dipropylcyclopenta[b]thienyl
dipropylcyclopenta[b]furanyl
dipropylcyclopenta[b]pyrrolyl
dipropylcyclopenta[b]phospholyl
tripropylcyclopenta[b]thienyl
tripropylcyclopenta[b]furanyl
tripropylcyclopenta[b]pyrrolyl
tripropylcyclopenta[b]phospholyl
butylcyclopenta[b]thienyl TABLE 1-continued butylcyclopenta[b]furanyl
butylcyclopenta[b]pyrrolyl
butylcyclopenta[b]phospholyl
dibutylcyclopenta[b]thienyl
dibutylcyclopenta[b]furanyl
dibutylcyclopenta[b]pyrrolyl
dibutylcyclopenta[b]phospholyl
tributylcyclopenta[b]thienyl
tributylcyclopenta[b]furanyl
tributylcyclopenta[b]pyrrolyl
tributylcyclopenta[b]phospholyl
ethylmethylcyclopenta[b]thienyl
ethylmethylcyclopenta[b]furanyl
ethylmethylcyclopenta[b]pyrrolyl
ethylmethylcyclopenta[b]phospholyl
methylpropylcyclopenta[b]thienyl
methylpropylcyclopenta[b]furanyl
methylpropylcyclopenta[b]pyrrolyl
methylpropylcyclopenta[b]phospholyl
butylmethylcyclopenta[b]thienyl
butylmethylcyclopenta[b]furanyl
butylmethylcyclopenta[b]pyrrolyl
butylmethylcyclopenta[b]phospholyl
cyclopenta[c]thienyl
cyclopenta[c]furanyl
cyclopenta[c]selenophenyl
cyclopenta[c]tellurophenyl
cyclopenta[c]pyrrolyl
cyclopenta[c]phospholyl
cyclopenta[c]arsolyl
cyclopenta[c]stibolyl
methylcyclopenta[c]thienyl
methylcyclopenta[c]furanyl
methylcyclopenta[c]selenophenyl
methylcyclopenta[c]tellurophenyl
methylcyclopenta[c]pyrrolyl
methylcyclopenta[c]phospholyl
methylcyclopenta[c]arsolyl
methylcyclopenta[c]stibolyl
dimethylcyclopenta[c]thienyl
dimethylcyclopenta[c]furanyl
dimethylcyclopenta[c]pyrrolyl
dimethylcyclopenta[c]phospholyl
trimethylcyclopenta[c]thienyl
trimethylcyclopenta[c]furanyl
trimethylcyclopenta[c]pyrrolyl
trimethylcyclopenta[c]phospholyl
tetramethylcyclopenta[c]thienyl
tetramethylcyclopenta[c]furanyl
tetramethylcyclopenta[c]pyrrolyl
tetramethylcyclopenta[c]phospholyl
pentamethylcyclopenta[c]pyrrolyl
pentamethylcyclopenta[c]phospholyl
ethylcyclopenta[c]thienyl
ethylcyclopenta[c]furanyl
ethylcyclopenta[c]pyrrolyl
ethylcyclopenta[c]phospholyl
diethylcyclopenta[c]thienyl
diethylcyclopenta[c]furanyl
diethylcyclopenta[c]pyrrolyl
diethylcyclopenta[c]phospholyl
triethylcyclopenta[c]thienyl
triethylcyclopenta[c]furanyl
triethylcyclopenta[c]pyrrolyl
triethylcyclopenta[c]phospholyl
propylcyclopenta[c]thienyl
propylcyclopenta[c]furanyl
propylcyclopenta[c]pyrrolyl
propylcyclopenta[c]phospholyl
dipropylcyclopenta[c]thienyl
dipropylcyclopenta[c]furanyl
dipropylcyclopenta[c]pyrrolyl
dipropylcyclopenta[c]phospholyl
tripropylcyclopenta[c]thienyl
tripropylcyclopenta[c]furanyl
tripropylcyclopenta[c]pyrrolyl
tripropylcyclopenta[c]phospholyl
butylcyclopenta[c]thienyl
butylcyclopenta[c]furanyl
butylcyclopenta[c]pyrrolyl
butylcyclopenta[c]phospholyl
dibutylcyclopenta[c]thienyl
dibutylcyclopenta[c]furanyl
dibutylcyclopenta[c]pyrrolyl
dibutylcyclopenta[c]phospholyl
tributylcyclopenta[c]thienyl
tributylcyclopenta[c]furanyl
tributylcyclopenta[c]pyrrolyl
tributylcyclopenta[c]phospholyl
ethylmethylcyclopenta[c]thienyl
ethylmethylcyclopenta[c]furanyl
ethylmethylcyclopenta[c]pyrrolyl
ethylmethylcyclopenta[c]phospholyl
methylpropylcyclopenta[c]thienyl
methylpropylcyclopenta[c]furanyl
methylpropylcyclopenta[c]pyrrolyl
methylpropylcyclopenta[c]phospholyl
butylmethylcyclopenta[c]thienyl
butylmethylcyclopenta[c]furanyl
butylmethylcyclopenta[c]pyrrolyl
butylmethylcyclopenta[c]phospholyl
indenyl
methylindenyl
dimethylindenyl
trimethylindenyl
tetramethylindenyl
pentamethylindenyl
hexamethylindenyl
ethylindenyl
diethylindenyl
triethylindenyl
propylindenyl
dipropylindenyl
tripropylindenyl
butylindenyl
dibutylindenyl
tributylindenyl
pentylindenyl
dipentylindenyl
tripentylindenyl
hexylindenyl
dihexylindenyl
trihexylindenyl
heptylindenyl
octylindenyl
nonylindenyl
decylindenyl
phenylindenyl
methylphenylindenyl
ethylphenylindenyl
propylphenylindenyl
butylphenylindenyl
pentylphenylindenyl
hexylphenylindenyl
heptylphenylindenyl
octylphenylindenyl
nonylphenylindenyl
decylphenylindenyl
dimethylphenylindenyl
trimethylphenylindenyl
dipropylphenylindenyl
methylpropylphenylindenyl
tolylindenyl
methyltolylindenyl
ethyltolylindenyl
propyltolylindenyl
butyltolylindenyl
pentyltolylindenyl
hexyltolylindenyl
heptyltolylindenyl
octyltolylindenyl
nonyltolylindenyl
decyltolylindenyl
dimethyltolylindenyl
trimethyltolylindenyl
dipropyltolylindenyl
methylpropyltolylindenyl
naphthylindenyl TABLE 1-continued methylnaphthylindenyl
ethylnaphthylindenyl
propylnaphthylindenyl
butylnaphthylindenyl
pentylnaphthylindenyl
hexylnaphthylindenyl
heptylnaphthylindenyl
octylnaphthylindenyl
nonylnaphthylindenyl
decylnaphthylindenyl
dimethylnaphthylindenyl
trimethylnaphthylindenyl
dipropylnaphthylindenyl
methylpropylnaphthylindenyl
(propylphenyl)indenyl
methyl(propylphenyl)indenyl
ethyl(propylphenyl)indenyl
propyl(propylphenyl)indenyl
butyl(propylphenyl)indenyl
dimethyl(propylphenyl)indenyl
trimethyl(propylphenyl)indenyl
methylpropyl(propylphenyl)indenyl
(dipropylphenyl)indenyl
methyl(dipropylphenyl)indenyl
ethyl(dipropylphenyl)indenyl
propyl(dipropylphenyl)indenyl
butyl(dipropylphenyl)indenyl
dimethyl(dipropylphenyl)indenyl
trimethyl(dipropylphenyl)indenyl
methylpropyl(dipropylphenyl)indenyl
(dimethylphenyl)indenyl
methyl(dimethylphenyl)indenyl
ethyl(dimethylphenyl)indenyl
propyl(dimethylphenyl)indenyl
butyl(dimethylphenyl)indenyl
trimethyl(dimethylphenyl)indenyl
trimethyl(dimethylphenyl)indenyl
methylpropyl(dimethylphenyl)indenyl
(trimethylphenyl)indenyl
methyl(trimethylphenyl)indenyl
ethyl(trimethylphenyl)indenyl
propyl(trimethylphenyl)indenyl
butyl(trimethylphenyl)indenyl
dimethyl(trimethylphenyl)indenyl
trimethyl(trimethylphenyl)indenyl
methylpropyl(trimethylphenyl)indenyl
trimethylsilylindenyl
trifluormethylindenyl
trifluoromethylphenylindenyl
(benzothiopheneyl)indenyl
(benzofuranyl)indenyl
(fluorophenyl)indenyl
(difluorophenyl)indenyl
(trifluorophenyl)indenyl
(tetrafluorophenyl)indenyl
(pentafluorophenyl)indenyl
(trifluoromethylphenyl)indenyl
(thienyl)indenyl
(furanyl)indenyl
(pyrrolyl)indenyl
(phospholyl)indenyl
(methylthienyl)indenyl
(methylfuranyl)indenyl
(methylpyrrolyl)indenyl
(methylphospholyl)indenyl
(dimethylthienyl)indenyl
(dimethylfuranyl)indenyl
(dimethylpyrrolyl)indenyl
(dimethylphospholyl)indenyl
(ethylthienyl)indenyl
(ethylfuranyl)indenyl
(ethylpyrrolyl)indenyl
(ethylphospholyl)indenyl
(propylthienyl)indenyl
(propylfuranyl)indenyl
(propylpyrrolyl)indenyl
(propylphospholyl)indenyl
(butylthienyl)indenyl
(butylfuranyl)indenyl
(butylpyrrolyl)indenyl
(butylphospholyl)indenyl
methyl(benzothiopheneyl)indenyl
methyl(benzofuranyl)indenyl
methyl(fluorophenyl)indenyl
methyl(difluorophenyl)indenyl
methyl(trifluorophenyl)indenyl
methyl(tetrafluorophenyl)indenyl
methyl(pentafluorophenyl)indenyl
methyl(trifluoromethylphenyl)indenyl
methyl(thienyl)indenyl
methyl(furanyl)indenyl
methyl(pyrrolyl)indenyl
methyl(phospholyl)indenyl
methyl(methylthienyl)indenyl
methyl(methylfuranyl)indenyl
methyl(methylpyrrolyl)indenyl
methyl(methylphospholyl)indenyl
methyl(dimethylthienyl)indenyl
methyl(dimethylfuranyl)indenyl
methyl(dimethylpyrrolyl)indenyl
methyl(dimethylphospholyl)indenyl
methyl(ethylthienyl)indenyl
methyl(ethylfuranyl)indenyl
methyl(ethylpyrrolyl)indenyl
methyl(ethylphospholyl)indenyl
methyl(propylthienyl)indenyl
methyl(propylfuranyl)indenyl
methyl(propylpyrrolyl)indenyl
methyl(propylphospholyl)indenyl
methyl(butylthienyl)indenyl
methyl(butylfuranyl)indenyl
methyl(butylpyrrolyl)indenyl
methyl(butylphospholyl)indenyl
propyl(benzothiopheneyl)indenyl
propyl(benzofuranyl)indenyl
propyl(fluorophenyl)indenyl
propyl(difluorophenyl)indenyl
propyl(trifluorophenyl)indenyl
propyl(tetrafluorophenyl)indenyl
propyl(pentafluorophenyl)indenyl
propyl(trifluoromethylphenyl)indenyl
propyl(thienyl)indenyl
propyl(furanyl)indenyl
propyl(pyrrolyl)indenyl
propyl(phospholyl)indenyl
propyl(methylthienyl)indenyl
propyl(methylfuranyl)indenyl
propyl(methylpyrrolyl)indenyl
propyl(methylphospholyl)indenyl
propyl(dimethylthienyl)indenyl
propyl(dimethylfuranyl)indenyl
propyl(dimethylpyrrolyl)indenyl
propyl(dimethylphospholyl)indenyl
propyl(ethylthienyl)indenyl
propyl(ethylfuranyl)indenyl
propyl(ethylpyrrolyl)indenyl
propyl(ethylphospholyl)indenyl
propyl(propylthienyl)indenyl
propyl(propylfuranyl)indenyl
propyl(propylpyrrolyl)indenyl
propyl(propylphospholyl)indenyl
propyl(butylthienyl)indenyl
propyl(butylfuranyl)indenyl
propyl(butylpyrrolyl)indenyl
propyl(butylphospholyl)indenyl
bromophenylindenyl
bromoindenyl
dibromoindenyl
bromomethylindenyl
bromoethylindenyl
bromopropylindenyl
bromobutylindenyl
bromodimethylindenyl
bromodiethylindenyl
bromodipropylindenyl
bromodibutylindenyl
bromomethylphenylindenyl
bromotolylindenyl

TABLE 1-continued bromocyclohexylindenyl
chlorophenylindenyl
chloroindenyl
dichloroindenyl
chloromethylindenyl
chloroethylindenyl
chloropropylindenyl
chlorobutylindenyl
chlorodimethylindenyl
chlorodiethylindenyl
chlorodipropylindenyl
chlorodibutylindenyl
chloromethylphenylindenyl
chlorotolylindenyl
tetrahydroindenyl
methyltetrahydroindenyl
dimethyltetrahydroindenyl
trimethyltetrahydroindenyl
tetramethyltetrahydroindenyl
pentamethyltetrahydroindenyl
hexamethyltetrahydroindenyl
ethyltetrahydroindenyl
propyltetrahydroindenyl
butyltetrahydroindenyl
pentyltetrahydroindenyl
hexyltetrahydroindenyl
heptyltetrahydroindenyl
octyltetrahydroindenyl
nonyltetrahydroindenyl
decyltetrahydroindenyl
phenyltetrahydroindenyl
methylphenyltetrahydroindenyl
ethylphenyltetrahydroindenyl
propylphenyltetrahydroindenyl
butylphenyltetrahydroindenyl
pentylphenyltetrahydroindenyl
hexylphenyltetrahydroindenyl
heptylphenyltetrahydroindenyl
octylphenyltetrahydroindenyl
nonylphenyltetrahydroindenyl
decylphenyltetrahydroindenyl
dimethylphenyltetrahydroindenyl
trimethylphenyltetrahydroindenyl
dipropylphenyltetrahydroindenyl
methylpropylphenyltetrahydroindenyl
tolyltetrahydroindenyl
methyltolyltetrahydroindenyl
ethyltolyltetrahydroindenyl
propyltolyltetrahydroindenyl
butyltolyltetrahydroindenyl
dimethyltolyltetrahydroindenyl
trimethyltolyltetrahydroindenyl
dipropyltolyltetrahydroindenyl
methylpropyltolyltetrahydroindenyl
naphthyltetrahydroindenyl
methylnaphthyltetrahydroindenyl
ethylnaphthyltetrahydroindenyl
propylnaphthyltetrahydroindenyl
butylnaphthyltetrahydroindenyl
dimethylnaphthyltetrahydroindenyl
trimethylnaphthyltetrahydroindenyl
dipropylnaphthyltetrahydroindenyl
methylpropylnaphthyltetrahydroindenyl
(propylphenyl)tetrahydroindenyl
methyl(propylphenyl)tetrahydroindenyl
ethyl(propylphenyl)tetrahydroindenyl
propyl(propylphenyl)tetrahydroindenyl
butyl(propylphenyl)tetrahydroindenyl
dimethyl(propylphenyl)tetrahydroindenyl
trimethyl(propylphenyl)tetrahydroindenyl
methylpropyl(propylphenyl)tetrahydroindenyl
(dipropylphenyl)tetrahydroindenyl
methyl(dipropylphenyl)tetrahydroindenyl
ethyl(dipropylphenyl)tetrahydroindenyl
propyl(dipropylphenyl)tetrahydroindenyl
butyl(dipropylphenyl)tetrahydroindenyl
dimethyl(dipropylphenyl)tetrahydroindenyl
trimethyl(dipropylphenyl)tetrahydroindenyl
methylpropyl(dipropylphenyl)tetrahydroindenyl
(dimethylphenyl)tetrahydroindenyl
methyl(dimethylphenyl)tetrahydroindenyl
ethyl(dimethylphenyl)tetrahydroindenyl
propyl(dimethylphenyl)tetrahydroindenyl
butyl(dimethylphenyl)tetrahydroindenyl
trimethyl(dimethylphenyl)tetrahydroindenyl
trimethyl(dimethylphenyl)tetrahydroindenyl
methylpropyl(dimethylphenyl)tetrahydroindenyl
(trimethylphenyl)tetrahydroindenyl
methyl(trimethylphenyl)tetrahydroindenyl
ethyl(trimethylphenyl)tetrahydroindenyl
propyl(trimethylphenyl)tetrahydroindenyl
butyl(trimethylphenyl)tetrahydroindenyl
dimethyl(trimethylphenyl)tetrahydroindenyl
trimethyl(trimethylphenyl)tetrahydroindenyl
methylpropyl(trimethylphenyl)tetrahydroindenyl
bromophenyltetrahydroindenyl
bromotetrahydroindenyl
dibromotetrahydroindenyl
bromomethyltetrahydroindenyl
bromoethyltetrahydroindenyl
bromopropyltetrahydroindenyl
bromobutyltetrahydroindenyl
bromodimethyltetrahydroindenyl
bromodiethyltetrahydroindenyl
bromodipropyltetrahydroindenyl
bromodibutyltetrahydroindenyl
bromomethylphenyltetrahydroindenyl
bromotolyltetrahydroindenyl
bromocyclohexyltetrahydroindenyl
cyclopentadienyl
methylcyclopentadienyl
dimethylcyclopentadienyl
trimethylcyclopentadienyl
tetramethylcyclopentadienyl
ethylcyclopentadienyl
diethylcyclopentadienyl
triethylcyclopentadienyl
tetraethylcyclopentadienyl
propylcyclopentadienyl
dipropylcyclopentadienyl
tripropylcyclopentadienyl
tetrapropylcyclopentadienyl
butylcyclopentadienyl
dibutylcyclopentadienyl
tributylcyclopentadienyl
tetrabutylcyclopentadienly
pentylcyclopentadienyl
dipentylcyclopentadienyl
tripentylcyclopentadienyl
tetrapentylcyclopentadienly
hexylcyclopentadienyl
dihexylcyclopentadienyl
trihexylcyclopentadienyl
tetrahexylcyclopentadienly
heptylcyclopentadienyl
diheptylcyclopentadienyl
octylcyclopentadienyl
dioctylcyclopentadienyl
nonylcyclopentadienyl
dinonylcyclopentadienyl
decylcyclopentadienyl
didecylcyclopentadienyl
undecylcyclopentadienyl
dodecylcyclopentadienyl
tridecylcyclopentadienyl
tetradecylcyclopentadienyl
pentadecylcyclopentadienyl
hexadecylcyclopentadienyl
heptadecylcyclopentadienyl
octadecylcyclopentadienyl
nonadecylcyclopentadienyl
eicosylcyclopentadienyl
heneicosylcyclopentadienyl
docosylcyclopentadienyl
tricosylcyclopentadienyl
tetracosylcyclopentadienyl
pentacosylcyclopentadienyl
hexacosylcyclopentadienyl TABLE 1-continued heptacosylcyclopentadienyl
octacosylcyclopentadienyl
nonacosylcyclopentadienyl
triacontylcyclopentadienyl
vinylcyclopentadienyl
allylcyclopentadienyl
propenylcyclopentadienyl
butenylcyclopentadienyl
propynylcyclopentadienyl
butynylcyclopentadienyl
cyclopropylcyclopentadienyl
cyclobutylcyclopentadienyl
cyclopentylcyclopentadienyl
cyclohexylcyclopentadienyl
phenylcyclopentadienyl
(dimethylphenyl)cyclopentadienyl
tolylcyclopentadienyl
benzylcyclopentadienyl
phenethylcyclopentadienyl
trimethylsilylcyclopentadienyl
trimethylgermylcyclopentadienyl
trimethylstannylcyclopentadienyl
triethylsilylcyclopentadienyl
dimethylethylsilylcyclopentadienyl
biphenylcyclopentadienyl
pyrenylcyclopentadienyl
trifluoromethylcyclopentadienyl
trifluoromethylmethylcyclopentadienyl
norbornylcyclopentadienyl
methylethylcyclopentadienyl
methylpropylcyclopentadienyl
methylbutylcyclopentadienyl
methylphenylcyclopentadienyl
methylcyclohexylcylopentadienyl
methyltolylcyclopentadienyl
trimethylsilylmethylcylopentadienyl
methylbenzylcylopentadienyl
methylphenethylcylopentadienyl
methylvinylcylopentadienyl
methylallylcylopentadienyl
(benzothipheneyl)cyclopentadienyl
(benzofuranyl)cyclopentadienyl
(fluorophenyl)cyclopentadienyl
(difluorophenyl)cyclopentadienyl
(trifluorophenyl)cyclopentadienyl
(tetrafluorophenyl)cyclopentadienyl
(pentafluorophenyl)cyclopentadienyl
(trifluoromethylphenyl)cyclopentadienyl
(thienyl)cyclopentadienyl
(furanyl)cyclopentadienyl
(pyrrolyl)cyclopentadienyl
(phospholyl)cyclopentadienyl
(methylthienyl)cyclopentadienyl
(methylfuranyl)cyclopentadienyl
(methylpyrrolyl)cyclopentadienyl
(methylphospholyl)cyclopentadienyl
(dimethylthienyl)cyclopentadienyl
(dimethylfuranyl)cyclopentadienyl
(dimethylpyrrolyl)cyclopentadienyl
(dimethylphospholyl)cyclopentadienyl
methyl(benzothipheneyl)cyclopentadienyl
methyl(benzofuranyl)cyclopentadienyl
methyl(fluorophenyl)cyclopentadienyl
methyl(difluorophenyl)cyclopentadienyl
methyl(trifluorophenyl)cyclopentadienyl
methyl(tetrafluorophenyl)cyclopentadienyl
methyl(pentafluorophenyl)cyclopentadienyl
methyl(trifluoromethylphenyl)cyclopentadienyl
methyl(thienyl)cyclopentadienyl
methyl(furanyl)cyclopentadienyl
methyl(pyrrolyl)cyclopentadienyl
methyl(phospholyl)cyclopentadienyl
methyl(methylthienyl)cyclopentadienyl
methyl(methylfuranyl)cyclopentadienyl
methyl(methylpyrrolyl)cyclopentadienyl
methyl(methylphospholyl)cyclopentadienyl
methyl(dimethylthienyl)cyclopentadienyl
methyl(dimethylfuranyl)cyclopentadienyl
methyl(dimethylpyrrolyl)cyclopentadienyl
methyl(dimethylphospholyl)cyclopentadienyl
bromophenylcyclopentadienyl
bromocyclopentadienyl
dibromocyclopentadienyl
bromomethylcyclopentadienyl
bromoethylcyclopentadienyl
bromopropylcyclopentadienyl
bromobutylcyclopentadienyl
bromodimethylcyclopentadienyl
bromodiethylcyclopentadienyl
bromodipropylcyclopentadienyl
bromodibutylcyclopentadienyl
bromomethylphenylcyclopentadienyl
bromotolylcyclopentadienyl
bromocyclohexylcyclopentadienyl
fluorenyl
methylfluorenyl
dimethylfluorenyl
trimethylfluorenyl
tetramethylfluorenyl
ethylfluorenyl
diethylfluorenyl
triethylfluorenyl
tetraethylfluorenyl
propylfluorenyl
dipropylfluorenyl
tripropylfluorenyl
tetrapropylfluorenyl
butylfluorenyl
dibutylfluorenyl
tributylfluorenyl
tetrabutylfluorenyl
pentylfluorenyl
dipentylfluorenyl
tripentylfluorenyl
tetrapentylfluorenyl
hexylfluorenyl
dihexylfluorenyl
trihexylfluorenyl
tetrahexylfluorenyl
heptylfluorenyl
diheptylfluorenyl
octylfluorenyl
dioctylfluorenyl
nonylfluorenyl
dinonylfluorenyl
decylfluorenyl
didecylfluorenyl
dodecylfluorenyl
didodecylfluorenyl
trifluoromethylfluorenyl
bis(trifluoromethyl)fluorenyl
trimethylsilylfluorenyl
bis(trimethylsilyl)fluorenyl
cyclohexylfluorenyl
bis(cyclohexyl)fluorenyl
phenylfluorenyl
diphenylfluorenyl
tolylfluorenyl
bis(tolyl)fluorenyl
octahydrofluorenyl
methyloctahydrofluorenyl
dimethyloctahydrofluorenyl
trimethyloctahydrofluorenyl
tetramethyloctahydrofluorenyl
ethyloctahydrofluorenyl
diethyloctahydrofluorenyl
propyloctahydrofluorenyl
dipropyloctahydrofluorenyl
butyloctahydrofluorenyl
dibutyloctahydrofluorenyl
pentyloctahydrofluorenyl
dipentyloctahydrofluorenyl
hexyloctahydrofluorenyl
dihexyloctahydrofluorenyl
heptyloctahydrofluorenyl
diheptyloctahydrofluorenyl
octyloctahydrofluorenyl
dioctyloctahydrofluorenyl
methyl(dimethylphospholyl)cyclopentadienyl TABLE 1-continued methyloctahydrodibenzyl[b,h]fluorenyl
dimethyloctahydrodibenzyl[b,h]fluorenyl
trimethyloctahydrodibenzyl[b,h]fluorenyl
tetramethyloctahydrodibenzyl[b,h]fluorenyl
pentamethyloctahydrodibenzyl[b,h]fluorenyl
hexamethyloctahydrodibenzyl[b,h]fluorenyl
heptamethyloctahydrodibenzyl[b,h]fluorenyl
octamethyloctahydrodibenzyl[b,h]fluorenyl
(benzothipheneyl)fluorenyl
(benzofuranyl)fluorenyl
(fluorophenyl)fluorenyl
(difluorophenyl)fluorenyl
(trifluorophenyl)fluorenyl
(tetrafluorophenyl)fluorenyl
(pentafluorophenyl)fluorenyl
(trifluoromethylphenyl)fluorenyl
(thienyl)fluorenyl
(furanyl)fluorenyl
(pyrrolyl)fluorenyl
(phospholyl)fluorenyl
(methylthienyl)fluorenyl
(methylfuranyl)fluorenyl
(methylpyrrolyl)fluorenyl
(methylphospholyl)fluorenyl
(dimethylthienyl)fluorenyl
(dimethylfuranyl)fluorenyl
(dimethylpyrrolyl)fluorenyl
(dimethylphospholyl)fluorenyl
bis(benzothipheneyl)fluorenyl
bis(benzofuranyl)fluorenyl
bis(fluorophenyl)fluorenyl
bis(difluorophenyl)fluorenyl
bis(trifluorophenyl)fluorenyl
bis(tetrafluorophenyl)fluorenyl
bis(pentafluorophenyl)fluorenyl
bis(trifluoromethylphenyl)fluorenyl
bis(thienyl)fluorenyl
bis(furanyl)fluorenyl
bis(pyrrolyl)fluorenyl
bis(phospholyl)fluorenyl
bis(methylthienyl)fluorenyl
bis(methylfuranyl)fluorenyl
bis(methylpyrrolyl)fluorenyl
bis(methylphospholyl)fluorenyl
bis(dimethylthienyl)fluorenyl
bis(dimethylfuranyl)fluorenyl
bis(dimethylpyrrolyl)fluorenyl
bis(dimethylphospholyl)fluorenyl
bromophenylfluorenyl
bromofluorenyl
dibromofluorenyl
bromomethylfluorenyl
bromoethylfluorenyl
bromopropylfluorenyl
bromobutylfluorenyl
bromodimethylfluorenyl
bromodiethylfluorenyl
bromodipropylfluorenyl
bromodibutylfluorenyl
bromomethylphenylfluorenyl
bromotolylfluorenyl
bromocyclohexylfluorenyl
dibromophenylfluorenyl
dibromofluorenyl
didibromofluorenyl
dibromomethylfluorenyl
dibromoethylfluorenyl
dibromopropylfluorenyl
dibromobutylfluorenyl
dibromodimethylfluorenyl
dibromodiethylfluorenyl
dibromodipropylfluorenyl
dibromodibutylfluorenyl
dibromomethylphenylfluorenyl
dibromotolylfluorenyl
dibromocyclohexylfluorenyl
azacyclopentadienyl
phosphacyclopentadienyl
stibacyclopentadienyl
arsacyclopentadienyl
boracyclopentadienyl
methylazacyclopentadienyl
methylphosphacyclopentadienyl
methylstibacyclopentadienyl
methylarsacyclopentadienyl
methylboracyclopentadienyl
1,2-diazacyclopentadienyl
1,2-diphosphacyclopentadienyl
1,2-distibacyclopentadienyl
1,2-diarsacyclopentadienyl
1,2-diboracyclopentadienyl
1,2-azaphosphacyclopentadienyl
1,2-azastibacyclopentadienyl
1,2-azarsacyclopentadienyl
1,2-azaboracyclopentadienyl
1,2-arsaphosphacyclopentadienyl
1,2-arsastibacyclopentadienyl
1,2-arsaboracyclopentadienyl
1,2-boraphosphacyclopentadienyl
1,2-borastibacyclopentadienyl
1,2-phosphastibacyclopentadienyl
1,3-diazacyclopentadienyl
1,3-diphosphacyclopentadienyl
1,3-distibacyclopentadienyl
1,3-diarsacyclopentadienyl
1,3-diboracyclopentadienyl
1,3-azaphosphacyclopentadienyl
1,3-azastibacyclopentadienyl
1,3-azarsacyclopentadienyl
1,3-azaboracyclopentadienyl
1,3-arsaphosphacyclopentadienyl
1,3-arsastibacyclopentadienyl
1,3-arsaboracyclopentadienyl
1,3-boraphosphacyclopentadienyl
1,3-borastibacyclopentadienyl
1,3-phosphastibacyclopentadienyl
pentadienyl
methylpentadienyl
dimethylpentadienyl
trimethylpentadienyl
tetramethylpentadienyl
pentamethylpentadienyl
hexamethylpentadienyl
allyl
methylallyl
dimethylallyl
trimethylallyl
tetramethylallyl
boratabenzene
methylboratabenzene
phenylboratabenzene
N,N-dimethylaminoboratabenzene
N,N-diethylaminoboratabenzene
N,N-dipropylaminoboratabenzene
$R^1$ $R^2$ $R^3$ $R^4$ $R^5$ $R^6$ $R^7$ $R^8$ $R^9$ $R'$ $R''$ $R^{4'}$ $R^{5'}$ and $R^{6'}$ hydrogen
methyl
ethyl
propyl
butyl
pentyl
hexyl
heptyl
octyl
nonyl
decyl
undecyl
dodecyl
tridecyl
tetradecyl
pentadecyl
hexadecyl
heptadecyl
octadecyl
nonadecyl
eicosyl TABLE 1-continued heneicosyl
docosyl
tricosyl
tetracosyl
pentacosyl
hexacosyl
heptacosyl
octacosyl
nonacosyl
triacontyl
vinyl
propenyl
butenyl
pentenyl
hexenyl
heptenyl
octenyl
nonenyl
decenyl
undecenyl
dodecenyl
tridecenyl
tetradecenyl
pentadecenyl
hexadecenyl
heptadecenyl
octadecenyl
nonadecenyl
eicosenyl
heneicosenyl
docosenyl
tricosenyl
tetracosenyl
pentacosenyl
hexacosenyl
heptacosenyl
octacosenyl
nonacosenyl
triacontenyl
propynyl
butynyl
pentynyl
hexynyl
heptynyl
octynyl
nonynyl
decynyl
undecynyl
dodecynyl
tridecynyl
tetradecynyl
pentadecynyl
hexadecynyl
heptadecynyl
octadecynyl
nonadecynyl
eicosynyl
heneicosynyl
docosynyl
tricosynyl
tetracosynyl
pentacosynyl
hexacosynyl
heptacosynyl
octacosynyl
nonacosynyl
triacontynyl
cyclopropyl
cyclobutyl
cyclopentyl
cyclohexyl
cycloheptyl
cyclooctyl
cyclononyl
cyclodecyl
cycloundecyl
cyclododecyl
cyclotetradecyl
cyclopentenyl TABLE 1-continued cyclohexenyl
cycloheptenyl
cyclooctenyl
cyclodecenyl
cyclododecenyl
methylcyclohexyl
ethylcyclohexyl
propylcyclohexyl
dimethylcyclohexyl
diethylcyclohexyl
dipropylcyclohexyl
phenyl
tolyl
mesityl
ethylphenyl
propylphenyl
butylphenyl
pentylphenyl
hexylphenyl
dimethylphenyl
trimethylphenyl
diethylphenyl
diethylmethylphenyl
dipropylphenyl
dipropylmethylphenyl
benzyl
phenethyl
napthyl
norbornyl
adamantyl
trifluoromethyl
methyltrifluoromethyl
trimethylsilyl
trimethylgermyl
trimethylstannyl
trimethylsilylmethyl
trimethylgermylmethyl
trimethylstannylmethyl
methoxymethyl
ethoxymethyl
propoxymethyl
butoxymethyl
phenoxymethyl
methylsulfanyl
ethylsulfanyl
propylsulfanyl
butylsulfanyl
phenylsulfanyl
dimethylaminomethyl
dimethylaminoethyl
diphenylaminomethyl
diphenylaminoethyl
phenylaminomethyl
phenylaminoethyl
methylaminomethyl
dimethylphosphinomethyl
dimethylphosphinoethyl
diphenylphosphinomethyl
phenylphosphinoethyl
methylphosphinomethyl
methoxy
ethoxy
propoxy
butoxy
dimethylamido
diethylamido
methylethylamido
phenoxy
benzoxy
methylphenoxy
ethylphenoxy
propylphenoxy
dimethylphenoxy
diethylphenoxy
dipropylphenoxy
methylbenzoxy
ethylbenzoxy
propylbenzoxy
dimethylbenzoxy TABLE 1-continued diethylbenzoxy
dipropylbenzoxy
perfluoroethyl
perfluoropropyl
perfluorobutyl
perfluoropentyl
perfluorohexyl
perfluoroheptyl
perfluorooctyl
perfluorononyl
perfluorodecyl
perfluoroundecyl
perfluorododecyl
perfluorotridecyl
perfluorotetradecyl
perfluoropentadecyl
perfluorohexadecyl
perfluoroheptadecyl
perfluorooctadecyl
perfluorononadecyl
perfluoroeicosyl
fluoromethyl
fluoroethyl
fluoropropyl
fluorobutyl
fluoropentyl
fluorohexyl
fluoroheptyl
fluorooctyl
fluorononyl
fluorodecyl
fluoroundecyl
fluorododecyl
fluorotridecyl
fluorotetradecyl
fluoropentadecyl
fluorohexadecyl
fluoroheptadecyl
fluorooctadecyl
fluorononadecyl
fluoroeicosyl
thienyl
furanyl
pyrrolyl
phospholyl
methylthienyl
methylfuranyl
methylpyrrolyl
methylphospholyl
ethylthienyl
ethylfuranyl
ethylpyrrolyl
ethylphospholyl
propylthienyl
propylfuranyl
propylpyrrolyl
propylphospholyl
butylthienyl
butylfuranyl
butylpyrrolyl
butylphospholyl
pentylthienyl
pentylfuranyl
pentylpyrrolyl
penylphospholyl
hexylthienyl
hexylfuranyl
hexylpyrrolyl
hexylphospholyl
heptylthienyl
heptylfuranyl
heptylpyrrolyl
heptylphospholyl
octylthienyl
octylfuranyl
octylpyrrolyl
octylphospholyl
nonylthienyl
nonylfuranyl TABLE 1-continued nonylpyrrolyl
nonylphospholyl
decylthienyl
decylfuranyl
decylpyrrolyl
decylphospholyl
undecylthienyl
undecylfuranyl
undecylpyrrolyl
undecylphospholyl
dodecylthienyl
dodecylfuranyl
dodecylpyrrolyl
dodecylphospholyl
dimethylthienyl
dimethylfuranyl
dimethylpyrrolyl
dimethylphospholyl
diethylthienyl
diethylfuranyl
diethylpyrrolyl
diethylphospholyl
dipropylthienyl
dipropylfuranyl
dipropylpyrrolyl
dipropylphospholyl
dibutylthienyl
dibutylfuranyl
dibutylpyrrolyl
dibutylphospholyl
dipentylthienyl
dipentylfuranyl
dipentylpyrrolyl
dipenylphospholyl
dihexylthienyl
dihexylfuranyl
dihexylpyrrolyl
dihexylphospholyl
trimethylthienyl
trimethylfuranyl
trimethylpyrrolyl
trimethylphospholyl
benzothiopheneyl
benzofuranyl
phenylthienyl
phenylfuranyl
phenylpyrrolyl
phenylphospholyl
tolylthienyl
tolylfuranyl
tolylpyrrolyl
tolylphospholyl
mesitylthienyl
mesitylfuranyl
mesitylpyrrolyl
mesitylphospholyl
fluorophenyl
difluorophenyl
trifluorophenyl
tetrafluorophenyl
pentafluorophenyl
trifluoromethylphenyl
fluorobenzyl
difluorobenzyl
trifluorobenzyl
tetrafluorobenzyl
pentafluorobenzyl
trifluoromethylbenzyl $R^1 R^2 R^3 R^4 R^5 R^6 R^7 R^8$ and $R^9$ bromo
chloro
fluoro $\underline{X}$ hydride
fluoride
chloride
bromide TABLE 1-continued iodide
methyl
ethyl
propyl
butyl
pentyl
hexyl
heptyl
octyl
nonyl
decyl
undecyl
dodecyl
tridecyl
tetradecyl
pentadecyl
hexadecyl
heptadecyl
octadecyl
nonadecyl
eicosyl
heneicosyl
docosyl
tricosyl
tetracosyl
pentacosyl
hexacosyl
heptacosyl
octacosyl
nonacosyl
triacontyl
vinyl
propenyl
butenyl
pentenyl
hexenyl
heptenyl
octenyl
nonenyl
decenyl
undecenyl
dodecenyl
tridecenyl
tetradecenyl
pentadecenyl
hexadecenyl
heptadecenyl
octadecenyl
nonadecenyl
eicosenyl
heneicosenyl
docosenyl
tricosenyl
tetracosenyl
pentacosenyl
hexacosenyl
heptacosenyl
octacosenyl
nonacosenyl
triacontenyl
propynyl
butynyl
pentynyl
hexynyl
heptynyl
octynyl
nonynyl
decynyl
undecynyl
dodecynyl
tridecynyl
tetradecynyl
pentadecynyl
hexadecynyl
heptadecynyl
octadecynyl
nonadecynyl
eicosynyl
heneicosynyl
docosynyl
tricosynyl
tetracosynyl
pentacosynyl
hexacosynyl
heptacosynyl
octacosynyl
nonacosynyl
triacontynyl
cyclopropyl
cyclobutyl
cyclopentyl
cyclohexyl
cycloheptyl
cyclooctyl
cyclononyl
cyclodecyl
cycloundecyl
cyclododecyl
cyclotetradecyl
cyclopentenyl
cyclohexenyl
cycloheptenyl
cyclooctenyl
cyclodecenyl
cyclododecenyl
methylcyclohexyl
ethylcyclohexyl
propylcyclohexyl
dimethylcyclohexyl
diethylcyclohexyl
dipropylcyclohexyl
phenyl
tolyl
mesityl
ethylphenyl
propylphenyl
butylphenyl
pentylphenyl
hexylphenyl
dimethylphenyl
trimethylphenyl
diethylphenyl
diethylmethylphenyl
dipropylphenyl
dipropylmethylphenyl
benzyl
phenethyl
napthyl
trifluoromethyl
methoxy
ethoxy
propoxy
butoxy
dimethylamido
diethylamido
methylethylamido
phenoxy
benzoxy
allyl
1,1-dimethyl allyl
acetylacetonate
1,1,1,5,5,5-hexa-
fluoroacetylacetonate
1,1,1-trifluoro-acetylacetonate
2-carboxymethyl allyl
1,1,1-trifluoro-5,5-di-
methylacetylacetonate
methoxymethyl
ethoxymethyl
propoxymethyl
butoxymethyl
phenoxymethyl
methylsulfanyl
ethylsulfanyl
propylsulfanyl
butylsulfanyl
phenylsulfanyl
dimethylaminomethyl

TABLE 1-continued dimethylaminoethyl
diphenylaminomethyl
diphenylaminoethyl
phenylaminomethyl
phenylaminoethyl
methylaminomethyl
dimethylphosphinomethyl
dimethylphosphinoethyl
diphenylphosphinomethyl
phenylphosphinoethyl
methylphosphinomethyl
trimethylsilylmethyl
trimethylgermylmethyl
trimethylstannylmethyl
fluoromethyl
fluoroethyl
fluoropropyl
fluorobutyl
fluoropentyl
fluorohexyl
fluoroheptyl
fluorooctyl
fluorononyl
fluorodecyl
fluoroundecyl
fluorododecyl
fluorotridecyl
fluorotetradecyl
fluoropentadecyl
fluorohexadecyl
fluoroheptadecyl
fluorooctadecyl
fluorononadecyl
fluoroeicosyl
fluorobenzyl
difluorobenzyl
trifluorobenzyl
tetrafluorobenzyl
pentafluorobenzyl
trifluoromethylbenzyl Both X methylidene
ethylidene
propylidene
tetramethylene
pentamethylene
hexamethylene
butadiene
methylbutadiene
dimethylbutadiene
pentadiene
methylpentadiene
dimethylpentadiene
hexadiene
methylhexadiene
dimethylhexadiene
propandiyl
butandiyl
pentandiyl
hexandiyl
heptandiyl
octandiyl
nonandiyl
decandiyl
dodecandiyl
tetradecandiyl
hexadecandiyl
octadecandiyl
azapropandiyl
azabutandiyl
azapentandiyl
azahexandiyl
azaheptandiyl
azaoctandiyl
azanonandiyl
azadecandiyl
azadodecandiyl
phosphapropandiyl

TABLE 1-continued phosphabutandiyl
phosphapentandiyl
thiapropandiyl
thiabutandiyl
thiapentandiyl
catecholate
butylcatecholate
diazabutandiyl
diazapentandiyl
diazahexandiyl
dioxabutandiyl
dioxapentandiyl
dioxahexandiyl The transition metal compounds of this invention can be racemic-like ansa-complexes or meso-like ansa-complexes depending on the selection of the bridge position and the selection of the cyclopentadienyl type ligands (i.e. substituted and unsubstituted cyclopentadienyl, heterocyclopentadienyl, indenyl, fluorenyl, heteroindenyl, heterofluorenyl ligands) bonded to the transition metal atom. The following discussion gives information of the complex type, but is not intended to delineate all possible combinations described herein. 4,4'-bridged bis-indenyl ligands (both symmetrically and unsymmetrically substituted) give racemic-like ansa-complexes. Bridged-4-indenyl-1-fluorenyl ligands and bridged 4-indenyl-4-fluorenyl ligands give racemic-like ansa-complexes even though they have C1 symmetry. 5,5'-bridged bis-indenyl ligands give meso-like ansa-complexes. Analogously, bridged-5-indenyl-2-fluorenyl ligands and bridged 5-indenyl-3-fluorenyl ligands give meso-like ansa-complexes. 4,5'-bridged bis-indenyl ligands, bridged 4-indenyl-2-fluorenyl ligands, bridged 4-indenyl-3-fluorenyl ligands, 1,2'-bridged bis-fluorenyl ligands, 1,3'-bis-fluorenyl ligands, 4,2'-bridged bis-fluorenyl ligands, and 4,3'-bridged bis-fluorenyl ligands give racemic-like ansa-complexes, however, their structures are close to being meso-like ansa-complexes. 4,1'-bridged bis-indenyl ligands and 4,2'-bridged bis-indenyl ligands give racemic-like ansa-complexes. It should be noted that substituents on the rings can further effect the symmetry of the molecules discussed above. By selection of the ligand types, the bridge positions and the substituents on the ligands, a wide variety of racemic-like and meso-like ansa-complexes can be prepared. Non-limiting examples of transition metal compounds M1 through M178 of this invention are illustrated in Table 2 where:

M is a group 3, 4, 5 or 6 transition metal atom, or a lanthanide metal atom, or actinide metal atom, preferably a Group 4 transition metal atom selected from titanium, zirconium or hafnium;

$R^1$, $R^2$, $R^3$, $R^4$, $R^5$, $R^6$, $R^7$, $R^8$, $R^9$, $R'$, $R^{4'}$, $R^{5'}$, and $R^{6'}$ are, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent $R^1$, $R^2$, $R^3$, $R^4$, $R^5$, $R^6$, $R^7$, $R^8$, $R^9$, $R'$, $R^{4'}$, $R^{5'}$, and $R^{6'}$ may join together to form a substituted or unsubstituted, saturated, partially unsaturated, or aromatic cyclic or polycyclic substituent;

Z is a Group 16 atom or a Group 15 atom, and preferably S, O, N, or P;

each z is zero or one, provided that when Z is a Group 15 atom, "z" is one, when Z is a Group 16 atom, "z" is zero, when Q is a Group 15 atom, "z" is one, and when a Q is a Group 16 atom, "z" is zero;

each Q, if present, is, independently, a Group 16 atom or a Group 15 atom, and preferably S, O, N, or P;

m, n, and p are independently zero or one, and m+n+p=1; when m or n or p is one, Q is present in the ring as a Group 16 or a Group 15 atom; when m or n or p is zero, Q is absent and is replaced by a ring carbon atom having a substituent R'';

Y is a Group 15 or 16 bridging heteroatom substituent, and Y is preferably S, O, NR' or PR'; in another embodiment, Y may consist of two Group 15 or 16 heteroatoms bonded in series with one heteroatom bonded to the indicated ring system, and the other heteroatom bonded to the other ligand (i.e. Y is O—O, S—S, R'N—NR', R'P—PR', O—S, O—NR', O—PR', S—NR', S—PR', or R'N—PR');

X are, independently, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from about 3 to about 20 carbon atoms; or both together can be an olefin, diolefin or aryne ligand; or when Lewis-acid activators, such as methylalumoxane, which are capable of donating an X ligand as described above to the transition metal component are used, both X may, independently, be a halogen, alkoxide, aryloxide, amide, phosphide or other univalent anionic ligand or both X can also be joined to form a anionic chelating ligand;

each R* is independently a hydrocarbyl or halocarbyl radical,

G is N, P, As, Sb or B; and

J is N, P, As, Sb or B.

TABLE 2

Transition metal compounds

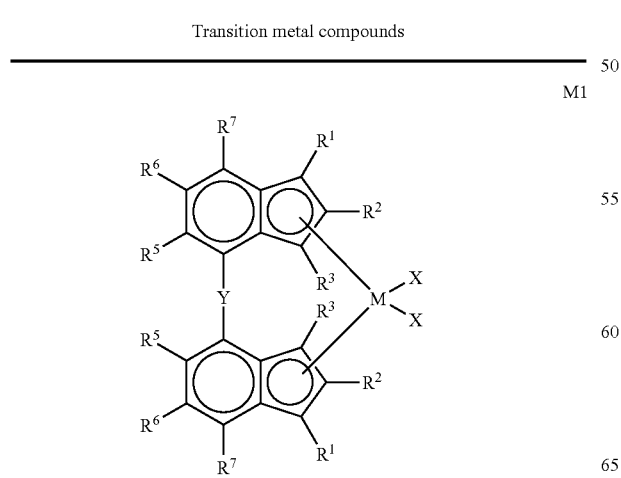

M1

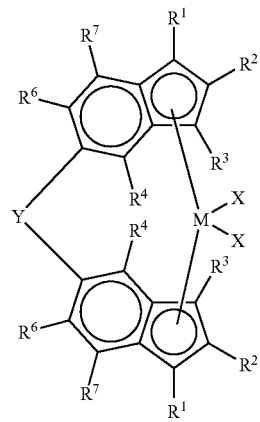

M2

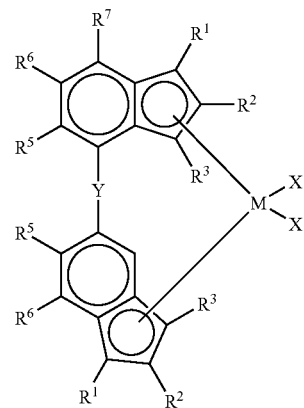

M3

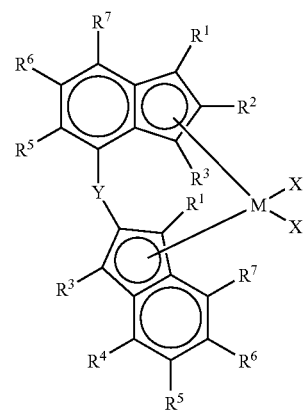

M4

TABLE 2-continued
Transition metal compounds
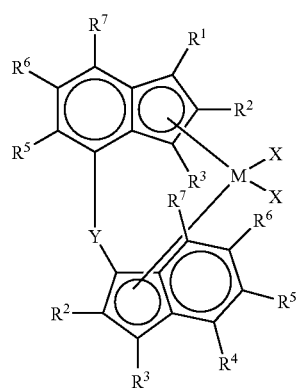 M5
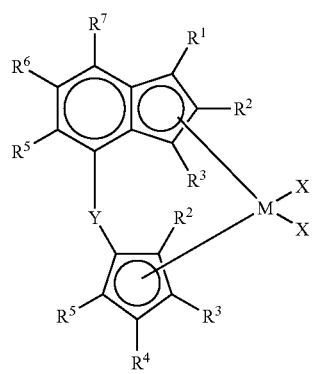 M6
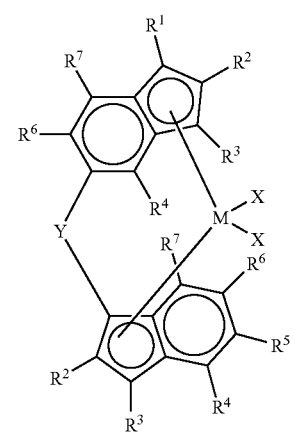 M7
TABLE 2-continued
Transition metal compounds
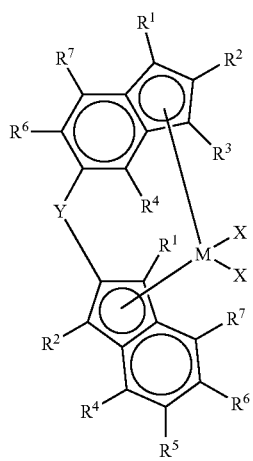 M8
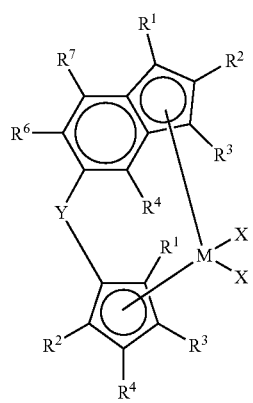 M9
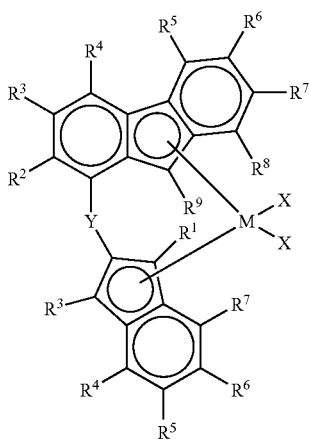 M10

TABLE 2-continued
Transition metal compounds
M11
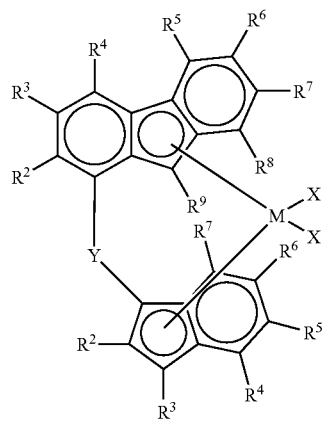
M12
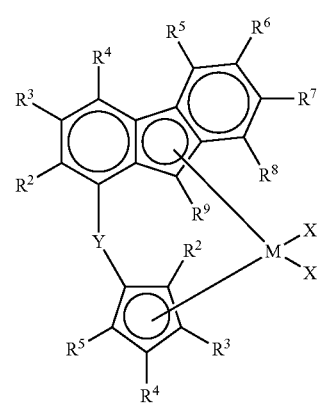
M13
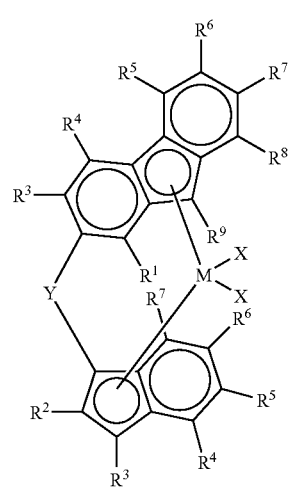
TABLE 2-continued
Transition metal compounds
M14
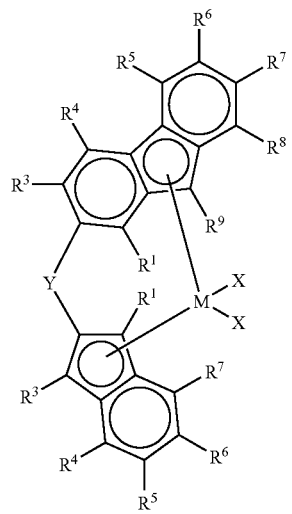
M15
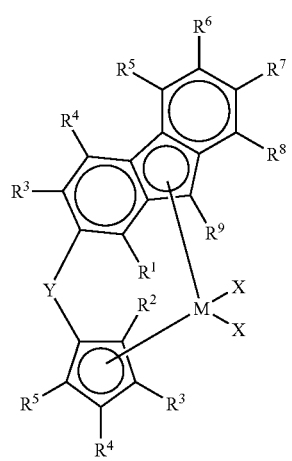
M16
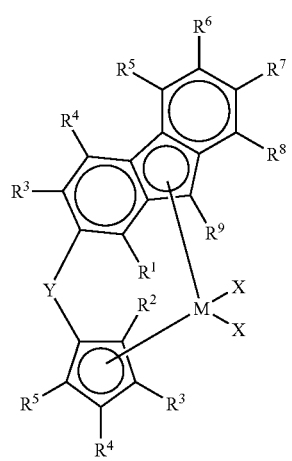

TABLE 2-continued
Transition metal compounds
M17
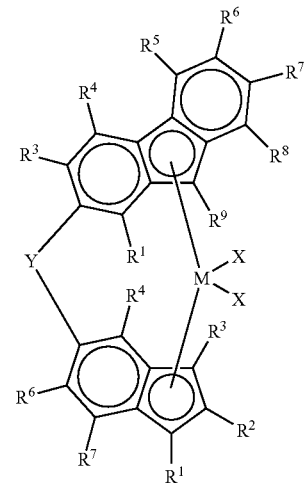
M18
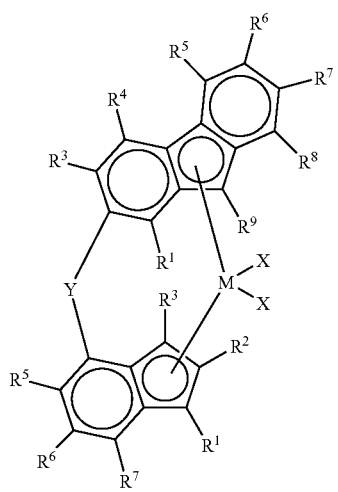
M19
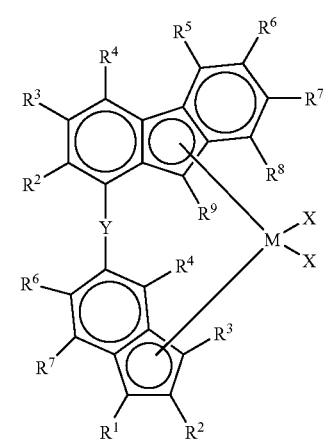
TABLE 2-continued
Transition metal compounds
M20
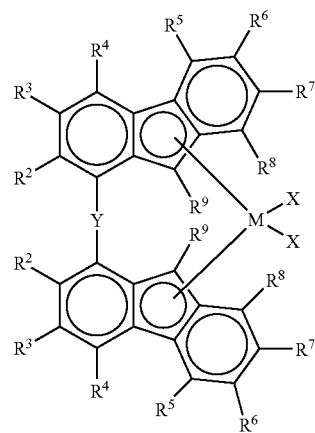
M21
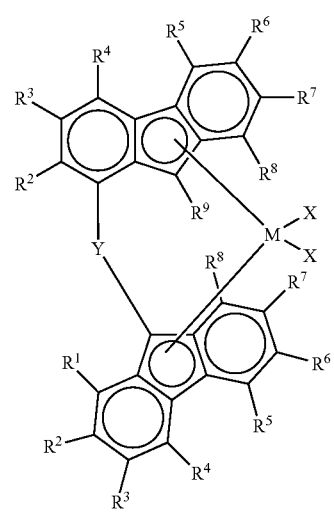
M22
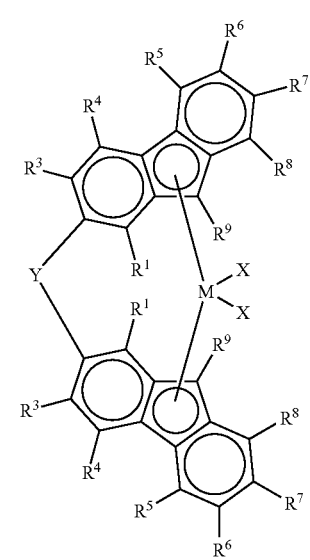

TABLE 2-continued
Transition metal compounds
M23
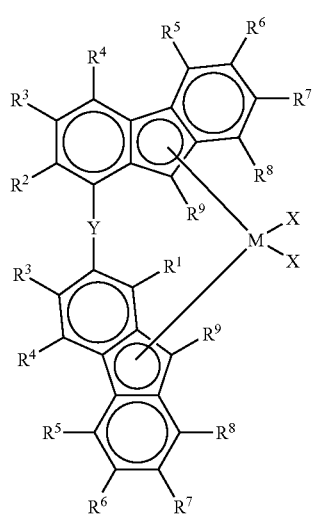
M24
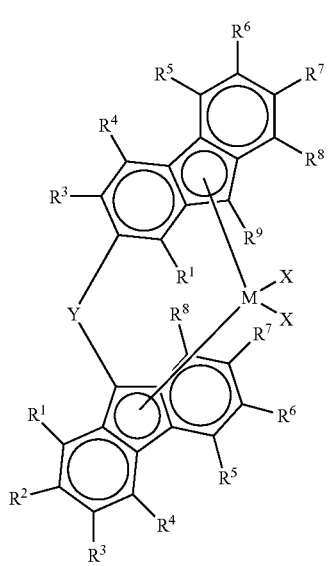
M25
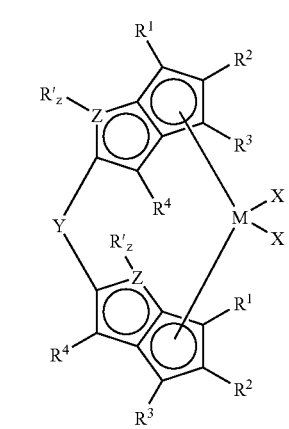
TABLE 2-continued
Transition metal compounds
M26
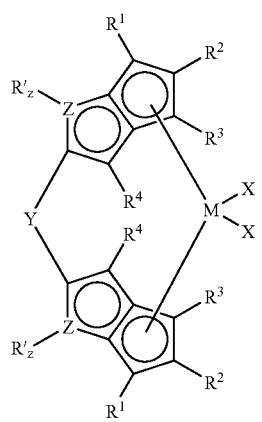
M27
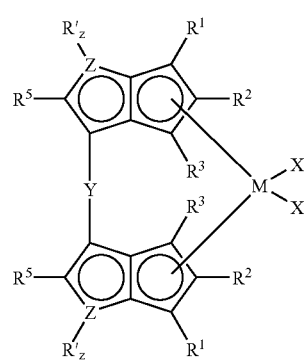
M28
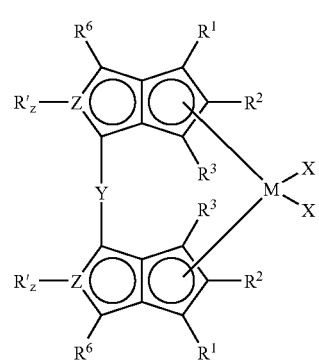

TABLE 2-continued
Transition metal compounds
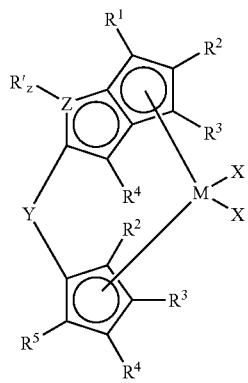
M29
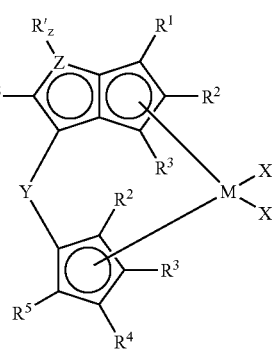
M30
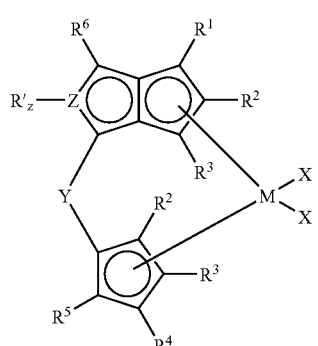
M31
TABLE 2-continued
Transition metal compounds
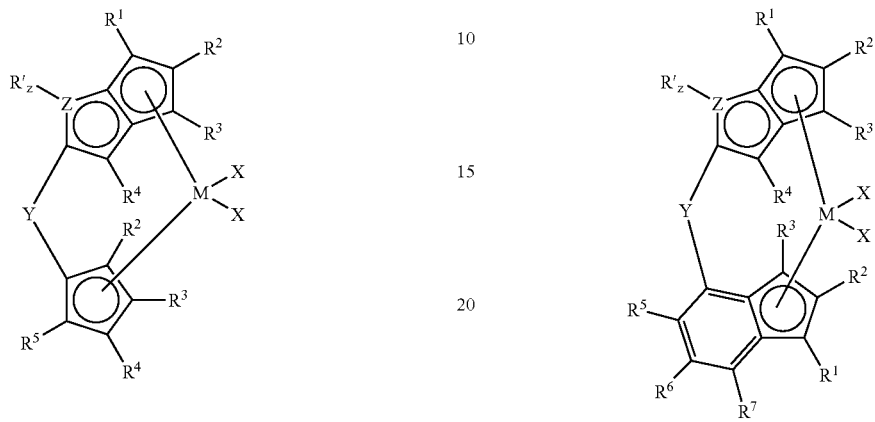
M32
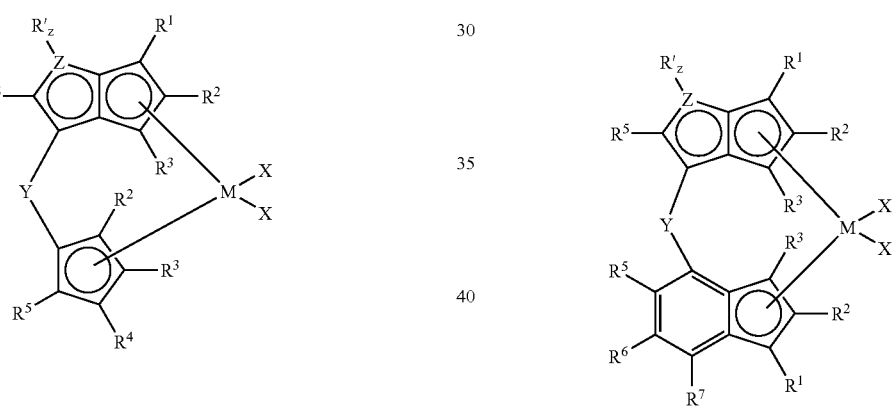
M33
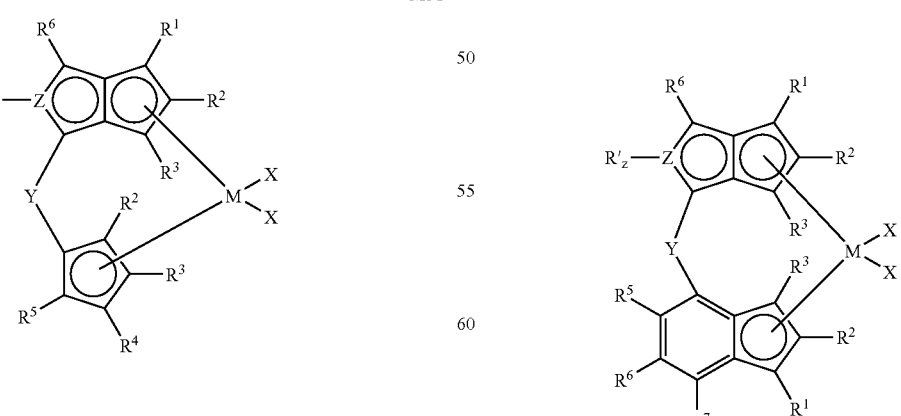
M34

TABLE 2-continued
Transition metal compounds
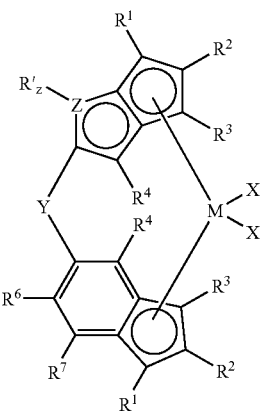
M35
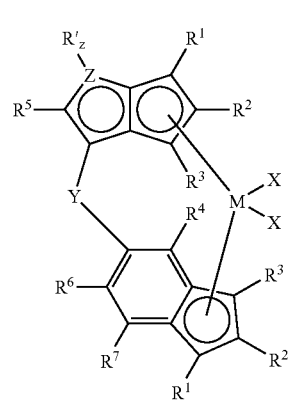
M36
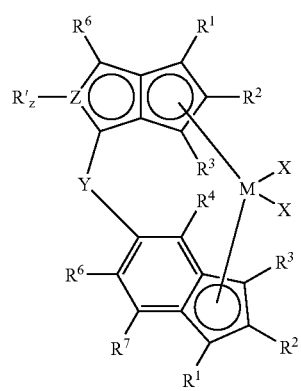
M37
TABLE 2-continued
Transition metal compounds
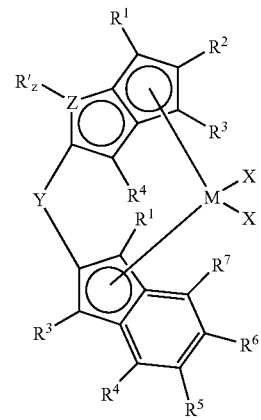
M38
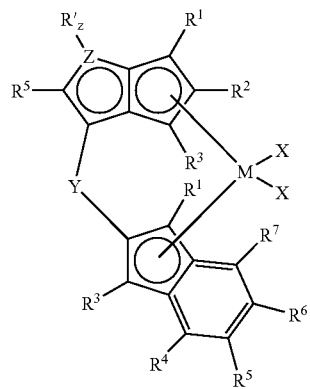
M39
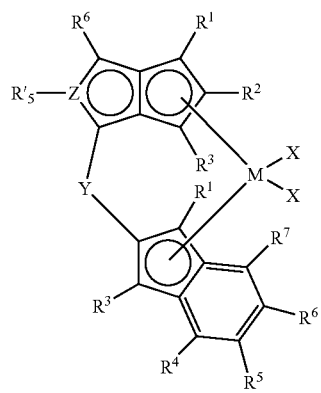
M40

TABLE 2-continued
Transition metal compounds
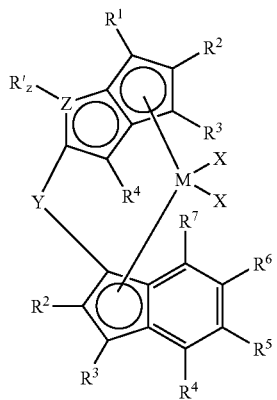
M41
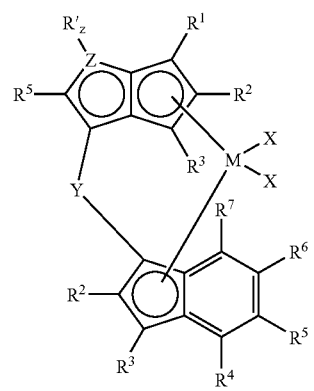
M42
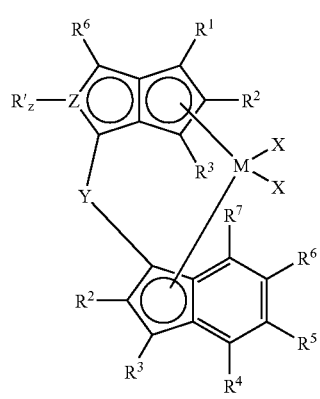
M43
TABLE 2-continued
Transition metal compounds
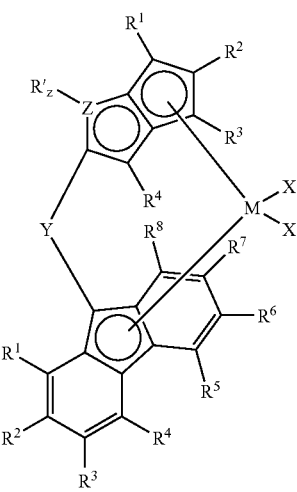
M44
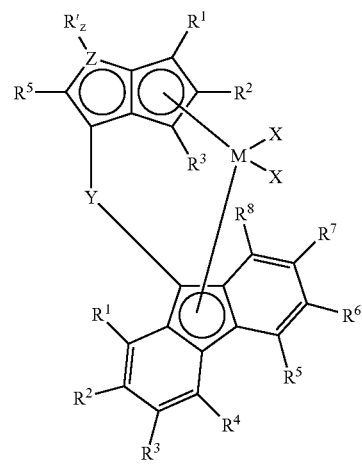
M45
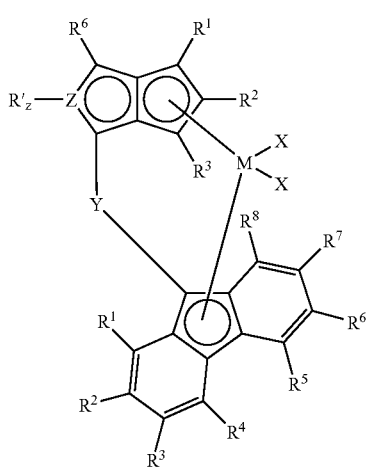
M46

TABLE 2-continued
Transition metal compounds
M47
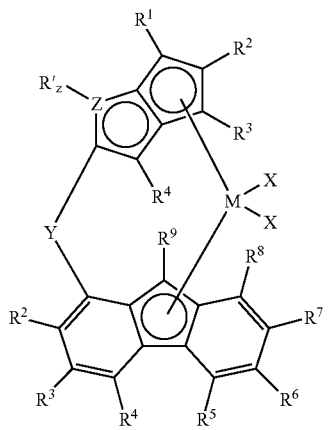
M48
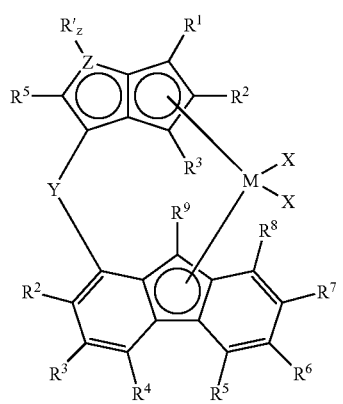
M49
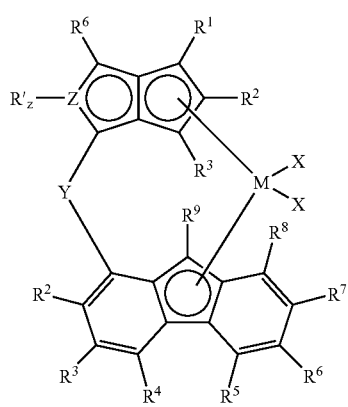
TABLE 2-continued
Transition metal compounds
M50
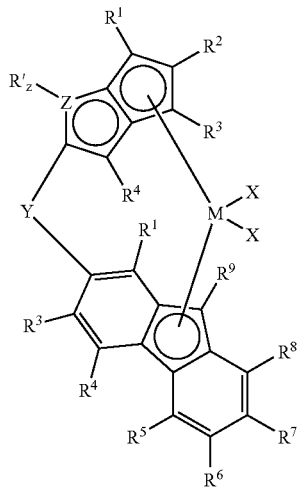
M51
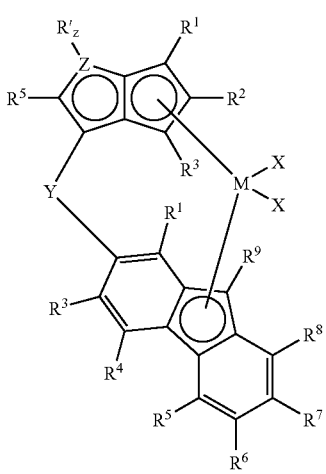
M52
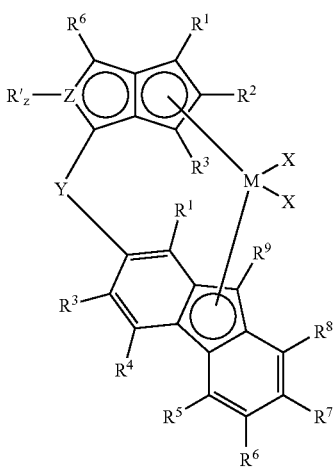

TABLE 2-continued
Transition metal compounds
M53
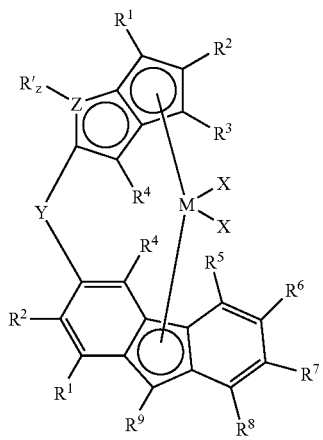
M54
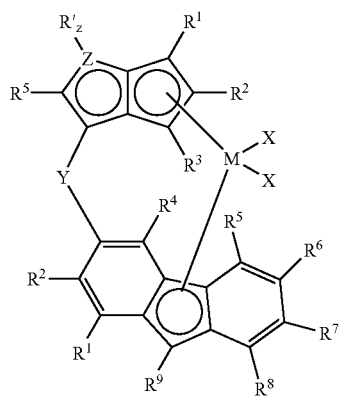
M55
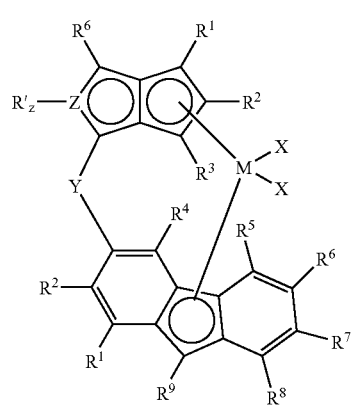
TABLE 2-continued
Transition metal compounds
M56
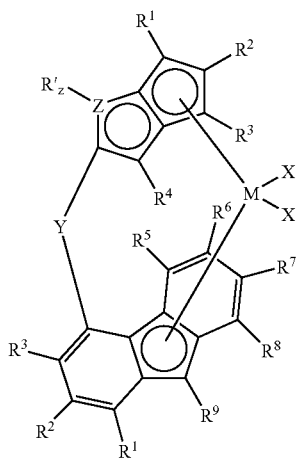
M57
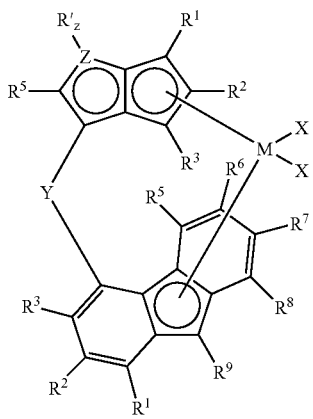
M58
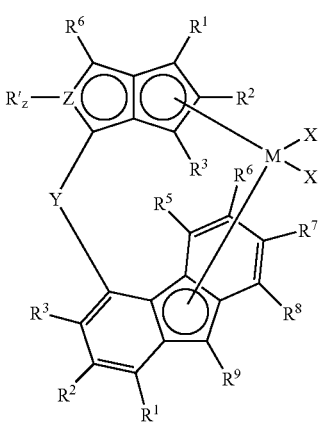

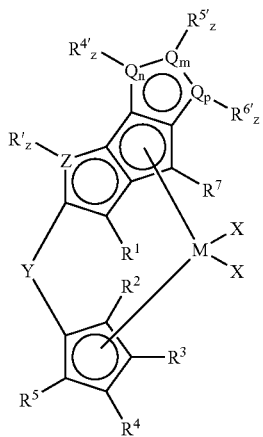

TABLE 2-continued
Transition metal compounds
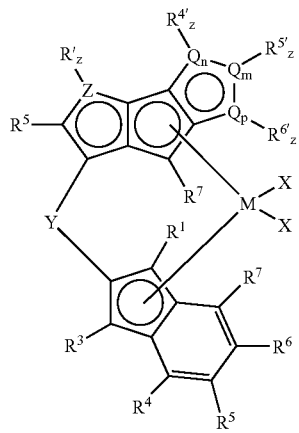
M65
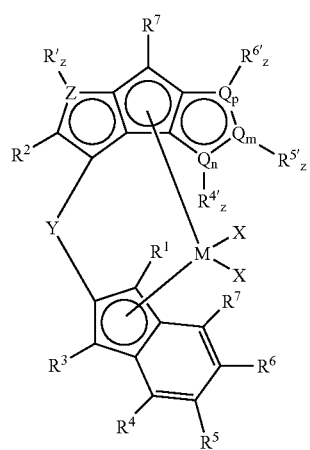
M66
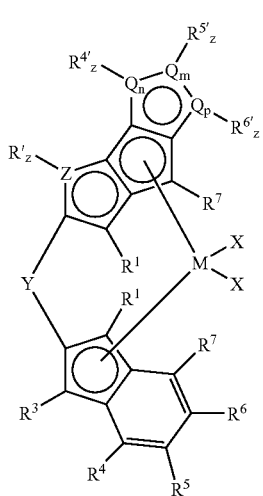
M67
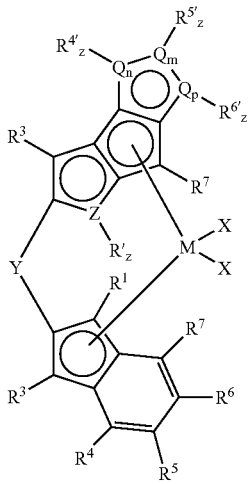
M68
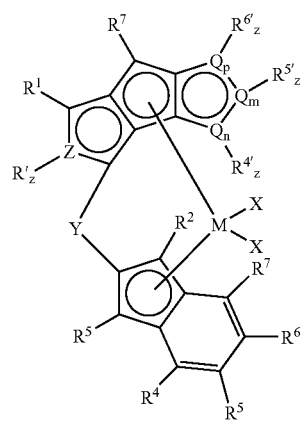
M69
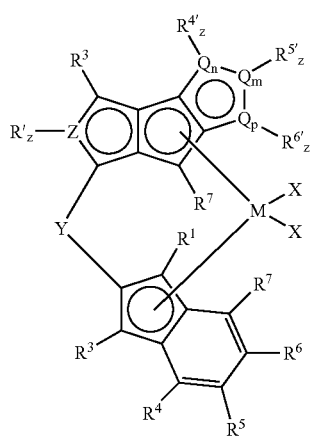
M70

TABLE 2-continued
Transition metal compounds
M71
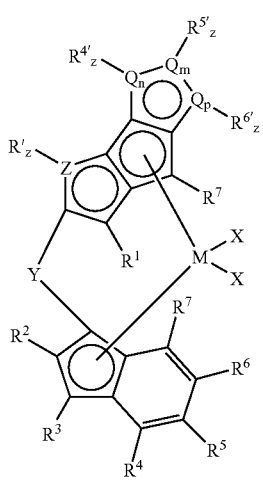
M72
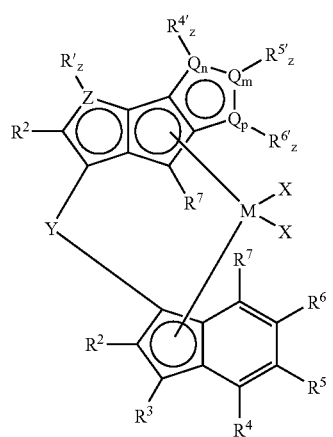
M73
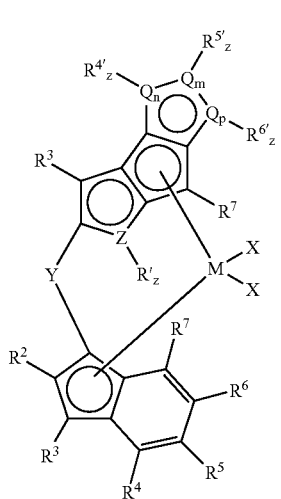
TABLE 2-continued
Transition metal compounds
M74
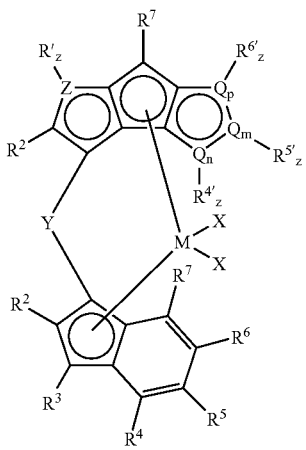
M75
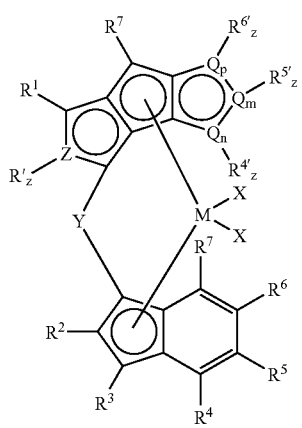
M76
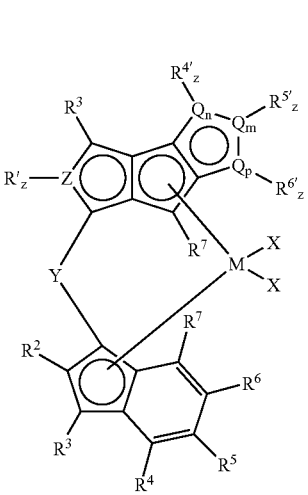

TABLE 2-continued
Transition metal compounds
M77
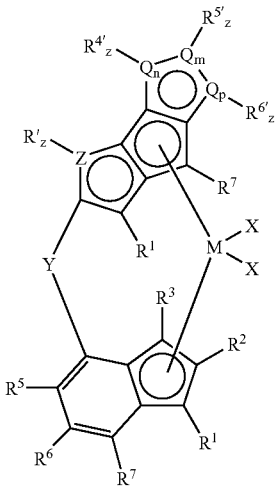
M78
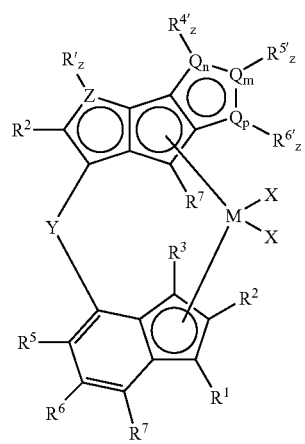
M79
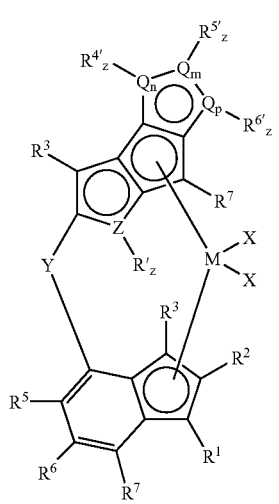
TABLE 2-continued
Transition metal compounds
M80
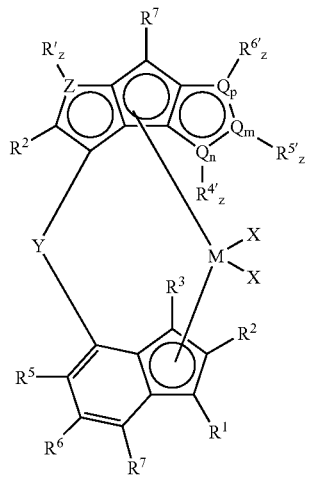
M81
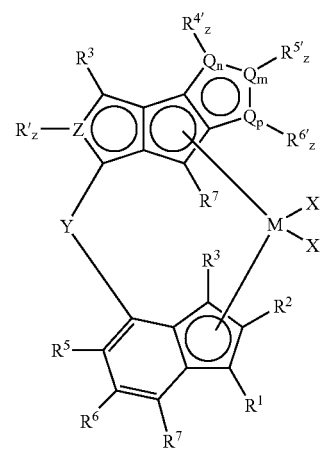
M82
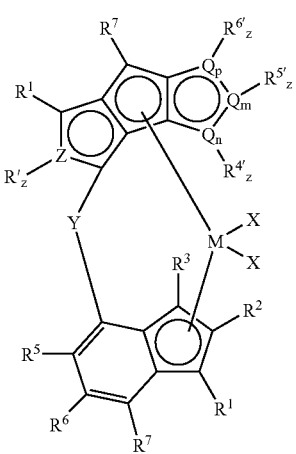

TABLE 2-continued
Transition metal compounds
M83
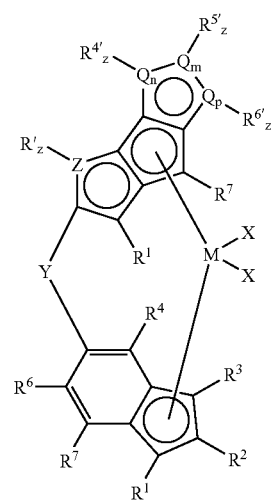
M84
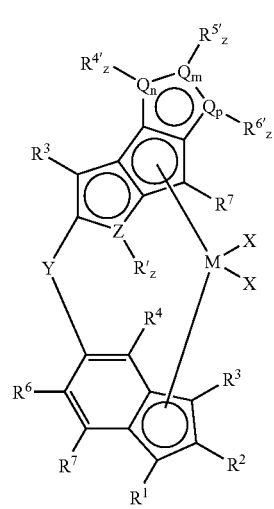
M85
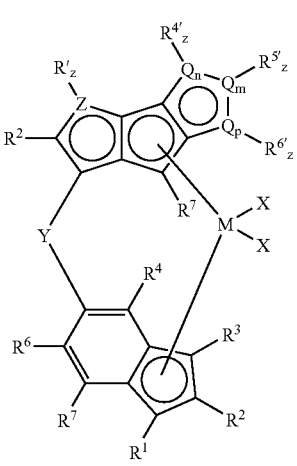
TABLE 2-continued
Transition metal compounds
M86
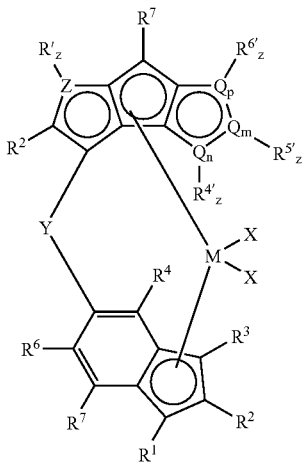
M87
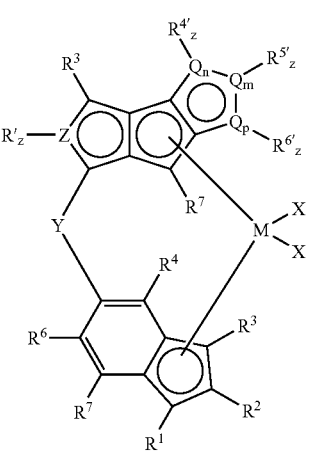
M88
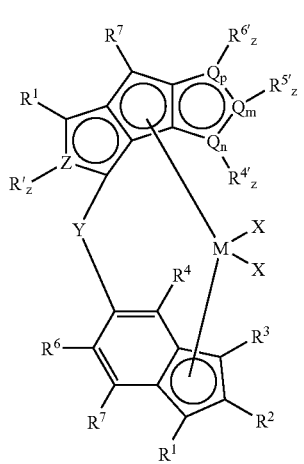

TABLE 2-continued
Transition metal compounds
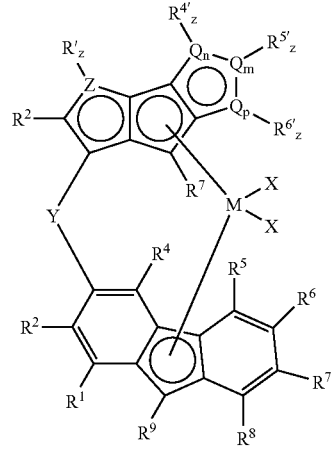
M89
M90
M91
M92
M93
M94

TABLE 2-continued
Transition metal compounds
M95
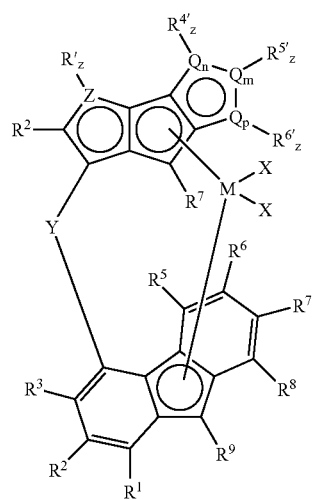
M96
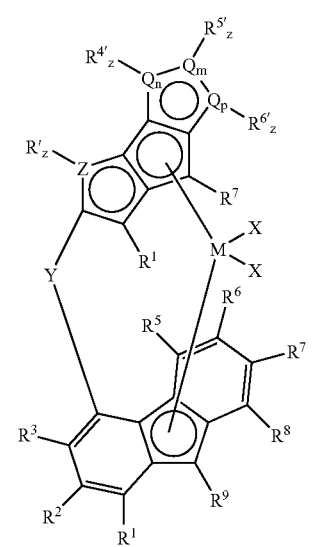
M97
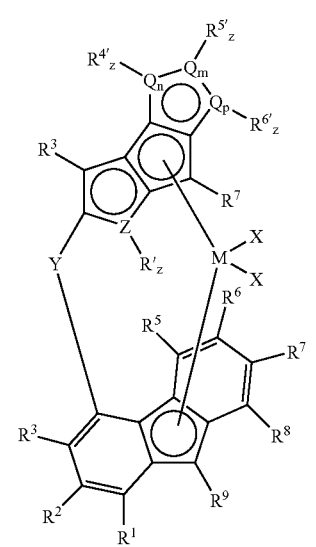
TABLE 2-continued
Transition metal compounds
M98
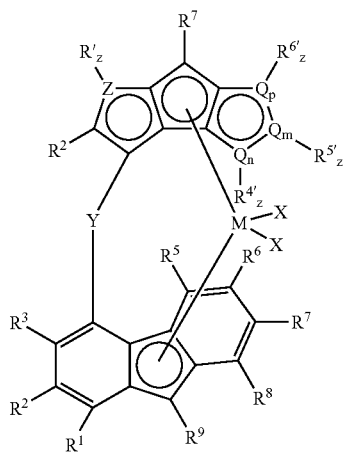
M99
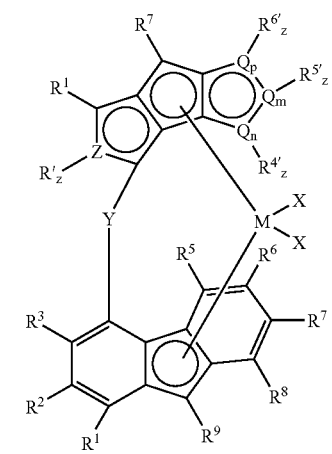
M100
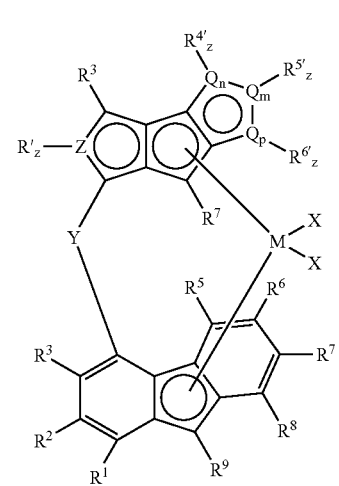

TABLE 2-continued
Transition metal compounds
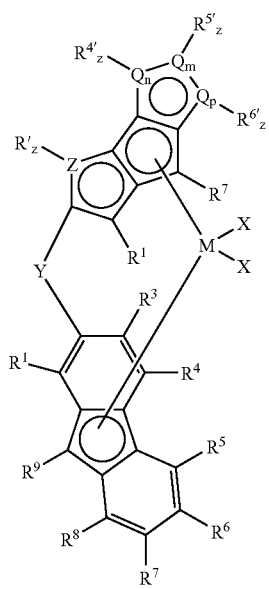
M101
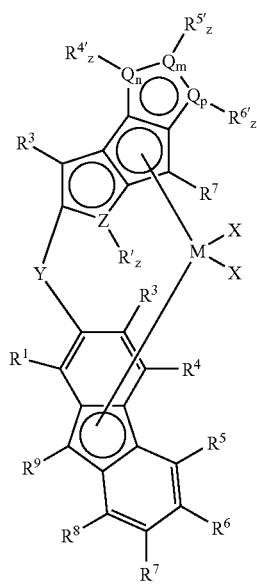
M103
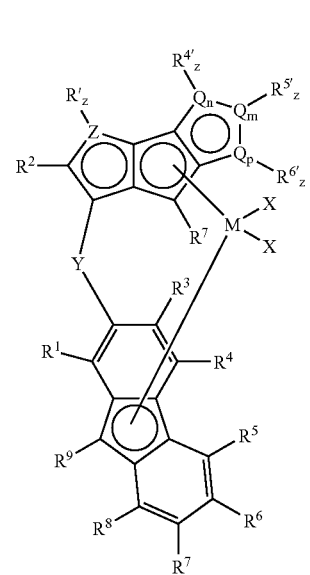
M102
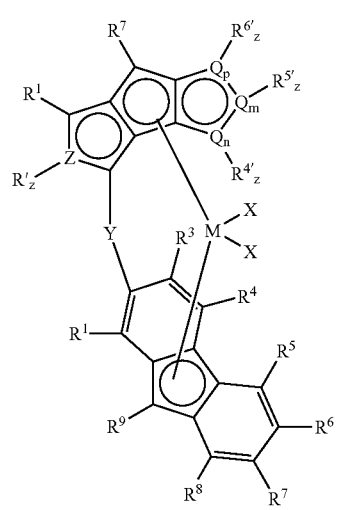
M104

TABLE 2-continued
Transition metal compounds
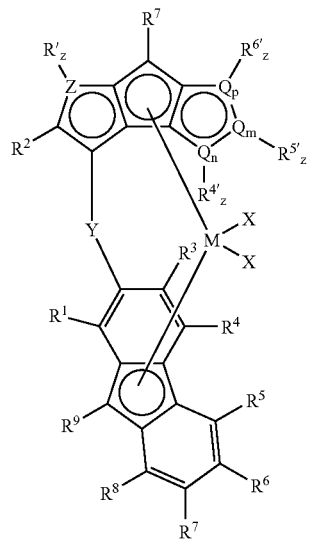
M105
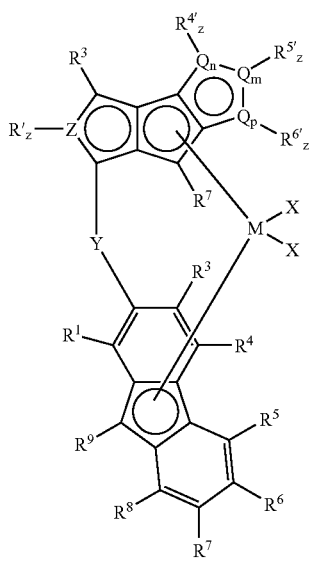
M106
TABLE 2-continued
Transition metal compounds
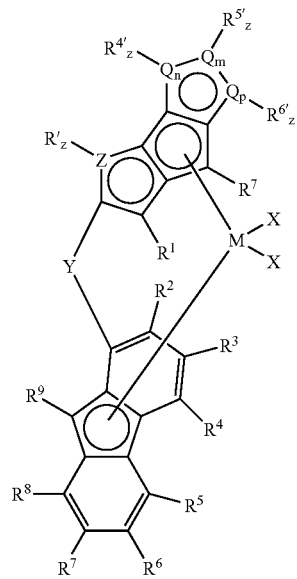
M107
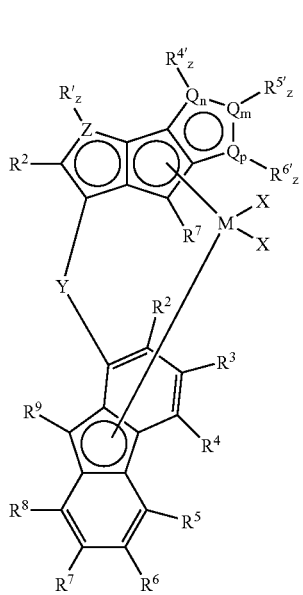
M108

TABLE 2-continued
Transition metal compounds
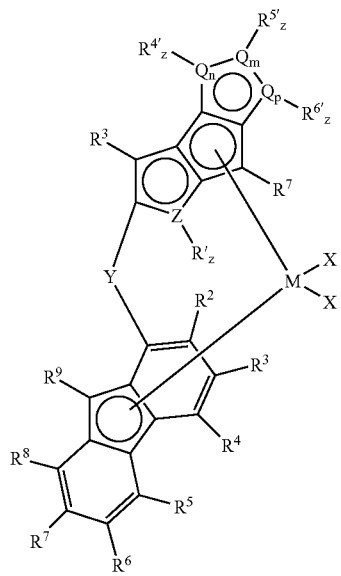
M109
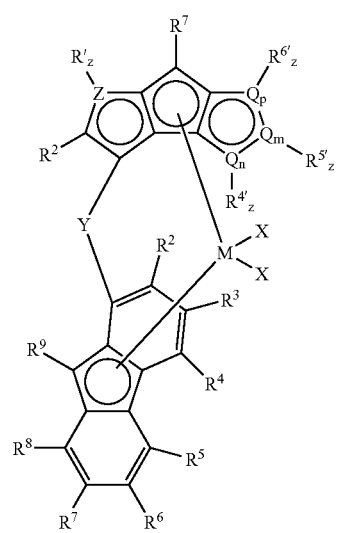
M110
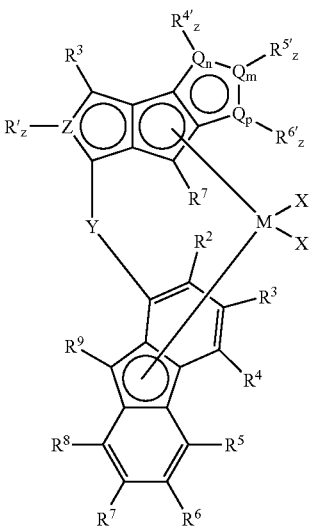
M111
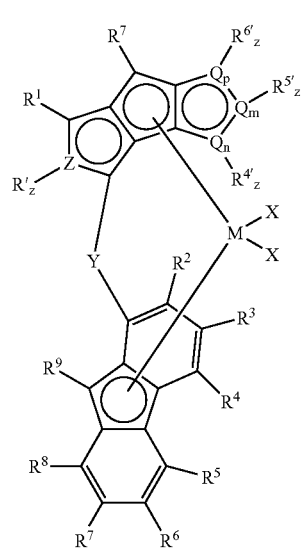
M112

TABLE 2-continued
Transition metal compounds
M113
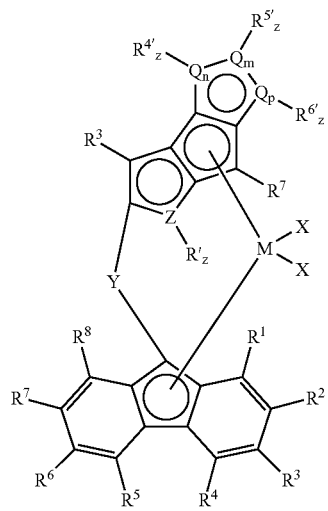
M114
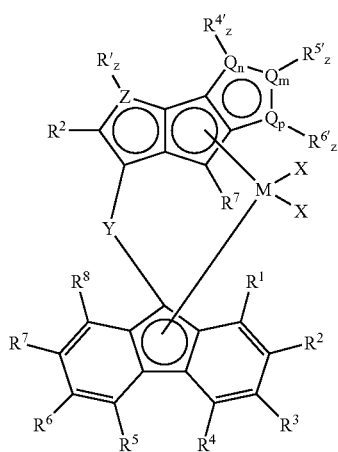
M115
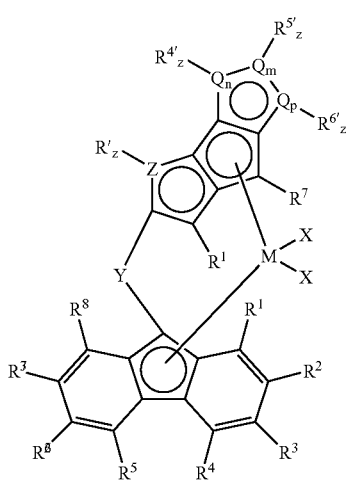
TABLE 2-continued
Transition metal compounds
M116
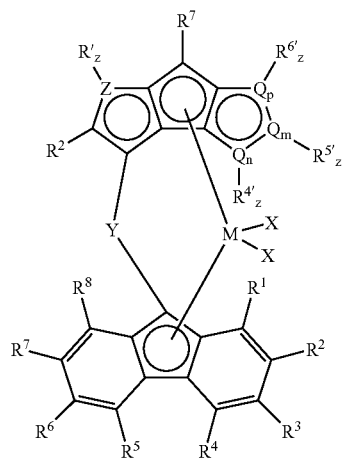
M117
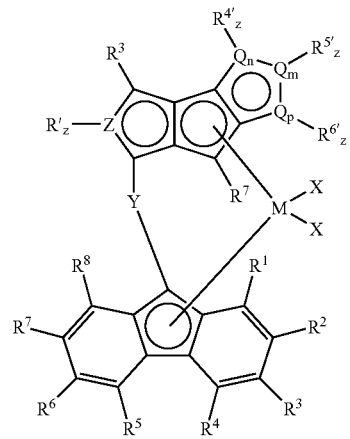
M118
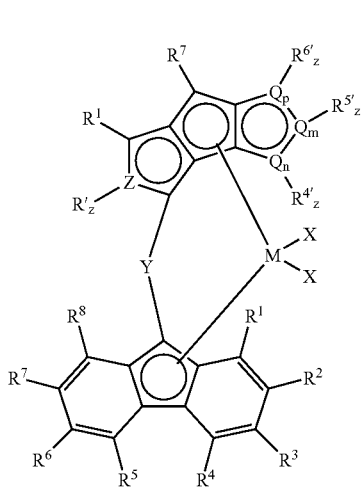

TABLE 2-continued
Transition metal compounds
M119
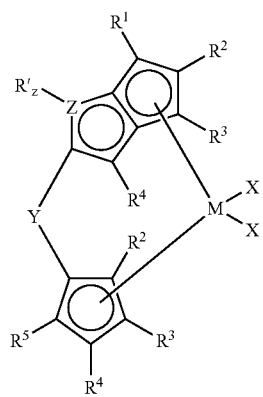
M120
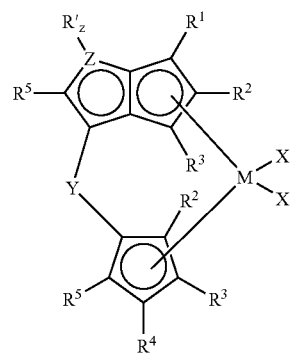
M121
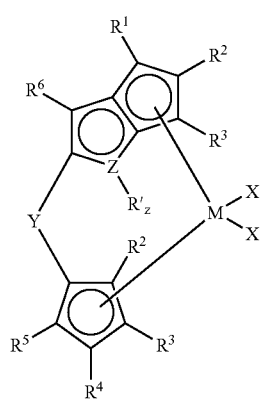
TABLE 2-continued
Transition metal compounds
M122
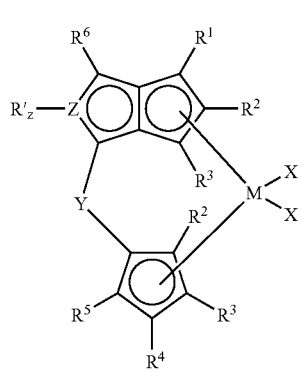
M123
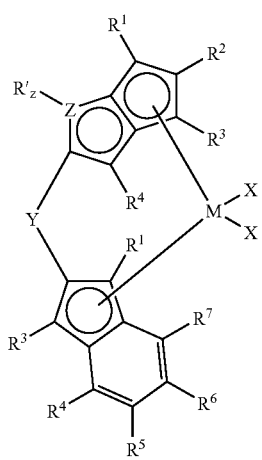
M124
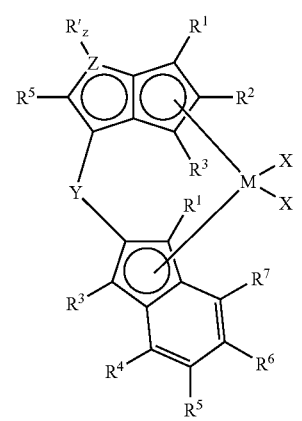

TABLE 2-continued
Transition metal compounds
M125
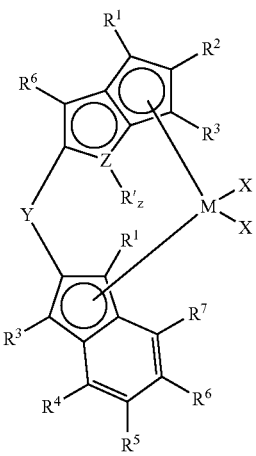
M126
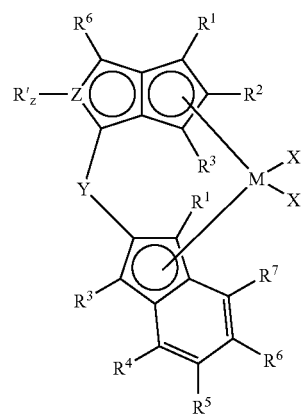
M127
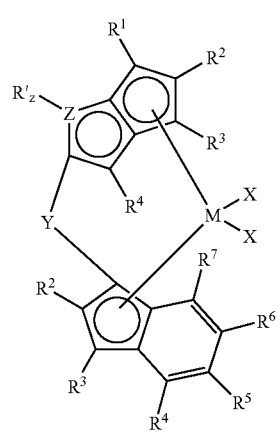
TABLE 2-continued
Transition metal compounds
M128
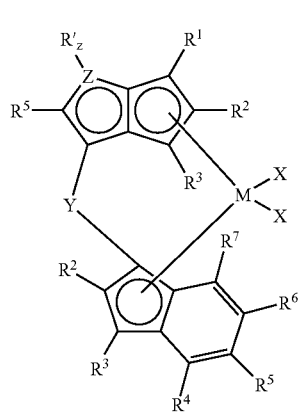
M129
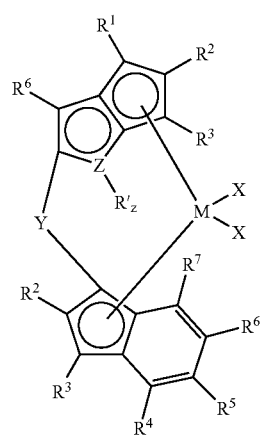
M130
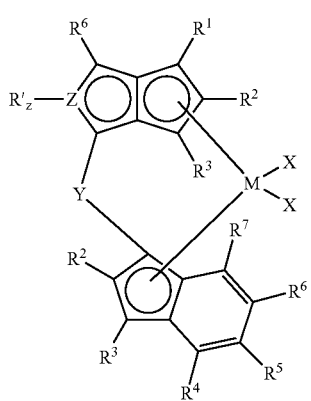

TABLE 2-continued
Transition metal compounds
M131
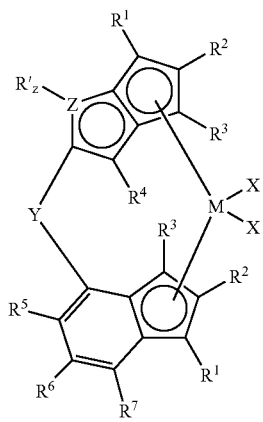
M132
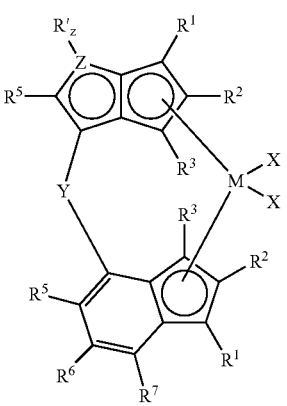
M133
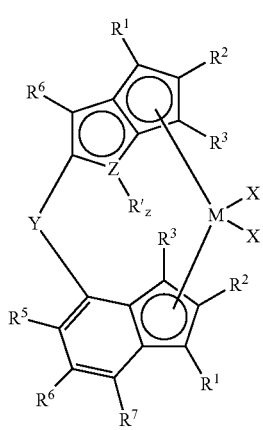
TABLE 2-continued
Transition metal compounds
M134
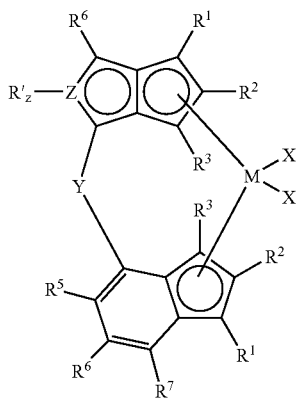
M135
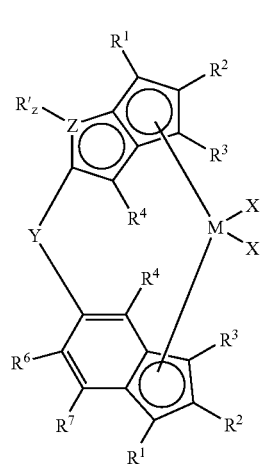
M136
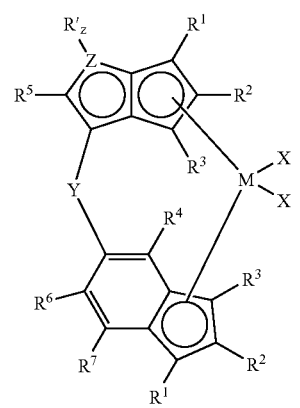

TABLE 2-continued
Transition metal compounds
M137
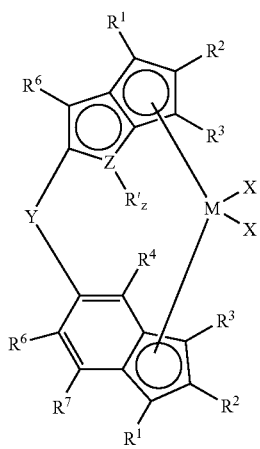
M138
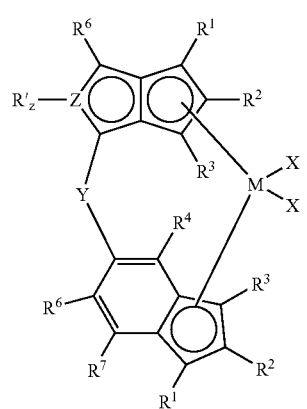
M139
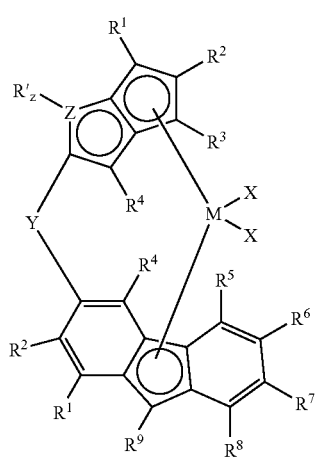
TABLE 2-continued
Transition metal compounds
M140
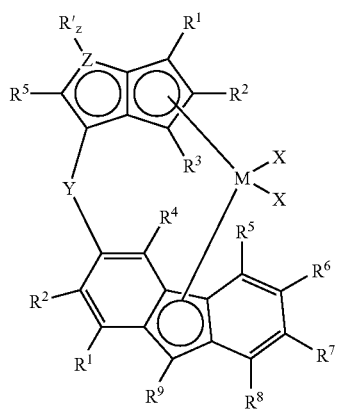
M141
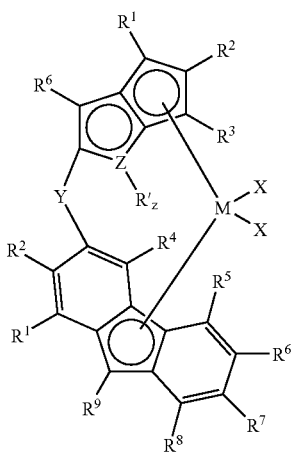
M142
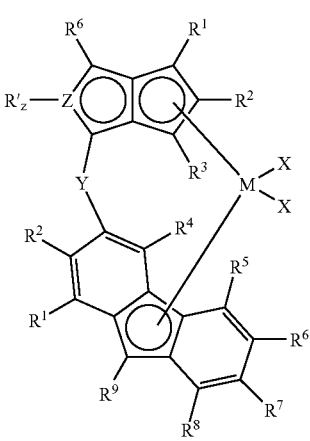

TABLE 2-continued
Transition metal compounds
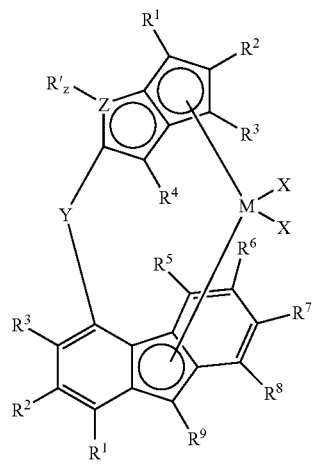
M143
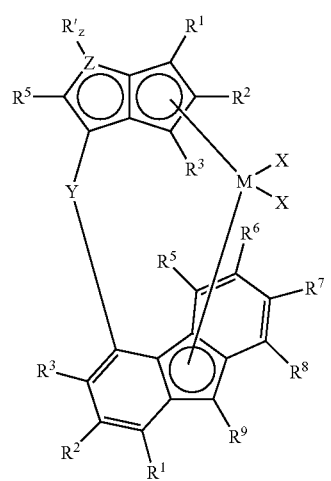
M144
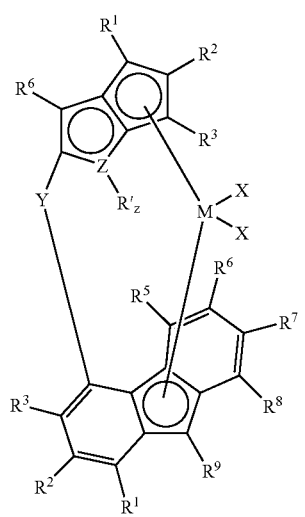
M145
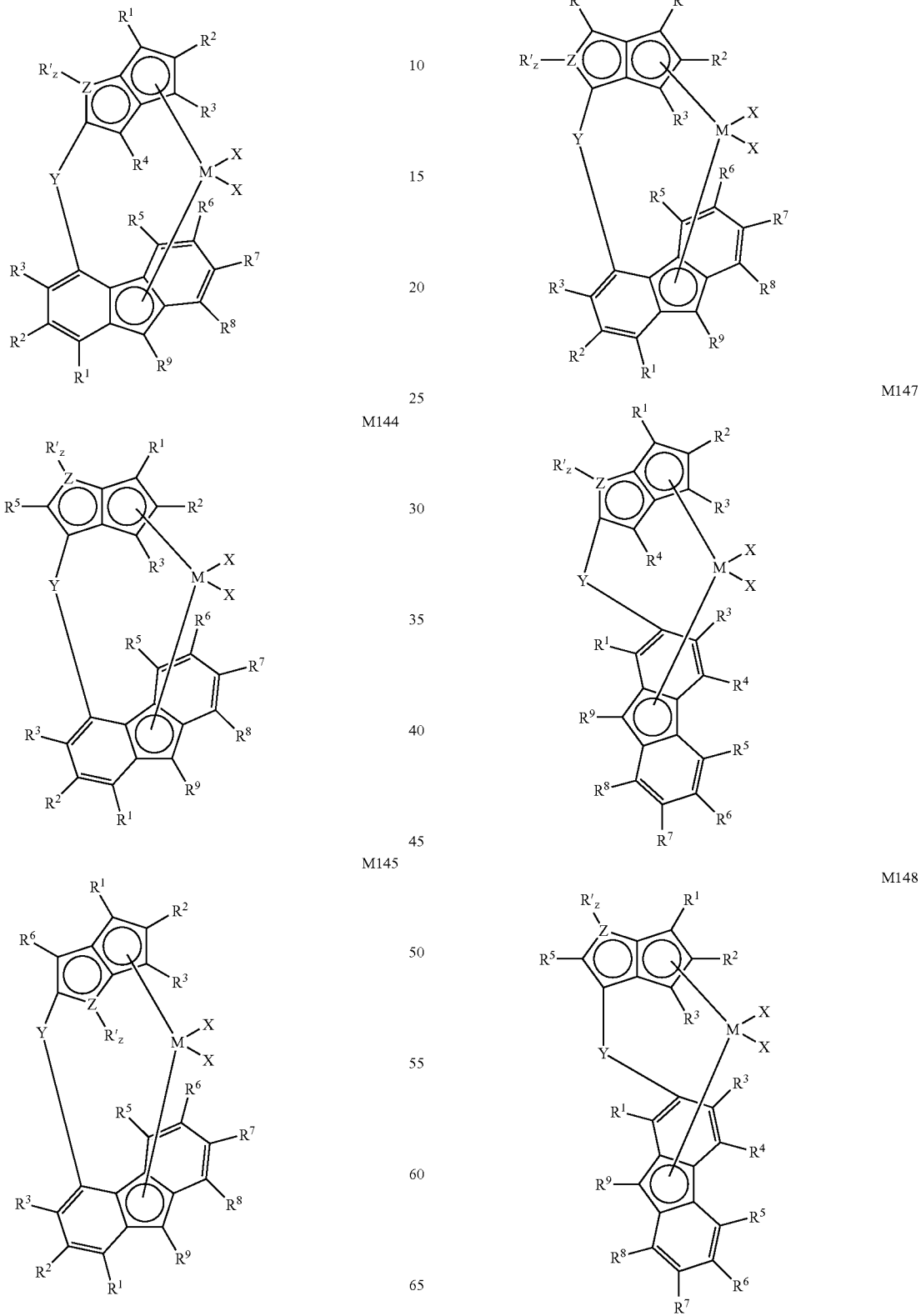
M146
M147
M148

TABLE 2-continued

Transition metal compounds

M149, M150, M151, M152, M153, M154

TABLE 2-continued

Transition metal compounds

M155, M156, M157, M158, M159, M160, M161

TABLE 2-continued
Transition metal compounds
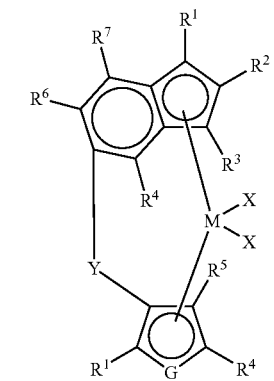
M162
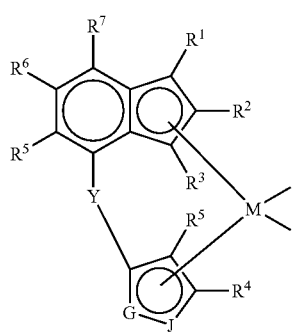
M163
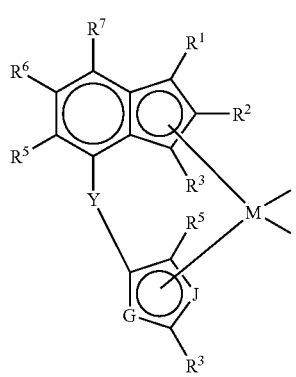
M164
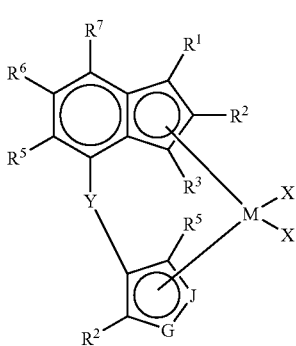
M165
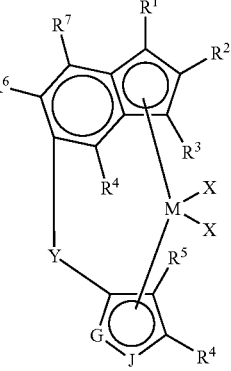
M166
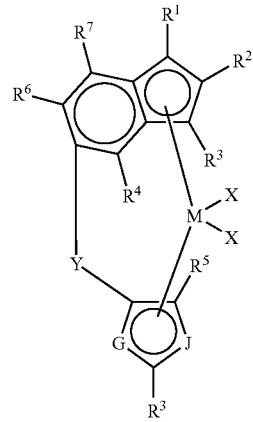
M167
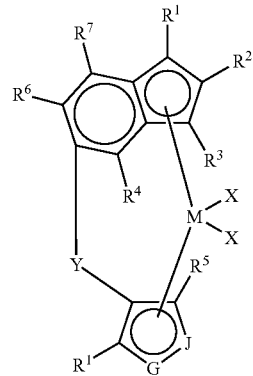
M168
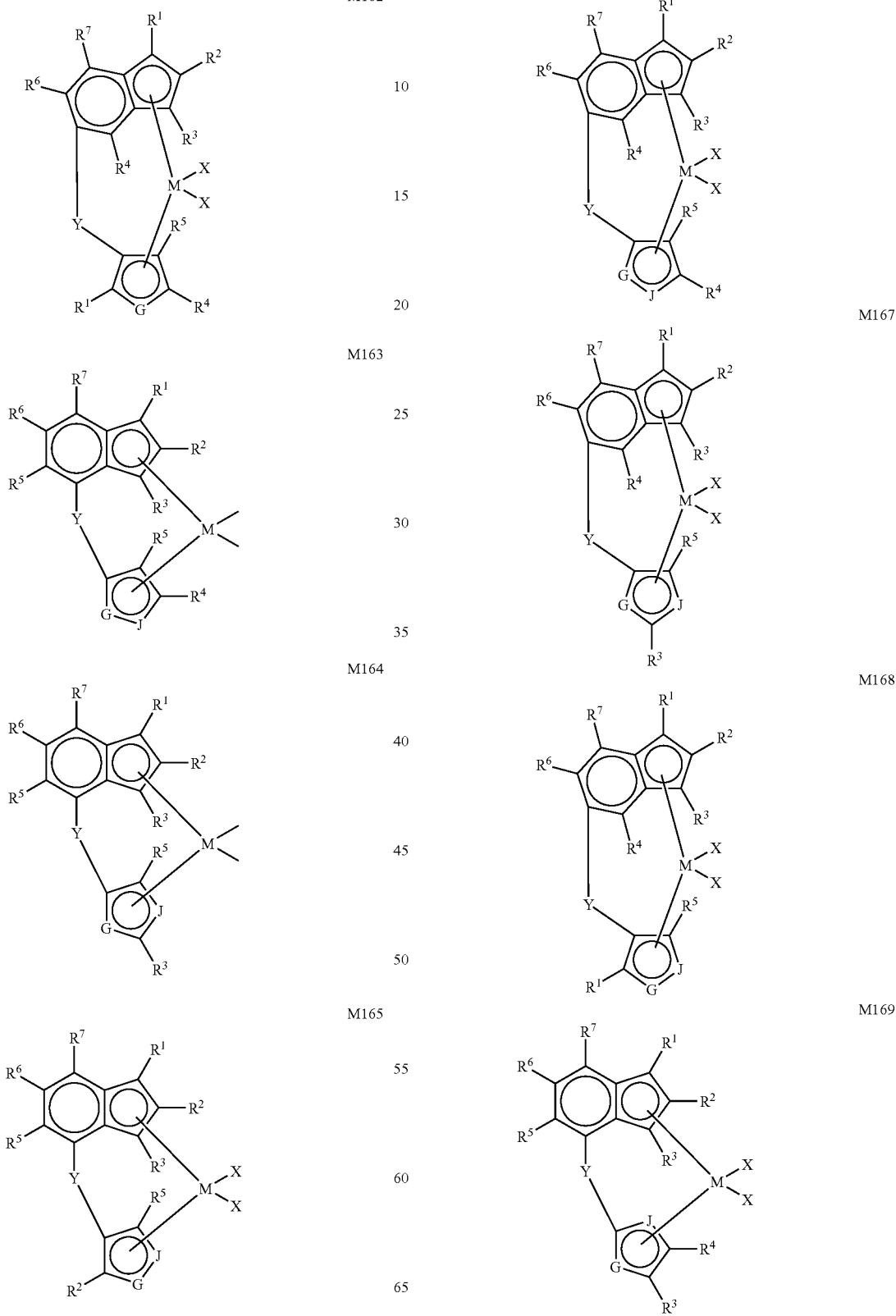
M169

TABLE 2-continued
Transition metal compounds
M170
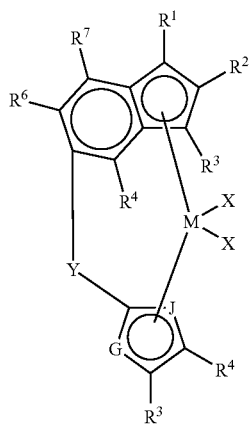
M171
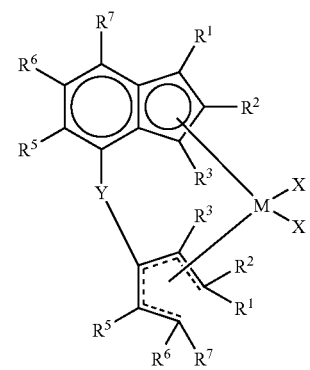
M172
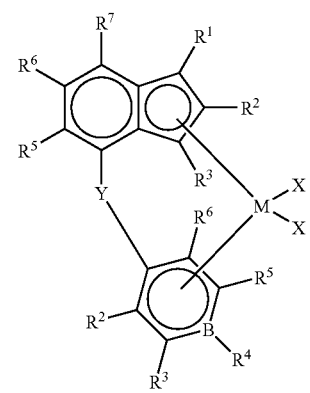
TABLE 2-continued
Transition metal compounds
M173
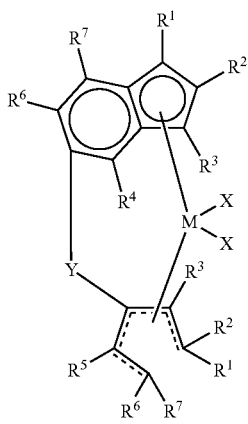
M174
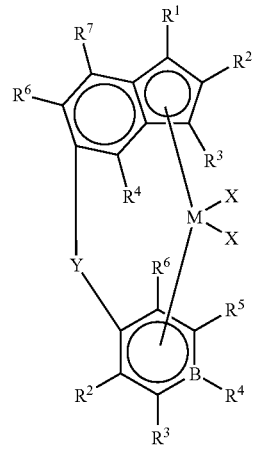
M175
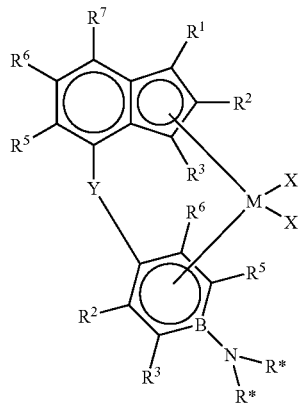

TABLE 2-continued

Transition metal compounds

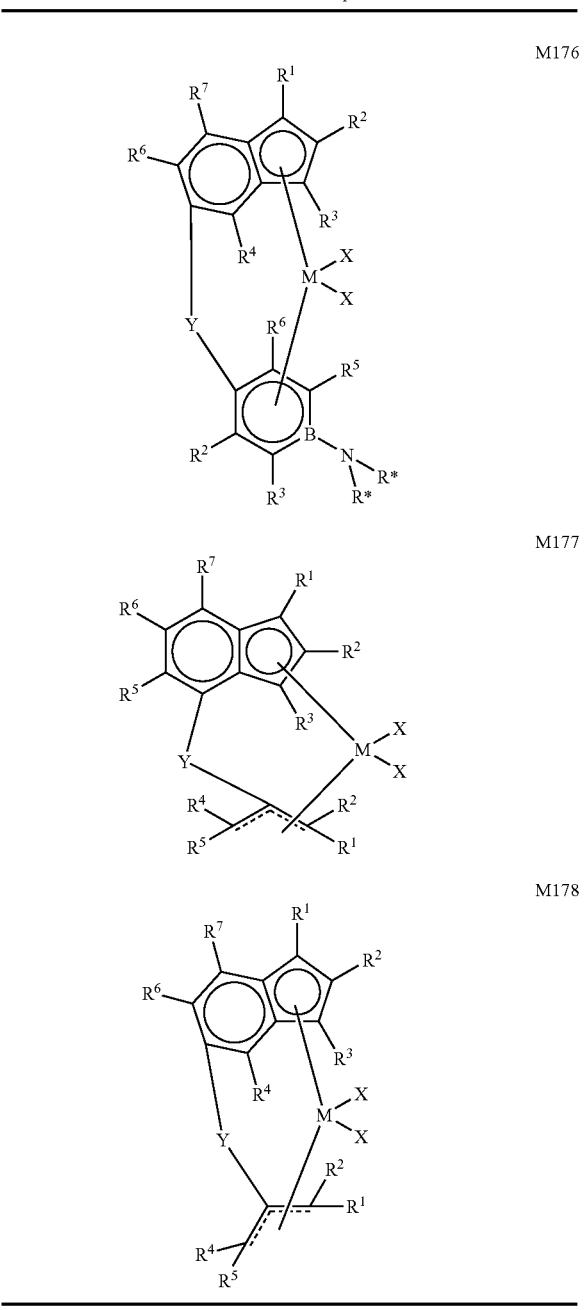

M176

M177

M178

The transition metal compounds of this invention may be prepared by at least two very distinct general routes. The first route involves making the desired ligand followed by a metallation reaction to form the metallocene. The second route involves doing coupling reactions, such as a Negishi coupling reaction, on a metallocene containing at least one bromine, chlorine or iodine substituent.

Synthetic Route 1:

Ligands with sulfur bridges can be prepared by reacting a "bromo-ligand" (Br-ligand) with hydrocarbyl lithium followed by a sulfur dihalide or other similarly functioning sulfur complex such as $S(O_2SPh)_2$, to form a "ligand-S-ligand". In some cases, further reaction is needed to form a metallocene precursor ligand, for example, conversion of a substituted indene from a substituted indane or indan-1-one. Examples of such reactions are illustrated below in Generic Reaction Schemes 1 and 2 and Reaction Schemes 1 through 5 where R is, independently, hydrogen, substituted or unsubstituted hydrocarbyl, substituted or unsubstituted fluorocarbyl, fluorine, substituted or unsubstituted silylcarbyl, or polar groups provided that R does not contain Cl, Br or I substituents; R* is hydrocarbyl, preferably alkyl, more preferably methyl or butyl; R** is, independently, substituted or unsubstituted hydrocarbyl; X* is halide, preferably chloride, but in some instances may also be a different mono anionic ligand; "ligand" (as in "bromo-ligand", and "ligand-S-ligand") is a substituted or unsubstituted indenyl ligand, a substituted or unsubstituted heteroindenyl ligand, a substituted or unsubstituted fluorenyl ligand, a substituted or unsubstituted heterofluorenyl ligand, a substituted or unsubstituted cyclopentadienyl or heterocyclopentadienyl ligand; "bromo-ligand" is a "ligand" substituted with a bromine atom at a $sp^2$ carbon atom of the "ligand", or alternatively substituted with a chlorine or iodine atom at a $sp^2$ carbon atom of the "ligand"; and "ligand-S-ligand" comprises two "ligands" as defined above, which may or may not be same, and are bridged by a sulfur atom, provided that at least one "ligand" is not a substituted or unsubstituted cyclopentadienyl or heterocyclopentadienyl ligand, and at least one "ligand" is bonded to the sulfur atom (such as described in the definition of E of formula (1), where Y is S). The designations "ligand 1" and "ligand 2" in the equations below are used to illustrate "ligands" that are not required to be identical. $^P$TosOH is para-toluenesulfonic acid.

Generic Reaction Scheme 1: Formation of a symmetrical ligand with a S-bridge.

2 Br-ligand $\xrightarrow{\begin{array}{l}\text{1. LiR*}\\\text{2. SX*}_2\\\text{3. further reaction to a}\\\quad\text{metallocene pre-cursor, if needed.}\end{array}}$

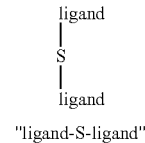

"ligand-S-ligand"

Generic Reaction Scheme 2: Formation of an unsymmetrical ligand with a S-bridge.

Br-ligand 1 + LiR*

Br-ligand 2 + LiR*

$\xrightarrow{\begin{array}{l}\text{1. SX*}_2\\\text{2. further reaction to a}\\\quad\text{metallocene pre-cursor, if needed.}\end{array}}$

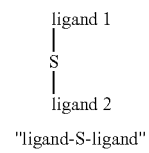

"ligand-S-ligand"

Reaction Scheme 1: Formation of a 4,4'-sulfur bridged bis-indene ligand from a 4-bromo-1-methoxyindane.

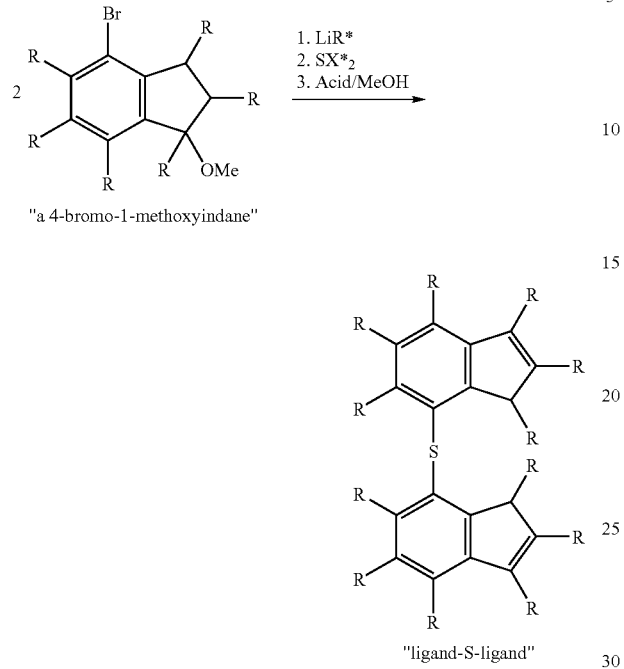

"a 4-bromo-1-methoxyindane"

"ligand-S-ligand"

Reaction Scheme 3: Formation of a 5,5'-sulfur bridged bis-indene ligand from a 5-bromo-1-methoxyindane.

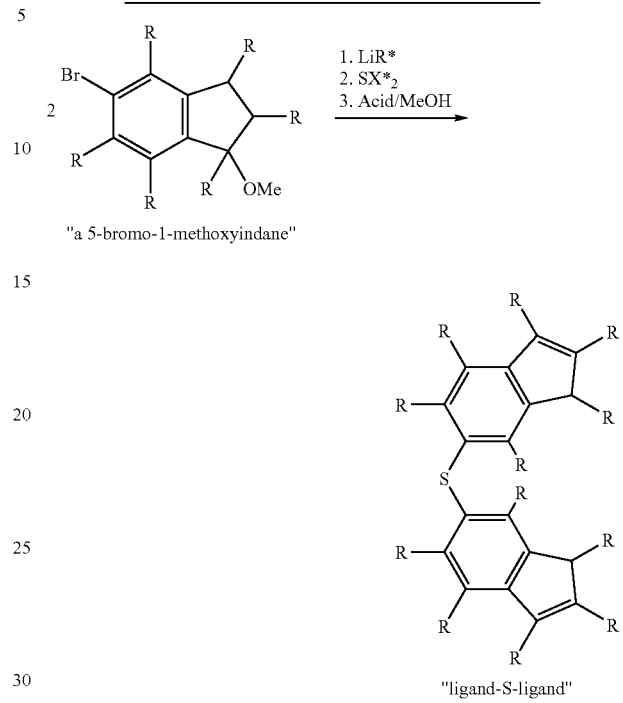

"a 5-bromo-1-methoxyindane"

"ligand-S-ligand"

Reaction Scheme 2: Formation of a 4,4'-sulfur bridged bis-indene ligand from a dioxalane-protected 4-bromo indanone.

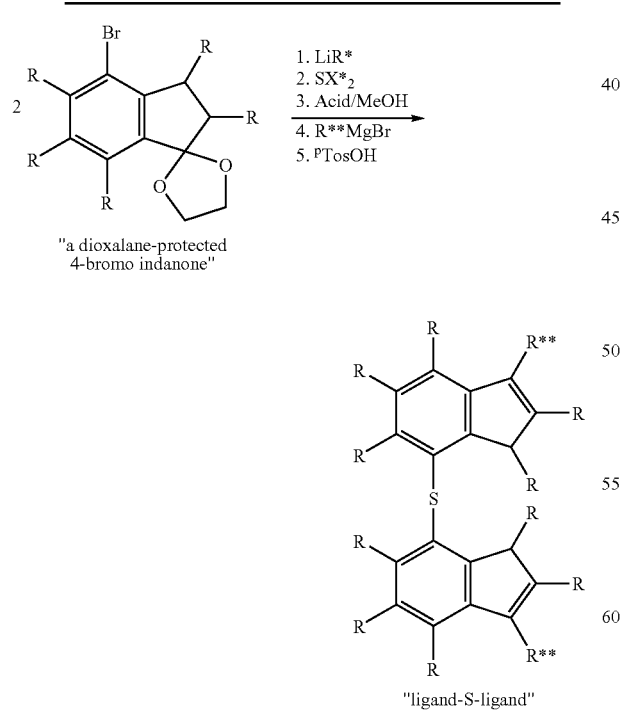

"a dioxalane-protected 4-bromo indanone"

"ligand-S-ligand"

Reaction Scheme 4: Formation of a sulfur bridged 4-indene-cyclopentadiene ligand from a dioxalane-protected 4-bromo indanone and a lithiated cyclopentadiene.

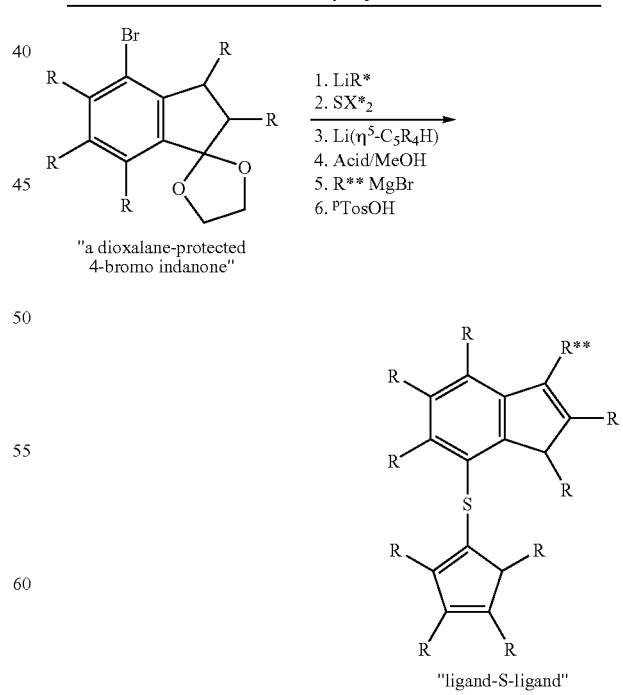

"a dioxalane-protected 4-bromo indanone"

"ligand-S-ligand"

Reaction Scheme 5: Formation of a 4,2'-sulfur bridged bis-indene ligand from a dioxalane-protected 4-bromo indanone and a lithiated indene.

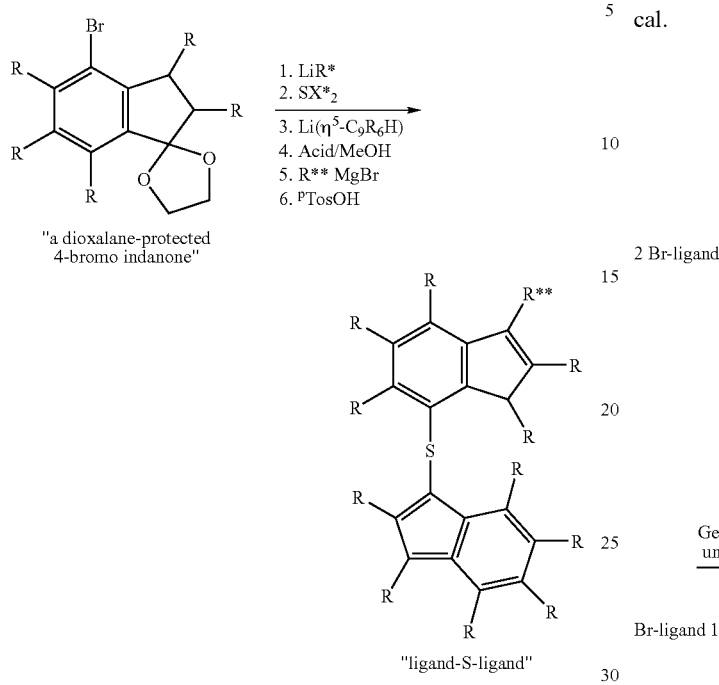

"ligand-S-ligand"

Ligands with phosphorous bridges can be prepared by reacting a "bromo-ligand" (Br-ligand) with and hydrocarbyl lithium followed by a hydrocarbyl phosphorous dihalide, to form a "ligand-P(R)-ligand" where R is, independently, substituted or unsubstituted hydrocarbyl. Additionally, phosphorus bridged ligands can be prepared by coupling two "bromo-ligands" using a palladium catalyst, a hydrocarbyl phosphine, and a base. It should be noted that the hydrocarbyl phosphine is used in this reaction. In some cases, further reaction is needed to form a metallocene precursor ligand, for example, conversion of a substituted indene from a substituted indane or indan-1-one. Examples of such reactions are illustrated below in Generic Reaction Schemes 3 and 5 and Reaction Schemes 6 through 10 where R is, independently, hydrogen, substituted or unsubstituted hydrocarbyl, substituted or unsubstituted fluorocarbyl, fluorine, substituted or unsubstituted silylcarbyl, or polar groups provided that R does not contain Cl, Br or I substituents; R* is hydrocarbyl, preferably alkyl, more preferably methyl or butyl; R** is, independently, substituted or unsubstituted hydrocarbyl; X* is halide, preferably chloride; "ligand" (as in "bromo-ligand", and "ligand-P(R)-ligand") is a substituted or unsubstituted indenyl ligand, a substituted or unsubstituted heteroindenyl ligand, a substituted or unsubstituted fluorenyl ligand, a substituted or unsubstituted heterofluorenyl ligand, or a substituted or unsubstituted cyclopentadienyl or heterocyclopentadienyl ligand; "bromo-ligand" is a "ligand" substituted with a bromine atom at a sp² carbon atom of the "ligand", or alternatively substituted with a chlorine or iodine atom at a sp² carbon atom of the "ligand"; and "ligand-P(R)-ligand" comprises two "ligand"s as defined above, which may or may not be same, and are bridged by a R-substituted phosphorous atom, provided that at least one "ligand" is not a substituted or unsubstituted cyclopentadienyl or heterocyclopentadienyl ligand, and at least one "ligand" is bonded to the R-substituted phosphorous atom as described in the definition of E of formula (1), where Y is P(R**). The designations "ligand 1" and "ligand 2" in the equations below are used to illustrate "ligands" that are not required to be identical.

Generic Reaction Scheme 3: Formation of a symmetrical ligand with a P(R**) bridge.

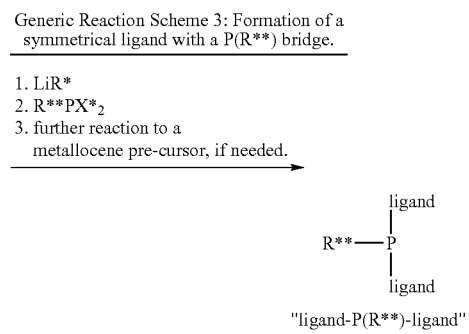

"ligand-P(R**)-ligand"

Generic Reaction Scheme 4: Formation of an unsymmetrical ligand with a P(R**) bridge.

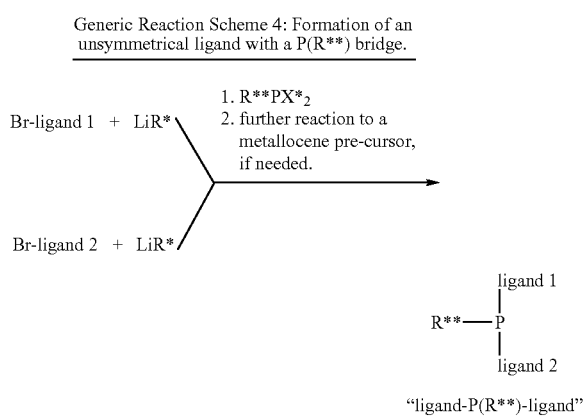

"ligand-P(R**)-ligand"

Generic Reaction Scheme 5: Formation of a symmetrical ligand with a P(R**) bridge.

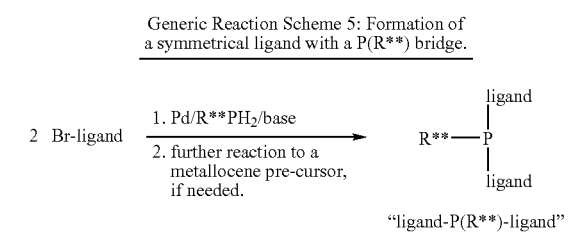

"ligand-P(R**)-ligand"

Reaction Scheme 6: Formation of a 4,4'-phosphorous bridged bis-indene ligand from a 4-bromo-1-methoxyindane.

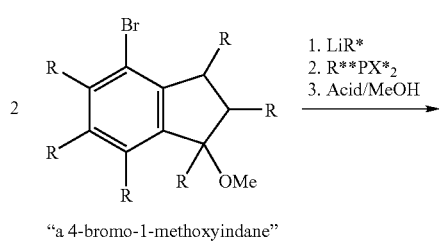

"a 4-bromo-1-methoxyindane"

-continued

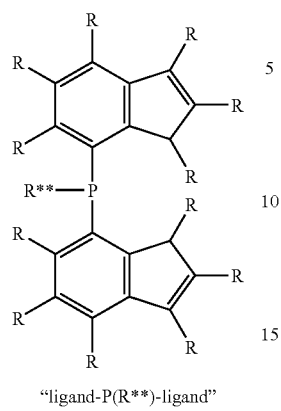

"ligand-P(R**)-ligand"

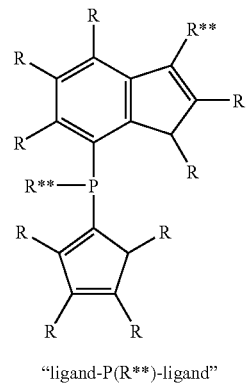

"ligand-P(R**)-ligand"

Reaction Scheme 7: Formation of a 5,5'-phosphorous bridged bis-indene ligand from a 5-bromo-1-methoxyindane.

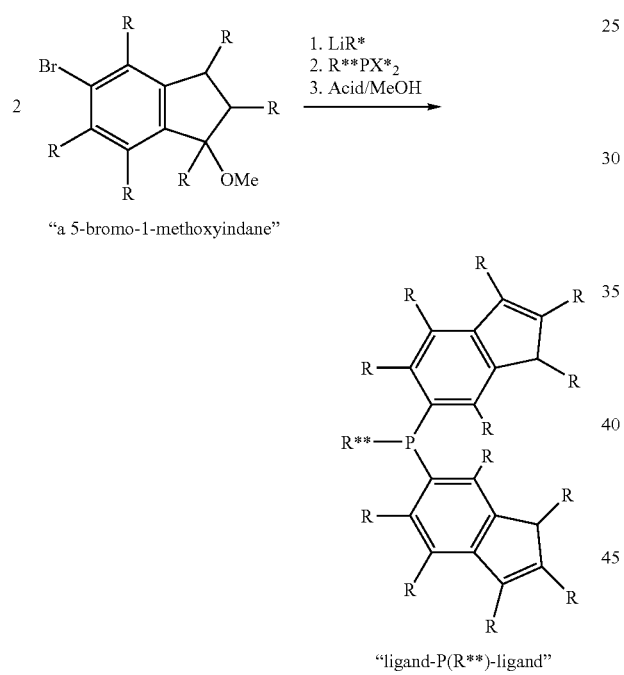

"a 5-bromo-1-methoxyindane"

"ligand-P(R**)-ligand"

Reaction Scheme 9: Formation of a 4,5'-phosphorous bridged bis-indene ligand from a 4-bromo-1-methoxyindane and a 5-bromo-1-methoxyindane.

"a 4-bromo-1-methoxyindane"

"a 5-bromo-1-methoxyindane"

1. LiR*
2. R**PX*$_2$
3. Acid/MeOH

Reaction Scheme 8: Formation of a phosphorous bridged 4-indene-cyclopentadiene ligand from a dioxalane-protected 4-bromo indanone and a lithiated cyclopentadiene.

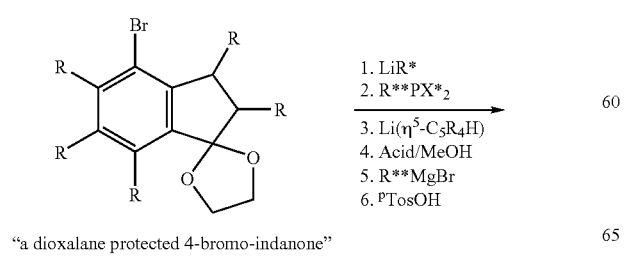

1. LiR*
2. R**PX*$_2$
3. Li($\eta^5$-C$_5$R$_4$H)
4. Acid/MeOH
5. R**MgBr
6. $^p$TosOH "a dioxalane protected 4-bromo-indanone"

"ligand-P(R**)-ligand"

Reaction Scheme 10: Formation of a 4,4'-phosphorous bridged bis-indene ligand from a 4-bromo indanone.

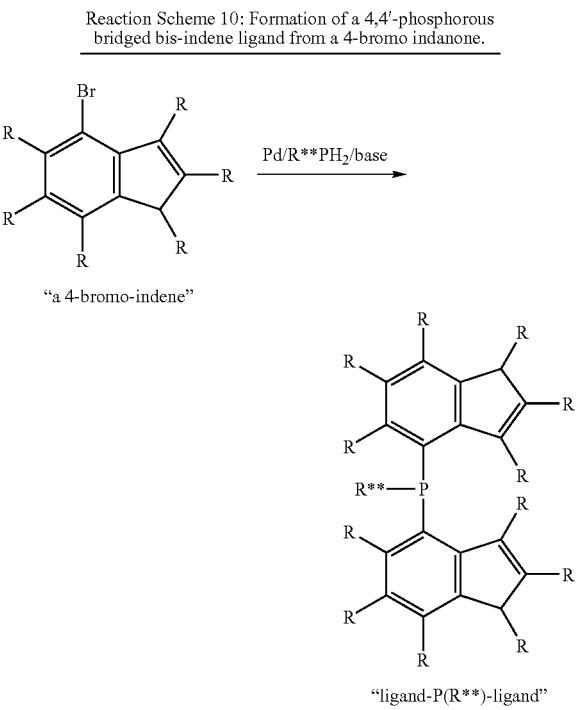

"a 4-bromo-indene"

"ligand-P(R**)-ligand"

Ligands with nitrogen bridges can be prepared by reacting a substituted or unsubstituted "bromo-ligand" (Br-ligand) with a hydrocarbyl amine in the presence of a Group 1 alkoxide such as potassium or lithium t-butoxide or a lithium amide such as lithium anilide or other base, such as $K_3PO_4$ or $Cs_2CO_3$, a palladium catalyst, such as palladium acetate or palladium dibenzylidenacetone used with a phosphine or phosphine-like reagent such as those selected among A-H (below), to form a "ligand-N(R)-ligand" where R is, independently, substituted or unsubstituted hydrocarbyl. Alternatively, a "bromo-ligand" can be reacted with a lithiated amine in the presence of a palladium catalyst such a palladium dibenzylidenacetone used with a phosphine or phosphine-like reagent such as those selected from A-H, to form a "primary amine substituted-ligand" (RNH-ligand) where R is, independently, substituted or unsubstituted hydrocarbyl. This "primary amine substituted ligand" can then be reacted with a "bromo-ligand" in the presence of a palladium catalyst such as palladium acetate used with a phosphine or phosphine-like reagent such as one selected from A-H, and a base. In some cases, further reaction is needed to form a metallocene precursor ligand, for example, conversion of a substituted indene from a substituted indane or indan-1-one. Examples of such reactions are illustrated below in Generic Reaction Schemes 6 and 7 and Reaction Schemes 11 through 13 where R is, independently, hydrogen, substituted or unsubstituted hydrocarbyl, substituted or unsubstituted fluorocarbyl, fluorine, substituted or unsubstituted silylcarbyl, or polar groups provided that R does not contain Cl, Br or I substituents; R* is hydrocarbyl, preferably alkyl, more preferably methyl or butyl; R** is, independently, substituted or unsubstituted hydrocarbyl; X* is halide, preferably chloride; "ligand" (as in "bromo-ligand", "primary amine substituted ligand" and "ligand-N(R)-ligand") is a substituted or unsubstituted indenyl ligand, a substituted or unsubstituted heteroindenyl ligand, a substituted or unsubstituted fluorenyl ligand, a substituted or unsubstituted heterofluorenyl ligand, or a substituted or unsubstituted cyclopentadienyl or heterocyclopentadienyl ligand; "bromo-ligand" is a "ligand" substituted with a bromine atom at a $sp^2$ carbon atom of the "ligand", or alternatively substituted with a chlorine or iodine atom at a $sp^2$ carbon atom of the "ligand"; "primary amine substituted ligand" is a "ligand" substituted with a primary amine substituent (—NHR) at a $sp^2$ carbon atom of the "ligand"; and "ligand-N(R)-ligand" comprises two "ligand"s as defined above, which may or may not be same, and are bridged by a R-substituted nitrogen atom, provided that at least one "ligand" is not a substituted or unsubstituted cyclopentadienyl or heterocyclopentadienyl ligand, and at least one "ligand" is bonded to the R-substituted nitrogen atom as described in the definition of E of formula (1), where Y is NR. The designations "ligand 1" and "ligand 2" in the equations below are used to illustrate "ligands" that are not required to be identical. It should be noted that for the coupling of ligands to form "ligand-N(R**)-ligand", some palladium catalysts that may be used do not require a phosphine reagent or phosphine-like reagent to be present. These palladium catalysts typically contain phosphine ligands bonded to palladium, such as bis(tri-tert-butyl)phosphine palladium.

Phosphine and Phosphine-like reagents (A through H) which are referred to as "Phosphine" in the reaction schemes below include:

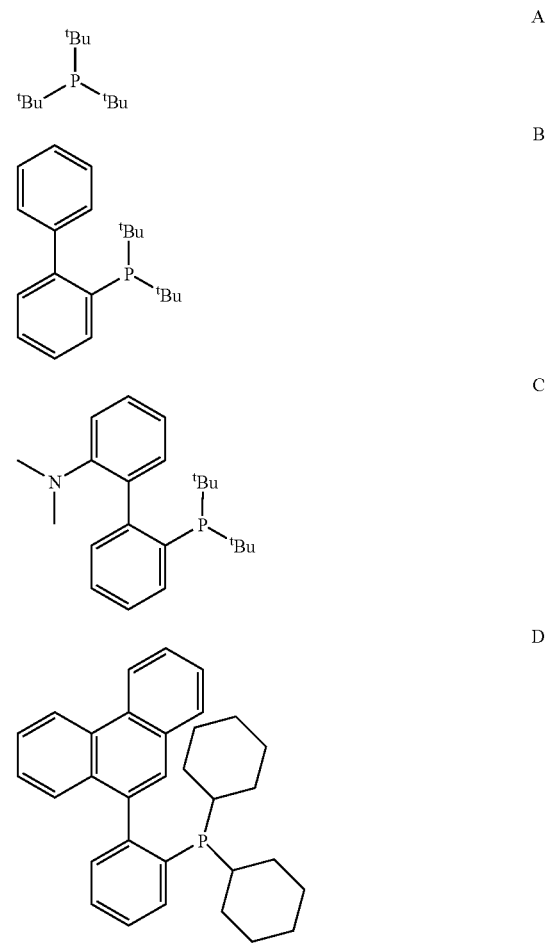

-continued

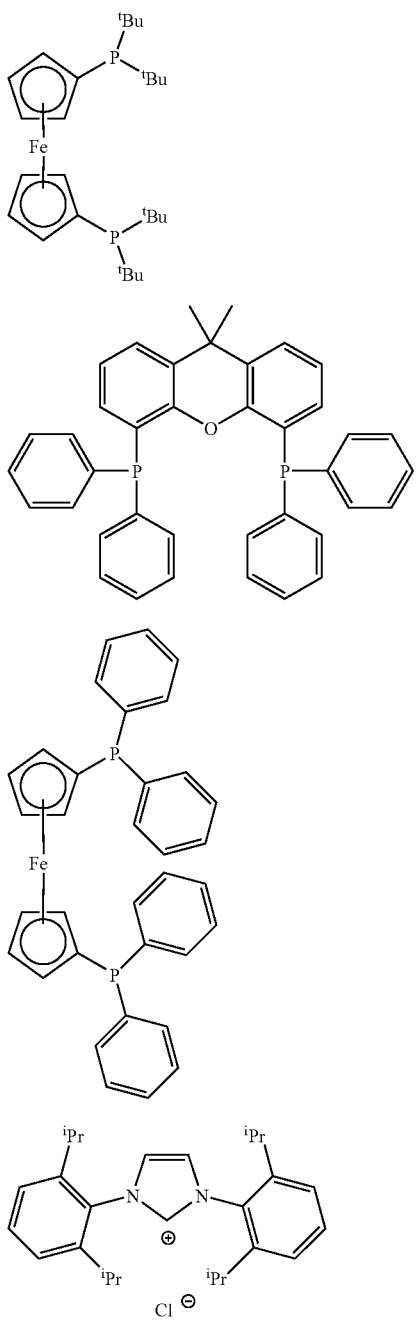

Other phosphines, including substituted phosphines may also be used, including polymer bound phosphines. Examples of commercially available polymeric bound phosphines include poly(ethylene glycol)triphenylphosphine; and dicyclohexylphenylphosphine, polymer-bound; (4-hydroxyphenyl)diphenylphosphine, polymer-bound; triphenylphosphine, polymer-supported; R-(+)-2,2'-bis(diphenylphosphino)-1,1'-binaphthalene, polymer-bound; S-(−)-2,2'-bis(diphenylphosphino)-1,1'-binaphthalene, polymer-bound (all available from Aldrich Chemical Company where the polymer-bound or polymer-supported is a divinylbenzene crosslinked polystyrene Generic Reaction Scheme 6: Formation of an unsymmetrical ligand with a N(R**) bridge.

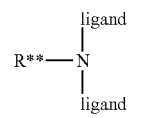

"ligand-N(R**)-ligand"

Generic Reaction Scheme 7: Formation of an optionally unsymmetrical ligand with a N(R**) bridge.

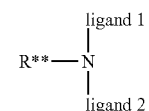

"ligand-N(R**)-ligand"

Reaction Scheme 11: Formation of a 4,4'-nitrogen bridged bis-indene ligand from a 4-bromo-1-methoxyindane.

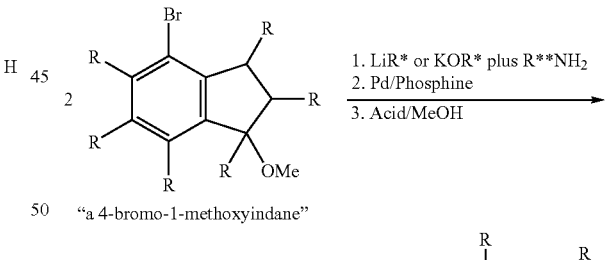

"a 4-bromo-1-methoxyindane"

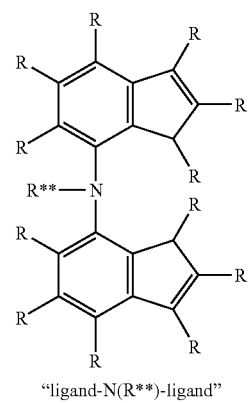

"ligand-N(R**)-ligand"

Reaction Scheme 12: Formation of a 4,4'-nitrogen bridged bis-indene ligand from a 4-bromo-1-methoxyindane via 4-hydrocarbylamino-1-methoxyindane.

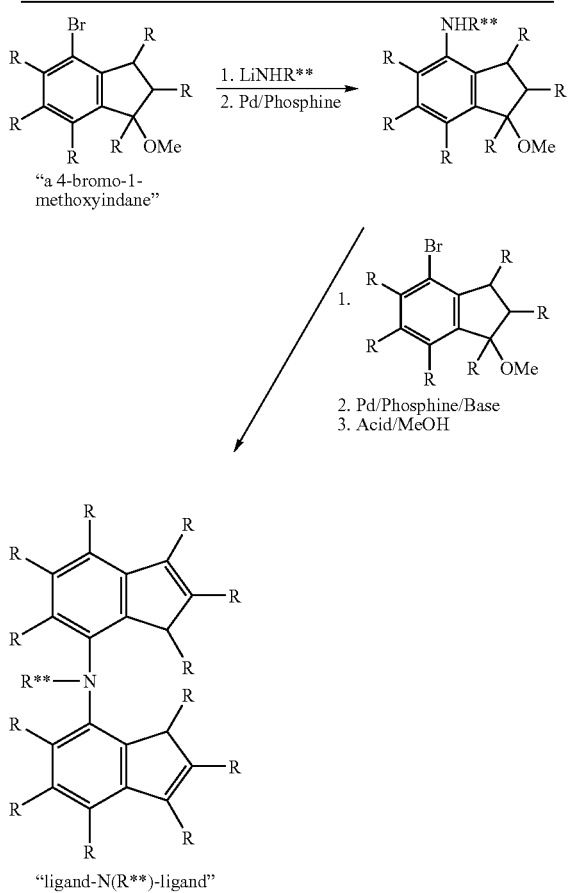

Reaction Scheme 13: Formation of a 4,5'-nitrogen bridged bis-indene ligand from a 4-bromo-1-methoxyindane and 5-bromo-1-methoxyindane.

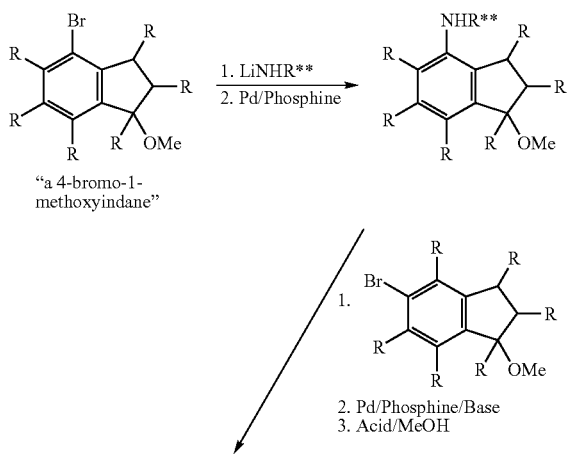

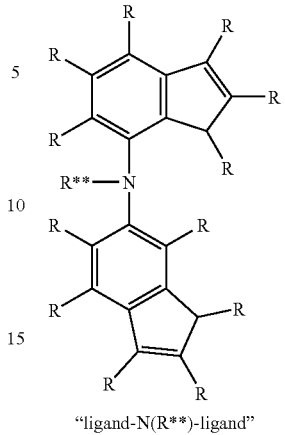

"ligand-N(R**)-ligand"

Ligands with oxygen bridges can be prepared by reacting a "bromo-ligand" (Br-ligand) with and hydrocarbyl lithium such as methyl or n-butyl lithium followed by a trialkoxyborate such as triisopropylborate, and subsequent addition of hydrogen peroxide and acid, to form a "hydroxy-ligand" (HO-ligand). The "hydroxy-ligand" is reacted with a "bromo-ligand" in the presence of a palladium catalyst such as palladium dibenzylidenacetone used with a phosphine or phosphine-like reagent such as one selected from A-H (above), and a base, to form a "ligand-O-ligand". In some cases, further reaction is needed to form a metallocene precursor ligand, for example, conversion of a substituted indene from a substituted indane or indan-1-one. Examples of such reactions are illustrated below in Generic Reaction Scheme 8 and Reaction Schemes 14 through 17 where R is, independently, hydrogen, substituted or unsubstituted hydrocarbyl, substituted or unsubstituted fluorocarbyl, fluorine, substituted or unsubstituted silylcarbyl, or polar groups provided that R does not contain Cl, Br or I substituents; R* is hydrocarbyl, preferably alkyl, more preferably methyl, propyl, or butyl; R** is, independently, substituted or unsubstituted hydrocarbyl; X* is halide, preferably chloride; "ligand" (as in "bromo-ligand", "hydroxy-ligand" and "ligand-O-ligand") is a substituted or unsubstituted indenyl ligand, a substituted or unsubstituted heteroindenyl ligand, a substituted or unsubstituted fluorenyl ligand, a substituted or unsubstituted heterofluorenyl ligand, or a substituted or unsubstituted cyclopentadienyl or heterocyclopentadienyl ligand; "bromo-ligand" is a "ligand" substituted with a bromine atom at a $sp^2$ carbon atom of the "ligand", or alternatively substituted with a chlorine or iodine atom at a $sp^2$ carbon atom of the "ligand"; "hydroxy-ligand" is a "ligand" substituted with a hydroxy substituent at a $sp^2$ carbon atom of the "ligand"; and "ligand-O-ligand" comprises two "ligand"s as defined above, which may or may not be same, and are bridged by an oxygen atom, provided that at least one "ligand" is not a substituted or unsubstituted cyclopentadienyl or heterocyclopentadienyl ligand, and at least one "ligand" is bonded to the oxygen atom as described in the definition of E of formula (1), where Y is O. The designations "ligand 1" and "ligand 2" in the equations below are used to illustrate "ligands" that are not required to be identical. It should be noted that for the coupling of ligands to form "ligand-O-ligand", some palladium catalysts that may be used do not require a phosphine reagent or phosphine-like reagent to be present. These palladium catalysts typically contain phosphine ligands bonded to palladium, such as bis(tri-tert-butyl)phosphine palladium.

Generic Reaction Scheme 8: Formation of an optionally unsymmetrical ligand with an oxygen bridge.

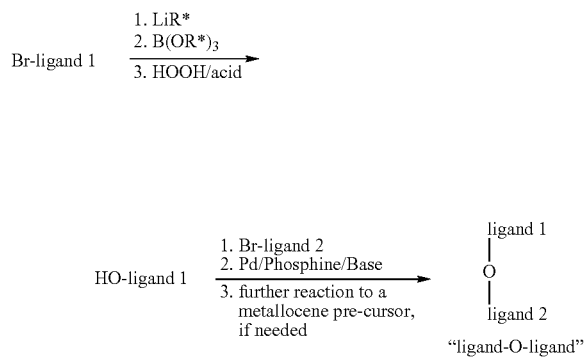

Reaction Scheme 14: Formation of a 4,4'-oxygen bridged bis-indene ligand from a 4-bromo-1-methoxyindane via 4-hydroxy-1-methoxyindane.

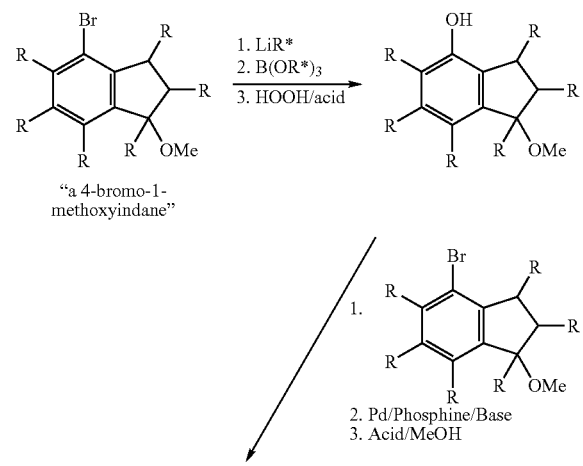

Reaction Scheme 15: Formation of a 4,5'-oxygen bridged bis-indene ligand from a 4-bromo-1-methoxyindane and a 5-bromo-1-methoxyindane.

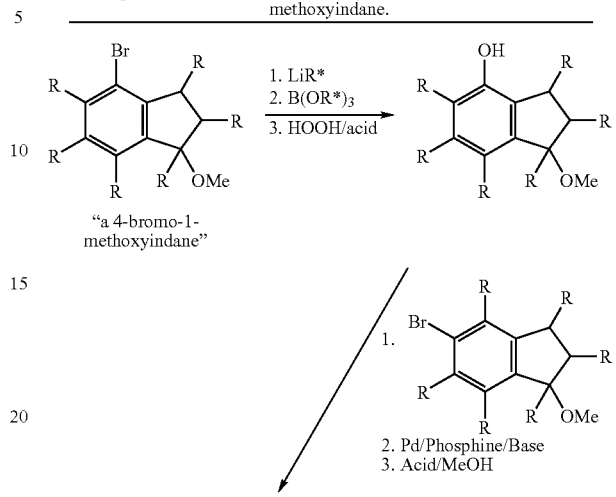

Reaction Scheme 16: Formation of a 5,5'-oxygen bridged bis-indene ligand from a 5-bromo-1-methoxyindane.

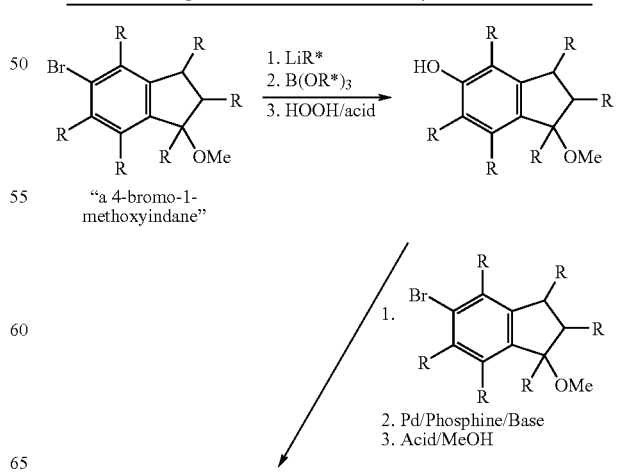

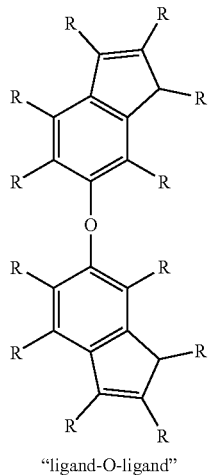

"ligand-O-ligand"

Reaction Scheme 17: Formation of an oxygen bridged 4-indene-cyclopentadiene ligand from a dioxalane-protected 4-bromo indanone and a dioxalane-protected bromo-cyclopentenone.

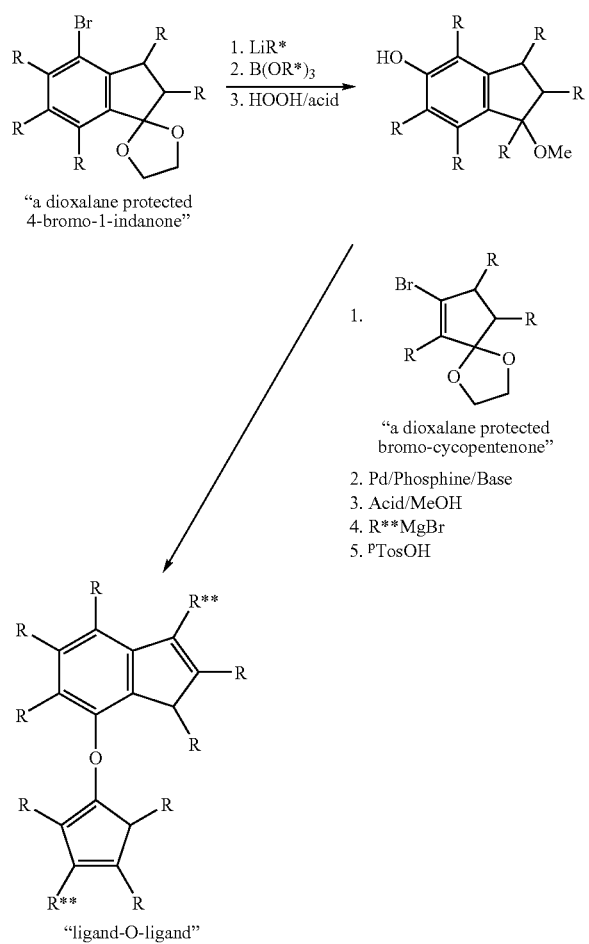

Preferred bromo ligands in Reaction Schemes 1-17 and Generic Reaction Schemes 1-8 are selected from:
4-bromo-1H-indene, 4-bromo-2-methyl-1H-indene, 4-bromo-3-methyl-1H-indene, 4-bromo-5-methyl-1H-indene, 4-bromo-6-methyl-1H-indene, 4-bromo-7-methyl-1H-indene, 4-bromo-2-ethyl-1H-indene, 4-bromo-3-ethyl-1H-indene, 4-bromo-5-ethyl-1H-indene, 4-bromo-6-ethyl-1H-indene, 4-bromo-7-ethyl-1H-indene, 4-bromo-2-propyl-1H-indene, 4-bromo-3-propyl-1H-indene, 4-bromo-5-propyl-1H-indene, 4-bromo-6-propyl-1H-indene, 4-bromo-7-propyl-1H-indene, 4-bromo-2-butyl-1H-indene, 4-bromo-3-butyl-1H-indene, 4-bromo-5-butyl-1H-indene, 4-bromo-6-butyl-1H-indene, 4-bromo-7-butyl-1H-indene, 4-bromo-2-pentyl-1H-indene, 4-bromo-3-pentyl-1H-indene, 4-bromo-5-pentyl-1H-indene, 4-bromo-6-pentyl-1H-indene, 4-bromo-7-pentyl-1H-indene, 4-bromo-2-hexyl-1H-indene, 4-bromo-3-hexyl-1H-indene, 4-bromo-5-hexyl-1H-indene, 4-bromo-6-hexyl-1H-indene, 4-bromo-7-hexyl-1H-indene, 4-bromo-2-heptyl-1H-indene, 4-bromo-3-heptyl-1H-indene, 4-bromo-5-heptyl-1H-indene, 4-bromo-6-heptyl-1H-indene, 4-bromo-7-heptyl-1H-indene, 4-bromo-2-octyl-1H-indene, 4-bromo-3-octyl-1H-indene, 4-bromo-5-octyl-1H-indene, 4-bromo-6-octyl-1H-indene, 4-bromo-7-octyl-1H-indene, 4-bromo-2-nonyl-1H-indene, 4-bromo-3-nonyl-1H-indene, 4-bromo-5-nonyl-1H-indene, 4-bromo-6-nonyl-1H-indene, 4-bromo-7-nonyl-1H-indene, 4-bromo-2-decyl-1H-indene, 4-bromo-3-decyl-1H-indene, 4-bromo-5-decyl-1H-indene, 4-bromo-6-decyl-1H-indene, 4-bromo-7-decyl-1H-indene, 4-bromo-2-phenyl-1H-indene, 4-bromo-3-phenyl-1H-indene, 4-bromo-5-phenyl-1H-indene, 4-bromo-6-phenyl-1H-indene, 4-bromo-7-phenyl-1H-indene, 4-bromo-2 mesityl-1H-indene, 4-bromo-3-mesityl-1H-indene, 4-bromo-5-mesityl-1H-indene, 4-bromo-6-mesityl-1H-indene, 4-bromo-7-mesityl-1H-indene, 4-bromo-2-mesityl-1H-indene, 4-bromo-3-mesityl-1H-indene, 4-bromo-5-mesityl-1H-indene, 4-bromo-6-mesityl-1H-indene, 4-bromo-7-mesityl-1H-indene, 4-bromo-2-naphthyl-1H-indene, 4-bromo-3-naphthyl-1H-indene, 4-bromo-5-naphthyl-1H-indene, 4-bromo-6-naphthyl-1H-indene, 4-bromo-7-naphthyl-1H-indene, 4-bromo-1,2-dimethyl-1H-indene, 4-bromo-1,3-dimethyl-1H-indene, 4-bromo-1,5-dimethyl-1H-indene, 4-bromo-1,6-dimethyl-1H-indene, 4-bromo-1,7-dimethyl-1H-indene, 4-bromo-2,3-dimethyl-1H-indene, 4-bromo-2,5-dimethyl-1H-indene, 4-bromo-2,6-dimethyl-1H-indene, 4-bromo-2,7-dimethyl-1H-indene, 4-bromo-3,5-dimethyl-1H-indene, 4-bromo-3,6-dimethyl-1H-indene, 4-bromo-3,7-dimethyl-1H-indene, 4-bromo-5,6-dimethyl-1H-indene, 4-bromo-5,7-dimethyl-1H-indene, 4-bromo-6,7-dimethyl-1H-indene, 4-bromo-1-methyl-2-phenyl-1H-indene, 4-bromo-1-methyl-3-phenyl-1H-indene, 4-bromo-1-methyl-5-phenyl-1H-indene, 4-bromo-1-methyl-6-phenyl-1H-indene, 4-bromo-1-methyl-7-phenyl-1H-indene, 4-bromo-2-methyl-3-phenyl-1H-indene, 4-bromo-2-methyl-5-phenyl-1H-indene, 4-bromo-2-methyl-6-phenyl-1H-indene, 4-bromo-2-methyl-7-phenyl-1H-indene, 4-bromo-3-methyl-5-phenyl-1H-indene, 4-bromo-3-methyl-6-phenyl-1H-indene, 4-bromo-3-methyl-7-phenyl-1H-indene, 4-bromo-5-methyl-6-phenyl-1H-indene, 4-bromo-5-methyl-7-phenyl-1H-indene, 4-bromo-6-methyl-7-phenyl-1H-indene, 4-bromo-2-methyl-1-phenyl-1H-indene, 4-bromo-3-methyl-1-phenyl-1H-indene, 4-bromo-5-methyl-1-phenyl-1H-indene, 4-bromo-6-methyl-1-phenyl-1H-indene, 4-bromo-7-methyl-1-phenyl-1H-indene, 4-bromo-1-propyl-2-phenyl-1H-indene, 4-bromo-1-propyl-3-phenyl-1H-indene, 4-bromo-1-propyl-5-phenyl-1H-indene, 4-bromo-1-propyl-6-phenyl-1H-indene, 4-bromo-1-propyl-7-phenyl-1H-indene, 4-bromo-2-propyl-3-phenyl-1H-indene, 4-bromo-2-propyl-5-phenyl-1H-indene, 4-bromo-2-propyl-6-phenyl-1H-indene, 4-bromo-2-propyl-7-phenyl-1H-indene, 4-bromo-3-propyl-5-phenyl-1H-indene, 4-bromo-3-propyl-6-phenyl-1H-indene, 4-bromo-3-propyl-7-phenyl-1H-indene, 4-bromo-5-propyl-6-phenyl-1H-indene, 4-bromo-5-propyl-7-phenyl-1H-indene, 4-bromo-6-propyl-7-phenyl-1H-indene, 4-bromo-2-propyl-1-phenyl-1H-indene, 4-bromo-3-propyl-1-phenyl-1H-indene, 4-bromo-5-propyl-1-phenyl-1H-indene, 4-bromo-6-propyl-1-phenyl-1H-indene, 4-bromo-7-propyl-1-phenyl-1H-indene, 4-bromo-1-methyl-2-tolyl-1H-indene, 4-bromo-1-methyl-3-tolyl-1H-indene, 4-bromo-1-methyl-5-tolyl-1H-indene, 4-bromo-1-methyl-6-tolyl-1H-indene, 4-bromo-1-methyl-7-tolyl-1H-indene, 4-bromo-2-methyl-3-tolyl-1H-indene, 4-bromo-2-methyl-5-tolyl-1H-indene, 4-bromo-2-methyl-6-tolyl-1H-indene, 4-bromo-2-methyl-7-tolyl-1H-indene, 4-bromo-3-methyl-5-tolyl-1H-indene, 4-bromo-3-methyl-6-tolyl-1H-indene, 4-bromo-3-methyl-7-tolyl-1H-indene, 4-bromo-5-methyl-6-tolyl-1H-indene, 4-bromo-5-methyl-7-tolyl-1H-indene, 4-bromo-6-methyl-7-tolyl-1H-indene, 4-bromo-2-methyl-1-tolyl-1H-indene, 4-bromo-3-methyl-1-tolyl-1H-indene, 4-bromo-5-methyl-1-tolyl-1H-indene, 4-bromo-6-methyl-1-tolyl-1H-indene, 4-bromo-7-methyl-1-tolyl-1H-indene, 4-bromo-1-methyl-2-naphthyl-1H-indene, 4-bromo-1-methyl-3-naphthyl-1H-indene, 4-bromo-1-methyl-5-naphthyl-1H-indene, 4-bromo-1-methyl-6-naphthyl-1H-indene, 4-bromo-1-methyl-7-naphthyl-1H-indene, 4-bromo-2-methyl-3-naphthyl-1H-indene, 4-bromo-2-methyl-5-naphthyl-1H-indene, 4-bromo-2-methyl-6-naphthyl-1H-indene, 4-bromo-2-methyl-7-naphthyl-1H-indene, 4-bromo-3-methyl-5-naphthyl-1H-indene, 4-bromo-3-methyl-6-naphthyl-1H-indene, 4-bromo-3-methyl-7-naphthyl-1H-indene, 4-bromo-5-methyl-6-naphthyl-1H-indene, 4-bromo-5-methyl-7-naphthyl-1H-indene, 4-bromo-6-methyl-7-naphthyl-1H-indene, 4-bromo-2-methyl-1-naphthyl-1H-indene, 4-bromo-3-methyl-1-naphthyl-1H-indene, 4-bromo-5-methyl-1-naphthyl-1H-indene, 4-bromo-6-methyl-1-naphthyl-1H-indene, 4-bromo-7-methyl-1-naphthyl-1H-indene, 4-bromo-1-methyl-2-mesityl-1H-indene, 4-bromo-1-methyl-3-mesityl-1H-indene, 4-bromo-1-methyl-5-mesityl-1H-indene, 4-bromo-1-methyl-6-mesityl-1H-indene, 4-bromo-1-methyl-7-mesityl-1H-indene, 4-bromo-2-methyl-3-mesityl-1H-indene, 4-bromo-2-methyl-5-mesityl-1H-indene, 4-bromo-2-methyl-6-mesityl-1H-indene, 4-bromo-2-methyl-7-mesityl-1H-indene, 4-bromo-3-methyl-5-mesityl-1H-indene, 4-bromo-3-methyl-6-mesityl-1H-indene, 4-bromo-3-methyl-7-mesityl-1H-indene, 4-bromo-5-methyl-6-mesityl-1H-indene, 4-bromo-5-methyl-7-mesityl-1H-indene, 4-bromo-6-methyl-7-mesityl-1H-indene, 4-bromo-2-methyl-1-mesityl-1H-indene, 4-bromo-3-methyl-1-mesityl-1H-indene, 4-bromo-5-methyl-1-mesityl-1H-indene, 4-bromo-6-methyl-1-mesityl-1H-indene, 4-bromo-7-methyl-1-mesityl-1H-indene, 4-bromo-1-methyl-2-(dimethylphenyl)-1H-indene, 4-bromo-1-methyl-3-(dimethylphenyl)-1H-indene, 4-bromo-1-methyl-5-(dimethylphenyl)-1H-indene, 4-bromo-1-methyl-6-(dimethylphenyl)-1H-indene, 4-bromo-1-methyl-7-(dimethylphenyl)-1H-indene, 4-bromo-2-methyl-3-(dimethylphenyl)-1H-indene, 4-bromo-2-methyl-5-(dimethylphenyl)-1H-indene, 4-bromo-2-methyl-6-(dimethylphenyl)-1H-indene, 4-bromo-2-methyl-7-(dimethylphenyl)-1H-indene, 4-bromo-3-methyl-5-(dimethylphenyl)-1H-indene, 4-bromo-3-methyl-6-(dimethylphenyl)-1H-indene, 4-bromo-3-methyl-7-(dimethylphenyl)-1H-indene, 4-bromo-5-methyl-6-(dimethylphenyl)-1H-indene, 4-bromo-5-methyl-7-(dimethylphenyl)-1H-indene, 4-bromo-6-methyl-7-(dimethylphenyl)-1H-indene, 4-bromo-2-methyl-1-(dimethylphenyl)-1H-indene, 4-bromo-3-methyl-1-(dimethylphenyl)-1H-indene, 4-bromo-5-methyl-1-(dimethylphenyl)-1H-indene, 4-bromo-6-methyl-1-(dimethylphenyl)-1H-indene, 4-bromo-7-methyl-1-(dimethylphenyl)-1H-indene, 4-bromo-1-methyl-2-(butylphenyl)-1H-indene, 4-bromo-1-methyl-3-(butylphenyl)-1H-indene, 4-bromo-1-methyl-5-(butylphenyl)-1H-indene, 4-bromo-1-methyl-6-(butylphenyl)-1H-indene, 4-bromo-1-methyl-7-(butylphenyl)-1H-indene, 4-bromo-2-methyl-3-(butylphenyl)-1H-indene, 4-bromo-2-methyl-5-(butylphenyl)-1H-indene, 4-bromo-2-methyl-6-(butylphenyl)-1H-indene, 4-bromo-2-methyl-7-(butylphenyl)-1H-indene, 4-bromo-3-methyl-5-(butylphenyl)-1H-indene, 4-bromo-3-methyl-6-(butylphenyl)-1H-indene, 4-bromo-3-methyl-7-(butylphenyl)-1H-indene, 4-bromo-5-methyl-6-(butylphenyl)-1H-indene, 4-bromo-5-methyl-7-(butylphenyl)-1H-indene, 4-bromo-6-methyl-7-(butylphenyl)-1H-indene, 4-bromo-2-methyl-1-(butylphenyl)-1H-indene, 4-bromo-3-methyl-1-(butylphenyl)-1H-indene, 4-bromo-5-methyl-1-(butylphenyl)-1H-indene, 4-bromo-6-methyl-1-(butylphenyl)-1H-indene, 4-bromo-7-methyl-1-(butylphenyl)-1H-indene, 4-bromo-2-fluoro-1H-indene, 4-bromo-3-fluoro-1H-indene, 4-bromo-5-fluoro-1H-indene, 4-bromo-6-fluoro-1H-indene, 4-bromo-7-fluoro-1H-indene, 4-bromo-2-methoxy-1H-indene, 4-bromo-3-methoxy-1H-indene, 4-bromo-5-methoxy-1H-indene, 4-bromo-6-methoxy-1H-indene, 4-bromo-7-methoxy-1H-indene, 4-bromo-2-methylsulfanyl-1H-indene, 4-bromo-3-methylsulfanyl-1H-indene, 4-bromo-5-methylsulfanyl-1H-indene, 4-bromo-6-methylsulfanyl-1H-indene, 4-bromo-7-methylsulfanyl-1H-indene, 4-bromo-1-trimethylsilyl-1H-indene, 4-bromo-2-trimethylsilyl-1H-indene, 4-bromo-3-trimethylsilyl-1H-indene, 4-bromo-5-trimethylsilyl-1H-indene, 4-bromo-6-trimethylsilyl-1H-indene, 4-bromo-7-trimethylsilyl-1H-indene, 4-bromo-2-trifluoromethyl-1H-indene, 4-bromo-3-trifluoromethyl-1H-indene, 4-bromo-5-trifluoromethyl-1H-indene, 4-bromo-6-trifluoromethyl-1H-indene, 4-bromo-7-trifluoromethyl-1H-indene, (4-bromo-1H-inden-2-yl)-dimethyl-amine, (4-bromo-1H-inden-3-yl)-dimethyl-amine, (4-bromo-1H-inden-5-yl)-dimethyl-amine, (4-bromo-1H-inden-6-yl)-dimethyl-amine, (4-bromo-1H-inden-7-yl)-dimethyl-amine, 4-bromo-2-methylsulfanyl-1H-indene, 4-bromo-3-methylsulfanyl-1H-indene, 4-bromo-5-methylsulfanyl-1H-indene, 4-bromo-6-methylsulfanyl-1H-indene, 4-bromo-7-methylsulfanyl-1H-indene, 2-(4-bromo-1H-inden-2-yl)-5-methyl-thiophene, 2-(4-bromo-1H-inden-3-yl)-5-methyl-thiophene, 2-(4-bromo-1H-inden-5-yl)-5-methyl-thiophene, 2-(4-bromo-1H-inden-6-yl)-5-methyl-thiophene, 2-(4-bromo-1H-inden-7-yl)-5-methyl-thiophene, 2-(4-bromo-1H-inden-2-yl)-thiophene, 2-(4-bromo-1H-inden-3-yl)-thiophene, 2-(4-bromo-1H-inden-5-yl)-thiophene, 2-(4-bromo-1H-inden-6-yl)-thiophene, 2-(4-bromo-1H-inden-7-yl)-thiophene, 2-(4-bromo-1H-inden-2-yl)-5-methyl-furan, 2-(4-bromo-1H-inden-3-yl)-5-methyl-furan, 2-(4-bromo-1H-inden-5-yl)-5-methyl-furan, 2-(4-bromo-1H-inden-6-yl)-5-methyl-furan, 2-(4-bromo-1H-inden-7-yl)-5-methyl-furan, 2-(4-bromo-1H-inden-2-yl)-furan, 2-(4-bromo-1H-inden-3-yl)-furan, 2-(4-bromo-1H-inden-5-yl)-furan, 2-(4-bromo-1H-inden- 6-yl)-furan, 2-(4-bromo-1H-inden-7-yl)-furan, 7-bromo-1H-indene, 7-bromo-2-methyl-1H-indene, 7-bromo-3-methyl-1H-indene, 7-bromo-5-methyl-1H-indene, 7-bromo-6-methyl-1H-indene, 7-bromo-4-methyl-1H-indene, 7-bromo-2-ethyl-1H-indene, 7-bromo-3-ethyl-1H-indene, 7-bromo-5-ethyl-1H-indene, 7-bromo-6-ethyl-1H-indene, 7-bromo-4-ethyl-1H-indene, 7-bromo-2-propyl-1H-indene, 7-bromo-3-propyl-1H-indene, 7-bromo-5-propyl-1H-indene, 7-bromo-6-propyl-1H-indene, 7-bromo-4-propyl-1H-indene, 7-bromo-2-butyl-1H-indene, 7-bromo-3-butyl-1H-indene, 7-bromo-5-butyl-1H-indene, 7-bromo-6-butyl-1H-indene, 7-bromo-4-butyl-1H-indene, 7-bromo-2-pentyl-1H-indene, 7-bromo-3-pentyl-1H-indene, 7-bromo-5-pentyl-1H-indene, 7-bromo-6-pentyl-1H-indene, 7-bromo-4-pentyl-1H-indene, 7-bromo-2-hexyl-1H-indene, 7-bromo-3-hexyl-1H-indene, 7-bromo-5-hexyl-1H-indene, 7-bromo-6-hexyl-1H-indene, 7-bromo-4-hexyl-1H-indene, 7-bromo-2-heptyl-1H-indene, 7-bromo-3-heptyl-1H-indene, 7-bromo-5-heptyl-1H-indene, 7-bromo-6-heptyl-1H-indene, 7-bromo-4-heptyl-1H-indene, 7-bromo-2-octyl-1H-indene, 7-bromo-3-octyl-1H-indene, 7-bromo-5-octyl-1H-indene, 7-bromo-6-octyl-1H-indene, 7-bromo-4-octyl-1H-indene, 7-bromo-2-nonyl-1H-indene, 7-bromo-3-nonyl-1H-indene, 7-bromo-5-nonyl-1H-indene, 7-bromo-6-nonyl-1H-indene, 7-bromo-4-nonyl-1H-indene, 7-bromo-2-decyl-1H-indene, 7-bromo-3-decyl-1H-indene, 7-bromo-5-decyl-1H-indene, 7-bromo-6-decyl-1H-indene, 7-bromo-4-decyl-1H-indene, 7-bromo-2-phenyl-1H-indene, 7-bromo-3-phenyl-1H-indene, 7-bromo-5-phenyl-1H-indene, 7-bromo-6-phenyl-1H-indene, 7-bromo-4-phenyl-1H-indene, 7-bromo-2-mesityl-1H-indene, 7-bromo-3-mesityl-1H-indene, 7-bromo-5-mesityl-1H-indene, 7-bromo-6-mesityl-1H-indene, 7-bromo-4-mesityl-1H-indene, 7-bromo-2-mesityl-1H-indene, 7-bromo-3-mesityl-1H-indene, 7-bromo-5-mesityl-1H-indene, 7-bromo-6-mesityl-1H-indene, 7-bromo-4-mesityl-1H-indene, 7-bromo-2-naphthyl-1H-indene, 7-bromo-3-naphthyl-1H-indene, 7-bromo-5-naphthyl-1H-indene, 7-bromo-6-naphthyl-1H-indene, 7-bromo-4-naphthyl-1H-indene, 7-bromo-1,2-dimethyl-1H-indene, 7-bromo-1,3-dimethyl-1H-indene, 7-bromo-1,5-dimethyl-1H-indene, 7-bromo-1,6-dimethyl-1H-indene, 7-bromo-1,4-dimethyl-1H-indene, 7-bromo-2,3-dimethyl-1H-indene, 7-bromo-2,5-dimethyl-1H-indene, 7-bromo-2,6-dimethyl-1H-indene, 7-bromo-2,4-dimethyl-1H-indene, 7-bromo-3,5-dimethyl-1H-indene, 7-bromo-3,6-dimethyl-1H-indene, 7-bromo-3,4-dimethyl-1H-indene, 7-bromo-5,6-dimethyl-1H-indene, 7-bromo-4,5-dimethyl-1H-indene, 7-bromo-4,6-dimethyl-1H-indene, 7-bromo-1-methyl-2-phenyl-1H-indene, 7-bromo-1-methyl-3-phenyl-1H-indene, 7-bromo-1-methyl-5-phenyl-1H-indene, 7-bromo-1-methyl-6-phenyl-1H-indene, 7-bromo-1-methyl-4-phenyl-1H-indene, 7-bromo-2-methyl-3-phenyl-1H-indene, 7-bromo-2-methyl-5-phenyl-1H-indene, 7-bromo-2-methyl-6-phenyl-1H-indene, 7-bromo-2-methyl-4-phenyl-1H-indene, 7-bromo-3-methyl-5-phenyl-1H-indene, 7-bromo-3-methyl-6-phenyl-1H-indene, 7-bromo-3-methyl-4-phenyl-1H-indene, 7-bromo-5-methyl-6-phenyl-1H-indene, 7-bromo-5-methyl-4-phenyl-1H-indene, 7-bromo-6-methyl-4-phenyl-1H-indene, 7-bromo-2-methyl-1-phenyl-1H-indene, 7-bromo-3-methyl-1-phenyl-1H-indene, 7-bromo-5-methyl-1-phenyl-1H-indene, 7-bromo-6-methyl-1-phenyl-1H-indene, 7-bromo-4-methyl-1-phenyl-1H-indene, 7-bromo-1-methyl-2-propyl-1H-indene, 7-bromo-1-methyl-3-propyl-1H-indene, 7-bromo-1-methyl-5-propyl-1H-indene, 7-bromo-1-methyl-6-propyl-1H-indene, 7-bromo-1-methyl-4-propyl-1H-indene, 7-bromo-2-methyl-3-propyl-1H-indene, 7-bromo-2-methyl-5-propyl-1H-indene, 7-bromo-2-methyl-6-propyl-1H-indene, 7-bromo-2-methyl-4-propyl-1H-indene, 7-bromo-3-methyl-5-propyl-1H-indene, 7-bromo-3-methyl-6-propyl-1H-indene, 7-bromo-3-methyl-4-propyl-1H-indene, 7-bromo-5-methyl-6-propyl-1H-indene, 7-bromo-5-methyl-4-propyl-1H-indene, 7-bromo-6-methyl-4-propyl-1H-indene, 7-bromo-2-methyl-1-propyl-1H-indene, 7-bromo-3-methyl-1-propyl-1H-indene, 7-bromo-5-methyl-1-propyl-1H-indene, 7-bromo-6-methyl-1-propyl-1H-indene, 7-bromo-4-methyl-1-propyl-1H-indene, 7-bromo-1-methyl-2-tolyl-1H-indene, 7-bromo-1-methyl-3-tolyl-1H-indene, 7-bromo-1-methyl-5-tolyl-1H-indene, 7-bromo-1-methyl-6-tolyl-1H-indene, 7-bromo-1-methyl-4-tolyl-1H-indene, 7-bromo-2-methyl-3-tolyl-1H-indene, 7-bromo-2-methyl-5-tolyl-1H-indene, 7-bromo-2-methyl-6-tolyl-1H-indene, 7-bromo-2-methyl-4-tolyl-1H-indene, 7-bromo-3-methyl-5-tolyl-1H-indene, 7-bromo-3-methyl-6-tolyl-1H-indene, 7-bromo-3-methyl-4-tolyl-1H-indene, 7-bromo-5-methyl-6-tolyl-1H-indene, 7-bromo-5-methyl-4-tolyl-1H-indene, 7-bromo-6-methyl-4-tolyl-1H-indene, 7-bromo-2-methyl-1-tolyl-1H-indene, 7-bromo-3-methyl-1-tolyl-1H-indene, 7-bromo-5-methyl-1-tolyl-1H-indene, 7-bromo-6-methyl-1-tolyl-1H-indene, 7-bromo-4-methyl-1-tolyl-1H-indene, 7-bromo-1-methyl-2-naphthyl-1H-indene, 7-bromo-1-methyl-3-naphthyl-1H-indene, 7-bromo-1-methyl-5-naphthyl-1H-indene, 7-bromo-1-methyl-6-naphthyl-1H-indene, 7-bromo-1-methyl-4-naphthyl-1H-indene, 7-bromo-2-methyl-3-naphthyl-1H-indene, 7-bromo-2-methyl-5-naphthyl-1H-indene, 7-bromo-2-methyl-6-naphthyl-1H-indene, 7-bromo-2-methyl-4-naphthyl-1H-indene, 7-bromo-3-methyl-5-naphthyl-1H-indene, 7-bromo-3-methyl-6-naphthyl-1H-indene, 7-bromo-3-methyl-4-naphthyl-1H-indene, 7-bromo-5-methyl-6-naphthyl-1H-indene, 7-bromo-5-methyl-4-naphthyl-1H-indene, 7-bromo-6-methyl-4-naphthyl-1H-indene, 7-bromo-2-methyl-1-naphthyl-1H-indene, 7-bromo-3-methyl-1-naphthyl-1H-indene, 7-bromo-5-methyl-1-naphthyl-1H-indene, 7-bromo-6-methyl-1-naphthyl-1H-indene, 7-bromo-4-methyl-1-naphthyl-1H-indene, 7-bromo-1-methyl-2-mesityl-1H-indene, 7-bromo-1-methyl-3-mesityl-1H-indene, 7-bromo-1-methyl-5-mesityl-1H-indene, 7-bromo-1-methyl-6-mesityl-1H-indene, 7-bromo-1-methyl-4-mesityl-1H-indene, 7-bromo-2-methyl-3-mesityl-1H-indene, 7-bromo-2-methyl-5-mesityl-1H-indene, 7-bromo-2-methyl-6-mesityl-1H-indene, 7-bromo-2-methyl-4-mesityl-1H-indene, 7-bromo-3-methyl-5-mesityl-1H-indene, 7-bromo-3-methyl-6-mesityl-1H-indene, 7-bromo-3-methyl-4-mesityl-1H-indene, 7-bromo-5-methyl-6-mesityl-1H-indene, 7-bromo-5-methyl-4-mesityl-1H-indene, 7-bromo-6-methyl-4-mesityl-1H-indene, 7-bromo-2-methyl-1-mesityl-1H-indene, 7-bromo-3-methyl-1-mesityl-1H-indene, 7-bromo-5-methyl-1-mesityl-1H-indene, 7-bromo-6-methyl-1-mesityl-1H-indene, 7-bromo-4-methyl-1-mesityl-1H-indene, 7-bromo-1-methyl-2-(dimethylphenyl)-1H-indene, 7-bromo-1-methyl-3-(dimethylphenyl)-1H-indene, 7-bromo-1-methyl-5-(dimethylphenyl)-1H-indene, 7-bromo-1-methyl-6-(dimethylphenyl)-1H-indene, 7-bromo-1-methyl-4-(dimethylphenyl)-1H-indene, 7-bromo-2-methyl-3-(dimethylphenyl)-1H-indene, 7-bromo-2-methyl-5-(dimethylphenyl)-1H-indene, 7-bromo-2-methyl-6-(dimethylphenyl)-1H-indene, 7-bromo-2-methyl-4-

(dimethylphenyl)-1H-indene, 7-bromo-3-methyl-5-(dimethylphenyl)-1H-indene, 7-bromo-3-methyl-6-(dimethylphenyl)-1H-indene, 7-bromo-3-methyl-4-(dimethylphenyl)-1H-indene, 7-bromo-5-methyl-6-(dimethylphenyl)-1H-indene, 7-bromo-5-methyl-4-(dimethylphenyl)-1H-indene, 7-bromo-6-methyl-4-(dimethylphenyl)-1H-indene, 7-bromo-2-methyl-1-(dimethylphenyl)-1H-indene, 7-bromo-3-methyl-1-(dimethylphenyl)-1H-indene, 7-bromo-5-methyl-1-(dimethylphenyl)-1H-indene, 7-bromo-6-methyl-1-(dimethylphenyl)-1H-indene, 7-bromo-4-methyl-1-(dimethylphenyl)-1H-indene, 7-bromo-1-methyl-2-(butylphenyl)-1H-indene, 7-bromo-1-methyl-3-(butylphenyl)-1H-indene, 7-bromo-1-methyl-5-(butylphenyl)-1H-indene, 7-bromo-1-methyl-6-(butylphenyl)-1H-indene, 7-bromo-1-methyl-4-(butylphenyl)-1H-indene, 7-bromo-2-methyl-3-(butylphenyl)-1H-indene, 7-bromo-2-methyl-5-(butylphenyl)-1H-indene, 7-bromo-2-methyl-6-(butylphenyl)-1H-indene, 7-bromo-2-methyl-4-(butylphenyl)-1H-indene, 7-bromo-3-methyl-5-(butylphenyl)-1H-indene, 7-bromo-3-methyl-6-(butylphenyl)-1H-indene, 7-bromo-3-methyl-4-(butylphenyl)-1H-indene, 7-bromo-5-methyl-6-(butylphenyl)-1H-indene, 7-bromo-5-methyl-4-(butylphenyl)-1H-indene, 7-bromo-6-methyl-4-(butylphenyl)-1H-indene, 7-bromo-2-methyl-1-(butylphenyl)-1H-indene, 7-bromo-3-methyl-1-(butylphenyl)-1H-indene, 7-bromo-5-methyl-1-(butylphenyl)-1H-indene, 7-bromo-6-methyl-1-(butylphenyl)-1H-indene, 7-bromo-4-methyl-1-(butylphenyl)-1H-indene, 7-bromo-2-fluoro-1H-indene, 7-bromo-3-fluoro-1H-indene, 7-bromo-5-fluoro-1H-indene, 7-bromo-6-fluoro-1H-indene, 7-bromo-4-fluoro-1H-indene, 7-bromo-2-methoxy-1H-indene, 7-bromo-3-methoxy-1H-indene, 7-bromo-5-methoxy-1H-indene, 7-bromo-6-methoxy-1H-indene, 7-bromo-4-methoxy-1H-indene, 7-bromo-2-methylsulfanyl-1H-indene, 7-bromo-3-methylsulfanyl-1H-indene, 7-bromo-5-methylsulfanyl-1H-indene, 7-bromo-6-methylsulfanyl-1H-indene, 7-bromo-4-methylsulfanyl-1H-indene, 7-bromo-1-trimethylsilyl-1H-indene, 7-bromo-2-trimethylsilyl-1H-indene, 7-bromo-3-trimethylsilyl-1H-indene, 7-bromo-5-trimethylsilyl-1H-indene, 7-bromo-6-trimethylsilyl-1H-indene, 7-bromo-1-trimethylsilyl-1H-indene, 7-bromo-2-trifluoromethyl-1H-indene, 7-bromo-3-trifluoromethyl-1H-indene, 7-bromo-5-trifluoromethyl-1H-indene, 7-bromo-6-trifluoromethyl-1H-indene, 7-bromo-4-trifluoromethyl-1H-indene, (7-bromo-1H-inden-2-yl)-dimethyl-amine, (7-bromo-1H-inden-3-yl)-dimethyl-amine, (7-bromo-1H-inden-5-yl)-dimethyl-amine, (7-bromo-1H-inden-6-yl)-dimethyl-amine, (7-bromo-1H-inden-4-yl)-dimethyl-amine, 7-bromo-2-methylsulfanyl-1H-indene, 7-bromo-3-methylsulfanyl-1H-indene, 7-bromo-5-methylsulfanyl-1H-indene, 7-bromo-6-methylsulfanyl-1H-indene, 7-bromo-4-methylsulfanyl-1H-indene, 2-(7-bromo-1H-inden-2-yl)-5-methyl-thiophene, 2-(7-bromo-1H-inden-3-yl)-5-methyl-thiophene, 2-(7-bromo-1H-inden-5-yl)-5-methyl-thiophene, 2-(7-bromo-1H-inden-6-yl)-5-methyl-thiophene, 2-(7-bromo-1H-inden-4-yl)-5-methyl-thiophene, 2-(7-bromo-1H-inden-2-yl)-thiophene, 2-(7-bromo-1H-inden-3-yl)-thiophene, 2-(7-bromo-1H-inden-5-yl)-thiophene, 2-(7-bromo-1H-inden-6-yl)-thiophene, 2-(7-bromo-1H-inden-4-yl)-thiophene, 2-(7-bromo-1H-inden-2-yl)-5-methyl-furan, 2-(7-bromo-1H-inden-3-yl)-5-methyl-furan, 2-(7-bromo-1H-inden-5-yl)-5-methyl-furan, 2-(7-bromo-1H-inden-6-yl)-5-methyl-furan, 2-(7-bromo-1H-inden-4-yl)-5-methyl-furan, 2-(7-bromo-1H-inden-2-yl)-furan, 2-(7-bromo-1H-inden-3-yl)-furan, 2-(7-bromo-1H-inden-5-yl)-furan, 2-(7-bromo-1H-inden-6-yl)-furan, 2-(7-bromo-1H-inden-4-yl)-furan, 5-bromo-1H-indene, 5-bromo-2-methyl-1H-indene, 5-bromo-3-methyl-1H-indene, 5-bromo-4-methyl-1H-indene, 5-bromo-6-methyl-1H-indene, 5-bromo-7-methyl-1H-indene, 5-bromo-2-ethyl-1H-indene, 5-bromo-3-ethyl-1H-indene, 5-bromo-4-ethyl-1H-indene, 5-bromo-6-ethyl-1H-indene, 5-bromo-7-ethyl-1H-indene, 5-bromo-2-propyl-1H-indene, 5-bromo-3-propyl-1H-indene, 5-bromo-4-propyl-1H-indene, 5-bromo-6-propyl-1H-indene, 5-bromo-7-propyl-1H-indene, 5-bromo-2-butyl-1H-indene, 5-bromo-3-butyl-1H-indene, 5-bromo-4-butyl-1H-indene, 5-bromo-6-butyl-1H-indene, 5-bromo-7-butyl-1H-indene, 5-bromo-2-pentyl-1H-indene, 5-bromo-3-pentyl-1H-indene, 5-bromo-4-pentyl-1H-indene, 5-bromo-6-pentyl-1H-indene, 5-bromo-7-pentyl-1H-indene, 5-bromo-2-hexyl-1H-indene, 5-bromo-3-hexyl-1H-indene, 5-bromo-4-hexyl-1H-indene, 5-bromo-6-hexyl-1H-indene, 5-bromo-7-hexyl-1H-indene, 5-bromo-2-heptyl-1H-indene, 5-bromo-3-heptyl-1H-indene, 5-bromo-4-heptyl-1H-indene, 5-bromo-6-heptyl-1H-indene, 5-bromo-7-heptyl-1H-indene, 5-bromo-2-octyl-1H-indene, 5-bromo-3-octyl-1H-indene, 5-bromo-4-octyl-1H-indene, 5-bromo-6-octyl-1H-indene, 5-bromo-7-octyl-1H-indene, 5-bromo-2-nonyl-1H-indene, 5-bromo-3-nonyl-1H-indene, 5-bromo-4-nonyl-1H-indene, 5-bromo-6-nonyl-1H-indene, 5-bromo-7-nonyl-1H-indene, 5-bromo-2-decyl-1H-indene, 5-bromo-3-decyl-1H-indene, 5-bromo-4-decyl-1H-indene, 5-bromo-6-decyl-1H-indene, 5-bromo-7-decyl-1H-indene, 5-bromo-2-phenyl-1H-indene, 5-bromo-3-phenyl-1H-indene, 5-bromo-4-phenyl-1H-indene, 5-bromo-6-phenyl-1H-indene, 5-bromo-7-phenyl-1H-indene, 5-bromo-2 mesityl-1H-indene, 5-bromo-3-mesityl-1H-indene, 5-bromo-4-mesityl-1H-indene, 5-bromo-6-mesityl-1H-indene, 5-bromo-7-mesityl-1H-indene, 5-bromo-2-mesityl-1H-indene, 5-bromo-3-mesityl-1H-indene, 5-bromo-4-mesityl-1H-indene, 5-bromo-6-mesityl-1H-indene, 5-bromo-7-mesityl-1H-indene, 5-bromo-2-naphthyl-1H-indene, 5-bromo-3-naphthyl-1H-indene, 5-bromo-4-naphthyl-1H-indene, 5-bromo-6-naphthyl-1H-indene, 5-bromo-7-naphthyl-1H-indene, 5-bromo-1,2-dimethyl-1H-indene, 5-bromo-1,3-dimethyl-1H-indene, 5-bromo-1,4-dimethyl-1H-indene, 5-bromo-1,6-dimethyl-1H-indene, 5-bromo-1,7-dimethyl-1H-indene, 5-bromo-2,3-dimethyl-1H-indene, 5-bromo-2,4-dimethyl-1H-indene, 5-bromo-2,6-dimethyl-1H-indene, 5-bromo-2,7-dimethyl-1H-indene, 5-bromo-3,4-dimethyl-1H-indene, 5-bromo-3,6-dimethyl-1H-indene, 5-bromo-3,7-dimethyl-1H-indene, 5-bromo-4,6-dimethyl-1H-indene, 5-bromo-4,7-dimethyl-1H-indene, 5-bromo-6,7-dimethyl-1H-indene, 5-bromo-1-methyl-2-phenyl-1H-indene, 5-bromo-1-methyl-3-phenyl-1H-indene, 5-bromo-1-methyl-4-phenyl-1H-indene, 5-bromo-1-methyl-6-phenyl-1H-indene, 5-bromo-1-methyl-7-phenyl-1H-indene, 5-bromo-2-methyl-3-phenyl-1H-indene, 5-bromo-2-methyl-4-phenyl-1H-indene, 5-bromo-2-methyl-6-phenyl-1H-indene, 5-bromo-2-methyl-7-phenyl-1H-indene, 5-bromo-3-methyl-4-phenyl-1H-indene, 5-bromo-3-methyl-6-phenyl-1H-indene, 5-bromo-3-methyl-7-phenyl-1H-indene, 5-bromo-4-methyl-6-phenyl-1H-indene, 5-bromo-4-methyl-7-phenyl-1H-indene, 5-bromo-6-methyl-7-phenyl-1H-indene, 5-bromo-2-methyl-1-phenyl-1H-indene, 5-bromo-3-methyl-1-phenyl-1H-indene, 5-bromo-4-methyl-1-phenyl-1H-indene, 5-bromo-6-methyl-1-phenyl-1H-indene, 5-bromo-7-methyl-1-phenyl-1H-indene, 5-bromo-1-propyl-2-phenyl-1H-indene, 5-bromo-1-propyl-3-phenyl-1H-indene, 5-bromo-1-propyl-4-phenyl-1H-indene, 5-bromo-1-propyl-6-phenyl-1H-indene, 5-bromo-1-propyl-7-phenyl-1H-indene, 5-bromo-2-propyl-3-phenyl-1H-indene, 5-bromo-2-propyl-4-phenyl-1H-indene, 5-bromo-2-propyl-6-phenyl-1H-indene, 5-bromo-2-propyl-7-phenyl-1H-indene, 5-bromo-3-propyl-4-phenyl-1H-indene, 5-bromo-3-propyl-6-phenyl-1H-indene, 5-bromo-3-propyl-7-phenyl-1H-indene, 5-bromo-4-propyl-6-phenyl-1H-indene, 5-bromo-4-propyl-7-phenyl-1H-indene, 5-bromo-6-propyl-7-phenyl-1H-indene, 5-bromo-2-propyl-1-phenyl-1H-indene, 5-bromo-3-propyl-1-phenyl-1H-indene, 5-bromo-4-propyl-1-phenyl-1H-indene, 5-bromo-6-propyl-1-phenyl-1H-indene, 5-bromo-7-propyl-1-phenyl-1H-indene, 5-bromo-1-methyl-2-tolyl-1H-indene, 5-bromo-1-methyl-3-tolyl-1H-indene, 5-bromo-1-methyl-4-tolyl-1H-indene, 5-bromo-1-methyl-6-tolyl-1H-indene, 5-bromo-1-methyl-7-tolyl-1H-indene, 5-bromo-2-methyl-3-tolyl-1H-indene, 5-bromo-2-methyl-4-tolyl-1H-indene, 5-bromo-2-methyl-6-tolyl-1H-indene, 5-bromo-2-methyl-7-tolyl-1H-indene, 5-bromo-3-methyl-4-tolyl-1H-indene, 5-bromo-3-methyl-6-tolyl-1H-indene, 5-bromo-3-methyl-7-tolyl-1H-indene, 5-bromo-4-methyl-6-tolyl-1H-indene, 5-bromo-4-methyl-7-tolyl-1H-indene, 5-bromo-6-methyl-7-tolyl-1H-indene, 5-bromo-2-methyl-1-tolyl-1H-indene, 5-bromo-3-methyl-1-tolyl-1H-indene, 5-bromo-4-methyl-1-tolyl-1H-indene, 5-bromo-6-methyl-1-tolyl-1H-indene, 5-bromo-7-methyl-1-tolyl-1H-indene, 5-bromo-1-methyl-2-naphthyl-1H-indene, 5-bromo-1-methyl-3-naphthyl-1H-indene, 5-bromo-1-methyl-4-naphthyl-1H-indene, 5-bromo-1-methyl-6-naphthyl-1H-indene, 5-bromo-1-methyl-7-naphthyl-1H-indene, 5-bromo-2-methyl-3-naphthyl-1H-indene, 5-bromo-2-methyl-4-naphthyl-1H-indene, 5-bromo-2-methyl-6-naphthyl-1H-indene, 5-bromo-2-methyl-7-naphthyl-1H-indene, 5-bromo-3-methyl-4-naphthyl-1H-indene, 5-bromo-3-methyl-6-naphthyl-1H-indene, 5-bromo-3-methyl-7-naphthyl-1H-indene, 5-bromo-4-methyl-6-naphthyl-1H-indene, 5-bromo-4-methyl-7-naphthyl-1H-indene, 5-bromo-6-methyl-7-naphthyl-1H-indene, 5-bromo-2-methyl-1-naphthyl-1H-indene, 5-bromo-3-methyl-1-naphthyl-1H-indene, 5-bromo-4-methyl-1-naphthyl-1H-indene, 5-bromo-6-methyl-1-naphthyl-1H-indene, 5-bromo-7-methyl-1-naphthyl-1H-indene, 5-bromo-1-methyl-2-mesityl-1H-indene, 5-bromo-1-methyl-3-mesityl-1H-indene, 5-bromo-1-methyl-4-mesityl-1H-indene, 5-bromo-1-methyl-6-mesityl-1H-indene, 5-bromo-1-methyl-7-mesityl-1H-indene, 5-bromo-2-methyl-3-mesityl-1H-indene, 5-bromo-2-methyl-4-mesityl-1H-indene, 5-bromo-2-methyl-6-mesityl-1H-indene, 5-bromo-2-methyl-7-mesityl-1H-indene, 5-bromo-3-methyl-4-mesityl-1H-indene, 5-bromo-3-methyl-6-mesityl-1H-indene, 5-bromo-3-methyl-7-mesityl-1H-indene, 5-bromo-4-methyl-6-mesityl-1H-indene, 5-bromo-4-methyl-7-mesityl-1H-indene, 5-bromo-6-methyl-7-mesityl-1H-indene, 5-bromo-2-methyl-1-mesityl-1H-indene, 5-bromo-3-methyl-1-mesityl-1H-indene, 5-bromo-4-methyl-1-mesityl-1H-indene, 5-bromo-6-methyl-1-mesityl-1H-indene, 5-bromo-7-methyl-1-mesityl-1H-indene, 5-bromo-1-methyl-2-(dimethylphenyl)-1H-indene, 5-bromo-1-methyl-3-(dimethylphenyl)-1H-indene, 5-bromo-1-methyl-4-(dimethylphenyl)-1H-indene, 5-bromo-1-methyl-6-(dimethylphenyl)-1H-indene, 5-bromo-1-methyl-7-(dimethylphenyl)-1H-indene, 5-bromo-2-methyl-3-(dimethylphenyl)-1H-indene, 5-bromo-2-methyl-4-(dimethylphenyl)-1H-indene, 5-bromo-2-methyl-6-(dimethylphenyl)-1H-indene, 5-bromo-2-methyl-7-(dimethylphenyl)-1H-indene, 5-bromo-3-methyl-4-(dimethylphenyl)-1H-indene, 5-bromo-3-methyl-6-(dimethylphenyl)-1H-indene, 5-bromo-3-methyl-7-(dimethylphenyl)-1H-indene, 5-bromo-4-methyl-6-(dimethylphenyl)-1H-indene, 5-bromo-4-methyl-7-(dimethylphenyl)-1H-indene, 5-bromo-6-methyl-7-(dimethylphenyl)-1H-indene, 5-bromo-2-methyl-1-(dimethylphenyl)-1H-indene, 5-bromo-3-methyl-1-(dimethylphenyl)-1H-indene, 5-bromo-4-methyl-1-(dimethylphenyl)-1H-indene, 5-bromo-6-methyl-1-(dimethylphenyl)-1H-indene, 5-bromo-7-methyl-1-(dimethylphenyl)-1H-indene, 5-bromo-1-methyl-2-(butylphenyl)-1H-indene, 5-bromo-1-methyl-3-(butylphenyl)-1H-indene, 5-bromo-1-methyl-4-(butylphenyl)-1H-indene, 5-bromo-1-methyl-6-(butylphenyl)-1H-indene, 5-bromo-1-methyl-7-(butylphenyl)-1H-indene, 5-bromo-2-methyl-3-(butylphenyl)-1H-indene, 5-bromo-2-methyl-4-(butylphenyl)-1H-indene, 5-bromo-2-methyl-6-(butylphenyl)-1H-indene, 5-bromo-2-methyl-7-(butylphenyl)-1H-indene, 5-bromo-3-methyl-4-(butylphenyl)-1H-indene, 5-bromo-3-methyl-6-(butylphenyl)-1H-indene, 5-bromo-3-methyl-7-(butylphenyl)-1H-indene, 5-bromo-4-methyl-6-(butylphenyl)-1H-indene, 5-bromo-4-methyl-7-(butylphenyl)-1H-indene, 5-bromo-6-methyl-7-(butylphenyl)-1H-indene, 5-bromo-2-methyl-1-(butylphenyl)-1H-indene, 5-bromo-3-methyl-1-(butylphenyl)-1H-indene, 5-bromo-4-methyl-1-(butylphenyl)-1H-indene, 5-bromo-6-methyl-1-(butylphenyl)-1H-indene, 5-bromo-7-methyl-1-(butylphenyl)-1H-indene, 5-bromo-2-fluoro-1H-indene, 5-bromo-3-fluoro-1H-indene, 5-bromo-4-fluoro-1H-indene, 5-bromo-6-fluoro-1H-indene, 5-bromo-7-fluoro-1H-indene, 5-bromo-2-methoxy-1H-indene, 5-bromo-3-methoxy-1H-indene, 5-bromo-4-methoxy-1H-indene, 5-bromo-6-methoxy-1H-indene, 5-bromo-7-methoxy-1H-indene, 5-bromo-2-methylsulfanyl-1H-indene, 5-bromo-3-methylsulfanyl-1H-indene, 5-bromo-4-methylsulfanyl-1H-indene, 5-bromo-6-methylsulfanyl-1H-indene, 5-bromo-7-methylsulfanyl-1H-indene, 5-bromo-1-trimethylsilyl-1H-indene, 5-bromo-2-trimethylsilyl-1H-indene, 5-bromo-3-trimethylsilyl-1H-indene, 5-bromo-4-trimethylsilyl-1H-indene, 5-bromo-6-trimethylsilyl-1H-indene, 5-bromo-7-trimethylsilyl-1H-indene, 5-bromo-2-trifluoromethyl-1H-indene, 5-bromo-3-trifluoromethyl-1H-indene, 5-bromo-4-trifluoromethyl-1H-indene, 5-bromo-6-trifluoromethyl-1H-indene, 5-bromo-7-trifluoromethyl-1H-indene, (5-bromo-1H-indene-2-yl)-dimethyl-amine, (5-bromo-1H-indene-3-yl)-dimethyl-amine, (5-bromo-1H-inden-4-yl)-dimethyl-amine, (5-bromo-1H-inden-6-yl)-dimethyl-amine, (5-bromo-1H-inden-7-yl)-dimethyl-amine, 5-bromo-2-methylsulfanyl-1H-indene, 5-bromo-3-methylsulfanyl-1H-indene, 5-bromo-4-methylsulfanyl-1H-indene, 5-bromo-6-methylsulfanyl-1H-indene, 5-bromo-7-methylsulfanyl-1H-indene, 2-(5-bromo-1H-inden-2-yl)-5-methyl-thiophene, 2-(5-bromo-1H-inden-3-yl)-5-methyl-thiophene, 2-(5-bromo-1H-inden-4-yl)-5-methyl-thiophene, 2-(5-bromo-1H-inden-6-yl)-5-methyl-thiophene, 2-(5-bromo-1H-inden-7-yl)-5-methyl-thiophene, 2-(5-bromo-1H-inden-2-yl)-thiophene, 2-(5-bromo-1H-inden-3-yl)-thiophene, 2-(5-bromo-1H-inden-4-yl)-thiophene, 2-(5-bromo-1H-inden-6-yl)-thiophene, 2-(5-bromo-1H-inden-7-yl)-thiophene, 2-(5-bromo-1H- inden-2-yl)-5-methyl-furan, 2-(5-bromo-1H-inden-3-yl)-5-methyl-furan, 2-(5-bromo-1H-inden-4-yl)-5-methyl-furan, 2-(5-bromo-1H-inden-6-yl)-5-methyl-furan, 2-(5-bromo-1H-inden-7-yl)-5-methyl-furan, 2-(5-bromo-1H-inden-2-yl)-furan, 2-(5-bromo-1H-inden-3-yl)-furan, 2-(5-bromo-1H-inden-4-yl)-furan, 2-(5-bromo-1H-inden-6-yl)-furan, 2-(5-bromo-1H-inden-7-yl)-furan, 6-bromo-1H-indene, 6-bromo-2-methyl-1H-indene, 6-bromo-3-methyl-1H-indene, 6-bromo-4-methyl-1H-indene, 6-bromo-5-methyl-1H-indene, 6-bromo-7-methyl-1H-indene, 6-bromo-2-ethyl-1H-indene, 6-bromo-3-ethyl-1H-indene, 6-bromo-4-ethyl-1H-indene, 6-bromo-5-ethyl-1H-indene, 6-bromo-7-ethyl-1H-indene, 6-bromo-2-propyl-1H-indene, 6-bromo-3-propyl-1H-indene, 6-bromo-4-propyl-1H-indene, 6-bromo-5-propyl-1H-indene, 6-bromo-7-propyl-1H-indene, 6-bromo-2-butyl-1H-indene, 6-bromo-3-butyl-1H-indene, 6-bromo-4-butyl-1H-indene, 6-bromo-5-butyl-1H-indene, 6-bromo-7-butyl-1H-indene, 6-bromo-2-pentyl-1H-indene, 6-bromo-3-pentyl-1H-indene, 6-bromo-4-pentyl-1H-indene, 6-bromo-5-pentyl-1H-indene, 6-bromo-7-pentyl-1H-indene, 6-bromo-2-hexyl-1H-indene, 6-bromo-3-hexyl-1H-indene, 6-bromo-4-hexyl-1H-indene, 6-bromo-5-hexyl-1H-indene, 6-bromo-7-hexyl-1H-indene, 6-bromo-2-heptyl-1H-indene, 6-bromo-3-heptyl-1H-indene, 6-bromo-4-heptyl-1H-indene, 6-bromo-5-heptyl-1H-indene, 6-bromo-7-heptyl-1H-indene, 6-bromo-2-octyl-1H-indene, 6-bromo-3-octyl-1H-indene, 6-bromo-4-octyl-1H-indene, 6-bromo-5-octyl-1H-indene, 6-bromo-7-octyl-1H-indene, 6-bromo-2-nonyl-1H-indene, 6-bromo-3-nonyl-1H-indene, 6-bromo-4-nonyl-1H-indene, 6-bromo-5-nonyl-1H-indene, 6-bromo-7-nonyl-1H-indene, 6-bromo-2-decyl-1H-indene, 6-bromo-3-decyl-1H-indene, 6-bromo-4-decyl-1H-indene, 6-bromo-5-decyl-1H-indene, 6-bromo-7-decyl-1H-indene, 6-bromo-2-phenyl-1H-indene, 6-bromo-3-phenyl-1H-indene, 6-bromo-4-phenyl-1H-indene, 6-bromo-5-phenyl-1H-indene, 6-bromo-7-phenyl-1H-indene, 6-bromo-2 mesityl-1H-indene, 6-bromo-3-mesityl-1H-indene, 6-bromo-4-mesityl-1H-indene, 6-bromo-5-mesityl-1H-indene, 6-bromo-7-mesityl-1H-indene, 6-bromo-2-mesityl-1H-indene, 6-bromo-3-mesityl-1H-indene, 6-bromo-4-mesityl-1H-indene, 6-bromo-5-mesityl-1H-indene, 6-bromo-7-mesityl-1H-indene, 6-bromo-2-naphthyl-1H-indene, 6-bromo-3-naphthyl-1H-indene, 6-bromo-4-naphthyl-1H-indene, 6-bromo-5-naphthyl-1H-indene, 6-bromo-7-naphthyl-1H-indene, 6-bromo-1,2-dimethyl-1H-indene, 6-bromo-1,3-dimethyl-1H-indene, 6-bromo-1,4-dimethyl-1H-indene, 6-bromo-1,5-dimethyl-1H-indene, 6-bromo-1,7-dimethyl-1H-indene, 6-bromo-2,3-dimethyl-1H-indene, 6-bromo-2,4-dimethyl-1H-indene, 6-bromo-2,5-dimethyl-1H-indene, 6-bromo-2,7-dimethyl-1H-indene, 6-bromo-3,4-dimethyl-1H-indene, 6-bromo-3,5-dimethyl-1H-indene, 6-bromo-3,7-dimethyl-1H-indene, 6-bromo-4,5-dimethyl-1H-indene, 6-bromo-4,7-dimethyl-1H-indene, 6-bromo-5,7-dimethyl-1H-indene, 6-bromo-1-methyl-2-phenyl-1H-indene, 6-bromo-1-methyl-3-phenyl-1H-indene, 6-bromo-1-methyl-4-phenyl-1H-indene, 6-bromo-1-methyl-5-phenyl-1H-indene, 6-bromo-1-methyl-7-phenyl-1H-indene, 6-bromo-2-methyl-3-phenyl-1H-indene, 6-bromo-2-methyl-4-phenyl-1H-indene, 6-bromo-2-methyl-5-phenyl-1H-indene, 6-bromo-2-methyl-7-phenyl-1H-indene, 6-bromo-3-methyl-4-phenyl-1H-indene, 6-bromo-3-methyl-5-phenyl-1H-indene, 6-bromo-3-methyl-7-phenyl-1H-indene, 6-bromo-4-methyl-5-phenyl-1H-indene, 6-bromo-4-methyl-7-phenyl-1H-indene, 6-bromo-5-methyl-7-phenyl-1H-indene, 6-bromo-2-methyl-1-phenyl-1H-indene, 6-bromo-3-methyl-1-phenyl-1H-indene, 6-bromo-4-methyl-1-phenyl-1H-indene, 6-bromo-5-methyl-1-phenyl-1H-indene, 6-bromo-7-methyl-1-phenyl-1H-indene, 6-bromo-1-propyl-2-phenyl-1H-indene, 6-bromo-1-propyl-3-phenyl-1H-indene, 6-bromo-1-propyl-4-phenyl-1H-indene, 6-bromo-1-propyl-5-phenyl-1H-indene, 6-bromo-1-propyl-7-phenyl-1H-indene, 6-bromo-2-propyl-3-phenyl-1H-indene, 6-bromo-2-propyl-4-phenyl-1H-indene, 6-bromo-2-propyl-5-phenyl-1H-indene, 6-bromo-2-propyl-7-phenyl-1H-indene, 6-bromo-3-propyl-4-phenyl-1H-indene, 6-bromo-3-propyl-5-phenyl-1H-indene, 6-bromo-3-propyl-7-phenyl-1H-indene, 6-bromo-4-propyl-5-phenyl-1H-indene, 6-bromo-4-propyl-7-phenyl-1H-indene, 6-bromo-5-propyl-7-phenyl-1H-indene, 6-bromo-2-propyl-1-phenyl-1H-indene, 6-bromo-3-propyl-1-phenyl-1H-indene, 6-bromo-4-propyl-1-phenyl-1H-indene, 6-bromo-5-propyl-1-phenyl-1H-indene, 6-bromo-7-propyl-1-phenyl-1H-indene, 6-bromo-1-methyl-2-tolyl-1H-indene, 6-bromo-1-methyl-3-tolyl-1H-indene, 6-bromo-1-methyl-4-tolyl-1H-indene, 6-bromo-1-methyl-5-tolyl-1H-indene, 6-bromo-1-methyl-7-tolyl-1H-indene, 6-bromo-2-methyl-3-tolyl-1H-indene, 6-bromo-2-methyl-4-tolyl-1H-indene, 6-bromo-2-methyl-5-tolyl-1H-indene, 6-bromo-2-methyl-7-tolyl-1H-indene, 6-bromo-3-methyl-4-tolyl-1H-indene, 6-bromo-3-methyl-5-tolyl-1H-indene, 6-bromo-3-methyl-7-tolyl-1H-indene, 6-bromo-4-methyl-5-tolyl-1H-indene, 6-bromo-4-methyl-7-tolyl-1H-indene, 6-bromo-5-methyl-7-tolyl-1H-indene, 6-bromo-2-methyl-1-tolyl-1H-indene, 6-bromo-3-methyl-1-tolyl-1H-indene, 6-bromo-4-methyl-1-tolyl-1H-indene, 6-bromo-5-methyl-1-tolyl-1H-indene, 6-bromo-7-methyl-1-tolyl-1H-indene, 6-bromo-1-methyl-2-naphthyl-1H-indene, 6-bromo-1-methyl-3-naphthyl-1H-indene, 6-bromo-1-methyl-4-naphthyl-1H-indene, 6-bromo-1-methyl-5-naphthyl-1H-indene, 6-bromo-1-methyl-7-naphthyl-1H-indene, 6-bromo-2-methyl-3-naphthyl-1H-indene, 6-bromo-2-methyl-4-naphthyl-1H-indene, 6-bromo-2-methyl-5-naphthyl-1H-indene, 6-bromo-2-methyl-7-naphthyl-1H-indene, 6-bromo-3-methyl-4-naphthyl-1H-indene, 6-bromo-3-methyl-5-naphthyl-1H-indene, 6-bromo-3-methyl-7-naphthyl-1H-indene, 6-bromo-4-methyl-5-naphthyl-1H-indene, 6-bromo-4-methyl-7-naphthyl-1H-indene, 6-bromo-5-methyl-7-naphthyl-1H-indene, 6-bromo-2-methyl-1-naphthyl-1H-indene, 6-bromo-3-methyl-1-naphthyl-1H-indene, 6-bromo-4-methyl-1-naphthyl-1H-indene, 6-bromo-5-methyl-1-naphthyl-1H-indene, 6-bromo-7-methyl-1-naphthyl-1H-indene, 6-bromo-1-methyl-2-mesityl-1H-indene, 6-bromo-1-methyl-3-mesityl-1H-indene, 6-bromo-1-methyl-4-mesityl-1H-indene, 6-bromo-1-methyl-5-mesityl-1H-indene, 6-bromo-1-methyl-7-mesityl-1H-indene, 6-bromo-2-methyl-3-mesityl-1H-indene, 6-bromo-2-methyl-4-mesityl-1H-indene, 6-bromo-2-methyl-5-mesityl-1H-indene, 6-bromo-2-methyl-7-mesityl-1H-indene, 6-bromo-3-methyl-4-mesityl-1H-indene, 6-bromo-3-methyl-5-mesityl-1H-indene, 6-bromo-3-methyl-7-mesityl-1H-indene, 6-bromo-4-methyl-5-mesityl-1H-indene, 6-bromo-4-methyl-7-mesityl-1H-indene, 6-bromo-5-methyl-7-mesityl-1H-indene, 6-bromo-2-methyl-1-mesityl-1H-indene, 6-bromo-3-methyl-1-mesityl-1H-indene, 6-bromo-4-methyl-1-mesityl-1H-indene, 6-bromo-5-methyl-1-mesityl-1H-indene, 6-bromo-7-methyl-1-mesityl-1H-indene, 6-bromo-1-methyl-2-(dimethylphenyl)-1H-indene, 6-bromo-1-methyl-3-(dimethylphenyl)-1H-indene, 6-bromo-1-methyl-4-

(dimethylphenyl)-1H-indene, (dimethylphenyl)-1H-indene, (dimethylphenyl)-1H-indene, (dimethylphenyl)-1H-indene, (dimethylphenyl)-1H-indene, (dimethylphenyl)-1H-indene, (dimethylphenyl)-1H-indene, (dimethylphenyl)-1H-indene, (dimethylphenyl)-1H-indene, (dimethylphenyl)-1H-indene, (dimethylphenyl)-1H-indene, (dimethylphenyl)-1H-indene, (dimethylphenyl)-1H-indene, (dimethylphenyl)-1H-indene, (dimethylphenyl)-1H-indene, (dimethylphenyl)-1H-indene, (dimethylphenyl)-1H-indene, (dimethylphenyl)-1H-indene, (butylphenyl)-1H-indene, (butylphenyl)-1H-indene, (butylphenyl)-1H-indene, (butylphenyl)-1H-indene, (butylphenyl)-1H-indene, (butylphenyl)-1H-indene, (butylphenyl)-1H-indene, (butylphenyl)-1H-indene, (butylphenyl)-1H-indene, (butylphenyl)-1H-indene, (butylphenyl)-1H-indene, (butylphenyl)-1H-indene, (butylphenyl)-1H-indene, (butylphenyl)-1H-indene, (butylphenyl)-1H-indene, (butylphenyl)-1H-indene, (butylphenyl)-1H-indene, (butylphenyl)-1H-indene, 6-bromo-1-methyl-5-(dimethylphenyl)-1H-indene, 6-bromo-1-methyl-7-(dimethylphenyl)-1H-indene, 6-bromo-2-methyl-3-(dimethylphenyl)-1H-indene, 6-bromo-2-methyl-4-(dimethylphenyl)-1H-indene, 6-bromo-2-methyl-5-(dimethylphenyl)-1H-indene, 6-bromo-2-methyl-7-(dimethylphenyl)-1H-indene, 6-bromo-3-methyl-4-(dimethylphenyl)-1H-indene, 6-bromo-3-methyl-5-(dimethylphenyl)-1H-indene, 6-bromo-3-methyl-7-(dimethylphenyl)-1H-indene, 6-bromo-4-methyl-5-(dimethylphenyl)-1H-indene, 6-bromo-4-methyl-7-(dimethylphenyl)-1H-indene, 6-bromo-5-methyl-7-(dimethylphenyl)-1H-indene, 6-bromo-2-methyl-1-(dimethylphenyl)-1H-indene, 6-bromo-3-methyl-1-(dimethylphenyl)-1H-indene, 6-bromo-4-methyl-1-(dimethylphenyl)-1H-indene, 6-bromo-5-methyl-1-(dimethylphenyl)-1H-indene, 6-bromo-7-methyl-1-(dimethylphenyl)-1H-indene, 6-bromo-1-methyl-2-(butylphenyl)-1H-indene, 6-bromo-1-methyl-3-(butylphenyl)-1H-indene, 6-bromo-1-methyl-4-(butylphenyl)-1H-indene, 6-bromo-1-methyl-5-(butylphenyl)-1H-indene, 6-bromo-1-methyl-7-(butylphenyl)-1H-indene, 6-bromo-2-methyl-3-(butylphenyl)-1H-indene, 6-bromo-2-methyl-4-(butylphenyl)-1H-indene, 6-bromo-2-methyl-5-(butylphenyl)-1H-indene, 6-bromo-2-methyl-7-(butylphenyl)-1H-indene, 6-bromo-3-methyl-4-(butylphenyl)-1H-indene, 6-bromo-3-methyl-5-(butylphenyl)-1H-indene, 6-bromo-3-methyl-7-(butylphenyl)-1H-indene, 6-bromo-4-methyl-5-(butylphenyl)-1H-indene, 6-bromo-4-methyl-7-(butylphenyl)-1H-indene, 6-bromo-5-methyl-7-(butylphenyl)-1H-indene, 6-bromo-2-methyl-1-(butylphenyl)-1H-indene, 6-bromo-3-methyl-1-(butylphenyl)-1H-indene, 6-bromo-4-methyl-1-(butylphenyl)-1H-indene, 6-bromo-5-methyl-1-(butylphenyl)-1H-indene, 6-bromo-7-methyl-1-(butylphenyl)-1H-indene, 6-bromo-2-fluoro-1H-indene, 6-bromo-3-fluoro-1H-indene, 6-bromo-4-fluoro-1H-indene, 6-bromo-5-fluoro-1H-indene, 6-bromo-7-fluoro-1H-indene, 6-bromo-2-methoxy-1H-indene, 6-bromo-3-methoxy-1H-indene, 6-bromo-4-methoxy-1H-indene, 6-bromo-5-methoxy-1H-indene, 6-bromo-7-methoxy-1H-indene, 6-bromo-2-methylsulfanyl-1H-indene, 6-bromo-3-methylsulfanyl-1H-indene, 6-bromo-4-methylsulfanyl-1H-indene, 6-bromo-5-methylsulfanyl-1H-indene, 6-bromo-7-methylsulfanyl-1H-indene, 6-bromo-1-trimethylsilyl-1H-indene, 6-bromo-2-trimethylsilyl-1H-indene, 6-bromo-3-trimethylsilyl-1H-indene, 6-bromo-4-trimethylsilyl-1H-indene, 6-bromo-5-trimethylsilyl-1H-indene, 6-bromo-7-trimethylsilyl-1H-indene, 6-bromo-2-trifluoromethyl-1H-indene, 6-bromo-3-trifluoromethyl-1H-indene, 6-bromo-4-trifluoromethyl-1H-indene, 6-bromo-5-trifluoromethyl-1H-indene, 6-bromo-7-trifluoromethyl-1H-indene, (6-bromo-1H-inden-2-yl)-dimethyl-amine, (6-bromo-1H-inden-3-yl)-dimethyl-amine, (6-bromo-1H-inden-4-yl)-dimethyl-amine, (6-bromo-1H-inden-5-yl)-dimethyl-amine, (6-bromo-1H-inden-7-yl)-dimethyl-amine, 6-bromo-2-methylsulfanyl-1H-indene, 6-bromo-3-methylsulfanyl-1H-indene, 6-bromo-4-methylsulfanyl-1H-indene, 6-bromo-5-methylsulfanyl-1H-indene, 6-bromo-7-methylsulfanyl-1H-indene, 2-(6-bromo-1H-inden-2-yl)-6-methyl-thiophene, 2-(6-bromo-1H-inden-3-yl)-5-methyl-thiophene, 2-(6-bromo-1H-inden-4-yl)-5-methyl-thiophene, 2-(6-bromo-1H-inden-5-yl)-6-methyl-thiophene, 2-(6-bromo-1H-inden-7-yl)-5-methyl-thiophene, 2-(6-bromo-1H-inden-2-yl)-thiophene, 2-(6-bromo-1H-inden-3-yl)-thiophene, 2-(6-bromo-1H-inden-4-yl)-thiophene, 2-(6-bromo-1H-inden-5-yl)-thiophene, 2-(6-bromo-1H-inden-7-yl)-thiophene, 2-(6-bromo-1H-inden-2-yl)-5-methyl-furan, 2-(6-bromo-1H-inden-3-yl)-5-methyl-furan, 2-(6-bromo-1H-inden-4-yl)-5-methyl-furan, 2-(6-bromo-1H-inden-5-yl)-5-methyl-furan, 2-(6-bromo-1H-inden-7-yl)-5-methyl-furan, 2-(6-bromo-1H-inden-2-yl)-furan, 2-(6-bromo-1H-inden-3-yl)-furan, 2-(6-bromo-1H-inden-4-yl)-furan, 2-(6-bromo-1H-inden-5-yl)-furan, 2-(6-bromo-1H-inden-7-yl)-furan, 4-bromo-5,6,7,8-tetrahydro-1H-cyclopenta[b]naphthalene, 4-bromo-1H-cyclopenta[b]naphthalene, 4-bromo-6,7,8,9-tetrahydro-1H-cyclopenta[a]naphthalene, 5-bromo-6,7,8,9-tetrahydro-1H-cyclopenta[a]naphthalene, 4-bromo-1H-cyclopenta[a]naphthalene, 5-bromo-1H-cyclopenta[a]naphthalene, 6-bromo-1H-cyclopenta[a]naphthalene, 7-bromo-1H-cyclopenta[a]naphthalene, 8-bromo-1H-cyclopenta[a]naphthalene, 9-bromo-1H-cyclopenta[a]naphthalene, 4-bromo-1-methyl-5,6,7,8-tetrahydro-1H-cyclopenta[b]naphthalene, 4-bromo-1-methyl-1H-cyclopenta[b]naphthalene, 4-bromo-1-methyl-6,7,8,9-tetrahydro-1H-cyclopenta[a]naphthalene, 5-bromo-1-methyl-6,7,8,9-tetrahydro-1H-cyclopenta[a]naphthalene, 4-bromo-1-methyl-1H-cyclopenta[a]naphthalene, 5-bromo-1-methyl-1H-cyclopenta[a]naphthalene, 4-bromo-2-methyl-5,6,7,8-tetrahydro-1H-cyclopenta[b]naphthalene, 4-bromo-2-methyl-1H-cyclopenta[b]naphthalene, 4-bromo-2-methyl-6,7,8,9-tetrahydro-1H-cyclopenta[a]naphthalene, 5-bromo-2-methyl-6,7,8,9-tetrahydro-1H-cyclopenta[a]naphthalene, 4-bromo-2-methyl-1H-cyclopenta[a]naphthalene, 5-bromo-2-methyl-1H-cyclopenta[a]naphthalene, 4-bromo-3-methyl-5,6,7,8-tetrahydro-1H-cyclopenta[b]naphthalene, 4-bromo-3-methyl-1H-cyclopenta[b]naphthalene, 4-bromo-3-methyl-6,7,8,9-tetrahydro-1H-cyclopenta[a]naphthalene, 5-bromo-3-methyl-6,7,8,9-tetrahydro-1H-cyclopenta[a]naphthalene, 4-bromo-3-methyl-1H-cyclopenta[a]naphthalene, 5-bromo-3-methyl-1H-cyclopenta[a]naphthalene, 4-bromo-1-ethyl-5,6,7,8-tetrahydro-1H-cyclopenta[b]naphthalene, 4-bromo-1-ethyl-1H-cyclopenta[b]naphthalene, 4-bromo-1-ethyl-6,7,8,9-tetrahydro-1H-cyclopenta[a]naphthalene, 5-bromo-1-ethyl-6,7,8,9-tetrahydro-1H-cyclopenta[a]naphthalene, 4-bromo-1-ethyl-1H-cyclopenta[a]naphthalene, 5-bromo-1-ethyl-1H-cyclopenta[a]naphthalene, 4-bromo-2-ethyl-5,6,7,8-tetrahydro-1H-cyclopenta[b]naphthalene, 4-bromo-2-ethyl-1H-cyclopenta[b]naphthalene, 4-bromo-2-ethyl-6,7,8,9-tetrahydro-1H-cyclopenta[a]naphthalene, 5-bromo-2-ethyl-6,7,8,9-tetrahydro-1H-cyclopenta[a]naphthalene, 4-bromo-2-ethyl-1H-cyclopenta[a]naphthalene, 5-bromo-2-ethyl-1H-cyclopenta[a]naphthalene, 4-bromo-3-ethyl-5,6,7,8-tetrahydro-1H-cyclopenta[b]naphthalene, 4-bromo-3-ethyl-1H-cyclopenta[b]naphthalene, 4-bromo-3-ethyl-6,7,8,9-tetrahydro-1H-cyclopenta[a]naphthalene, 5-bromo-3-ethyl-6,7,8,9-tetrahydro-1H-cyclopenta[a]naphthalene, 4-bromo-3-ethyl-1H-cyclopenta[a]naphthalene, 5-bromo-3-ethyl-1H-cyclopenta[a]naphthalene, 4-bromo-1-propyl-5,6,7,8-tetrahydro-1H-cyclopenta[b]naphthalene, 4-bromo-1-propyl-1H-cyclopenta[b]naphthalene, 4-bromo-1-propyl-6,7,8,9-tetrahydro-1H-cyclopenta[a]naphthalene, 5-bromo-1-propyl-6,7,8,9-tetrahydro-1H-cyclopenta[a]naphthalene, 4-bromo-1-propyl-1H-cyclopenta[a]naphthalene, 5-bromo-1-propyl-1H-cyclopenta[a]naphthalene, 4-bromo-2-propyl-5,6,7,8H-tetrahydro-1H-cyclopenta[b]naphthalene, 4-bromo-2-propyl-1H-cyclopenta[b]naphthalene, 4-bromo-2-propyl-6,7,8,9-tetrahydro-1H-cyclopenta[a]naphthalene, 5-bromo-2-propyl-6,7,8,9-tetrahydro-1H-cyclopenta[a]naphthalene, 4-bromo-2-propyl-1H-cyclopenta[a]naphthalene, 5-bromo-2-propyl-1H-cyclopenta[a]naphthalene, 4-bromo-3-propyl-5,6,7,8-tetrahydro-1H-cyclopenta[b]naphthalene, 4-bromo-3-propyl-1H-cyclopenta[b]naphthalene, 4-bromo-3-propyl-6,7,8,9-tetrahydro-1H-cyclopenta[a]naphthalene, 5-bromo-3-propyl-6,7,8,9-tetrahydro-1H-cyclopenta[a]naphthalene, 4-bromo-3-propyl-1H-cyclopenta[a]naphthalene, 5-bromo-3-propyl-1H-cyclopenta[a]naphthalene, 9-bromo-5,6,7,8-tetrahydro-1H-cyclopenta[b]naphthalene, 9-bromo-1H-cyclopenta[b]naphthalene, 4-bromo-6,7,8,9-tetrahydro-3H-cyclopenta[a]naphthalene, 5-bromo-6,7,8,9-tetrahydro-3H-cyclopenta[a]naphthalene, 4-bromo-3H-cyclopenta[a]naphthalene, 5-bromo-3H-cyclopenta[a]naphthalene, 9-bromo-1-methyl-5,6,7,8-tetrahydro-1H-cyclopenta[b]naphthalene, 9-bromo-1-methyl-1H-cyclopenta[b]naphthalene, 4-bromo-1-methyl-6,7,8,9-tetrahydro-3H-cyclopenta[a]naphthalene, 5-bromo-1-methyl-6,7,8,9-tetrahydro-3H-cyclopenta[a]naphthalene, 4-bromo-1-methyl-3H-cyclopenta[a]naphthalene, 5-bromo-1-methyl-3H-cyclopenta[a]naphthalene, 9-bromo-2-methyl-5,6,7,8-tetrahydro-1H-cyclopenta[b]naphthalene, 9-bromo-2-methyl-1H-cyclopenta[b]naphthalene, 4-bromo-2-methyl-6,7,8,9-tetrahydro-3H-cyclopenta[a]naphthalene, 5-bromo-2-methyl-6,7,8,9-tetrahydro-3H-cyclopenta[a]naphthalene, 4-bromo-2-methyl-3H-cyclopenta[a]naphthalene, 5-bromo-2-methyl-3H-cyclopenta[a]naphthalene, 9-bromo-3-methyl-5,6,7,8-tetrahydro-1H-cyclopenta[b]naphthalene, 9-bromo-3-methyl-1H-cyclopenta[b]naphthalene, 4-bromo-3-methyl-6,7,8,9-tetrahydro-3H-cyclopenta[a]naphthalene, 5-bromo-3-methyl-6,7,8,9-tetrahydro-3H-cyclopenta[a]naphthalene, 4-bromo-3-methyl-3H-cyclopenta[a]naphthalene, 5-bromo-3-methyl-3H-cyclopenta[a]naphthalene, 9-bromo-1-ethyl-5,6,7,8-tetrahydro-1H-cyclopenta[b]naphthalene, 9-bromo-1-ethyl-1H-cyclopenta[b]naphthalene, 4-bromo-1-ethyl-6,7,8,9-tetrahydro-3H-cyclopenta[a]naphthalene, 5-bromo-1-ethyl-6,7,8,9-tetrahydro-3H-cyclopenta[a]naphthalene, 4-bromo-1-ethyl-3H-cyclopenta[a]naphthalene, 5-bromo-1-ethyl-3H-cyclopenta[a]naphthalene, 9-bromo-2-ethyl-5,6,7,8-tetrahydro-1H-cyclopenta[b]naphthalene, 9-bromo-2-ethyl-1H-cyclopenta[b]naphthalene, 4-bromo-2-ethyl-6,7,8,9-tetrahydro-3H-cyclopenta[a]naphthalene, 5-bromo-2-ethyl-6,7,8,9-tetrahydro-3H-cyclopenta[a]naphthalene, 4-bromo-2-ethyl-3H-cyclopenta[a]naphthalene, 5-bromo-2-ethyl-3H-cyclopenta[a]naphthalene, 9-bromo-3-ethyl-5,6,7,8-tetrahydro-1H-cyclopenta[b]naphthalene, 9-bromo-3-ethyl-1H-cyclopenta[b]naphthalene, 4-bromo-3-ethyl-6,7,8,9-tetrahydro-3H-cyclopenta[a]naphthalene, 5-bromo-3-ethyl-6,7,8,9-tetrahydro-3H-cyclopenta[a]naphthalene, 4-bromo-3-ethyl-3H-cyclopenta[a]naphthalene, 5-bromo-3-ethyl-3H-cyclopenta[a]naphthalene, 9-bromo-1-propyl-5,6,7,8-tetrahydro-1H-cyclopenta[b]naphthalene, 9-bromo-1-propyl-1H-cyclopenta[b]naphthalene, 4-bromo-1-propyl-6,7,8,9-tetrahydro-3H-cyclopenta[a]naphthalene, 5-bromo-1-propyl-6,7,8,9-tetrahydro-3H-cyclopenta[a]naphthalene, 4-bromo-1-propyl-3H-cyclopenta[a]naphthalene, 5-bromo-1-propyl-3H-cyclopenta[a]naphthalene, 9-bromo-2-propyl-5,6,7,8-tetrahydro-1H-cyclopenta[b]naphthalene, 9-bromo-2-propyl-1H-cyclopenta[b]naphthalene, 4-bromo-2-propyl-6,7,8,9-tetrahydro-3H-cyclopenta[a]naphthalene, 5-bromo-2-propyl-6,7,8,9-tetrahydro-3H-cyclopenta[a]naphthalene, 4-bromo-2-propyl-3H-cyclopenta[a]naphthalene, 5-bromo-2-propyl-3H-cyclopenta[a]naphthalene, 9-bromo-3-propyl-5,6,7,8-tetrahydro-1H-cyclopenta[b]naphthalene, 9-bromo-3-propyl-1H-cyclopenta[b]naphthalene, 4-bromo-3-propyl-6,7,8,9-tetrahydro-3H-cyclopenta[a]naphthalene, 5-bromo-3-propyl-6,7,8,9-tetrahydro-3H-cyclopenta[a]naphthalene, 4-bromo-3-propyl-3H-cyclopenta[a]naphthalene, 5-bromo-3-propyl-3H-cyclopenta[a]naphthalene, 3-bromo-6H-cyclopenta[b]thiophene, 3-bromo-5-methyl-6H-cyclopenta[b]thiophene, 3-bromo-4-methyl-6H-cyclopenta[b]thiophene, 3-bromo-6-methyl-6H-cyclopenta[b]thiophene, 3-bromo-5-ethyl-6H-cyclopenta[b]thiophene, 3-bromo-4-ethyl-6H-cyclopenta[b]thiophene, 3-bromo-6-ethyl-6H-cyclopenta[b]thiophene, 3-bromo-5-propyl-6H-cyclopenta[b]thiophene, 3-bromo-4-propyl-6H-cyclopenta[b]thiophene, 3-bromo-6-propyl-6H-cyclopenta[b]thiophene, 2-bromo-6H-cyclopenta[b]thiophene, 2-bromo-5-methyl-6H-cyclopenta[b]thiophene, 2-bromo-4-methyl-6H-cyclopenta[b]thiophene, 2-bromo-6-methyl-6H-cyclopenta[b]thiophene, 2-bromo-5-ethyl-6H-cyclopenta[b]thiophene, 2-bromo-4-ethyl-6H-cyclopenta[b]thiophene, 2-bromo-6-ethyl-6H-cyclopenta[b]thiophene, 2-bromo-5-propyl-6H-cyclopenta[b]thiophene, 2-bromo-4-propyl-6H-cyclopenta[b]thiophene, 2-bromo-6-propyl-6H-cyclopenta[b]thiophene, 3-bromo-6H-cyclopenta[b]furan, 3-bromo-5-methyl-6H-cyclopenta[b]furan, 3-bromo-4-methyl-6H-cyclopenta[b]furan, 3-bromo-6-methyl-6H-cyclopenta[b]furan, 3-bromo-5-ethyl-6H-cyclopenta[b]furan, 3-bromo-4-ethyl-6H-cyclopenta[b]furan, 3-bromo-6-ethyl-6H-cyclopenta[b]furan, 3-bromo-5-propyl-6H-cyclopenta[b]furan, 3-bromo-4-propyl-6H-cyclopenta[b]furan, 3-bromo-6-propyl-6H-cyclopenta[b]furan, 2-bromo-6H-cyclopenta[b]furan, 2-bromo-5-methyl-6H-cyclopenta[b]furan, 2-bromo-4-methyl-6H-cyclopenta[b]furan, 2-bromo-6-methyl-6H-cyclopenta[b]furan, 2-bromo-5-ethyl-6H-cyclopenta[b]furan, 2-bromo-4-ethyl-6H-cyclopenta[b]furan, 2-bromo-6-ethyl-6H-cyclopenta[b]furan, 2-bromo-5-propyl-6H-cyclopenta[b]furan, 2-bromo-4-propyl-6H-cyclopenta[b]furan, 2-bromo-6-propyl-6H-cyclopenta[b]furan, 3-bromo-1-methyl-1,6-dihydro-cyclopenta[b]pyrrole, 2-bromo-1-methyl-1,6-dihydro-cyclopenta[b]pyrrole, 3-bromo-1,5-dimethyl-1,6-dihydro-cyclopenta[b]pyrrole, 2-bromo-1,5-dimethyl-1,6-dihydro-cyclopenta[b]pyrrole, 3-bromo-1-methyl-5-ethyl-1,6-dihydro-cyclopenta[b]pyrrole, 2-bromo-1-methyl-5-ethyl-1,6-dihydro-cyclopenta[b]pyrrole, 3-bromo-1-methyl-5-propyl-1,6-dihydro-cyclopenta[b]pyrrole, 2-bromo-1-methyl-5-propyl-1,6-dihydro-cyclopenta[b]pyrrole, 3-bromo-1-phenyl-1,6-dihydro-cyclopenta[b]pyrrole, 2-bromo-1-phenyl-1,6-dihydro-cyclopenta[b]pyrrole, 3-bromo-1-phenyl-5-methyl-1,6-dihydro-cyclopenta[b]pyrrole, 2-bromo-1-phenyl-5-methyl-1,6-dihydro-cyclopenta[b]pyrrole, 3-bromo-1-phenyl-5-ethyl-1,6-dihydro-cyclopenta[b]pyrrole, 2-bromo-1-phenyl-5-ethyl-1,6-dihydro-cyclopenta[b]pyrrole, 3-bromo-1-phenyl-5-propyl-1,6-dihydro-cyclopenta[b]pyrrole, 2-bromo-1-phenyl-5-propyl-1,6-dihydro-cyclopenta[b]pyrrole, 3-bromo-1-methyl-1,6-dihydro-cyclopenta[b]phosphole, 2-bromo-1-methyl-1,6-dihydro-cyclopenta[b]phosphole, 3-bromo-1,5-dimethyl-1,6-dihydro-cyclopenta[b]phosphole, 2-bromo-1,5-dimethyl-1,6-dihydro-cyclopenta[b]phosphole, 3-bromo-1-methyl-5-ethyl-1,6-dihydro-cyclopenta[b]phosphole, 2-bromo-1-methyl-5-ethyl-1,6-dihydro-cyclopenta[b]phosphole, 3-bromo-1-methyl-5-propyl-1,6-dihydro-cyclopenta[b]phosphole, 2-bromo-1-methyl-5-propyl-1,6-dihydro-cyclopenta[b]phosphole, 3-bromo-1-phenyl-1,6-dihydro-cyclopenta[b]phosphole, 2-bromo-1-phenyl-1,6-dihydro-cyclopenta[b]phosphole, 3-bromo-1-phenyl-5-methyl-1,6-dihydro-cyclopenta[b]phosphole, 2-bromo-1-phenyl-5-methyl-1,6-dihydro-cyclopenta[b]phosphole, 3-bromo-1-phenyl-5-ethyl-1,6-dihydro-cyclopenta[b]phosphole, 2-bromo-1-phenyl-5-ethyl-1,6-dihydro-cyclopenta[b]phosphole, 3-bromo-1-phenyl-5-propyl-1,6-dihydro-cyclopenta[b]phosphole, 2-bromo-1-phenyl-5-propyl-1,6-dihydro-cyclopenta[b]phosphole, 1-bromo-3-methyl-4H-cyclopenta[c]thiophene, 1-bromo-3-ethyl-4H-cyclopenta[c]thiophene, 1-bromo-3-propyl-4H-cyclopenta[c]thiophene, 1-bromo-3-methyl-4H-cyclopenta[c]furan, 1-bromo-3-ethyl-4H-cyclopenta[c]furan, 1-bromo-3-propyl-4H-cyclopenta[c]furan, 3-bromo-1-methyl-1,6-dihydro-cyclopentapyrazole, 3-bromo-1-ethyl-1,6-dihydro-cyclopentapyrazole, 3-bromo-1-propyl-1,6-dihydro-cyclopentapyrazole, 4-bromo-7H-[1]pyrindine, 4-bromo-7H-[2]pyrindine, 4-bromo-7H-cyclopentapyrimidine, 4-bromo-7H-cyclopenta[b]phosphinine, 5-bromo-7H-[1]pyrindine, 5-bromo-7H-[2]pyrindine, 5-bromo-7H-cyclopenta[b]phosphinine, 1-bromo-9H-fluorene, 2-bromo-9H-fluorene, 3-bromo-9H-fluorene, 4-bromo-9H-fluorene, 7-bromo-8H-1-thia-cyclopenta[a]indene, 7-bromo-8H-2-thia-cyclopenta[a]indene, 7-bromo-8H-3-thia-cyclopenta[a]indene, 3-bromo-8H-1-thia-cyclopenta[a]indene, 1-bromo-8H-2-thia-cyclopenta[a]indene, 7-bromo-8H-1-oxa-cyclopenta[a]indene, 7-bromo-8H-2-oxa-cyclopenta[a]indene, 7-bromo-8H-3-oxa-cyclopenta[a]indene, 3-bromo-8H-1-oxa-cyclopenta[a]indene, 1-bromo-8H-2-oxa-cyclopenta[a]indene, 4-bromo-5H-indeno[1,2-b]pyridine, 8-bromo-9H-2,6-diaza-fluorene, 1-bromo-3-methyl-3,8-dihydro-3-aza-cyclopenta[a]indene, 1-bromo-3-phenyl-3,8-dihydro-3-aza-cyclopenta[a]indene, 7-bromo-8H-1-thia-6-aza-cyclopenta[a]indene, 7-bromo-1-methyl-1,8-dihydro-1,6-diaza-cyclopenta[a]indene, 3-bromo-7H-cyclopenta[1,2-b;3,4-c']dithiophene, 3-bromo-7H-cyclopenta[1,2-b;3,4-b']dithiophene, 3-bromo-7H-cyclopenta[1,2-b;4,3-b']dithiophene, 3-bromo-4-methyl-4,7-dihydro-1-thia-4-aza-cyclopenta[a]pentalene, 3-bromo-5-methyl-5,7-dihydro-1-thia-5-aza-cyclopenta[a]pentalene, 3-bromo-6-methyl-6,7-dihydro-1-thia-6-aza-cyclopenta[a]pentalene, 3-bromo-4-phenyl-4,7-dihydro-1-thia-4-aza-cyclopenta[a]pentalene, 3-bromo-5-phenyl-5,7-dihydro-1-thia-5-aza-cyclopenta[a]pentalene, 3-bromo-6-phenyl-6,7-dihydro-1-thia-6-aza-cyclopenta[a]pentalene, 4-bromo-1H-phosphindole, 4-bromo-2-methyl-1H-phosphindole, 4-bromo-3-methyl-1H-phosphindole, 4-bromo-5-methyl-1H-phosphindole, 4-bromo-6-methyl-1H-phosphindole, 4-bromo-7-methyl-1H-phosphindole, 4-bromo-2-ethyl-1H-phosphindole, 4-bromo-3-ethyl-1H-phosphindole, 4-bromo-5-ethyl-1H-phosphindole, 4-bromo-6-ethyl-1H-phosphindole, 4-bromo-7-ethyl-1H-phosphindole, 4-bromo-2-propyl-1H-phosphindole, 4-bromo-3-propyl-1H-phosphindole, 4-bromo-5-propyl-1H-phosphindole, 4-bromo-6-propyl-1H-phosphindole, 4-bromo-7-propyl-1H-phosphindole, 6-bromo-3H-benzo[c][1,2]azaborole, 6-bromo-3-methyl-3H-benzo[c][1,2]azaborole, 6-bromo-4-methyl-3H-benzo[c][1,2]azaborole, 6-bromo-5-methyl-3H-benzo[c][1,2]azaborole, 6-bromo-7-methyl-3H-benzo[c][1,2]azaborole, 6-bromo-3-ethyl-3H-benzo[c][1,2]azaborole, 6-bromo-4-ethyl-3H-benzo[c][1,2]azaborole, 6-bromo-5-ethyl-3H-benzo[c][1,2]azaborole, 6-bromo-7-ethyl-3H-benzo[c][1,2]azaborole, 6-bromo-3-propyl-3H-benzo[c][1,2]azaborole, 6-bromo-4-propyl-3H-benzo[c][1,2]azaborole, 6-bromo-5-propyl-3H-benzo[c][1,2]azaborole, 6-bromo-7-propyl-3H-benzo[c][1,2]azaborole, 5-bromo-1H-isoindole, 5-bromo-1-methyl-1H-isoindole, 5-bromo-3-methyl-1H-isoindole, 5-bromo-4-methyl-1H-isoindole, 5-bromo-6-methyl-1H-isoindole, 5-bromo-7-methyl-1H-isoindole, 5-bromo-1-ethyl-1H-isoindole, 5-bromo-3-ethyl-1H-isoindole, 5-bromo-4-ethyl-1H-isoindole, 5-bromo-6-ethyl-1H-isoindole, 5-bromo-7-ethyl-1H-isoindole, 5-bromo-1-propyl-1H-isoindole, 5-bromo-3-propyl-1H-isoindole, 5-bromo-4-propyl-1H-isoindole, 5-bromo-6-propyl-1H-isoindole, 5-bromo-7-propyl-1H-isoindole, 6-bromo-3H-benzo[b]cyclopenta[d]thiophene, 5-bromo-3H-benzo[b]cyclopenta[d]thiophene, 7-bromo-3H-benzo[b]cyclopenta[d]thiophene, and 7-bromo-3H-benzo[b]cyclopenta[d]thiophene. Another list of preferred compounds includes all of the above compounds where "bromo" is replaced with "chloro". Another list of preferred compounds includes all of the above compounds where "bromo" is replaced with "iodo".

The metallocene precursor ligands ("ligand-S-ligand", "ligand-O-ligand", "ligand-N(R)-ligand", and "ligand-P(R)-ligand" as defined above), typically are converted to a dianionic metallocene precursor ligands or a reactive metallocene precursor ligands prior to reaction with a transition metal compound to form an invention metallocene compound. Non-limiting examples of these reactions are illustrated in Generic Reaction Schemes 9 through 13 where ligand 1 and ligand 2 have the same definition as "ligand" as defined above, R**, R*, and X* are as previously defined; Y is a Group 15 or 16 bridging heteroatom substituent bonded through the heteroatom, and preferably selected from S, O, N(R), or P(R); $M^1$ is a Group 1 atom and is preferably lithium; $M^2$ is a Group 2 atom and is preferably magnesium; M is a Group 3, 4, 5, or 6 transition metal atom or lanthanide metal atom or actinide metal atom, preferably a Group 4 transition metal atom selected from titanium, zirconium or hafnium; $R^\#$ is a hydrocarbyl and is preferably methyl, ethyl, propyl, or butyl; Sn is tin; and Si is silicon.

Metallation reactions between a dianionic metallocene precursor ligand and a transition metal compound, preferably a transition metal halide, are illustrated in Generic Reaction Schemes 14 through 16.

Metallation reactions between a reactive metallocene precursor ligand and a transition metal compound, preferably a transition metal halide, are illustrated in Generic Reaction Schemes 17 through 18.

Metallation reactions between a metallocene precursor ligand and a transition metal amide is illustrated in Generic Reaction Scheme 19. The resulting metallocene diamide can be used as a catalyst precursor, or can be converted to a metallocene dihalide by reaction with HX* where H is hydrogen and X* is halide.

Generic Reaction Scheme 9: Reaction of a metallocene precursor ligand with a Group 1 metal hydrocarbyl compound to form a dianionic metallocene precursor ligand. For this reaction, $M^1$ is preferably lithium, and R* is preferably n-butyl or methyl.

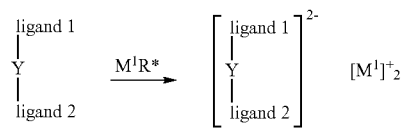

Generic Reaction Scheme 10: Reaction of a metallocene precursor ligand with a Group 2 metal hydrocarbyl compound to form a dianionic metallocene precursor ligand.

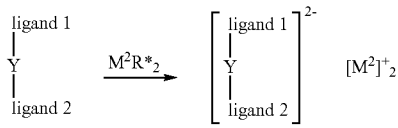

Generic Reaction Scheme 11: Reaction of a metallocene precursor ligand with a Group 2 hydrocarbyl halide (a Grignard reagent) to form a dianionic metallocene precursor ligand. In this reaction $M^2$ is preferably magnesium, $R^*$ is preferably methyl, ethyl, propyl or butyl, and $X^*$ is preferably chloride or bromide.

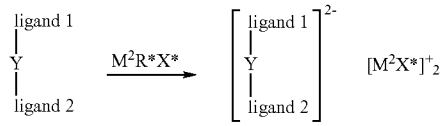

Generic Reaction Scheme 12: Reaction of a metallocene precursor ligand with a Group 1 hydrocarbyl compound followed by reaction with a trihydrocarbyltin halide to form reactive metallocene precursor ligand. In this reaction $M^1$ is preferably lithium, $R^*$ is preferably n-butyl or methyl, $R^\#$ is preferably methyl, ethyl, propyl or butyl with ethyl being most preferred, and $X^*$ is preferably chloride.

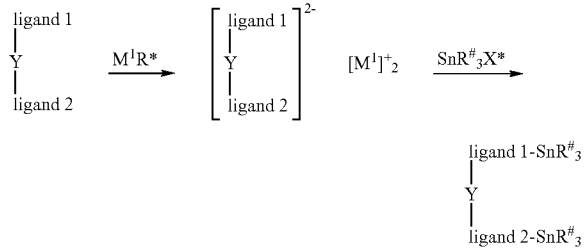

Generic Reaction Scheme 13: Reaction of a metallocene precursor ligand with a Group 1 hydrocarbyl compound followed by reaction with a trihydrocarbylsilicon halide to form reactive metallocene precursor ligand. In this reaction $M^1$ is preferably lithium, $R^*$ is preferably n-butyl or methyl, $R^\#$ is preferably methyl, ethyl, propyl or butyl with methyl being most preferred, and $X^*$ is preferably chloride.

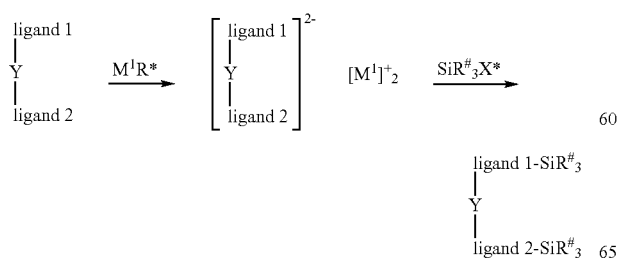

Generic Reaction Scheme 14: Reaction of a cationic Group 1 metal stabilized dianionic metallocene precursor ligand with a metal halide to form a metallocene. In this reaction $M^1$ is preferably lithium, M is preferably titanium, zirconium or hafnium, and $X^*$ is preferably chloride.

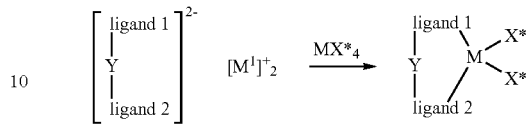

Generic Reaction Scheme 15: Reaction of a cationic Group 2 metal stabilized dianionic metallocene precursor ligand with a transition metal halide to form a metallocene. In this reaction $M^2$ is preferably magnesium, M is preferably titanium, zirconium or hafnium, and $X^*$ is preferably chloride.

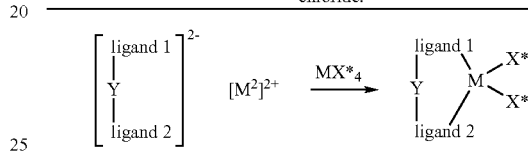

Generic Reaction Scheme 16: Reaction of a cationic Group 2 halide stabilized dianionic metallocene precursor ligand with a metal halide to form a metallocene. In this reaction $M^2$ is preferably magnesium, M is preferably titanium, zirconium or hafnium, and $X^*$ is preferably chloride or bromide.

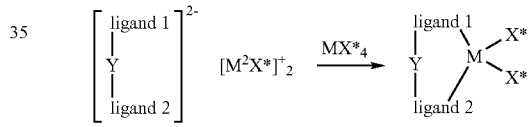

Generic Reaction Scheme 17: Reaction of a trihydrocarbyltin based reactive metallocene precursor ligand with a metal halide to form a metallocene
In this reaction M is preferably titanium, zirconium or hafnium, $R^\#$ is preferably methyl, ethyl, propyl, or butyl with ethyl being most preferred, and $X^*$ is preferably chloride.

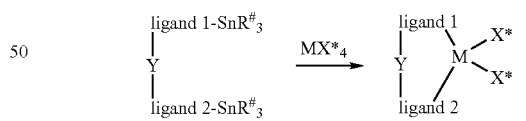

Generic Reaction Scheme 18: Reaction of a trihydrocarbylsilicon based reactive metallocene precursor ligand with a metal halide to form a metallocene. In this reaction M is preferably titanium, zirconium or hafnium, $R^\#$ is preferably methyl, ethyl, propyl, or butyl with methyl being most preferred, and $X^*$ is preferably chloride.

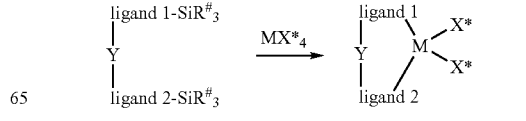

Generic Reaction Scheme 19: Reaction of a metallocene precursor ligand with a metal amide to form a metallocene diamide which optionally can further be reacted with an acid halide to from a metallocene dihalide. In this reaction M is preferably titanium, zirconium or hafnium, R** is preferably methyl, ethyl, propyl, or butyl, and X* is preferably chloride.

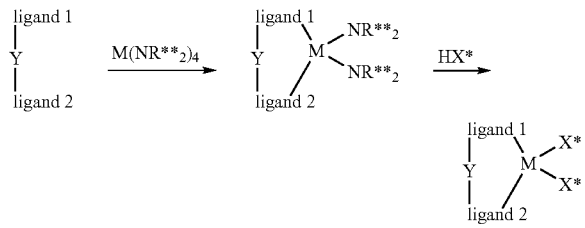

Synthetic Route 2:

This novel synthetic route involves coupling reactions, such as a Negishi coupling reaction, on a metallocene containing at least one bromide substituent. The bromine substituted metallocene ligand precursors, "Br-ligand-Y-ligand-Br" or "Br-ligand-Y-ligand" where Y is S, O, N(R), P(R), can be made by methods previously illustrated above. This method is referred to as the indirect bromination method.

Additionally, 4,4'-bridged "Br-ligand-Y-ligand-Br" can be prepared by coupling two "Br-ligands" in the 4,4' positions as previously illustrated, followed by reaction of bromine, and then acid/MeOH to form a metallocene precursor ligand. For this reaction, when Y is $N(R^{})$ or $P(R^{})$ and $R^{}$ is aryl, the aryl ring should be substituted in the 4-position to prevent bromination of R, unless this is desired. This route also requires that the "ligand-Y-ligand" to be brominated is not a substituted or unsubstituted indene, but rather a substituted or unsubstituted indane, such as a 1-methoxyindane or a dioxalane protected 1-indanone. This method is referred to as the direct bromination method.

More specific, but non-limiting, examples are illustrated below in Generic Reaction Schemes 20-25 (indirect bromination method) and Generic Reaction Schemes 26-29 (direct bromination method) and Reaction Schemes 18-19 (indirect bromination method) and Reaction Schemes 10-23 (direct bromination method), following the teachings from above, and where R is, independently, hydrogen, substituted or unsubstituted hydrocarbyl, substituted or unsubstituted fluorocarbyl, fluorine, substituted or unsubstituted silylcarbyl, or polar groups provided that R does not contain Cl, Br or I substituents; R* is hydrocarbyl, preferably alkyl, more preferably methyl, propyl or butyl; R** is, independently, substituted or unsubstituted hydrocarbyl; X* is halide, preferably chloride; "ligand" (as in "dibromo-ligand" ($Br_2$-ligand), "bromo-ligand" (Br-ligand), "hydroxy-ligand" (HO-ligand), "primary amine substituted-ligand" (RNH-ligand), "Br-ligand-Y-ligand-Br", and "Br-ligand-Y-ligand") is a substituted or unsubstituted indenyl ligand, a substituted or unsubstituted heteroindenyl ligand, a substituted or unsubstituted fluorenyl ligand, a substituted or unsubstituted heterofluorenyl ligand, or a substituted or unsubstituted cyclopentadienyl or heterocyclopentadienyl ligand; "bromo-ligand" is a "ligand" substituted with a bromine atom at a $sp^2$ carbon atom of the "ligand", or alternatively substituted with a chlorine or iodine atom at a $sp^2$ carbon atom of the "ligand"; "dibromo-ligand" is a "ligand" substituted with two bromine atoms, each at a $sp^2$ carbon atom of the "ligand", or alternatively substituted with a two chlorine atoms, or two iodine atoms, or one bromine atom and one chlorine atom, or one bromine atom and one iodine atom, or one chlorine atom and one iodine atom at each at a $sp^2$ carbon atom of the "ligand"; "primary amine substituted ligand" is a "ligand" substituted with a primary amine substituent (—NHR) at a $sp^2$ carbon atom of the "ligand"; "hydroxy-ligand" is a "ligand substituted" with a hydroxy substituent at a $sp^2$ carbon atom of the "ligand"; "Br-ligand-Y-ligand-Br" comprises two "ligand" s as defined above, which may or may not be same, and are bridged by a Y atom, provided that at least one "ligand" is not a substituted or unsubstituted cyclopentadienyl or heterocyclopentadienyl ligand, and at least one "ligand"s bonded to the Y atom as described in the definition of E of formula (1), and additionally, each "ligand" is bonded to a bromine atom at a $sp^2$ carbon atom of the "ligand"; and "Br-ligand-Y-ligand" comprises two "ligand"s as defined above, which may or may not be same, and are bridged by a Y atom, provided that at least one "ligand" is not a substituted or unsubstituted cyclopentadienyl or heterocyclopentadienyl ligand, and at least one "ligand" is bonded to the Y atom as described in the definition of E of formula (1), and additionally, one "ligand" is bonded to a bromine atom at a $sp^2$ carbon atom of the "ligand";. The designations "ligand 1", "ligand 2", "ligand-Br 1", and "ligand-Br 2" in the equations below are used to illustrate "ligands" that are not required to be identical.

Generic Reaction Scheme 20: Formation of a symmetrical bromine substituted ligand with a S-bridge.

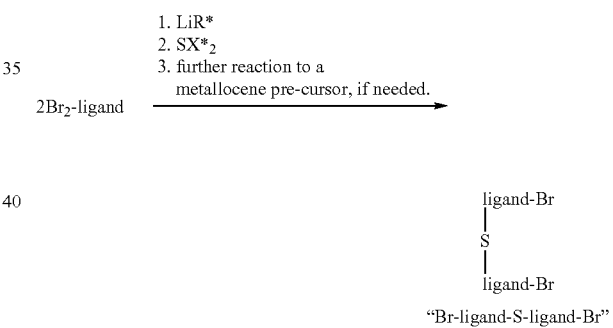

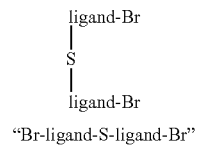

"Br-ligand-S-ligand-Br"

Generic Reaction Scheme 21: Formation of an unsymmetrical bromine substituted ligand with a S-bridge.

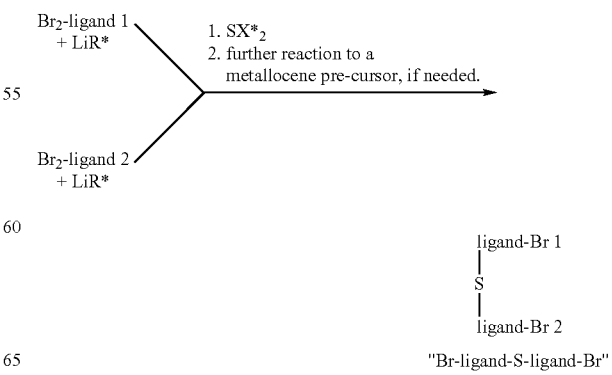

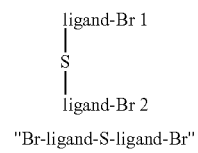

"Br-ligand-S-ligand-Br"

Generic Reaction Scheme 22: Formation of an unsymmetrical bromine substituted ligand with a S-bridge.

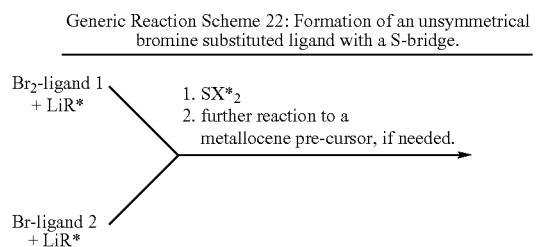

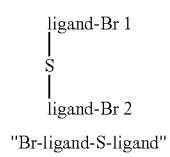

"Br-ligand-S-ligand"

Generic Reaction Scheme 23: Formation of a symmetrical bromine substituted ligand with a phosphorous bridge.

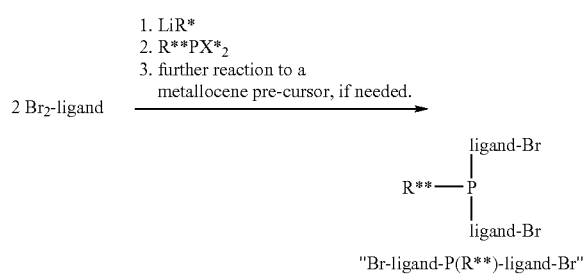

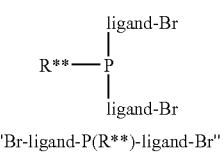

"Br-ligand-P(R**)-ligand-Br"

Generic Reaction Scheme 24: Formation of an unsymmetrical bromine substituted ligand with a phosphorous bridge.

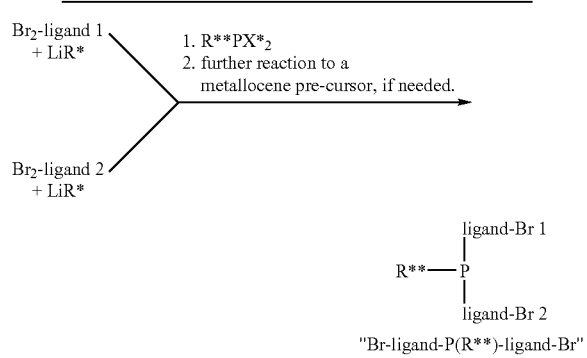

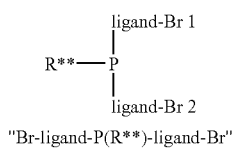

"Br-ligand-P(R**)-ligand-Br"

Generic Reaction Scheme 25: Formation of an unsymmetrical bromine substituted ligand with a phosphorous bridge.

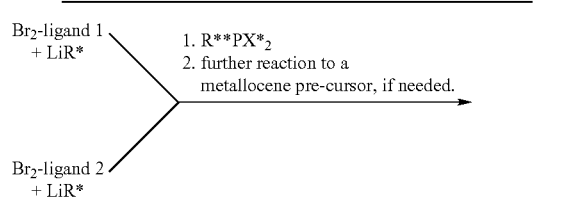

-continued

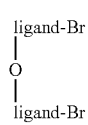

"Br-ligand-P(R**)-ligand"

Generic Reaction Scheme 26: Formation of a bromine substituted ligand with a sulfur bridge.

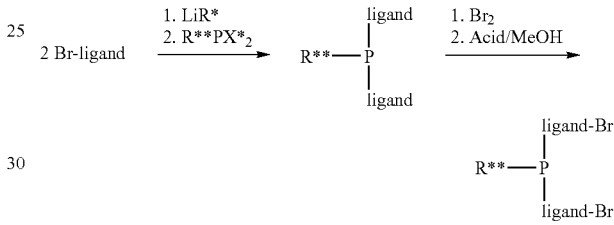

Generic Reaction Scheme 27: Formation of a bromine substituted ligand with a phosphorous bridge.

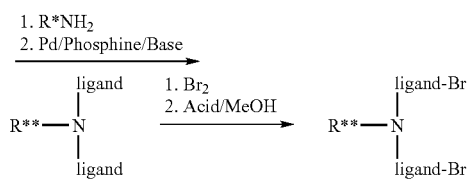

Generic Reaction Scheme 28: Formation of a bromine substituted ligand with a nitrogen bridge.

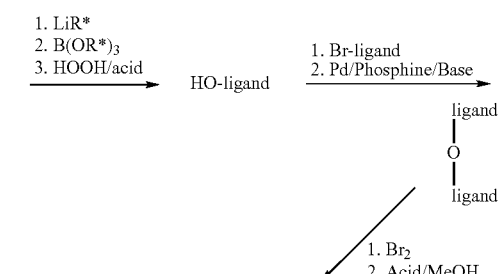

Generic Reaction Scheme 29: Formation of a bromine substituted ligand with a oxygen bridge.

Reaction Scheme 18: Formation of a 4,4'-sulfur bridged bis-indene ligand from a 4,7-dibromo-1-methoxyindane.

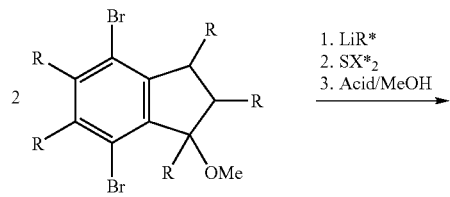

"a 4,7-dibromo-1-methoxyindane"

Reaction Scheme 20: Formation of a 4,4'-sulfur bridged bis-indene ligand from a 4-bromo-1-methoxyindane.

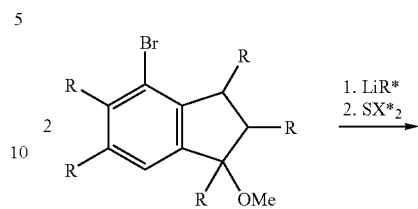

"a 4-bromo-1-methoxyindane"

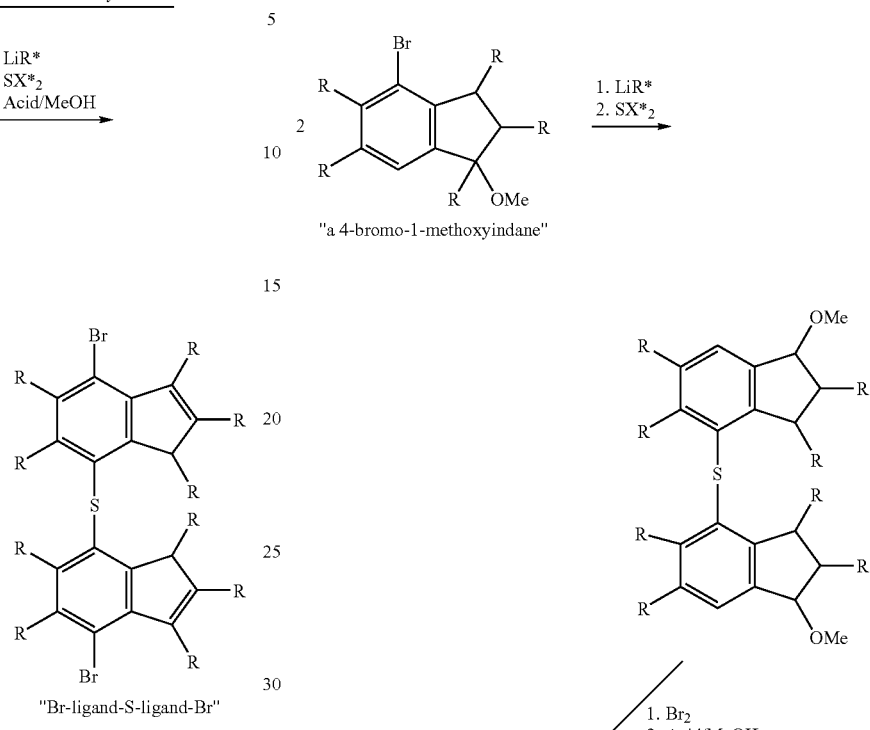

"Br-ligand-S-ligand-Br"

Reaction Scheme 19: Formation of a 4,4'-phosphorous bridged bis-indene ligand from a 4,7-dibromo-1-methoxyindane.

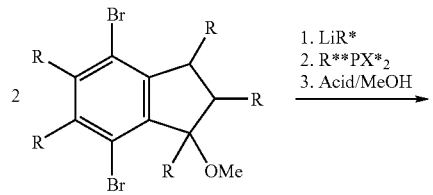

"a 4,7-dibromo-1-methoxyindane"

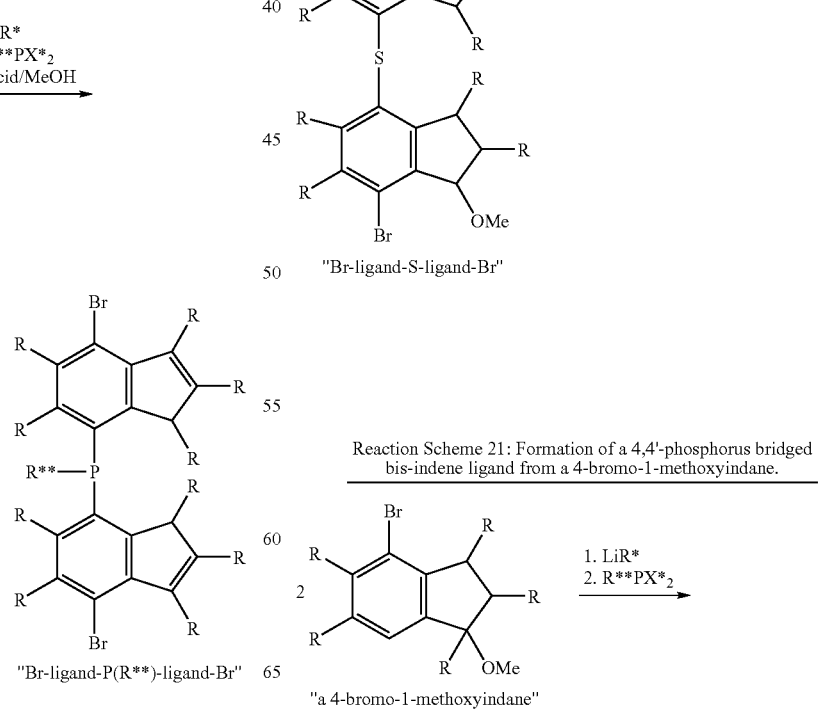

"Br-ligand-P(R**)-ligand-Br"

Reaction Scheme 21: Formation of a 4,4'-phosphorus bridged bis-indene ligand from a 4-bromo-1-methoxyindane.

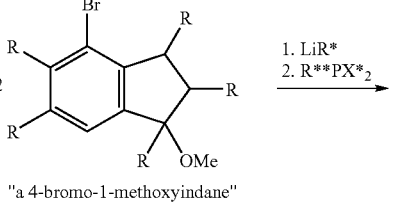

"a 4-bromo-1-methoxyindane"

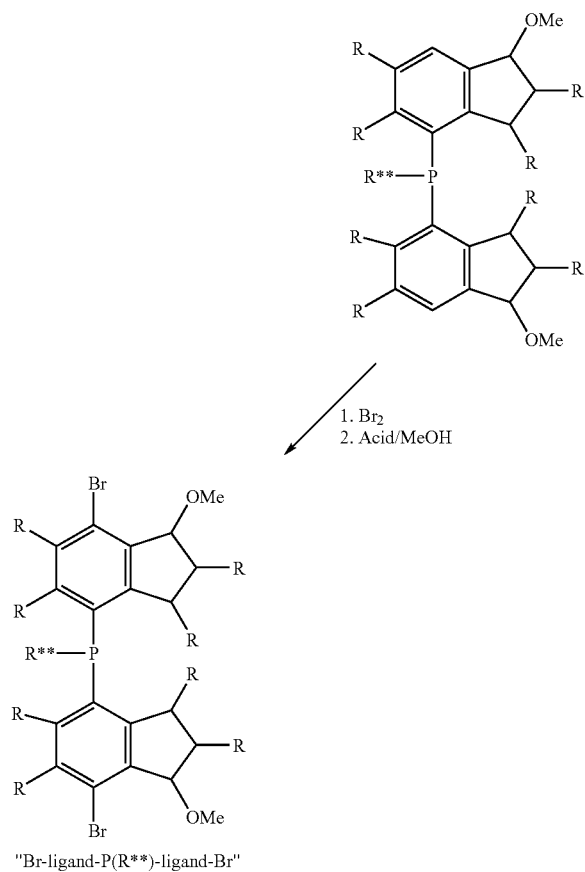

"Br-ligand-P(R**)-ligand-Br"

Reaction Scheme 22: Formation of a 4,4'-oxygen bridged bis-indene ligand from a 4-bromo-1-methoxyindane.

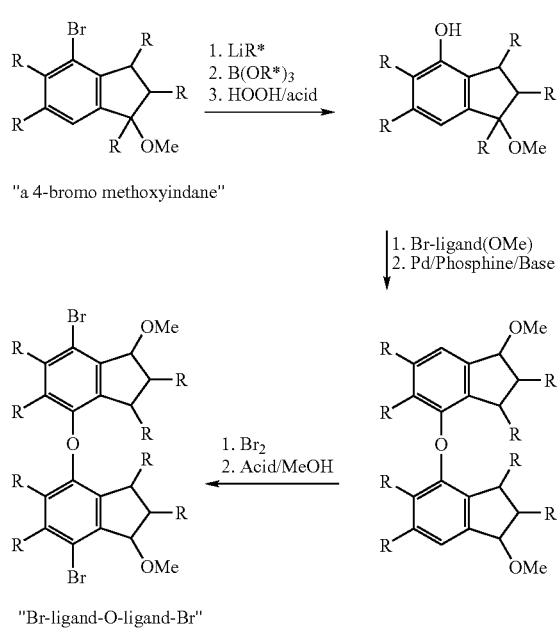

"Br-ligand-O-ligand-Br"

Reaction Scheme 23: Formation of a 4,4'-nitrogen bridged bis-indene ligand from a 4-bromo-1-methoxyindane.

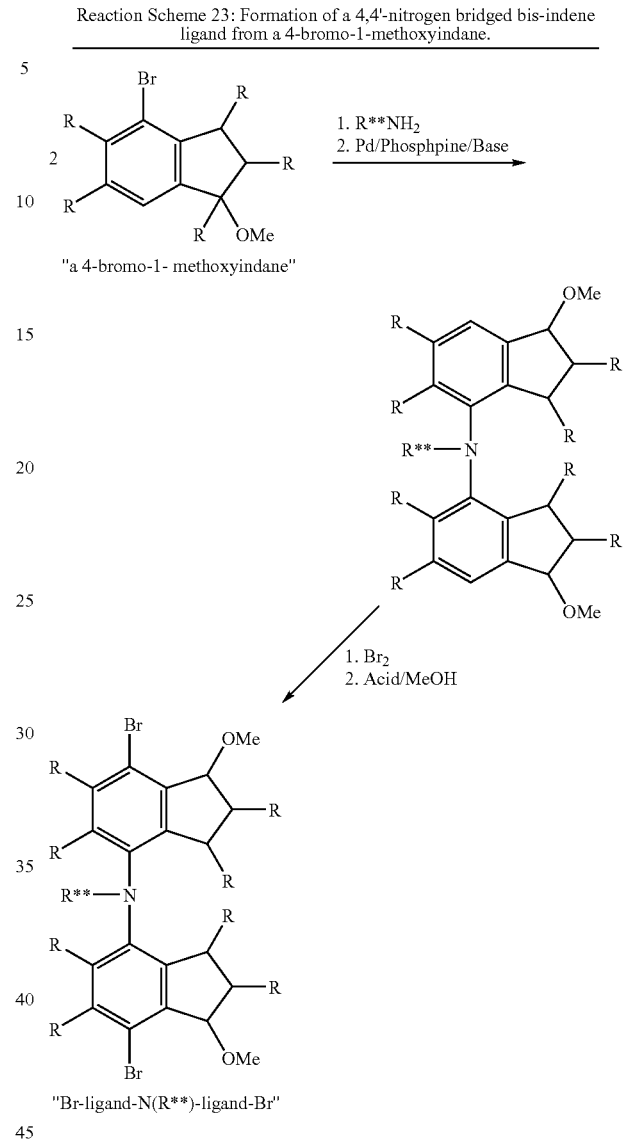

"Br-ligand-N(R**)-ligand-Br"

The metallocene precursor ligands ("Br-ligand-S-ligand-Br", "Br-ligand-O-ligand-Br", "Br-ligand-N(R)-ligand-Br", and "Br-ligand-P(R)-ligand-Br" as defined above), typically are converted to a dianionic metallocene precursor ligands or a reactive metallocene precursor ligands prior to reaction with a transition metal compound to form an invention metallocene compound. These reactions are illustrated in Generic Reaction Schemes 8 through 13 where ligand 1 and or ligand 2 are replaced by ligand-Br and or ligand-Br 1 and or ligand-Br 2. Use of Generic Reaction Scheme 12 is preferred.

The subsequent metallation reactions are preformed as illustrated in Generic Reaction Schemes 14 through 19 where ligand 1 and or ligand 2 are replaced by ligand-Br and or ligand-Br 1 and or ligand-Br 2. Use of Generic Reaction Scheme 17 is preferred.

The Negishi coupling reactions on the bromine substituted metallocenes follows Generic Reaction Schemes 30 and 31 and are illustrated below where M is as defined in formulae 2-17, Y is S, O, N(R), P(R); R** is, independently, substituted or unsubstituted hydrocarbyl; X* is halide, preferably chloride, bromide or iodide; "ligand" (as in "Br-ligand-Y-ligand-Br", "Br-ligand-Y-ligand", "R-ligand-Y-ligand-R", and "R-ligand-Y-ligand") is a substituted or unsubstituted indenyl ligand, a substituted or unsubstituted heteroindenyl ligand, a substituted or unsubstituted fluorenyl ligand, a substituted or unsubstituted heterofluorenyl ligand, or a substituted or unsubstituted cyclopentadienyl or heterocyclopentadienyl ligand; "Br-ligand-Y-ligand-Br" comprises two "ligand"s as defined above, which may or may not be same, and are bridged by a Y atom, provided that at least one "ligand" is not a substituted or unsubstituted cyclopentadienyl or heterocyclopentadienyl ligand, and at least one "ligand" is bonded to the Y atom as described in the definition of E of formula (1), and additionally, each "ligand" is bonded to a bromine atom at a sp$^2$ carbon atom of the "ligand", or alternatively substituted with a chlorine or iodine atom at the sp$^2$ carbon of each "ligand"; "Br-ligand-Y-ligand" comprises two "ligand"s as defined above, which may or may not be same, and are bridged by a Y atom, provided that at least one "ligand" is not a substituted or unsubstituted cyclopentadienyl or heterocyclopentadienyl ligand, and at least one "ligand" is bonded to the Y atom as described in the definition of E of formula (1), and additionally, one "ligand" is bonded to a bromine atom at a sp$^2$ carbon atom of the "ligand", or alternatively substituted with a chlorine or iodine atom at the sp$^2$ carbon of the "ligand"; "R-ligand-Y-ligand-R" comprises two "ligand"s as defined above, which may or may not be same, and are bridged by a Y atom, provided that at least one "ligand" is not a substituted or unsubstituted cyclopentadienyl or heterocyclopentadienyl ligand, and at least one "ligand" is bonded to the Y atom as described in the definition of E of formula (1), and additionally, each "ligand" is bonded to a R substituent; and "R-ligand-Y-ligand" comprises two "ligand"s as defined above, which may or may not be same, and are bridged by a Y atom, provided that at least one "ligand" is not a substituted or unsubstituted cyclopentadienyl or heterocyclopentadienyl ligand, and at least one "ligand" is bonded to the Y atom as described in the definition of E of formula (1), and additionally, one "ligand" is bonded to a R substituent.

The Negishi coupling reaction uses a substituted or unsubstituted hydrocarbyl zinc reagent (R**ZnX* or R**$_2$Zn where X* and R** are as previously defined) with a palladium catalyst such as bis(tri-tert-butylphosphine)palladium to react with the bromine substituent(s) on the metallocene. After reaction, trimethylsilyl chloride is added to react with excess organozinc reagent present. The entire reaction mixture is then evaporated to dryness and THF contamination of the metallocene product is eliminated by refluxing the metallocene in toluene.

When the metallocene bridge, Y, is P(R), it is first oxidized to P(=O)R using air or another soft oxidizing agent. After the Negishi coupling reaction, the metallocene bridge, P(=O)R, is reduced back to P(R) using trichlorosilane. Alternatively, the metallocene bridge, P(R), can be reacted with elemental sulfur or selenium to from the respective P(=S)R and P(=Se)R metallocene bridges. After the Negishi coupling reaction, the P(=S)R and P(=Se)R metallocene bridges can be reduced back to P(R) using trichlorosilane. (THF is tetrahydrofuran).

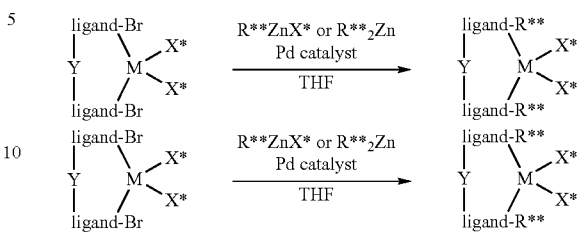

Generic Reaction Scheme 30: Negishi coupling reaction on a metallocene.

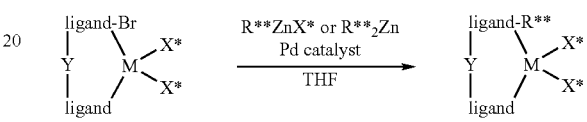

Generic Reaction Scheme 31: Negishi coupling reaction on a metallocene.

Palladium catalysts that may be used in the Negishi coupling reaction on a metallocene include bis(tri-tert-butyl) phosphine palladium, bis(tricyclohexylphosphine) palladium, trans-dichlorbis(tricyclohexylphosphine) palladium (II), trans-dichlorbis(triphenylphosphine) palladium(II), trans-dichlorbis(tri-o-tolylphosphine) palladium(II), tetrakis (triphenylphosphine)palladium (0), dichloro[1,1'-bis(diphenylphosphino)ferrocene]palladium (II), or palladium compounds such as palladium(II) acetate, palladium(0) dibenzylideneacetone, palladium (II) chloride, palladium (II) bromide, palladium (II) iodide, allyl palladium chloride dimer, palladium (II) trifluoroacetate, bis(tri-o-tolylphosphine) palladium (II) chloride, dichloro(1,5-cyclooctadiene) palladium (II), dichlorobis(benzonitrile) palladium (II), dichlorobis(acetonitrile) palladium (II), bis(2-methylallyl) palladium chloride dimer, crotyl palladium chloride dimer, tris(dibenzylideneacetone) dipalladium (0), or dichlorobis (benzonitrile)palladium (II) used in combination with any of the phosphine and phosphine like reagents (A through H) listed above. When the metallocene is substituted with an iodo ligand, any of the palladium compounds listed above will work to catalyze the coupling reaction even in the absence of phosphine and phosphine like reagents.

Preferred palladium catalysts that may be used in the Negishi coupling reaction on a metallocene include bis(tri-tert-butyl)phosphine palladium, or palladium(II) acetate, palladium(0) dibenzylideneacetone used in combination with any of the phosphine and phosphine like reagents (A through H) listed above.

Organozinc reagents, R**ZnX* or R**$_2$Zn, that may be used in the Negishi coupling reaction are those where X* selected from chloride, bromide or iodide, and where R** is, independently, selected from methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl;

halocarbyls and all isomers of halocarbyls including perfluoropropyl, perfluorobutyl, perfluoropentyl, perfluorohexyl, perfluoroheptyl, perfluorooctyl, perfluorononyl, perfluorodecyl, perfluoroundecyl, perfluorododecyl, perfluorotridecyl, perfluorotetradecyl, perfluoropentadecyl, perfluorohexadecyl, perfluoroheptadecyl, perfluorooctadecyl, perfluorononadecyl, perfluoroeicosyl, perfluoroheneicosyl, perfluorodocosyl, perfluorotricosyl, perfluorotetracosyl, perfluoropentacosyl, perfluorohexacosyl, perfluoroheptacosyl, perfluorooctacosyl, perfluorononacosyl, perfluorotriacontyl, perfluorobutenyl, perfluorobutynyl, fluoropropyl, fluorobutyl, fluoropentyl, fluorohexyl, fluoroheptyl, fluorooctyl, fluorononyl, fluorodecyl, fluoroundecyl, fluorododecyl, fluorotridecyl, fluorotetradecyl, fluoropentadecyl, fluorohexadecyl, fluoroheptadecyl, fluorooctadecyl, fluorononadecyl, fluoroeicosyl, fluoroheneicosyl, fluorodocosyl, fluorotricosyl, fluorotetracosyl, fluoropentacosyl, fluorohexacosyl, fluoroheptacosyl, fluorooctacosyl, fluorononacosyl, fluorotriacontyl, difluorobutyl, trifluorobutyl, tetrafluorobutyl, pentafluorobutyl, hexafluorobutyl, heptafluorobutyl, octafluorobutyl;

substituted hydrocarbyl radicals and all isomers of substituted hydrocarbyl radicals including methoxymethyl, methoxyethyl, methoxypropyl, methoxybutyl, methoxypentyl, methoxyhexyl, methoxyheptyl, methoxyoctyl, methoxynonyl, methoxydecyl, methoxyundecyl, methoxydodecyl, methoxytridecyl, methoxytetradecyl, methoxypentadecyl, methoxyhexadecyl, methoxyheptadecyl, methoxyoctadecyl, methoxynonadecyl, methoxyeicosyl, methoxyheneicosyl, methoxydocosyl, methoxytricosyl, methoxytetracosyl, methoxypentacosyl, methoxyhexacosyl, methoxyheptacosyl, methoxyoctacosyl, methoxynonacosyl, methoxytriacontyl, ethoxymethyl, ethoxyethyl, ethoxypropyl, ethoxybutyl, ethoxypentyl, ethoxyhexyl, ethoxyheptyl, ethoxyoctyl, ethoxynonyl, ethoxydecyl, ethoxyundecyl, ethoxydodecyl, ethoxytridecyl, ethoxytetradecyl, ethoxypentadecyl, ethoxyhexadecyl, ethoxyheptadecyl, methoxyoctadecyl, ethoxynonadecyl, ethoxyeicosyl, ethoxyheneicosyl, ethoxydocosyl, ethoxytricosyl, ethoxytetracosyl, ethoxypentacosyl, ethoxyhexacosyl, ethoxyheptacosyl, methoxyoctacosyl, ethoxynonacosyl, ethoxytriacontyl, propoxymethyl, propoxyethyl, propoxypropyl, propoxybutyl, propoxypentyl, propoxyhexyl, propoxyheptyl, propoxyoctyl, propoxynonyl, propoxydecyl, propoxyundecyl, propoxydodecyl, propoxytridecyl, propoxytetradecyl, propoxypentadecyl, propoxyhexadecyl, propoxyheptadecyl, mpropoxyoctadecyl, propoxynonadecyl, propoxyeicosyl, propoxyheneicosyl, propoxydocosyl, propoxytricosyl, propoxytetracosyl, propoxypentacosyl, propoxyhexacosyl, propoxyheptacosyl, mpropoxyoctacosyl, propoxynonacosyl, propoxytriacontyl, butoxymethyl, butoxyethyl, butoxypropyl, butoxybutyl, butoxypentyl, butoxyhexyl, butoxyheptyl, butoxyoctyl, butoxynonyl, butoxydecyl, butoxyundecyl, butoxydodecyl, butoxytridecyl, butoxytetradecyl, butoxypentadecyl, butoxyhexadecyl, butoxyheptadecyl, butoxyoctadecyl, butoxynonadecyl, butoxyeicosyl, butoxyheneicosyl, butoxydocosyl, butoxytricosyl, butoxytetracosyl, butoxypentacosyl, butoxyhexacosyl, butoxyheptacosyl, butoxyoctacosyl, butoxynonacosyl, butoxytriacontyl, dimethylaminopropyl, dimethylaminobutyl, dimethylaminopentyl, dimethylaminohexyl, dimethylaminoheptyl, dimethylaminooctyl, dimethylaminononyl, dimethylaminodecyl, dimethylaminoundecyl, dimethylaminododecyl, dimethylaminotridecyl, dimethylaminotetradecyl, dimethylaminopentadecyl, dimethylaminohexadecyl, dimethylaminoheptadecyl, dimethylaminooctadecyl, dimethylaminononadecyl, dimethylaminoeicosyl, dimethylaminoheneicosyl, dimethylaminodocosyl, dimethylaminotricosyl, dimethylaminotetracosyl, dimethylaminopentacosyl, dimethylaminohexacosyl, dimethylaminoheptacosyl, dimethylaminooctacosyl, dimethylaminononacosyl, dimethylaminotriacontyl, methoxybenzyl, ethoxybenzyl, propoxybenzyl, butoxybenzyl, methoxyphenyl, ethoxyphenyl, propoxyphenyl, butoxyphenyl, dimethylaminobenzyl, diethylaminobenzyl, dipropylaminobenzyl, dibutylaminobenzyl, dimethylaminophenyl, diethylaminophenyl, dipropylaminophenyl, dibutylaminophenyl, methylthiobenzyl, ethylthiobenzyl, propylthiobenzyl, butylthiobenzyl, methylthiophenyl, ethylthiophenyl, propylthiophenyl, butylthiophenyl, dimethylphosphinobenzyl, diethylphosphinobenzyl, dipropylphosphinobenzyl, dibutylphosphinobenzyl, methoxychlorophenyl, methoxybromophenyl, methoxyiodophenyl, methoxyfluorophenyl, ethoxychlorophenyl, ethoxybromophenyl, ethoxyiodophenyl, ethoxyfluorophenyl, propoxychlorophenyl, propoxybromophenyl, propoxyiodophenyl, propoxyfluorophenyl, butoxychlorophenyl, butoxybromophenyl, butoxyiodophenyl, butoxyfluorophenyl, dimethylchloroaminophenyl, diethylchloroaminophenyl, dipropoxychlorophenyl, dibutoxychlorophenyl, dimethylbromoaminophenyl, diethylbromoaminophenyl, dipropoxybromophenyl, dibutoxybromophenyl, dimethyliodoaminophenyl, diethyliodoaminophenyl, dipropoxyiodophenyl, dibutoxyiodophenyl, dimethylfluoroaminophenyl, diethylfluoroaminophenyl, dipropoxyfluorophenyl, dibutoxyfluorophenyl, dimethylaminochlorophenyl, diethylaminochlorophenyl, dipropylaminochlorophenyl, dibutylaminochlorophenyl, dimethylaminobromophenyl, diethylaminobromophenyl, dipropylaminobromophenyl, dibutylaminobromophenyl, dimethylaminoiodophenyl, diethylaminoiodophenyl, dipropylaminoiodophenyl, dibutylaminoiodophenyl, dimethylaminofluorophenyl, diethylaminofluorophenyl, dipropylaminofluorophenyl, dibutylaminofluorophenyl, methylthiochlorophenyl, ethylthiochlorophenyl, propylthiochlorophenyl, butylthiochlorophenyl, methylthiobromophenyl, ethylthiobromophenyl, propylthiobromophenyl, butylthiobromophenyl, methylthioiodophenyl, ethylthioiodophenyl, propylthioiodophenyl, butylthioiodophenyl, methylthiofluorophenyl, ethylthiofluorophenyl, propylthiofluorophenyl, butylthiofluorophenyl, benzoyl acid methyl ester, benzoyl acid ethyl ester, benzoyl acid propyl ester, benzoyl acid butyl ester, and the like; all isomers of silylcarbyl radicals including trimethylsilylpropyl, trimethylsilylbutyl, trimethylsilylpentyl, trimethylsilylhexyl, trimethylsilylheptyl, trimethylsilyloctyl, trimethylsilylnonyl, trimethylsilyldecyl, trimethylsilylundecyl, trimethylsilyldodecyl, trimethylsilyltridecyl, trimethylsilyltetradecyl, trimethylsilylpentadecyl, trimethylsilylhexadecyl, trimethylsilylheptadecyl, trimethylsilyloctadecyl, trimethylsilylnonadecyl, trimethylsilyleicosyl, trimethylsilylheneicosyl, trimethylsilyldocosyl, trimethylsilyltricosyl, trimethylsilyltetracosyl, trimethylsilylpentacosyl, trimethylsilylhexacosyl, trimethylsilylheptacosyl, trimethylsilyloctacosyl, trimethylsilylnonacosyl, trimethylsilyltriacontyl, dimethylphenylsilylpropyl, dimethylphenylsilylbutyl, dimethylphenylsilylpentyl, dimethylphenylsilylhexyl, dimethylphenylsilylheptyl, dimethylphenylsilyloctyl, dimethylphenylsilylnonyl, dimethylphenylsilyldecyl, dimethylphenylsilylundecyl, dimethylphenylsilyldodecyl, dimethylphenylsilyltridecyl, dimethylphenylsilyltetradecyl, dimethylphenylsilylpentadecyl, dimethylphenylsilylhexadecyl, dimethylphenylsilylheptadecyl, dimethylphenylsilyloctadecyl, dimethylphenylsilylnonadecyl, dimethylphenylsilyleicosyl, dimethylphenylsilylheneicosyl, dimethylphenylsilyldocosyl, dimethylphenylsilyltricosyl, dimethylphenylsilyltetracosyl, dimethylphenylsilylpentacosyl, dimethylphenylsilylhexacosyl, dimethylphenylsilylheptacosyl, dimethylphenylsilyloctacosyl, dimethylphenylsilylnonacosyl, dimethylphenylsilyltriacontyl, triethylsilylpropyl, triethylsilylbutyl, triethylsilylpentyl, triethylsilylhexyl, triethylsilylheptyl, triethylsilyloctyl, triethylsilylnonyl, triethylsilyldecyl, triethylsilylundecyl, triethylsilyldodecyl, triethylsilyltridecyl, triethylsilyltetradecyl, triethylsilylpentadecyl, triethylsilylhexadecyl, triethylsilylheptadecyl, triethylsilyloctadecyl, triethylsilylnonadecyl, triethylsilyleicosyl, triethylsilylheneicosyl, triethylsilyldocosyl, triethylsilyltricosyl, triethylsilyltetracosyl, triethylsilylpentacosyl, triethylsilylhexacosyl, triethylsilylheptacosyl, triethylsilyloctacosyl, triethylsilylnonacosyl, triethylsilyltriacontyl, 1,1-dimethylsilolanyl, 1,1-dimethyl-silinanyl, 1,1-dimethyl-silepanyl, 1,1-diethyl-silolanyl, 1,1-diethyl-silinanyl, 1,1-diethyl-silepanyl and the like;

phenyl and isomers of methylphenyl, ethylphenyl, propylphenyl, butylphenyl, pentylphenyl, hexylphenyl, heptylphenyl, octylphenyl, nonylphenyl, decylphenyl, undecylphenyl, dodecylphenyl, tridecylphenyl, tetradecylphenyl, pentadecylphenyl, hexadecylphenyl, heptadecylphenyl, octadecylphenyl, nonadecylphenyl, eicosylphenyl, heneicosylphenyl, docosylphenyl, tricosylphenyl, tetracosylphenyl, pentacosylphenyl, hexacosylphenyl, heptacosylphenyl, octacosylphenyl, nonacosylphenyl, triacontylphenyl, dimethylphenyl, diethylphenyl, dipropylphenyl, dibutylphenyl, dipentylphenyl, dihexylphenyl, diheptylphenyl, dioctylphenyl, dinonylphenyl, didecylphenyl, diundecylphenyl, didodecylphenyl, trimethylphenyl, triethylphenyl, tripropylphenyl, tributylphenyl, tripentylphenyl, trihexylphenyl, triheptylphenyl, trioctylphenyl, trinonylphenyl, tridecylphenyl, triundecylphenyl, tridodecylphenyl, tetramethylphenyl, tetraethylphenyl, tetrapropylphenyl, tetrabutylphenyl, tetrapentylphenyl, tetrahexylphenyl, pentamethylphenyl, pentaethylphenyl, pentapropylphenyl, pentabutylphenyl, ethylmethylphenyl, methylpropylphenyl, butylmethylphenyl, methylpentylphenyl, hexylmethylphenyl, heptylmethylphenyl, methyloctylphenyl, nonylmethylphenyl, decylmethylphenyl, methylundecylphenyl, dodecylmethylphenyl, dimethylethylphenyl, dimethylpropylphenyl, butyldimethylphenyl, dimethylpentylphenyl, dimethylhexylphenyl, dimethylheptylphenyl, dimethyloctylphenyl, dimethylnonylphenyl, decyldimethylphenyl, dimethylundecylphenyl, dimethyldodecylphenyl, diethylmethylphenyl, diethylpropylphenyl, butyldiethylphenyl, diethylpentylphenyl, diethylhexylphenyl, diethylheptylphenyl, diethyloctylphenyl, diethylnonylphenyl, decyldiethylphenyl, diethylundecylphenyl, diethyldodecylphenyl, dipropylmethylphenyl, dipropylethylphenyl, butyldipropylphenyl, dipropylpentylphenyl, dipropylhexylphenyl, dipropylheptylphenyl, dipropyloctylphenyl, dipropylnonylphenyl, decyldipropylphenyl, dipropylundecylphenyl, dipropyldodecylphenyl, dibutylmethylphenyl, dibutylethylphenyl, dibutylpropylphenyl, dibutylpentylphenyl, dibutylhexylphenyl, dibutylheptylphenyl, dibutyloctylphenyl, dibutylnonylphenyl, decyldibutylphenyl, dibutylundecylphenyl, dibutyldodecylphenyl, vinylphenyl, propenylphenyl, butenylphenyl, methylvinylphenyl, trimethylsilylphenyl, trimethylgermylphenyl, trifluoromethylphenyl, bis(triflouromethyl)phenyl and the like;

halo substituted phenyl and all isomers of halo substituted phenyl (where halo is, independently, fluoro, chloro, and iodo) including halophenyl, dihalophenyl, trihalophenyl, tetrahalophenyl, and pentahalophenyl; from all isomers of halo substituted hydrocarbyl substituted phenyl (where halo is, independently, fluoro, chloro, and iodo) including halomethylphenyl, dihalomethylphenyl, trihalomethylphenyl, tetrahalomethylphenyl, haloethlyphenyl, dihaloethylphenyl, trihaloethylphenyl, tetrahaloethylphenyl, halopropylphenyl, dihalopropylphenyl, trihalopropylphenyl, tetrahalopropylphenyl, halobutylphenyl, dihalobutylphenyl, trihalobutylphenyl, tetrahalobutylphenyl, dihalodimethylphenyl, dihalo(trifluoromethyl)phenyl and the like;

from all isomers of benzyl, and all isomers of hydrocarbyl substituted benzyl including methylbenzyl, dimethylbenzyl, trimethylbenzyl, tetramethylbenzyl, pentamethylbenzyl ethylbenzyl, diethylbenzyl, triethylbenzyl, tetraethylbenzyl, pentaethylbenzyl, propylbenzyl, dipropylbenzyl, tripropylbenzyl, tetrapropylbenzyl, pentapropylbenzyl butylbenzyl, dibutylbenzyl, tributylbenzyl, tetrabutylbenzyl, pentabutylbenzyl, hexylbenzyl, dihexylbenzyl, trihexylbenzyl, tetrahexylbenzyl, pentahexylbenzyl, dimethylethylbenzyl, dimethylpropylbenzyl, dimethylbutylbenzyl, dimethylpentylbenzyl, dimethylhexylbenzyl, diethylmethylbenzyl, diethylpropylbenzyl, diethylbutylbenzyl, diethylpentylbenzyl, diethylhexylbenzyl, dipropylmethylbenzyl, dipropylethylbenzyl, dipropylbutylbenzyl, dipropylpentylbenzyl, dipropylhexylbenzyl, dibutylmethylbenzyl, dibutylethylbenzyl, dibutylpropylbenzyl, dibutylpentylbenzyl, dibutylhexylbenzyl, methylethylbenzyl, methylpropylbenzyl, methylbutylbenzyl, methylpentylbenzyl, methylhexylbenzyl, ethylpropylbenzyl, ethylbutylbenzyl, ethylpentylbenzyl, ethylhexylbenzyl, propylbutylbenzyl, propylpentylbenzyl, propylhexylbenzyl, butylpentylbenzyl, butylhexylbenzyl, trimethylsilylbenzyl, bis(trimethylsilyl)benzyl, trimethylgermylbenzyl, diphenylmethyl and the like;

trihydrocarbyl-silyl, -germyls, -stannyls and -plumbyls including trimethylsilyl, trimethylgermyl, trimethylstannyl, trimethylplumbyl, triethylsilyl, triethylgermyl, dimethylethylsilyl, dimethylethylgermyl, diethylmethylsilyl, diethylmethylgermyl, triphenylsilyl, triphenylgermyl, and all isomers of tripropylsilyl, tripropylgermyl, tributylsilyl, tributylgermyl, tris(trifluormethyl)silyl, bis(perfluoromethyl)methylsilyl, and the like;

all isomers of hydrocarbyl substituted isomers of polycyclic areneyls including pyrenyl, aceanthrylenyl, acenaphthylene, acephenanthrylenyl, azulenyl biphenylenyl, chrysenyl, coronenyl, fluoranthenyl, fluorenyl, heptacenyl, heptalenyl, heptaphenyl, hexacenyl, hexaphenyl, as-indacenyl, s-indecenyl, indenyl, ovalenyl, pentacenyl, pentalenyl, pentaphenyl, perylenyl, phenalenyl, phenanthrenyl, picenyl, pleiadenyl, pyranhrenyl, rubicenyl, naphthacenyl, tetraphenylenyl, trinaphthylenyl, triphenylenyl, hexahelicenyl, naphthyl, anthracenyl, dibenza[a,b]anthracenyl, indanyl, acenaphthenyl, cholanthrenyl, aceanthrenyl, acephenanthrenyl, 1,2,3,4-tetrahydronapthalene, fullerenyl, and the like;

all isomers of hydrocarbyl substituted alicyclic, monocyclic and polycyclic hydrocarbon rings including cyclopropyl, cyclobutyl, cyclopentyl, cyclohexyl, cyclohexenyl, cycloheptyl, cyclooctyl, cyclononyl, cyclodecyl, cycloundecyl, and cyclododecyl, dimethylcyclohexyl, norbornyl, norbornenyl, adamantyl, cubanyl, prismanyl, spiro[4,5]decanyl, and the like;

all isomers of heterocycles and hydrocarbyl substituted heterocycles including acridarsinyl, acridinyl, acridophosphinyl, 1H-acrindolinyl, anthrazinyl, anthyridinyl, arsanthridinyl, arsindolyl, arsindolizinyl, arsinolinyl, arsinolizinyl, benzofuranyl, carbazolyl, β-carbolinyl, chromenyl, thiochromenyl, cinnolinyl, furanyl (also called furyl), imidazolyl, indazolyl, indolyl, indolizinyl, isoarsindolyl, isoarsinolinyl, isobenzofuranyl, isochromenyl, isothiochromenyl, isoindolyl, isophosphindolyl, isophosphinolinyl, isoquinolinyl, isothiazolyl, isoxazolyl, naphthyridinyl, oxazolyl, perimidinyl, phenanthrazinyl, phenanthridinyl, phenanthrolinyl, phenazinyl, phosphanthridinyl, phosphindolyl, phosphindolizinyl, phosphinolizinyl, phthalazinyl, pteridinyl, phthaloperinyl, purinyl, pyranyl, thiopyranal, pyrazinyl, pyrazolyl, pyridazinyl, pyridinyl, pyrindinyl, pyrimidinyl, pyrrolyl, pyrrolizinyl, quinazolinyl, quindolinyl, 1H-quinindolinyl, quinolinyl, quinolizinyl, quinoxalinyl, selenophenyl, thebenidinyl, thiazolyl, thiophenyl (also called thienyl), triphenodioxazinyl, triphenodithiazinyl, xanthenyl, chromanyl, thiochromanyl, imidazolidinyl, indolinyl, isochromanyl, isothiochromanyl, isoindolinyl, morpholinyl, piperazinyl, piperidinyl, pyrozolidinyl, pyrrolidinyl, quinuclidinyl, methylthiopehnyl, methylfuranyl, ethylthiopehnyl, ethylfuranyl, propylthiopehnyl, propylfuranyl, butylthiopehnyl, butylfuranyl, pentylthiopehnyl, pentylfuranyl, hexylthiopehnyl, hexylfuiranyl, dimethylacridarsinyl, dimethylacridinyl, dimethylacridophosphinyl, dimethyl-1H-acrindolinyl, dimethylanthrazinyl, dimethylanthyridinyl, dimethylarsanthridinyl, dimethylarsindolyl, dimethylarsindolizinyl, dimethylarsinolinyl, dimethylarsinolizinyl, dibutylbenzofuiranyl, dibutylcarbazolyl, dibutyl-β-carbolinyl, dibutylchromenyl, dibutylthiochromenyl, butylcinnolinyl, dibutylfuranyl, dimethylimidazolyl, dimethylindazolyl, dipropylindolyl, dipropylindolizinyl, dimethylisoarsindolyl, methylisoarsinolinyl, dimethylisobenzofuranyl, diphenylisochromenyl, dibutylisothiochromenyl, phenylisoindolyl, butylisophosphindolyl, dibutylisophosphinolinyl, dimethylisoquinolinyl, methylisothiazolyl, butylisoxazolyl, butylnaphthyridinyl, dimethyloxazolyl, methylphenylperimidinyl, tetrabutylphenanthrazinyl, propylphenanthridinyl, dibutylphenanthrolinyl, tetramethylphenazinyl, butylphosphanthridinyl, phenylphosphindolyl, dimethylphosphindolizinyl, methylphosphinolizinyl, dibutylphthalazinyl, trimethylpteridinyl, methylphthaloperinyl, dimethylpurinyl, dibutylpyranyl, dibutylthiopyranal, trimethylpyrazinyl, phenylpyrazolyl, dipropylpyridazinyl, dimethylpyridinyl, methylpropylpyrindinyl, triethylpyrimidinyl, dibutylpyrrolyl, diethylpyrrolizinyl, dibutylquinazolinyl, dibutylquindolinyl, dibutyl-1H-quinindolinyl, dimethylquinolinyl, propylquinolizinyl, methylquinoxalinyl, methylbutylselenophenyl, methylthebenidinyl, dimethylthiazolyl, trimethylthiophenyl, dibutyltriphenodioxazinyl, dibutyltriphenodithiazinyl, dibutylxanthenyl, trimethylchromanyl, dimethylthiochromanyl, dimethylimidazolidinyl, dimethylindolinyl, dibutylisochromanyl, dibutylisothiochromanyl, phenylisoindolinyl, dibutylmorpholinyl, dimethylpiperazinyl, dimethylpiperidinyl, dimethylpyrozolidinyl, dimethylpyrrolidinyl, bipyridyl, pyrido[2,1,6-de]quinolizinyl, hexamethylquinuclidinyl, 5,7-dioxa-6-phosphadibenzo[a, c]cycloheptene-6-oxide, 9-oxa-10-phosphaphenanthrene-10-oxide and the like.

Preferred zinc reagents include: methyl zinc chloride, phenyl zinc chloride, para-tolyl zinc chloride, para-tert-butylphenyl zinc chloride, biphenyl zinc chloride, meta-tolyl zinc chloride, ortho-tolyl zinc chloride, ortho-methoxyphenyl zinc chloride, para-fluorophenyl zinc chloride, meta-trifluoromethylphenyl zinc chloride, mesityl zinc chloride, 1-naphthyl zinc chloride, 2-thienyl zinc chloride, 2-furyl zinc chloride, 1-benzothien-2-yl zinc chloride, 1-benzofur-2-yl zinc chloride, 5-methyl-2-thienyl zinc chloride, and 5-methyl-2-furyl zinc chloride.

Preferred bromine substituted metallocenes include those metallocenes comprising one or more of the bromo ligands described above as preferred in Reaction Schemes 1-17 and Generic Reaction Schemes 1-8. In particular titanocenes, hafnocenes, and zirconocenes comprising such bromo ligands are preferred.

While the Negishi coupling reactions are preferred, other palladium catalyzed coupling reactions such as the Kumada reaction (using R**MgX*, Ni catalyzed), the Suzuki reaction (using NaBPh$_4$/LiBR$_3$Ar), the Stille reaction (using R$_3$SnAr), the Heck reaction (using H$_2$C=CHR), and the Sonogashira reaction (using HC≡CR) may be used, where Ar is an arene, R** is as defined above, X* is chlorine, bromine and iodine.

The transfer-agent will normally be an organometallic transfer-agent comprising a RM' fragment, where the metal M' is selected from boron, tin, magnesium, lithium, aluminum, silicon, copper, and zinc, and R is selected from hydrocarbyl, substituted hydrocarbyl, halocarbyl, substituted halocarbyl, silylcarbyl, or a germylcarbyl radical. Alternatively, the transfer-agent can be an organic molecule RH where R is as described above. Preferred examples of R** include methyl, ethyl, n-propyl, isopropyl, n-butyl, sec-butyl, isobutyl, tert-butyl, cyclopentyl, cyclohexyl, benzyl, 4-methylbenzyl, 4-methoxybenzyl, 4-trifluoromethyl, diphenylmethyl, adamantyl, cyclohexenyl, isopropenyl, 2-phenylethenyl, trimethylsilylmethyl, neopentyl, methoxymethyl, 3-methoxypropyl, dimethylaminomethyl, diphenylphosphinomethyl, 2-pyridyl, 4-pyridyl, 2-thienyl, 2-benzothienyl, 2-benzofuryl, 3-(N-methylindolyl), phenyl, 2-methylphenyl, 3-methylphenyl, 4-methylphenyl, 4-tert-butylphenyl, 2,6-dimethylphenyl, 2,6-diisopropylphenyl, 3,5-dimethylphenyl, 2,5-dimethylphenyl, 3,5-diisopropylphenyl, 3,5-di-tert-butylphenyl, 2-isopropylphenyl, 3-trifluoromethylphenyl, 4-fluorophenyl, 4-methoxyphenyl, 2-methoxyphenyl, 4-dimethylaminophenyl, 1-naphthyl, 2-naphthyl, and pentafluorophenyl.

Different cross-coupling reactions can be used to produce substituted metallocene compounds according to the process described herein. Generic reaction schemes for coupling reactions are illustrated below where M, X, Y, y, are as previously defined.

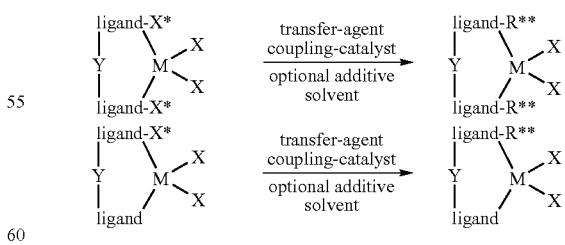

Essentially, the processes described above for producing the substituted transition metal compounds, particularly substituted metallocene compounds, involve a coupling reaction or cross-coupling reaction in which a transfer-agent comprising a RM' unit, or an organic molecule RH, is reacted with an a transition metal compound comprising at least one ligand having a halogen or sulfonate substituent directly bonded to any $sp^2$ carbon atom at a bondable ring position of said ligand, where said substituted ligand is represented by ligand-X* where X* is chloro, bromo, iodo or sulfonate (sulfonate=$OSO_2G$ where G is a hydrocarbyl or halocarbyl), usually in the presence of a coupling-catalyst or combination of coupling-catalysts and, when required, in the presence of additives, to produce a substituted transition metal compound wherein the ligand(s) of said substituted transition metal compound is represented by ligand-R. The transfer-agent, comprising a RM' unit, contains the nucleophile R** to be transferred to ligand-X*, as well as a metal-containing fragment M'. Typical metals "M'" useful herein include Al, Zr, Si, B, Li, Mg, Sn, Cu, Zn, and mixtures thereof. R** is substituted or unsubstituted hydrocarbyl, substituted or unsubstituted halocarbyl, substituted or unsubstituted silylcarbyl, or substituted or unsubstituted germylcarbyl radical. Ligand-X* includes, but is not limited to, substituted or unsubstituted indenyl ligand, a substituted or unsubstituted heteroindenyl ligand, a substituted or unsubstituted fluorenyl ligand, a substituted or unsubstituted heterofluorenyl ligand, or a substituted or unsubstituted cyclopentadienyl or heterocyclopentadienyl ligand. Coupling-catalysts are catalytic reagents that promote the reaction and are typically selected from nickel, palladium, copper, silver and cobalt compounds. The additives are compounds that enhance the coupling reaction by, for example, increasing regioselectivity, increasing enantioselectivity, suppressing undesired side reactions, activating the coupling-catalyst or other reagents, regenerating the coupling-catalyst, stabilizing the coupling-catalyst or intermediates, coordinating counterions, or accelerating the coupling reaction.

Transfer agents include but are not limited to boron reagents such as $R**B(OR*^{\#})_2$, $R**B(OR*^{\#})$ or $R**B(R*^{\#})_2$, where $R*^{\#}$ is, independently, hydrogen or hydrocarbyl, and two or more $R*^{190}$ may join together to form a substituted or unsubstituted saturated, partially saturated or aromatic cyclic or polycyclic ring structure; tin reagents such as $R**SnR*^{\#\#}_3$, where R* is an alkyl, preferably methyl or butyl; copper reagents such as RCu; magnesium reagents such as RMgX*, where X* is Cl or Br; zinc reagents such as RZnX or R**ZnR*, where X is Cl or Br; aluminum alkyls; lithium reagents such as LiR; zirconium reagents such as $RZrCp_2Cl$; and organosilanes such as $RSiX*'_n R*'_{3-n}$, where R*' is an alkyl or aryl group, X*' is a halide, preferably F and n=0-3.

Catalysts for coupling reactions include but are not limited to nickel complexes such as nickel(II) chloride, nickel(II) bromide, (2,2'-bipyridine)dibromonickel(II), dichlorobis(triphenylphosphine)nickel(II), dibromobis(triphenylphosphine)nickel(II), dichloro[1,2-bis(diphenylphosphino)ethane]nickel(II), dichloro[1,3-bis(diphenylphosphino)propane]nickel(II), dichloro[1,1'-bis(diphenylphosphino)ferrocene]nickel(II), bis(1,5-cyclooctadiene)nickel(0), tetrakis(triphenylphosphine)nickel(0), and nickel(II) acetylacetonate; palladium-phoshine complexes such as bis(tri (tert-butyl)phosphine)palladium, bis(tricyclohexylphosphine)palladium, bis(tri(iso-propyl)phosphine)palladium, dichlorobis(tri(iso-propyl)phosphine)palladium(II), dichlorobis(tri(o-tolyl) phoshine)palladium(II), trans-dichlorobis (tricyclohexylphosphine)palladium(II), trans-dichlorobis (triphenylphosphine)palladium(II), trans-dichlorobis(tri-o-tolylphosphine) palladium(II), tetrakis(triphenylphosphine) palladium(0), tetrakis(tri(o-tolyl)phosphine)palladium(0), dichloro[1,1'-bis(diphenylphosphino)ferrocene]palladium (II), dichloro[1,2-bis(diphenylphosphino)ethane]palladium (II), dichloro[1,3-bis(diphenylphosphino)propane]palladium(II), dichloro[1,4-bis(diphenylphosphino)butane]palladium(II), dichlorobis(triphenylphosphine)palladium(II) polymer bound or tetrakis(triphenylphosphine)palladium(0) polymer bound (both are available from Aldrich Chemical Company where the polymer is a divinylbenzene crosslinked polystyrene), benzylbis(triphenylphosphine)palladium(II) chloride, trans-di(µ-acetato)bis[o-(di(o-tolyl)phosphino) benzyl]dipalladium(II), and trans-di(µ-acetato)bis[o-(dimesityl-phosphino)benzyl]dipalladium(II);

palladium compounds such as palladium(II) acetate, palladium(0) dibenzylideneacetone, palladium(II) chloride, palladium(II) bromide, palladium(II) iodide, palladium(II) acetylacetonate, allylpalladium chloride dimer, bis(2-methylallyl) palladium chloride dimer, crotylpalladium chloride dimer, palladium(II) trifluoroacetate, dichloro(1,5-cyclooctadiene) palladium(II), dichlorobis(benzonitrile)palladium(II), dichlorobis(acetonitrile)palladium(II), and tris(dibenzylideneacetone)dipalladium(0);

copper catalysts such as copper(I) cyanide, copper(I) chloride, copper(I) iodide, copper(I) trifluoroacetate, copper(II) fluoride, copper(I) chloride, and copper(II) iodide;

silver catalysts such as silver(I) iodide; and cobalt catalysts such as cobalt(II) bromide, and cobalt(II) acetylacetonate.

Additives include but are not limited to bases such as sodium methoxide, sodium ethoxide, potassium tert-butoxide, lithium hydroxide, sodium hydroxide, potassium hydroxide, barium hydroxide, thallium hydroxide, triethylamine, ethyldiisopropylamine, benzyldimethylamine, propylamine, butylamine, diethylamine, diisopropylamine, sodium acetate, potassium acetate, sodium carbonate, potassium carbonate, cesium carbonate, calcium carbonate, thallium carbonate, sodium bicarbonate, potassium phosphate, pyridine, N-methylpyrrolidinone, piperidine, 2,2,5,5,6-pentamethylpiperidine, pyrrolidine, diaza[2.2.2]bicyclooctane, and any of the phosphine and phosphine like reagents (A through H) listed above/below; salts such as lithium chloride, sodium chloride, potassium chloride, sodium bromide, sodium iodide, potassium fluoride, cesium fluoride, tetrabutylammonium fluoride, tetrabutylammonium chloride, tetrabutylammonium bromide, tetraethylammonium chloride, tetrapropylammonium bromide, benzyltriethylammonium bromide, benzyltrioctylammonium chloride, tris(diethylamino)sulfonium difluoro(trimethyl)silicate, nickel(II) bromide, silver(I) carbonate, silver(I) phosphate, silver(I) nitrate, silver (I) acetate, silver trifluoroacetate, silver(I) oxide, thallium(I) carbonate, thallium(I) acetate, zinc(II) chloride, zinc(II) bromide, copper(I) cyanide, copper(I) chloride, copper(I) bromide, copper(I) iodide, copper(II) chloride, and copper(II) oxide; and other reagents such as chlorotrimethylsilane, 18-crown-6, triphenylarsine, and triphenylantimony.

In another embodiment this invention relates to ligands represented by the formula:

HE-Y-AH, or $R_3SnE$-Y-$ASnR_3$, or $R_3SiE$-Y-$ASiR_3$, wherein:

H is hydrogen; Sn is tin; Si is silicon; each R is, independently, a hydrocarbyl group; preferably methyl, ethyl, propyl or butyl, E is: 1) a substituted or unsubstituted indenyl ligand that is bonded to Y through the four, five, six or seven position of the indenyl ring, or 2) a substituted or unsubstituted heteroindenyl ligand that is bonded to Y through the four, five or six position of the heteroindenyl ring, provided that the bonding position is not the same as the position of the ring heteroatom, or 3) a substituted or unsubstituted fluorenyl ligand that is bonded to Y through the one, two, three, four, five, six, seven or eight position of the fluorenyl ring, or 4) a substituted or unsubstituted heterofluorenyl ligand that is bonded to Y through the one, two, three, four, five or six position of the heteroindenyl ring, provided that the bonding position is not the same as the position of the ring heteroatom;

A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, a substituted or unsubstituted heterofluorenyl ligand, or other mono-anionic ligand; and Y is a Group 15 or 16 bridging heteroatom substituent that is bonded via the heteroatom to E and A.

Mixed Catalysts

Mixed catalyst systems can also be used, for example, the invention catalyst can be used in conjunction with a "second catalyst" in the same reactor or in a series of reactors where the invention catalyst produces oligomers, macromers, or polymers with olefinic end-groups, and the "second catalyst" incorporates these oligomers, macromers, or polymers into a polymer backbone as a copolymer with other monomers, such as ethylene, propylene, butene, and other C2 to C20 olefins. Alternatively, the invention catalyst can be used in conjunction with a second catalyst in the same reactor or in a series of reactors where the second catalyst produces oligomers, macromers, or polymers with olefinic end-groups, and the invention catalyst incorporates these oligomers, macromers, or polymers into a polymer backbone as a copolymer with other monomers, such as ethylene, propylene, butene, and other C2 to C20 olefins. The "second catalyst" can be of the same family as the invention catalyst, or can be from a completely different catalyst family. Likewise, the invention catalyst can be used in conjunction with a "second catalyst" in the same reactor or in a series of reactors where the invention catalyst and the "second catalyst" produces mixtures or blends of polymers.

Invention polymerization catalyst systems can comprise additional olefin polymerization catalysts, sometimes referred to as the "second catalyst". These additional olefin polymerization catalysts are any of those well known in the art to catalyze the olefin to polyolefin reaction. Some invention catalysts systems include Group-4-6 metallocenes as additional olefin polymerization catalysts. Metallocenes include (un)bridged compounds containing one (mono(cyclopentadienyl) metallocenes) or two (bis(cyclopentadienyl) metallocenes) (un)substituted cyclopentadienyl ligand(s). In bridged metallocenes, a single, cyclopentadienyl ligand connects to a heteroatom ligand with both coordinating to the metal center, or two cyclopentadienyl ligands connect together with both cyclopentadienyl ligands coordinating to the metal center. Typical catalysts and their precursors are well known in the art. Suitable description appears in the patent literature, for example U.S. Pat. Nos. 4,871,705, 4,937,299, 5,324,800, EP-A-0418044, EP-A-0591756, WO-A-92/00333 and WO-A-94/01471. Some embodiments select the metallocene compounds from mono- or bis-cyclopentadienyl-substituted, Group-4, -5, and -6 metals in which cyclopentadienyls are (un)substituted with one or more groups or are bridged to each other or to a metal-coordinated heteroatom. Some embodiments select similar metallocene compounds except they are not necessarily bridged to each other or to a metal-coordinated heteroatom. See U.S. Pat. Nos. 5,278,264 and 5,304,614.

Some invention catalysts systems include the following additional olefin polymerization catalysts. Metallocene compounds suitable for linear polyethylene or ethylene-containing copolymer production (where copolymer means comprising at least two different monomers) are essentially those disclosed in WO-A-92/00333, WO 97/44370 and U.S. Pat. Nos. 5,001,205, 5,057,475, 5,198,401, 5,304,614, 5,308,816 and 5,324,800. Selection of metallocene compounds for isotactic or syndiotactic polypropylene blend production, and their syntheses, are well-known in the patent and academic literature, e.g. *Journal of Organometallic Chemistry* 369, 359-370 (1989). Typically, those catalysts are stereorigid, asymmetric, chiral, or bridged-chiral metallocenes. Invention activators are suited for activating these types of catalyst precursors.

Likewise, some invention catalysts systems include the following additional olefin polymerization catalysts: mono-cyclopentadienyl metallocenes with Group-15 or -16 heteroatoms connected, through a bridging group, to a cyclopentadienyl-ligand ring carbon. Both the cyclopentadienyl Cp-ligand and the heteroatom connect to a transition metal. Some embodiments select a Group-4 transition metal. Additionally, unbridged monocyclopentadienyl, heteroatom-containing Group-4 components of WO 97/22639 will function with this invention. Moreover, transition metal systems with high-oxidation-state, Group-5-10 transition-metal centers are known and can serve as the additional olefin polymerization catalysts with invention catalyst systems.

Invention catalyst systems can use non-cyclopentadienyl, Group-4-5 precursor compounds as the additional olefin polymerization catalysts. Non-cyclopentadienyl, Group-4-5 precursor compounds are activable to stable, discrete cationic complexes include those containing bulky, chelating, diamide ligands, such as described in U.S. Pat. No. 5,318,935 and "Conformationally Rigid Diamide Complexes: Synthesis and Structure of Tantalum (III) Alkyne Derivatives", D. H. McConville, et al, *Organometallics* 1995, 14, 3154-3156. U.S. Pat. No. 5,318,935 describes bridged and unbridged, bis-amido catalyst compounds of Group-4 metals capable of α-olefins polymerization. Bridged bis(arylamido) Group-4 compounds for olefin polymerization are described by D. H. McConville, et al., in *Organometallics* 1995, 14, 5478-5480. Synthetic methods and compound characterization are presented. Further work appearing in D. H. McConville, et al, *Macromolecules* 1996, 29, 5241-5243, describes bridged bis (arylamido) Group-4 compounds that are polymerization catalysts for 1-hexene. Additional invention-suitable transition-metal compounds include those described in WO 96/40805. Cationic Group-3- or Lanthanide olefin polymerization complexes are disclosed in copending U.S. application Ser. No. 09/408,050, filed 29 Sep. 1999, and its equivalent PCT/US99/22690. A monoanionic bidentate ligand and two monoanionic ligands stabilize those catalyst precursors; they are activable with this invention ionic cocatalysts. Other suitable Group-4-5 non-metallocene catalysts are bimetallocyclic catalyst compounds comprising two independently selected Group-4-5 metal atoms directly linked through two bridging groups to form cyclic compounds.

Invention catalyst systems can use transition metal catalyst precursors that have a 2+ oxidation state as the additional olefin polymerization catalyst. Typical $Ni^{2+}$ and $Pd^{2+}$ complexes are diimines, see "New Pd(II)- and Ni(II)-Based Catalysts for Polymerization of Ethylene and α-Olefins", M. Brookhart, et al, *J. Am. Chem. Soc.*, 1995, 117, 6414-6415, WO 96/23010 and WO 97/02298. See additionally the related bis(imino) Group-8 and -9 organometallic compounds described by V. C. Gibson and others in "Novel olefin polymerization catalysts based on iron and cobalt", Chem. Commun., 849-850, 1998.

For a review of other potential catalysts used in combination or series with the invention catalysts, see S. D. Ittel and L. K. Johnson, Chem. Rev. 2000, 1000, 1169 and V. C. Gibson and S. K. Spitzmesser, Chem. Rev. 2003, 103, 283.

Activators and Catalyst Activation

The catalyst precursors, when activated by a commonly known activator such as methyl alumoxane, form active catalysts for the polymerization or oligomerization of olefins. Activators that may be used include alumoxanes such as methyl alumoxane, modified methyl alumoxane, ethyl alumoxane, iso-butyl alumoxane and the like; Lewis acid activators include triphenyl boron, tris-perfluorophenyl boron, tris-perfluorophenyl aluminum and the like; Ionic activators include dimethylanilinium tetrakis perfluorophenyl borate, triphenyl carbonium tetrakis perfluorophenyl borate, dimethylanilinium tetrakis perfluorophenyl aluminate, and the like.

A co-activator is a compound capable of alkylating the transition metal complex, such that when used in combination with an activator, an active catalyst is formed. Co-activators include alumoxanes such as methyl alumoxane, modified alumoxanes such as modified methyl alumoxane, and aluminum alkyls such trimethyl aluminum, tri-isobutyl aluminum, triethyl aluminum, and tri-isopropyl aluminum. Co-activators are typically only used in combination with Lewis acid activators and ionic activators when the pre-catalyst is not a dihydrocarbyl or dihydride complex.

The alumoxane component useful as an activator typically is an oligomeric aluminum compound represented by the general formula $(R^x—Al—O)_n$, which is a cyclic compound, or $R^x(R^x—Al—O)_nAlR^x{}_2$, which is a linear compound. In the general alumoxane formula, $R^x$ is independently a $C_1$-$C_{20}$ alkyl radical, for example, methyl, ethyl, propyl, butyl, pentyl, isomers thereof, and the like, and "n" is an integer from 1-50. Most preferably, $R^x$ is methyl and "n" is at least 4. Methyl alumoxane and modified methyl alumoxanes are most preferred. For further descriptions see, EP 0 279 586, EP 0 594 218, EP 0 561 476, WO94/10180 and U.S. Pat. Nos. 4,665,208, 4,874,734, 4,908,463, 4,924,018, 4,952,540, 4,968,827, 5,041,584, 5,091,352, 5,103,031, 5,157,137, 5,204,419, 5,206,199, 5,235,081, 5,248,801, 5,329,032, 5,391,793, and 5,416,229.

When an alumoxane or modified alumoxane is used, the catalyst-precursor-to-activator molar ratio is from about 1:3000 to 10:1; alternatively, 1:2000 to 10:1; alternatively 1:1000 to 10:1; alternatively, 1:500 to 1:1; alternatively 1:300 to 1:1; alternatively 1:200 to 1:1; alternatively 1:100 to 1:1; alternatively 1:50 to 1:1; alternatively 1:10 to 1:1. When the activator is an alumoxane (modified or unmodified), some embodiments select the maximum amount of activator at a 5000-fold molar excess over the catalyst precursor (per metal catalytic site). The preferred minimum activator-to-catalyst-precursor ratio is 1:1 molar ratio.

Ionic activators (at times used in combination with a co-activator) may be used in the practice of this invention. Preferably, discrete ionic activators such as $[Me_2PhNH][B(C_6F_5)_4]$, $[Ph_3C][B(C_6F_5)_4]$, $[Me_2PhNH][B((C_6H_3\text{-}3,5\text{-}(CF_3)_2))_4]$, $[Ph_3C][B((C_6H_3\text{-}3,5\text{-}(CF_3)_2))_4]$, $[NH_4][B(C_6H_5)_4]$ or Lewis acidic activators such as $B(C_6F_5)_3$ or $B(C_6H_5)_3$ can be used. Preferred co-activators, when used, are alumoxanes such as methyl alumoxane, modified alumoxanes such as modified methyl alumoxane, and aluminum alkyls such as tri-isobutyl aluminum, and trimethyl aluminum.

It is within the scope of this invention to use an ionizing or stoichiometric activator, neutral or ionic, such as tri(n-butyl) ammonium tetrakis (pentafluorophenyl) borate, a trisperfluorophenyl boron metalloid precursor or a trisperfluoronaphthyl boron metalloid precursor, polyhalogenated heteroborane anions (WO 98/43983), boric acid (U.S. Pat. No. 5,942,459) or combination thereof.

Examples of neutral stoichiometric activators include tri-substituted boron, tellurium, aluminum, gallium and indium or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, naphthyl or mixtures thereof. Even more preferably, the three groups are halogenated, preferably fluorinated, aryl groups. Most preferably, the neutral stoichiometric activator is trisperfluorophenyl boron or trisperfluoronaphthyl boron.

Ionic stoichiometric activator compounds may contain an active proton, or some other cation associated with, but not coordinated to, or only loosely coordinated to, the remaining ion of the ionizing compound. Such compounds and the like are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are herein fully incorporated by reference.

Ionic catalysts can be prepared by reacting a transition metal compound with an activator, such as $B(C_6F_6)_3$, which upon reaction with the hydrolyzable ligand (X') of the transition metal compound forms an anion, such as $([B(C_6F_5)_3(X')]^-)$, which stabilizes the cationic transition metal species generated by the reaction. The catalysts can be, and preferably are, prepared with activator components which are ionic compounds or compositions. However preparation of activators utilizing neutral compounds is also contemplated by this invention.

Compounds useful as an activator component in the preparation of the ionic catalyst systems used in the process of this invention comprise a cation, which is preferably a Bronsted acid capable of donating a proton, and a compatible non-coordinating anion which anion is relatively large (bulky), capable of stabilizing the active catalyst species which is formed when the two compounds are combined and said anion will be sufficiently labile to be displaced by olefinic diolefinic and acetylenically unsaturated substrates or other neutral Lewis bases such as ethers, nitriles and the like. Two classes of compatible non-coordinating anions have been disclosed in EPA 277,003 and EPA 277,004 published 1988: 1) anionic coordination complexes comprising a plurality of lipophilic radicals covalently coordinated to and shielding a central charge-bearing metal or metalloid core, and 2) anions comprising a plurality of boron atoms such as carboranes, metallacarboranes and boranes.

In a preferred embodiment, the stoichiometric activators include a cation and an anion component, and may be represented by the following formula:

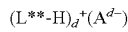

wherein L** is an neutral Lewis base;

H is hydrogen;

(L**-H)$^+$ is a Bronsted acid

A$^{d-}$ is a non-coordinating anion having the charge d− d is an integer from 1 to 3.

The cation component, (L**-H)$_d^+$ may include Bronsted acids such as protons or protonated Lewis bases or reducible Lewis acids capable of protonating or abstracting a moiety, such as an alkyl or aryl, from the precatalyst after alkylation.

The activating cation (L-H)$_d^+$ may be a Bronsted acid, capable of donating a proton to the alkylated transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxomiuns from ethers such as dimethyl ether, diethyl ether, tetrahydrofuran and dioxane, sulfoniums from thioethers, such as diethyl thioethers and tetrahydrothiophene, and mixtures thereof. The activating cation (L-H)$_d^+$ may also be a moiety such as silver, tropylium, carbeniums, ferroceniums and mixtures, preferably carboniums and ferroceniums; most preferably triphenyl carbonium.

The anion component A$^{d-}$ include those having the formula [M$^{k+}$Q$_n$]$^{d-}$ wherein k is an integer from 1 to 3; n is an integer from 2-6; n−k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than one occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable A$^{d-}$ also include diboron compounds as disclosed in U.S. Pat. No. 5,447,895, which is fully incorporated herein by reference.

Illustrative, but not limiting examples of boron compounds which may be used as an activating cocatalyst in combination with a co-activator in the preparation of the improved catalysts of this invention are tri-substituted ammonium salts such as: trimethylammonium tetraphenylborate, triethylammonium tetraphenylborate, tripropylammonium tetraphenylborate, tri(n-butyl)ammonium tetraphenylborate, tri(tert-butyl) ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis (pentafluorophenyl)borate, trimethylammonium tetrakis-(2,3,4,6-tetrafluorophenyl) borate, triethylammonium tetrakis-(2,3,4,6-tetrafluorophenyl)borate, tripropylammonium tetrakis-(2,3,4,6-tetrafluorophenyl)borate, tri(n-butyl) ammonium tetrakis-(2,3,4,6-tetrafluorophenyl)borate, dimethyl(tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis -(2,3,4,6-tetrafluorophenyl) borate, trimethylammonium tetrakis(perfluoronaphtyl) borate, triethylammonium tetrakis(perfluoronaphthyl) borate, tripropylammonium tetrakis(perfluoronaphthyl) borate, tri(n-butyl)ammonium tetrakis(perfluoronaphthyl) borate, tri(tert-butyl)ammonium tetrakis(perfluoronaphthyl) borate, N,N-dimethylanilinium tetrakis(perfluoronaphthyl) borate, N,N-diethylanilinium tetrakis(perfluoronaphthyl) borate, N,N-dimethyl-(2,4,6-trimethylanilinium) tetrakis (perfluoronaphthyl)borate, trimethylammonium tetrakis (perfluorobiphenyl)borate, triethylammonium tetrakis (perfluorobiphenyl)borate, tripropylammonium tetrakis (perfluorobiphenyl)borate, tri(n-butyl)ammonium tetrakis (perfluorobiphenyl)borate, tri(tert-butyl)ammonium tetrakis (perfluorobiphenyl)borate, N,N-dimethylanilinium tetrakis (perfluorobiphenyl)borate, N,N-diethylanilinium tetrakis (perfluorobiphenyl)borate, N,N-dimethyl-(2,4,6-trimethylanilinium) tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(tert-butyl) ammonium tetrakis(3,5-bis(trifluoromethyl)phenyl)borate, N,N-dimethylanilinium tetrakis(3,5-bis(trifluoromethyl) phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, and dialkyl ammonium salts such as: di-(iso-propyl)ammonium tetrakis(pentafluorophenyl)borate, and dicyclohexylammonium tetrakis(pentafluorophenyl)borate; and other salts such as tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis (pentafluorophenyl)borate, triethylsilylium tetrakis (pentafluorophenyl)borate, benzene(diazonium) tetrakis (pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, tropillium tetrakis (perfluoronaphthyl)borate, triphenylcarbenium tetrakis(perfluoronaphthyl)borate, triphenylphosphonium tetrakis(perfluoronaphthyl)borate, triethylsilylium tetrakis (perfluoronaphthyl)borate, benzene(diazonium) tetrakis (perfluoronaphthyl)borate, tropillium tetrakis (perfluorobiphenyl)borate, triphenylcarbenium tetrakis (perfluorobiphenyl)borate, triphenylphosphonium tetrakis (perfluorobiphenyl)borate, triethylsilylium tetrakis (perfluorobiphenyl)borate, benzene(diazonium) tetrakis (perfluorobiphenyl)borate, tropillium tetrakis(3,5-bis (trifluoromethyl)phenyl)borate, triphenylcarbenium tetrakis (3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, and benzene(diazonium) tetrakis(3,5-bis(trifluoromethyl)phenyl)borate.

Most preferably, the ionic stoichiometric activator ($L^{**}$-$H)_d^+$ ($A^{d-}$) is N,N-dimethylanilinium tetrakis(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, or triphenylcarbenium tetra(perfluorophenyl)borate.

In a preferred embodiment, the activator is trispentafluorophenylborane.

Invention catalyst precursors can also be activated with cocatalysts or activators that comprise non-coordinating anions containing metalloid-free cyclopentadienide ions. These are described in U.S. Patent Publication 2002/0058765 A1, published on 16 May 2002, and for the instant invention, require the addition of a co-activator to the catalyst precursor.

The term "non-coordinating anion" (NCA) means an anion that does not coordinate to the catalyst metal cation or that does coordinate to the metal cation, but only weakly. An NCA coordinates weakly enough that a neutral Lewis base, such as an olefinically or acetylenically unsaturated monomer can displace it from the catalyst center. "Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Non-coordinating anions useful in accordance with this invention are those that are compatible, stabilize the transition metal complex cation in the sense of balancing its ionic charge at +1, yet retain sufficient lability to permit displacement by an ethylenically or acetylenically unsaturated monomer during polymerization. These types of cocatalysts sometimes use scavengers such as but not limited to tri-iso-butyl aluminum, tri-n-octyl aluminum, tri-n-hexyl aluminum, triethylaluminum or trimethylaluminum.

Invention process also can employ cocatalyst compounds or activator compounds that are initially neutral Lewis acids but form a cationic metal complex and a noncoordinating anion, or a zwitterionic complex upon reaction with the alkylated transition metal compounds. The alkylated invention compound is formed from the reaction of the catalyst precursor and the co-activator. For example, tris(pentafluorophenyl) boron or aluminum act to abstract a hydrocarbyl ligand to yield an invention cationic transition metal complex and stabilizing noncoordinating anion, see EP-A-0 427 697 and EP-A-0 520 732 for illustrations of analogous Group-4 metallocene compounds. Also, see the methods and compounds of EP-A-0 495 375. For formation of zwitterionic complexes using analogous Group 4 compounds, see U.S. Pat. Nos. 5,624,878; 5,486,632; and 5,527,929.

Additional neutral Lewis-acids are known in the art and are suitable for abstracting formal anionic ligands. See in particular the review article by E. Y.-X. Chen and T. J. Marks, "Cocatalysts for Metal-Catalyzed Olefin Polymerization: Activators, Activation Processes, and Structure-Activity Relationships", *Chem. Rev.*, 100, 1391-1434 (2000).

When the cations of noncoordinating anion precursors are Bronsted acids such as protons or protonated Lewis bases (excluding water), or reducible Lewis acids such as ferrocenium or silver cations, or alkali or alkaline earth metal cations such as those of sodium, magnesium or lithium, the catalyst-precursor-to-activator molar ratio may be any ratio. Combinations of the described activator compounds may also be used for activation.

When an ionic or neutral stoichiometric activator is used, the catalyst-precursor-to-activator molar ratio is from 1:10 to 1:1; 1:10 to 10:1; 1:10 to 2:1; 1:10 to 3:1; 1:10 to 5:1; 1:2 to 1.2:1; 1:2 to 10:1; 1:2 to 2:1; 1:2 to 3:1; 1:2 to 5:1; 1:3 to 1.2:1; 1:3 to 10:1; 1:3 to 2:1; 1:3 to 3:1; 1:3 to 5:1; 1:5 to 1:1; 1:5 to 10:1; 1:5 to 2:1; 1:5 to 3:1; 1:5 to 5:1; 1:1 to 1:1.2. The catalyst-precursor-to-co-activator molar ratio is from 1:100 to 100:1; 1:75 to 75:1; 1:50 to 50:1; 1:25 to 25:1; 1:15 to 15:1; 1:10 to 10:1; 1:5 to 5:1, 1:2 to 2:1; 1:100 to 1:1; 1:75 to 1:1; 1:50 to 1:1; 1:25 to 1:1; 1:15 to 1:1; 1:10 to 1:1; 1:5 to 1:1; 1:2 to 1:1; 1:10 to 2:1.

Preferred activators and activator/co-activator combinations include methylalumoxane, modified methylalumoxane, mixtures of methylalumoxane with dimethylanilinium tetrakis(pentafluorophenyl)borate or tris(pentafluorophenyl) boron, and mixtures of trimethyl aluminum with dimethylanilinium tetrakis(pentafluorophenyl)borate or tris (pentafluorophenyl)boron In some embodiments, scavenging compounds are used with stoichiometric activators. Typical aluminum or boron alkyl components useful as scavengers are represented by the general formula $R^xJZ_2$ where J is aluminum or boron, $R^x$ is as previously defined above, and each Z is independently $R^x$ or a different univalent anionic ligand such as halogen (Cl, Br, I), alkoxide ($OR^x$) and the like. Most preferred aluminum alkyls include triethylaluminum, diethylaluminum chloride, tri-isobutylaluminum, tri-n-octylaluminum, tri-n-hexylaluminum, trimethylaluminum and the like. Preferred boron alkyls include triethylboron. Scavenging compounds may also be alumoxanes and modified alumoxanes including methylalumoxane and modified methylalumoxane.

Supported Catalysts

The catalyst compounds of this invention may be placed upon a support. To prepare uniform supported catalysts, the catalyst precursor preferably dissolves in the chosen solvent. The term "uniform supported catalyst" means that the catalyst precursor, the activator and or the activated catalyst approach uniform distribution upon the support's accessible surface area, including the interior pore surfaces of porous supports. Some embodiments of supported catalysts prefer uniform supported catalysts; other embodiments show no such preference.

Invention supported catalyst systems may be prepared by any method effective to support other coordination catalyst systems, effective meaning that the catalyst so prepared can be used for oligomerizing or polymerizing olefin in a heterogenous process. The catalyst precursor, activator, co-activator if needed, suitable solvent, and support may be added in any order or simultaneously.

By one method, the activator, dissolved in an appropriate solvent such as toluene may be stirred with the support material for 1 minute to 10 hours. The total solution volume may be greater than the pore volume of the support, but some embodiments limit the total solution volume below that needed to form a gel or slurry (about 90% to 400%, preferably about 100-200% of the pore volume). The mixture is optionally heated from 30-200° C. during this time. The catalyst precursor may be added to this mixture as a solid, if a suitable solvent is employed in the previous step, or as a solution. Or alternatively, this mixture can be filtered, and the resulting solid mixed with a catalyst precursor solution. Similarly, the mixture may be vacuum dried and mixed with a catalyst precursor solution. The resulting catalyst mixture is then stirred for 1 minute to 10 hours, and the catalyst is either filtered from the solution and vacuum dried or evaporation alone removes the solvent.

Alternatively, the catalyst precursor and activator may be combined in solvent to form a solution. Then the support is added, and the mixture is stirred for 1 minute to 10 hours. The total solution volume may be greater than the pore volume of the support, but some embodiments limit the total solution volume below that needed to form a gel or slurry (about 90% to 400%, preferably about 100-200% of the pore volume). After stirring, the residual solvent is removed under vacuum, typically at ambient temperature and over 10-16 hours. But greater or lesser times and temperatures are possible.

The catalyst precursor may also be supported absent the activator; in that case, the activator (and co-activator if needed) is added to a slurry process's liquid phase. For example, a solution of catalyst precursor may be mixed with a support material for a period of about 1 minute to 10 hours. The resulting precatalyst mixture may be filtered from the solution and dried under vacuum, or evaporation alone removes the solvent. The total, catalyst-precursor-solution volume may be greater than the support's pore volume, but some embodiments limit the total solution volume below that needed to form a gel or slurry (about 90% to 400%, preferably about 100-200% of the pore volume).

Additionally, two or more different catalyst precursors may be placed on the same support using any of the support methods disclosed above. Likewise, two or more activators or an activator and co-activator may be placed on the same support.

Suitable solid particle supports are typically comprised of polymeric or refractory oxide materials, each being preferably porous. Any support material that has an average particle size greater than 10 µm is suitable for use in this invention. Various embodiments select a porous support material, such as for example, talc, inorganic oxides, inorganic chlorides, for example magnesium chloride and resinous support materials such as polystyrene polyolefin or polymeric compounds or any other organic support material and the like. Some embodiments select inorganic oxide materials as the support material including Group-2, -3, -4, -5, -13, or -14 metal or metalloid oxides. Some embodiments select the catalyst support materials to include silica, alumina, silica-alumina, and their mixtures. Other inorganic oxides may serve either alone or in combination with the silica, alumina, or silica-alumina. These are magnesia, titania, zirconia, and the like. Lewis acidic materials such as montmorillonite and similar clays may also serve as a support. In this case, the support can optionally double as the activator component. But additional activator may also be used.

The support material may be pretreated by any number of methods. For example, inorganic oxides may be calcined, chemically treated with dehydroxylating agents such as aluminum alkyls and the like, or both.

As stated above, polymeric carriers will also be suitable in accordance with the invention, see for example the descriptions in WO 95/15815 and U.S. Pat No. 5,427,991. The methods disclosed may be used with the catalyst complexes, activators or catalyst systems of this invention to adsorb or absorb them on the polymeric supports, particularly if made up of porous particles, or may be chemically bound through functional groups bound to or in the polymer chains.

Invention catalyst carriers may have a surface area of from 10-700 m$^2$/g, a pore volume of 0.1-4.0 cc/g and an average particle size of 10-500 µm. Some embodiments select a surface area of 50-500 m$^2$/g, a pore volume of 0.5-3.5 cc/g, or an average particle size of 20-200 µm. Other embodiments select a surface area of 100-400 m$^2$/g, a pore volume of 0.8-3.0 cc/g, and an average particle size of 30-100 µm. Invention carriers typically have a pore size of 10-1000 Angstroms, alternatively 50-500 Angstroms, or 75-350 Angstroms.

Invention catalysts are generally deposited on the support at a loading level of 10-100 micromoles of catalyst precursor per gram of solid support; alternately 20-80 micromoles of catalyst precursor per gram of solid support; or 40-60 micromoles of catalyst precursor per gram of support. But greater or lesser values may be used provided that the total amount of solid catalyst precursor does not exceed the support's pore volume.

Invention catalysts can be supported for gas-phase, bulk, or slurry polymerization, or otherwise as needed. Numerous support methods are known for catalysts in the olefin polymerization art, particularly alumoxane-activated catalysts; all are suitable for this invention's broadest practice. See, for example, U.S. Pat. Nos. 5,057,475 and 5,227,440. An example of supported ionic catalysts appears in WO 94/03056. U.S. Pat. No. 5,643,847 and WO 96/04319A describe a particularly effective method. A bulk or slurry process using this invention's supported metal complexes activated with alumoxane can be used for ethylene-propylene rubber as described in U.S. Pat. Nos. 5,001,205 and 5,229,478. Additionally, those processes suit this invention's catalyst systems. Both polymers and inorganic oxides may serve as supports, as is known in the art. See U.S. Pat. Nos. 5,422,325, 5,427,991, 5,498,582 and 5,466,649, and international publications WO 93/11172 and WO 94/07928.

Monomers

In a preferred embodiment the catalyst compounds of this invention are used to polymerize or oligomerize any unsaturated monomer or monomers. Preferred monomers include $C_2$ to $C_{100}$ olefins, preferably $C_2$ to $C_{60}$ olefins, preferably $C_2$ to $C_{40}$ olefins preferably $C_2$ to $C_{20}$ olefins, preferably $C_2$ to $C_{12}$ olefins. In some embodiments preferred monomers include linear, branched or cyclic alpha-olefins, preferably $C_2$ to $C_{100}$ alpha-olefins, preferably $C_2$ to $C_{60}$ alpha-olefins, preferably $C_2$ to $C_{40}$ alpha-olefins preferably $C_2$ to $C_{20}$ alpha-olefins, preferably $C_2$ to $C_{12}$ alpha-olefins. Preferred olefin monomers may be one or more of ethylene, propylene, butene, pentene, hexene, heptene, octene, nonene, decene, dodecene, 4-methylpentene-1, 3-methylpentene-1,3,5,5-trimethylhexene-1, and 5-ethylnonene-1.

In another embodiment the polymer produced herein is a copolymer of one or more linear or branched $C_3$ to $C_{30}$ prochiral alpha-olefins or $C_5$ to $C_{30}$ ring containing olefins or combinations thereof capable of being polymerized by either stereospecific and non-stereospecific catalysts. Prochiral, as used herein, refers to monomers that favor the formation of isotactic or syndiotactic polymer when polymerized using stereospecific catalyst(s).

Preferred monomers may also include aromatic-group-containing monomers containing up to 30 carbon atoms. Suitable aromatic-group-containing monomers comprise at least one aromatic structure, preferably from one to three, more preferably a phenyl, indenyl, fluorenyl, or naphthyl moiety. The aromatic-group-containing monomer further comprises at least one polymerizable double bond such that after polymerization, the aromatic structure will be pendant from the polymer backbone. The aromatic-group containing monomer may further be substituted with one or more hydrocarbyl groups including but not limited to $C_1$ to $C_{10}$ alkyl groups.

Additionally two adjacent substitutions may be joined to form a ring structure. Preferred aromatic-group-containing monomers contain at least one aromatic structure appended to a polymerizable olefinic moiety. Particularly preferred aromatic monomers include styrene, alpha-methylstyrene, para-alkylstyrenes, vinyltoluenes, vinylnaphthalene, allyl benzene, and indene, especially styrene, para-methylstyrene, 4-phenyl-1-butene and allyl benzene.

Non aromatic cyclic group containing monomers are also preferred. These monomers can contain up to 30 carbon atoms. Suitable non-aromatic cyclic group containing monomers preferably have at least one polymerizable olefinic group that is either pendant on the cyclic structure or is part of the cyclic structure. The cyclic structure may also be further substituted by one or more hydrocarbyl groups such as, but not limited to, $C_1$ to $C_{10}$ alkyl groups. Preferred non-aromatic cyclic group containing monomers include vinylcyclohexane, vinylcyclohexene, cyclopentadiene, cyclopentene, 4-methylcyclopentene, cyclohexene, 4-methylcyclohexene, cyclobutene, vinyladamantane, norbornene, 5-methylnorbornene, 5-ethylnorbornene, 5-propylnorbornene, 5-butylylnorbornene, 5-pentylnorbornene, 5-hexylnorbornene, 5-heptylnorbornene, 5-octylnorbornene, 5-nonylnorbornene, 5-decylnorbornene, 5-phenylnorbornene, vinylnorbornene, ethylidene norbornene, 5,6-dimethylnorbornene, 5,6-dibutylnorbornene and the like.

Preferred diolefin monomers useful in this invention include any hydrocarbon structure, preferably $C_4$ to $C_{30}$, having at least two unsaturated bonds, wherein at least one, typically two, of the unsaturated bonds are readily incorporated into a polymer by either a stereospecific or a non-stereospecific catalyst(s). It is further preferred that the diolefin monomers be selected from alpha-omega-diene monomers (i.e. di-vinyl monomers). More preferably, the diolefin monomers are linear di-vinyl monomers, most preferably those containing from 4 to 30 carbon atoms. Examples of preferred dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, particularly preferred dienes include 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Preferred cyclic dienes include cyclopentadiene, vinylnorbornene, norbornadiene, ethylidene norbornene, divinylbenzene, dicyclopentadiene or higher ring containing diolefins with or without substituents at various ring positions.

Non-limiting examples of preferred polar unsaturated monomers useful in this invention include nitro substituted monomers including 6-nitro-1-hexene; amine substituted monomers including N-methylallylamine, N-allylcyclopentylamine, and N-allyl-hexylamine; ketone substituted monomers including methyl vinyl ketone, ethyl vinyl ketone, and 5-hexen-2-one; aldehyde substituted monomers including acrolein, 2,2-dimethyl-4-pentenal, undecylenic aldehyde, and 2,4-dimethyl-2,6-heptadienal; alcohol substituted monomers including allyl alcohol, 7-octen-1-ol, 7-octene-1,2-diol, 10-undecen-1-ol, 10-undecene-1,2-diol, 2-methyl-3-buten-1-ol; acetal, epoxide and or ether substituted monomers including 4-hex-5-enyl-2,2-dimethyl-[1,3]dioxolane, 2,2-dimethyl-4-non-8-enyl-[1,3]dioxolane, acrolein dimethyl acetal, butadiene monoxide, 1,2-epoxy-7-octene, 1,2-epoxy-9-decene, 1,2-epoxy-5-hexene, 2-methyl-2-vinyloxirane, allyl glycidyl ether, 2,5-dihydrofuran, 2-cyclopenten-1-one ethylene ketal, 11-methoxyundec-1-ene, and 8-methoxyoct-1-ene; sulfur containing monomers including allyl disulfide; acid and ester substituted monomers including acrylic acid, vinylacetic acid, 4-pentenoic acid, 2,2-dimethyl-4-pentenoic acid, 6-heptenoic acid, trans-2,4-pentadienoic acid, 2,6-heptadienoic acid, methyl acrylate, ethyl acrylate, tert-butyl acrylate, n-butyl acrylate, methacrylic acid, methyl methacrylate, ethyl methacrylate, tert-butyl methacrylate, n-butyl methacrylate, hydroxypropyl acrylate, acetic acid oct-7-enyl ester, non-8-enoic acid methyl ester, acetic acid undec-10-enyl ester, dodec-11-enoic acid methyl ester, propionic acid undec-10-enyl ester, dodec-11-enoic acid ethyl ester, and nonylphenoxypolyetheroxy acrylate; siloxy containing monomers including trimethyloct-7-enyloxy silane, and trimethylundec-10-enyloxy silane, polar functionalized norbornene monomers including 5-norbornene-2-carbonitrile, 5-norbornene-2-carboxaldehyde, 5-norbornene-2-carboxylic acid, cis-5-norbornene-endo-2,3-dicarboxylic acid, 5-norbornene-2,2,-dimethanol, cis-5-norbornene-endo-2,3-dicarboxylic anhydride, 5-norbornene-2-endo-3-endo-dimethanol, 5-norbornene-2-endo-3-exo-dimethanol, 5-norbornene-2-methanol, 5-norbornene-2-ol, 5-norbornene-2-yl acetate, 1-[2-(5-norbornene-2-yl)ethyl]-3,5,7,9,11,13,15-heptacyclopentylpentacyclo[9.5.1.1$^{3,9}$.1$^{5,15}$. 1$^{7,13}$]octasiloxane, 2-benzoyl-5-norbornene, 2-acetyl-5-norbornene, 7-syn methoxymethyl-5-norbornen-2-one, 5-norbornen-2-ol, and 5-norbornen-2-yloxy-trimethylsilane, and partially fluorinated monomers including nonafluoro-1-hexene, allyl-1,1,2,2, -tetrafluoroethyl ether, 2,2,3,3-tetrafluoro-non-8-enoic acid ethyl ester, 1,1,2,2-tetrafluoro-2-(1,1,2,2-tetrafluoro-oct-7-enyloxy)-ethanesulfonyl fluoride, acrylic acid 2,2,3,3,4,4,5,5,6,6,7,7,8,8,8-pentadecafluoro-octyl ester, and 1,1,2,2-tetrafluoro-2-(1,1,2,2,3,3,4,4-octafluoro-dec-9-enyloxy)-ethanesulfonyl fluoride. In an embodiment herein, the process described herein is used to produce an oligomer of any of the monomers listed above. Preferred oligomers include oligomers of any $C_2$ to $C_{20}$ olefins, preferably $C_2$ to $C_{12}$ alpha-olefins, most preferably oligomers comprising ethylene, propylene and or butene are prepared. A preferred feedstock for the oligomerization process is the alpha-olefin, ethylene. But other alpha-olefins, including but not limited to propylene and 1-butene, may also be used alone or combined with ethylene. Preferred alpha-olefins include any $C_2$ to $C_{40}$ alpha-olefin, preferably and $C_2$ to $C_{20}$ alpha-olefin, preferably any $C_2$ to $C_{12}$ alpha-olefin, preferably ethylene, propylene, and butene, most preferably ethylene. Dienes may be used in the processes described herein, preferably alpha-omega-dienes are used alone or in combination with mono-alpha olefins.

In a preferred embodiment the process described herein may be used to produce homopolymers or copolymers. (For the purposes of this invention and the claims thereto a copolymer may comprise two, three, four or more different monomer units.) Preferred polymers produced herein include homopolymers or copolymers of any of the above monomers. In a preferred embodiment the polymer is a homopolymer of any $C_2$ to $C_{12}$ alpha-olefin. Preferably the polymer is a homopolymer of ethylene or a homopolymer of propylene. In another embodiment the polymer is a copolymer comprising ethylene and one or more of any of the monomers listed above. In another embodiment the polymer is a copolymer comprising propylene and one or more of any of the monomers listed above. In another preferred embodiment the homopolymers or copolymers described, additionally comprise one or more diolefin comonomers, preferably one or more $C_4$ to $C_{40}$ diolefins.

In another preferred embodiment the polymer produced herein is a copolymer of ethylene and one or more $C_3$ to $C_{20}$ linear, branched or cyclic monomers, preferably one or more $C_3$ to $C_{12}$ linear, branched or cyclic alpha-olefins. Preferably the polymer produced herein is a copolymer of ethylene and one or more of propylene, butene, pentene, hexene, heptene, octene, nonene, decene, dodecene, 4-methylpentene-1,3-methylpentene-1,3,5,5-trimethylhexene-1, cyclopentene, 4-methylcyclopentene, cyclohexene, and 4-methylcyclohexene.

In another preferred embodiment the polymer produced herein is a copolymer of propylene and one or more $C_2$ or $C_4$ to $C_{20}$ linear, branched or cyclic monomers, preferably one or more $C_2$ or $C_4$ to $C_{12}$ linear, branched or cyclic alpha-olefins. Preferably the polymer produced herein is a copolymer of propylene and one or more of ethylene, butene, pentene, hexene, heptene, octene, nonene, decene, dodecene, 4-methylpentene-1, 3-methylpentene-1, and 3,5,5-trimethylhexene-1. In a preferred embodiment, the polymer produced herein is a homopolymer of norbornene or a copolymer of norbornene and a substituted norbornene, including polar functionalised norbornenes.

In a preferred embodiment the copolymers described herein comprise at least 50 mole % of a first monomer and up to 50 mole % of other monomers. In another embodiment, the polymer comprises: a first monomer present at from 40 to 95 mole %, preferably 50 to 90 mole %, preferably 60 to 80 mole %, and a comonomer present at from 5 to 60 mole %, preferably 10 to 40 mole %, more preferably 20 to 40 mole %, and a termonomer present at from 0 to 10 mole %, more preferably from 0.5 to 5 mole %, more preferably 1 to 3 mole %.

In a preferred embodiment the first monomer comprises one or more of any $C_3$ to $C_8$ linear branched or cyclic alpha-olefins, including propylene, butene, (and all isomers thereof), pentene (and all isomers thereof), hexene (and all isomers thereof), heptene (and all isomers thereof), and octene (and all isomers thereof). Preferred monomers include propylene, 1-butene, 1-hexene, 1-octene, cyclopentene, cyclohexene, cyclooctene, hexadiene, cyclohexadiene and the like.

In a preferred embodiment the comonomer comprises one or more of any $C_2$ to $C_{40}$ linear, branched or cyclic alpha-olefins (provided ethylene, if present, is present at 5 mole % or less), including ethylene, propylene, butene, pentene, hexene, heptene, and octene, nonene, decene, undecene, dodecene, hexadecene, butadiene, hexadiene, heptadiene, pentadiene, octadiene, nonadiene, decadiene, dodecadiene, styrene, 3,5,5-trimethylhexene-1,3-methylpentene-1,4-methylpentene-1, cyclopentadiene, and cyclohexene.

In a preferred embodiment the termonomer comprises one or more of any $C_2$ to $C_{40}$ linear, branched or cyclic alpha-olefins, (provided ethylene, if present, is present at 5 mole % or less), including ethylene, propylene, butene, pentene, hexene, heptene, and octene, nonene, decene, undecene, dodecene, hexadecene, butadiene, hexadiene, heptadiene, pentadiene, octadiene, nonadiene, decadiene, dodecadiene, styrene, 3,5,5-trimethylhexene-1,3-methylpentene-1,4-methylpentene-1, cyclopentadiene, and cyclohexene.

In a preferred embodiment the polymers described above further comprise one or more dienes at up to 10 weight %, preferably at 0.00001 to 1.0 weight %, preferably 0.002 to 0.5 weight %, even more preferably 0.003 to 0.2 weight %, based upon the total weight of the composition. In some embodiments 500 ppm or less of diene is added to the polymerization, preferably 400 ppm or less, preferably or 300 ppm or less. In other embodiments at least 50 ppm of diene is added to the polymerization, or 100 ppm or more, or 150 ppm or more.

Polymerization Processes

Invention catalyst complexes are useful in polymerizing unsaturated monomers conventionally known to undergo metallocene-catalyzed polymerization such as solution, slurry, gas-phase, and high-pressure polymerization. Typically one or more transition metal compounds, one or more activators, and one or more monomers are contacted to produce polymer. These catalysts may be supported and as such will be particularly useful in the known, fixed-bed, moving-bed, fluid-bed, slurry, solution, or bulk operating modes conducted in single, series, or parallel reactors.

One or more reactors in series or in parallel may be used in the present invention. The transition metal compound, activator and when required, co-activator, may be delivered as a solution or slurry, either separately to the reactor, activated in-line just prior to the reactor, or preactivated and pumped as an activated solution or slurry to the reactor. Polymerizations are carried out in either single reactor operation, in which monomer, comonomers, catalyst/activator/co-activator, optional scavenger, and optional modifiers are added continuously to a single reactor or in series reactor operation, in which the above components are added to each of two or more reactors connected in series. The catalyst components can be added to the first reactor in the series. The catalyst component may also be added to both reactors, with one component being added to first reaction and another component to other reactors. In one preferred embodiment, the precatalyst is activated in the reactor in the presence of olefin.

Ethylene-alpha-olefin (including ethylene-cyclic olefin and ethylene-alpha-olefin-diolefin) elastomers of high molecular weight and low crystallinity can be prepared utilizing the catalysts of the invention under traditional solution processes or by introducing ethylene gas into a slurry utilizing the alpha-olefin or cyclic olefin or mixture thereof with other monomers, polymerizable and not, as a polymerization diluent in which the catalyst suspension is suspended. Typical ethylene pressures will be between 10 and 1000 psig (69-6895 kPa) and the polymerization diluent temperature will typically be between −10 and 160° C. The process can be carried out in a stirred tank reactor or a tubular reactor, or more than one reactor operated in series or in parallel. See the general disclosure of U.S. Pat. No. 5,001,205 for general process conditions. All documents are incorporated by reference for description of polymerization processes, ionic activators and useful scavenging compounds.

The invention catalyst compositions can be used individually or can be mixed with other known polymerization catalysts to prepare polymer blends. Monomer and catalyst selection allows polymer blend preparation under conditions analogous to those using individual catalysts. Polymers having increased MWD for improved processing and other traditional benefits available from polymers made with mixed catalyst systems can thus be achieved.

Generally, when using invention catalysts, particularly when they are immobilized on a support, the complete catalyst system will additionally comprise one or more scavenging compounds. Here, the term scavenging compound means a compound that removes polar impurities from the reaction environment. These impurities adversely affect catalyst activity and stability. Typically, purifying steps are usually used before introducing reaction components to a reaction vessel. But such steps will rarely allow polymerization without using some scavenging compounds. Normally, the polymerization process will still use at least small amounts of scavenging compounds.

Typically, the scavenging compound will be an organometallic compound such as the Group-13 organometallic compounds of U.S. Pat. Nos. 5,153,157, 5,241,025 and WO-A-91/09882, WO-A-94/03506, WO-A-93/14132, and that of WO 95/07941. Exemplary compounds include triethyl aluminum, triethyl borane, tri-iso-butyl aluminum, methyl alumoxane, iso-butyl alumoxane, and tri-n-octyl aluminum. Those scavenging compounds having bulky or $C_6$-$C_{20}$ linear hydrocarbyl substituents connected to the metal or metalloid center usually minimize adverse interaction with the active catalyst. Examples include triethylaluminum, but more preferably, bulky compounds such as tri-iso-butyl aluminum, tri-iso-prenyl aluminum, and long-chain linear alkyl-substituted aluminum compounds, such as tri-n-hexyl aluminum, tri-n-octyl aluminum, or tri-n-dodecyl aluminum. When alumoxane is used as the activator, any excess over that needed for activation will scavenge impurities and additional scavenging compounds may be unnecessary. Alumoxanes also may be added in scavenging quantities with other activators, e.g., methylalumoxane, $[Me_2HNPh]^+[B(pfP)_4]^-$ or $B(pfp)_3$ (perfluorophenyl=pfp=$C_6F_5$).

In terms of polymer density, the polymers capable of production in accordance the invention, can range from about 0.85 to about 0.95, preferably from 0.87 to 0.93, more preferably 0.89 to 0.920. Polymer molecular weights can range from about 3000 Mn to about 2,000,000 Mn or greater. Molecular weight distributions can range from about 1.1 to about 50.0, with molecular weight distributions from 1.2 to about 5.0 being more typical. Pigments, antioxidants and other additives, as is known in the art, may be added to the polymer.

Gas Phase Polymerization

Generally, in a fluidized gas bed process used for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661 and 5,668,228 all of which are fully incorporated herein by reference.)

The reactor pressure in a gas phase process may vary from about 10 psig (69 kPa) to about 500 psig (3448 kPa), preferably from about 100 psig (690 kPa) to about 500 psig (3448 kPa), preferably in the range of from about 200 psig (1379 kPa) to about 400 psig (2759 kPa), more preferably in the range of from about 250 psig (1724 kPa) to about 350 psig (2414 kPa).

The reactor temperature in the gas phase process may vary from about 30° C. to about 120° C., preferably from about 60° C. to about 115° C., more preferably in the range of from about 70° C. to 110° C., and most preferably in the range of from about 70° C. to about 95° C. In another embodiment when high density polyethylene is desired then the reactor temperature is typically between 70 and 105° C.

The productivity of the catalyst or catalyst system in a gas phase system is influenced by the partial pressure of the main monomer. The preferred mole percent of the main monomer, ethylene or propylene, preferably ethylene, is from about 25 to 90 mole percent and the comonomer partial pressure is in the range of from about 138 kPa to about 517 kPa, preferably about 517 kPa to about 2069 kPa, which are typical conditions in a gas phase polymerization process. Also in some systems the presence of comonomer can increase productivity.

In a preferred embodiment, the reactor utilized in the present invention is capable of producing more than 500 lbs of polymer per hour (227 Kg/hr) to about 200,000 lbs/hr (90,900 Kg/hr) or higher, preferably greater than 1000 lbs/hr (455 Kg/hr), more preferably greater than 10,000 lbs/hr (4540 Kg/hr), even more preferably greater than 25,000 lbs/hr (11,300 Kg/hr), still more preferably greater than 35,000 lbs/hr (15,900 Kg/hr), still even more preferably greater than 50,000 lbs/hr (22,700 Kg/hr) and preferably greater than 65,000 lbs/hr (29,000 Kg/hr) to greater than 100,000 lbs/hr (45,500 Kg/hr), and most preferably over 100,000 lbs/hr (45,500 Kg/hr).

Other gas phase processes contemplated by the process of the invention include those described in U.S. Pat. Nos. 5,627,242, 5,665,818 and 5,677,375, and European publications EP-A-0 794 200, EP-A-0 802 202 and EP-B-634 421 all of which are herein fully incorporated by reference.

In another preferred embodiment the catalyst system in is liquid form and is introduced into the gas phase reactor into a resin particle lean zone. For information on how to introduce a liquid catalyst system into a fluidized bed polymerization into a particle lean zone, please see U.S. Pat. No. 5,693,727, which is incorporated by reference herein.

Slurry Phase Polymerization

A slurry polymerization process generally operates between 1 to about 50 atmosphere pressure range (15 psig to 735 psig, 103 kPa to 5068 kPa) or even greater and temperatures in the range of 0° C. to about 120° C. In a slurry polymerization, a suspension of solid, particulate polymer is formed in a liquid polymerization diluent medium to which monomer and comonomers along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process should be operated above the reaction diluent critical temperature and pressure. Preferably, a hexane or an isobutane medium is employed.

In one embodiment, a preferred polymerization technique of the invention is referred to as a particle form polymerization, or a slurry process where the temperature is kept below the temperature at which the polymer goes into solution. Such technique is well known in the art, and described in for instance U.S. Pat. No. 3,248,179 which is fully incorporated herein by reference. The preferred temperature in the particle form process is within the range of about 85° C. to about 110° C. Two preferred polymerization methods for the slurry process are those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484, which is herein fully incorporated by reference.

In another embodiment, the slurry process is carried out continuously in a loop reactor. The catalyst, as a slurry in isobutane or as a dry free flowing powder, is injected regularly to the reactor loop, which is itself filled with circulating slurry of growing polymer particles in a diluent of isobutane containing monomer and comonomer. Hydrogen, optionally, may be added as a molecular weight control. The reactor is maintained at a pressure of 3620 kPa to 4309 kPa and at a temperature in the range of about 60° C. to about 104° C. depending on the desired polymer melting characteristics. Reaction heat is removed through the loop wall since much of the reactor is in the form of a double-jacketed pipe. The slurry is allowed to exit the reactor at regular intervals or continuously to a heated low pressure flash vessel, rotary dryer and a nitrogen purge column in sequence for removal of the isobutane diluent and all unreacted monomer and comonomers. The resulting hydrocarbon free powder is then compounded for use in various applications.

In another embodiment, the reactor used in the slurry process of the invention is capable of and the process of the invention is producing greater than 2000 lbs of polymer per hour (907 Kg/hr), more preferably greater than 5000 lbs/hr (2268 Kg/hr), and most preferably greater than 10,000 lbs/hr (4540 Kg/hr). In another embodiment the slurry reactor used in the process of the invention is producing greater than 15,000 lbs of polymer per hour (6804 Kg/hr), preferably greater than 25,000 lbs/hr (11,340 Kg/hr) to about 100,000 lbs/hr (45,500 Kg/hr).

In another embodiment in the slurry process of the invention the total reactor pressure is in the range of from 400 psig (2758 kPa) to 800 psig (5516 kPa), preferably 450 psig (3103 kPa) to about 700 psig (4827 kPa), more preferably 500 psig (3448 kPa) to about 650 psig (4482 kPa), most preferably from about 525 psig (3620 kPa) to 625 psig (4309 kPa).

In yet another embodiment in the slurry process of the invention the concentration of predominant monomer in the reactor liquid medium is in the range of from about 1 to 10 weight percent, preferably from about 2 to about 7 weight percent, more preferably from about 2.5 to about 6 weight percent, most preferably from about 3 to about 6 weight percent.

Another process of the invention is where the process, preferably a slurry or gas phase process is operated in the absence of or essentially free of any scavengers, such as triethylaluminum, trimethylaluminum, tri-iso-butylaluminum and tri-n-hexylaluminum and diethyl aluminum chloride, dibutyl zinc and the like. This process is described in PCT publication WO 96/08520 and U.S. Pat. No. 5,712,352, which are herein fully incorporated by reference.

In another embodiment the process is run with scavengers. Typical scavengers include trimethyl aluminum, tri-iso-butyl aluminum and an excess of alumoxane or modified alumoxane.

In a preferred embodiment, hydrogen or other chain termination agent (such as phenyl silane) are added to the slurry polymerization.

Homogeneous, Bulk or Solution Phase Polymerization

The catalysts described herein can be used advantageously in homogeneous solution processes. Generally this involves polymerization in a continuous reactor in which the polymer formed and the starting monomer and catalyst materials supplied, are agitated to reduce or avoid concentration gradients. Suitable processes operate above the melting point of the polymers at high pressures, from 1 to 3000 bar (10-30,000 MPa), in which the monomer acts as diluent or in solution polymerization using a solvent.

Temperature control in the reactor is obtained by balancing the heat of polymerization and with reactor cooling by reactor jackets or cooling coils to cool the contents of the reactor, auto refrigeration, pre-chilled feeds, vaporization of liquid medium (diluent, monomers or solvent) or combinations of all three. Adiabatic reactors with pre-chilled feeds may also be used. The reactor temperature depends on the catalyst used. In general, the reactor temperature preferably can vary between about 0° C. and about 160° C., more preferably from about 10° C. to about 140° C., and most preferably from about 40° C. to about 120° C. In series operation, the second reactor temperature is preferably higher than the first reactor temperature. In parallel reactor operation, the temperatures of the two reactors are independent. The pressure can vary from about 1 mm Hg to 2500 bar (25,000 MPa), preferably from 0.1 bar to 1600 bar (1-16,000 MPa), most preferably from 1.0 to 500 bar (10-5000 MPa).

Each of these processes may also be employed in single reactor, parallel or series reactor configurations. The liquid processes comprise contacting olefin monomers with the above described catalyst system in a suitable diluent or solvent and allowing said monomers to react for a sufficient time to produce the desired polymers. Hydrocarbon solvents are suitable, both aliphatic and aromatic. Alkanes, such as hexane, pentane, isopentane, and octane, are preferred.

The process can be carried out in a continuous stirred tank reactor, batch reactor, or plug flow reactor, or more than one reactor operated in series or parallel. These reactors may have or may not have internal cooling and the monomer feed may or may not be refrigerated. See the general disclosure of U.S. Pat. No. 5,001,205 for general process conditions. See also, international application WO 96/33227 and WO 97/22639.

Medium and High Pressure Polymerizations

In the high pressure process for the polymerization of ethylene alone or in combination with $C_3$ to $C_{10}$ alpha-olefins and optionally other copolymerizable olefins, the temperature of the medium within which the polymerization reaction occurs is at least 120° C. and preferably above 140° C. and may range to 350° C., but below the decomposition temperature of said polymer product, typically from 310° C. to 325° C. Preferably, the polymerization is completed at a temperature within the range of 130° C. to 230° C. The polymerization is completed at a pressure above 200 bar (20 MPa), and generally at a pressure within the range of 500 bar (50 MPa) to 3500 bar (350 MPa). Preferably, the polymerization is completed at a pressure within the range from 800 bar (80 MPa) to 2500 bar (250 MPa).

For medium pressure process, the temperature within which the polymerization reaction occurs is at least 80° C. and ranges from 80° C. to 250° C., preferably from 100° C. to 220° C., and should for a given polymer in the reactor, be above the melting point of said polymer so as to maintain the fluidity of the polymer-rich phase. The pressure can be varied between 100 and 1000 bar for ethylene homopolymers and from 30 bar (3 MPa) to 1000 bar (100 MPa), especially 50 bar (5 MPa) to 500 bar (50 MPa) for processes producing ethylene copolymers containing $C_3$ to $C_{10}$ olefins and optionally other copolymerizable olefins.

More recently, polymerization conditions for high pressure and or temperature polymerizations to prepare propylene homopolymers and copolymers of propylene with $C_3$ to $C_{10}$ olefins and optionally other copolymerizable olefins have been reported. See U.S. patent application Ser. No. 60/431,185 filed Dec. 5, 2002; Ser. No. 60/431,077, filed Dec. 5, 2002; and Ser. No. 60/412,541, filed Sep. 20, 2002.

After polymerization and deactivation of the catalyst, the polymer product can be recovered by processes well known in the art. Any excess reactants may be flashed off from the polymer and the polymer obtained extruded into water and cut into pellets or other suitable comminuted shapes. For general process conditions, see the general disclosure of U.S.

Pat. Nos. 5,084,534, 5,408,017, 6,127,497, 6,255,410, which are incorporated herein by reference.

A set of exemplary catalyst precursors is set out below. These are by way of example only and are not intended to list every catalyst precursor that is within the scope of the invention.

Examples of preferred pre-catalysts include:
4,4'-oxadiyl-bis($\eta^5$-1-naphthylindenyl)zirconium dichloride,
4,4'-sulfandiyl-bis($\eta^5$-1-naphthylindenyl)zirconium dichloride,
4,4'-phenylphosphindiyl-bis($\eta^5$-1-naphthylindenyl)zirconium dichloride,
4,4'-sulfandiyl-bis($\eta^5$-2-methyl-1-phenylindenyl)zirconium dichloride,
4,4'-sulfandiyl-bis($\eta^5$-1-phenylindenyl)zirconium dichloride,
4,4'-sulfandiyl-bis($\eta^5$-1-phenylindenyl)zirconium dichloride,
4,4'-sulfandiyl-bis($\eta^5$-indenyl)zirconium dichloride,
4,4'-sulfandiyl-bis($\eta^5$-fluorenyl)zirconium dichloride,
4,4'-sulfandiyl-bis($\eta^5$-2-methylindenyl)zirconium dichloride,
4,4'-sulfandiyl-bis($\eta^5$-2,7-dimethylindenyl)zirconium dichloride,
4,4'-sulfandiyl-bis($\eta^5$-7-ethyl-2-methylindenyl)zirconium dichloride,
4,4'-sulfandiyl-bis($\eta^5$-7-propyl-2-methylindenyl)zirconium dichloride,
4,4'-sulfandiyl-bis($\eta^5$-7-butyl-2-methylindenyl)zirconium dichloride,
4,4'-sulfandiyl-bis($\eta^5$-7-hexyl-2-methylindenyl)zirconium dichloride,
4,4'-sulfandiyl-bis($\eta^5$-7-phenylindenyl)zirconium dichloride,
4,4'-sulfandiyl-bis($\eta^5$-7-phenyl-2-methylindenyl)zirconium dichloride,
4,4'-sulfandiyl-bis($\eta^5$-2-methyl-7-p-tolyl-indenyl)zirconium dichloride,
4,4'-sulfandiyl-bis($\eta^5$-2-methyl-7-m-tolylindenyl)zirconium dichloride,
4,4'-sulfandiyl-bis($\eta^5$-2-methyl-7-o-tolylindenyl)zirconium dichloride,
4,4'-sulfandiyl-bis[$\eta^5$-2-methyl-7-(2,4-dimethylphenyl)indenyl]zirconium dichloride,
4,4'-sulfandiyl-bis($\eta^5$-2-methyl-7-mesitylindenyl)zirconium dichloride,
4,4'-sulfandiyl-bis($\eta^5$-7-mesitylindenyl)zirconium dichloride,
4,4'-sulfandiyl-bis[$\eta^5$-2-methyl-7-(4-tert-butylphenyl)indenyl]zirconium dichloride,
4,4'-sulfandiyl-bis($\eta^5$-7-bromo-2-methylindenyl)zirconium dichloride,
4,4'-sulfandiyl-bis($\eta^5$-7-mesityl-2-methylindenyl)zirconium dichloride,
4,4'-sulfandiyl-bis[$\eta^5$-2-methyl-7-(5-methyl-thien-2-yl)indenyl]zirconium dichloride,
4,4'-sulfandiyl-bis[$\eta^5$-2-methyl-7-(5-methyl-furan-2-yl)indenyl]zirconium dichloride,
4,4'-sulfandiyl-bis[$\eta^5$-2-methyl-7-(2-benzothiopheneyl)indenyl]zirconium dichloride,
4,4'-sulfandiyl-bis[$\eta^5$-2-methyl-7-(2-benzofuranyl)indenyl]zirconium dichloride,
4,4'-sulfandiyl-bis[$\eta^5$-2-methyl-7-(4-fluorophenyl)indenyl]zirconium dichloride,
4,4'-sulfandiyl-bis[$\eta^5$-2-methyl-7-(3-trifluoromethylphenyl)indenyl]zirconium dichloride,
4,4'-sulfandiyl-bis($\eta^5$-7-p-tolyl-indenyl)zirconium dichloride,
4,4'-sulfandiyl-bis($\eta^5$-7-m-tolylindenyl)zirconium dichloride,
4,4'-sulfandiyl-bis[$\eta^5$-7-(4-tert-butylphenyl)indenyl]zirconium dichloride,
4,4'-sulfandiyl-bis[$\eta^5$-7-(5-methyl-thien-2-yl)indenyl]zirconium dichloride,
4,4'-sulfandiyl-bis[$\eta^5$-7-(5-methyl-furan-2-yl)indenyl]zirconium dichloride,
4,4'-sulfandiyl-bis[$\eta^5$-7-(2-benzothipheneyl)indenyl]zirconium dichloride,
4,4'-sulfandiyl-bis[$\eta^5$-7-(2-benzofuranyl)indenyl]zirconium dichloride,
4,4'-sulfandiyl-bis[$\eta^5$-7-(4-fluorophenyl)indenyl]zirconium dichloride,
4,4'-sulfandiyl-bis[$\eta^5$-7-(3-trifluoromethylphenyl)indenyl]zirconium dichloride,
4,4'-sulfandiyl-bis($\eta^5$-2-isopropyl-7-phenylindenyl)zirconium dichloride,
4,4'-sulfandiyl-bis($\eta^5$-2-isopropyl-7-p-tolyl-indenyl)zirconium dichloride,
4,4'-sulfandiyl-bis($\eta^5$-2-isopropyl-7-m-tolylindenyl)zirconium dichloride,
4,4'-sulfandiyl-bis[$\eta^5$-2-isopropyl-7-(4-tert-butylphenyl)indenyl]zirconium dichloride,
4,4'-sulfandiyl-bis[$\eta^5$-2-isopropyl-7-(5-methyl-thien-2-yl)indenyl]zirconium dichloride,
4,4'-sulfandiyl-bis[$\eta^5$-2-isopropyl-7-(5-methyl-furan-2-yl)indenyl]zirconium dichloride,
4,4'-sulfandiyl-bis[$\eta^5$-2-isopropyl-7-(2-benzothipheneyl)indenyl]zirconium dichloride,
4,4'-sulfandiyl-bis[$\eta^5$-2-isopropyl-7-(2-benzofuranyl)indenyl]zirconium dichloride,
4,4'-sulfandiyl-bis[$\eta^5$-2-isopropyl-7-(4-fluorophenyl)indenyl]zirconium dichloride,
4,4'-sulfandiyl-bis[$\eta^5$-2-isopropyl-7-(3-trifluoromethylphenyl)indenyl]zirconium dichloride,
4,4'-oxadiyl-bis($\eta^5$-1-phenylindenyl)zirconium dichloride,
4,4'-oxadiyl-bis($\eta^5$-1-phenylindenyl)zirconium dichloride,
4,4'-oxadiyl-bis($\eta^5$-indenyl)zirconium dichloride,
4,4'-oxadiyl-bis($\eta^5$-fluorenyl)zirconium dichloride,
4,4'-oxadiyl-bis($\eta^5$-2-methylindenyl)zirconium dichloride,
4,4'-oxadiyl-bis($\eta^5$-2,7-dimethylindenyl)zirconium dichloride,
4,4'-oxadiyl-bis($\eta^5$-7-ethyl-2-methylindenyl)zirconium dichloride,
4,4'-oxadiyl-bis($\eta^5$-7-propyl-2-methylindenyl)zirconium dichloride,
4,4'-oxadiyl-bis($\eta^5$-7-butyl-2-methylindenyl)zirconium dichloride,
4,4'-oxadiyl-bis($\eta^5$-7-hexyl-2-methylindenyl)zirconium dichloride,
4,4'-oxadiyl-bis($\eta^5$-7-phenylindenyl)zirconium dichloride,
4,4'-oxadiyl-bis($\eta^5$-7-phenyl-2-methylindenyl)zirconium dichloride,
4,4'-oxadiyl-bis($\eta^5$-2-methyl-7-p-tolyl-indenyl)zirconium dichloride,
4,4'-oxadiyl-bis($\eta^5$-2-methyl-7-m-tolylindenyl)zirconium dichloride,
4,4'-oxadiyl-bis($\eta^5$-2-methyl-7-o-tolylindenyl)zirconium dichloride,
4,4'-oxadiyl-bis[$\eta^5$-2-methyl-7-(2,4-dimethylphenyl)indenyl]zirconium dichloride,
4,4'-oxadiyl-bis($\eta^5$-2-methyl-7-mesitylindenyl)zirconium dichloride,
4,4'-oxadiyl-bis($\eta^5$-7-mesitylindenyl)zirconium dichloride, 4,4'-oxadiyl-bis[$\eta^5$-2-methyl-7-(4-tert-butylphenyl)indenyl]zirconium dichloride,
4,4'-oxadiyl-bis($\eta^5$-7-bromo-2-methylindenyl)zirconium dichloride,
4,4'-oxadiyl-bis($\eta^5$-7-mesityl-2-methylindenyl)zirconium dichloride,
4,4'-oxadiyl-bis[$\eta^5$-2-methyl-7-(5-methyl-thien-2-yl)indenyl]zirconium dichloride,
4,4'-oxadiyl-bis[$\eta^5$-2-methyl-7-(5-methyl-furan-2-yl)indenyl]zirconium dichloride,
4,4'-oxadiyl-bis[$\eta^5$-2-methyl-7-(2-benzothiopheneyl)indenyl]zirconium dichloride,
4,4'-oxadiyl-bis[$\eta^5$-2-methyl-7-(2-benzofuranyl)indenyl]zirconium dichloride,
4,4'-oxadiyl-bis[$\eta^5$-2-methyl-7-(4-fluorophenyl)indenyl]zirconium dichloride,
4,4'-oxadiyl-bis[$\eta^5$-2-methyl-7-(3-trifluoromethylphenyl)indenyl]zirconium dichloride,
4,4'-oxadiyl-bis($\eta^5$-7-p-tolyl-indenyl)zirconium dichloride,
4,4'-oxadiyl-bis($\eta^5$-7-m-tolylindenyl)zirconium dichloride,
4,4'-oxadiyl-bis[$\eta^5$-7-(4-tert-butylphenyl)indenyl]zirconium dichloride,
4,4'-oxadiyl-bis[$\eta^5$-7-(5-methyl-thien-2-yl)indenyl]zirconium dichloride,
4,4'-oxadiyl-bis[$\eta^5$-7-(5-methyl-furan-2-yl)indenyl]zirconium dichloride,
4,4'-oxadiyl-bis[$\eta^5$-7-(2-benzothiopheneyl)indenyl]zirconium dichloride,
4,4'-oxadiyl-bis[$\eta^5$-7-(2-benzofuranyl)indenyl]zirconium dichloride,
4,4'-oxadiyl-bis[$\eta^5$-7-(4-fluorophenyl)indenyl]zirconium dichloride,
4,4'-oxadiyl-bis[$\eta^5$-7-(3-trifluoromethylphenyl)indenyl]zirconium dichloride,
4,4'-oxadiyl-bis($\eta^5$-2-isopropyl-7-phenylindenyl)zirconium dichloride,
4,4'-oxadiyl-bis($\eta^5$-2-isopropyl-7-p-tolyl-indenyl)zirconium dichloride,
4,4'-oxadiyl-bis($\eta^5$-2-isopropyl-7-m-tolylindenyl)zirconium dichloride,
4,4'-oxadiyl-bis[$\eta^5$-2-isopropyl-7-(4-tert-butylphenyl)indenyl]zirconium dichloride,
4,4'-oxadiyl-bis[$\eta^5$-2-isopropyl-7-(5-methyl-thien-2-yl)indenyl]zirconium dichloride,
4,4'-oxadiyl-bis[$\eta^5$-2-isopropyl-7-(5-methyl-furan-2-yl)indenyl]zirconium dichloride,
4,4'-oxadiyl-bis[$\eta^5$-2-isopropyl-7-(2-benzothiopheneyl)indenyl]zirconium dichloride,
4,4'-oxadiyl-bis[$\eta^5$-2-isopropyl-7-(2-benzofuranyl)indenyl]zirconium dichloride,
4,4'-oxadiyl-bis[$\eta^5$-2-isopropyl-7-(4-fluorophenyl)indenyl]zirconium dichloride,
4,4'-oxadiyl-bis[$\eta^5$-2-isopropyl-7-(3-trifluoromethylphenyl)indenyl]zirconium dichloride,
4,4'-phenylazandiyl-bis($\eta^5$-1-phenylindenyl)zirconium dichloride,
4,4'-phenylazandiyl-bis($\eta^5$-1-phenylindenyl)zirconium dichloride,
4,4'-phenylazandiyl-bis($\eta^5$-indenyl)zirconium dichloride,
4,4'-phenylazandiyl-bis($\eta^5$-fluorenyl)zirconium dichloride,
4,4'-phenylazandiyl-bis($\eta^5$-2-methylindenyl)zirconium dichloride,
4,4'-phenylazandiyl-bis($\eta^5$-2,7-dimethylindenyl)zirconium dichloride,
4,4'-phenylazandiyl-bis($\eta^5$-7-ethyl-2-methylindenyl)zirconium dichloride,
4,4'-phenylazandiyl-bis($\eta^5$-7-propyl-2-methylindenyl)zirconium dichloride,
4,4'-phenylazandiyl-bis($\eta^5$-7-butyl-2-methylindenyl)zirconium dichloride,
4,4'-phenylazandiyl-bis($\eta^5$-7-hexyl-2-methylindenyl)zirconium dichloride,
4,4'-phenylazandiyl-bis($\eta^5$-7-phenylindenyl)zirconium dichloride,
4,4'-phenylazandiyl-bis($\eta^5$-7-phenyl-2-methylindenyl)zirconium dichloride,
4,4'-phenylazandiyl-bis($\eta^5$-2-methyl-7-p-tolyl-indenyl)zirconium dichloride,
4,4'-phenylazandiyl-bis($\eta^5$-2-methyl-7-m-tolylindenyl)zirconium dichloride,
4,4'-phenylazandiyl-bis($\eta^5$-2-methyl-7-o-tolylindenyl)zirconium dichloride,
4,4'-phenylazandiyl-bis[$\eta^5$-2-methyl-7-(2,4-dimethylphenyl)indenyl]zirconium dichloride,
4,4'-phenylazandiyl-bis($\eta^5$-2-methyl-7-mesitylindenyl)zirconium dichloride,
4,4'-phenylazandiyl-bis($\eta^5$-7-mesitylindenyl)zirconium dichloride,
4,4'-phenylazandiyl-bis[$\eta^5$-2-methyl-7-(4-tert-butylphenyl)indenyl]zirconium dichloride,
4,4'-phenylazandiyl-bis($\eta^5$-7-bromo-2-methylindenyl)zirconium dichloride,
4,4'-phenylazandiyl-bis($\eta^5$-7-mesityl-2-methylindenyl)zirconium dichloride,
4,4'-phenylazandiyl-bis[$\eta^5$-2-methyl-7-(5-methyl-thien-2-yl)indenyl]zirconium dichloride,
4,4'-phenylazandiyl-bis[$\eta^5$-2-methyl-7-(5-methyl-furan-2-yl)indenyl]zirconium dichloride,
4,4'-phenylazandiyl-bis[$\eta^5$-2-methyl-7-(2-benzothiopheneyl)indenyl]zirconium dichloride,
4,4'-phenylazandiyl-bis[$\eta^5$-2-methyl-7-(2-benzofuranyl)indenyl]zirconium dichloride,
4,4'-phenylazandiyl-bis[$\eta^5$-2-methyl-7-(4-fluorophenyl)indenyl]zirconium dichloride,
4,4'-phenylazandiyl-bis[$\eta^5$-2-methyl-7-(3-trifluoromethylphenyl)indenyl]zirconium dichloride,
4,4'-phenylazandiyl-bis($\eta^5$-7-p-tolyl-indenyl)zirconium dichloride,
4,4'-phenylazandiyl-bis($\eta^5$-7-m-tolylindenyl)zirconium dichloride,
4,4'-phenylazandiyl-bis[$\eta^5$-7-(4-tert-butylphenyl)indenyl]zirconium dichloride,
4,4'-phenylazandiyl-bis[$\eta^5$-7-(5-methyl-thien-2-yl)indenyl]zirconium dichloride,
4,4'-phenylazandiyl-bis[$\eta^5$-7-(5-methyl-furan-2-yl)indenyl]zirconium dichloride,
4,4'-phenylazandiyl-bis[$\eta^5$-7-(2-benzothiopheneyl)indenyl]zirconium dichloride,
4,4'-phenylazandiyl-bis[$\eta^5$-7-(2-benzofuranyl)indenyl]zirconium dichloride,
4,4'-phenylazandiyl-bis[$\eta^5$-7-(4-fluorophenyl)indenyl]zirconium dichloride,
4,4'-phenylazandiyl-bis[$\eta^5$-7-(3-trifluoromethylphenyl)indenyl]zirconium dichloride,
4,4'-phenylazandiyl-bis($\eta^5$-2-isopropyl-7-phenylindenyl)zirconium dichloride,
4,4'-phenylazandiyl-bis($\eta^5$-2-isopropyl-7-p-tolyl-indenyl)zirconium dichloride,
4,4'-phenylazandiyl-bis($\eta^5$-2-isopropyl-7-m-tolylindenyl)zirconium dichloride,
4,4'-phenylazandiyl-bis[$\eta^5$-2-isopropyl-7-(4-tert-butylphenyl)indenyl]zirconium dichloride, 4,4'-phenylazandiyl-bis[η⁵-2-isopropyl-7-(5-methyl-thien-2-yl)indenyl]zirconium dichloride,
4,4'-phenylazandiyl-bis[η⁵-2-isopropyl-7-(5-methyl-furan-2-yl)indenyl]zirconium dichloride,
4,4'-phenylazandiyl-bis[η⁵-2-isopropyl-7-(2-benzothiopheneyl)indenyl]zirconium dichloride,
4,4'-phenylazandiyl-bis[η⁵-2-isopropyl-7-(2-benzofuranyl)indenyl]zirconium dichloride,
4,4'-phenylazandiyl-bis[η⁵-2-isopropyl-7-(4-fluorophenyl)indenyl]zirconium dichloride,
4,4'-phenylazandiyl-bis[η⁵-2-isopropyl-7-(3-trifluoromethylphenyl)indenyl]zirconium dichloride,
4,4'-methylazandiyl-bis(η⁵-1-phenylindenyl)zirconium dichloride,
4,4'-methylazandiyl-bis(η⁵-1-phenylindenyl)zirconium dichloride,
4,4'-methylazandiyl-bis(η⁵-indenyl)zirconium dichloride,
4,4'-methylazandiyl-bis(η⁵-fluorenyl)zirconium dichloride,
4,4'-methylazandiyl-bis(η⁵-2-methylindenyl)zirconium dichloride,
4,4'-methylazandiyl-bis(η⁵-2,7-dimethylindenyl)zirconium dichloride,
4,4'-methylazandiyl-bis(η⁵-7-ethyl-2-methylindenyl)zirconium dichloride,
4,4'-methylazandiyl-bis(η⁵-7-propyl-2-methylindenyl)zirconium dichloride,
4,4'-methylazandiyl-bis(η⁵-7-butyl-2-methylindenyl)zirconium dichloride,
4,4'-methylazandiyl-bis(η⁵-7-hexyl-2-methylindenyl)zirconium dichloride,
4,4'-methylazandiyl-bis(η⁵-7-phenylindenyl)zirconium dichloride,
4,4'-methylazandiyl-bis(η⁵-7-phenyl-2-methylindenyl)zirconium dichloride,
4,4'-methylazandiyl-bis(η⁵-2-methyl-7-p-tolyl-indenyl)zirconium dichloride,
4,4'-methylazandiyl-bis(η⁵-2-methyl-7-m-tolylindenyl)zirconium dichloride,
4,4'-methylazandiyl-bis(η⁵-2-methyl-7-o-tolylindenyl)zirconium dichloride,
4,4'-methylazandiyl-bis[η⁵-2-methyl-7-(2,4-dimethylphenyl)indenyl]zirconium dichloride,
4,4'-methylazandiyl-bis[η⁵-2-methyl-7-(4-tert-butylphenyl)indenyl]zirconium dichloride,
4,4'-methylazandiyl-bis(η⁵-7-bromo-2-methylindenyl)zirconium dichloride,
4,4'-methylazandiyl-bis(η⁵-7-mesityl-2-methylindenyl)zirconium dichloride,
4,4'-methylazandiyl-bis[η⁵-2-methyl-7-(5-methyl-thien-2-yl)indenyl]zirconium dichloride,
4,4'-methylazandiyl-bis[η⁵-2-methyl-7-(5-methyl-furan-2-yl)indenyl]zirconium dichloride,
4,4'-methylazandiyl-bis[η⁵-2-methyl-7-(2-benzothiopheneyl)indenyl]zirconium dichloride,
4,4'-methylazandiyl-bis[η⁵-2-methyl-7-(2-benzofuranyl)indenyl]zirconium dichloride,
4,4'-methylazandiyl-bis[η⁵-2-methyl-7-(4-fluorophenyl)indenyl]zirconium dichloride,
4,4'-methylazandiyl-bis[η⁵-2-methyl-7-(3-trifluoromethylphenyl)indenyl]zirconium dichloride,
4,4'-methylazandiyl-bis(η⁵-7-p-tolyl-indenyl)zirconium dichloride,
4,4'-methylazandiyl-bis(η⁵-7-m-tolylindenyl)zirconium dichloride,
4,4'-methylazandiyl-bis[η⁵-7-(4-tert-butylphenyl)indenyl]zirconium dichloride,
4,4'-methylazandiyl-bis[η⁵-7-(5-methyl-thien-2-yl)indenyl]zirconium dichloride,
4,4'-methylazandiyl-bis[η⁵-7-(5-methyl-furan-2-yl)indenyl]zirconium dichloride,
4,4'-methylazandiyl-bis[η⁵-7-(2-benzothiopheneyl)indenyl]zirconium dichloride,
4,4'-methylazandiyl-bis[η⁵-7-(2-benzofuranyl)indenyl]zirconium dichloride,
4,4'-methylazandiyl-bis[η⁵-7-(4-fluorophenyl)indenyl]zirconium dichloride,
4,4'-methylazandiyl-bis[η⁵-7-(3-trifluoromethylphenyl)indenyl]zirconium dichloride,
4,4'-methylazandiyl-bis(η⁵-2-isopropyl-7-phenylindenyl)zirconium dichloride,
4,4'-methylazandiyl-bis(η⁵-2-isopropyl-7-p-tolyl-indenyl)zirconium dichloride,
4,4'-methylazandiyl-bis(η⁵-2-isopropyl-7-m-tolylindenyl)zirconium dichloride,
4,4'-methylazandiyl-bis[η⁵-2-isopropyl-7-(4-tert-butylphenyl)indenyl]zirconium dichloride,
4,4'-methylazandiyl-bis[η⁵-2-isopropyl-7-(5-methyl-thien-2-yl)indenyl]zirconium dichloride,
4,4'-methylazandiyl-bis[η⁵-2-isopropyl-7-(5-methyl-furan-2-yl)indenyl]zirconium dichloride,
4,4'-methylazandiyl-bis[η⁵-2-isopropyl-7-(2-benzothiopheneyl)indenyl]zirconium dichloride,
4,4'-methylazandiyl-bis[η⁵-2-isopropyl-7-(2-benzofuranyl)indenyl]zirconium dichloride,
4,4'-methylazandiyl-bis[η⁵-2-isopropyl-7-(4-fluorophenyl)indenyl]zirconium dichloride,
4,4'-methylazandiyl-bis[η⁵-2-isopropyl-7-(3-trifluoromethylphenyl)indenyl]zirconium dichloride,
4,4'-phenylphosphindiyl-bis(η⁵-1-phenylindenyl)zirconium dichloride,
4,4'-phenylphosphindiyl-bis(η⁵-1-phenylindenyl)zirconium dichloride,
4,4'-phenylphosphindiyl-bis(η⁵-indenyl)zirconium dichloride,
4,4'-phenylphosphindiyl-bis(η⁵-fluroenyl)zirconium dichloride,
4,4'-phenylphosphindiyl-bis(η⁵-2-methylindenyl)zirconium dichloride,
4,4'-phenylphosphindiyl-bis(η⁵-2,7-dimethylindenyl)zirconium dichloride,
4,4'-phenylphosphindiyl-bis(η⁵-7-ethyl-2-methylindenyl)zirconium dichloride,
4,4'-phenylphosphindiyl-bis(η⁵-7-propyl-2-methylindenyl)zirconium dichloride,
4,4'-phenylphosphindiyl-bis(η⁵-7-butyl-2-methylindenyl)zirconium dichloride,
4,4'-phenylphosphindiyl-bis(η⁵-7-hexyl-2-methylindenyl)zirconium dichloride,
4,4'-phenylphosphindiyl-bis(η⁵-7-phenylindenyl)zirconium dichloride,
4,4'-phenylphosphindiyl-bis(η⁵-7-phenyl-2-methylindenyl)zirconium dichloride,
4,4'-phenylphosphindiyl-bis(η⁵-2-methyl-7-p-tolyl-indenyl)zirconium dichloride,
4,4'-phenylphosphindiyl-bis(η⁵-2-methyl-7-m-tolylindenyl)zirconium dichloride,
4,4'-phenylphosphindiyl-bis(η⁵-2-methyl-7-o-tolylindenyl)zirconium dichloride,
4,4'-phenylphosphindiyl-bis[η⁵-2-methyl-7-(2,4-dimethylphenyl)indenyl]zirconium dichloride,
4,4'-phenylphosphindiyl-bis(η⁵-2-methyl-7-mesitylindenyl)zirconium dichloride, 4,4'-phenylphosphindiyl-bis($\eta^5$-7-mesitylindenyl)zirconium dichloride,
4,4'-phenylphosphindiyl-bis[$\eta^5$-2-methyl-7-(4-tert-butylphenyl)indenyl]zirconium dichloride,
4,4'-phenylphosphindiyl-bis($\eta^5$-7-bromo-2-methylindenyl)zirconium dichloride,
4,4'-phenylphosphindiyl-bis($\eta^5$-7-mesityl-2-methylindenyl)zirconium dichloride,
4,4'-phenylphosphindiyl-bis[$\eta^5$-2-methyl-7-(5-methyl-thien-2-yl)indenyl]zirconium dichloride,
4,4'-phenylphosphindiyl-bis[$\eta^5$-2-methyl-7-(5-methyl-furan-2-yl)indenyl]zirconium dichloride,
4,4'-phenylphosphindiyl-bis[$\eta^5$-2-methyl-7-(2-benzothiopheneyl)indenyl]zirconium dichloride,
4,4'-phenylphosphindiyl-bis[$\eta^5$-2-methyl-7-(2-benzofuranyl)indenyl]zirconium dichloride,
4,4'-phenylphosphindiyl-bis[$\eta^5$-2-methyl-7-(4-fluorophenyl)indenyl]zirconium dichloride,
4,4'-phenylphosphindiyl-bis[$\eta^5$-2-methyl-7-(3-trifluoromethylphenyl)indenyl]zirconium dichloride,
4,4'-phenylphosphindiyl-bis($\eta^5$-7-p-tolyl-indenyl)zirconium dichloride,
4,4'-phenylphosphindiyl-bis($\eta^5$-7-m-tolylindenyl)zirconium dichloride,
4,4'-phenylphosphindiyl-bis[$\eta^5$-7-(4-tert-butylphenyl)indenyl]zirconium dichloride,
4,4'-phenylphosphindiyl-bis[$\eta^5$-7-(5-methyl-thien-2-yl)indenyl]zirconium dichloride,
4,4'-phenylphosphindiyl-bis[$\eta^5$-7-(5-methyl-furan-2-yl)indenyl]zirconium dichloride,
4,4'-phenylphosphindiyl-bis[$\eta^5$-7-(2-benzothiopheneyl)indenyl]zirconium dichloride,
4,4'-phenylphosphindiyl-bis[$\eta^5$-7-(2-benzofuranyl)indenyl]zirconium dichloride,
4,4'-phenylphosphindiyl-bis[$\eta^5$-7-(4-fluorophenyl)indenyl]zirconium dichloride,
4,4'-phenylphosphindiyl-bis[$\eta^5$-7-(3-trifluoromethylphenyl)indenyl]zirconium dichloride,
4,4'-phenylphosphindiyl-bis($\eta^5$-2-isopropyl-7-phenylindenyl)zirconium dichloride,
4,4'-phenylphosphindiyl-bis($\eta^5$-2-isopropyl-7-p-tolyl-indenyl)zirconium dichloride,
4,4'-phenylphosphindiyl-bis($\eta^5$-2-isopropyl-7-m-tolylindenyl)zirconium dichloride,
4,4'-phenylphosphindiyl-bis[$\eta^5$-2-isopropyl-7-(4-tert-butylphenyl)indenyl]zirconium dichloride,
4,4'-phenylphosphindiyl-bis[$\eta^5$-2-isopropyl-7-(5-methyl-thien-2-yl)indenyl]zirconium dichloride,
4,4'-phenylphosphindiyl-bis[$\eta^5$-2-isopropyl-7-(5-methyl-furan-2-yl)indenyl]zirconium dichloride,
4,4'-phenylphosphindiyl-bis[$\eta^5$-2-isopropyl-7-(2-benzothiopheneyl)indenyl]zirconium dichloride,
4,4'-phenylphosphindiyl-bis[$\eta^5$-2-isopropyl-7-(2-benzofuranyl)indenyl]zirconium dichloride,
4,4'-phenylphosphindiyl-bis[$\eta^5$-2-isopropyl-7-(4-fluorophenyl)indenyl]zirconium dichloride,
4,4'-phenylphosphindiyl-bis[$\eta^5$-2-isopropyl-7-(3-trifluoromethylphenyl)indenyl]zirconium dichloride,
4,4'-methylphosphindiyl-bis($\eta^5$-1-phenylindenyl)zirconium dichloride,
4,4'-methylphosphindiyl-bis($\eta^5$-1-phenylindenyl)zirconium dichloride,
4,4'-methylphosphindiyl-bis($\eta^5$-indenyl)zirconium dichloride,
4,4'-methylphosphindiyl-bis($\eta^5$-fluroenyl)zirconium dichloride,
4,4'-methylphosphindiyl-bis($\eta^5$-2-methylindenyl)zirconium dichloride,
4,4'-methylphosphindiyl-bis($\eta^5$-2,7-dimethylindenyl)zirconium dichloride,
4,4'-methylphosphindiyl-bis($\eta^5$-7-ethyl-2-methylindenyl)zirconium dichloride,
4,4'-methylphosphindiyl-bis($\eta^5$-7-propyl-2-methylindenyl)zirconium dichloride,
4,4'-methylphosphindiyl-bis($\eta^5$-7-butyl-2-methylindenyl)zirconium dichloride,
4,4'-methylphosphindiyl-bis($\eta^5$-7-hexyl-2-methylindenyl)zirconium dichloride,
4,4'-methylphosphindiyl-bis($\eta^5$-7-phenylindenyl)zirconium dichloride,
4,4'-methylphosphindiyl-bis($\eta^5$-7-phenyl-2-methylindenyl)zirconium dichloride,
4,4'-methylphosphindiyl-bis($\eta^5$-2-methyl-7-p-tolyl-indenyl)zirconium dichloride,
4,4'-methylphosphindiyl-bis($\eta^5$-2-methyl-7-m-tolylindenyl)zirconium dichloride,
4,4'-methylphosphindiyl-bis($\eta^5$-2-methyl-7-o-tolylindenyl)zirconium dichloride,
4,4'-methylphosphindiyl-bis[$\eta^5$-2-methyl-7-(2,4-dimethylphenyl)indenyl]zirconium dichloride,
4,4'-methylphosphindiyl-bis[$\eta^5$-2-methyl-7-(4-tert-butylphenyl)indenyl]zirconium dichloride,
4,4'-methylphosphindiyl-bis($\eta^5$-7-bromo-2-methylindenyl)zirconium dichloride,
4,4'-methylphosphindiyl-bis($\eta^5$-7-mesityl-2-methylindenyl)zirconium dichloride,
4,4'-methylphosphindiyl-bis[$\eta^5$-2-methyl-7-(5-methyl-thien-2-yl)indenyl]zirconium dichloride,
4,4'-methylphosphindiyl-bis[$\eta^5$-2-methyl-7-(5-methyl-furan-2-yl)indenyl]zirconium dichloride,
4,4'-methylphosphindiyl-bis[$\eta^5$-2-methyl-7-(2-benzothiopheneyl)indenyl]zirconium dichloride,
4,4'-methylphosphindiyl-bis[$\eta^5$-2-methyl-7-(2-benzofuranyl)indenyl]zirconium dichloride,
4,4'-methylphosphindiyl-bis[$\eta^5$-2-methyl-7-(4-fluorophenyl)indenyl]zirconium dichloride,
4,4'-methylphosphindiyl-bis[$\eta^5$-2-methyl-7-(3-trifluoromethylphenyl)indenyl]zirconium dichloride,
4,4'-methylphosphindiyl-bis($\eta^5$-7-p-tolyl-indenyl)zirconium dichloride,
4,4'-methylphosphindiyl-bis($\eta^5$-7-m-tolylindenyl)zirconium dichloride,
4,4'-methylphosphindiyl-bis[$\eta^5$-7-(4-tert-butylphenyl)indenyl]zirconium dichloride,
4,4'-methylphosphindiyl-bis[$\eta^5$-7-(5-methyl-thien-2-yl)indenyl]zirconium dichloride,
4,4'-methylphosphindiyl-bis[$\eta^5$-7-(5-methyl-furan-2-yl)indenyl]zirconium dichloride,
4,4'-methylphosphindiyl-bis[$\eta^5$-7-(2-benzothiopheneyl)indenyl]zirconium dichloride,
4,4'-methylphosphindiyl-bis[$\eta^5$-7-(2-benzofuranyl)indenyl]zirconium dichloride,
4,4'-methylphosphindiyl-bis[$\eta^5$-7-(4-fluorophenyl)indenyl]zirconium dichloride,
4,4'-methylphosphindiyl-bis[$\eta^5$-7-(3-trifluoromethylphenyl)indenyl]zirconium dichloride,
4,4'-methylphosphindiyl-bis($\eta^5$-2-isopropyl-7-phenylindenyl)zirconium dichloride,
4,4'-methylphosphindiyl-bis($\eta^5$-2-isopropyl-7-p-tolyl-indenyl)zirconium dichloride,
4,4'-methylphosphindiyl-bis($\eta^5$-2-isopropyl-7-m-tolylindenyl)zirconium dichloride, 4,4'-methylphosphindiyl-bis[$\eta^5$-2-isopropyl-7-(4-tert-butylphenyl)indenyl]zirconium dichloride,
4,4'-methylphosphindiyl-bis[$\eta^5$-2-isopropyl-7-(5-methyl-thien-2-yl)indenyl]zirconium dichloride,
4,4'-methylphosphindiyl-bis[$\eta^5$-2-isopropyl-7-(5-methyl-furan-2-yl)indenyl]zirconium dichloride,
4,4'-methylphosphindiyl-bis[$\eta^5$-2-isopropyl-7-(2-benzothiopheneyl)indenyl]zirconium dichloride,
4,4'-methylphosphindiyl-bis[$\eta^5$-2-isopropyl-7-(2-benzofuranyl)indenyl]zirconium dichloride,
4,4'-methylphosphindiyl-bis[$\eta^5$-2-isopropyl-7-(4-fluorophenyl)indenyl]zirconium dichloride,
4,4'-methylphosphindiyl-bis[$\eta^5$-2-isopropyl-7-(3-trifluoromethylphenyl)indenyl]zirconium dichloride,
5,5'-oxadiyl-bis($\eta^5$-1-naphthylindenyl)zirconium dichloride,
5,5'-sulfandiyl-bis($\eta^5$-1-naphthylindenyl)zirconium dichloride,
5,5'-phenylphosphindiyl-bis($\eta^5$-1-naphthylindenyl)zirconium dichloride,
5,5'-sulfandiyl-bis($\eta^5$-2-methyl-1-phenylindenyl)zirconium dichloride,
5,5'-sulfandiyl-bis($\eta^5$-1-phenylindenyl)zirconium dichloride,
5,5'-sulfandiyl-bis($\eta^5$-1-phenylindenyl)zirconium dichloride,
5,5'-sulfandiyl-bis($\eta^5$-indenyl)zirconium dichloride,
5,5'-sulfandiyl-bis(($\eta^5$-fluroenyl)zirconium dichloride,
5,5'-sulfandiyl-bis($\eta^5$-2-methylindenyl)zirconium dichloride,
5,5'-sulfandiyl-bis($\eta^5$-2,7-dimethylindenyl)zirconium dichloride,
5,5'-sulfandiyl-bis($\eta^5$-7-ethyl-2-methylindenyl)zirconium dichloride,
5,5'-sulfandiyl-bis($\eta^5$-7-propyl-2-methylindenyl)zirconium dichloride,
5,5'-sulfandiyl-bis($\eta^5$-7-butyl-2-methylindenyl)zirconium dichloride,
5,5'-sulfandiyl-bis($\eta^5$-7-hexyl-2-methylindenyl)zirconium dichloride,
5,5'-sulfandiyl-bis($\eta^5$-7-phenylindenyl)zirconium dichloride,
5,5'-sulfandiyl-bis($\eta^5$-7-phenyl-2-methylindenyl)zirconium dichloride,
5,5'-sulfandiyl-bis($\eta^5$-2-methyl-7-p-tolyl-indenyl)zirconium dichloride,
5,5'-sulfandiyl-bis($\eta^5$-2-methyl-7-m-tolylindenyl)zirconium dichloride,
5,5'-sulfandiyl-bis($\eta^5$-2-methyl-7-o-tolylindenyl)zirconium dichloride,
5,5'-sulfandiyl-bis[$\eta^5$-2-methyl-7-(2,4-dimethylphenyl)indenyl]zirconium dichloride,
5,5'-sulfandiyl-bis[$\eta^5$-2-methyl-7-(4-tert-butylphenyl)indenyl]zirconium dichloride,
5,5'-sulfandiyl-bis($\eta^5$-7-bromo-2-methylindenyl)zirconium dichloride,
5,5'-sulfandiyl-bis($\eta^5$-7-mesityl-2-methylindenyl)zirconium dichloride,
5,5'-sulfandiyl-bis[$\eta^5$-2-methyl-7-(5-methyl-thien-2-yl)indenyl]zirconium dichloride,
5,5'-sulfandiyl-bis[$\eta^5$-2-methyl-7-(5-methyl-furan-2-yl)indenyl]zirconium dichloride,
5,5'-sulfandiyl-bis[$\eta^5$-2-methyl-7-(2-benzothiopheneyl)indenyl]zirconium dichloride,
5,5'-sulfandiyl-bis[$\eta^5$-2-methyl-7-(2-benzofuranyl)indenyl]zirconium dichloride,
5,5'-sulfandiyl-bis[$\eta^5$-2-methyl-7-(4-fluorophenyl)indenyl]zirconium dichloride,
5,5'-sulfandiyl-bis[$\eta^5$-2-methyl-7-(3-trifluoromethylphenyl)indenyl]zirconium dichloride,
5,5'-sulfandiyl-bis($\eta^5$-7-p-tolyl-indenyl)zirconium dichloride,
5,5'-sulfandiyl-bis($\eta^5$-7-m-tolylindenyl)zirconium dichloride,
5,5'-sulfandiyl-bis[$\eta^5$-7-(4-tert-butylphenyl)indenyl]zirconium dichloride,
5,5'-sulfandiyl-bis[$\eta^5$-7-(5-methyl-thien-2-yl)indenyl]zirconium dichloride,
5,5'-sulfandiyl-bis[$\eta^5$-7-(5-methyl-furan-2-yl)indenyl]zirconium dichloride,
5,5'-sulfandiyl-bis[$\eta^5$-7-(2-benzothiopheneyl)indenyl]zirconium dichloride,
5,5'-sulfandiyl-bis[$\eta^5$-7-(2-benzofaranyl)indenyl]zirconium dichloride,
5,5'-sulfandiyl-bis[$\eta^5$-7-(4-fluorophenyl)indenyl]zirconium dichloride,
5,5'-sulfandiyl-bis[$\eta^5$-7-(3-trifluoromethylphenyl)indenyl]zirconium dichloride,
5,5'-sulfandiyl-bis($\eta^5$-2-isopropyl-7-phenylindenyl)zirconium dichloride,
5,5'-sulfandiyl-bis($\eta^5$-2-isopropyl-7-p-tolyl-indenyl)zirconium dichloride,
5,5'-sulfandiyl-bis($\eta^5$-2-isopropyl-7-m-tolylindenyl)zirconium dichloride,
5,5'-sulfandiyl-bis[$\eta^5$-2-isopropyl-7-(4-tert-butylphenyl)indenyl]zirconium dichloride,
5,5'-sulfandiyl-bis[$\eta^5$-2-isopropyl-7-(5-methyl-thien-2-yl)indenyl]zirconium dichloride,
5,5'-sulfandiyl-bis[$\eta^5$-2-isopropyl-7-(5-methyl-furan-2-yl)indenyl]zirconium dichloride,
5,5'-sulfandiyl-bis[$\eta^5$-2-isopropyl-7-(2-benzothiopheneyl)indenyl]zirconium dichloride,
5,5'-sulfandiyl-bis[$\eta^5$-2-isopropyl-7-(2-benzofuranyl)indenyl]zirconium dichloride,
5,5'-sulfandiyl-bis[$\eta^5$-2-isopropyl-7-(4-fluorophenyl)indenyl]zirconium dichloride,
5,5'-sulfandiyl-bis[$\eta^5$-2-isopropyl-7-(3-trifluoromethylphenyl)indenyl]zirconium dichloride,
5,5'-oxadiyl-bis($\eta^5$-1-phenylindenyl)zirconium dichloride,
5,5'-oxadiyl-bis($\eta^5$-1-phenylindenyl)zirconium dichloride,
5,5'-oxadiyl-bis($\eta^5$-indenyl)zirconium dichloride,
5,5'-oxadiyl-bis($\eta^5$-fluroenyl)zirconium dichloride,
5,5'-oxadiyl-bis($\eta^5$-2-methylindenyl)zirconium dichloride,
5,5'-oxadiyl-bis($\eta^5$-2,7-dimethylindenyl)zirconium dichloride,
5,5'-oxadiyl-bis($\eta^5$-7-ethyl-2-methylindenyl)zirconium dichloride,
5,5'-oxadiyl-bis($\eta^5$-7-propyl-2-methylindenyl)zirconium dichloride,
5,5'-oxadiyl-bis($\eta^5$-7-butyl-2-methylindenyl)zirconium dichloride,
5,5'-oxadiyl-bis($\eta^5$-7-hexyl-2-methylindenyl)zirconium dichloride,
5,5'-oxadiyl-bis($\eta^5$-7-phenylindenyl)zirconium dichloride,
5,5'-oxadiyl-bis($\eta^5$-7-phenyl-2-methylindenyl)zirconium dichloride,
5,5'-oxadiyl-bis($\eta^5$-2-methyl-7-p-tolyl-indenyl)zirconium dichloride,
5,5'-oxadiyl-bis($\eta^5$-2-methyl-7-m-tolylindenyl)zirconium dichloride,
5,5'-oxadiyl-bis($\eta^5$-2-methyl-7-o-tolylindenyl)zirconium dichloride, 5,5'-oxadiyl-bis[$\eta^5$-2-methyl-7-(2,4-dimethylphenyl)indenyl]zirconium dichloride,
5,5'-oxadiyl-bis[$\eta^5$-2-methyl-7-(4-tert-butylphenyl)indenyl]zirconium dichloride,
5,5'-oxadiyl-bis($\eta^5$-7-bromo-2-methylindenyl)zirconium dichloride,
5,5'-oxadiyl-bis($\eta^5$-7-mesityl-2-methylindenyl)zirconium dichloride,
5,5'-oxadiyl-bis[$\eta^5$-2-methyl-7-(5-methyl-thien-2-yl)indenyl]zirconium dichloride,
5,5'-oxadiyl-bis[$\eta^5$-2-methyl-7-(5-methyl-furan-2-yl)indenyl]zirconium dichloride,
5,5'-oxadiyl-bis[$\eta^5$-2-methyl-7-(2-benzothiopheneyl)indenyl]zirconium dichloride,
5,5'-oxadiyl-bis[$\eta^5$-2-methyl-7-(2-benzofuranyl)indenyl]zirconium dichloride,
5,5'-oxadiyl-bis[$\eta^5$-2-methyl-7-(4-fluorophenyl)indenyl]zirconium dichloride,
5,5'-oxadiyl-bis[$\eta^5$-2-methyl-7-(3-trifluoromethylphenyl)indenyl]zirconium dichloride,
5,5'-oxadiyl-bis($\eta^5$-7-p-tolyl-indenyl)zirconium dichloride,
5,5'-oxadiyl-bis($\eta^5$-7-m-tolylindenyl)zirconium dichloride,
5,5'-oxadiyl-bis($\eta^5$-7-(4-tert-butylphenyl)indenyl]zirconium dichloride,
5,5'-oxadiyl-bis[$\eta^5$-7-(5-methyl-thien-2-yl)indenyl]zirconium dichloride,
5,5'-oxadiyl-bis[$\eta^5$-7-(5-methyl-furan-2-yl)indenyl]zirconium dichloride,
5,5'-oxadiyl-bis[$\eta^5$-7-(2-benzothiopheneyl)indenyl]zirconium dichloride,
5,5'-oxadiyl-bis[$\eta^5$-7-(2-benzofuranyl)indenyl]zirconium dichloride,
5,5'-oxadiyl-bis[$\eta^5$-7-(4-fluorophenyl)indenyl]zirconium dichloride,
5,5'-oxadiyl-bis[$\eta^5$-7-(3-trifluoromethylphenyl)indenyl]zirconium dichloride,
5,5'-oxadiyl-bis($\eta^5$-2-isopropyl-7-phenylindenyl)zirconium dichloride,
5,5'-oxadiyl-bis($\eta^5$-2-isopropyl-7-p-tolyl-indenyl)zirconium dichloride,
5,5'-oxadiyl-bis($\eta^5$-2-isopropyl-7-m-tolylindenyl)zirconium dichloride,
5,5'-oxadiyl-bis[$\eta^5$-2-isopropyl-7-(4-tert-butylphenyl)indenyl]zirconium dichloride,
5,5'-oxadiyl-bis[$\eta^5$-2-isopropyl-7-(5-methyl-thien-2-yl)indenyl]zirconium dichloride,
5,5'-oxadiyl-bis[$\eta^5$-2-isopropyl-7-(5-methyl-furan-2-yl)indenyl]zirconium dichloride,
5,5'-oxadiyl-bis[$\eta^5$-2-isopropyl-7-(2-benzothiopheneyl)indenyl]zirconium dichloride,
5,5'-oxadiyl-bis[$\eta^5$-2-isopropyl-7-(2-benzofuranyl)indenyl]zirconium dichloride,
5,5'-oxadiyl-bis[$\eta^5$-2-isopropyl-7-(4-fluorophenyl)indenyl]zirconium dichloride,
5,5'-oxadiyl-bis[$\eta^5$-2-isopropyl-7-(3-trifluoromethylphenyl)indenyl]zirconium dichloride,
5,5'-phenylazandiyl-bis($\eta^5$-1-phenylindenyl)zirconium dichloride,
5,5'-phenylazandiyl-bis($\eta^5$-1-phenylindenyl)zirconium dichloride,
5,5'-phenylazandiyl-bis($\eta^5$-indenyl)zirconium dichloride,
5,5'-phenylazandiyl-bis($\eta^5$-fluroenyl)zirconium dichloride,
5,5'-phenylazandiyl-bis($\eta^5$-2-methylindenyl)zirconium dichloride,
5,5'-phenylazandiyl-bis($\eta^5$-2,7-dimethylindenyl)zirconium dichloride,
5,5'-phenylazandiyl-bis($\eta^5$-7-ethyl-2-methylindenyl)zirconium dichloride,
5,5'-phenylazandiyl-bis($\eta^5$-7-propyl-2-methylindenyl)zirconium dichloride,
5,5'-phenylazandiyl-bis($\eta^5$-7-butyl-2-methylindenyl)zirconium dichloride,
5,5'-phenylazandiyl-bis($\eta^5$-7-hexyl-2-methylindenyl)zirconium dichloride,
5,5'-phenylazandiyl-bis($\eta^5$-7-phenylindenyl)zirconium dichloride,
5,5'-phenylazandiyl-bis($\eta^5$-7-phenyl-2-methylindenyl)zirconium dichloride,
5,5'-phenylazandiyl-bis[$\eta^5$-2-methyl-7-p-tolyl-indenyl]zirconium dichloride,
5,5'-phenylazandiyl-bis[$\eta^5$-2-methyl-7-m-tolylindenyl]zirconium dichloride,
5,5'-phenylazandiyl-bis[$\eta^5$-2-methyl-7-o-tolylindenyl]zirconium dichloride,
5,5'-phenylazandiyl-bis[$\eta^5$-2-methyl-7-(2,4-dimethylphenyl)indenyl]zirconium dichloride,
5,5'-phenylazandiyl-bis[$\eta^5$-2-methyl-7-(4-tert-butylphenyl)indenyl]zirconium dichloride,
5,5'-phenylazandiyl-bis($\eta^5$-7-bromo-2-methylindenyl)zirconium dichloride,
5,5'-phenylazandiyl-bis($\eta^5$-7-mesityl-2-methylindenyl)zirconium dichloride,
5,5'-phenylazandiyl-bis[$\eta^5$-2-methyl-7-(5-methyl-thien-2-yl)indenyl]zirconium dichloride,
5,5'-phenylazandiyl-bis[$\eta^5$-2-methyl-7-(5-methyl-furan-2-yl)indenyl]zirconium dichloride,
5,5'-phenylazandiyl-bis[$\eta^5$-2-methyl-7-(2-benzothiopheneyl)indenyl]zirconium dichloride,
5,5'-phenylazandiyl-bis[$\eta^5$-2-methyl-7-(2-benzofuranyl)indenyl]zirconium dichloride,
5,5'-phenylazandiyl-bis[$\eta^5$-2-methyl-7-(4-fluorophenyl)indenyl]zirconium dichloride,
5,5'-phenylazandiyl-bis[$\eta^5$-2-methyl-7-(3-trifluoromethylphenyl)indenyl]zirconium dichloride,
5,5'-phenylazandiyl-bis($\eta^5$-7-p-tolyl-indenyl)zirconium dichloride,
5,5'-phenylazandiyl-bis($\eta^5$-7-m-tolylindenyl)zirconium dichloride,
5,5'-phenylazandiyl-bis[$\eta^5$-7-(4-tert-butylphenyl)indenyl]zirconium dichloride,
5,5'-phenylazandiyl-bis[$\eta^5$-7-(5-methyl-thien-2-yl)indenyl]zirconium dichloride,
5,5'-phenylazandiyl-bis[$\eta^5$-7-(5-methyl-furan-2-yl)indenyl]zirconium dichloride,
5,5'-phenylazandiyl-bis[$\eta^5$-7-(2-benzothiopheneyl)indenyl]zirconium dichloride,
5,5'-phenylazandiyl-bis[$\eta^5$-7-(2-benzofuranyl)indenyl]zirconium dichloride,
5,5'-phenylazandiyl-bis[$\eta^5$-7-(4-fluorophenyl)indenyl]zirconium dichloride,
5,5'-phenylazandiyl-bis[$\eta^5$-7-(3-trifluoromethylphenyl)indenyl]zirconium dichloride,
5,5'-phenylazandiyl-bis($\eta^5$-2-isopropyl-7-phenylindenyl)zirconium dichloride,
5,5'-phenylazandiyl-bis($\eta^5$-2-isopropyl-7-p-tolyl-indenyl)zirconium dichloride,
5,5'-phenylazandiyl-bis($\eta^5$-2-isopropyl-7-m-tolylindenyl)zirconium dichloride,
5,5'-phenylazandiyl-bis[$\eta^5$-2-isopropyl-7-(4-tert-butylphenyl)indenyl]zirconium dichloride,
5,5'-phenylazandiyl-bis[$\eta^5$-2-isopropyl-7-(5-methyl-thien-2-yl)indenyl]zirconium dichloride, 5,5'-phenylazandiyl-bis[η⁵-2-isopropyl-7-(5-methyl-furan-2-yl)indenyl]zirconium dichloride,
5,5'-phenylazandiyl-bis[η⁵-2-isopropyl-7-(2-benzothiopheneyl)indenyl]zirconium dichloride,
5,5'-phenylazandiyl-bis[η⁵-2-isopropyl-7-(2-benzofaranyl)indenyl]zirconium dichloride,
5,5'-phenylazandiyl-bis[η⁵-2-isopropyl-7-(4-fluorophenyl)indenyl]zirconium dichloride,
5,5'-phenylazandiyl-bis[η⁵-2-isopropyl-7-(3-trifluoromethylphenyl)indenyl]zirconium dichloride,
5,5'-methylazandiyl-bis(η⁵-1-phenylindenyl)zirconium dichloride,
5,5'-methylazandiyl-bis(η⁵-1-phenylindenyl)zirconium dichloride,
5,5'-methylazandiyl-bis(η⁵-indenyl)zirconium dichloride,
5,5'-methylazandiyl-bis(η⁵-fluroenyl)zirconium dichloride,
5,5'-methylazandiyl-bis(η⁵-2-methylindenyl)zirconium dichloride,
5,5'-methylazandiyl-bis(η⁵-2,7-dimethylindenyl)zirconium dichloride,
5,5'-methylazandiyl-bis(η⁵-7-ethyl-2-methylindenyl)zirconium dichloride,
5,5'-methylazandiyl-bis(η⁵-7-propyl-2-methylindenyl)zirconium dichloride,
5,5'-methylazandiyl-bis(η⁵-7-butyl-2-methylindenyl)zirconium dichloride,
5,5'-methylazandiyl-bis(η⁵-7-hexyl-2-methylindenyl)zirconium dichloride,
5,5'-methylazandiyl-bis(η⁵-7-phenylindenyl)zirconium dichloride,
5,5'-methylazandiyl-bis(η⁵-7-phenyl-2-methylindenyl)zirconium dichloride,
5,5'-methylazandiyl-bis(η⁵-2-methyl-7-p-tolyl-indenyl)zirconium dichloride,
5,5'-methylazandiyl-bis(η⁵-2-methyl-7-m-tolylindenyl)zirconium dichloride,
5,5'-methylazandiyl-bis(η⁵-2-methyl-7-o-tolylindenyl)zirconium dichloride,
5,5'-methylazandiyl-bis[η⁵-2-methyl-7-(2,4-dimethylphenyl)indenyl]zirconium dichloride,
5,5'-methylazandiyl-bis[η⁵-2-methyl-7-(4-tert-butylphenyl)indenyl]zirconium dichloride,
5,5'-methylazandiyl-bis(η⁵-7-bromo-2-methylindenyl)zirconium dichloride,
5,5'-methylazandiyl-bis(η⁵-7-mesityl-2-methylindenyl)zirconium dichloride,
5,5'-methylazandiyl-bis[η⁵-2-methyl-7-(5-methyl-thien-2-yl)indenyl]zirconium dichloride,
5,5'-methylazandiyl-bis[η⁵-2-methyl-7-(5-methyl-furan-2-yl)indenyl]zirconium dichloride,
5,5'-methylazandiyl-bis[η⁵-2-methyl-7-(2-benzothiopheneyl)indenyl]zirconium dichloride,
5,5'-methylazandiyl-bis[η⁵-2-methyl-7-(2-benzofuranyl)indenyl]zirconium dichloride,
5,5'-methylazandiyl-bis[η⁵-2-methyl-7-(4-fluorophenyl)indenyl]zirconium dichloride,
5,5'-methylazandiyl-bis[η⁵-2-methyl-7-(3-trifluoromethylphenyl)indenyl]zirconium dichloride,
5,5'-methylazandiyl-bis(η⁵-7-p-tolyl-indenyl)zirconium dichloride,
5,5'-methylazandiyl-bis(η⁵-7-m-tolylindenyl)zirconium dichloride,
5,5'-methylazandiyl-bis[η⁵-7-(4-tert-butylphenyl)indenyl]zirconium dichloride,
5,5'-methylazandiyl-bis[η⁵-7-(5-methyl-thien-2-yl)indenyl]zirconium dichloride,
5,5'-methylazandiyl-bis[η⁵-7-(5-methyl-furan-2-yl)indenyl]zirconium dichloride,
5,5'-methylazandiyl-bis[η⁵-7-(2-benzothiopheneyl)indenyl]zirconium dichloride,
5,5'-methylazandiyl-bis[η⁵-7-(2-benzofuranyl)indenyl]zirconium dichloride,
5,5'-methylazandiyl-bis[η⁵-7-(4-fluorophenyl)indenyl]zirconium dichloride,
5,5'-methylazandiyl-bis[η⁵-7-(3-trifluoromethylphenyl)indenyl]zirconium dichloride,
5,5'-methylazandiyl-bis(η⁵-2-isopropyl-7-phenylindenyl)zirconium dichloride,
5,5'-methylazandiyl-bis(η⁵-2-isopropyl-7-p-tolyl-indenyl)zirconium dichloride,
5,5'-methylazandiyl-bis(η⁵-2-isopropyl-7-m-tolylindenyl)zirconium dichloride,
5,5'-methylazandiyl-bis[η⁵-2-isopropyl-7-(4-tert-butylphenyl)indenyl]zirconium dichloride,
5,5'-methylazandiyl-bis[η⁵-2-isopropyl-7-(5-methyl-thien-2-yl)indenyl]zirconium dichloride,
5,5'-methylazandiyl-bis[η⁵-2-isopropyl-7-(5-methyl-furan-2-yl)indenyl]zirconium dichloride,
5,5'-methylazandiyl-bis[η⁵-2-isopropyl-7-(2-benzothiopheneyl)indenyl]zirconium dichloride,
5,5'-methylazandiyl-bis[η⁵-2-isopropyl-7-(2-benzofuranyl)indenyl]zirconium dichloride,
5,5'-methylazandiyl-bis[η⁵-2-isopropyl-7-(4-fluorophenyl)indenyl]zirconium dichloride,
5,5'-methylazandiyl-bis[η⁵-2-isopropyl-7-(3-trifluoromethylphenyl)indenyl]zirconium dichloride,
5,5'-phenylphosphindiyl-bis(η⁵-1-phenylindenyl)zirconium dichloride,
5,5'-phenylphosphindiyl-bis(η⁵-1-phenylindenyl)zirconium dichloride,
5,5'-phenylphosphindiyl-bis(η⁵-indenyl)zirconium dichloride,
5,5'-phenylphosphindiyl-bis(η⁵-fluroenyl)zirconium dichloride,
5,5'-phenylphosphindiyl-bis(η⁵-2-methylindenyl)zirconium dichloride,
5,5'-phenylphosphindiyl-bis(η⁵-2,7-dimethylindenyl)zirconium dichloride,
5,5'-phenylphosphindiyl-bis(η⁵-7-ethyl-2-methylindenyl)zirconium dichloride,
5,5'-phenylphosphindiyl-bis(η⁵-7-propyl-2-methylindenyl)zirconium dichloride,
5,5'-phenylphosphindiyl-bis(η⁵-7-butyl-2-methylindenyl)zirconium dichloride,
5,5'-phenylphosphindiyl-bis(η⁵-7-hexyl-2-methylindenyl)zirconium dichloride,
5,5'-phenylphosphindiyl-bis(η⁵-7-phenylindenyl)zirconium dichloride,
5,5'-phenylphosphindiyl-bis(η⁵-7-phenyl-2-methylindenyl)zirconium dichloride,
5,5'-phenylphosphindiyl-bis(η⁵-2-methyl-7-p-tolyl-indenyl)zirconium dichloride,
5,5'-phenylphosphindiyl-bis(η⁵-2-methyl-7-m-tolylindenyl)zirconium dichloride,
5,5'-phenylphosphindiyl-bis(η⁵-2-methyl-7-o-tolylindenyl)zirconium dichloride,
5,5'-phenylphosphindiyl-bis[η⁵-2-methyl-7-(2,4-dimethylphenyl)indenyl]zirconium dichloride,
5,5'-phenylphosphindiyl-bis[η⁵-2-methyl-7-(4-tert-butylphenyl)indenyl]zirconium dichloride,
5,5'-phenylphosphindiyl-bis(15-7-bromo-2-methylindenyl)zirconium dichloride, 5,5'-phenylphosphindiyl-bis($\eta^5$-7-mesityl-2-methylindenyl) zirconium dichloride,
5,5'-phenylphosphindiyl-bis[$\eta^5$-2-methyl-7-(5-methyl-thien-2-yl)indenyl]zirconium dichloride,
5,5'-phenylphosphindiyl-bis[$\eta^5$-2-methyl-7-(5-methyl-furan-2-yl)indenyl]zirconium dichloride,
5,5'-phenylphosphindiyl-bis[$\eta^5$-2-methyl-7-(2-benzothiopheneyl)indenyl]zirconium dichloride,
5,5'-phenylphosphindiyl-bis[$\eta^5$-2-methyl-7-(2-benzofuranyl)indenyl]zirconium dichloride,
5,5'-phenylphosphindiyl-bis[$\eta^5$-2-methyl-7-(4-fluorophenyl)indenyl]zirconium dichloride,
5,5'-phenylphosphindiyl-bis[$\eta^5$-2-methyl-7-(3-trifluoromethylphenyl)indenyl]zirconium dichloride,
5,5'-phenylphosphindiyl-bis($\eta^5$-7-p-tolyl-indenyl)zirconium dichloride,
5,5'-phenylphosphindiyl-bis($\eta^5$-7-m-tolylindenyl)zirconium dichloride,
5,5'-phenylphosphindiyl-bis[$\eta^5$-7-(4-tert-butylphenyl)indenyl]zirconium dichloride,
5,5'-phenylphosphindiyl-bis[$\eta^5$-7-(5-methyl-thien-2-yl)indenyl]zirconium dichloride,
5,5'-phenylphosphindiyl-bis[$\eta^5$-7-(5-methyl-furan-2-yl)indenyl]zirconium dichloride,
5,5'-phenylphosphindiyl-bis[$\eta^5$-7-(2-benzothiopheneyl)indenyl]zirconium dichloride,
5,5'-phenylphosphindiyl-bis[$\eta^5$-7-(2-benzofuranyl)indenyl]zirconium dichloride,
5,5'-phenylphosphindiyl-bis[$\eta^5$-7-(4-fluorophenyl)indenyl]zirconium dichloride,
5,5'-phenylphosphindiyl-bis[$\eta^5$-7-(3-trifluoromethylphenyl)indenyl]zirconium dichloride,
5,5'-phenylphosphindiyl-bis($\eta^5$-2-isopropyl-7-phenylindenyl)zirconium dichloride,
5,5'-phenylphosphindiyl-bis($\eta^5$-2-isopropyl-7-p-tolyl-indenyl)zirconium dichloride,
5,5'-phenylphosphindiyl-bis($\eta^5$-2-isopropyl-7-m-tolylindenyl)zirconium dichloride,
5,5'-phenylphosphindiyl-bis[$\eta^5$-2-isopropyl-7-(4-tert-butylphenyl)indenyl]zirconium dichloride,
5,5'-phenylphosphindiyl-bis[$\eta^5$-2-isopropyl-7-(5-methyl-thien-2-yl)indenyl]zirconium dichloride,
5,5'-phenylphosphindiyl-bis[$\eta^5$-2-isopropyl-7-(5-methyl-furan-2-yl)indenyl]zirconium dichloride,
5,5'-phenylphosphindiyl-bis[$\eta^5$-2-isopropyl-7-(2-benzothiopheneyl)indenyl]zirconium dichloride,
5,5'-phenylphosphindiyl-bis[$\eta^5$-2-isopropyl-7-(2-benzofuranyl)indenyl]zirconium dichloride,
5,5'-phenylphosphindiyl-bis[$\eta^5$-2-isopropyl-7-(4-fluorophenyl)indenyl]zirconium dichloride,
5,5'-phenylphosphindiyl-bis[$\eta^5$-2-isopropyl-7-(3-trifluoromethylphenyl)indenyl]zirconium dichloride,
5,5'-methylphosphindiyl-bis($\eta^5$-1-phenylindenyl)zirconium dichloride,
5,5'-methylphosphindiyl-bis($\eta^5$-1-phenylindenyl)zirconium dichloride,
5,5'-methylphosphindiyl-bis($\eta^5$-indenyl)zirconium dichloride,
5,5'-methylphosphindiyl-bis($\eta^5$-fluroenyl)zirconium dichloride,
5,5'-methylphosphindiyl-bis($\eta^5$-2-methylindenyl)zirconium dichloride,
5,5'-methylphosphindiyl-bis($\eta^5$-2,7-dimethylindenyl)zirconium dichloride,
5,5'-methylphosphindiyl-bis($\eta^5$-7-ethyl-2-methylindenyl)zirconium dichloride,
5,5'-methylphosphindiyl-bis($\eta^5$-7-propyl-2-methylindenyl) zirconium dichloride,
5,5'-methylphosphindiyl-bis($\eta^5$-7-butyl-2-methylindenyl) zirconium dichloride,
5,5'-methylphosphindiyl-bis($\eta^5$-7-hexyl-2-methylindenyl) zirconium dichloride,
5,5'-methylphosphindiyl-bis($\eta^5$-7-phenylindenyl)zirconium dichloride,
5,5'-methylphosphindiyl-bis($\eta^5$-7-phenyl-2-methylindenyl) zirconium dichloride,
5,5'-methylphosphindiyl-bis($\eta^5$-2-methyl-7-p-tolyl-indenyl)zirconium dichloride,
5,5'-methylphosphindiyl-bis($\eta^5$-2-methyl-7-m-tolylindenyl) zirconium dichloride,
5,5'-methylphosphindiyl-bis($\eta^5$-2-methyl-7-o-tolylindenyl) zirconium dichloride,
5,5'-methylphosphindiyl-bis[$\eta^5$-2-methyl-7-(2,4-dimethylphenyl)indenyl]zirconium dichloride,
5,5'-methylphosphindiyl-bis[$\eta^5$-2-methyl-7-(4-tert-butylphenyl)indenyl]zirconium dichloride,
5,5'-methylphosphindiyl-bis($\eta^5$-7-bromo-2-methylindenyl) zirconium dichloride,
5,5'-methylphosphindiyl-bis($\eta^5$-7-mesityl-2-methylindenyl) zirconium dichloride,
5,5'-methylphosphindiyl-bis[$\eta^5$-2-methyl-7-(5-methyl-thien-2-yl)indenyl]zirconium dichloride,
5,5'-methylphosphindiyl-bis[$\eta^5$-2-methyl-7-(5-methyl-furan-2-yl)indenyl]zirconium dichloride,
5,5'-methylphosphindiyl-bis[$\eta^5$-2-methyl-7-(2-benzothiopheneyl)indenyl]zirconium dichloride,
5,5'-methylphosphindiyl-bis[$\eta^5$-2-methyl-7-(2-benzofuranyl)indenyl]zirconium dichloride,
5,5'-methylphosphindiyl-bis[$\eta^5$-2-methyl-7-(4-fluorophenyl)indenyl]zirconium dichloride,
5,5'-methylphosphindiyl-bis[$\eta^5$-2-methyl-7-(3-trifluoromethylphenyl)indenyl]zirconium dichloride,
5,5'-methylphosphindiyl-bis($\eta^5$-7-p-tolyl-indenyl)zirconium dichloride,
5,5'-methylphosphindiyl-bis($\eta^5$-7-m-tolylindenyl)zirconium dichloride,
5,5'-methylphosphindiyl-bis[$\eta^5$-7-(4-tert-butylphenyl)indenyl]zirconium dichloride,
5,5'-methylphosphindiyl-bis[$\eta^5$-7-(5-methyl-thien-2-yl)indenyl]zirconium dichloride,
5,5'-methylphosphindiyl-bis[$\eta^5$-7-(5-methyl-furan-2-yl)indenyl]zirconium dichloride,
5,5'-methylphosphindiyl-bis[$\eta^5$-7-(2-benzothiopheneyl)indenyl]zirconium dichloride,
5,5'-methylphosphindiyl-bis[$\eta^5$-7-(2-benzofuranyl)indenyl] zirconium dichloride,
5,5'-methylphosphindiyl-bis[$\eta^5$-7-(4-fluorophenyl)indenyl] zirconium dichloride,
5,5'-methylphosphindiyl-bis[$\eta^5$-7-(3-trifluoromethylphenyl)indenyl]zirconium dichloride,
5,5'-methylphosphindiyl-bis($\eta^5$-2-isopropyl-7-phenylindenyl)zirconium dichloride,
5,5'-methylphosphindiyl-bis($\eta^5$-2-isopropyl-7-p-tolyl-indenyl)zirconium dichloride,
5,5'-methylphosphindiyl-bis($\eta^5$-2-isopropyl-7-m-tolylindenyl)zirconium dichloride,
5,5'-methylphosphindiyl-bis[$\eta^5$-2-isopropyl-7-(4-tert-butylphenyl)indenyl]zirconium dichloride,
5,5'-methylphosphindiyl-bis[$\eta^5$-2-isopropyl-7-(5-methyl-thien-2-yl)indenyl]zirconium dichloride,
5,5'-methylphosphindiyl-bis[$\eta^5$-2-isopropyl-7-(5-methyl-furan-2-yl)indenyl]zirconium dichloride, 5,5'-methylphosphindiyl-bis[η⁵-2-isopropyl-7-(2-benzothiopheneyl)indenyl]zirconium dichloride,
5,5'-methylphosphindiyl-bis[η⁵-2-isopropyl-7-(2-benzofuranyl)indenyl]zirconium dichloride,
5,5'-methylphosphindiyl-bis[η⁵-2-isopropyl-7-(4-fluorophenyl)indenyl]zirconium dichloride,
5,5'-methylphosphindiyl-bis[η⁵-2-isopropyl-7-(3-trifluoromethylphenyl)indenyl]zirconium dichloride,
4,5'-oxadiyl-bis(η⁵-1-naphthylindenyl)zirconium dichloride,
4,5'-sulfandiyl-bis(η⁵-1-naphthylindenyl)zirconium dichloride,
4,5'-phenylphosphindiyl-bis(η⁵-1-naphthylindenyl)zirconium dichloride,
4,5'-sulfandiyl-bis(η⁵-2-methyl-1-phenylindenyl)zirconium dichloride,
4,5'-sulfandiyl-bis(η⁵-1-phenylindenyl)zirconium dichloride,
4,5'-sulfandiyl-bis(η⁵-1-phenylindenyl)zirconium dichloride,
4,5'-sulfandiyl-bis(η⁵-indenyl)zirconium dichloride,
4,5'-sulfandiyl-bis(η⁵-fluroenyl)zirconium dichloride,
4,5'-sulfandiyl-bis(η⁵-2-methylindenyl)zirconium dichloride,
4,5'-sulfandiyl-bis(η⁵-2,7-dimethylindenyl)zirconium dichloride,
4,5'-sulfandiyl-bis(η⁵-7-ethyl-2-methylindenyl)zirconium dichloride,
4,5'-sulfandiyl-bis(η⁵-7-propyl-2-methylindenyl)zirconium dichloride,
4,5'-sulfandiyl-bis(η⁵-7-butyl-2-methylindenyl)zirconium dichloride,
4,5'-sulfandiyl-bis(η⁵-7-hexyl-2-methylindenyl)zirconium dichloride,
4,5'-sulfandiyl-bis(η⁵-7-phenylindenyl)zirconium dichloride,
4,5'-sulfandiyl-bis(η⁵-7-phenyl-2-methylindenyl)zirconium dichloride,
4,5'-sulfandiyl-bis(η⁵-2-methyl-7-p-tolyl-indenyl)zirconium dichloride,
4,5'-sulfandiyl-bis(η⁵-2-methyl-7-m-tolylindenyl)zirconium dichloride,
4,5'-sulfandiyl-bis(η⁵-2-methyl-7-o-tolylindenyl)zirconium dichloride,
4,5'-sulfandiyl-bis[η⁵-2-methyl-7-(2,4-dimethylphenyl)indenyl]zirconium dichloride,
4,5'-sulfandiyl-bis[η⁵-2-methyl-7-(4-tert-butylphenyl)indenyl]zirconium dichloride,
4,5'-sulfandiyl-bis(η⁵-7-bromo-2-methylindenyl)zirconium dichloride,
4,5'-sulfandiyl-bis(η⁵-7-mesityl-2-methylindenyl)zirconium dichloride,
4,5'-sulfandiyl-bis[η⁵-2-methyl-7-(5-methyl-thien-2-yl)indenyl]zirconium dichloride,
4,5'-sulfandiyl-bis[η⁵-2-methyl-7-(5-methyl-furan-2-yl)indenyl]zirconium dichloride,
4,5'-sulfandiyl-bis[η⁵-2-methyl-7-(2-benzothiopheneyl)indenyl]zirconium dichloride,
4,5'-sulfandiyl-bis[η⁵-2-methyl-7-(2-benzofuranyl)indenyl]zirconium dichloride,
4,5'-sulfandiyl-bis[η⁵-2-methyl-7-(4-fluorophenyl)indenyl]zirconium dichloride,
4,5'-sulfandiyl-bis[η⁵-2-methyl-7-(3-trifluoromethylphenyl)indenyl]zirconium dichloride,
4,5'-sulfandiyl-bis(η⁵-7-p-tolyl-indenyl)zirconium dichloride,
4,5'-sulfandiyl-bis(η⁵-7-m-tolylindenyl)zirconium dichloride,
4,5'-sulfandiyl-bis[η⁵-7-(4-tert-butylphenyl)indenyl]zirconium dichloride,
4,5'-sulfandiyl-bis[η⁵-7-(5-methyl-thien-2-yl)indenyl]zirconium dichloride,
4,5'-sulfandiyl-bis[η⁵-7-(5-methyl-furan-2-yl)indenyl]zirconium dichloride,
4,5'-sulfandiyl-bis[η⁵-7-(2-benzothiopheneyl)indenyl]zirconium dichloride,
4,5'-sulfandiyl-bis[η⁵-7-(2-benzofuranyl)indenyl]zirconium dichloride,
4,5'-sulfandiyl-bis[η⁵-7-(4-fluorophenyl)indenyl]zirconium dichloride,
4,5'-sulfandiyl-bis[η⁵-7-(3-trifluoromethylphenyl)indenyl]zirconium dichloride,
4,5'-sulfandiyl-bis(η⁵-2-isopropyl-7-phenylindenyl)zirconium dichloride,
4,5'-sulfandiyl-bis(η⁵-2-isopropyl-7-p-tolyl-indenyl)zirconium dichloride,
4,5'-sulfandiyl-bis(η⁵-2-isopropyl-7-m-tolylindenyl)zirconium dichloride,
4,5'-sulfandiyl-bis[η⁵-2-isopropyl-7-(4-tert-butylphenyl)indenyl]zirconium dichloride,
4,5'-sulfandiyl-bis[η⁵-2-isopropyl-7-(5-methyl-thien-2-yl)indenyl]zirconium dichloride,
4,5'-sulfandiyl-bis[η⁵-2-isopropyl-7-(5-methyl-furan-2-yl)indenyl]zirconium dichloride,
4,5'-sulfandiyl-bis[η⁵-2-isopropyl-7-(2-benzothiopheneyl)indenyl]zirconium dichloride,
4,5'-sulfandiyl-bis[η⁵-2-isopropyl-7-(2-benzofuranyl)indenyl]zirconium dichloride,
4,5'-sulfandiyl-bis[η⁵-2-isopropyl-7-(4-fluorophenyl)indenyl]zirconium dichloride,
4,5'-sulfandiyl-bis[η⁵-2-isopropyl-7-(3-trifluoromethylphenyl)indenyl]zirconium dichloride,
4,5'-oxadiyl-bis(η⁵-1-phenylindenyl)zirconium dichloride,
4,5'-oxadiyl-bis(η⁵-1-phenylindenyl)zirconium dichloride,
4,5'-oxadiyl-bis(η⁵-indenyl)zirconium dichloride,
4,5'-oxadiyl-bis(η⁵-fluroenyl)zirconium dichloride,
4,5'-oxadiyl-bis(η⁵-2-methylindenyl)zirconium dichloride,
4,5'-oxadiyl-bis(η⁵-2,7-dimethylindenyl)zirconium dichloride,
4,5'-oxadiyl-bis(η⁵-7-ethyl-2-methylindenyl)zirconium dichloride,
4,5'-oxadiyl-bis(η⁵-7-propyl-2-methylindenyl)zirconium dichloride,
4,5'-oxadiyl-bis(η⁵-7-butyl-2-methylindenyl)zirconium dichloride,
4,5'-oxadiyl-bis(η⁵-7-hexyl-2-methylindenyl)zirconium dichloride,
4,5'-oxadiyl-bis(η⁵-7-phenylindenyl)zirconium dichloride,
4,5'-oxadiyl-bis(η⁵-7-phenyl-2-methylindenyl)zirconium dichloride,
4,5'-oxadiyl-bis(η⁵-2-methyl-7-p-tolyl-indenyl)zirconium dichloride,
4,5'-oxadiyl-bis(η⁵-2-methyl-7-m-tolylindenyl)zirconium dichloride,
4,5'-oxadiyl-bis(η⁵-2-methyl-7-o-tolylindenyl)zirconium dichloride,
4,5'-oxadiyl-bis[η⁵-2-methyl-7-(2,4-dimethylphenyl)indenyl]zirconium dichloride,
4,5'-oxadiyl-bis[η⁵-2-methyl-7-(4-tert-butylphenyl)indenyl]zirconium dichloride,
4,5'-oxadiyl-bis(η⁵-7-bromo-2-methylindenyl)zirconium dichloride, 4,5'-oxadiyl-bis(η⁵-7-mesityl-2-methylindenyl)zirconium dichloride,
4,5'-oxadiyl-bis[η⁵-2-methyl-7-(5-methyl-thien-2-yl)indenyl]zirconium dichloride,
4,5'-oxadiyl-bis[η⁵-2-methyl-7-(5-methyl-furan-2-yl)indenyl]zirconium dichloride,
4,5'-oxadiyl-bis[η⁵-2-methyl-7-(2-benzothiopheneyl)indenyl]zirconium dichloride,
4,5'-oxadiyl-bis[η⁵-2-methyl-7-(2-benzofuranyl)indenyl]zirconium dichloride,
4,5'-oxadiyl-bis[η⁵-2-methyl-7-(4-fluorophenyl)indenyl]zirconium dichloride,
4,5'-oxadiyl-bis[η⁵-2-methyl-7-(3-trifluoromethylphenyl)indenyl]zirconium dichloride,
4,5'-oxadiyl-bis(η⁵-7-p-tolyl-indenyl)zirconium dichloride,
4,5'-oxadiyl-bis(η⁵-7-m-tolylindenyl)zirconium dichloride,
4,5'-oxadiyl-bis[η⁵-7-(4-tert-butylphenyl)indenyl]zirconium dichloride,
4,5'-oxadiyl-bis[η⁵-7-(5-methyl-thien-2-yl)indenyl]zirconium dichloride,
4,5'-oxadiyl-bis[η⁵-7-(5-methyl-furan-2-yl)indenyl]zirconium dichloride,
4,5'-oxadiyl-bis[η⁵-7-(2-benzothiopheneyl)indenyl]zirconium dichloride,
4,5'-oxadiyl-bis[η⁵-7-(2-benzofuranyl)indenyl]zirconium dichloride,
4,5'-oxadiyl-bis[η⁵-7-(4-fluorophenyl)indenyl]zirconium dichloride,
4,5'-oxadiyl-bis[η⁵-7-(3-trifluoromethylphenyl)indenyl]zirconium dichloride,
4,5'-oxadiyl-bis(η⁵-2-isopropyl-7-phenylindenyl)zirconium dichloride,
4,5'-oxadiyl-bis(η⁵-2-isopropyl-7-p-tolyl-indenyl)zirconium dichloride,
4,5'-oxadiyl-bis(η⁵-2-isopropyl-7-m-tolylindenyl)zirconium dichloride,
4,5'-oxadiyl-bis[η⁵-2-isopropyl-7-(4-tert-butylphenyl)indenyl]zirconium dichloride,
4,5'-oxadiyl-bis[η⁵-2-isopropyl-7-(5-methyl-thien-2-yl)indenyl]zirconium dichloride,
4,5'-oxadiyl-bis[η⁵-2-isopropyl-7-(5-methyl-furan-2-yl)indenyl]zirconium dichloride,
4,5'-oxadiyl-bis[η⁵-2-isopropyl-7-(2-benzothiopheneyl)indenyl]zirconium dichloride,
4,5'-oxadiyl-bis[η⁵-2-isopropyl-7-(2-benzofuranyl)indenyl]zirconium dichloride,
4,5'-oxadiyl-bis[η⁵-2-isopropyl-7-(4-fluorophenyl)indenyl]zirconium dichloride,
4,5'-oxadiyl-bis[η⁵-2-isopropyl-7-(3-trifluoromethylphenyl)indenyl]zirconium dichloride,
4,5'-phenylazandiyl-bis(η⁵-1-phenylindenyl)zirconium dichloride,
4,5'-phenylazandiyl-bis(η⁵-1-phenylindenyl)zirconium dichloride,
4,5'-phenylazandiyl-bis(η⁵-indenyl)zirconium dichloride,
4,5'-phenylazandiyl-bis(η⁵-fluroenyl)zirconium dichloride,
4,5'-phenylazandiyl-bis(η⁵-2-methylindenyl)zirconium dichloride,
4,5'-phenylazandiyl-bis(η⁵-2,7-dimethylindenyl)zirconium dichloride,
4,5'-phenylazandiyl-bis(η⁵-7-ethyl-2-methylindenyl)zirconium dichloride,
4,5'-phenylazandiyl-bis(η⁵-7-propyl-2-methylindenyl)zirconium dichloride,
4,5'-phenylazandiyl-bis(η⁵-7-butyl-2-methylindenyl)zirconium dichloride,
4,5'-phenylazandiyl-bis(η⁵-7-hexyl-2-methylindenyl)zirconium dichloride,
4,5'-phenylazandiyl-bis(η⁵-7-phenylindenyl)zirconium dichloride,
4,5'-phenylazandiyl-bis(η⁵-7-phenyl-2-methylindenyl)zirconium dichloride,
4,5'-phenylazandiyl-bis(η⁵-2-methyl-7-p-tolyl-indenyl)zirconium dichloride,
4,5'-phenylazandiyl-bis(η⁵-2-methyl-7-m-tolylindenyl)zirconium dichloride,
4,5'-phenylazandiyl-bis(η⁵-2-methyl-7-o-tolylindenyl)zirconium dichloride,
4,5'-phenylazandiyl-bis[η⁵-2-methyl-7-(2,4-dimethylphenyl)indenyl]zirconium dichloride,
4,5'-phenylazandiyl-bis[η⁵-2-methyl-7-(4-tert-butylphenyl)indenyl]zirconium dichloride,
4,5'-phenylazandiyl-bis(η⁵-7-bromo-2-methylindenyl)zirconium dichloride,
4,5'-phenylazandiyl-bis(η⁵-7-mesityl-2-methylindenyl)zirconium dichloride,
4,5'-phenylazandiyl-bis[η⁵-2-methyl-7-(5-methyl-thien-2-yl)indenyl]zirconium dichloride,
4,5'-phenylazandiyl-bis[η⁵-2-methyl-7-(5-methyl-furan-2-yl)indenyl]zirconium dichloride,
4,5'-phenylazandiyl-bis[η⁵-2-methyl-7-(2-benzothiopheneyl)indenyl]zirconium dichloride,
4,5'-phenylazandiyl-bis[η⁵-2-methyl-7-(2-benzofuranyl)indenyl]zirconium dichloride,
4,5'-phenylazandiyl-bis[η⁵-2-methyl-7-(4-fluorophenyl)indenyl]zirconium dichloride,
4,5'-phenylazandiyl-bis[η⁵-2-methyl-7-(3-trifluoromethylphenyl)indenyl]zirconium dichloride,
4,5'-phenylazandiyl-bis(η⁵-7-p-tolyl-indenyl)zirconium dichloride,
4,5'-phenylazandiyl-bis(η⁵-7-m-tolylindenyl)zirconium dichloride,
4,5'-phenylazandiyl-bis[η⁵-7-(4-tert-butylphenyl)indenyl]zirconium dichloride,
4,5'-phenylazandiyl-bis[η⁵-7-(5-methyl-thien-2-yl)indenyl]zirconium dichloride,
4,5'-phenylazandiyl-bis[η⁵-7-(5-methyl-furan-2-yl)indenyl]zirconium dichloride,
4,5'-phenylazandiyl-bis[η⁵-7-(2-benzothiopheneyl)indenyl]zirconium dichloride,
4,5'-phenylazandiyl-bis[η⁵-7-(2-benzofuranyl)indenyl]zirconium dichloride,
4,5'-phenylazandiyl-bis[η⁵-7-(4-fluorophenyl)indenyl]zirconium dichloride,
4,5'-phenylazandiyl-bis[η⁵-7-(3-trifluoromethylphenyl)indenyl]zirconium dichloride,
4,5'-phenylazandiyl-bis(η⁵-2-isopropyl-7-phenylindenyl)zirconium dichloride,
4,5'-phenylazandiyl-bis(η⁵-2-isopropyl-7-p-tolyl-indenyl)zirconium dichloride,
4,5'-phenylazandiyl-bis(η⁵-2-isopropyl-7-m-tolylindenyl)zirconium dichloride,
4,5'-phenylazandiyl-bis[η⁵-2-isopropyl-7-(4-tert-butylphenyl)indenyl]zirconium dichloride,
4,5'-phenylazandiyl-bis[η⁵-2-isopropyl-7-(5-methyl-thien-2-yl)indenyl]zirconium dichloride,
4,5'-phenylazandiyl-bis[η⁵-2-isopropyl-7-(5-methyl-furan-2-yl)indenyl]zirconium dichloride,
4,5'-phenylazandiyl-bis[η⁵-2-isopropyl-7-(2-benzothiopheneyl)indenyl]zirconium dichloride,
4,5'-phenylazandiyl-bis[η⁵-2-isopropyl-7-(2-benzofuranyl)indenyl]zirconium dichloride, 4,5'-phenylazandiyl-bis[η⁵-2-isopropyl-7-(4-fluorophenyl) indenyl]zirconium dichloride,
4,5'-phenylazandiyl-bis[η⁵-2-isopropyl-7-(3-trifluoromethylphenyl)indenyl]zirconium dichloride,
4,5'-methylazandiyl-bis(η⁵-1-phenylindenyl)zirconium dichloride,
4,5'-methylazandiyl-bis(η⁵-1-phenylindenyl)zirconium dichloride,
4,5'-methylazandiyl-bis(η⁵-indenyl)zirconium dichloride,
4,5'-methylazandiyl-bis(η⁵-fluroenyl)zirconium dichloride,
4,5'-methylazandiyl-bis(η⁵-2-methylindenyl)zirconium dichloride,
4,5'-methylazandiyl-bis(η⁵-2,7-dimethylindenyl)zirconium dichloride,
4,5'-methylazandiyl-bis(η⁵-7-ethyl-2-methylindenyl)zirconium dichloride,
4,5'-methylazandiyl-bis(η⁵-7-propyl-2-methylindenyl)zirconium dichloride,
4,5'-methylazandiyl-bis(η⁵-7-butyl-2-methylindenyl)zirconium dichloride,
4,5'-methylazandiyl-bis(η⁵-7-hexyl-2-methylindenyl)zirconium dichloride,
4,5'-methylazandiyl-bis(η⁵-7-phenylindenyl)zirconium dichloride,
4,5'-methylazandiyl-bis(η⁵-7-phenyl-2-methylindenyl)zirconium dichloride,
4,5'-methylazandiyl-bis(η⁵-2-methyl-7-p-tolyl-indenyl)zirconium dichloride,
4,5'-methylazandiyl-bis(η⁵-2-methyl-7-m-tolylindenyl)zirconium dichloride,
4,5'-methylazandiyl-bis(η⁵-2-methyl-7-o-tolyl)zirconium dichloride,
4,5'-methylazandiyl-bis[η⁵-2-methyl-7-(2,4-dimethylphenyl)indenyl]zirconium dichloride,
4,5'-methylazandiyl-bis[η⁵-2-methyl-7-(4-tert-butylphenyl)indenyl]zirconium dichloride,
4,5'-methylazandiyl-bis(η⁵-7-bromo-2-methylindenyl)zirconium dichloride,
4,5'-methylazandiyl-bis(η⁵-7-mesityl-2-methylindenyl)zirconium dichloride,
4,5'-methylazandiyl-bis[η⁵-2-methyl-7-(5-methyl-thien-2-yl)indenyl]zirconium dichloride,
4,5'-methylazandiyl-bis[η⁵-2-methyl-7-(5-methyl-furan-2-yl)indenyl]zirconium dichloride,
4,5'-methylazandiyl-bis[η⁵-2-methyl-7-(2-benzothiopheneyl)indenyl]zirconium dichloride,
4,5'-methylazandiyl-bis[η⁵-2-methyl-7-(2-benzofuranyl)indenyl]zirconium dichloride,
4,5'-methylazandiyl-bis[η⁵-2-methyl-7-(4-fluorophenyl)indenyl]zirconium dichloride,
4,5'-methylazandiyl-bis[η⁵-2-methyl-7-(3-trifluoromethylphenyl)indenyl]zirconium dichloride,
4,5'-methylazandiyl-bis(η⁵-7-p-tolyl-indenyl)zirconium dichloride,
4,5'-methylazandiyl-bis(η⁵-7-m-tolylindenyl)zirconium dichloride,
4,5'-methylazandiyl-bis[η⁵-7-(4-tert-butylphenyl)indenyl]zirconium dichloride,
4,5'-methylazandiyl-bis[η⁵-7-(5-methyl-thien-2-yl)indenyl]zirconium dichloride,
4,5'-methylazandiyl-bis[η⁵-7-(5-methyl-furan-2-yl)indenyl]zirconium dichloride,
4,5'-methylazandiyl-bis[η⁵-7-(2-benzothiopheneyl)indenyl]zirconium dichloride,
4,5'-methylazandiyl-bis[η⁵-7-(2-benzofuranyl)indenyl]zirconium dichloride,
4,5'-methylazandiyl-bis[η⁵-7-(4-fluorophenyl)indenyl]zirconium dichloride,
4,5'-methylazandiyl-bis[η⁵-7-(3-trifluoromethylphenyl)indenyl]zirconium dichloride,
4,5'-methylazandiyl-bis(η⁵-2-isopropyl-7-phenylindenyl)zirconium dichloride,
4,5'-methylazandiyl-bis(η⁵-2-isopropyl-7-p-tolyl-indenyl)zirconium dichloride,
4,5'-methylazandiyl-bis(η⁵-2-isopropyl-7-m-tolylindenyl)zirconium dichloride,
4,5'-methylazandiyl-bis[η⁵-2-isopropyl-7-(4-tert-butylphenyl)indenyl]zirconium dichloride,
4,5'-methylazandiyl-bis[η⁵-2-isopropyl-7-(5-methyl-thien-2-yl)indenyl]zirconium dichloride,
4,5'-methylazandiyl-bis[η⁵-2-isopropyl-7-(5-methyl-furan-2-yl)indenyl]zirconium dichloride,
4,5'-methylazandiyl-bis[η⁵-2-isopropyl-7-(2-benzothiopheneyl)indenyl]zirconium dichloride,
4,5'-methylazandiyl-bis[η⁵-2-isopropyl-7-(2-benzofuranyl) indenyl]zirconium dichloride,
4,5'-methylazandiyl-bis[η⁵-2-isopropyl-7-(4-fluorophenyl)indenyl]zirconium dichloride,
4,5'-methylazandiyl-bis[η⁵-2-isopropyl-7-(3-trifluoromethylphenyl)indenyl]zirconium dichloride,
4,5'-phenylphosphindiyl-bis(η⁵-1-phenylindenyl)zirconium dichloride,
4,5'-phenylphosphindiyl-bis(η⁵-1-phenylindenyl)zirconium dichloride,
4,5'-phenylphosphindiyl-bis(η⁵-indenyl)zirconium dichloride,
4,5'-phenylphosphindiyl-bis(η⁵-fluroenyl)zirconium dichloride,
4,5'-phenylphosphindiyl-bis(η⁵-2-methylindenyl)zirconium dichloride,
4,5'-phenylphosphindiyl-bis(η⁵-2,7-dimethylindenyl)zirconium dichloride,
4,5'-phenylphosphindiyl-bis(η⁵-7-ethyl-2-methylindenyl)zirconium dichloride,
4,5'-phenylphosphindiyl-bis(η⁵-7-propyl-2-methylindenyl)zirconium dichloride,
4,5'-phenylphosphindiyl-bis(η⁵-7-butyl-2-methylindenyl)zirconium dichloride,
4,5'-phenylphosphindiyl-bis(η⁵-7-hexyl-2-methylindenyl)zirconium dichloride,
4,5'-phenylphosphindiyl-bis(η⁵-7-phenylindenyl)zirconium dichloride,
4,5'-phenylphosphindiyl-bis(η⁵-7-phenyl-2-methylindenyl)zirconium dichloride,
4,5'-phenylphosphindiyl-bis(η⁵-2-methyl-7-p-tolyl-indenyl)zirconium dichloride,
4,5'-phenylphosphindiyl-bis(η⁵-2-methyl-7-m-tolylindenyl)zirconium dichloride,
4,5'-phenylphosphindiyl-bis(η⁵-2-methyl-7-o-tolylindenyl)zirconium dichloride,
4,5'-phenylphosphindiyl-bis[η⁵-2-methyl-7-(2,4-dimethylphenyl)indenyl]zirconium dichloride,
4,5'-phenylphosphindiyl-bis[η⁵-2-methyl-7-(4-tert-butylphenyl)indenyl]zirconium dichloride,
4,5'-phenylphosphindiyl-bis(η⁵-7-bromo-2-methylindenyl)zirconium dichloride,
4,5'-phenylphosphindiyl-bis(η⁵-7-mesityl-2-methylindenyl)zirconium dichloride,
4,5'-phenylphosphindiyl-bis[η⁵-2-methyl-7-(5-methyl-thien-2-yl)indenyl]zirconium dichloride,
4,5'-phenylphosphindiyl-bis[η⁵-2-methyl-7-(5-methyl-furan-2-yl)indenyl]zirconium dichloride, 4,5'-phenylphosphindiyl-bis[η$^5$-2-methyl-7-(2-benzothiopheneyl)indenyl]zirconium dichloride,
4,5'-phenylphosphindiyl-bis[η$^5$-2-methyl-7-(2-benzofuranyl)indenyl]zirconium dichloride,
4,5'-phenylphosphindiyl-bis[η$^5$-2-methyl-7-(4-fluorophenyl)indenyl]zirconium dichloride,
4,5'-phenylphosphindiyl-bis[η$^5$-2-methyl-7-(3-trifluoromethylphenyl)indenyl]zirconium dichloride,
4,5'-phenylphosphindiyl-bis(η$^5$-7-p-tolyl-indenyl)zirconium dichloride,
4,5'-phenylphosphindiyl-bis(η$^5$-7-m-tolylindenyl)zirconium dichloride,
4,5'-phenylphosphindiyl-bis[η$^5$-7-(4-tert-butylphenyl)indenyl]zirconium dichloride,
4,5'-phenylphosphindiyl-bis[η$^5$-7-(5-methyl-thien-2-yl)indenyl]zirconium dichloride,
4,5'-phenylphosphindiyl-bis[η$^5$-7-(5-methyl-furan-2-yl)indenyl]zirconium dichloride,
4,5'-phenylphosphindiyl-bis[η$^5$-7-(2-benzothiopheneyl)indenyl]zirconium dichloride,
4,5'-phenylphosphindiyl-bis[η$^5$-7-(2-benzofuranyl)indenyl]zirconium dichloride,
4,5'-phenylphosphindiyl-bis[η$^5$-7-(4-fluorophenyl)indenyl]zirconium dichloride,
4,5'-phenylphosphindiyl-bis[η$^5$-7-(3-trifluoromethylphenyl)indenyl]zirconium dichloride,
4,5'-phenylphosphindiyl-bis(η$^5$-2-isopropyl-7-phenylindenyl)zirconium dichloride,
4,5'-phenylphosphindiyl-bis(η$^5$-2-isopropyl-7-p-tolyl-indenyl)zirconium dichloride,
4,5'-phenylphosphindiyl-bis(η$^5$-2-isopropyl-7-m-tolylindenyl)zirconium dichloride,
4,5'-phenylphosphindiyl-bis[η$^5$-2-isopropyl-7-(4-tert-butylphenyl)indenyl]zirconium dichloride,
4,5'-phenylphosphindiyl-bis[η$^5$-2-isopropyl-7-(5-methyl-thien-2-yl)indenyl]zirconium dichloride,
4,5'-phenylphosphindiyl-bis[η$^5$-2-isopropyl-7-(5-methyl-furan-2-yl)indenyl]zirconium dichloride,
4,5'-phenylphosphindiyl-bis[η$^5$-2-isopropyl-7-(2-benzothiopheneyl)indenyl]zirconium dichloride,
4,5'-phenylphosphindiyl-bis[η$^5$-2-isopropyl-7-(2-benzofuranyl)indenyl]zirconium dichloride,
4,5'-phenylphosphindiyl-bis[η$^5$-2-isopropyl-7-(4-fluorophenyl)indenyl]zirconium dichloride,
4,5'-phenylphosphindiyl-bis[η$^5$-2-isopropyl-7-(3-trifluoromethylphenyl)indenyl]zirconium dichloride,
4,5'-methylphosphindiyl-bis[η$^5$-1-phenylindenyl]zirconium dichloride,
4,5'-methylphosphindiyl-bis[η$^5$-1-phenylindenyl]zirconium dichloride,
4,5'-methylphosphindiyl-bis(η$^5$-indenyl)zirconium dichloride,
4,5'-methylphosphindiyl-bis(η$^5$-fluroenyl)zirconium dichloride,
4,5'-methylphosphindiyl-bis(η$^5$-2-methylindenyl)zirconium dichloride,
4,5'-methylphosphindiyl-bis(η$^5$-2,7-dimethylindenyl)zirconium dichloride,
4,5'-methylphosphindiyl-bis(η$^5$-7-ethyl-2-methylindenyl)zirconium dichloride,
4,5'-methylphosphindiyl-bis(η$^5$-7-propyl-2-methylindenyl)zirconium dichloride,
4,5'-methylphosphindiyl-bis(η$^5$-7-butyl-2-methylindenyl)zirconium dichloride,
4,5'-methylphosphindiyl-bis(η$^5$-7-hexyl-2-methylindenyl)zirconium dichloride,
4,5'-methylphosphindiyl-bis(η$^5$-7-phenylindenyl)zirconium dichloride,
4,5'-methylphosphindiyl-bis(η$^5$-7-phenyl-2-methylindenyl)zirconium dichloride,
4,5'-methylphosphindiyl-bis(η$^5$-2-methyl-7-p-tolyl-indenyl)zirconium dichloride,
4,5'-methylphosphindiyl-bis(η$^5$-2-methyl-7-m-tolylindenyl)zirconium dichloride,
4,5'-methylphosphindiyl-bis(η$^5$-2-methyl-7-o-tolylindenyl)zirconium dichloride,
4,5'-methylphosphindiyl-bis[η$^5$-2-methyl-7-(2,4-dimethylphenyl)indenyl]zirconium dichloride,
4,5'-methylphosphindiyl-bis[η$^5$-2-methyl-7-(4-tert-butylphenyl)indenyl]zirconium dichloride,
4,5'-methylphosphindiyl-bis(η$^5$-7-bromo-2-methylindenyl)zirconium dichloride,
4,5'-methylphosphindiyl-bis(η$^5$-7-mesityl-2-methylindenyl)zirconium dichloride,
4,5'-methylphosphindiyl-bis[η$^5$-2-methyl-7-(5-methyl-thien-2-yl)indenyl]zirconium dichloride,
4,5'-methylphosphindiyl-bis[η$^5$-2-methyl-7-(5-methyl-furan-2-yl)indenyl]zirconium dichloride,
4,5'-methylphosphindiyl-bis[η$^5$-2-methyl-7-(2-benzothiopheneyl)indenyl]zirconium dichloride,
4,5'-methylphosphindiyl-bis[η$^5$-2-methyl-7-(2-benzofuranyl)indenyl]zirconium dichloride,
4,5'-methylphosphindiyl-bis[η$^5$-2-methyl-7-(4-fluorophenyl)indenyl]zirconium dichloride,
4,5'-methylphosphindiyl-bis[η$^5$-2-methyl-7-(3-trifluoromethylphenyl)indenyl]zirconium dichloride,
4,5'-methylphosphindiyl-bis(η$^5$-7-p-tolyl-indenyl)zirconium dichloride,
4,5'-methylphosphindiyl-bis(η$^5$-7-m-tolylindenyl)zirconium dichloride,
4,5'-methylphosphindiyl-bis[η$^5$-7-(4-tert-butylphenyl)indenyl]zirconium dichloride,
4,5'-methylphosphindiyl-bis[η$^5$-7-(5-methyl-thien-2-yl)indenyl]zirconium dichloride,
4,5'-methylphosphindiyl-bis[η$^5$-7-(5-methyl-furan-2-yl)indenyl]zirconium dichloride,
4,5'-methylphosphindiyl-bis[η$^5$-7-(2-benzothiopheneyl)indenyl]zirconium dichloride,
4,5'-methylphosphindiyl-bis[η$^5$-7-(2-benzofuranyl)indenyl]zirconium dichloride,
4,5'-methylphosphindiyl-bis[η$^5$-7-(4-fluorophenyl)indenyl]zirconium dichloride,
4,5'-methylphosphindiyl-bis[η$^5$-7-(3-trifluoromethylphenyl)indenyl]zirconium dichloride,
4,5'-methylphosphindiyl-bis(η$^5$-2-isopropyl-7-phenylindenyl)zirconium dichloride,
4,5'-methylphosphindiyl-bis(η$^5$-2-isopropyl-7-p-tolyl-indenyl)zirconium dichloride,
4,5'-methylphosphindiyl-bis(η$^5$-2-isopropyl-7-m-tolylindenyl)zirconium dichloride,
4,5'-methylphosphindiyl-bis[η$^5$-2-isopropyl-7-(4-tert-butylphenyl)indenyl]zirconium dichloride,
4,5'-methylphosphindiyl-bis[η$^5$-2-isopropyl-7-(5-methyl-thien-2-yl)indenyl]zirconium dichloride,
4,5'-methylphosphindiyl-bis[η$^5$-2-isopropyl-7-(5-methyl-furan-2-yl)indenyl]zirconium dichloride,
4,5'-methylphosphindiyl-bis[η$^5$-2-isopropyl-7-(2-benzothiopheneyl)indenyl]zirconium dichloride,
4,5'-methylphosphindiyl-bis[η$^5$-2-isopropyl-7-(2-benzofuranyl)indenyl]zirconium dichloride,
4,5'-methylphosphindiyl-bis[η$^5$-2-isopropyl-7-(4-fluorophenyl)indenyl]zirconium dichloride, 4,5'-methylphosphindiyl-bis[$\eta^5$-2-isopropyl-7-(3-trifluoromethylphenyl)indenyl]zirconium dichloride,
4,4'-sulfandiyl-bis($\eta^5$-2-methylindenyl)zirconium dimethyl,
4,4'-sulfandiyl-bis($\eta^5$-indenyl)zirconium dimethyl,
4,4'-phenylazandiyl-bis($\eta^5$-2-methylindenyl)zirconium dimethyl,
4,4'-phenylphosphindiyl-bis($\eta^5$-2-methylindenyl)zirconium dimethyl,
4,4'-oxadiyl-bis($\eta^5$-1-phenylindenyl)zirconium dichloride,
4,4'-sulfandiyl-bis($\eta^5$-1-phenylindenyl)zirconium dimethyl,
4,4'-phenylphosphindiyl-bis($\eta^5$-1-phenylindene)zirconium dimethyl,
4,4'-phenylazandiyl-bis($\eta^5$-1-phenylindenyl)zirconium dimethyl,
4,4'-oxadiyl-bis($\eta^5$-1-naphthylindenyl)zirconium dichloride,
4,4'-sulfandiyl-bis($\eta^5$-1-naphthylindenyl)zirconium dimethyl,
4,4'-phenylphosphindiyl-bis($\eta^5$-1-naphthylindenyl)zirconium dimethyl,
4,4'-sulfandiyl-bis($\eta^5$-2-methyl-1-phenylindenyl)zirconium dimethyl,
4,4'-sulfandiyl-bis($\eta^5$-7-bromo-2-methylindenyl)zirconium dimethyl,
4,4'-sulfandiyl-bis($\eta^5$-2,7-dimethylindenyl)zirconium dimethyl,
4,4'-sulfandiyl-bis($\eta^5$-7-phenyl-2-methylindenyl)zirconium dimethyl,
4,4'-sulfandiyl-bis($\eta^5$-2-methyl-7-p-tolyl-indenyl)zirconium dimethyl,
4,4'-sulfandiyl-bis($\eta^5$-2-methyl-7-m-tolylindenyl)zirconium dimethyl,
4,4'-sulfandiyl-bis[$\eta^5$-2-methyl-7-(4-tert-butylphenyl)indenyl]zirconium dimethyl,
4,4'-sulfandiyl-bis($\eta^5$-7-mesityl-2-methylindenyl)zirconium dimethyl,
4,4'-sulfandiyl-bis[$\eta^5$-2-methyl-7-(5-methyl-thien-2-yl)indenyl]zirconium dimethyl,
4,4'-sulfandiyl-bis[$\eta^5$-2-methyl-7-(5-methyl-furan-2-yl)indenyl]zirconium dimethyl,
4,4'-sulfandiyl-bis[$\eta^5$-2-methyl-7-(2-benzothiopheneyl)indenyl]zirconium dimethyl,
4,4'-sulfandiyl-bis[$\eta^5$-2-methyl-7-(2-benzofuranyl)indenyl]zirconium dimethyl,
4,4'-sulfandiyl-bis[$\eta^5$-2-methyl-7-(4-fluorophenyl)indenyl]zirconium dimethyl,
4,4'-sulfandiyl-bis[$\eta^5$-2-methyl-7-(3-trifluoromethylphenyl)indenyl]zirconium dimethyl,
4,4'-sulfandiyl-bis($\eta^5$-2-methylindenyl)zirconium dibenzyl,
4,4'-sulfandiyl-bis($\eta^5$-indenyl)zirconium dibenzyl,
4,4'-phenylazandiyl-bis($\eta^5$-2-methylindenyl)zirconium dibenzyl,
4,4'-phenylphosphindiyl-bis($\eta^5$-2-methylindenyl)zirconium dibenzyl,
4,4'-oxadiyl-bis($\eta^5$-1-phenylindenyl)zirconium dibenzyl,
4,4'-sulfandiyl-bis($\eta^5$-1-phenylindenyl)zirconium dibenzyl,
4,4'-phenylphosphindiyl-bis($\eta^5$-1-phenylindene)zirconium dibenzyl,
4,4'-phenylazandiyl-bis($\eta^5$-1-phenylindenyl)zirconium dibenzyl,
4,4'-oxadiyl-bis($\eta^5$-1-naphthylindenyl)zirconium dibenzyl,
4,4'-sulfandiyl-bis($\eta^5$-1-naphthylindenyl)zirconium dibenzyl,
4,4'-phenylphosphindiyl-bis($\eta^5$-1-naphthylindenyl)zirconium dibenzyl,
4,4'-sulfandiyl-bis($\eta^5$-2-methyl-1-phenylindenyl)zirconium dibenzyl,
4,4'-sulfandiyl-bis($\eta^5$-7-bromo-2-methylindenyl)zirconium dibenzyl,
4,4'-sulfandiyl-bis($\eta^5$-2,7-dimethylindenyl)zirconium dibenzyl,
4,4'-sulfandiyl-bis($\eta^5$-7-phenyl-2-methylindenyl)zirconium dibenzyl,
4,4'-sulfandiyl-bis($\eta^5$-2-methyl-7-p-tolyl-indenyl)zirconium dibenzyl,
4,4'-sulfandiyl-bis($\eta^5$-2-methyl-7-m-tolylindenyl)zirconium dibenzyl,
4,4'-sulfandiyl-bis[$\eta^5$-2-methyl-7-(4-tert-butylphenyl)indenyl]zirconium dibenzyl,
4,4'-sulfandiyl-bis($\eta^5$-7-mesityl-2-methylindenyl)zirconium dibenzyl,
4,4'-sulfandiyl-bis[$\eta^5$-2-methyl-7-(5-methyl-thien-2-yl)indenyl]zirconium dibenzyl,
4,4'-sulfandiyl-bis[$\eta^5$-2-methyl-7-(5-methyl-furan-2-yl)indenyl]zirconium dibenzyl,
4,4'-sulfandiyl-bis[$\eta^5$-2-methyl-7-(2-benzothiopheneyl)indenyl]zirconium dibenzyl,
4,4'-sulfandiyl-bis[$\eta^5$-2-methyl-7-(2-benzofuranyl)indenyl]zirconium dibenzyl,
4,4'-sulfandiyl-bis[$\eta^5$-2-methyl-7-(4-fluorophenyl)indenyl]zirconium dibenzyl,
4,4'-sulfandiyl-bis[$\eta^5$-2-methyl-7-(3-trifluoromethylphenyl)indenyl]zirconium dibenzyl,
4,4'-sulfandiyl-bis($\eta^5$-2-methylindenyl)hafnium dichloride,
4,4'-sulfandiyl-bis($\eta^5$-indenyl)hafnium dichloride,
4,4'-phenylazandiyl-bis($\eta^5$-2-methylindenyl)hafnium dichloride,
4,4'-phenylphosphindiyl-bis($\eta^5$-2-methylindenyl)hafnium dichloride,
4,4'-oxadiyl-bis($\eta^5$-1-phenylindenyl)hafnium dichloride,
4,4'-sulfandiyl-bis($\eta^5$-1-phenylindenyl)hafnium dichloride,
4,4'-phenylphosphindiyl-bis($\eta^5$-1-phenylindene)hafnium dichloride,
4,4'-phenylazandiyl-bis($\eta^5$-1-phenylindenyl)hafnium dichloride,
4,4'-oxadiyl-bis($\eta^5$-1-naphthylindenyl)hafnium dichloride,
4,4'-sulfandiyl-bis($\eta^5$-1-naphthylindenyl)hafnium dichloride,
4,4'-phenylphosphindiyl-bis($\eta^5$-1-naphthylindenyl)hafnium dichloride,
4,4'-sulfandiyl-bis($\eta^5$-2-methyl-1-phenylindenyl)hafnium dichloride,
4,4'-sulfandiyl-bis($\eta^5$-7-bromo-2-methylindenyl)hafnium dichloride,
4,4'-sulfandiyl-bis($\eta^5$-2,7-dimethylindenyl)hafnium dichloride,
4,4'-sulfandiyl-bis($\eta^5$-7-phenyl-2-methylindenyl)hafnium dichloride,
4,4'-sulfandiyl-bis($\eta^5$-2-methyl-7-p-tolyl-indenyl)hafnium dichloride,
4,4'-sulfandiyl-bis($\eta^5$-2-methyl-7-m-tolylindenyl)hafnium dichloride,
4,4'-sulfandiyl-bis[($\eta^5$-2-methyl-7-(4-tert-butylphenyl)indenyl]hafnium dichloride,
4,4'-sulfandiyl-bis($\eta^5$-7-mesityl-2-methylindenyl)hafnium dichloride,
4,4'-sulfandiyl-bis[$\eta^5$-2-methyl-7-(5-methyl-thien-2-yl)indenyl]hafnium dichloride,
4,4'-sulfandiyl-bis[$\eta^5$-2-methyl-7-(5-methyl-furan-2-yl)indenyl]hafnium dichloride,
4,4'-sulfandiyl-bis[$\eta^5$-2-methyl-7-(2-benzothiopheneyl)indenyl]hafnium dichloride,
4,4'-sulfandiyl-bis[$\eta^5$-2-methyl-7-(2-benzofuranyl)indenyl]hafnium dichloride, 4,4'-sulfandiyl-bis[η⁵-2-methyl-7-(4-fluorophenyl)indenyl]
hafnium dichloride,
4,4'-sulfandiyl-bis[η5-2-methyl-7-(3-trifluoromethylphenyl)indenyl]hafnium dichloride,
4,4'-sulfandiyl-bis(η⁵-2-methylindenyl)hafnium dimethyl,
4,4'-sulfandiyl-bis(η⁵-indenyl)hafnium dimethyl,
4,4'-phenylazandiyl-bis(η⁵-2-methylindenyl)hafnium dimethyl,
4,4'-phenylphosphindiyl-bis(η⁵-2-methylindenyl)hafnium dimethyl,
4,4'-oxadiyl-bis(η⁵-1-phenylindenyl)hafnium dichloride,
4,4'-sulfandiyl-bis(η⁵-1-phenylindenyl)hafnium dimethyl,
4,4'-phenylphosphindiyl-bis(η⁵-1-phenylindene)hafnium dimethyl,
4,4'-phenylazandiyl-bis(η⁵-1-phenylindenyl)hafnium dimethyl,
4,4'-oxadiyl-bis(η⁵-1-naphthylindenyl)hafnium dichloride,
4,4'-sulfandiyl-bis(η⁵-1-naphthylindenyl)hafnium dimethyl,
4,4'-phenylphosphindiyl-bis(η⁵-1-naphthylindenyl)hafnium dimethyl,
4,4'-sulfandiyl-bis(η⁵-2-methyl-1-phenylindenyl)hafnium dimethyl,
4,4'-sulfandiyl-bis(η⁵-7-bromo-2-methylindenyl)hafnium dimethyl,
4,4'-sulfandiyl-bis(η⁵-2,7-dimethylindenyl)hafnium dimethyl,
4,4'-sulfandiyl-bis(η⁵-7-phenyl-2-methylindenyl)hafnium dimethyl,
4,4'-sulfandiyl-bis(η⁵-2-methyl-7-p-tolyl-indenyl)hafnium dimethyl,
4,4'-sulfandiyl-bis(η⁵-2-methyl-7-m-tolylindenyl)hafnium dimethyl,
4,4'-sulfandiyl-bis[η⁵-2-methyl-7-(4-tert-butylphenyl)indenyl]hafnium dimethyl,
4,4'-sulfandiyl-bis(η⁵-7-mesityl-2-methylindenyl)hafnium dimethyl,
4,4'-sulfandiyl-bis[η⁵-2-methyl-7-(5-methyl-thien-2-yl)indenyl]hafnium dimethyl,
4,4'-sulfandiyl-bis[η⁵-2-methyl-7-(5-methyl-furan-2-yl)indenyl]hafnium dimethyl,
4,4'-sulfandiyl-bis[η⁵-2-methyl-7-(2-benzothiopheneyl)indenyl]hafnium dimethyl,
4,4'-sulfandiyl-bis[η⁵-2-methyl-7-(2-benzofuranyl)indenyl]hafnium dimethyl,
4,4'-sulfandiyl-bis[η⁵-2-methyl-7-(4-fluorophenyl)indenyl]hafnium dimethyl,
4,4'-sulfandiyl-bis[η⁵-2-methyl-7-(3-trifluoromethylphenyl)indenyl]hafnium dimethyl,
sulfandiyl-4-(η⁵-2-methylindenyl)-4'-(indenyl)zirconium dichloride,
sulfandiyl-4-(η⁵-2-methylindenyl)-4'-(η⁵-1-phenylindenyl)zirconium dichloride,
sulfandiyl-4-(η⁵-2-methylindenyl)-4'-(η⁵-1-naphthylindenyl)zirconium dichloride,
sulfandiyl-4-(η⁵-2-methylindenyl)-4'-(η⁵-7-bromo-2-methylindenyl)zirconium dichloride,
sulfandiyl-4-(η⁵-2-methylindenyl)-4'-(η⁵-7-bromo-indenyl)zirconium dichloride,
sulfandiyl-4-(η⁵-2-methylindenyl)-4'-(η⁵-2,7-dimethylindenyl)zirconium dichloride,
sulfandiyl-4-(η⁵-2-methylindenyl)-4'-(η⁵-7-phenyl-2-methylindenyl)zirconium dichloride,
sulfandiyl-4-(η⁵-2-methylindenyl)-4'-(η⁵-2-methyl-7-p-tolyl-indenyl)zirconium dichloride,
sulfandiyl-4-(η⁵-2-methylindenyl)-4'-(η⁵-2-methyl-7-m-tolylindenyl)zirconium dichloride,
sulfandiyl-4-(η⁵-2-methylindenyl)-4'-[η⁵-2-methyl-7-(4-tert-butylphenyl)indenyl]zirconium dichloride,
sulfandiyl-4-(η⁵-2-methylindenyl)-4'-[η⁵-2-methyl-7-(5-methyl-thien-2-yl)indenyl]zirconium dichloride,
sulfandiyl-4-(η⁵-2-methylindenyl)-4'-[η⁵-2-methyl-7-(5-methyl-furan-2-yl)indenyl]zirconium dichloride,
sulfandiyl-4-(η⁵-2-methylindenyl)-4'-[η⁵-2-methyl-7-(2-benzothiopheneyl)indenyl]zirconium dichloride,
sulfandiyl-4-(η⁵-2-methylindenyl)-4'-[η⁵-2-methyl-7-(2-benzofuranyl)indenyl]zirconium dichloride,
sulfandiyl-4-(η⁵-2-methylindenyl)-4'-[η⁵-2-methyl-7-(4-fluorophenyl)indenyl]zirconium dichloride,
sulfandiyl-4-(η⁵-2-methylindenyl)-4'-[η⁵-2-methyl-7-(3-trifluoromethylphenyl)indenyl]zirconium dichloride,
sulfandiyl-4-(η⁵-indenyl)-4'-(η⁵-1-phenylindenyl)zirconium dichloride,
sulfandiyl-4-(η⁵-indenyl)-4'-(η⁵-1-naphthylindenyl)zirconium dichloride,
sulfandiyl-4-(η⁵-indenyl)-4'-(η⁵-7-bromo-2-methylindenyl)zirconium dichloride,
sulfandiyl-4-(η⁵-indenyl)-4'-(η⁵-7-bromo-indenyl)zirconium dichloride,
sulfandiyl-4-(η⁵-indenyl)-4'-(η⁵-2,7-dimethylindenyl)zirconium dichloride,
sulfandiyl-4-(η⁵-indenyl)-4'-(η⁵-7-phenyl-2-methylindenyl)zirconium dichloride,
sulfandiyl-4-(η⁵-indenyl)-4'-(η⁵-2-methyl-7-p-tolyl-indenyl)zirconium dichloride,
sulfandiyl-4-(η⁵-indenyl)-4'-(η⁵-2-methyl-7-m-tolylindenyl)zirconium dichloride,
sulfandiyl-4-(η⁵-indenyl)-4'-[η⁵-2-methyl-7-(4-tert-butylphenyl)indenyl]zirconium dichloride,
sulfandiyl-4-(η⁵-indenyl)-4'-[η⁵-2-methyl-7-(5-methyl-thien-2-yl)indenyl]zirconium dichloride,
sulfandiyl-4-(η⁵-indenyl)-4'-[η⁵-2-methyl-7-(5-methyl-furan-2-yl)indenyl]zirconium dichloride,
sulfandiyl-4-(η⁵-indenyl)-4'-[η⁵-2-methyl-7-(2-benzothiopheneyl)indenyl]zirconium dichloride,
sulfandiyl-4-(η⁵-indenyl)-4'-[η⁵-2-methyl-7-(2-benzofuranyl)indenyl]zirconium dichloride,
sulfandiyl-4-(η⁵-indenyl)-4'-[η⁵-2-methyl-7-(4-fluorophenyl)indenyl]zirconium dichloride,
sulfandiyl-4-(η⁵-indenyl)-4'-[η⁵-2-methyl-7-(3-trifluoromethylphenyl)indenyl]zirconium dichloride,
sulfandiyl-4-(η⁵-1-phenylindenyl)-4'-(η⁵-1-naphthylindenyl)zirconium dichloride,
sulfandiyl-4-(η⁵-1-phenylindenyl)-4'-(η⁵-7-bromo-2-methylindenyl)zirconium dichloride,
sulfandiyl-4-(η⁵-1-phenylindenyl)-4'-(η⁵-7-bromoindenyl)zirconium dichloride,
sulfandiyl-4-(η⁵-1-phenylindenyl)-4'-(η⁵-2,7-dimethylindenyl)zirconium dichloride,
sulfandiyl-4-(η⁵-1-phenylindenyl)-4'-(η⁵-7-phenyl-2-methylindenyl)zirconium dichloride,
sulfandiyl-4-(η⁵-1-phenylindenyl)-4'-(η⁵-2-methyl-7-p-tolyl-indenyl)zirconium dichloride,
sulfandiyl-4-(η⁵-1-phenylindenyl)-4'-(η⁵-2-methyl-7-m-tolylindenyl)zirconium dichloride,
sulfandiyl-4-(η⁵-1-phenylindenyl)-4'-[η⁵-2-methyl-7-(4-tert-butylphenyl)indenyl]zirconium dichloride,
sulfandiyl-4-(η⁵-1-phenylindenyl)-4'-[η⁵-2-methyl-7-(5-methyl-thien-2-yl)indenyl]zirconium dichloride,
sulfandiyl-4-(η⁵-1-phenylindenyl)-4'-[η⁵-2-methyl-7-(5-methyl-furan-2-yl)indenyl]zirconium dichloride,
sulfandiyl-4-(η⁵-1-phenylindenyl)-4'-[η⁵-2-methyl-7-(2-benzothiopheneyl)indenyl]zirconium dichloride, sulfandiyl-4-($\eta^5$-1-phenylindenyl)-4'-[$\eta^5$-2-methyl-7-(2-benzofuranyl)indenyl]zirconium dichloride,
sulfandiyl-4-($\eta^5$-1-phenylindenyl)-4'-[$\eta^5$-2-methyl-7-(4-fluorophenyl)indenyl]zirconium dichloride,
sulfandiyl-4-($\eta^5$-1-phenylindenyl)-4'-[$\eta^5$-2-methyl-7-(3-trifluoromethylphenyl)indenyl]zirconium dichloride,
sulfandiyl-4-($\eta^5$-1-naphthylindenyl)-4'-($\eta^5$-7-bromo-2-methylindenyl)zirconium dichloride,
sulfandiyl-4-($\eta^5$-1-naphthylindenyl)-4'-($\eta^5$-7-bromoindenyl)zirconium dichloride,
sulfandiyl-4-($\eta^5$-1-naphthylindenyl)-4'-($\eta^5$-2,7-dimethylindenyl)zirconium dichloride,
sulfandiyl-4-($\eta^5$-1-naphthylindenyl)-4'-($\eta^5$-7-phenyl-2-methylindenyl)zirconium dichloride,
sulfandiyl-4-($\eta^5$-1-naphthylindenyl)-4'-($\eta^5$-2-methyl-7-p-tolyl-indenyl)zirconium dichloride,
sulfandiyl-4-($\eta^5$-1-naphthylindenyl)-4'-($\eta^5$-2-methyl-7-m-tolylindenyl)zirconium dichloride,
sulfandiyl-4-($\eta^5$-1-naphthylindenyl)-4'-[$\eta^5$-2-methyl-7-(4-tert-butylphenyl)indenyl]zirconium dichloride,
sulfandiyl-4-($\eta^5$-1-naphthylindenyl)-4'-[$\eta^5$-2-methyl-7-(5-methyl-thien-2-yl)indenyl]zirconium dichloride,
sulfandiyl-4-($\eta^5$-1-naphthylindenyl)-4'-[$\eta^5$-2-methyl-7-(5-methyl-furan-2-yl)indenyl]zirconium dichloride,
sulfandiyl-4-($\eta^5$-1-naphthylindenyl)-4'-[$\eta^5$-2-methyl-7-(2-benzothiopheneyl)indenyl]zirconium dichloride,
sulfandiyl-4-($\eta^5$-1-naphthylindenyl)-4'-[$\eta^5$-2-methyl-7-(2-benzofuranyl)indenyl]zirconium dichloride,
sulfandiyl-4-($\eta^5$-1-naphthylindenyl)-4'-[$\eta^5$-2-methyl-7-(4-fluorophenyl)indenyl]zirconium dichloride,
sulfandiyl-4-($\eta^5$-1-naphthylindenyl)-4'-[$\eta^5$-2-methyl-7-(3-trifluoromethylphenyl)indenyl]zirconium dichloride,
sulfandiyl-4-($\eta^5$-7-bromo-2-methylindenyl)-4'-($\eta^5$-7-bromoindenyl)zirconium dichloride,
sulfandiyl-4-($\eta^5$-7-bromo-2-methylindenyl)-4'-($\eta^5$-2,7-dimethylindenyl)zirconium dichloride,
sulfandiyl-4-($\eta^5$-7-bromo-2-methylindenyl)-4'-($\eta^5$-7-phenyl-2-methylindenyl)zirconium dichloride,
sulfandiyl-4-($\eta^5$-7-bromo-2-methylindenyl)-4'-($\eta^5$-2-methyl-7-p-tolyl-indenyl)zirconium dichloride,
sulfandiyl-4-($\eta^5$-7-bromo-2-methylindenyl)-4'-($\eta^5$-2-methyl-7-m-tolylindenyl)zirconium dichloride,
sulfandiyl-4-($\eta^5$-7-bromo-2-methylindenyl)-4'-[$\eta^5$-2-methyl-7-(4-tert-butylphenyl)indenyl]zirconium dichloride,
sulfandiyl-4-($\eta^5$-7-bromo-2-methylindenyl)-4'-[$\eta^5$-2-methyl-7-(5-methyl-thien-2-yl)indenyl]zirconium dichloride,
sulfandiyl-4-($\eta^5$-7-bromo-2-methylindenyl)-4'-[$\eta^5$-2-methyl-7-(5-methyl-furan-2-yl)indenyl]zirconium dichloride,
sulfandiyl-4-($\eta^5$-7-bromo-2-methylindenyl)-4'-[$\eta^5$-2-methyl-7-(2-benzothiopheneyl)indenyl]zirconium dichloride,
sulfandiyl-4-($\eta^5$-7-bromo-2-methylindenyl)-4'-[$\eta^5$-2-methyl-7-(2-benzofuranyl)indenyl]zirconium dichloride,
sulfandiyl-4-($\eta^5$-7-bromo-2-methylindenyl)-4'-[$\eta^5$-2-methyl-7-(4-fluorophenyl)indenyl]zirconium dichloride,
sulfandiyl-4-($\eta^5$-7-bromo-2-methylindenyl)-4'-[$\eta^5$-2-methyl-7-(3-trifluoromethylphenyl)indenyl]zirconium dichloride,
sulfandiyl-4-($\eta^5$-7-bromoindenyl)-4'-($\eta^5$-2,7-dimethylindenyl)zirconium dichloride,
sulfandiyl-4-($\eta^5$-7-bromoindenyl)-4'-($\eta^5$-7-phenyl-2-methylindenyl)zirconium dichloride,
sulfandiyl-4-($\eta^5$-7-bromoindenyl)-4'-($\eta^5$-2-methyl-7-p-tolyl-indenyl)zirconium dichloride,
sulfandiyl-4-($\eta^5$-7-bromoindenyl)-4'-($\eta^5$-2-methyl-7-m-tolylindenyl)zirconium dichloride,
sulfandiyl-4-($\eta^5$-7-bromoindenyl)-4'-[$\eta^5$-2-methyl-7-(4-tert-butylphenyl)indenyl]zirconium dichloride,
sulfandiyl-4-($\eta^5$-7-bromoindenyl)-4'-[$\eta^5$-2-methyl-7-(5-methyl-thien-2-yl)indenyl]zirconium dichloride,
sulfandiyl-4-($\eta^5$-7-bromoindenyl)-4'-[$\eta^5$-2-methyl-7-(5-methyl-furan-2-yl)indenyl]zirconium dichloride,
sulfandiyl-4-($\eta^5$-7-bromoindenyl)-4'-[$\eta^5$-2-methyl-7-(2-benzothiopheneyl)indenyl]zirconium dichloride,
sulfandiyl-4-($\eta^5$-7-bromoindenyl)-4'-[$\eta^5$-2-methyl-7-(2-benzofuranyl)indenyl]zirconium dichloride,
sulfandiyl-4-($\eta^5$-7-bromoindenyl)-4'-[$\eta^5$-2-methyl-7-(4-fluorophenyl)indenyl]zirconium dichloride,
sulfandiyl-4-($\eta^5$-7-bromoindenyl)-4'-[$\eta^5$-2-methyl-7-(3-trifluoromethylphenyl)indenyl]zirconium dichloride,
sulfandiyl-4-($\eta^5$-2,7-dimethylindenyl)-4'-($\eta^5$-7-phenyl-2-methylindenyl)zirconium dichloride,
sulfandiyl-4-($\eta^5$-2,7-dimethylindenyl)-4'-($\eta^5$-2-methyl-7-p-tolyl-indenyl)zirconium dichloride,
sulfandiyl-4-($\eta^5$-2,7-dimethylindenyl)-4'-($\eta^5$-2-methyl-7-m-tolylindenyl)zirconium dichloride,
sulfandiyl-4-($\eta^5$-2,7-dimethylindenyl)-4'-[$\eta^5$-2-methyl-7-(4-tert-butylphenyl)indenyl]zirconium dichloride,
sulfandiyl-4-($\eta^5$-2,7-dimethylindenyl)-4'-[$\eta^5$-2-methyl-7-(5-methyl-thien-2-yl)indenyl]zirconium dichloride,
sulfandiyl-4-($\eta^5$-2,7-dimethylindenyl)-4'-[$\eta^5$-2-methyl-7-(5-methyl-furan-2-yl)indenyl]zirconium dichloride,
sulfandiyl-4-($\eta^5$-2,7-dimethylindenyl)-4'-[$\eta^5$-2-methyl-7-(2-benzothiopheneyl)indenyl]zirconium dichloride,
sulfandiyl-4-($\eta^5$-2,7-dimethylindenyl)-4'-[$\eta^5$-2-methyl-7-(2-benzofuranyl)indenyl]zirconium dichloride,
sulfandiyl-4-($\eta^5$-2,7-dimethylindenyl)-4'-[$\eta^5$-2-methyl-7-(4-fluorophenyl)indenyl]zirconium dichloride,
sulfandiyl-4-($\eta^5$-2,7-dimethylindenyl)-4'-[$\eta^5$-2-methyl-7-(3-trifluoromethylphenyl)indenyl]zirconium dichloride,
sulfandiyl-4-($\eta^5$-7-phenyl-2-methylindenyl)-4'-($\eta^5$-2-methyl-7-p-tolyl-indenyl)zirconium dichloride,
sulfandiyl-4-($\eta^5$-7-phenyl-2-methylindenyl)-4'-($\eta^5$-2-methyl-7-m-tolylindenyl)zirconium dichloride,
sulfandiyl-4-($\eta^5$-7-phenyl-2-methylindenyl)-4'-[$\eta^5$-2-methyl-7-(4-tert-butylphenyl)indenyl]zirconium dichloride,
sulfandiyl-4-($\eta^5$-7-phenyl-2-methylindenyl)-4'-[$\eta^5$-2-methyl-7-(5-methyl-thien-yl)indenyl]zirconium dichloride,
sulfandiyl-4-($\eta^5$-7-phenyl-2-methylindenyl)-4'-[$\eta^5$-2-methyl-7-(5-methyl-furan-2-yl)indenyl]zirconium dichloride,
sulfandiyl-4-($\eta^5$-7-phenyl-2-methylindenyl)-4'-[$\eta^5$-2-methyl-7-(2-benzothiopheneyl)indenyl]zirconium dichloride,
sulfandiyl-4-($\eta^5$-7-phenyl-2-methylindenyl)-4'-[$\eta^5$-2-methyl-7-(2-benzofuranyl)indenyl]zirconium dichloride,
sulfandiyl-4-($\eta^5$-7-phenyl-2-methylindenyl)-4'-[$\eta^5$-2-methyl-7-(4-fluorophenyl)indenyl]zirconium dichloride,
sulfandiyl-4-($\eta^5$-7-phenyl-2-methylindenyl)-4'-[$\eta^5$-2-methyl-7-(3-trifluoromethylphenyl)indenyl]zirconium dichloride,
sulfandiyl-4-($\eta^5$-2-methyl-7-p-tolylindenyl)-4'-($\eta^5$-2-methyl-7-m-tolylindenyl)zirconium dichloride,
sulfandiyl-4-($\eta^5$-2-methyl-7-p-tolylindenyl)-4'-[$\eta^5$-2-methyl-7-(4-tert-butylphenyl)indenyl]zirconium dichloride,
sulfandiyl-4-($\eta^5$-2-methyl-7-p-tolylindenyl)-4'-[$\eta^5$-2-methyl-7-(5-methyl-thien-2-yl)indenyl]zirconium dichloride,
sulfandiyl-4-($\eta^5$-2-methyl-7-p-tolylindenyl)-4'-[$\eta^5$-2-methyl-7-(5-methyl-furan-2-yl)indenyl]zirconium dichloride, sulfandiyl-4-(η⁵-2-methyl-7-p-tolylindenyl)-4'-[η⁵-2-methyl-7-(2-benzothiopheneyl)indenyl]zirconium dichloride,
sulfandiyl-4-(η⁵-2-methyl-7-p-tolylindenyl)-4'-[η⁵-2-methyl-7-(2-benzofuranyl)indenyl]zirconium dichloride,
sulfandiyl-4-(η⁵-2-methyl-7-p-tolylindenyl)-4'-[η⁵-2-methyl-7-(4-fluorophenyl)indenyl]zirconium dichloride,
sulfandiyl-4-(η⁵-2-methyl-7-p-tolylindenyl)-4'-[η⁵-2-methyl-7-(3-trifluoromethylphenyl)indenyl]zirconium dichloride,
sulfandiyl-4-(η⁵-2-methyl-7-m-tolylindenyl)-4'-[η⁵-2-methyl-7-(4-tert-butylphenyl)indenyl]zirconium dichloride,
sulfandiyl-4-(η⁵-2-methyl-7-m-tolylindenyl)-4'-[η⁵-2-methyl-7-(5-methyl-thien-2-yl)indenyl]zirconium dichloride,
sulfandiyl-4-(η⁵-2-methyl-7-m-tolylindenyl)-4'-[η⁵-2-methyl-7-(5-methyl-furan-2-yl)indenyl]zirconium dichloride,
sulfandiyl-4-(η⁵-2-methyl-7-m-tolylindenyl)-4'-[η⁵-2-methyl-7-(2-benzothiopheneyl)indenyl]zirconium dichloride,
sulfandiyl-4-(η⁵-2-methyl-7-m-tolylindenyl)-4'-[η⁵-2-methyl-7-(2-benzofuranyl)indenyl]zirconium dichloride,
sulfandiyl-4-(η⁵-2-methyl-7-m-tolylindenyl)-4'-[η⁵-2-methyl-7-(4-fluorophenyl)indenyl]zirconium dichloride,
sulfandiyl-4-(η⁵-2-methyl-7-m-tolylindenyl)-4'-[η⁵-2-methyl-7-(3-trifluoromethylphenyl)indenyl]zirconium dichloride,
sulfandiyl-4-[η⁵-2-methyl-7-(4-tert-butylphenyl)indenyl]-4'-[η⁵-2-methyl-7-(5-methyl-thien-2-yl)indenyl]zirconium dichloride,
sulfandiyl-4-[η⁵-2-methyl-7-(4-tert-butylphenyl)indenyl]-4'-[η⁵-2-methyl-7-(5-methyl-furan-2-yl)indenyl]zirconium dichloride,
sulfandiyl-4-[η⁵-2-methyl-7-(4-tert-butylphenyl)indenyl]-4'-[η⁵-2-methyl-7-(2-benzothiopheneyl)indenyl]zirconium dichloride,
sulfandiyl-4-[η⁵-2-methyl-7-(4-tert-butylphenyl)indenyl]-4'-[η⁵-2-methyl-7-(2-benzofuranyl)indenyl]zirconium dichloride,
sulfandiyl-4-[η⁵-2-methyl-7-(4-tert-butylphenyl)indenyl]-4'-[η⁵-2-methyl-7-(4-fluorophenyl)indenyl]zirconium dichloride,
sulfandiyl-4-[η⁵-2-methyl-7-(4-tert-butylphenyl)indenyl]-4'-[η⁵-2-methyl-7-(3-trifluoromethylphenyl)indenyl]zirconium dichloride,
sulfandiyl-4-[η⁵-2-methyl-7-(5-methyl-thien-2-yl)indenyl]-4'-[η⁵-2-methyl-7-(5-methyl-furan-2-yl)indenyl]zirconium dichloride,
sulfandiyl-4-[η⁵-2-methyl-7-(5-methyl-thien-2-yl)indenyl]-4'-[η⁵-2-methyl-7-(2-benzothiopheneyl)indenyl]zirconium dichloride,
sulfandiyl-4-[η⁵-2-methyl-7-(5-methyl-thien-2-yl)indenyl]-4'-[η⁵-2-methyl-7-(2-benzofuranyl)indenyl]zirconium dichloride,
sulfandiyl-4-[η⁵-2-methyl-7-(5-methyl-thien-2-yl)indenyl]-4'-[η⁵-2-methyl-7-(4-fluorophenyl)indenyl]zirconium dichloride,
sulfandiyl-4-[η⁵-2-methyl-7-(5-methyl-thien-2-yl)indenyl]-4'-[η⁵-2-methyl-7-(3-trifluoromethylphenyl)indenyl]zirconium dichloride,
sulfandiyl-4-[η⁵-2-methyl-7-(5-methyl-furan-2-yl)indenyl]-4'-[η⁵-2-methyl-7-(2-benzothiopheneyl)indenyl]zirconium dichloride,
sulfandiyl-4-[η⁵-2-methyl-7-(5-methyl-furan-2-yl)indenyl]-4'-[η⁵-2-methyl-7-(2-benzofuranyl)indenyl]zirconium dichloride,
sulfandiyl-4-[η⁵-2-methyl-7-(5-methyl-furan-2-yl)indenyl]-4'-[η⁵-2-methyl-7-(4-fluorophenyl)indenyl]zirconium dichloride,
sulfandiyl-4-[η⁵-2-methyl-7-(5-methyl-furan-2-yl)indenyl]-4'-[η⁵-2-methyl-7-(3-trifluoromethylphenyl)indenyl]zirconium dichloride,
sulfandiyl-4-[η⁵-2-methyl-7-(5-methyl-2-benzothiopheneyl)indenyl]-4'-[η⁵-2-methyl-7-(2-benzofuranyl)indenyl]zirconium dichloride,
sulfandiyl-4-[η⁵-2-methyl-7-(5-methyl-2-benzothiopheneyl)indenyl]-4'-[η⁵-2-methyl-7-(4-fluorophenyl)indenyl]zirconium dichloride,
sulfandiyl-4-[η⁵-2-methyl-7-(5-methyl-2-benzothiopheneyl)indenyl]-4'-[η⁵-2-methyl-7-(3-trifluoromethylphenyl)indenyl]zirconium dichloride,
sulfandiyl-4-[η⁵-2-methyl-7-(5-methyl-2-benzofuranyl)indenyl]-4'-[η⁵-2-methyl-7-(4-fluorophenyl)indenyl]zirconium dichloride,
sulfandiyl-4-[η⁵-2-methyl-7-(5-methyl-2-benzofuranyl)indenyl]-4'-[η⁵-2-methyl-7-(3-trifluoromethylphenyl)indenyl]zirconium dichloride,
sulfandiyl-4-[η⁵-2-methyl-7-(3-trifluoromethylphenyl)indenyl]-4'-[η⁵-2-methyl-7-(3-trifluoromethylphenyl)indenyl]zirconium dichloride,
oxadiyl-4-(η⁵-2-methylindenyl)-4'-(indenyl)zirconium dichloride,
oxadiyl-4-(η⁵-2-methylindenyl)-4'-(η⁵-1-phenylindenyl)zirconium dichloride,
oxadiyl-4-(η⁵-2-methylindenyl)-4'-(η⁵-1-naphthylindenyl)zirconium dichloride,
oxadiyl-4-(η⁵-2-methylindenyl)-4'-(η⁵-7-bromo-2-methylindenyl)zirconium dichloride,
oxadiyl-4-(η⁵-2-methylindenyl)-4'-(η⁵-7-bromo-indenyl)zirconium dichloride,
oxadiyl-4-(η⁵-2-methylindenyl)-4'-(η⁵-2,7-dimethylindenyl)zirconium dichloride,
oxadiyl-4-(η⁵-2-methylindenyl)-4'-(η⁵-7-phenyl-2-methylindenyl)zirconium dichloride,
oxadiyl-4-(η⁵-2-methylindenyl)-4'-(η⁵-2-methyl-7-p-tolylindenyl)zirconium dichloride,
oxadiyl-4-(η⁵-2-methylindenyl)-4'-(η⁵-2-methyl-7-m-tolylindenyl)zirconium dichloride,
oxadiyl-4-(η⁵-2-methylindenyl)-4'-[η⁵-2-methyl-7-(4-tert-butylphenyl)indenyl]zirconium dichloride,
oxadiyl-4-(η⁵-2-methylindenyl)-4'-[η⁵-2-methyl-7-(5-methyl-thien-2-yl)indenyl]zirconium dichloride,
oxadiyl-4-(η⁵-2-methylindenyl)-4'-[η⁵-2-methyl-7-(5-methyl-furan-2-yl)indenyl]zirconium dichloride,
oxadiyl-4-(η⁵-2-methylindenyl)-4'-[η⁵-2-methyl-7-(2-benzothiopheneyl)indenyl]zirconium dichloride,
oxadiyl-4-(η⁵-2-methylindenyl)-4'-[η⁵-2-methyl-7-(2-benzofuranyl)indenyl]zirconium dichloride,
oxadiyl-4-(η⁵-2-methylindenyl)-4'-[η⁵-2-methyl-7-(4-fluorophenyl)indenyl]zirconium dichloride,
oxadiyl-4-(η⁵-2-methylindenyl)-4'-[η⁵-2-methyl-7-(3-trifluoromethylphenyl)indenyl]zirconium dichloride,
oxadiyl-4-(η⁵-indenyl)-4'-(η⁵-1-phenylindenyl)zirconium dichloride,
oxadiyl-4-(η⁵-indenyl)-4'-(η⁵-1-naphthylindenyl)zirconium dichloride,
oxadiyl-4-(η⁵-indenyl)-4'-(η⁵-7-bromo-2-methylindenyl)zirconium dichloride,
oxadiyl-4-(η⁵-indenyl)-4'-(η⁵-7-bromo-indenyl)zirconium dichloride,
oxadiyl-4-(η⁵-indenyl)-4'-(η⁵-2,7-dimethylindenyl)zirconium dichloride, oxadiyl-4-($\eta^5$-indenyl)-4'-($\eta^5$-7-phenyl-2-methylindenyl)zirconium dichloride,
oxadiyl-4-($\eta^5$-indenyl)-4'-($\eta^5$-2-methyl-7-p-tolyl-indenyl)zirconium dichloride,
oxadiyl-4-($\eta^5$-indenyl)-4'-($\eta^5$-2-methyl-7-m-tolylindenyl)zirconium dichloride,
oxadiyl-4-($\eta^5$-indenyl)-4'-[$\eta^5$-2-methyl-7-(4-tert-butylphenyl)indenyl]zirconium dichloride,
oxadiyl-4-($\eta^5$-indenyl)-4'-[$\eta^5$-2-methyl-7-(5-methyl-thien-2-yl)indenyl]zirconium dichloride,
oxadiyl-4-($\eta^5$-indenyl)-4'-[$\eta^5$-2-methyl-7-(5-methyl-furan-2-yl)indenyl]zirconium dichloride,
oxadiyl-4-($\eta^5$-indenyl)-4'-[$\eta^5$-2-methyl-7-(2-benzothiopheneyl)indenyl]zirconium dichloride,
oxadiyl-4-($\eta^5$-indenyl)-4'-[$\eta^5$-2-methyl-7-(2-benzofuranyl)indenyl]zirconium dichloride,
oxadiyl-4-($\eta^5$-indenyl)-4'-[$\eta^5$-2-methyl-7-(4-fluorophenyl)indenyl]zirconium dichloride,
oxadiyl-4-($\eta^5$-indenyl)-4'-[$\eta^5$-2-methyl-7-(3-trifluoromethylphenyl)indenyl]zirconium dichloride,
oxadiyl-4-($\eta^5$-1-phenylindenyl)-4'-($\eta^5$-1-naphthylindenyl)zirconium dichloride,
oxadiyl-4-($\eta^5$-1-phenylindenyl)-4'-($\eta^5$-7-bromo-2-methylindenyl)zirconium dichloride,
oxadiyl-4-($\eta^5$-1-phenylindenyl)-4'-($\eta^5$-7-bromoindenyl)zirconium dichloride,
oxadiyl-4-($\eta^5$-1-phenylindenyl)-4'-($\eta^5$-2,7-dimethylindenyl)zirconium dichloride,
oxadiyl-4-($\eta^5$-1-phenylindenyl)-4'-($\eta^5$-7-phenyl-2-methylindenyl)zirconium dichloride,
oxadiyl-4-($\eta^5$-1-phenylindenyl)-4'-($\eta^5$-2-methyl-7-p-tolyl-indenyl)zirconium dichloride,
oxadiyl-4-($\eta^5$-1-phenylindenyl)-4'-($\eta^5$-2-methyl-7-m-tolyl-indenyl)zirconium dichloride,
oxadiyl-4-($\eta^5$-1-phenylindenyl)-4'-[$\eta^5$-2-methyl-7-(4-tert-butylphenyl)indenyl]zirconium dichloride,
oxadiyl-4-($\eta^5$-1-phenylindenyl)-4'-[$\eta^5$-2-methyl-7-(5-methyl-thien-2-yl)indenyl]zirconium dichloride,
oxadiyl-4-($\eta^5$-1-phenylindenyl)-4'-[$\eta^5$-2-methyl-7-(5-methyl-furan-2-yl)indenyl]zirconium dichloride,
oxadiyl-4-($\eta^5$-1-phenylindenyl)-4'-[$\eta^5$-2-methyl-7-(2-benzothiopheneyl)indenyl]zirconium dichloride,
oxadiyl-4-($\eta^5$-1-phenylindenyl)-4'-[$\eta^5$-2-methyl-7-(2-benzofuranyl)indenyl]zirconium dichloride,
oxadiyl-4-($\eta^5$-1-phenylindenyl)-4'-[$\eta^5$-2-methyl-7-(4-fluorophenyl)indenyl]zirconium dichloride,
oxadiyl-4-($\eta^5$-1-phenylindenyl)-4'-[$\eta^5$-2-methyl-7-(3-trifluoromethylphenyl)indenyl]zirconium dichloride,
oxadiyl-4-($\eta^5$-1-naphthylindenyl)-4'-($\eta^5$-7-bromo-2-methylindenyl)zirconium dichloride,
oxadiyl-4-($\eta^5$-1-naphthylindenyl)-4'-($\eta^5$-7-bromoindenyl)zirconium dichloride,
oxadiyl-4-($\eta^5$-1-naphthylindenyl)-4'-($\eta^5$-2,7-dimethylindenyl)zirconium dichloride,
oxadiyl-4-($\eta^5$-1-naphthylindenyl)-4'-($\eta^5$-7-phenyl-2-methylindenyl)zirconium dichloride,
oxadiyl-4-($\eta^5$-1-naphthylindenyl)-4'-($\eta^5$-2-methyl-7-p-tolyl-indenyl)zirconium dichloride,
oxadiyl-4-($\eta^5$-1-naphthylindenyl)-4'-($\eta^5$-2-methyl-7-m-tolylindenyl)zirconium dichloride,
oxadiyl-4-($\eta^5$-1-naphthylindenyl)-4'-[$\eta^5$-2-methyl-7-(4-tert-butylphenyl)indenyl]zirconium dichloride,
oxadiyl-4-($\eta^5$-1-naphthylindenyl)-4'-[$\eta^5$-2-methyl-7-(5-methyl-thien-2-yl)indenyl]zirconium dichloride,
oxadiyl-4-($\eta^5$-1-naphthylindenyl)-4'-[$\eta^5$-2-methyl-7-(5-methyl-furan-2-yl)indenyl]zirconium dichloride,
oxadiyl-4-($\eta^5$-1-naphthylindenyl)-4'-[$\eta^5$-2-methyl-7-(2-benzothiopheneyl)indenyl]zirconium dichloride,
oxadiyl-4-($\eta^5$-1-naphthylindenyl)-4'-[$\eta^5$-2-methyl-7-(2-benzofuranyl)indenyl]zirconium dichloride,
oxadiyl-4-($\eta^5$-1-naphthylindenyl)-4'-[$\eta^5$-2-methyl-7-(4-fluorophenyl)indenyl]zirconium dichloride,
oxadiyl-4-($\eta^5$-1-naphthylindenyl)-4'-[$\eta^5$-2-methyl-7-(3-trifluoromethylphenyl)indenyl]zirconium dichloride,
oxadiyl-4-($\eta^5$-7-bromo-2-methylindenyl)-4'-($\eta^5$-7-bromoindenyl)zirconium dichloride,
oxadiyl-4-($\eta^5$-7-bromo-2-methylindenyl)-4'-($\eta^5$-2,7-dimethylindenyl)zirconium dichloride,
oxadiyl-4-($\eta^5$-7-bromo-2-methylindenyl)-4'-($\eta^5$-7-phenyl-2-methylindenyl)zirconium dichloride,
oxadiyl-4-($\eta^5$-7-bromo-2-methylindenyl)-4'-($\eta^5$-2-methyl-7-p-tolyl-indenyl)zirconium dichloride,
oxadiyl-4-($\eta^5$-7-bromo-2-methylindenyl)-4'-($\eta^5$-2-methyl-7-m-tolylindenyl)zirconium dichloride,
oxadiyl-4-($\eta^5$-7-bromo-2-methylindenyl)-4'-[$\eta^5$-2-methyl-7-(4-tert-butylphenyl)indenyl]zirconium dichloride,
oxadiyl-4-($\eta^5$-7-bromo-2-methylindenyl)-4'-[$\eta^5$-2-methyl-7-(5-methyl-thien-2-yl)indenyl]zirconium dichloride,
oxadiyl-4-($\eta^5$-7-bromo-2-methylindenyl)-4'-[$\eta^5$-2-methyl-7-(5-methyl-furan-2-yl)indenyl]zirconium dichloride,
oxadiyl-4-($\eta^5$-7-bromo-2-methylindenyl)-4'-[$\eta^5$-2-methyl-7-(2-benzothiopheneyl)indenyl]zirconium dichloride,
oxadiyl-4-($\eta^5$-7-bromo-2-methylindenyl)-4'-[$\eta^5$-2-methyl-7-(2-benzofuranyl)indenyl]zirconium dichloride,
oxadiyl-4-($\eta^5$-7-bromo-2-methylindenyl)-4'-[$\eta^5$-2-methyl-7-(4-fluorophenyl)indenyl]zirconium dichloride,
oxadiyl-4-($\eta^5$-7-bromo-2-methylindenyl)-4'-[$\eta^5$-2-methyl-7-(3-trifluoromethylphenyl)indenyl]zirconium dichloride,
oxadiyl-4-($\eta^5$-7-bromoindenyl)-4'-($\eta^5$-2,7-dimethylindenyl)zirconium dichloride,
oxadiyl-4-($\eta^5$-7-bromoindenyl)-4'-($\eta^5$-7-phenyl-2-methylindenyl)zirconium dichloride,
oxadiyl-4-($\eta^5$-7-bromoindenyl)-4'-($\eta^5$-2-methyl-7-p-tolyl-indenyl)zirconium dichloride,
oxadiyl-4-($\eta^5$-7-bromoindenyl)-4'-($\eta^5$-2-methyl-7-m-tolyl-indenyl)zirconium dichloride,
oxadiyl-4-($\eta^5$-7-bromoindenyl)-4'-[$\eta^5$-2-methyl-7-(4-tert-butylphenyl)indenyl]zirconium dichloride,
oxadiyl-4-($\eta^5$-7-bromoindenyl)-4'-[$\eta^5$-2-methyl-7-(5-methyl-thien-2-yl)indenyl]zirconium dichloride,
oxadiyl-4-($\eta^5$-7-bromoindenyl)-4'-[$\eta^5$-2-methyl-7-(5-methyl-furan-2-yl)indenyl]zirconium dichloride,
oxadiyl-4-($\eta^5$-7-bromoindenyl)-4'-[$\eta^5$-2-methyl-7-(2-benzothiopheneyl)indenyl]zirconium dichloride,
oxadiyl-4-($\eta^5$-7-bromoindenyl)-4'-[$\eta^5$-2-methyl-7-(2-benzofuranyl)indenyl]zirconium dichloride,
oxadiyl-4-($\eta^5$-7-bromoindenyl)-4'-[$\eta^5$-2-methyl-7-(4-fluorophenyl)indenyl]zirconium dichloride,
oxadiyl-4-($\eta^5$-7-bromoindenyl)-4'-[$\eta^5$-2-methyl-7-(3-trifluoromethylphenyl)indenyl]zirconium dichloride,
oxadiyl-4-($\eta^5$-2,7-dimethylindenyl)-4'-($\eta^5$-7-phenyl-2-methylindenyl)zirconium dichloride,
oxadiyl-4-($\eta^5$-2,7-dimethylindenyl)-4'-($\eta^5$-2-methyl-7-p-tolyl-indenyl)zirconium dichloride,
oxadiyl-4-($\eta^5$-2,7-dimethylindenyl)-4'-($\eta^5$-2-methyl-7-m-tolylindenyl)zirconium dichloride,
oxadiyl-4-($\eta^5$-2,7-dimethylindenyl)-4'-[$\eta^5$-2-methyl-7-(4-tert-butylphenyl)indenyl]zirconium dichloride,
oxadiyl-4-($\eta^5$-2,7-dimethylindenyl)-4'-[$\eta^5$-2-methyl-7-(5-methyl-thien-2-yl)indenyl]zirconium dichloride,
oxadiyl-4-($\eta^5$-2,7-dimethylindenyl)-4'-[$\eta^5$-2-methyl-7-(5-methyl-furan-2-yl)indenyl]zirconium dichloride, oxadiyl-4-(η⁵-2,7-dimethylindenyl)-4'-[η⁵-2-methyl-7-(2-benzothiopheneyl)indenyl]zirconium dichloride,
oxadiyl-4-(η⁵-2,7-dimethylindenyl)-4'-[η⁵-2-methyl-7-(2-benzofuranyl)indenyl]zirconium dichloride,
oxadiyl-4-(η⁵-2,7-dimethylindenyl)-4'-[η⁵-2-methyl-7-(4-fluorophenyl)indenyl]zirconium dichloride,
oxadiyl-4-(η⁵-2,7-dimethylindenyl)-4'-[η⁵-2-methyl-7-(3-trifluoromethylphenyl)indenyl]zirconium dichloride,
oxadiyl-4-(η⁵-7-phenyl-2-methylindenyl)-4'-(η⁵-2-methyl-7-p-tolyl-indenyl)zirconium dichloride,
oxadiyl-4-(η⁵-7-phenyl-2-methylindenyl)-4'-(η⁵-2-methyl-7-m-tolylindenyl)zirconium dichloride,
oxadiyl-4-(η⁵-7-phenyl-2-methylindenyl)-4'-[η⁵-2-methyl-7-(4-tert-butylphenyl)indenyl]zirconium dichloride,
oxadiyl-4-(η⁵-7-phenyl-2-methylindenyl)-4'-[η⁵-2-methyl-7-(5-methyl-thien-2-yl)indenyl]zirconium dichloride,
oxadiyl-4-(η⁵-7-phenyl-2-methylindenyl)-4'-[η⁵-2-methyl-7-(5-methyl-furan-2-yl)indenyl]zirconium dichloride,
oxadiyl-4-(η⁵-7-phenyl-2-methylindenyl)-4'-[η⁵-2-methyl-7-(2-benzothiopheneyl)indenyl]zirconium dichloride,
oxadiyl-4-(η⁵-7-phenyl-2-methylindenyl)-4'-[η⁵-2-methyl-7-(2-benzofuranyl)indenyl]zirconium dichloride,
oxadiyl-4-(η⁵-7-phenyl-2-methylindenyl)-4'-[η⁵-2-methyl-7-(4-fluorophenyl)indenyl]zirconium dichloride,
oxadiyl-4-(η⁵-7-phenyl-2-methylindenyl)-4'-[η⁵-2-methyl-7-(3-trifluoromethylphenyl)indenyl]zirconium dichloride,
oxadiyl-4-(η⁵-2-methyl-7-p-tolylindenyl)-4'-(η⁵-2-methyl-7-m-tolylindenyl)zirconium dichloride,
oxadiyl-4-(η⁵-2-methyl-7-p-tolylindenyl)-4'-[η⁵-2-methyl-7-(4-tert-butylphenyl)indenyl]zirconium dichloride,
oxadiyl-4-(η⁵-2-methyl-7-p-tolylindenyl)-4'-[η⁵-2-methyl-7-(5-methyl-thien-2-yl)indenyl]zirconium dichloride,
oxadiyl-4-(η⁵-2-methyl-7-p-tolylindenyl)-4'-[η⁵-2-methyl-7-(5-methyl-furan-2-yl)indenyl]zirconium dichloride,
oxadiyl-4-(η⁵-2-methyl-7-p-tolylindenyl)-4'-[η⁵-2-methyl-7-(2-benzothiopheneyl)indenyl]zirconium dichloride,
oxadiyl-4-(η⁵-2-methyl-7-p-tolylindenyl)-4'-[η⁵-2-methyl-7-(2-benzofuranyl)indenyl]zirconium dichloride,
oxadiyl-4-(η⁵-2-methyl-7-p-tolylindenyl)-4'-[η⁵-2-methyl-7-(4-fluorophenyl)indenyl]zirconium dichloride,
oxadiyl-4-(η⁵-2-methyl-7-p-tolylindenyl)-4'-[η⁵-2-methyl-7-(3-trifluoromethylphenyl)indenyl]zirconium dichloride,
oxadiyl-4-(η⁵-2-methyl-7-m-tolylindenyl)-4'-[η⁵-2-methyl-7-(4-tert-butylphenyl)indenyl]zirconium dichloride,
oxadiyl-4-(η⁵-2-methyl-7-m-tolylindenyl)-4'-[η⁵-2-methyl-7-(5-methyl-thien-2-yl)indenyl]zirconium dichloride,
oxadiyl-4-(η⁵-2-methyl-7-m-tolylindenyl)-4'-[η⁵-2-methyl-7-(5-methyl-furan-2-yl)indenyl]zirconium dichloride,
oxadiyl-4-(η⁵-2-methyl-7-m-tolylindenyl)-4'-[η⁵-2-methyl-7-(2-benzothiopheneyl)indenyl]zirconium dichloride,
oxadiyl-4-(η⁵-2-methyl-7-m-tolylindenyl)-4'-[η⁵-2-methyl-7-(2-benzofuranyl)indenyl]zirconium dichloride,
oxadiyl-4-(η⁵-2-methyl-7-m-tolylindenyl)-4'-[η⁵-2-methyl-7-(4-fluorophenyl)indenyl]zirconium dichloride,
oxadiyl-4-(η⁵-2-methyl-7-m-tolylindenyl)-4'-[η⁵-2-methyl-7-(3-trifluoromethylphenyl)indenyl]zirconium dichloride,
oxadiyl-4-[η⁵-2-methyl-7-(4-tert-butylphenyl)indenyl]-4'-[η⁵-2-methyl-7-(5-methyl-thien-2-yl)indenyl]zirconium dichloride,
oxadiyl-4-[η⁵-2-methyl-7-(4-tert-butylphenyl)indenyl]-4'-[η⁵-2-methyl-7-(5-methyl-furan-2-yl)indenyl]zirconium dichloride,
oxadiyl-4-[η⁵-2-methyl-7-(4-tert-butylphenyl)indenyl]-4'-[η⁵-2-methyl-7-(2-benzothiopheneyl)indenyl]zirconium dichloride,
oxadiyl-4-[η⁵-2-methyl-7-(4-tert-butylphenyl)indenyl]-4'-[η⁵-2-methyl-7-(2-benzofuranyl)indenyl]zirconium dichloride,
oxadiyl-4-[η⁵-2-methyl-7-(4-tert-butylphenyl)indenyl]-4'-[η⁵-2-methyl-7-(4-fluorophenyl)indenyl]zirconium dichloride,
oxadiyl-4-[η⁵-2-methyl-7-(4-tert-butylphenyl)indenyl]-4'-[η⁵-2-methyl-7-(3-trifluoromethylphenyl)indenyl]zirconium dichloride,
oxadiyl-4-[η⁵-2-methyl-7-(5-methyl-thien-2-yl)indenyl]-4'-[η⁵-2-methyl-7-(5-methyl-furan-2-yl)indenyl]zirconium dichloride,
oxadiyl-4-[η⁵-2-methyl-7-(5-methyl-thien-2-yl)indenyl]-4'-[η⁵-2-methyl-7-(2-benzothiopheneyl)indenyl]zirconium dichloride,
oxadiyl-4-[η⁵-2-methyl-7-(5-methyl-thien-2-yl)indenyl]-4'-[η⁵-2-methyl-7-(2-benzofuranyl)indenyl]zirconium dichloride,
oxadiyl-4-[η⁵-2-methyl-7-(5-methyl-thien-2-yl)indenyl]-4'-[η⁵-2-methyl-7-(4-fluorophenyl)indenyl]zirconium dichloride,
oxadiyl-4-[η⁵-2-methyl-7-(5-methyl-thien-2-yl)indenyl]-4'-[η⁵-2-methyl-7-(3-trifluoromethylphenyl)indenyl]zirconium dichloride,
oxadiyl-4-[η⁵-2-methyl-7-(5-methyl-furan-2-yl)indenyl]-4'-[η⁵-2-methyl-7-(2-benzothiopheneyl)indenyl]zirconium dichloride,
oxadiyl-4-[η⁵-2-methyl-7-(5-methyl-furan-2-yl)indenyl]-4'-[η⁵-2-methyl-7-(2-benzofuranyl)indenyl]zirconium dichloride,
oxadiyl-4-[η⁵-2-methyl-7-(5-methyl-furan-2-yl)indenyl]-4'-[η⁵-2-methyl-7-(4-fluorophenyl)indenyl]zirconium dichloride,
oxadiyl-4-[η⁵-2-methyl-7-(5-methyl-furan-2-yl)indenyl]-4'-[η⁵-2-methyl-7-(3-trifluoromethylphenyl)indenyl]zirconium dichloride,
oxadiyl-4-[η⁵-2-methyl-7-(5-methyl-2-benzothiopheneyl)indenyl]-4'-[η⁵-2-methyl-7-(2-benzofuranyl)indenyl]zirconium dichloride,
oxadiyl-4-[η⁵-2-methyl-7-(5-methyl-2-benzothiopheneyl)indenyl]-4'-[η⁵-2-methyl-7-(4-fluorophenyl)indenyl]zirconium dichloride,
oxadiyl-4-[η⁵-2-methyl-7-(5-methyl-2-benzothiopheneyl)indenyl]-4'-[η⁵-2-methyl-7-(3-trifluoromethylphenyl)indenyl]zirconium dichloride,
oxadiyl-4-[η⁵-2-methyl-7-(5-methyl-2-benzofuranyl)indenyl]-4'-[η⁵-2-methyl-7-(4-fluorophenyl)indenyl]zirconium dichloride,
oxadiyl-4-[η⁵-2-methyl-7-(5-methyl-2-benzofuranyl)indenyl]-4'-[η⁵-2-methyl-7-(3-trifluoromethylphenyl)indenyl]zirconium dichloride,
oxadiyl-4-[η⁵-2-methyl-7-(3-trifluoromethylphenyl)indenyl]-4'-[η⁵-2-methyl-7-(3-trifluoromethylphenyl)indenyl]zirconium dichloride,
phenylazandiyl-4-(η⁵-2-methylindenyl)-4'-(indenyl)zirconium dichloride,
phenylazandiyl-4-(η⁵-2-methylindenyl)-4'-(η⁵-1-phenylindenyl)zirconium dichloride,
phenylazandiyl-4-(η⁵-2-methylindenyl)-4'-(η⁵-1-naphthylindenyl)zirconium dichloride,
phenylazandiyl-4-(η⁵-2-methylindenyl)-4'-(η⁵-7-bromo-2-methylindenyl)zirconium dichloride,
phenylazandiyl-4-(η⁵-2-methylindenyl)-4'-(η⁵-7-bromo-indenyl)zirconium dichloride,
phenylazandiyl-4-(η⁵-2-methylindenyl)-4'-(η⁵-2,7-dimethylindenyl)zirconium dichloride, phenylazandiyl-4-($\eta^5$-2-methylindenyl)-4'-($\eta^5$-7-phenyl-2-methylindenyl)zirconium dichloride,
phenylazandiyl-4-($\eta^5$-2-methylindenyl)-4'-($\eta^5$-2-methyl-7-p-tolyl-indenyl)zirconium dichloride,
phenylazandiyl-4-($\eta^5$-2-methylindenyl)-4'-($\eta^5$-2-methyl-7-m-tolylindenyl)zirconium dichloride,
phenylazandiyl-4-($\eta^5$-2-methylindenyl)-4'-[$\eta^5$-2-methyl-7-(4-tert-butylphenyl)indenyl]zirconium dichloride,
phenylazandiyl-4-($\eta^5$-2-methylindenyl)-4'-[$\eta^5$-2-methyl-7-(5-methyl-thien-2-yl)indenyl]zirconium dichloride,
phenylazandiyl-4-($\eta^5$-2-methylindenyl)-4'-[$\eta^5$-2-methyl-7-(5-methyl-furan-2-yl)indenyl]zirconium dichloride,
phenylazandiyl-4-($\eta^5$-2-methylindenyl)-4'-[$\eta^5$-2-methyl-7-(2-benzothiopheneyl)indenyl]zirconium dichloride,
phenylazandiyl-4-($\eta^5$-2-methylindenyl)-4'-[$\eta^5$-2-methyl-7-(2-benzofuranyl)indenyl]zirconium dichloride,
phenylazandiyl-4-($\eta^5$-2-methylindenyl)-4'-[$\eta^5$-2-methyl-7-(4-fluorophenyl)indenyl]zirconium dichloride,
phenylazandiyl-4-($\eta^5$-2-methylindenyl)-4'-[$\eta^5$-2-methyl-7-(3-trifluoromethylphenyl)indenyl]zirconium dichloride,
phenylazandiyl-4-($\eta^5$-indenyl)-4'-($\eta^5$-1-phenylindenyl)zirconium dichloride,
phenylazandiyl-4-($\eta^5$-indenyl)-4'-($\eta^5$-1-naphthylindenyl)zirconium dichloride,
phenylazandiyl-4-($\eta^5$-indenyl)-4'-($\eta^5$-7-bromo-2-methylindenyl)zirconium dichloride,
phenylazandiyl-4-($\eta^5$-indenyl)-4'-($\eta^5$-7-bromo-indenyl)zirconium dichloride,
phenylazandiyl-4-($\eta^5$-indenyl)-4'-($\eta^5$-2,7-dimethylindenyl)zirconium dichloride,
phenylazandiyl-4-($\eta^5$-indenyl)-4'-($\eta^5$-7-phenyl-2-methylindenyl)zirconium dichloride,
phenylazandiyl-4-($\eta^5$-indenyl)-4'-($\eta^5$-2-methyl-7-p-tolyl-indenyl)zirconium dichloride,
phenylazandiyl-4-($\eta^5$-indenyl)-4'-($\eta^5$-2-methyl-7-m-tolyl-indenyl)zirconium dichloride,
phenylazandiyl-4-($\eta^5$-indenyl)-4'-[$\eta^5$-2-methyl-7-(4-tert-butylphenyl)indenyl]zirconium dichloride,
phenylazandiyl-4-($\eta^5$-indenyl)-4'-[$\eta^5$-2-methyl-7-(5-methyl-thien-2-yl)indenyl]zirconium dichloride,
phenylazandiyl-4-($\eta^5$-indenyl)-4'-[$\eta^5$-2-methyl-7-(5-methyl-furan-2-yl)indenyl]zirconium dichloride,
phenylazandiyl-4-($\eta^5$-indenyl)-4'-[$\eta^5$-2-methyl-7-(2-benzothiopheneyl)indenyl]zirconium dichloride,
phenylazandiyl-4-($\eta^5$-indenyl)-4'-[$\eta^5$-2-methyl-7-(2-benzofuranyl)indenyl]zirconium dichloride,
phenylazandiyl-4-($\eta^5$-indenyl)-4'-[$\eta^5$-2-methyl-7-(4-fluorophenyl)indenyl]zirconium dichloride,
phenylazandiyl-4-($\eta^5$-indenyl)-4'-[$\eta^5$-2-methyl-7-(3-trifluoromethylphenyl)indenyl]zirconium dichloride,
phenylazandiyl-4-($\eta^5$-1-phenylindenyl)-4'-($\eta^5$-1-naphthyl-indenyl)zirconium dichloride,
phenylazandiyl-4-($\eta^5$-1-phenylindenyl)-4'-($\eta^5$-7-bromo-2-methylindenyl)zirconium dichloride,
phenylazandiyl-4-($\eta^5$-1-phenylindenyl)-4'-($\eta^5$-7-bromoindenyl)zirconium dichloride,
phenylazandiyl-4-($\eta^5$-1-phenylindenyl)-4'-($\eta^5$-2,7-dimethylindenyl)zirconium dichloride,
phenylazandiyl-4-($\eta^5$-1-phenylindenyl)-4'-($\eta^5$-7-phenyl-2-methylindenyl)zirconium dichloride,
phenylazandiyl-4-($\eta^5$-1-phenylindenyl)-4'-($\eta^5$-2-methyl-7-p-tolyl-indenyl)zirconium dichloride,
phenylazandiyl-4-($\eta^5$-1-phenylindenyl)-4'-($\eta^5$-2-methyl-7-m-tolylindenyl)zirconium dichloride,
phenylazandiyl-4-($\eta^5$-1-phenylindenyl)-4'-[$\eta^5$-2-methyl-7-(4-tert-butylphenyl)indenyl]zirconium dichloride,
phenylazandiyl-4-($\eta^5$-1-phenylindenyl)-4'-[$\eta^5$-2-methyl-7-(5-methyl-thien-2-yl)indenyl]zirconium dichloride,
phenylazandiyl-4-($\eta^5$-1-phenylindenyl)-4'-[$\eta^5$-2-methyl-7-(5-methyl-furan-2-yl)indenyl]zirconium dichloride,
phenylazandiyl-4-($\eta^5$-1-phenylindenyl)-4'-[$\eta^5$-2-methyl-7-(2-benzothiopheneyl)indenyl]zirconium dichloride,
phenylazandiyl-4-($\eta^5$-1-phenylindenyl)-4'-[$\eta^5$-2-methyl-7-(2-benzofuranyl)indenyl]zirconium dichloride,
phenylazandiyl-4-($\eta^5$-1-phenylindenyl)-4'-[$\eta^5$-2-methyl-7-(4-fluorophenyl)indenyl]zirconium dichloride,
phenylazandiyl-4-($\eta^5$-1-phenylindenyl)-4'-[$\eta^5$-2-methyl-7-(3-trifluoromethylphenyl)indenyl]zirconium dichloride,
phenylazandiyl-4-($\eta^5$-1-naphthylindenyl)-4'-($\eta^5$-7-bromo-2-methylindenyl)zirconium dichloride,
phenylazandiyl-4-($\eta^5$-1-naphthylindenyl)-4'-($\eta^5$-7-bromoindenyl)zirconium dichloride,
phenylazandiyl-4-($\eta^5$-1-naphthylindenyl)-4'-($\eta^5$-2,7-dimethylindenyl)zirconium dichloride,
phenylazandiyl-4-($\eta^5$-1-naphthylindenyl)-4'-($\eta^5$-7-phenyl-2-methylindenyl)zirconium dichloride,
phenylazandiyl-4-($\eta^5$-1-naphthylindenyl)-4'-($\eta^5$-2-methyl-7-p-tolyl-indenyl)zirconium dichloride,
phenylazandiyl-4-($\eta^5$-1-naphthylindenyl)-4'-($\eta^5$-2-methyl-7-m-tolylindenyl)zirconium dichloride,
phenylazandiyl-4-($\eta^5$-1-naphthylindenyl)-4'-[$\eta^5$-2-methyl-7-(4-tert-butylphenyl)indenyl]zirconium dichloride,
phenylazandiyl-4-($\eta^5$-1-naphthylindenyl)-4'-[$\eta^5$-2-methyl-7-(5-methyl-thien-2-yl)indenyl]zirconium dichloride,
phenylazandiyl-4-($\eta^5$-1-naphthylindenyl)-4'-[$\eta^5$-2-methyl-7-(5-methyl-furan-2-yl)indenyl]zirconium dichloride,
phenylazandiyl-4-($\eta^5$-1-naphthylindenyl)-4'-[$\eta^5$-2-methyl-7-(2-benzothiopheneyl)indenyl]zirconium dichloride,
phenylazandiyl-4-($\eta^5$-1-naphthylindenyl)-4'-[$\eta^5$-2-methyl-7-(2-benzofuranyl)indenyl]zirconium dichloride,
phenylazandiyl-4-($\eta^5$-1-naphthylindenyl)-4'-[$\eta^5$-2-methyl-7-(4-fluorophenyl)indenyl]zirconium dichloride,
phenylazandiyl-4-($\eta^5$-1-naphthylindenyl)-4'-[$\eta^5$-2-methyl-7-(3-trifluoromethylphenyl)indenyl]zirconium dichloride,
phenylazandiyl-4-($\eta^5$-7-bromo-2-methylindenyl)-4'-($\eta^5$-7-bromoindenyl)zirconium dichloride,
phenylazandiyl-4-($\eta^5$-7-bromo-2-methylindenyl)-4'-($\eta^5$-2,7-dimethylindenyl)zirconium dichloride,
phenylazandiyl-4-($\eta^5$-7-bromo-2-methylindenyl)-4'-($\eta^5$-7-phenyl-2-methylindenyl)zirconium dichloride,
phenylazandiyl-4-($\eta^5$-7-bromo-2-methylindenyl)-4'-($\eta^5$-2-methyl-7-p-tolyl-indenyl)zirconium dichloride,
phenylazandiyl-4-($\eta^5$-7-bromo-2-methylindenyl)-4'-($\eta^5$-2-methyl-7-m-tolylindenyl)zirconium dichloride,
phenylazandiyl-4-($\eta^5$-7-bromo-2-methylindenyl)-4'-[$\eta^5$-2-methyl-7-(4-tert-butylphenyl)indenyl]zirconium dichloride,
phenylazandiyl-4-($\eta^5$-7-bromo-2-methylindenyl)-4'-[$\eta^5$-2-methyl-7-(5-methyl-thien-2-yl)indenyl]zirconium dichloride,
phenylazandiyl-4-($\eta^5$-7-bromo-2-methylindenyl)-4'-[$\eta^5$-2-methyl-7-(5-methyl-furan-2-yl)indenyl]zirconium dichloride,
phenylazandiyl-4-($\eta^5$-7-bromo-2-methylindenyl)-4'-[$\eta^5$-2-methyl-7-(2-benzothiopheneyl)indenyl]zirconium dichloride,
phenylazandiyl-4-($\eta^5$-7-bromo-2-methylindenyl)-4'-[$\eta^5$-2-methyl-7-(2-benzofuranyl)indenyl]zirconium dichloride,
phenylazandiyl-4-($\eta^5$-7-bromo-2-methylindenyl)-4'-[$\eta^5$-2-methyl-7-(4-fluorophenyl)indenyl]zirconium dichloride,
phenylazandiyl-4-($\eta^5$-7-bromo-2-methylindenyl)-4'-[$\eta^5$-2-methyl-7-(3-trifluoromethylphenyl)indenyl]zirconium dichloride, phenylazandiyl-4-($\eta^5$-7-bromoindenyl)-4'-($\eta^5$-2,7-dimethylindenyl)zirconium dichloride,
phenylazandiyl-4-($\eta^5$-7-bromoindenyl)-4'-($\eta^5$-7-phenyl-2-methylindenyl)zirconium dichloride,
phenylazandiyl-4-($\eta^5$-7-bromoindenyl)-4'-($\eta^5$-2-methyl-7-p-tolyl-indenyl)zirconium dichloride,
phenylazandiyl-4-($\eta^5$-7-bromoindenyl)-4'-($\eta^5$-2-methyl-7-m-tolylindenyl)zirconium dichloride,
phenylazandiyl-4-($\eta^5$-7-bromoindenyl)-4'-[$\eta^5$-2-methyl-7-(4-tert-butylphenyl)indenyl]zirconium dichloride,
phenylazandiyl-4-($\eta^5$-7-bromoindenyl)-4'-[$\eta^5$-2-methyl-7-(5-methyl-thien-2-yl)indenyl]zirconium dichloride,
phenylazandiyl-4-($\eta^5$-7-bromoindenyl)-4'-[$\eta^5$-2-methyl-7-(5-methyl-furan-2-yl)indenyl]zirconium dichloride,
phenylazandiyl-4-($\eta^5$-7-bromoindenyl)-4'-[$\eta^5$-2-methyl-7-(2-benzothiopheneyl)indenyl]zirconium dichloride,
phenylazandiyl-4-($\eta^5$-7-bromoindenyl)-4'-[$\eta^5$-2-methyl-7-(2-benzofuranyl)indenyl]zirconium dichloride,
phenylazandiyl-4-($\eta^5$-7-bromoindenyl)-4'-[$\eta^5$-2-methyl-7-(4-fluorophenyl)indenyl]zirconium dichloride,
phenylazandiyl-4-($\eta^5$-7-bromoindenyl)-4'-[$\eta^5$-2-methyl-7-(3-trifluoromethylphenyl)indenyl]zirconium dichloride,
phenylazandiyl-4-($\eta^5$-2,7-dimethylindenyl)-4'-($\eta^5$-7-phenyl-2-methylindenyl)zirconium dichloride,
phenylazandiyl-4-($\eta^5$-2,7-dimethylindenyl)-4'-($\eta^5$-2-methyl-7-p-tolyl-indenyl)zirconium dichloride,
phenylazandiyl-4-($\eta^5$-2,7-dimethylindenyl)-4'-($\eta^5$-2-methyl-7-m-tolylindenyl)zirconium dichloride,
phenylazandiyl-4-($\eta^5$-2,7-dimethylindenyl)-4'-[$\eta^5$-2-methyl-7-(4-tert-butylphenyl)indenyl]zirconium dichloride,
phenylazandiyl-4-($\eta^5$-2,7-dimethylindenyl)-4'-[$\eta^5$-2-methyl-7-(5-methyl-thien-2-yl)indenyl]zirconium dichloride,
phenylazandiyl-4-($\eta^5$-2,7-dimethylindenyl)-4'-[$^5$-2-methyl-7-(5-methyl-furan-2-yl)indenyl]zirconium dichloride,
phenylazandiyl-4-($\eta^5$-2,7-dimethylindenyl)-4'-[$\eta^5$-2-methyl-7-(2-benzothiopheneyl)indenyl]zirconium dichloride,
phenylazandiyl-4-($\eta^5$-2,7-dimethylindenyl)-4'-[$\eta^5$-2-methyl-7-(2-benzofuranyl)indenyl]zirconium dichloride,
phenylazandiyl-4-($\eta^5$-2,7-dimethylindenyl)-4'-[$\eta^5$-2-methyl-7-(4-fluorophenyl)indenyl]zirconium dichloride,
phenylazandiyl-4-($\eta^5$-2,7-dimethylindenyl)-4'-[$\eta^5$-2-methyl-7-(3-trifluoromethylphenyl)indenyl]zirconium dichloride,
phenylazandiyl-4-($\eta^5$-7-phenyl-2-methylindenyl)-4'-($\eta^5$-2-methyl-7-p-tolyl-indenyl)zirconium dichloride,
phenylazandiyl-4-($\eta^5$-7-phenyl-2-methylindenyl)-4'-($\eta^5$-2-methyl-7-m-tolylindenyl)zirconium dichloride,
phenylazandiyl-4-($\eta^5$-7-phenyl-2-methylindenyl)-4'-[$\eta^5$-2-methyl-7-(4-tert-butylphenyl)indenyl]zirconium dichloride,
phenylazandiyl-4-($\eta^5$-7-phenyl-2-methylindenyl)-4'-[$\eta^5$-2-methyl-7-(5-methyl-thien-2-yl)indenyl]zirconium dichloride,
phenylazandiyl-4-($\eta^5$-7-phenyl-2-methylindenyl)-4'-[$\eta^5$-2-methyl-7-(5-methyl-furan-2-yl)indenyl]zirconium dichloride,
phenylazandiyl-4-($\eta^5$-7-phenyl-2-methylindenyl)-4'-[$\eta^5$-2-methyl-7-(2-benzothiopheneyl)indenyl]zirconium dichloride,
phenylazandiyl-4-($\eta^5$-7-phenyl-2-methylindenyl)-4'-[$\eta^5$-2-methyl-7-(2-benzofuranyl)indenyl]zirconium dichloride,
phenylazandiyl-4-($\eta^5$-7-phenyl-2-methylindenyl)-4'-[$\eta^5$-2-methyl-7-(4-fluorophenyl)indenyl]zirconium dichloride,
phenylazandiyl-4-($\eta^5$-7-phenyl-2-methylindenyl)-4'-[$\eta^5$-2-methyl-7-(3-trifluoromethylphenyl)indenyl]zirconium dichloride,
phenylazandiyl-4-($\eta^5$-2-methyl-7-p-tolylindenyl)-4'-($\eta^5$-2-methyl-7-m-tolylindenyl)zirconium dichloride,
phenylazandiyl-4-($\eta^5$-2-methyl-7-p-tolylindenyl)-4'-[$\eta^5$-2-methyl-7-(4-tert-butylphenyl)indenyl]zirconium dichloride,
phenylazandiyl-4-($\eta^5$-2-methyl-7-p-tolylindenyl)-4'-[$\eta^5$-2-methyl-7-(5-methyl-thien-2-yl)indenyl]zirconium dichloride,
phenylazandiyl-4-($\eta^5$-2-methyl-7-p-tolylindenyl)-4'-[$\eta^5$-2-methyl-7-(5-methyl-furan-2-yl)indenyl]zirconium dichloride,
phenylazandiyl-4-($\eta^5$-2-methyl-7-p-tolylindenyl)-4'-[$\eta^5$-2-methyl-7-(2-benzothiopheneyl)indenyl]zirconium dichloride,
phenylazandiyl-4-($\eta^5$-2-methyl-7-p-tolylindenyl)-4'-[$\eta^5$-2-methyl-7-(2-benzofuranyl)indenyl]zirconium dichloride,
phenylazandiyl-4-($\eta^5$-2-methyl-7-p-tolylindenyl)-4'-[$\eta^5$-2-methyl-7-(4-fluorophenyl)indenyl]zirconium dichloride,
phenylazandiyl-4-($\eta^5$-2-methyl-7-p-tolylindenyl)-4'-[$\eta^5$-2-methyl-7-(3-trifluoromethylphenyl)indenyl]zirconium dichloride,
phenylazandiyl-4-($\eta^5$-2-methyl-7-m-tolylindenyl)-4'-[$\eta^5$-2-methyl-7-(4-tert-butylphenyl)indenyl]zirconium dichloride,
phenylazandiyl-4-($\eta^5$-2-methyl-7-m-tolylindenyl)-4'-[$\eta^5$-2-methyl-7-(5-methyl-thien-2-yl)indenyl]zirconium dichloride,
phenylazandiyl-4-($\eta^5$-2-methyl-7-m-tolylindenyl)-4'-[$\eta^5$-2-methyl-7-(5-methyl-furan-2-yl)indenyl]zirconium dichloride,
phenylazandiyl-4-($\eta^5$-2-methyl-7-m-tolylindenyl)-4'-[$\eta^5$-2-methyl-7-(2-benzothiopheneyl)indenyl]zirconium dichloride,
phenylazandiyl-4-($\eta^5$-2-methyl-7-m-tolylindenyl)-4'-[$\eta^5$-2-methyl-7-(2-benzofuranyl)indenyl]zirconium dichloride,
phenylazandiyl-4-($\eta^5$-2-methyl-7-m-tolylindenyl)-4'-[$\eta^5$-2-methyl-7-(4-fluorophenyl)indenyl]zirconium dichloride,
phenylazandiyl-4-($\eta^5$-2-methyl-7-m-tolylindenyl)-4'-[$\eta^5$-2-methyl-7-(3-trifluoromethylphenyl)indenyl]zirconium dichloride,
phenylazandiyl-4-[$\eta^5$-2-methyl-7-(4-tert-butylphenyl)indenyl]-4'-[$\eta^5$-2-methyl-7-(5-methyl-thien-2-yl)indenyl]zirconium dichloride,
phenylazandiyl-4-[$\eta^5$-2-methyl-7-(4-tert-butylphenyl)indenyl]-4'-[$\eta^5$-2-methyl-7-(5-methyl-furan-2-yl)indenyl]zirconium dichloride,
phenylazandiyl-4-[$\eta^5$-2-methyl-7-(4-tert-butylphenyl)indenyl]-4'-[$\eta^5$-2-methyl-7-(2-benzothiopheneyl)indenyl]zirconium dichloride,
phenylazandiyl-4-[$\eta^5$-2-methyl-7-(4-tert-butylphenyl)indenyl]-4'-[$\eta^5$-2-methyl-7-(2-benzofuranyl)indenyl]zirconium dichloride,
phenylazandiyl-4-[$\eta^5$-2-methyl-7-(4-tert-butylphenyl)indenyl]-4'-[$\eta^5$-2-methyl-7-(4-fluorophenyl)indenyl]zirconium dichloride,
phenylazandiyl-4-[$\eta^5$-2-methyl-7-(4-tert-butylphenyl)indenyl]-4'-[$\eta^5$-2-methyl-7-(3-trifluoromethylphenyl)indenyl]zirconium dichloride,
phenylazandiyl-4-[$\eta^5$-2-methyl-7-(5-methyl-thien-2-yl)indenyl]-4'-[$\eta^5$-2-methyl-7-(5-methyl-furan-2-yl)indenyl]zirconium dichloride,
phenylazandiyl-4-[$\eta^5$-2-methyl-7-(5-methyl-thien-2-yl)indenyl]-4'-[$\eta^5$-2-methyl-7-(2-benzothiopheneyl)indenyl]zirconium dichloride, phenylazandiyl-4-[$\eta^5$-2-methyl-7-(5-methyl-thien-2-yl)indenyl]-4'-[$\eta^5$-2-methyl-7-(2-benzofuranyl)indenyl]zirconium dichloride,
phenylazandiyl-4-[$\eta^5$-2-methyl-7-(5-methyl-thien-2-yl)indenyl]-4'-[$\eta^5$-2-methyl-7-(4-fluorophenyl)indenyl]zirconium dichloride,
phenylazandiyl-4-[$\eta^5$-2-methyl-7-(5-methyl-thien-2-yl)indenyl]-4'-[$\eta^5$-2-methyl-7-(3-trifluoromethylphenyl)indenyl]zirconium dichloride,
phenylazandiyl-4-[$\eta^5$-2-methyl-7-(5-methyl-furan-2-yl)indenyl]-4'-[$\eta^5$-2-methyl-7-(2-benzothiopheneyl)indenyl]zirconium dichloride,
phenylazandiyl-4-[$\eta^5$-2-methyl-7-(5-methyl-furan-2-yl)indenyl]-4'-[$\eta^5$-2-methyl-7-(2-benzofuranyl)indenyl]zirconium dichloride,
phenylazandiyl-4-[$\eta^5$-2-methyl-7-(5-methyl-furan-2-yl)indenyl]-4'-[$\eta^5$-2-methyl-7-(4-fluorophenyl)indenyl]zirconium dichloride,
phenylazandiyl-4-[$\eta^5$-2-methyl-7-(5-methyl-furan-2-yl)indenyl]-4'-[$\eta^5$-2-methyl-7-(3-trifluoromethylphenyl)indenyl]zirconium dichloride,
phenylazandiyl-4-[$\eta^5$-2-methyl-7-(5-methyl-2-benzothiopheneyl)indenyl]-4'-[$\eta^5$-2-methyl-7-(2-benzofuranyl)indenyl]zirconium dichloride,
phenylazandiyl-4-[$\eta^5$-2-methyl-7-(5-methyl-2-benzothiopheneyl)indenyl]-4'-[$\eta^5$-2-methyl-7-(4-fluorophenyl)indenyl]zirconium dichloride,
phenylazandiyl-4-[$\eta^5$-2-methyl-7-(5-methyl-2-benzothiopheneyl)indenyl]-4'-[$\eta^5$-2-methyl-7-(3-trifluoromethylphenyl)indenyl]zirconium dichloride,
phenylazandiyl-4-[$\eta^5$-2-methyl-7-(5-methyl-2-benzofuranyl)indenyl]-4'-[$\eta^5$-2-methyl-7-(4-fluorophenyl)indenyl]zirconium dichloride,
phenylazandiyl-4-[$\eta^5$-2-methyl-7-(5-methyl-2-benzofuranyl)indenyl]-4'-[$\eta^5$-2-methyl-7-(3-trifluoromethylphenyl)indenyl]zirconium dichloride,
phenylazandiyl-4-[$\eta^5$-2-methyl-7-(3-trifluoromethylphenyl)indenyl]-4'-[$\eta^5$-2-methyl-7-(3-trifluoromethylphenyl)indenyl]zirconium dichloride,
phenylphosphindiyl-4-($\eta^5$-2-methylindenyl)-4'-(indenyl)zirconium dichloride,
phenylphosphindiyl-4-($\eta^5$-2-methylindenyl)-4'-($\eta^5$-1-phenylindenyl)zirconium dichloride,
phenylphosphindiyl-4-($\eta^5$-2-methylindenyl)-4'-($\eta^5$-1-naphthylindenyl)zirconium dichloride,
phenylphosphindiyl-4-($\eta^5$-2-methylindenyl)-4'-($\eta^5$-7-bromo-2-methylindenyl)zirconium dichloride,
phenylphosphindiyl-4-($\eta^5$-2-methylindenyl)-4'-($\eta^5$-7-bromo-indenyl)zirconium dichloride,
phenylphosphindiyl-4-($\eta^5$-2-methylindenyl)-4'-($\eta^5$-2,7-dimethylindenyl)zirconium dichloride,
phenylphosphindiyl-4-($\eta^5$-2-methylindenyl)-4'-($\eta^5$-7-phenyl-2-methylindenyl)zirconium dichloride,
phenylphosphindiyl-4-($\eta^5$-2-methylindenyl)-4'-($\eta^5$-2-methyl-7-p-tolyl-indenyl)zirconium dichloride,
phenylphosphindiyl-4-($\eta^5$-2-methylindenyl)-4'-($\eta^5$-2-methyl-7-m-tolylindenyl)zirconium dichloride,
phenylphosphindiyl-4-($\eta^5$-2-methylindenyl)-4'-[$\eta^5$-2-methyl-7-(4-tert-butylphenyl)indenyl]zirconium dichloride,
phenylphosphindiyl-4-($\eta^5$-2-methylindenyl)-4'-[$\eta^5$-2-methyl-7-(5-methyl-thien-2-yl)indenyl]zirconium dichloride,
phenylphosphindiyl-4-($\eta^5$-2-methylindenyl)-4'-[$\eta^5$-2-methyl-7-(5-methyl-furan-2-yl)indenyl]zirconium dichloride,
phenylphosphindiyl-4-($\eta^5$-2-methylindenyl)-4'-[$\eta^5$-2-methyl-7-(2-benzothiopheneyl)indenyl]zirconium dichloride,
phenylphosphindiyl-4-($\eta^5$-2-methylindenyl)-4'-[$\eta^5$-2-methyl-7-(2-benzofuranyl)indenyl]zirconium dichloride,
phenylphosphindiyl-4-($\eta^5$-2-methylindenyl)-4'-[$\eta^5$-2-methyl-7-(4-fluorophenyl)indenyl]zirconium dichloride,
phenylphosphindiyl-4-($\eta^5$-2-methylindenyl)-4'-[$\eta^5$-2-methyl-7-(3-trifluoromethylphenyl)indenyl]zirconium dichloride,
phenylphosphindiyl-4-($\eta^5$-indenyl)-4'-($\eta^5$-1-phenylindenyl)zirconium dichloride,
phenylphosphindiyl-4-($\eta^5$-indenyl)-4'-($\eta^5$-1-naphthylindenyl)zirconium dichloride,
phenylphosphindiyl-4-($\eta^5$-indenyl)-4'-($\eta^5$-7-bromo-2-methylindenyl)zirconium dichloride,
phenylphosphindiyl-4-($\eta^5$-indenyl)-4'-($\eta^5$-7-bromo-indenyl)zirconium dichloride,
phenylphosphindiyl-4-($\eta^5$-indenyl)-4'-($\eta^5$-2,7-dimethylindenyl)zirconium dichloride,
phenylphosphindiyl-4-($\eta^5$-indenyl)-4'-($\eta^5$-7-phenyl-2-methylindenyl)zirconium dichloride,
phenylphosphindiyl-4-($\eta^5$-indenyl)-4'-($\eta^5$-2-methyl-7-p-tolyl-indenyl)zirconium dichloride,
phenylphosphindiyl-4-($\eta^5$-indenyl)-4'-($\eta^5$-2-methyl-7-m-tolylindenyl)zirconium dichloride,
phenylphosphindiyl-4-($\eta^5$-indenyl)-4'-[$\eta^5$-2-methyl-7-(4-tert-butylphenyl)indenyl]zirconium dichloride,
phenylphosphindiyl-4-($\eta^5$-indenyl)-4'-[$\eta^5$-2-methyl-7-(5-methyl-thien-2-yl)indenyl]zirconium dichloride,
phenylphosphindiyl-4-($\eta^5$-indenyl)-4'-[$\eta^5$-2-methyl-7-(5-methyl-furan-2-yl)indenyl]zirconium dichloride,
phenylphosphindiyl-4-($\eta^5$-indenyl)-4'-[$\eta^5$-2-methyl-7-(2-benzothiopheneyl)indenyl]zirconium dichloride,
phenylphosphindiyl-4-($\eta^5$-indenyl)-4'-[$\eta^5$-2-methyl-7-(2-benzofuranyl)indenyl]zirconium dichloride,
phenylphosphindiyl-4-($\eta^5$-indenyl)-4'-[$\eta^5$-2-methyl-7-(4-fluorophenyl)indenyl]zirconium dichloride,
phenylphosphindiyl-4-($\eta^5$-indenyl)-4'-[$\eta^5$-2-methyl-7-(3-trifluoromethylphenyl)indenyl]zirconium dichloride,
phenylphosphindiyl-4-($\eta^5$-1-phenylindenyl)-4'-($\eta^5$-1-naphthylindenyl)zirconium dichloride,
phenylphosphindiyl-4-($\eta^5$-1-phenylindenyl)-4'-($\eta^5$-7-bromo-2-methylindenyl)zirconium dichloride,
phenylphosphindiyl-4-($\eta^5$-1-phenylindenyl)-4'-($\eta^5$-7-bromoindenyl)zirconium dichloride,
phenylphosphindiyl-4-($\eta^5$-1-phenylindenyl)-4'-($\eta^5$-2,7-dimethylindenyl)zirconium dichloride,
phenylphosphindiyl-4-($\eta^5$-1-phenylindenyl)-4'-($\eta^5$-7-phenyl-2-methylindenyl)zirconium dichloride,
phenylphosphindiyl-4-($\eta^5$-1-phenylindenyl)-4'-($\eta^5$-2-methyl-7-p-tolyl-indenyl)zirconium dichloride,
phenylphosphindiyl-4-($\eta^5$-1-phenylindenyl)-4'-($\eta^5$-2-methyl-7-m-tolylindenyl)zirconium dichloride,
phenylphosphindiyl-4-($\eta^5$-1-phenylindenyl)-4'-[$\eta^5$-2-methyl-7-(4-tert-butylphenyl)indenyl]zirconium dichloride,
phenylphosphindiyl-4-($\eta^5$-1-phenylindenyl)-4'-[$\eta^5$-2-methyl-7-(5-methyl-thien-2-yl)indenyl]zirconium dichloride,
phenylphosphindiyl-4-($\eta^5$-1-phenylindenyl)-4'-[$\eta^5$-2-methyl-7-(5-methyl-furan-2-yl)indenyl]zirconium dichloride,
phenylphosphindiyl-4-($\eta^5$-1-phenylindenyl)-4'-[$\eta^5$-2-methyl-7-(2-benzothiopheneyl)indenyl]zirconium dichloride,
phenylphosphindiyl-4-($\eta^5$-1-phenylindenyl)-4'-[$\eta^5$-2-methyl-7-(2-benzofuranyl)indenyl]zirconium dichloride, phenylphosphindiyl-4-($\eta^5$-1-phenylindenyl)-4'-[$\eta^5$-2-methyl-7-(4-fluorophenyl)indenyl]zirconium dichloride,
phenylphosphindiyl-4-($\eta^5$-1-phenylindenyl)-4'-[$\eta^5$-2-methyl-7-(3-trifluoromethylphenyl)indenyl]zirconium dichloride,
phenylphosphindiyl-4-($\eta^5$-1-naphthylindenyl)-4'-($\eta^5$-7-bromo-2-methylindenyl)zirconium dichloride,
phenylphosphindiyl-4-($\eta^5$-1-naphthylindenyl)-4'-($\eta^5$-7-bromoindenyl)zirconium dichloride,
phenylphosphindiyl-4-($\eta^5$-1-naphthylindenyl)-4'-($\eta^5$-2,7-dimethylindenyl)zirconium dichloride,
phenylphosphindiyl-4-($\eta^5$-1-naphthylindenyl)-4'-($\eta^5$-7-phenyl-2-methylindenyl)zirconium dichloride,
phenylphosphindiyl-4-($\eta^5$-1-naphthylindenyl)-4'-($\eta^5$-2-methyl-7-p-tolyl-indenyl)zirconium dichloride,
phenylphosphindiyl-4-($\eta^5$-1-naphthylindenyl)-4'-($\eta^5$-2-methyl-7-m-tolylindenyl)zirconium dichloride,
phenylphosphindiyl-4-($\eta^5$-1-naphthylindenyl)-4'-[$\eta^5$-2-methyl-7-(4-tert-butylphenyl)indenyl]zirconium dichloride,
phenylphosphindiyl-4-($\eta^5$-1-naphthylindenyl)-4'-[$\eta^5$-2-methyl-7-(5-methyl-thien-2-yl)indenyl]zirconium dichloride,
phenylphosphindiyl-4-($\eta^5$-1-naphthylindenyl)-4'-[$\eta^5$-2-methyl-7-(5-methyl-furan-2-yl)indenyl]zirconium dichloride,
phenylphosphindiyl-4-($\eta^5$-1-naphthylindenyl)-4'-[$\eta^5$-2-methyl-7-(2-benzothiopheneyl)indenyl]zirconium dichloride,
phenylphosphindiyl-4-($\eta^5$-1-naphthylindenyl)-4'-[$\eta^5$-2-methyl-7-(2-benzofuranyl)indenyl]zirconium dichloride,
phenylphosphindiyl-4-($\eta^5$-1-naphthylindenyl)-4'-[$\eta^5$-2-methyl-7-(4-fluorophenyl)indenyl]zirconium dichloride,
phenylphosphindiyl-4-($\eta^5$-1-naphthylindenyl)-4'-[$\eta^5$-2-methyl-7-(3-trifluoromethylphenyl)indenyl]zirconium dichloride,
phenylphosphindiyl-4-($\eta^5$-7-bromo-2-methylindenyl)-4'-($\eta^5$-7-bromoindenyl)zirconium dichloride,
phenylphosphindiyl-4-($\eta^5$-7-bromo-2-methylindenyl)-4'-($\eta^5$-2,7-dimethylindenyl)zirconium dichloride,
phenylphosphindiyl-4-($\eta^5$-7-bromo-2-methylindenyl)-4'-($\eta^5$-7-phenyl-2-methylindenyl)zirconium dichloride,
phenylphosphindiyl-4-($\eta^5$-7-bromo-2-methylindenyl)-4'-($\eta^5$-2-methyl-7-p-tolyl-indenyl)zirconium dichloride,
phenylphosphindiyl-4-($\eta^5$-7-bromo-2-methylindenyl)-4'-($\eta^5$-2-methyl-7-m-tolylindenyl)zirconium dichloride,
phenylphosphindiyl-4-($\eta^5$-7-bromo-2-methylindenyl)-4'-[$\eta^5$-2-methyl-7-(4-tert-butylphenyl)indenyl]zirconium dichloride,
phenylphosphindiyl-4-($\eta^5$-7-bromo-2-methylindenyl)-4'-[$\eta^5$-2-methyl-7-(5-methyl-thien-2-yl)indenyl]zirconium dichloride,
phenylphosphindiyl-4-($\eta^5$-7-bromo-2-methylindenyl)-4'-[$\eta^5$-2-methyl-7-(5-methyl-furan-2-yl)indenyl]zirconium dichloride,
phenylphosphindiyl-4-($\eta^5$-7-bromo-2-methylindenyl)-4'-[$\eta^5$-2-methyl-7-(2-benzothiopheneyl)indenyl]zirconium dichloride,
phenylphosphindiyl-4-($\eta^5$-7-bromo-2-methylindenyl)-4'-[$\eta^5$-2-methyl-7-(2-benzofuranyl)indenyl]zirconium dichloride,
phenylphosphindiyl-4-($\eta^5$-7-bromo-2-methylindenyl)-4'-[$\eta^5$-2-methyl-7-(4-fluorophenyl)indenyl]zirconium dichloride,
phenylphosphindiyl-4-($\eta^5$-7-bromo-2-methylindenyl)-4'-[$\eta^5$-2-methyl-7-(3-trifluoromethylphenyl)indenyl]zirconium dichloride,
phenylphosphindiyl-4-($\eta^5$-7-bromoindenyl)-4'-($\eta^5$-2,7-dimethylindenyl)zirconium dichloride,
phenylphosphindiyl-4-($\eta^5$-7-bromoindenyl)-4'-($\eta^5$-7-phenyl-2-methylindenyl)zirconium dichloride,
phenylphosphindiyl-4-($\eta^5$-7-bromoindenyl)-4'-($\eta^5$-2-methyl-7-p-tolyl-indenyl)zirconium dichloride,
phenylphosphindiyl-4-($\eta^5$-7-bromoindenyl)-4'-($\eta^5$-2-methyl-7-m-tolylindenyl)zirconium dichloride,
phenylphosphindiyl-4-($\eta^5$-7-bromoindenyl)-4'-[$\eta^5$-2-methyl-7-(4-tert-butylphenyl)indenyl]zirconium dichloride,
phenylphosphindiyl-4-($\eta^5$-7-bromoindenyl)-4'-[$\eta^5$-2-methyl-7-(5-methyl-thien-2-yl)indenyl]zirconium dichloride,
phenylphosphindiyl-4-($\eta^5$-7-bromoindenyl)-4'-[$\eta^5$-2-methyl-7-(5-methyl-furan-2-yl)indenyl]zirconium dichloride,
phenylphosphindiyl-4-($\eta^5$-7-bromoindenyl)-4'-[$\eta^5$-2-methyl-7-(2-benzothiopheneyl)indenyl]zirconium dichloride,
phenylphosphindiyl-4-($\eta^5$-7-bromoindenyl)-4'-[$\eta^5$-2-methyl-7-(2-benzofuranyl)indenyl]zirconium dichloride,
phenylphosphindiyl-4-($\eta^5$-7-bromoindenyl)-4'-[$\eta^5$-2-methyl-7-(4-fluorophenyl)indenyl]zirconium dichloride,
phenylphosphindiyl-4-($\eta^5$-7-bromoindenyl)-4'-[$\eta^5$-2-methyl-7-(3-trifluoromethylphenyl)indenyl]zirconium dichloride,
phenylphosphindiyl-4-($\eta^5$-2,7-dimethylindenyl)-4'-($\eta^5$-7-phenyl-2-methylindenyl)zirconium dichloride,
phenylphosphindiyl-4-($\eta^5$-2,7-dimethylindenyl)-4'-($\eta^5$-2-methyl-7-p-tolyl-indenyl)zirconium dichloride,
phenylphosphindiyl-4-($\eta^5$-2,7-dimethylindenyl)-4'-($\eta^5$-2-methyl-7-m-tolylindenyl)zirconium dichloride,
phenylphosphindiyl-4-($\eta^5$-2,7-dimethylindenyl)-4'-[$\eta^5$-2-methyl-7-(4-tert-butylphenyl)indenyl]zirconium dichloride,
phenylphosphindiyl-4-($\eta^5$-2,7-dimethylindenyl)-4'-[$\eta^5$-2-methyl-7-(5-methyl-thien-2-yl)indenyl]zirconium dichloride,
phenylphosphindiyl-4-($\eta^5$-2,7-dimethylindenyl)-4'-[$\eta^5$-2-methyl-7-(5-methyl-furan-2-yl)indenyl]zirconium dichloride,
phenylphosphindiyl-4-($\eta^5$-2,7-dimethylindenyl)-4'-[$\eta^5$-2-methyl-7-(2-benzothiopheneyl)indenyl]zirconium dichloride,
phenylphosphindiyl-4-($\eta^5$-2,7-dimethylindenyl)-4'-[$\eta^5$-2-methyl-7-(2-benzofuranyl)indenyl]zirconium dichloride,
phenylphosphindiyl-4-($\eta^5$-2,7-dimethylindenyl)-4'-[$\eta^5$-2-methyl-7-(4-fluorophenyl)indenyl]zirconium dichloride,
phenylphosphindiyl-4-($\eta^5$-2,7-dimethylindenyl)-4'-[$\eta^5$-2-methyl-7-(3-trifluoromethylphenyl)indenyl]zirconium dichloride,
phenylphosphindiyl-4-($\eta^5$-7-phenyl-2-methylindenyl)-4'-($\eta^5$-2-methyl-7-p-tolyl-indenyl)zirconium dichloride,
phenylphosphindiyl-4-($\eta^5$-7-phenyl-2-methylindenyl)-4'-($\eta^5$-2-methyl-7-m-tolylindenyl)zirconium dichloride,
phenylphosphindiyl-4-($\eta^5$-7-phenyl-2-methylindenyl)-4'-[$\eta^5$-2-methyl-7-(4-tert-butylphenyl)indenyl]zirconium dichloride,
phenylphosphindiyl-4-($\eta^5$-7-phenyl-2-methylindenyl)-4'-[$\eta^5$-2-methyl-7-(5-methyl-thien-2-yl)indenyl]zirconium dichloride,
phenylphosphindiyl-4-($\eta^5$-7-phenyl-2-methylindenyl)-4'-[$\eta^5$-2-methyl-7-(5-methyl-furan-2-yl)indenyl]zirconium dichloride,
phenylphosphindiyl-4-($\eta^5$-7-phenyl-2-methylindenyl)-4'-[$\eta^5$-2-methyl-7-(2-benzothiopheneyl)indenyl]zirconium dichloride, phenylphosphindiyl-4-($\eta^5$-7-phenyl-2-methylindenyl)-4'-[$\eta^5$-2-methyl-7-(2-benzofuranyl)indenyl]zirconium dichloride,
phenylphosphindiyl-4-($\eta^5$-7-phenyl-2-methylindenyl)-4'-[$\eta^5$-2-methyl-7-(4-fluorophenyl)indenyl]zirconium dichloride,
phenylphosphindiyl-4-($\eta^5$-7-phenyl-2-methylindenyl)-4'-[$\eta^5$-2-methyl-7-(3-trifluoromethylphenyl)indenyl]zirconium dichloride,
phenylphosphindiyl-4-($\eta^5$-2-methyl-7-p-tolylindenyl)-4'-($\eta^5$-2-methyl-7-m-tolylindenyl)zirconium dichloride,
phenylphosphindiyl-4-($\eta^5$-2-methyl-7-p-tolylindenyl)-4'-[$\eta^5$-2-methyl-7-(4-tert-butylphenyl)indenyl]zirconium dichloride,
phenylphosphindiyl-4-($\eta^5$-2-methyl-7-p-tolylindenyl)-4'-[$\eta^5$-2-methyl-7-(5-methyl-thien-2-yl)indenyl]zirconium dichloride,
phenylphosphindiyl-4-($\eta^5$-2-methyl-7-p-tolylindenyl)-4'-[$\eta^5$-2-methyl-7-(5-methyl-furan-2-yl)indenyl]zirconium dichloride,
phenylphosphindiyl-4-($\eta^5$-2-methyl-7-p-tolylindenyl)-4'-[$\eta^5$-2-methyl-7-(2-benzothiopheneyl)indenyl]zirconium dichloride,
phenylphosphindiyl-4-($\eta^5$-2-methyl-7-p-tolylindenyl)-4'-[$\eta^5$-2-methyl-7-(2-benzofuranyl)indenyl]zirconium dichloride,
phenylphosphindiyl-4-($\eta^5$-2-methyl-7-p-tolylindenyl)-4'-[$\eta^5$-2-methyl-7-(4-fluorophenyl)indenyl]zirconium dichloride,
phenylphosphindiyl-4-($\eta^5$-2-methyl-7-p-tolylindenyl)-4'-[$\eta^5$-2-methyl-7-(3-trifluoromethylphenyl)indenyl]zirconium dichloride,
phenylphosphindiyl-4-($\eta^5$-2-methyl-7-m-tolylindenyl)-4'-[$\eta^5$-2-methyl-7-(4-tert-butylphenyl)indenyl]zirconium dichloride,
phenylphosphindiyl-4-($\eta^5$-2-methyl-7-m-tolylindenyl)-4'-[$\eta^5$-2-methyl-7-(5-methyl-thien-2-yl)indenyl]zirconium dichloride,
phenylphosphindiyl-4-($\eta^5$-2-methyl-7-m-tolylindenyl)-4'-[$\eta^5$-2-methyl-7-(5-methyl-furan-2-yl)indenyl]zirconium dichloride,
phenylphosphindiyl-4-($\eta^5$-2-methyl-7-m-tolylindenyl)-4'-[$\eta^5$-2-methyl-7-(2-benzothiopheneyl)indenyl]zirconium dichloride,
phenylphosphindiyl-4-($\eta^5$-2-methyl-7-m-tolylindenyl)-4'-[$\eta^5$-2-methyl-7-(2-benzofuranyl)indenyl]zirconium dichloride,
phenylphosphindiyl-4-($\eta^5$-2-methyl-7-m-tolylindenyl)-4'-[$\eta^5$-2-methyl-7-(4-fluorophenyl)indenyl]zirconium dichloride,
phenylphosphindiyl-4-($\eta^5$-2-methyl-7-m-tolylindenyl)-4'-[$\eta^5$-2-methyl-7-(3-trifluoromethylphenyl)indenyl]zirconium dichloride,
phenylphosphindiyl-4-[$\eta^5$-2-methyl-7-(4-tert-butylphenyl)indenyl]-4'-[$\eta^5$-2-methyl-7-(5-methyl-thien-2-yl)indenyl]zirconium dichloride,
phenylphosphindiyl-4-[$\eta^5$-2-methyl-7-(4-tert-butylphenyl)indenyl]-4'-[$\eta^5$-2-methyl-7-(5-methyl-furan-2-yl)indenyl]zirconium dichloride,
phenylphosphindiyl-4-[$\eta^5$-2-methyl-7-(4-tert-butylphenyl)indenyl]-4'-[$\eta^5$-2-methyl-7-(2-benzothiopheneyl)indenyl]zirconium dichloride,
phenylphosphindiyl-4-[$\eta^5$-2-methyl-7-(4-tert-butylphenyl)indenyl]-4'-[$\eta^5$-2-methyl-7-(2-benzofuranyl)indenyl]zirconium dichloride,
phenylphosphindiyl-4-[$\eta^5$-2-methyl-7-(4-tert-butylphenyl)indenyl]-4'-[$\eta^5$-2-methyl-7-(4-fluorophenyl)indenyl]zirconium dichloride,
phenylphosphindiyl-4-[$\eta^5$-2-methyl-7-(4-tert-butylphenyl)indenyl]-4'-[$\eta^5$-2-methyl-7-(3-trifluoromethylphenyl)indenyl]zirconium dichloride,
phenylphosphindiyl-4-[$\eta^5$-2-methyl-7-(5-methyl-thien-2-yl)indenyl]-4'-[$\eta^5$-2-methyl-7-(5-methyl-furan-2-yl)indenyl]zirconium dichloride,
phenylphosphindiyl-4-[$\eta^5$-2-methyl-7-(5-methyl-thien-2-yl)indenyl]-4'-[$\eta^5$-2-methyl-7-(2-benzothiopheneyl)indenyl]zirconium dichloride,
phenylphosphindiyl-4-[$\eta^5$-2-methyl-7-(5-methyl-thien-2-yl)indenyl]-4'-[$\eta^5$-2-methyl-7-(2-benzofuranyl)indenyl]zirconium dichloride,
phenylphosphindiyl-4-[$\eta^5$-2-methyl-7-(5-methyl-thien-2-yl)indenyl]-4'-[$\eta^5$-2-methyl-7-(4-fluorophenyl)indenyl]zirconium dichloride,
phenylphosphindiyl-4-[$\eta^5$-2-methyl-7-(5-methyl-thien-2-yl)indenyl]-4'-[$\eta^5$-2-methyl-7-(3-trifluoromethylphenyl)indenyl]zirconium dichloride,
phenylphosphindiyl-4-[$\eta^5$-2-methyl-7-(5-methyl-furan-2-yl)indenyl]-4'-[$\eta^5$-2-methyl-7-(2-benzothiopheneyl)indenyl]zirconium dichloride,
phenylphosphindiyl-4-[$\eta^5$-2-methyl-7-(5-methyl-furan-2-yl)indenyl]-4'-[$\eta^5$-2-methyl-7-(2-benzofuranyl)indenyl]zirconium dichloride,
phenylphosphindiyl-4-[$\eta^5$-2-methyl-7-(5-methyl-furan-2-yl)indenyl]-4'-[$\eta^5$-2-methyl-7-(4-fluorophenyl)indenyl]zirconium dichloride,
phenylphosphindiyl-4-[$\eta^5$-2-methyl-7-(5-methyl-furan-2-yl)indenyl]-4'-[$\eta^5$-2-methyl-7-(3-trifluoromethylphenyl)indenyl]zirconium dichloride,
phenylphosphindiyl-4-[$\eta^5$-2-methyl-7-(5-methyl-2-benzothiopheneyl)indenyl]-4'-[$\eta^5$-2-methyl-7-(2-benzofuranyl)indenyl]zirconium dichloride,
phenylphosphindiyl-4-[$\eta^5$-2-methyl-7-(5-methyl-2-benzothiopheneyl)indenyl]-4'-[$\eta^5$-2-methyl-7-(4-fluorophenyl)indenyl]zirconium dichloride,
phenylphosphindiyl-4-[$\eta^5$-2-methyl-7-(5-methyl-2-benzothiopheneyl)indenyl]-4'-[$\eta^5$-2-methyl-7-(3-trifluoromethylphenyl)indenyl]zirconium dichloride,
phenylphosphindiyl-4-[$\eta^5$-2-methyl-7-(5-methyl-2-benzofuranyl)indenyl]-4'-[$\eta^5$-2-methyl-7-(4-fluorophenyl)indenyl]zirconium dichloride,
phenylphosphindiyl-4-[$\eta^5$-2-methyl-7-(5-methyl-2-benzofuranyl)indenyl]-4'-[$\eta^5$-2-methyl-7-(3-trifluoromethylphenyl)indenyl]zirconium dichloride,
phenylphosphindiyl-4-[$\eta^5$-2-methyl-7-(3-trifluoromethylphenyl)indenyl]-4'-[$\eta^5$-2-methyl-7-(3-trifluoromethylphenyl)indenyl]zirconium dichloride,
phenylphosphindiyl-($\eta^5$-cyclopentadienyl)-4-(2-methylindenyl)zirconium dichloride,
phenylphosphindiyl-($\eta^5$-cyclopentadienyl)-4-(indenyl)zirconium dichloride,
phenylphosphindiyl-($\eta^5$-cyclopentadienyl)-4-($\eta^5$-7-bromo-2-methylindenyl)zirconium dichloride,
phenylphosphindiyl-($\eta^5$-cyclopentadienyl)-4-($\eta^5$-7-bromo-indenyl)zirconium dichloride,
phenylphosphindiyl-($\eta^5$-cyclopentadienyl)-4-($\eta^5$-2,7-dimethylindenyl)zirconium dichloride,
phenylphosphindiyl-($\eta^5$-cyclopentadienyl)-4-($\eta^5$-7-phenyl-2-methylindenyl)zirconium dichloride,
phenylphosphindiyl-($\eta^5$-cyclopentadienyl)-4-($\eta^5$-2-methyl-7-p-tolyl-indenyl)zirconium dichloride,
phenylphosphindiyl-($\eta^5$-cyclopentadienyl)-4-($\eta^5$-2-methyl-7-m-tolylindenyl)zirconium dichloride, phenylphosphindiyl-4-(η⁵-fluorenyl)-4'-(2-methylindenyl) zirconium dichloride,
phenylphosphindiyl-4-(η⁵-fluorenyl)-4'-(indenyl)zirconium dichloride,
phenylphosphindiyl-4-(η⁵-fluorenyl)-4'-(η⁵-7-bromo-2-methylindenyl)zirconium dichloride,
phenylphosphindiyl-4-(η⁵-fluorenyl)-4'-(η⁵-7-bromo-indenyl)zirconium dichloride,
phenylphosphindiyl-4-(η⁵-fluorenyl)-4'-(η⁵-2,7-dimethylindenyl)zirconium dichloride,
phenylphosphindiyl-4-(η⁵-fluorenyl)-4'-(η⁵-7-phenyl-2-methylindenyl)zirconium dichloride,
phenylphosphindiyl-4-(η⁵-fluorenyl)-4'-(η⁵-2-methyl-7-p-tolyl-indenyl)zirconium dichloride,
phenylphosphindiyl-4-(η⁵-fluorenyl)-4'-(η⁵-2-methyl-7-m-tolylindenyl)zirconium dichloride,
phenylphosphindiyl-4-(η⁵-2-methylindenyl)-4'-(indenyl) hafnium dichloride,
phenylphosphindiyl-4-(η⁵-2-methylindenyl)-4'-(η⁵-7-bromo-2-methylindenyl)hafnium dichloride,
phenylphosphindiyl-4-(η⁵-2-methylindenyl)-4'-(η⁵-7-bromo-indenyl)hafnium dichloride,
phenylphosphindiyl-4-(η⁵-2-methylindenyl)-4'-(η⁵-2,7-dimethylindenyl)hafnium dichloride,
phenylphosphindiyl-4-(η⁵-2-methylindenyl)-4'-(η⁵-7-phenyl-2-methylindenyl)hafnium dichloride,
phenylphosphindiyl-4-(η⁵-2-methylindenyl)-4'-(η⁵-2-methyl-7-p-tolyl-indenyl)hafnium dichloride,
phenylphosphindiyl-4-(η⁵-2-methylindenyl)-4'-(η⁵-2-methyl-7-m-tolylindenyl)hafnium dichloride,
phenylphosphindiyl-4-(η⁵-2-methylindenyl)-4'-(indenyl) hafnium dimethyl,
phenylphosphindiyl-4-(η⁵-2-methylindenyl)-4'-(η⁵-7-bromo-2-methylindenyl)hafnium dimethyl,
phenylphosphindiyl-4-(η⁵-2-methylindenyl)-4'-(η⁵-7-bromo-indenyl)hafnium dimethyl,
phenylphosphindiyl-4-(η⁵-2-methylindenyl)-4'-(η⁵-2,7-dimethylindenyl)hafnium dimethyl,
phenylphosphindiyl-4-(η⁵-2-methylindenyl)-4'-(η⁵-7-phenyl-2-methylindenyl)hafnium dimethyl,
phenylphosphindiyl-4-(η⁵-2-methylindenyl)-4'-(η⁵-2-methyl-7-p-tolyl-indenyl)hafnium dimethyl,
phenylphosphindiyl-4-(η⁵-2-methylindenyl)-4'-(η⁵-2-methyl-7-m-tolylindenyl)hafnium dimethyl,
phenylphosphindiyl-4-(η⁵-2-methylindenyl)-4'-(indenyl) zirconium dimethyl,
phenylphosphindiyl-4-(η⁵-2-methylindenyl)-4'-(η⁵-7-bromo-2-methylindenyl)zirconium dimethyl,
phenylphosphindiyl-4-(η⁵-2-methylindenyl)-4'-(η⁵-7-bromo-indenyl)zirconium dimethyl,
phenylphosphindiyl-4-(η⁵-2-methylindenyl)-4'-(η⁵-2,7-dimethylindenyl)zirconium dimethyl,
phenylphosphindiyl-4-(η⁵-2-methylindenyl)-4'-(η⁵-7-phenyl-2-methylindenyl)zirconium dimethyl,
phenylphosphindiyl-4-(η⁵-2-methylindenyl)-4'-(η⁵-2-methyl-7-p-tolyl-indenyl)zirconium dimethyl,
phenylphosphindiyl-4-(η⁵-2-methylindenyl)-4'-(η⁵-2-methyl-7-m-tolylindenyl)zirconium dimethyl,
sulfandiyl-(η⁵-cyclopentadienyl)-4-(2-methylindenyl)zirconium dichloride,
sulfandiyl-(η⁵-cyclopentadienyl)-4-(indenyl)zirconium dichloride,
sulfandiyl-(η⁵-cyclopentadienyl)-4-(η⁵-7-bromo-2-methylindenyl)zirconium dichloride,
sulfandiyl-(η⁵-cyclopentadienyl)-4-(η⁵-7-bromo-indenyl)zirconium dichloride,
sulfandiyl-(η⁵-cyclopentadienyl)-4-(η⁵-2,7-dimethylindenyl)zirconium dichloride,
sulfandiyl-(η⁵-cyclopentadienyl)-4-(η⁵-7-phenyl-2-methylindenyl)zirconium dichloride,
sulfandiyl-(η⁵-cyclopentadienyl)-4-(η⁵-2-methyl-7-p-tolyl-indenyl)zirconium dichloride,
sulfandiyl-(η⁵-cyclopentadienyl)-4-(η⁵-2-methyl-7-m-tolyl-indenyl)zirconium dichloride,
sulfandiyl-4-(η⁵-fluorenyl)-4'-(2-methylindenyl)zirconium dichloride,
sulfandiyl-4-(η⁵-fluorenyl)-4'-(indenyl)zirconium dichloride,
sulfandiyl-4-(η⁵-fluorenyl)-4'-(η⁵-7-bromo-2-methylindenyl)zirconium dichloride,
sulfandiyl-4-(η⁵-fluorenyl)-4'-(η⁵-7-bromo-indenyl)zirconium dichloride,
sulfandiyl-4-(η⁵-fluorenyl)-4'-(η⁵-2,7-dimethylindenyl)zirconium dichloride,
sulfandiyl-4-(η⁵-fluorenyl)-4'-(η⁵-7-phenyl-2-methylindenyl)zirconium dichloride,
sulfandiyl-4-(η⁵-fluorenyl)-4'-(η⁵-2-methyl-7-p-tolyl-indenyl)zirconium dichloride,
sulfandiyl-4-(η⁵-fluorenyl)-4'-(η⁵-2-methyl-7-m-tolylindenyl)zirconium dichloride,
sulfandiyl-4-(η⁵-2-methylindenyl)-4'-(indenyl)hafnium dichloride,
sulfandiyl-4-(η⁵-2-methylindenyl)-4'-(η⁵-7-bromo-2-methylindenyl)hafnium dichloride,
sulfandiyl-4-(η⁵-2-methylindenyl)-4'-(η⁵-7-bromo-indenyl) hafnium dichloride,
sulfandiyl-4-(η⁵-2-methylindenyl)-4'-(η⁵-2,7-dimethylindenyl)hafnium dichloride,
sulfandiyl-4-(η⁵-2-methylindenyl)-4'-(η⁵-7-phenyl-2-methylindenyl)hafnium dichloride,
sulfandiyl-4-(η⁵-2-methylindenyl)-4'-(η⁵-2-methyl-7-p-tolyl-indenyl)hafnium dichloride,
sulfandiyl-4-(η⁵-2-methylindenyl)-4'-(η⁵-2-methyl-7-m-tolylindenyl)hafnium dichloride,
sulfandiyl-4-(η⁵-2-methylindenyl)-4'-(indenyl)hafnium dimethyl,
sulfandiyl-4-(η⁵-2-methylindenyl)-4'-(η⁵-7-bromo-2-methylindenyl)hafnium dimethyl,
sulfandiyl-4-(η⁵-2-methylindenyl)-4'-(η⁵-7-bromo-indenyl) hafnium dimethyl,
sulfandiyl-4-(η⁵-2-methylindenyl)-4'-(η⁵-2,7-dimethylindenyl)hafnium dimethyl,
sulfandiyl-4-(η⁵-2-methylindenyl)-4'-(η⁵-7-phenyl-2-methylindenyl)hafnium dimethyl,
sulfandiyl-4-(η⁵-2-methylindenyl)-4'-(η⁵-2-methyl-7-p-tolyl-indenyl)hafnium dimethyl,
sulfandiyl-4-(η⁵-2-methylindenyl)-4'-(η⁵-2-methyl-7-m-tolylindenyl)hafnium dimethyl,
sulfandiyl-4-(η⁵-2-methylindenyl)-4'-(indenyl)zirconium dimethyl,
sulfandiyl-4-(η⁵-2-methylindenyl)-4'-(η⁵-7-bromo-2-methylindenyl)zirconium dimethyl,
sulfandiyl-4-(η⁵-2-methylindenyl)-4'-(η⁵-7-bromo-indenyl) zirconium dimethyl,
sulfandiyl-4-(η⁵-2-methylindenyl)-4'-(η⁵-2,7-dimethylindenyl)zirconium dimethyl,
sulfandiyl-4-(η⁵-2-methylindenyl)-4'-(η⁵-7-phenyl-2-methylindenyl)zirconium dimethyl,
sulfandiyl-4-(η⁵-2-methylindenyl)-4'-(η⁵-2-methyl-7-p-tolyl-indenyl)zirconium dimethyl,
sulfandiyl-4-(η⁵-2-methylindenyl)-4'-(η⁵-2-methyl-7-m-tolylindenyl)zirconium dimethyl, oxadiyl-(η$^5$-cyclopentadienyl)-4-(2-methylindenyl)zirconium dichloride,
oxadiyl-(η$^5$-cyclopentadienyl)-4-(indenyl)zirconium dichloride,
oxadiyl-(η$^5$-cyclopentadienyl)-4-(η$^5$-7-bromo-2-methylindenyl)zirconium dichloride,
oxadiyl-(η$^5$-cyclopentadienyl)-4-(η$^5$-7-bromo-indenyl)zirconium dichloride,
oxadiyl-(η$^5$-cyclopentadienyl)-4-(η$^5$-2,7-dimethylindenyl)zirconium dichloride,
oxadiyl-(η$^5$-cyclopentadienyl)-4-(η$^5$-7-phenyl-2-methylindenyl)zirconium dichloride,
oxadiyl-(η$^5$-cyclopentadienyl)-4-(η$^5$-2-methyl-7-p-tolyl-indenyl)zirconium dichloride,
oxadiyl-(η$^5$-cyclopentadienyl)-4-(η$^5$-2-methyl-7-m-tolylindenyl)zirconium dichloride,
oxadiyl-4-(η$^5$-fluorenyl)-4'-(2-methylindenyl)zirconium dichloride,
oxadiyl-4-(η$^5$-fluorenyl)-4'-(indenyl)zirconium dichloride,
oxadiyl-4-(η$^5$-fluorenyl)-4'-(η$^5$-7-bromo-2-methylindenyl)zirconium dichloride,
oxadiyl-4-(η$^5$-fluorenyl)-4'-(η$^5$-7-bromo-indenyl)zirconium dichloride,
oxadiyl-4-(η$^5$-fluorenyl)-4'-(η$^5$-2,7-dimethylindenyl)zirconium dichloride,
oxadiyl-4-(η$^5$-fluorenyl)-4'-(η$^5$-7-phenyl-2-methylindenyl)zirconium dichloride,
oxadiyl-4-(η$^5$-fluorenyl)-4'-(η$^5$-2-methyl-7-p-tolyl-indenyl)zirconium dichloride,
oxadiyl-4-(η$^5$-fluorenyl)-4'-(η$^5$-2-methyl-7-m-tolylindenyl)zirconium dichloride,
oxadiyl-4-(η$^5$-2-methylindenyl)-4'-(indenyl)hafnium dichloride,
oxadiyl-4-(η$^5$-2-methylindenyl)-4'-(η$^5$-7-bromo-2-methylindenyl)hafnium dichloride,
oxadiyl-4-(η$^5$-2-methylindenyl)-4'-(η$^5$-7-bromo-indenyl)hafnium dichloride,
oxadiyl-4-(η$^5$-2-methylindenyl)-4'-(η$^5$-2,7-dimethylindenyl)hafnium dichloride,
oxadiyl-4-(η$^5$-2-methylindenyl)-4'-(η$^5$-7-phenyl-2-methylindenyl)hafnium dichloride,
oxadiyl-4-(η$^5$-2-methylindenyl)-4'-(η$^5$-2-methyl-7-p-tolyl-indenyl)hafnium dichloride,
oxadiyl-4-(η$^5$-2-methylindenyl)-4'-(η$^5$-2-methyl-7-m-tolyl-indenyl)hafnium dichloride,
oxadiyl-4-(η$^5$-2-methylindenyl)-4'-(indenyl)hafnium dimethyl,
oxadiyl-4-(η$^5$-2-methylindenyl)-4'-(η$^5$-7-bromo-2-methylindenyl)hafnium dimethyl,
oxadiyl-4-(η$^5$-2-methylindenyl)-4'-(η$^5$-7-bromo-indenyl)hafnium dimethyl,
oxadiyl-4-(η$^5$-2-methylindenyl)-4'-(η$^5$-2,7-dimethylindenyl)hafnium dimethyl,
oxadiyl-4-(η$^5$-2-methylindenyl)-4'-(η$^5$-7-phenyl-2-methylindenyl)hafnium dimethyl,
oxadiyl-4-(η$^5$-2-methylindenyl)-4'-(η$^5$-2-methyl-7-p-tolyl-indenyl)hafnium dimethyl,
oxadiyl-4-(η$^5$-2-methylindenyl)-4'-(η$^5$-2-methyl-7-m-tolyl-indenyl)hafnium dimethyl,
oxadiyl-4-(η$^5$-2-methylindenyl)-4'-(indenyl)zirconium dimethyl,
oxadiyl-4-(η$^5$-2-methylindenyl)-4'-(η$^5$-7-bromo-2-methyl-indenyl)zirconium dimethyl,
oxadiyl-4-(η$^5$-2-methylindenyl)-4'-(η$^5$-7-bromo-indenyl)zirconium dimethyl,
oxadiyl-4-(η$^5$-2-methylindenyl)-4'-(η$^5$-2,7-dimethylindenyl)zirconium dimethyl,
oxadiyl-4-(η$^5$-2-methylindenyl)-4'-(η$^5$-7-phenyl-2-methylindenyl)zirconium dimethyl,
oxadiyl-4-(η$^5$-2-methylindenyl)-4'-(η$^5$-2-methyl-7-p-tolyl-indenyl)zirconium dimethyl,
oxadiyl-4-(η$^5$-2-methylindenyl)-4'-(η$^5$-2-methyl-7-m-tolyl-indenyl)zirconium dimethyl,
phenylazandiyl-(η$^5$-cyclopentadienyl)-4-(2-methylindenyl)zirconium dichloride,
phenylazandiyl-(η$^5$-cyclopentadienyl)-4-(indenyl)zirconium dichloride,
phenylazandiyl-(η$^5$-cyclopentadienyl)-4-(η$^5$-7-bromo-2-methylindenyl)zirconium dichloride,
phenylazandiyl-(η$^5$-cyclopentadienyl)-4-(η$^5$-7-bromo-indenyl)zirconium dichloride,
phenylazandiyl-(η$^5$-cyclopentadienyl)-4-(η$^5$-2,7-dimethylindenyl)zirconium dichloride,
phenylazandiyl-(η$^5$-cyclopentadienyl)-4-(η$^5$-7-phenyl-2-methylindenyl)zirconium dichloride,
phenylazandiyl-(η$^5$-cyclopentadienyl)-4-(η$^5$-2-methyl-7-p-tolyl-indenyl)zirconium dichloride,
phenylazandiyl-(η$^5$-cyclopentadienyl)-4-(η$^5$-2-methyl-7-m-tolylindenyl)zirconium dichloride,
phenylazandiyl-4-(η$^5$-fluorenyl)-4'-(2-methylindenyl)zirconium dichloride,
phenylazandiyl-4-(η$^5$-fluorenyl)-4'-(indenyl)zirconium dichloride,
phenylazandiyl-4-(η$^5$-fluorenyl)-4'-(η$^5$-7-bromo-2-methylindenyl)zirconium dichloride,
phenylazandiyl-4-(η$^5$-fluorenyl)-4'-(η$^5$-7-bromo-indenyl)zirconium dichloride,
phenylazandiyl-4-(η$^5$-fluorenyl)-4'-(η$^5$-2,7-dimethylindenyl)zirconium dichloride,
phenylazandiyl-4-(η$^5$-fluorenyl)-4'-(η$^5$-7-phenyl-2-methylindenyl)zirconium dichloride,
phenylazandiyl-4-(η$^5$-fluorenyl)-4'-(η$^5$-2-methyl-7-p-tolyl-indenyl)zirconium dichloride,
phenylazandiyl-4-(η$^5$-fluorenyl)-4'-(η$^5$-2-methyl-7-m-tolyl-indenyl)zirconium dichloride,
phenylazandiyl-4-(η$^5$-2-methylindenyl)-4'-(indenyl)hafnium dichloride,
phenylazandiyl-4-(η$^5$-2-methylindenyl)-4'-(η$^5$-7-bromo-2-methylindenyl)hafnium dichloride,
phenylazandiyl-4-(η$^5$-2-methylindenyl)-4'-(η$^5$-7-bromo-indenyl)hafnium dichloride,
phenylazandiyl-4-(η$^5$-2-methylindenyl)-4'-(η$^5$-2,7-dimethylindenyl)hafnium dichloride,
phenylazandiyl-4-(η$^5$-2-methylindenyl)-4'-(η$^5$-7-phenyl-2-methylindenyl)hafnium dichloride,
phenylazandiyl-4-(η$^5$-2-methylindenyl)-4'-(η$^5$-2-methyl-7-p-tolyl-indenyl)hafnium dichloride,
phenylazandiyl-4-(η$^5$-2-methylindenyl)-4'-(15-2-methyl-7-m-tolylindenyl)hafnium dichloride,
phenylazandiyl-4-(η$^5$-2-methylindenyl)-4'-(indenyl) hafnium dimethyl,
phenylazandiyl-4-(η$^5$-2-methylindenyl)-4'-(η$^5$-7-bromo-2-methylindenyl)hafnium dimethyl,
phenylazandiyl-4-(η$^5$-2-methylindenyl)-4'-(η$^5$-7-bromo-indenyl)hafnium dimethyl,
phenylazandiyl-4-(η$^5$-2-methylindenyl)-4'-(η$^5$-2,7-dimethylindenyl)hafnium dimethyl,
phenylazandiyl-4-(η$^5$-2-methylindenyl)-4'-(η$^5$-7-phenyl-2-methylindenyl)hafnium dimethyl,
phenylazandiyl-4-(η$^5$-2-methylindenyl)-4'-(η$^5$-2-methyl-7-p-tolyl-indenyl)hafnium dimethyl,
phenylazandiyl-4-(η$^5$-2-methylindenyl)-4'-(η$^5$-2-methyl-7-m-tolylindenyl)hafnium dimethyl, phenylazandiyl-4-($\eta^5$-2-methylindenyl)-4'-(indenyl)zirconium dimethyl,
phenylazandiyl-4-($\eta^5$-2-methylindenyl)-4'-($\eta^5$-7-bromo-2-methylindenyl)zirconium dimethyl,
phenylazandiyl-4-($\eta^5$-2-methylindenyl)-4'-($\eta^5$-7-bromo-indenyl)zirconium dimethyl,
phenylazandiyl-4-($\eta^5$-2-methylindenyl)-4'-($\eta^5$-2,7-dimethylindenyl)zirconium dimethyl,
phenylazandiyl-4-($\eta^5$-2-methylindenyl)-4'-($\eta^5$-7-phenyl-2-methylindenyl)zirconium dimethyl,
phenylazandiyl-4-($\eta^5$-2-methylindenyl)-4'-($\eta^5$-2-methyl-7-p-tolyl-indenyl)zirconium dimethyl, and
phenylazandiyl-4-($\eta^5$-2-methylindenyl)-4'-($\eta^5$-2-methyl-7-m-tolylindenyl)zirconium dimethyl.

Particularly preferred pre-catalysts include:
4,4'-sulfandiyl-bis($\eta^5$-2-methylindenyl)zirconium dichloride,
4,4'-sulfandiyl-bis($\eta^5$-indenyl)zirconium dichloride,
4,4'-phenylazandiyl-bis($\eta^5$-2-methylindenyl)zirconium dichloride,
4,4'-phenylphosphindiyl-bis($\eta^5$-2-methylindenyl)zirconium dichloride,
4,4'-oxadiyl-bis($\eta^5$-1-phenylindenyl)zirconium dichloride,
4,4'-sulfandiyl-bis($\eta^5$-1-phenylindenyl)zirconium dichloride,
4,4'-phenylphosphindiyl-bis($\eta^5$-1-phenylindene)zirconium dichloride,
4,4'-phenylazandiyl-bis($\eta^5$-1-phenylindenyl)zirconium dichloride,
4,4'-oxadiyl-bis($\eta^5$-1-naphthylindenyl)zirconium dichloride,
4,4'-sulfandiyl-bis($\eta^5$-1-naphthylindenyl)zirconium dichloride,
4,4'-phenylphosphindiyl-bis($\eta^5$-1-naphthylindenyl)zirconium dichloride,
4,4'-sulfandiyl-bis($\eta^5$-2-methyl-1-phenylindenyl)zirconium dichloride,
4,4'-sulfandiyl-bis($\eta^5$-7-bromo-2-methylindenyl)zirconium dichloride,
4,4'-sulfandiyl-bis($\eta^5$-2,7-dimethylindenyl)zirconium dichloride,
4,4'-sulfandiyl-bis($\eta^5$-7-phenyl-2-methylindenyl)zirconium dichloride,
4,4'-sulfandiyl-bis($\eta^5$-2-methyl-7-p-tolyl-indenyl)zirconium dichloride,
4,4'-sulfandiyl-bis($\eta^5$-2-methyl-7-m-tolylindenyl)zirconium dichloride,
4,4'-sulfandiyl-bis[$\eta^5$-2-methyl-7-(4-tert-butylphenyl)indenyl]zirconium dichloride,
4,4'-sulfandiyl-bis($\eta^5$-7-mesityl-2-methylindenyl)zirconium dichloride,
4,4'-sulfandiyl-bis[$\eta^5$-2-methyl-7-(5-methyl-thien-2-yl)indenyl]zirconium dichloride,
4,4'-sulfandiyl-bis[$\eta^5$-2-methyl-7-(5-methyl-furan-2-yl)indenyl]zirconium dichloride,
4,4'-sulfandiyl-bis[$\eta^5$-2-methyl-7-(2-benzothiopheneyl)indenyl]zirconium dichloride,
4,4'-sulfandiyl-bis[$\eta^5$-2-methyl-7-(2-benzofuranyl)indenyl]zirconium dichloride,
4,4'-sulfandiyl-bis[$\eta^5$-2-methyl-7-(4-fluorophenyl)indenyl]zirconium dichloride, and
4,4'-sulfandiyl-bis[$\eta^5$-2-methyl-7-(3-trifluoromethylphenyl)indenyl]zirconium dichloride.

Another list of particularly preferred compounds includes all of the above compounds where "zirconium" is replaced with "hafnium". Another list of particularly preferred compounds includes all of the above compounds where "zirconium" is replaced with "titanium". Another list of particularly preferred compounds includes all of the above compounds where "dichloride" is replaced with "dimethyl". Another list of particularly preferred compounds includes all of the above compounds where "zirconium" is replaced with "hafnium" and "dichloride" is replaced with "dimethyl". Another list of particularly preferred compounds includes all of the above compounds where "zirconium" is replaced with "titanium" and "dichloride" is replaced with "dimethyl".

Preferred compounds include:
4,4'-sulfandiyl-bis($\eta^5$-2,7-dimethylindenyl)zirconium dichloride,
4,4'-sulfandiyl-bis($\eta^5$-7-phenyl-2-methylindenyl)zirconium dichloride,
4,4'-sulfandiyl-bis($\eta^5$-7-(p-tolyl)-2-methylindenyl)zirconium dichloride,
4,4'-sulfandiyl-bis($\eta^5$-7-(m-tolyl)-2-methylindenyl)zirconium dichloride,
4,4'-sulfandiyl-bis($\eta^5$-7-(4-t-butylphenyl)-2-methylindenyl)zirconium dichloride,
4,4'-sulfandiyl-bis($\eta^5$-7-mesityl-2-methylindenyl)zirconium dichloride,
4,4'-sulfandiyl-bis($\eta^5$-7-(5-methyl-2-thienyl)-2-methylindenyl)zirconium dichloride,
4,4'-sulfandiyl-bis($\eta^5$-7-(5-methyl-2-furyl)-2-methylindenyl)zirconium dichloride,
4,4'-sulfandiyl-bis($\eta^5$-7-(2-benzothienyl)-2-methylindenyl)zirconium dichloride,
4,4'-sulfandiyl-bis($\eta^5$-7-(2-benzofuryl)-2-methylindenyl)zirconium dichloride,
4,4'-sulfandiyl-bis($\eta^5$-7-(4-fluorophenyl)-2-methylindenyl)zirconium dichloride,
4,4'-sulfandiyl-bis($\eta^5$-7-(3-trifluoromethylphenyl)-2-methylindenyl)zirconium dichloride,
4,4'-sulfandiyl-bis($\eta^5$-7-(2,5-dimethylphenyl)-2-methylindenyl)zirconium dichloride,
4,4'-sulfandiyl-bis($\eta^5$-7-(4-biphenyl)-2-methylindenyl)zirconium dichloride,
4,4'-sulfandiyl-bis($\eta^5$-2,7-dimethylindenyl)zirconium dichloride,
4,4'-sulfandiyl-bis($\eta^5$-7-phenyl-2-methylindenyl)hafnium dichloride,
4,4'-sulfandiyl-bis($\eta^5$-7-(p-tolyl)-2-methylindenyl)hafnium dichloride,
4,4'-sulfandiyl-bis($\eta^5$-7-(m-tolyl)-2-methylindenyl)hafnium dichloride,
4,4'-sulfandiyl-bis($\eta^5$-7-(4-t-butylphenyl)-2-methylindenyl)hafnium dichloride,
4,4'-sulfandiyl-bis($\eta^5$-7-mesityl-2-methylindenyl)hafnium dichloride,
4,4'-sulfandiyl-bis($\eta^5$-7-(5-methyl-2-thienyl)-2-methylindenyl)hafnium dichloride,
4,4'-sulfandiyl-bis($\eta^5$-7-(-methyl-2-furyl)-2-methylindenyl)hafnium dichloride,
4,4'-sulfandiyl-bis($\eta^5$-7-(2-benzothienyl)-2-methylindenyl)hafnium dichloride,
4,4'-sulfandiyl-bis($\eta^5$-7-(2-benzofuryl)-2-methylindenyl)hafnium dichloride,
4,4'-sulfandiyl-bis($\eta^5$-7-(4-fluorophenyl)-2-methylindenyl)hafnium dichloride,
4,4'-sulfandiyl-bis($\eta^5$-7-(3-trifluoromethylphenyl)-2-methylindenyl)hafnium dichloride,
4,4'-sulfandiyl-bis($\eta^5$-7-(2,5-dimethylphenyl)-2-methylindenyl)hafnium dichloride,
4,4'-sulfandiyl-bis($\eta^5$-7-(4-biphenyl)-2-methylindenyl)hafnium dichloride, 4,4'-tolylazandiyl-bis($\eta^5$-2,7-dimethylindenyl)zirconium dichloride,
4,4'-tolylazandiyl-bis($\eta^5$-7-p-tolyl)-2-methylindenyl)zirconium dichloride,
4,4'-tolylazandiyl-bis($\eta^5$-2,7-dimethylindenyl)hafnium dichloride,
4,4'-tolylazandiyl-bis($\eta^5$-7-(p-tolyl)-2-methylindenyl) hafnium dichloride,
4,4'-oxadiyl-bis($\eta^5$-2,7-dimethylindenyl)zirconium dichloride,
4,4'-oxadiyl-bis($\eta^5$-7-(-tolyl)-2-methylindenyl)zirconium dichloride,
4,4'-oxadiyl-bis($\eta^5$-7-(4-dimethylaminophenyl)-2-methylindenyl)zirconium dichloride,
4,4'-oxadiyl-bis($\eta^5$-7-(2-benzofuryl)-2-methylindenyl)zirconium dichloride,
4,4'-oxadiyl-bis($\eta^5$-7-(2-benzothienyl)-2-methylindenyl) zirconium dichloride,
4,4'-oxadiyl-bis($\eta^5$-2,7-dimethylindenyl)hafnium dichloride,
4,4'-oxadiyl-bis($\eta^5$-7-(p-tolyl)-2-methylindenyl)hafnium dichloride,
4,4'-oxadiyl-bis($\eta^5$-7-(4-dimethylaminophenyl)-2-methylindenyl)hafnium dichloride,
4,4'-oxadiyl-bis($\eta^5$-7-(2-benzofuryl)-2-methylindenyl) hafnium dichloride, and
4,4'-oxadiyl-bis($\eta^5$-7-(2-benzothienyl)-2-methylindenyl) hafnium dichloride.

EXPERIMENTAL

Synthesis of Pre-Catalysts

All manipulations with air and moisture sensitive compounds were performed either in an atmosphere of thoroughly purified argon using a standard Schlenk technique or in a controlled atmosphere Glove Box (Vacuum Atmospheres Co.). Tetrahydrofuran (THF, Merck=Merck KGBA, Darmstadt, Germany) and diethyl ether (Merck) for synthesis were purified by distillation over LiAlH$_4$, and stored over sodium benzophenone ketyl under an inert atmosphere; prior to use, the solvents were distilled from the benzophenone ketyl. Hydrocarbon solvents such as benzene (Merck), toluene (Merck) and hexanes (Merck) were typically distilled over CaH$_2$, and were stored over Na/K alloy under an inert atmosphere; prior to use, the solvents were distilled from the Na/K alloy. Methylene chloride (and CCl$_2$D$_2$ for NMR measurements) was distilled and stored over CaH$_2$ under an inert atmosphere; prior to use, the solvent was distilled from the CaH$_2$. Chloroform-d was distilled over P$_4$O$_{10}$ and stored over molecular sieves (3 Å). Anhydrous ethanol (Merck), methanol (Merck), methyl-tert-butyl ether (Acros=Acros Organics), acetone (Merck), chloroform (Merck), dimethylsulfoxide (DMSO, Acros), hexanes (Acros), CCl$_4$(Acros), acetic acid (Acros), 50% H$_2$O$_2$(Merck), para-toluenesulfonic acid (Aldrich=Aldrich Chemical Co.), anhydrous ZrCl$_4$(Aldrich), ZrCl$_4$(THF)$_2$(Aldrich), CuBr (Acros), 2.0 M "BuLi in hexanes (Chemetall=Chemetall Chemical Products), 2.0 M 4-tert-butylbromophenylmagnesium bromide in ether (Aldrich), 2.0M methylzinc chloride in THF (Aldrich), 1.0 M phenylmagnesium bromide in THF (Aldrich), 1.0 M p-tolylmagnesium bromide in THF (Aldrich), 1.0 M m-tolylmagnesium chloride in THF (Aldrich), mesityl bromide (Acros), bromobenzene (Acros), 1-bromonaphthalene (Acros), 2-methylthiophene (Fluka Chemical Corp.=Fluka), 2-methylfuran (Aldrich), 2-methyl-4-bromoaniline (Aldrich), Et$_3$SnCl (Alfa Aesar), anhydrous K$_2$CO$_3$(Merck), Pd(OAc)$_2$ (Strem=Strem Chemical Co., OAc=acetate), Pd(dba)$_2$(Aldrich, dba=dibenzylideneacetone), 0.5 M ZnCl$_2$ in THF (Aldrich), Pd(P$^2$Bu$_3$)$_2$(Strem), PhPCl$_2$(Aldrich), aniline (Acros), potassium tert-butoxide (Acros), tris(tert-butyl)phosphine (Aldrich), N-{2'-[di(tert-butyl)phosphino][1,1'-biphenyl]-2-yl}-N,N-dimethylamine (Strem), NaBH$_4$ (Acros), anhydrous powdered AlCl$_3$(Merck), triisopropylborate (Alfa Aesar), K$_3$PO$_4$(Fluka), P$_4$O$_{10}$(Merck), N-bromosuccinimide (Acros), methyl iodide (Acros), benzoyl peroxide (Aldrich), ethylene glycol (Merck), diethyl 2-methylmalonate (Acros), diethyl malonate (Acros), 2-bromobenzyl bromide (Aldrich), 2,5-dimethylphenylmagnesium bromide, 0.5 M in THF (Aldrich), 4-biphenylmagnesium bromide, 0.5 M in THF (Aldrich), Silica Gel 60, 40-63 µm (Merck and Fluka) were used as obtained. Celite 503(Fluka) was dried in vacuum at 180° C. (PhSO$_2$)S was synthesized from SCl$_2$ and sodium salt of benzenesulphonic acid in toluene [Inaoka, S.; Collard, D. M. *J. Mater. Chem*, 1999, 9, 1719.]. Mesitylmagnesium bromide in THF was obtained from magnesium turnings (Aldrich) and mesityl bromide in THF at reflux. Sulfur dichloride (Aldrich) and thionyl chloride (Merck) were distilled before use. Trichloromethylsilane (Merck) was distilled in the presence of quinoline in argon to eliminate HCl.

Analytical and semi-preparative liquid chromatography was performed using Waters Delta 600 HPLC system including 996 Photodiode Array Detector, Nova-Pack C18or HR Silica (60 A, 6 µm, 3.9 and 19×300 mm) and Symmetry C18 (5 µm, 4.6×250 mm) columns. MPHPLC was performed using MPHPLC glass columns and fittings (Ace Glass), PD5130 pump drive equipped with J1 gear-well pump head (Heidolph), 996 Photodiode Array Detector and Fraction Collector II (Waters Corp.). $^1$H, $^{13}$C, and $^{31}$P spectra were recorded with a Brucker DPX-300 for 1-10% solutions in deuterated solvents. Chemical shifts for $^1$H and $^{13}$C were measured relatively to tetramethylsilane (TMS). Chemical shifts for $^{31}$P were measured relatively to H$_3$PO$_4$. In $^1$H NMR spectra, the assignment was made on the evidence of double resonance and Nuclear Overhauser Effect (NOE) experiments. C, H microanalyses were done using CHN—O-Rapid analyzer (Heraecus Ltd., Banau, Germany).

Example 1

Synthesis of 4,4'-sulfandiyl-bis($\eta^5$-2-methylindenyl) zirconium dichloride (S2)

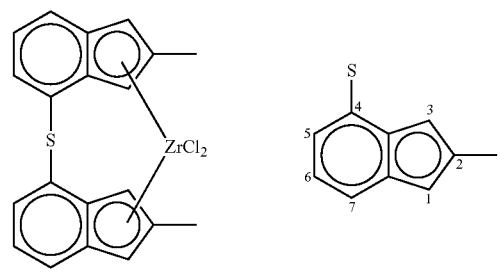

4-bromo-2-methyl-1-indanone via 3-(2-bromophenyl)-2-methylpropionyl chloride via 3-(2-bromophenyl)-2-methylpropionic acid

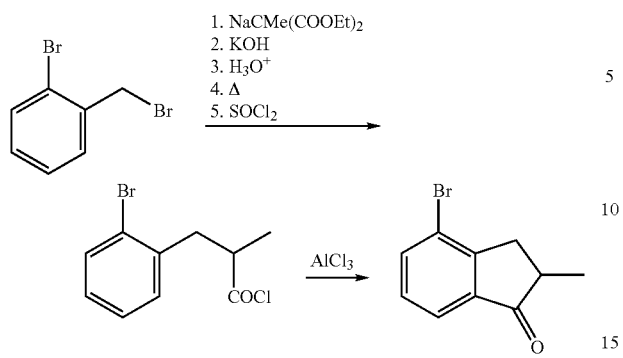

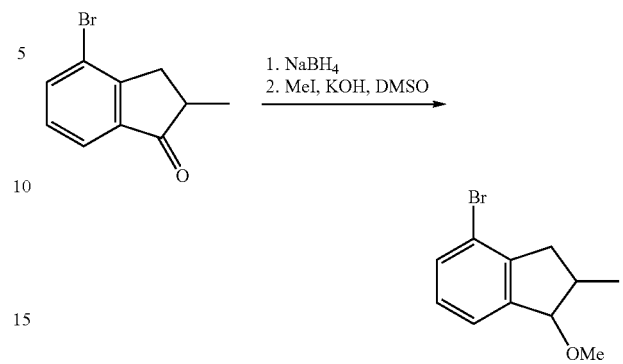

In a three-necked round-bottom 2000 ml flask equipped with a reflux condenser, a pressure-equalizing dropping funnel, and magnetic stirring bar, 20.5 g (0.89 mol) of sodium metal was dissolved in 450 ml of dry ethanol. To the resulting solution, 155 g (0.89 mol) of diethyl 2-methylmalonate in 150 ml of dry ethanol was added dropwise within 15 min. This mixture was stirred for 15 min; then, 186 g (0.89 mol) of o-bromobenzyl bromide was added with vigorous stirring at such a rate, so that the reaction mixture was maintained at a gentle reflux. Additionally, this mixture was refluxed for 4 hours, then cooled to room temperature. A solution of 151 g of KOH in 400 ml of water was added. This mixture was refluxed for 3 hours to saponificate the ester formed. Ethanol and water were distilled off. To the residue, 500 ml of water and, then, 12 M HCl (to pH 1) were added. Crude 2-(2-bromophenyl)-2-methylmalonic acid precipitated, was separated, washed with 2×200 ml of cold water, and dried overnight on a watch glass. This crude, substituted methylmalonic acid was decarboxylated by heating for 2 hours at 160° C. to form crude 3-(2-bromophenyl)-2-methylpropionic acid (and $CO_2$ as a byproduct). The crude 3-(2-bromophenyl)-2-methylpropionic acid was used without further purification. A mixture of this acid and 160 ml of $SOCl_2$ was stirred for 24 hours at ambient temperature. Thionyl chloride was distilled off. The crude 3-(2-bromophenyl)-2-methylpropionyl chloride dissolved in 270 ml of $CH_2Cl_2$ was added dropwise with vigorous stirring to a suspension of 136 g (1.02 mol) of $AlCl_3$ in 1350 ml of $CH_2Cl_2$ for 1 hour at 0° C. Then, this mixture was refluxed for 3 hours, cooled to ambient temperature, and poured on 500 cm$^3$ of ice. The organic layer was separated. The aqueous layer was extracted with 3×300 ml of methyl-tert-butyl ether. The combined extract was dried over $K_2CO_3$ and evaporated to dryness. Fractional distillation gave 4-bromo-2-methyl-1-indanone, b.p. 131-134° C./2 mm Hg. Yield, 125.5 g (75%) of a colorless solid.

Anal. calc. for $C_{10}H_9BrO$: C, 53.36; H, 4.03. Found: C, 53.19; H, 3.98.

$^1$H NMR (300 MHz, $CDCl_3$): δ 7.76 (d, J=7.6 Hz, 1H, 7-H), 7.71 (d, J=7.6 Hz, 1H, 5-H), 7.28 (t, J=7.6 Hz, 1H, 6-H), 3.36 (dd, J=17.5 Hz, J=7.6 Hz, 1H, 3-H), 2.70-2.82 (m, 1H, 2-H), 2.67 (dd, J=17.5 Hz, J=3.8 Hz, 1H, 3'-H), 1.34 (d, J=7.3 Hz, 3H, 2-Me).

$^{13}$C NMR (75 MHz, $CDCl_3$): δ 208.3, 152.9, 138.2, 137.2, 129.0, 122.6, 122.0, 41.8, 35.7, 16.0.

4-Bromo-1-methoxy-2-methylindane

To a solution of 149.5 g (0.664 mol) of 4-bromo-2-methyl-1-indanone in 900 ml of THF-methanol (2:1, vol.), 37.6 g (0.995 mol) of $NaBH_4$ was added in small portions at vigorous stirring for 1.5 hours at 5° C. This mixture was stirred at room temperature for 12 hours and then added to 2 L of cold water. The hydrogenation product was extracted with 5×200 ml of dichloromethane, and the combined extract was evaporated to dryness. To 149 g (2.65 mol) of KOH in 420 ml of DMSO, 188 g (82.5 ml, 1.33 mol) of MeI, and a solution of crude 4-bromo-2-methylindan-1-ol in 220 ml of DMSO were added. This mixture was stirred for 2 hours at ambient temperature; then, 92.0 g (40.4 ml, 0.664 mol) of MeI was added, and the mixture was additionally stirred for 2 hours. The resulting mixture was added to 2.5 L of cold water. The crude product was extracted with 5×200 ml of dichloromethane. The combined extract was dried over $Na_2SO_4$ and, then, evaporated to dryness. Fractional distillation gave a mixture of two diastereomeric compounds, b.p. 108° C./3 mm Hg. Yield, 148.5 g (93%) of a colorless oil.

Anal. calc. for $C_{11}H_{13}BrO$: C, 54.79; H, 5.43. Found: C, 54.86; H, 5.40.

$^1$H NMR (300 MHz, $CDCl_3$): δ 7.41 (d, J=7.9 Hz, 1H, 5-H of cis-product), 7.40 (d, J=7.9 Hz, 1H, 5-H of trans-product), 7.31 (d, J=7.2 Hz, 1H, 7-H of cis-product), 7.29 (d, J=7.2 Hz, 1H, 7-H of trans-product), 7.08 (m, 1H, 6-H of cis-product), 7.07 (m, 1H, 6-H of trans-product), 4.57 (d, J=5.8 Hz, 1H, CHOMe of trans-product), 4.45 (d, J=4.2 Hz, 1H, CHOMe of cis-product), 3.45 (m, 3H, OMe of cis-product), 3.40 (m, 3H, OMe of trans-product), 2.40-3.30 (m, 6H, $CH_2$ and CHMe of cis-products), 1.18 (m, 3H, CHMe of cis-product), 1.11 (m, 3H, CHMe of trans-product).

$^{13}$C{$^1$H} NMR (75 MHz, $CDCl_3$): δ 144.6, 144.1, 143.7, 143.4, 131.3, 131.2, 128.2, 127.8, 124.1, 123.9, 120.4 (two resonances), 91.9, 86.6, 56.9, 56.5, 39.7, 39.5, 39.0, 37.9, 19.2, 13.4.

Bis(2-methyl-1H-inden-7-yl)sulfide

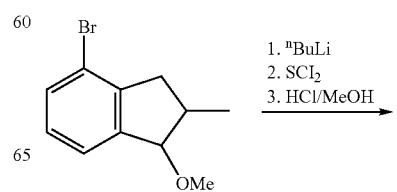

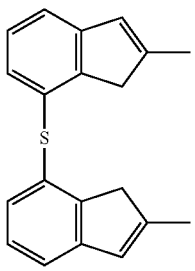

Under an argon atmosphere, to a solution of 47.6 g (177 mmol) of 4-bromo-1-methoxy-2-methylindane in 400 ml of THF, 70.7 ml of 2.5 M ⁿBuLi (177 mmol) in hexanes was added at vigorous stirring for 1 hour at −78° C. Then, a solution of 9.54 g (92.7 mmol) of $SCl_2$ in 40 ml of hexanes was added at this temperature. The reaction mixture was slowly warmed, and then 50 ml of a saturated aqueous solution of NaCl was added. The organic layer was separated; the aqueous layer was extracted with 2×25 ml of ether. The combined extract was evaporated to dryness. The yellowish oil of crude 1-methoxy-4-[1-methoxy-2-methyl-2,3-dihydro-1H-inden-4-yl)sulfanyl]2-2 methylindane was dried in vacuum. This methoxyindane was demethoxylated in a mixture of 200 ml of 16 M HCl and 200 ml of methanol for 8 hours at reflux. The product was extracted with 3×150 ml of $CH_2Cl_2$. The combined extract was washed with 2×100 ml of water, dried over $K_2CO_3$, and evaporated to dryness. The analytically pure product, bis(2-methyl-1H-inden-7-yl)sulfide, was isolated by flash chromatography on Silica Gel 60 (40-64 μm, d 50 mm, l 450 mm, eluant: hexanes-$CH_2Cl_2$=3:1). Yield, 12.8 g (50%) of a white solid.

Anal. calc. for $C_{20}H_{18}S$: C, 82.71; H, 6.25. Found: C, 82.57; H, 6.14.

$^1$H NMR (300 MHz, $CDCl_3$): δ 7.16 (d, J=2.1 Hz, 2H), 7.15 (d, J=6.7 Hz, 2H), 6.94 (dd, J=6.7 Hz, J=2.1 Hz, 2H), 6.49 (q, J=1.5 Hz, 2H, 3,3'-H), 3.24 (s, 4H, 1,1'-$CH_2$), 2.14 (d, J=1.5 Hz, 6H, 2,2'-Me).

$^{13}C\{^1H\}$ NMR (75 MHz, $CDCl_3$): δ 146.6, 146.5, 144.1, 129.0, 127.6, 127.2, 126.9, 126.3, 125.9, 118.9, 118.5, 42.5, 16.8, 16.7.

4,4'-sulfandiyl-bis(η$^5$-2-methylindenyl)zirconium dichloride (S2)

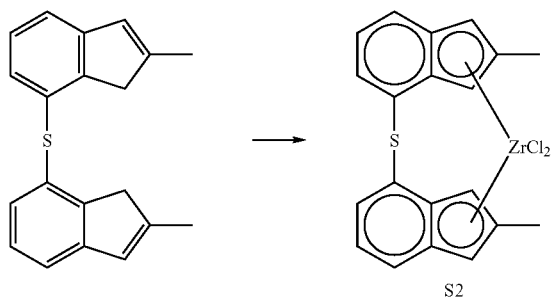

Under an argon atmosphere, to a solution of 8.00 g (27.6 mmol) of bis(2-methyl-1H-inden-7-yl)sulfide in 250 ml of toluene, 24.0 ml of 2.5 M (60.0 mmol) ⁿBuLi in hexanes was added at vigorous stirring at ambient temperature. This mixture was stirred for 9 hours; then, 35 ml of ether and 15.7 g (65.0 mmol) of triethyltin chloride were added. The mixture was stirred for 12 hours and then filtered through Celite 503. The filtrate was evaporated to ca. 150 ml, and 6.74 g (28.9 mmol) of $ZrCl_4$ was added. The suspension was stirred for 2 hours at ambient temperature and 10 hours at reflux. The solution was cooled to ambient temperature and filtered through glass frit (G4). The filtrate was evaporated to dryness, and 200 ml of hexanes was added to the residue. The orange precipitate was filtered off (50° C., glass frit G4), washed with 2×100 ml of hot (50° C.) hexanes, and dried in vacuum. This procedure gave 6.80 g of the product, 4,4'-sulfandiyl-bis (η$^5$-2-methylindenyl)zirconium dichloride. An additional amount of the product was obtained by low temperature (−30° C.) crystallization of the combined filtrate. Yield, 8.32 g (67%).

Anal. calc. for $C_{20}H_{16}Cl_2SZr$: C, 53.32; H, 3.58. Found: C, 53.49; H, 3.66.

$^1$H NMR (300 MHz, $CD_2Cl_2$): δ 7.67 (dd, J=6.9 Hz, J=1.0 Hz, 2H, 6,6'-H), 7.53 (dt, J=8.5 Hz, J=0.9 Hz, 2H, 4,4'-H), 7.18 (dd, J=8.5 Hz, J=6.9 Hz, 2H, 5,5'-H), 6.33 (m, 2H, 3,3'-H), 4.48 (m, 2H, 1,1'-H), 2.04 (s, 6H, 2,2'-Me).

Example 2

Synthesis of 4,4'-sulfandiyl-bis(η$^5$-indenyl)zirconium dichloride (S1)

4-Bromoindan-1-one via 3-(2-bromophenyl)propionyl chloride via 3-(2-bromophenyl)propionic acid

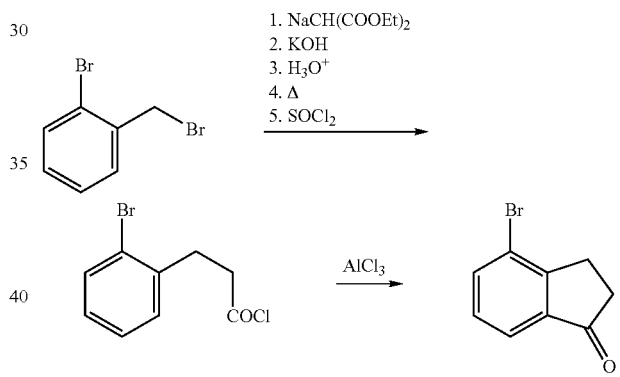

In a three-necked round-bottom 2000 ml flask equipped with a reflux condenser, a pressure-equalizing dropping funnel, and magnetic stirring bar, 26.4 g (1.15 mol) of sodium metal was dissolved in 850 ml of dry ethanol. To the resulting solution, 184 g (1.15 mol) of diethyl malonate was added dropwise within 15 min. This mixture was stirred for 15 min; then, added dropwise to a solution of 239 g (0.96 mol) of 2-bromobenzylbromide with vigorous stirring over 3 hours. Additionally, this mixture was refluxed for 3 hours, and then cooled to room temperature. To this mixture, a solution of 230 g of KOH in 600 ml of water was added. This mixture was refluxed for 3 hours to saponificate the ester formed. Ethanol was distilled off. To the residue, cold water was added to a volume equal to ca. 2000 cm$^3$. Then, 12 M HCl (to pH 1) was added. The substituted malonic acid precipitated, and was separated, washed with 2×150 ml of cold water, and dried overnight on watch glass. Crude 3-(2-bromophenyl)propionic acid was obtained after decarboxylation of this substituted methylmalonic acid by heating it in a round bottom flask for 1 hour at 130° C. The crude 3-(2-bromophenyl)propionic acid was used without further purification. A mixture of this acid and 174 ml of $SOCl_2$ in 1200 ml of dry dichloromethane was refluxed for 3 hours. Dichloromethane and thionyl chloride were distilled off. Fractional distillation gave 153 g of 3-(2-bromophenyl)propionyl chloride, b.p. 118-130° C./7 mm. This product dissolved in 250 ml of $CH_2Cl_2$, was added dropwise with vigorous stirring to a suspension of 90.7 g (0.68 mol) of $AlCl_3$ in 1200 ml of $CH_2Cl_2$ for 1 hour at 0° C. Then, this mixture was refluxed for 3 hours, cooled to ambient temperature, and poured on 600 cm³ of ice. The organic layer was separated. The aqueous layer was extracted with 3×200 ml of methyl-tert-butyl ether. The combined extract was dried over K2CO3 and evaporated to dryness. Fractional distillation using a hot condenser (no cooling water used) gave 4-bromoindan-1-one, b.p. 183° C./39 mm Hg. Yield 116 g (89%) of yellowish solid, m.p. 95° C.

Anal. calc. for C9H7BrO: C, 51.22; H, 3.34. Found: C, 51.30; H, 3.39.

1H NMR (300 MHz, CDCl3): δ 7.71 (dd, J=7.6 Hz, J=0.9 Hz, 1H, 5-H), 7.66 (m, 1H, 7-H), 7.24 (m, 1H, 6-H), 3.04 (m, 2H, 3-CH2), 2.69 (m, 2H, 2-CH2).

13C{1H} NMR (75 MHz, CDCl3): δ 205.8, 154.6, 139.0, 137.2, 129.0, 122.5, 122.2, 36.0, 26.9.

4-Bromo-1-methoxyindane

To a solution of 100 g (0.474 mol) of 4-bromo-1-indanone in 530 ml of THF-methanol (2:1, vol.), 26.8 g (0.709 mol) of $NaBH_4$ was added in small portions at vigorous stirring for 1.5 hours at 5° C. This mixture was stirred at room temperature for 12 hours and then added to 1 L of cold water. The hydrogenation product was extracted with 4×200 ml of dichloromethane, and the combined extract was evaporated to dryness. To 108 g (1.93 mol) of KOH in 700 ml of DMSO, 135 g (59.2 ml, 0.948 mol) MeI, and a solution of crude 4-bromoindan-1-ol in 300 ml of DMSO were added. This mixture was stirred for 2 hours at ambient temperature; then, 67.2 g (29.5 ml, 0.473 mol) of MeI was added, and the mixture was additionally stirred for 2 hours. The resulting mixture was added to 2 L of cold water. The crude product was extracted with 5×200 ml of dichloromethane. The combined extract was dried over $Na_2SO_4$ and, then, evaporated to dryness. Fractional distillation gave 4-bromo-1-methoxyindane, b.p. 94° C./2 mm Hg. Yield, 100 g (93%) of a colorless oil.

Anal. calc. for $C_{10}H_{11}BrO$: C, 52.89; H, 4.88. Found: C, 52.74; H, 4.81.

$^1$H NMR (300 MHz, CDCl$_3$): δ 4.88 (dd, J=6.7 Hz, J=4.3 Hz, CHOMe), 3.40 (s, 3H, OMe), 3.07 (ddd, J=16.6 Hz, J=8.5 Hz, J=5.9 Hz, 1H, CHH'CHH'CHOMe), 2.83 (ddd, J=16.6 Hz, J=8.6 Hz, J=5.3 Hz, 1H, CHH'CHH'CHOMe), 2.35 (m, 1H, CHH'CHOMe), 2.09 (m, 1H, CHH'CHOMe).

$^{13}$C{$^1$H} NMR (75 MHz, CDCl$_3$): δ 144.4, 144.2, 131.4, 128.1, 123.8, 120.2, 85.1, 56.1, 31.6, 30.9.

Bis(1H-inden-7-yl)sulfide

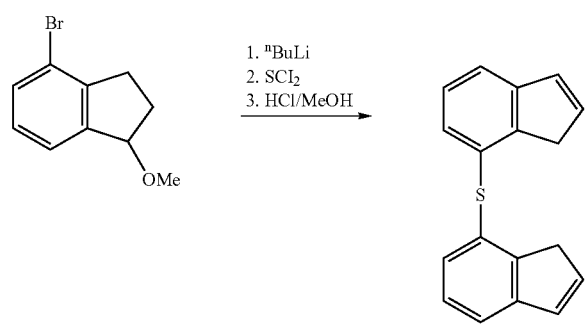

Under an argon atmosphere, following the procedure described for bis(2-methyl-1H-inden-7-yl)sulfide, 35.9 g (158 mmol) of 4-bromo-1-methoxyindane in 250 ml of THF, 63.2 ml of 2.5 M "BuLi (158 mmol) in hexanes, and 8.53 g (82.8 mmol) of $SCl_2$ in 20 ml of hexanes gave crude 1-methoxy-4-[(1-methoxy-2,3-dihydro-1H-inden-4-yl)sulfanyl]indane, which was demethoxylated in a mixture of 150 ml of 16 M HCl and 150 ml of methanol for 10 hours at reflux. The product was isolated by flash chromatography on Silica Gel 60 (40-63 μm, d 65 mm, 1 400 mm, eluant:hexanes-$CH_2Cl_2$=3:1). Yield, 14.6 g (71%).

Anal. calc. for $C_{18}H_{14}S$: C, 82.40; H, 5.38. Found: C, 82.49; H, 5.43.

$^1$H NMR (300 MHz, CDCl$_3$): δ7.64 (dd, J=7.6 Hz, J=0.8 Hz, 2H, 4,4'-H), 7.51 (t, J=7.6 Hz, 2H, 5,5'-H), 7.38 (dd, J=7.6 Hz, J=0.8 Hz, 6,6'-H), 7.20 (dt, J=5.6 Hz, J=1.9 Hz, 2H, 3,3'-H), 6.87 (dt, J=5.6 Hz, J=1.9 Hz, 2H, 2,2'-H), 3.64 (t, J=1.9 Hz, 1,1'-CH$_2$).

$^{13}$C{$^1$H} NMR (75 MHz, CDCl$_3$): δ 145.4, 144.6, 134.6, 131.8, 129.6, 127.4, 127.3, 120.1, 38.9.

4,4'-sulfandiyl-bis($\eta^5$-indenyl)zirconium dichloride (S1)

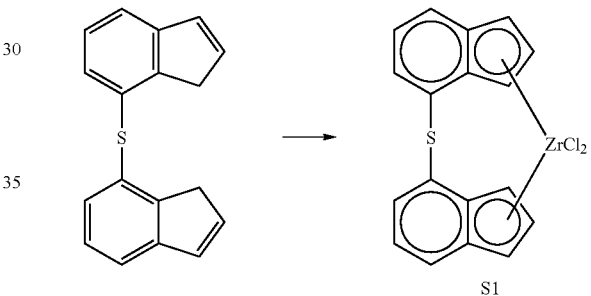

Under an argon atmosphere, to a solution of 7.29 g (27.8 mmol) of bis(1H-inden-7-yl)sulfide in 250 ml of toluene, 25.0 ml of 2.5 M (62.5 mmol) "BuLi in hexanes was added at vigorous stirring. This solution was stirred for 4 hours; then, 15.7 g (65.0 mmol) of triethyltin chloride was added. This mixture was stirred overnight and then filtered through Celite 503. The filtrate was evaporated to ca. 250 ml; and 6.74 g (28.9 mmol) of $ZrCl_4$ was added. This mixture was stirred for 1 hour at room temperature, then 7 hours at 100° C. and filtered through glass frit (G4) at 80-90° C. Crystals precipitated from the filtrate at ambient temperature, were separated, washed with cold toluene, and dried in vacuum. The filtrate was evaporated to ca. 70 ml. An additional amount of the crystalline product was obtained from this filtrate at 5° C. Yield, 6.11 g (52%).

Anal. calc. for $C_{18}H_{12}Cl_2SZr$: C, 51.17; H, 2.86. Found: C, 51.32; H, 2.93.

$^1$H NMR (300 MHz, CD$_2$Cl$_2$): δ 7.78 (dd, J=7.1 Hz, J=0.9 Hz, 2H, 5,5'-H), 7.66 (dt, J=8.4 Hz, J=0.9 Hz, 2H, 7,7'-H), 7.28 (dd, J=8.4 Hz, J=7.1 Hz, 2H, 6,6'-H), 6.75 (t, J=3.7 Hz, 2H, 1,1'-H), 6.57 (dd, J=3.7 Hz, J=2.3 Hz, 2H, 2,2'-H), 4.80 (m, 2H, 3,3'-H).

$^{13}$C{$^1$H} NMR (75 MHz, CD$_2$Cl$_2$): δ 136.1, 130.3, 129.8, 129.4, 127.1, 125.0, 120.8, 111.2, 102.7.

Example 3

Synthesis of 4,4'-phenylazandiyl-bis($\eta^5$-2-methylindenyl)zirconium dichloride (N2)

N,N-Bis(2-methyl-1H-inden-7-yl)-N-phenylamine

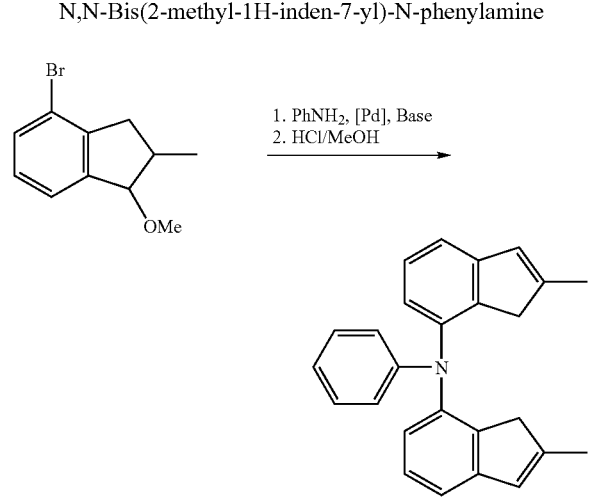

Under an argon atmosphere, a mixture of 2.79 g (30 mmol) of aniline, 14.5 g (60 mmol) of 4-bromo-1-methoxy-2-methylindane, 20.2 g (180 mmol) of $^t$BuOK, 30 ml of 0.2 M (6.0 mmol) solution of P$^t$Bu$_3$ in toluene, and 180 ml toluene, 0.67 g (3.0 mmol) of Pd(OAc)$_2$ was added. This mixture was stirred for 8 hours at 100° C. Then, this mixture was washed with 600 ml of water, and organic layer was separated. The aqueous layer was extracted with 3×150 ml of methyl-tert-butyl ether. To the combined extract, 250 ml of methanol and 150 ml of 10 M HCl were added; and the resulting mixture was refluxed for 7 hours. Sodium bicarbonate (ca. 130 g) was added in small portions until carbon dioxide evolved. The product, N,N-bis(2-methyl-1H-inden-7-yl)-N-phenylamine, was isolated by flash chromatography on Silica Gel 60 (40-63 μm, d 50 mm, l 400 mm, eluant:hexanes-dichloromethane=1:1, vol.) Yield, 7.84 g (80%) of a yellowish oil.

Anal. calc. for C$_{26}$H$_{23}$N: C, 89.36; H, 6.63. Found: C, 89.21; H, 6.55.

$^1$H NMR (300 MHz, CDCl$_3$): δ 7.10-7.18 (m, 4H, 5,5', 6,6'-H in indenyl), 6.99-7.04 (m, 2H, 2,6-H in Ph), 6.85-6.90 (m, 3H, 3,4,6-H in Ph), 6.84 (d, J=7.9 Hz, 2H, 4,4'-H in indenyl), 6.40 (m, 2H, 3,3'-H in indenyl), 2.71 (br.s, 4H, 1,1'-CH$_2$ in indenyl), 1.98 (s, 6H, 2,2'-Me in indenyl).

$^{13}$C{$^1$H} NMR (75 MHz, CDCl$_3$): δ 147.6, 147.3, 146.1, 141.9, 137.4, 128.7, 127.6, 126.7, 121.7, 121.2, 120.8, 116.0, 41.7, 16.7.

Synthesis of 4,4'-phenylazandiyl-bis($\eta^5$-2-methylindenyl)zirconium dichloride (N2)

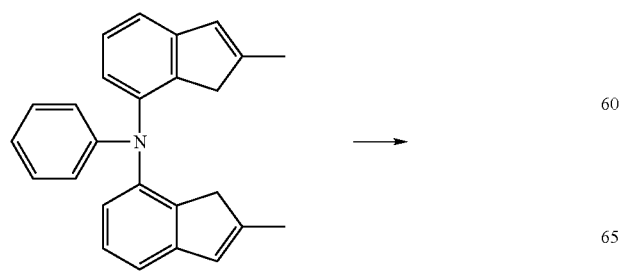

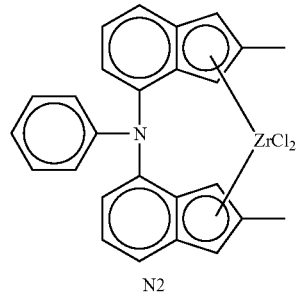

Under an argon atmosphere, to a solution of 7.79 g (22.3 mmol) of N,N-bis(2-methyl-1H-inden-7-yl)-N-phenylamine in a mixture of 200 ml of toluene and 40 ml of ether, 19.2 ml of 2.5 M (48.0 mmol) $^n$BuLi in hexanes was added by syringe at ambient temperature. This mixture was stirred for one day; then, 14.5 g (60.0 mmol) of Et$_3$SnCl was added. The resulting mixture was stirred for 24 hours and, then, evaporated to a volume ca. 150 ml. This mixture was filtered through Celite 503. To the filtrate 5.20 g (22.3 mmol) of ZrCl$_4$ was added. The resulting mixture was refluxed for 12 hours. Crystals that precipitated at room temperature were collected, washed with 20 ml of cold toluene, and dried in vacuum. Yield, 5.41 g (48%) of an orange crystalline solid.

Anal. calc. for C$_{26}$H$_{21}$Cl$_2$NZr: C, 61.28; H, 4.15. Found: C, 61.37; H, 4.22.

$^1$H NMR (300 MHz, CD$_2$Cl$_2$): δ 7.30-7.35 (m, 5H, Ph), 7.23 (dd, J=7.4 Hz, J=1.5 Hz, 2H, 5,5'-H in indenyl), 7.20 (t, J=7.4 Hz, 2H, 6,6'-H in indenyl), 7.09 (m, 2H, 7,7'-H in indenyl), 6.32 (dd, J=2.4 Hz, J=0.6 Hz, 2H, 1,1'-H in indenyl), 4.53 (d, J=2.4 Hz, 2H, 3,3'-H in indenyl), 2.06 (s, 6H, 2,2'-Me in indenyl).

$^{13}$C{$^1$H} NMR (75 MHz, CD$_2$Cl$_2$): δ 149.2, 145.8, 142.1, 132.3, 131.1, 128.8, 125.0, 123.1, 121.2, 120.7, 118.4, 112.5, 107.3, 103.0, 18.0.

The X-ray crystal structure of this compound was determined, and its molecular structure is represented in FIG. 1.

Example 4

Synthesis of 4,4'-phenylphosphindiyl-bis($\eta^5$-2-methylindenyl)zirconium dichloride (P2)

Bis(1-methoxy-2-methyl-2,3-dihydro-1H-inden-4-yl)(phenyl)phosphine

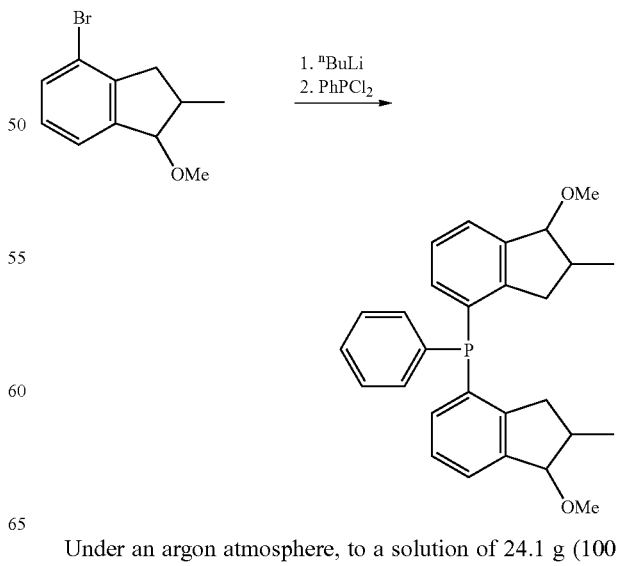

Under an argon atmosphere, to a solution of 24.1 g (100 mmol) of 4-bromo-1-methoxy-2-methylindane in 300 ml of THF, 61.0 ml of 1.64 M "BuLi (100 mmol) in hexanes was added at vigorous stirring for 1 hour at −78° C. To this mixture, a solution of 13.6 ml (17.9 g, 50 mmol) of PhPCl$_2$ in 35 ml of THF was added. Then, this mixture was warmed to ambient temperature, and 50 ml of a saturated aqueous solution of NaCl was added. The organic layer was separated. The aqueous layer was extracted with 2×25 ml of ether. The combined extract was evaporated to dryness. The yellowish oil obtained was dried in vacuum (0.01 mm Hg) at 40° C. Yield, 21.3 g (99%) of crude product, bis(1-methoxy-2-methyl-2,3-dihydro-1H-inden-4-yl)(phenyl)phosphine, which was further used without an additional purification.

Anal. calc. for C$_{28}$H$_{31}$O$_2$P: C, 78.12; H, 7.26. Found: C, 78.38; H, 7.40.

$^{31}$P {$^1$H} NMR (121 MHz, CDCl$_3$): δ −58.47, −58.51, −58.64, −58.78.

Bis(2-methyl-1H-inden-7-yl)(phenyl)phosphine

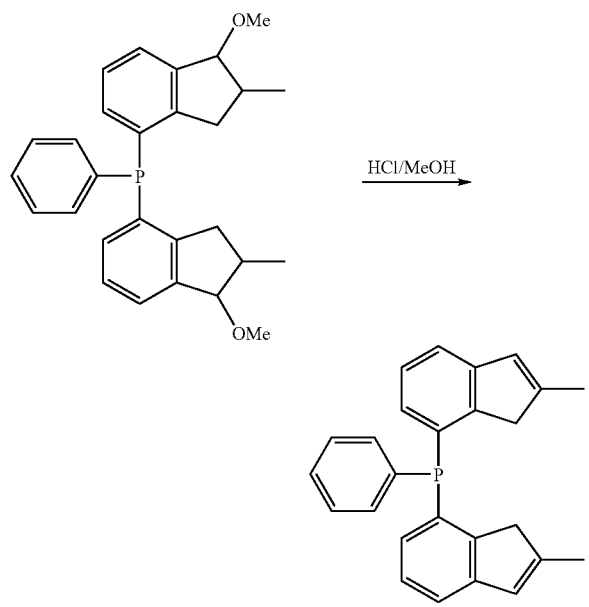

A mixture of 21.3 g (49.5 mmol) of crude bis(1-methoxy-2-methyl-2,3-dihydro-1H-inden-4-yl)(phenyl)phosphine, 100 ml of 16 M HCl, and 150 ml of methanol was refluxed for 5 hours. This mixture was cooled to ambient temperature, and 100 ml of water was added. The white precipitate that formed was filtered off and dried in vacuum. Yield, 15.0 g (82%) of a white solid.

Anal. calc. for C$_{26}$H$_{23}$P: C, 85.22; H, 6.33. Found: C, 85.34; H, 6.20.

$^1$H NMR (300 MHz, CDCl$_3$): δ 7.31-7.36 (m, 5H, 6,6'-H in indenyl and 3,4,5-H in Ph), 7.25 (d, J=7.3 Hz, 2,6-H in Ph), 7.14 (t, J=7.5 Hz, 5,5'-H in indenyl), 6.64 (ddd, J=7.5 Hz, J=5.2 Hz, J=0.8 Hz, 2H, 4,4'-H in indenyl), 6.50 (m, 2H, 3,3'-H), 3.23 (s, 4H, 1,1'-CH$_2$), 2.10 (d, J=0.8 Hz, 6H, 2,2'-Me).

$^{13}$C{$^1$H} NMR (75 MHz, CDCl$_3$): δ 148.0 (d, J=25.9 Hz), 146.6, 145.6 (d, J=7.6 Hz), 135.1 (d, J=9.2 Hz), 134.0 (d, J=19.8 Hz), 130.2 (d, J=10.7 Hz), 128.6 (d, J=16.8 Hz), 128.5, 127.5, 126.8, 126.7, 120.2, 42.8 (d, J=10.7 Hz), 16.7.

$^{31}$P{$^1$H} NMR (121 MHz, CDCl$_3$): δ −25.3.

Synthesis of 4,4'-phenylphosphindiyl-bis(η$^5$-2-methylindenyl)zirconium dichloride (P2)

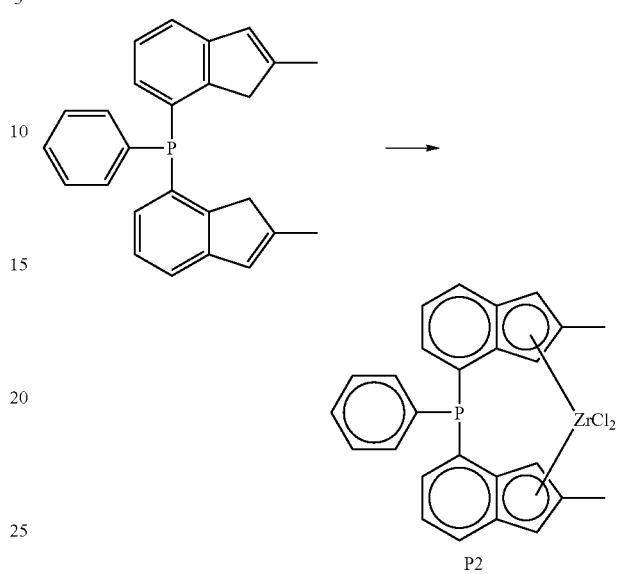

P2

Under an argon atmosphere, to a solution of 11.1 g (30.3 mmol) of bis(2-methyl-1H-inden-7-yl)(phenyl)phosphine in 200 ml of toluene, 24.2 ml of 2.5 M (60.6 mmol) "BuLi in hexanes was added over 1 hour with vigorous stirring. The suspension formed was stirred for 1.5 hours; and, then, 10 ml of ether and 15.0 g (62.2 mmol) of triethyltin chloride were added. The resulting mixture was stirred for 1 hour, evaporated to ca. 60 ml, and refluxed for an additional 2 hours. Then, 100 ml of toluene was added, and the resulting mixture was filtered through Celite 503. To the filtrate, 7.00 g (30.0 mmol) of ZrCl$_4$ was added. This mixture was stirred for 24 hours at ambient temperature, refluxed for 10 hours, cooled to ambient temperature, and then filtered through a glass frit (G4). The precipitate was washed with 2×40 ml of toluene. This procedure gave 6.02 g of yellow crystalline product, 4,4'-phenylphosphindiyl-bis(η$^5$-2-methylindenyl)zirconium dichloride. An additional portion of the product was obtained by crystallization from the filtrate at −30° C. Yield, 8.19 g (51%).

Anal. calc. for C$_{26}$H$_{21}$Cl$_2$PZr: C, 59.31; H, 4.02. Found: C, 59.48; H, 4.11.

$^1$H NMR (300 MHz, CD$_2$Cl$_2$): δ 8.07 (ddd, J$_{PH}$=14.9 Hz, J=6.8 Hz, J=1.1 Hz, 1H, 4-H in PPh), 6.75 (m, 1H, 5'-H in indenyl), 7.54-7.60 (m, 2H, 2,6-H in PhP), 7.50 (m, 1H, 5'-H in indenyl), 7.41-7.46 (m, 3H, 6'-H in indenyl and 3,5-H in PhP), 7.25 (ddd, J$_{PH}$=8.4 Hz, J=6.7 Hz, J=1.5 Hz, 1H, 7-H in indenyl), 7.10 (ddd, ddd, J$_{PH}$=7.0 Hz, J=4.2 Hz, J=1.0 Hz, 1H, 6'-H in indenyl), 7.03 (ddd, J$_{PH}$=8.4 Hz, J=6.9 Hz, J=1.5 Hz, 1H, 7'-H in indenyl), 6.36 (m, 1H, 1-H in indenyl), 6.34 (m, 1H, 1'-H in indenyl), 4.38 (m, 1H, 3-H), 4.13 (m, 1H, 3'-H), 2.05 (s, 3H, 2-Me in indenyl), 1.98 (s, 3H, 2'-Me in indenyl).

$^{31}$P{$^1$H} NMR (121 MHz, CD$_2$Cl$_2$): δ −9.0.

Figure 2:
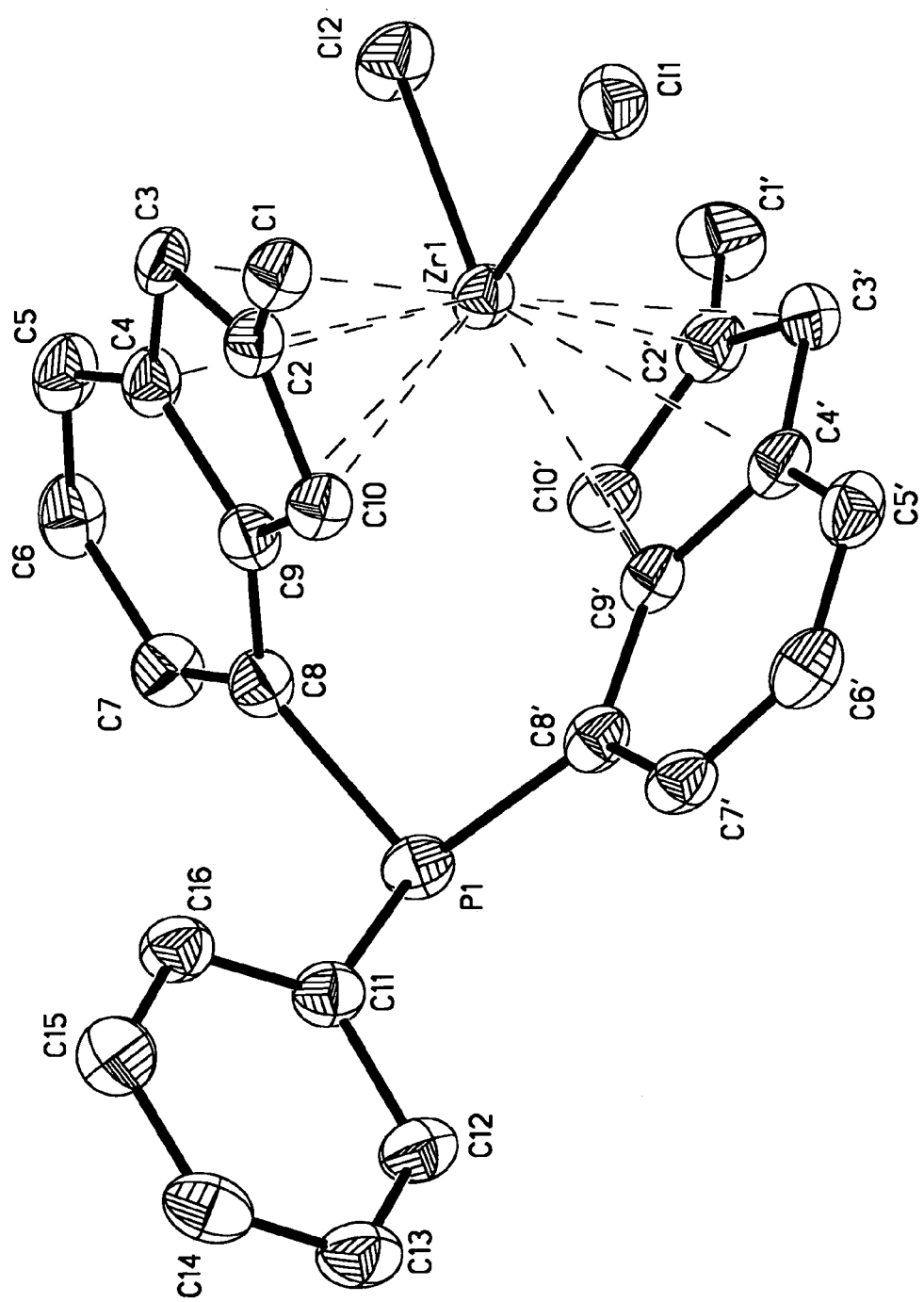
FIG. 2 is a drawing of 4,4'-phenylphosphindiyl-bis($\eta^5$-2-methylindenyl)zirconium dichloride (P2)

The X-ray crystal structure of this compound was determined, and its molecular structure is represented in FIG. 2.

Example 5

Synthesis of 4,4'-oxadiyl-bis($\eta^5$-1-phenylindenyl) zirconium dichloride (O3)

4-Bromo-1-methoxy-1-phenylindane

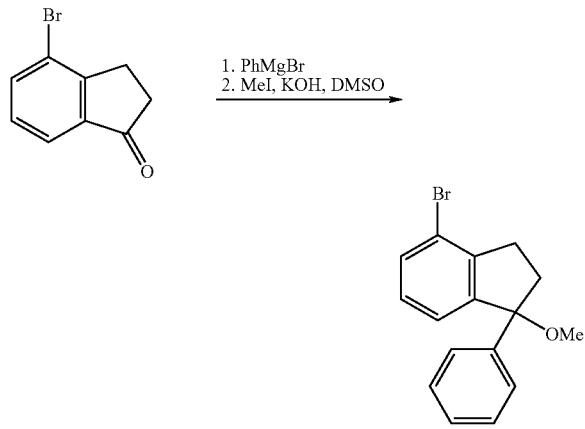

Under an argon atmosphere, to a solution of PhMgBr obtained from 7.60 g (0.31 mol) of Mg and 50.0 g (0.32 mol) of PhBr in 200 ml of THF, a solution of 43.9 g (0.21 mol) of 4-bromo-1-indanone in 400 ml of THF was added dropwise with vigorous stirring at −10° C. This mixture was additionally stirred overnight at ambient temperature. Then, 300 ml of ether was added, the resulting mixture was cooled to 0° C., and 200 ml of cold water was added. The organic layer was separated, and aqueous layer was extracted with 5×200 ml of ether. The combined extract was evaporated to dryness. To 47.5 g (0.85 mol) of KOH in 425 ml of DMSO, 26.0 ml (59.1 g, 0.42 mol) of MeI, and, then, the above obtained crude alcohol in 200 ml of DMSO were added with vigorous stirring at 10° C. The reaction mixture was stirred for 2 hours at ambient temperature; then, 26.0 ml (59.1 g, 0.42 mol) of MeI was added, and the reaction mixture was additionally stirred for 2 hours. The resulting mixture was added to 2 L of cold water. The crude product was extracted with 5×200 ml of dichloromethane. The combined extract was dried over Na$_2$SO$_4$ and, then, evaporated to dryness. The product, 4-bromo-1-methoxy-1-phenylindane, was isolated by flash chromatography on Silica Gel 60 (40-63 μm, d 55 mm, l 400 mm, eluant:hexanes:dichloromethane, 1:1, vol.). Yield, 47.0 g (75%) of a yellowish oil.

Anal. calc. for C$_{16}$H$_{15}$BrO: C, 63.38; H, 4.99. Found: C, 63.47; H, 5.06.

$^1$H NMR (300 MHz, C$_6$D$_6$): δ 7.31-7.35 (m, 2H, 2,6-H in Ph), 7.30 (dd, J=7.8 Hz, J=1.0 Hz, 1H, 5-H in C$_6$H$_3$), 7.14-7.19 (m, 2H, 3,5-H in Ph), 7.06-7.21 (m, 1H, 4-H in Ph), 6.89 (m, 1H, 7-H in C$_6$H$_3$), 6.70 (m, 1H, 6-H in C$_6$H$_3$), 3.04 (m, 1H, CHH'CHH'CPh), 2.87 (s, 3H, OMe), 2.80 (ddd, J=16.6 Hz, J=8.8 Hz, J=3.2 Hz, 1H, CHH'CHH'CPh), 2.39 (ddd, J=13.7 Hz, J=8.1 Hz, J=3.2 Hz, 1H, CHH'CHH'CPh), 2.07 (ddd, J=13.7 Hz, J=8.8 Hz, J=7.6 Hz, 1H, CHH'CHH'CPh).

$^{13}$C{$^1$H} NMR (75 MHz, C$_6$D$_6$): δ 146.3, 146.1, 144.7, 131.7, 128.5, 128.1, 127.2, 126.6, 125.3, 120.9, 91.9, 51.4, 41.5, 32.2.

7-Bromo-3-phenyl-1H-indene

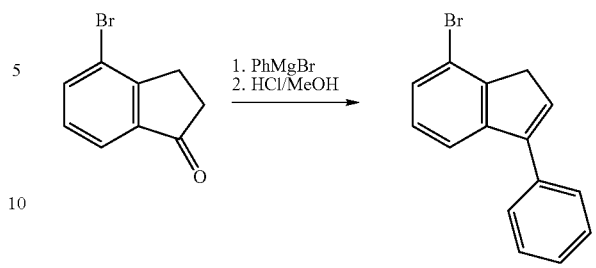

Under an argon atmosphere, to a solution of PhMgBr in THF [obtained from 7.60 g (0.312 mol) of magnesium turnings, 50.0 g (0.318 mmol) of bromobenzene, and 200 ml of THF], a solution of 43.9 g (0.208 mol) of 4-bromoindan-1-one in 400 ml of THF was added dropwise with vigorous stirring at −10° C. This mixture was stirred overnight at room temperature; and, then, 300 ml of ether was added. The resulting mixture was cooled to 0° C., and 200 ml of cold water and then 200 ml of 12 M HCl were added. The organic layer was separated; and the aqueous layer was extracted with 2×200 ml of dichloromethane. The combined extract was dried over K$_2$CO$_3$ and then evaporated to dryness. The product was isolated by flash chromatography on Silica Gel 60 (40-63 μm, d 65 mm, 400 mm, eluant:hexanes) and then recrystallized from hexanes. Yield, 48.4 g (86%) of a white crystalline solid.

Anal. calc. for C$_{15}$H$_{11}$Br: C, 66.44; H, 4.09. Found: C, 66.39; H, 4.02.

$^1$H NMR (300 MHz, CDCl$_3$): δ 7.58-7.62 (m, 2H, 2,6-H in Ph), 7.56 (dd, J=Hz, J=Hz, 6-H in indenyl), 7.46-7.52 (m; 2H, 3,5-H in Ph), 7.39-7.45 (m, 2H, 4-H in indenyl and 4-H in Ph), 7.23 (t, J=7.8 Hz, 5-H in indenyl), 6.65 (t, J=2.2 Hz, 1H, 2-H in indenyl), 3.52 (d, J=2.2 Hz, 2H, CH$_2$).

$^{13}$C{$^1$H} NMR (75 MHz, CDCl$_3$): δ 145.4, 145.2, 144.6, 135.6, 131.1, 128.5, 128.0, 127.9, 127.7, 127.6, 119.3, 119.1, 39.7.

3-Phenyl-1H-inden-7-ol

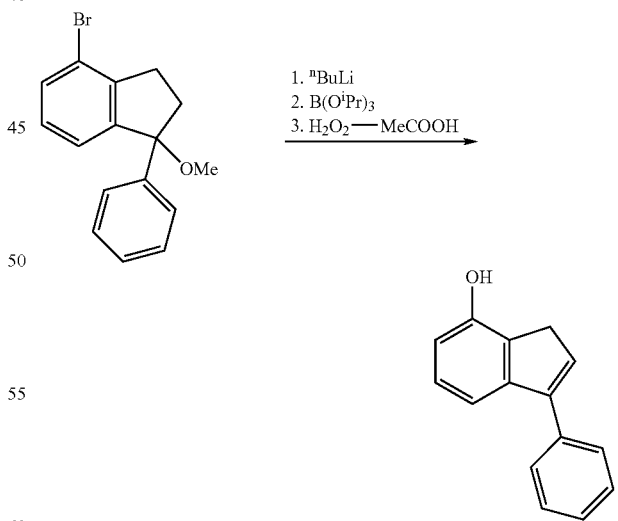

Under an argon atmosphere, to a solution of 21.0 g (69.3 mmol) of 4-bromo-1-methoxy-1-phenylindane in 200 ml of THF, 27.7 ml of 2.5 M $^n$BuLi (69.3 mmol) in hexanes was added with vigorous stirring for 1 hour at −78° C. Then, 24.0 ml (19.5 g, 104 mmol) of triisopropylborate was added at this temperature. The resulting mixture was slowly warmed to ambient temperature, and then 5.96 ml (6.25 g, 104 mmol) of glacial acetic acid was added. The resulting mixture was cooled to 0° C., and then 14.7 ml of 16% $H_2O_2$ was added. This mixture was stirred for ca. 30 min at room temperature, and then 300 ml of water was added. The product was extracted with 3×150 ml of $CH_2Cl_2$. The combined extract was dried over $Na_2SO_4$ and evaporated to dryness. The analytically pure product, 3-phenyl-1H-inden-7-ol, was obtained by flash chromatography on Silica Gel 60 (40-63 μm, d 50 mm, l 350 mm, eluant: hexanes-$CH_2Cl_2$=4:1). Yield, 9.68 g (67%).

Anal. calc. for $C_{15}H_{12}O$: C, 86.51; H, 5.81. Found: C, 86.40; H, 5.73.

$^1$H NMR (300 MHz, $CDCl_3$): δ 7.56-7.61 (m, 2H, 2,6-H in Ph), 7.41-7.47 (m, 2H, 3,5-H in Ph), 7.34-7.39 (m, 1H, 4-H in Ph), 7.19-7.26 (m, 2H, 4,5-H in indenyl), 6.73 (dd, J=6.7 Hz, J=2.1 Hz, 1H, 6-H in indenyl), 6.58 (t, J=2.2 Hz, 1H, 2-H in indenyl), 4.78 (br.s, 1H, OH), 3.46 (d, J=2.2 Hz, 2H, 1-$CH_2$ in indenyl).

$^{13}C\{^1H\}$ NMR (75 MHz, $CDCl_3$): δ 151.3, 146.2, 145.4, 136.0, 130.5, 129.3, 128.4, 128.0, 127.7, 127.5, 113.8, 112.2, 34.7.

[1,1'-biphenyl]-2-yl}-N,N-dimethylamine was added. This mixture was stirred for 8 hours at 100° C. Then, 300 ml of water was added, the organic layer was separated, and the aqueous layer was extracted with 3×75 ml of $CH_2Cl_2$. The combined extract was washed with 2×100 ml of water, dried over $K_2CO_3$, and evaporated to dryness. The analytically pure product, bis(3-phenyl-1H-inden-7-yl)ether, was obtained using flash chromatography on Silica Gel 60 (40-63 μm, d 50 mm, 1250 mm, eluant: $CH_2Cl_2$). Yield, 3.56 g (35%) of a white solid.

Anal. calc. for $C_{30}H_{22}O$: C, 90.42; H, 5.56. Found: C, 90.33; H, 5.48.

$^1$H NMR (300 MHz, $CDCl_3$): δ 7.60-7.66 (m, 4H, 2,2',6,6'-H in Ph), 7.35-7.52 (m, 2H, 4,4'-H in indenyl and 3,3',4,4',5,5'-H in Ph), 7.29 (t, J=7.9 Hz, 2H, 5,5'-H in indenyl), 6.86 (dd, J=7.9 Hz, J=0.7 Hz, 2H, 6,6'-H in indenyl), 6.60 (t, J=2.1 Hz, 2H, 2,2'-H in indenyl), 3.49 (d, J=2.1 Hz, 4H, 1,1'-$CH_2$ in indenyl).

$^{13}C\{^1H\}$ NMR (75 MHz, $CDCl_3$): δ 152.7, 146.5, 145.1, 136.0, 133.9, 131.3, 128.6, 128.0, 127.7, 127.6, 116.0, 115.0, 35.7.

Bis(3-phenyl-1H-inden-7-yl) ether 4,4'-oxadiyl-bis($\eta^5$-1-phenylindenyl)zirconium dichloride (O3)

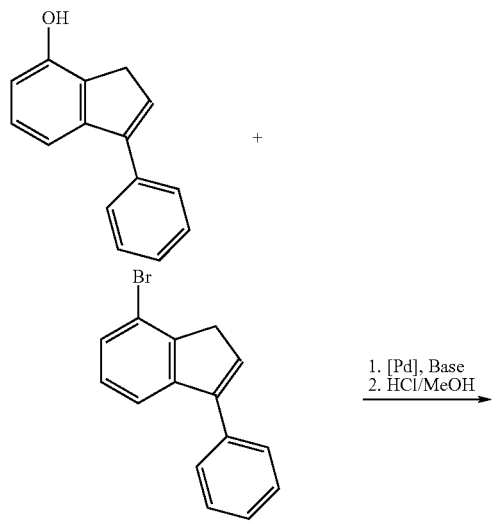

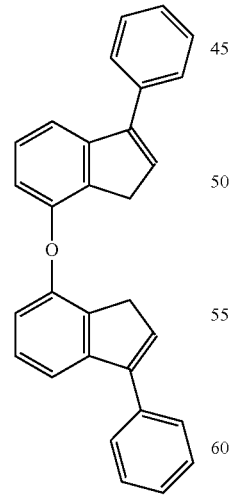

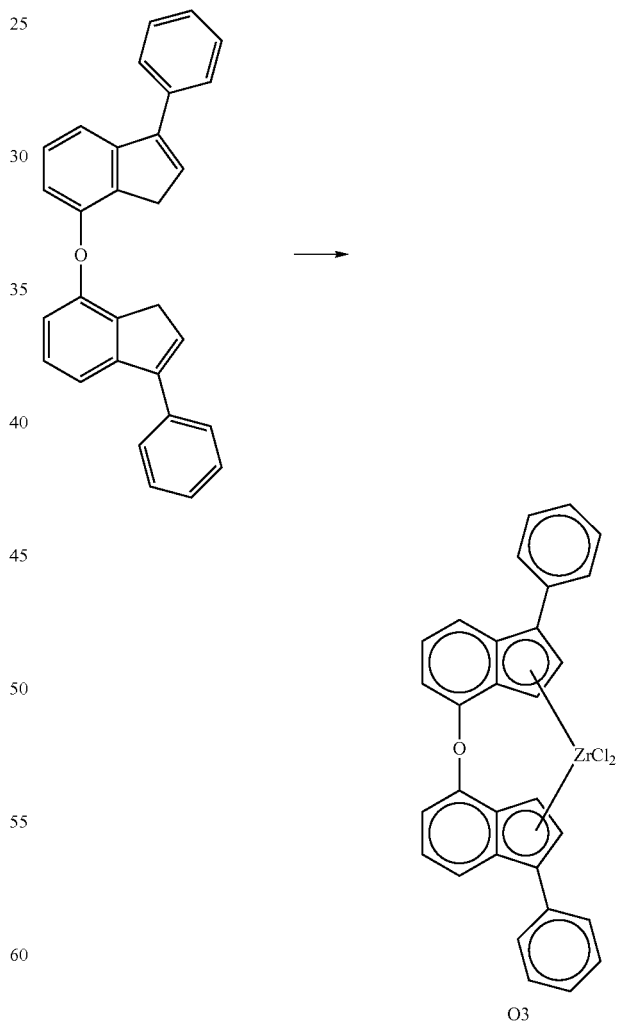

O3

Under an argon atmosphere, to a mixture of 6.90 g (25.5 mmol) of 7-bromo-3-phenyl-1H-indene, 5.30 g (25.5 mmol) of 3-phenyl-1H-inden-7-ol, 10.8 g (51 mmol) $K_3PO_4$, and 100 ml of toluene, a mixture of 300 mg (0.52 mmol) Pd(dba)$_2$ and 348 mg (1.02 mmol) of N-{2'-[di(tert-butyl)phosphino]

Under an argon atmosphere, to a solution of 5.64 g (14.2 mmol) of bis(3-phenyl-1H-inden-7-yl) ether in 200 ml of toluene, 12.0 ml of 2.5 M (30.0 mmol) $^n$BuLi in hexanes was added with vigorous stirring at ambient temperature. This mixture was stirred for 5 hours; then, 7.50 g (31.1 mmol) of triethyltin chloride was added. The resulting mixture was stirred overnight and then filtered through Celite 503. The filtrate was evaporated to ca. 180 ml; then, 3.30 g (14.2 mmol) of $ZrCl_4$ was added. The suspension was stirred for 1 hour at ambient temperature and then 7 hours at 100° C. The resulting red mixture was filtered through glass frit (G4) at 100° C. Crystals precipitated at 5° C., and were separated, washed with cold toluene, and dried in vacuum. Yield, 2.20 g (28%) of a yellow crystalline product.

Anal. calc. for $C_{30}H_{20}Cl_2OZr$: C, 64.50; H, 3.61. Found: C, 64.67; H, 3.70.

$^1$H NMR (300 MHz, $CD_2Cl_2$): δ 7.79 (m, 2H, 6,6'-H in indenyl), 7.62-7.69 (m, 4H, 2,2',6,6'-H in Ph), 7.38-7.51 (m, 8H, 5,5',7,7'-H in indenyl and 3,3',5,5'-H in Ph), 7.28-7.36 (m, 2H, 4,4'-H in Ph), 6.85 (d, J=3.4 Hz, 2H, 2,2'-H in indenyl), 4.66 (m, 2H, 1,1'-H in indenyl).

$^{13}C\{^1H\}$ NMR (75 MHz, $CDCl_3$): δ 161.1, 135.3, 130.5, 130.4, 130.2, 129.6, 129.4, 128.5, 126.6, 121.2, 116.5, 115.1, 100.8.

Example 6

Synthesis of 4,4'-sulfandiyl-bis($\eta^5$-1-phenylindenyl) zirconium dichloride (S3)

Bis(3-phenyl-1H-inden-7-yl)sulfide

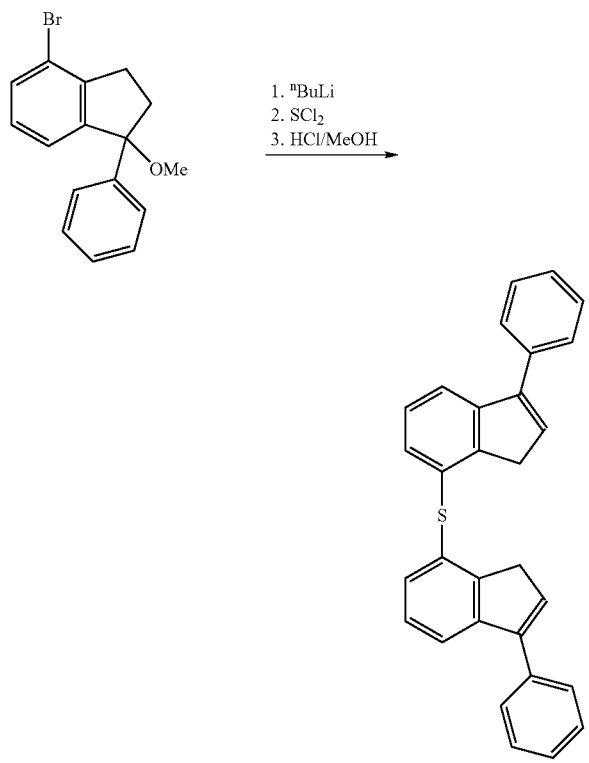

Under an argon atmosphere, following the procedure described for bis(2-methyl-1H-inden-7-yl)sulfide, 30.5 g (101 mmol) of 4-bromo-1-methoxy-1-phenylindane in 200 ml of THF, 40.3 ml of 2.5 M $^n$BuLi (101 mmol) in hexanes, and 5.45 g (53 mmol) of $SCl_2$ gave crude 1-methoxy-4-[(1-methoxy-1-phenyl-2,3-dihydro-1H-inden-4-yl)sulfanyl]-1-phenylindane, which was demethoxylated in a mixture of 150 ml of 16 M HCl and 150 ml of MeOH for 10 hours at reflux. The analytically pure product, bis(3-phenyl-1H-inden-7-yl) sulfide, was obtained by flash chromatography on Silica Gel 60 (40-63 (m, d 65 mm, l 450 mm, eluant: hexanes-CH2Cl2=3:1. Yield, 17.7 g (85%).

Anal. calc. for C30H22S: C, 86.92; H, 5.35. Found: C, 87.09; H, 5.42.

$^1$H NMR (300 MHz, CDCl3): δ 7.58-7.63 (m, 4H, 2,2',6, 6'-H in Ph), 7.52 (dd, J=7.6 Hz, J=1.0 Hz, 2H, 4,4'-H in indenyl), 7.43-7.49 (m, 4H, 3,3',5,5'-H in Ph), 7.35-7.41 (m, 4,4'-H in Ph), 7.28 (m, 2H, 5,5'-H in indenyl), 7.17 (d, J=0.9 Hz, 2H, 6,6'-H in indenyl), 6.61 (t, J=2.2 Hz, 2H, 2,2'-H in indenyl), 3.48 (d, J=2.2 Hz, 4H, 1,1'-CH2 in indenyl).

$^{13}C\{1H\}$ NMR (75 MHz, CDCl3): δ 145.6, 145.0, 144.6, 135.9, 131.1, 129.9, 128.5, 127.64 (two resonances), 127.58, 127.3, 119.5, 38.0.

4,4'-sulfandiyl-bis((5-1-phenylindenyl)zirconium dichloride (S3)

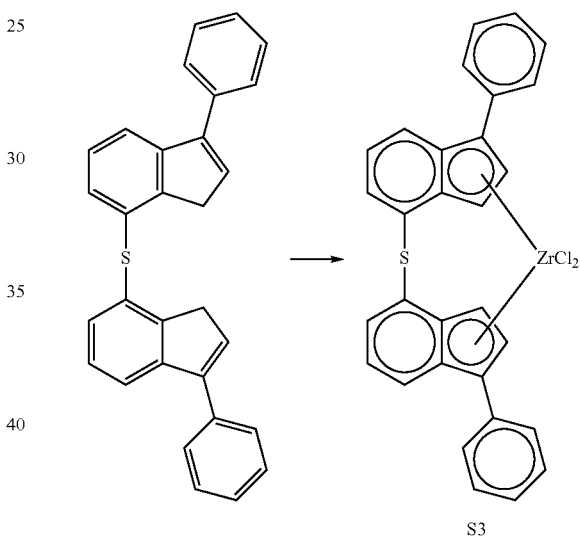

S3

Under an argon atmosphere, to a solution of 7.94 g (19.2 mmol) of bis(3-phenyl-1H-inden-7-yl)sulfide in 200 ml of toluene, 15.4 ml of 2.5 M (38.5 mmol) $^n$BuLi in hexanes was added with vigorous stirring at ambient temperature. This mixture was stirred for 9 hours; then, 9.31 g (38.6 mmol) of triethyltin chloride was added. The resulting mixture was stirred for 12 hours and then filtered through Celite 503. To the filtrate, 4.46 g (19.1 mmol) of ZrCl4 was added. This mixture was stirred for 1 hour at ambient temperature and 7 hours at reflux. Crystals that precipitated from this red solution at ambient temperature were separated, washed with 2×25 ml of toluene, and dried in vacuum. Yield, 7.28 g (66%) of a yellow crystalline product.

Anal. calc. for $C_{30}H_{20}Cl_2SZr$: C, 62.70; H, 3.51. Found: C, 62.88; H, 3.60.

$^1$H NMR (300 MHz, $CD_2Cl_2$): δ 7.96 (m, 2H, 5,5'-H in indenyl), 7.85 (m, 2H, 7,7'-H in indenyl), 7.66-7.72 (m, 4H, 2,2', 6,6'-H in Ph), 7.37-7.45 (m, 6H, 6,6'-H in indenyl and 3,3',5,5'-H in Ph), 7.27-7.35 (m, 2H, 4,4'-H in Ph), 6.89 (m, 2H, 2,2'-H in indenyl), 4.95 (m, 2H, 1,1'-H in indenyl).

$^{13}$C{$^1$H} NMR (75 MHz, CD$_2$Cl$_2$): δ 137.9, 135.5, 130.8, 130.3, 130.2, 129.8, 129.3, 128.8, 128.2, 125.8, 125.2, 122.5, 104.1.

Example 7

Synthesis of 4,4'-phenylphosphindiyl-bis(η$^5$-1-phenylindenyl)zirconium dichloride (P3)

Phenyl[bis(3-phenyl-1H-inden-7-yl)]phosphine

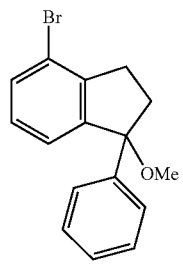

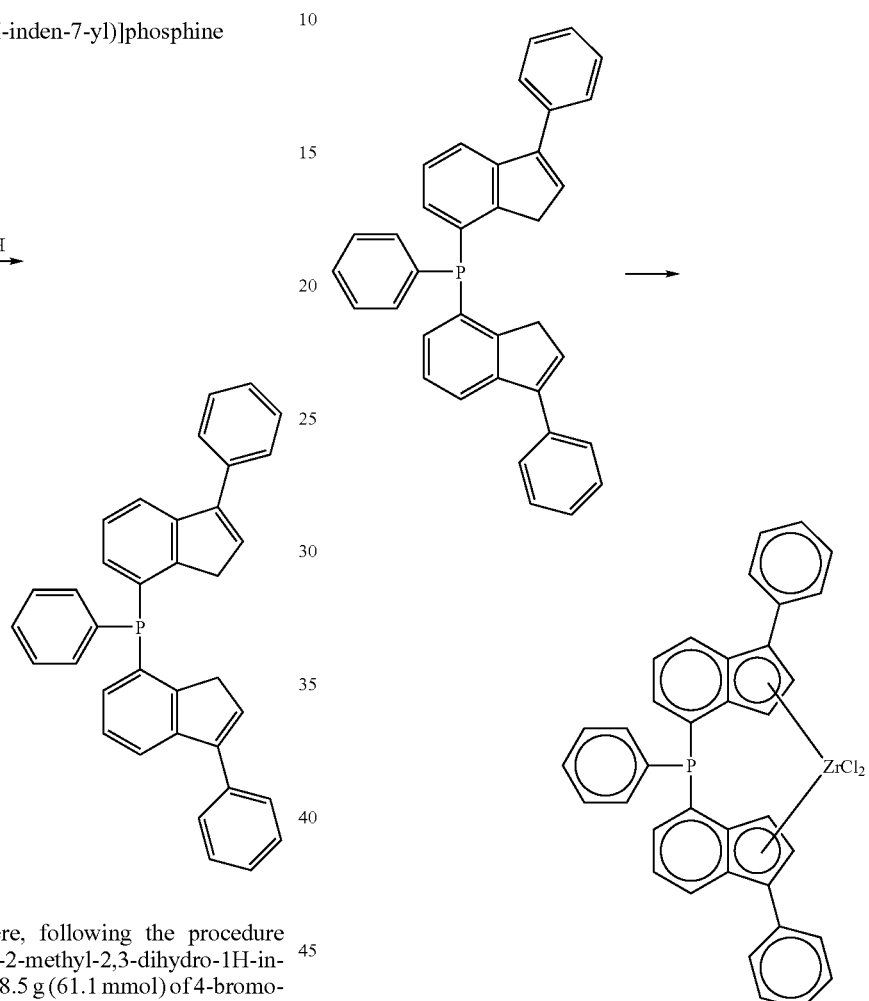

Under an argon atmosphere, following the procedure described for bis(1-methoxy-2-methyl-2,3-dihydro-1H-inden-4-yl)(phenyl)phosphine, 18.5 g (61.1 mmol) of 4-bromo-1-methoxy-1-phenylindane in 200 ml of THF, 24.5 ml of 2.5 M "BuLi (61.3 mmol) in hexanes, and 4.15 ml (5.47 g, 30.6 mmol) PhPCl$_2$ gave crude bis(1-methoxy-1-phenyl-2,3-dihydro-1H-inden-4-yl)(phenyl)phosphine, which then was demethoxylated in a mixture of 170 ml of 16 M HCl and 170 ml of methanol for 3 hours at reflux. The analytically pure product was isolated by flash chromatography on Silica Gel 60 (40-63 μm, d 50 mm, 1 400 mm, eluant: hexanes-CH$_2$Cl$_2$=2:1). Yield, 8.22 g (55%).

Anal. calc. for C$_{36}$H$_{27}$P: C, 88.14; H, 5.55. Found: C, 88.05; H, 5.48.

$^1$H NMR (300 MHz, CDCl$_3$): δ 7.58-7.63 (m, 4H, 2,2',6,6'-H in 3-Ph of indenyl), 7.33-7.48 (m, 13H, 4,4'-H in indenyl, 3,3',4,4',5,5'-H in 3-Ph of indenyl, and PPh), 7.27 (t, J=7.6 Hz, 2H, 5,5'-H in indenyl), 6.85 (ddd, J=7.6 Hz, J=5.1 Hz, J=1.0 Hz, 2H, 6,6'-H in indenyl), 6.57 (t, J=2.1 Hz, 2H, 2,2'-H in indenyl), 3.46 (d, J=2.1 Hz, 4H, 1,1'-CH$_2$ in indenyl).

$^{13}$C{$^1$H} NMR (75 MHz, CDCl$_3$): δ 149.5 (d, J=26.9 Hz), 144.9 (d, J=1.9 Hz), 143.7 (d, J=6.4 Hz), 136.1 (d, J=1.5 Hz), 134.9 (d, J=9.5 Hz), 134.2 (d, J=20.2 Hz), 131.3 (d, J=1.5 Hz), 131.2, 129.1 (d, J=2.3 Hz), 128.9, 128.7, 128.6, 127.8, 127.6, 126.8 (d, J=1.7 Hz), 121.0, 38.4 (d, J=11.6 Hz).

$^{31}$P{$^1$H} NMR (121 MHz, CDCl$_3$): δ −26.8.

4,4'-phenylphosphindiyl-bis(η$^5$-1-phenylindene) zirconium dichloride (P3)

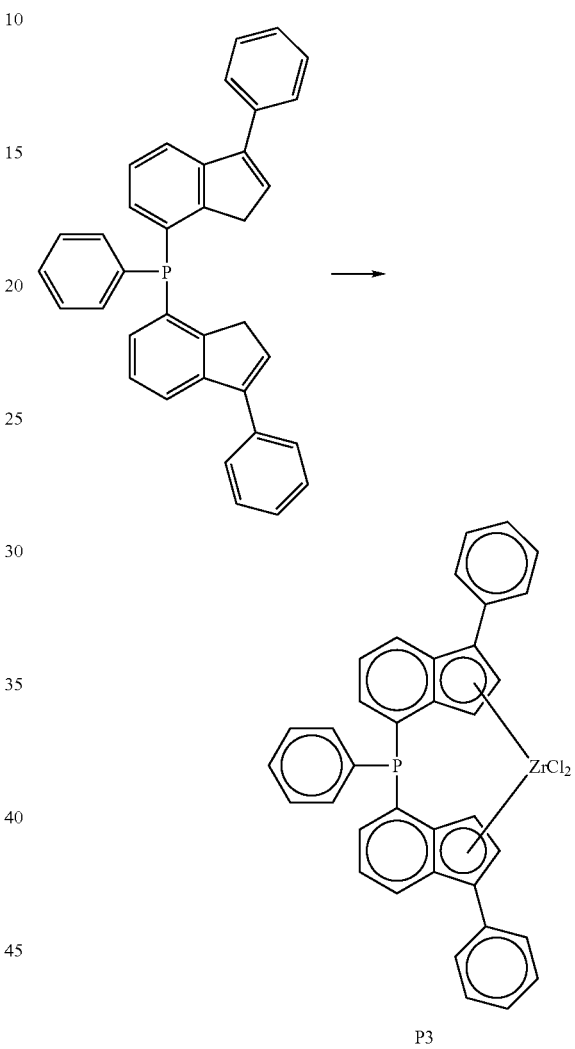

P3

Under an argon atmosphere, to a solution of 8.05 g (16.4 mmol) of phenyl[bis(3-phenyl-1H-inden-7-yl)]phosphine in 200 ml of toluene, 14.5 ml of 2.5 M (36.3 mmol) "BuLi in hexanes was added with vigorous stirring at ambient temperature. This mixture was stirred for 5 hours; then, 9.00 g (37.3 mmol) of triethyltin chloride was added. The resulting mixture was stirred overnight and then filtered through Celite 503. The filtrate was evaporated to ca. 180 ml; then, 3.82 g (16.4 mmol) of ZrCl$_4$ was added. The suspension was stirred for 1 hour at ambient temperature and 7 hours at 100° C. The obtained orange solution was filtered through glass a frit (G4) and then evaporated to ca. 50 ml. To this solution, 100 ml of hexanes was added. The yellow precipitate that formed was separated, washed with cold hexanes, and dried in vacuum. Yield, 6.82 g (64%). Analytically pure product was obtained by recrystallization from hexanes.

Anal. calc. for $C_{36}H_{25}Cl_2PZr$: C, 66.45; H, 3.87. Found: C, 66.56; H, 3.93.

$^1$H NMR (300 MHz, $CD_2Cl_2$): δ 8.29 (ddd, $J_{PH}$=15.0 Hz, J=6.6 Hz, J=0.8 Hz, 1H, 4-H in PhP), 8.18 (m, 1H, 5'-H in indenyl), 7.23-7.96 (m, 19H, 6,6',7',7'-H in indenyl, PhP, and 1,1'-Ph in indenyl), 6.83 (dd, $J_{PH}$=6.9 Hz, J=3.5 Hz, 2H, 2,2'-H in indenyl), 4.81 (dd, J=3.5 Hz, $J_{PH}$=0.6 Hz, 1H, 3-H in indenyl), 4.71 (d, J=3.5 Hz, 1H, 3'-H in indenyl).

$^{31}P\{^1H\}$ NMR (121 MHz, $CD_2Cl_2$): δ -7.7.

Example 8

Synthesis of 4,4'-phenylazandiyl-bis($\eta^5$-1-phenylindenyl)zirconium dichloride (N3)

1-Methoxy-N,1-diphenyl-4-indanamine

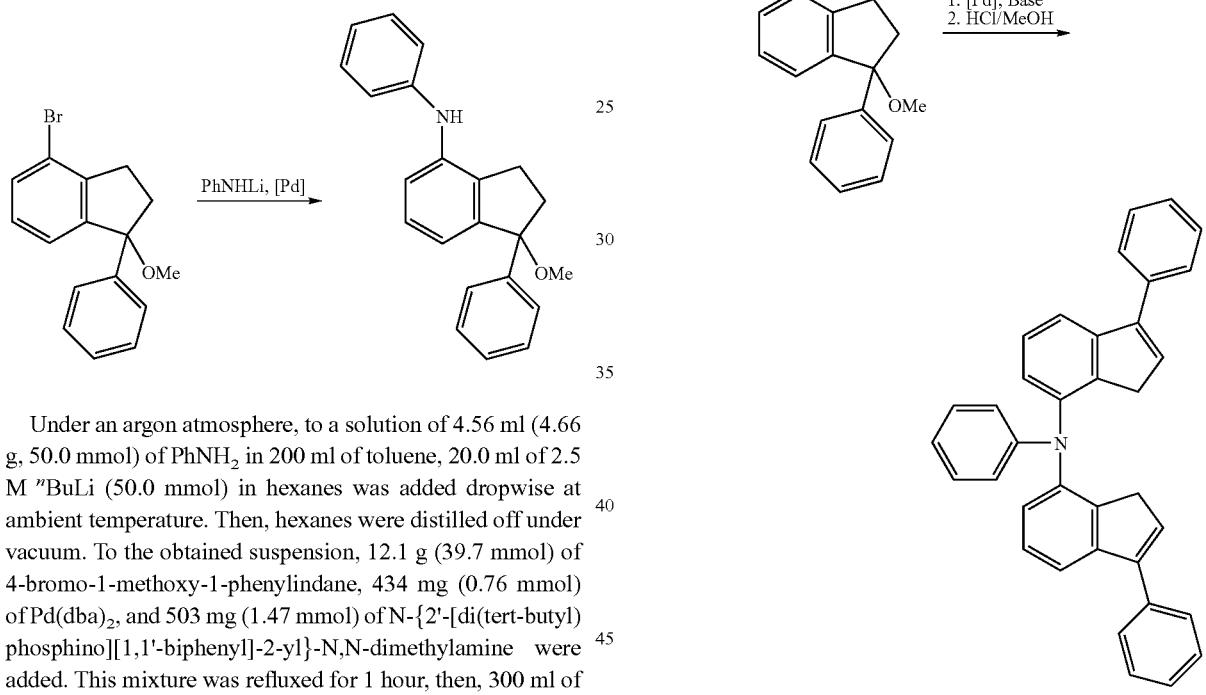

Under an argon atmosphere, to a solution of 4.56 ml (4.66 g, 50.0 mmol) of $PhNH_2$ in 200 ml of toluene, 20.0 ml of 2.5 M $^n$BuLi (50.0 mmol) in hexanes was added dropwise at ambient temperature. Then, hexanes were distilled off under vacuum. To the obtained suspension, 12.1 g (39.7 mmol) of 4-bromo-1-methoxy-1-phenylindane, 434 mg (0.76 mmol) of $Pd(dba)_2$, and 503 mg (1.47 mmol) of N-{2'-[di(tert-butyl)phosphino][1,1'-biphenyl]-2-yl}-N,N-dimethylamine were added. This mixture was refluxed for 1 hour, then, 300 ml of water was added. The organic layer was separated; the aqueous layer was extracted with 3×75 ml of ether. The combined extract was dried over $Na_2SO_4$ and, then, evaporated to dryness. The analytically pure 1-methoxy-N,1-diphenyl-4-indanamine was obtained by flash chromatography on Silica Gel 60 (40-63 μm, d 50 mm, 1300 mm, eluant: $CH_2Cl_2$). Yield, 12.5 g (99%).

Anal. calc. for $C_{22}H_{21}NO$: C, 83.78; H, 6.71. Found: C, 83.71; H, 6.77.

$^1$H NMR (300 MHz, $C_6D_6$): δ 6.84-7.61 (m, 13H, 5,6,7-H in indenyl, PhN, and PhC), 5.13 (br.s, 1H, NH), 3.12 (s, 3H, OMe), 2.81 (dt, J=15.3 Hz, J=7.7 Hz, 1H, CHH'COMe), 2.60 (ddd, J=13.2 Hz, J=7.7 Hz, J=2.6 Hz, 1H, CHH'CHH'COMe), 2.45 (ddd, J=15.3 Hz, J=8.5 Hz, J=2.6 Hz, 1H, CHH'CHH'COMe), 2.24 (m, 1H, CHH'COMe).

$^{13}C\{^1H\}$ NMR (75 MHz, $C_6D_6$): δ 145.3, 145.0, 143.5, 140.3, 135.3, 129.6, 128.4, 127.5, 127.1, 126.9, 121.4, 119.7, 118.6, 116.6, 91.6, 51.6, 42.9, 27.9.

N,N-Bis[3-(1-phenyl)-1H-inden-7-yl]-N-phenylamine

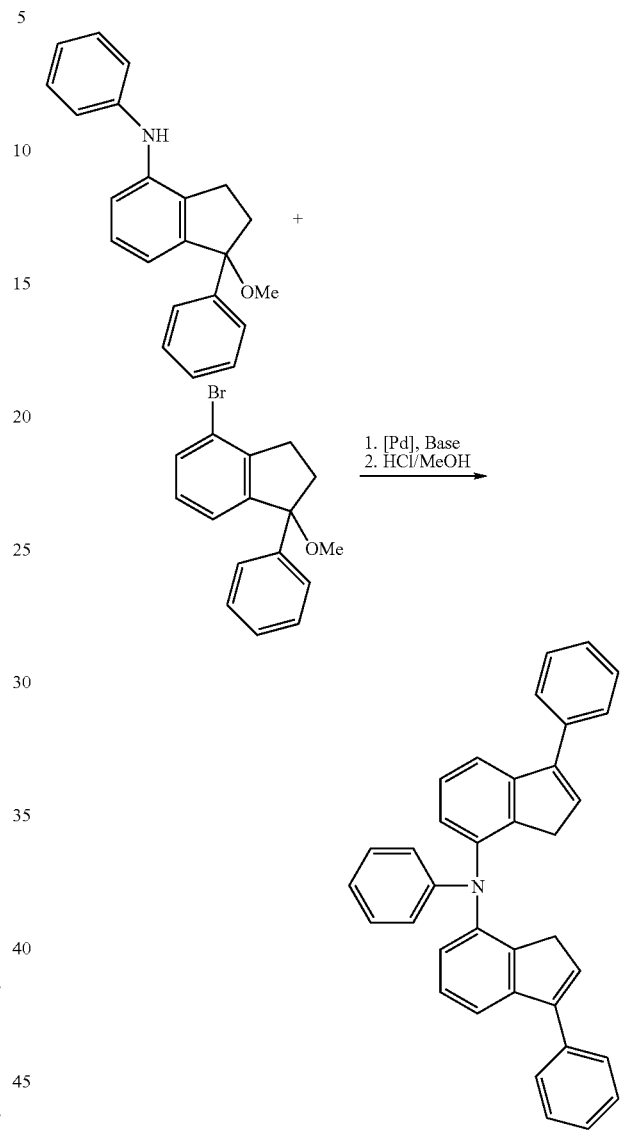

To a mixture of 12.2 g (50.5 mmol) of 4-bromo-1-methoxy-1-phenylindane, 9.93 g (55.6 mmol) of 3-(1-phenyl)-N-phenyl-1H-inden-7-amine, 21.4 g (101 mmol) of $K_3PO_4$, and 200 ml of toluene, a mixture of 227 mg (1.01 mmol) of $Pd(OAc)_2$ and 518 mg (1.52 mmol) N-{2'-[di(tert-butyl)phosphino][1,1'-biphenyl]-2-yl}-N,N-dimethylamine was added. The resulting mixture was stirred for 24 hours at 100° C. To this mixture 300 ml of water was added, and then the organic layer was separated, and the aqueous layer was extracted with 3×75 ml of $CH_2Cl_2$. The combined extract was dried over $Na_2SO_4$ and evaporated to dryness. The crude N,N-bis(1-methoxy-1-phenyl-2,3-dihydro-1H-inden-4-yl)-N-phenylamine was isolated using a short column with Silica Gel 60 (40-63 μm, d 50 mm, 180 mm, eluant: $CH_2Cl_2$). This product was demethoxylated in a mixture of 170 ml of 16 M HCl and 170 ml of methanol for 7 hours at reflux. The product was extracted with 3×150 ml of $CH_2Cl_2$. The combined extract was washed with 2×100 ml of water, dried over $K_2CO_3$, and evaporated to dryness. The analytically pure product was isolated by flash chromatography on Silica Gel 60 (40-63 μm, d 50 mm, l 350 mm, eluant:hexanes-CH$_2$Cl$_2$=3:1). Yield, 7.61 g (55%) of a white solid.

Anal. calc. for C$_{36}$H$_{27}$N: C, 91.30; H, 5.75. Found: C, 91.13; H, 5.66.

$^1$H NMR (300 MHz, CDCl$_3$): δ 7.58-7.63 (m, 4H, 2,2',6,6'-H of 3-Ph in indenyl), 7.34-7.49 (m, 8H, 4,4'-H in indenyl and 3,3',4,4',5,5'-H of 3-Ph in indenyl), 7.30 (t, J=7.8 Hz, 2H, 5,5'-H in indenyl), 7.20-7.25 (m, 2H, 3,5-H in NPh), 7.07 (d, J=7.8 Hz, 2H, 6,6'-H in indenyl), 6.93-7.03 (m, 3H, 2,4,6-H in NPh), 6.44 (t, J=2.1 Hz, 2H, 2,2'-H in indenyl), 2.96 (d, J=2.1 Hz, 4H, 1,1'-CH$_2$ in indenyl).

$^{13}$C{$^1$H} NMR (75 MHz, CDCl$_3$): δ 147.4, 145.9, 144.8, 142.8, 139.1, 136.1, 131.2, 129.0, 128.5, 127.8, 127.7, 127.5, 123.0, 121.8, 121.3, 116.8, 37.4.

4,4'-phenylazandiyl-bis(η$^5$-1-phenylindenyl)zirconium dichloride (N3)

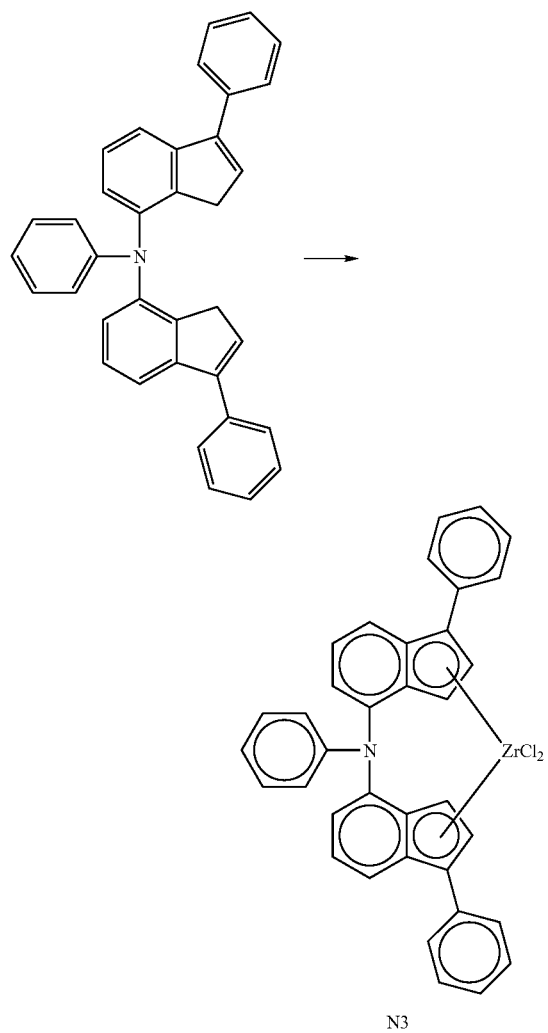

N3

Under an argon atmosphere, to a solution of 7.96 g (16.8 mmol) of N,N-bis[3-(1-phenyl)-1H-inden-7-yl]-N-phenylamine in 200 ml of THF, 13.5 ml of 2.5 M (33.8 mmol) $^n$BuLi in hexanes was added with vigorous stirring at −78° C. Then, the solution was stirred for 30 min at room temperature, cooled to −30° C., and 6.34 g (16.8 mmol) of ZrCl$_4$(THF)$_2$ was added. This mixture was stirred for 12 hours at room temperature and then evaporated to dryness. To the residue, 200 ml of toluene was added, and the resulting mixture was refluxed for 5 hours. The precipitate formed was filtered off and then washed with 5×100 ml of hot toluene. Crystals precipitated at 5° C., and were separated and dried in vacuum. Yield, 2.92 g (27%) of a red crystalline solid.

Anal. calc. for C$_{36}$H$_{25}$Cl$_2$NZr: C, 68.23; H, 3.98. Found: C, 68.44; H, 4.07.

$^1$H NMR (300 MHz, CD$_2$Cl$_2$): δ 7.74 (dt, J=8.0 Hz, J=1.0 Hz, 2H, 5,5'-H in indenyl), 7.86-7.71 (m, 4H, 2,2',6,6'-H of 1,1'-Ph in indenyl), 7.35-7.46 (m, 13H, 6,6',7,7'-H in indenyl, 3,3',5,5'-H of 1,1'-Ph in indenyl, and PhN), 7.27-7.34 (m, 2H, 4,4'-H of 1,1'-Ph in indenyl), 6.88 (d, J=3.4 Hz, 2H, 2,2'-H in indenyl), 5.03 (dd, J=3.4 Hz, J=1.0 Hz, 2H, 3,3'-H in indenyl).

$^{13}$C{$^1$H} NMR (75 MHz, CD$_2$Cl$_2$): δ 150.1, 146.0, 135.6, 131.3, 130.32, 130.25, 130.16, 129.9, 129.2, 128.71, 128.69, 125.7, 125.6, 123.8, 120.6, 119.3, 102.2.

Example 9

Synthesis of 4,4'-oxadiyl-bis(η$^5$-1-naphthylindenyl) zirconium dichloride (O4)

4-Bromo-1-(1-naphthyl)-2,3-dihydro-1H-inden-1-yl methyl ether

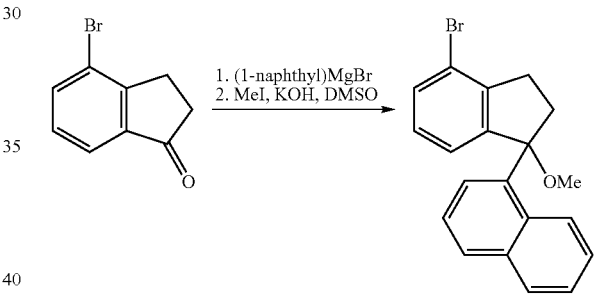

Under an argon atmosphere, to a mixture of naphthylmagnesium bromide obtained from 7.59 g (0.31 mol) of Mg and 65.0 g (0.32 mol) of naphthyl bromide in 300 ml of THF and 400 ml of benzene, 43.9 g (0.21 mol) of powdered 4-bromo-1-indanone was added at ambient temperature. The mixture was stirred overnight. Then, 300 ml of ether was added, the resulting mixture was cooled to 0° C., and 200 ml of cold water was added. The organic layer was separated, and the aqueous layer was extracted with 5×200 ml of ether. The combined extract was evaporated to dryness. To 47.5 g (0.85 mol) of KOH in 425 ml of DMSO, 26.0 ml (59.1 g, 0.42 mol) of MeI, and then, the above obtained crude alcohol in 200 ml of DMSO were added with vigorous stirring at 10° C. The reaction mixture was stirred for 2 hours at ambient temperature; then, 26.0 ml (59.1 g, 0.42 mol) of MeI was added, and the reaction mixture was additionally stirred for 2 hours. The resulting mixture was added to 2 L of cold water. The crude product was extracted with 5×200 ml of dichloromethane. The combined extract was dried over Na$_2$SO$_4$ and, then, evaporated to dryness. The product was isolated by flash chromatography on Silica Gel 60 (40-63 μm, d 55 mm, l 400 mm, eluant: hexanes:dichloromethane, 1:1, vol.). Yield, 58.3 g (79%) of a yellowish oil.

Anal. calc. for C$_{20}$H$_{17}$BrO: C, 68.00; H, 4.85. Found: C, 68.17; H, 4.93.

¹H NMR (300 MHz, C₆D₆): δ 7.31-7.35 (m, 2H, 2,6-H in Ph), 7.30 (dd, J=7.8 Hz, J=1.0 Hz, 1H, 5-H in C₆H₃), 7.14-7.19 (m, 2H, 3,5-H in Ph), 7.06-7.21 (m, 1H, 4-H in Ph), 6.89 (m, 1H, 7-H in C₆H₃), 6.70 (m, 1H, 6-H in C₆H₃), 3.08 (m, 1H, CHH'CHH'CPh), 2.91 (s, 3H, OMe), 2.76 (ddd, J=16.6 Hz, J=8.7 Hz, J=4.0 Hz, 1H, CHH'CHH'CPh), 2.67 (ddd, J=13.9 Hz, J=8.2 Hz, J=4.0 Hz, 1H, CHH'CHH'CPh), 2.42 (ddd, J=13.9 Hz, J=8.7 Hz, J=6.7 Hz, 1H, CHH'CHH'CPh).

¹³C{¹H} NMR (75 MHz, C₆D₆): δ 146.1, 145.8, 139.2, 135.4, 131.9, 131.7, 129.3, 129.1, 127.2, 126.2, 125.9, 125.7, 125.6, 124.9, 121.3, 93.6, 51.2, 39.6, 32.2.

3-(1-Naphthyl)-1H-inden-7-ol

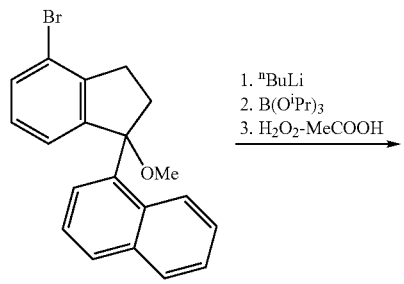

Under an argon atmosphere, to a solution of 12.3 g (34.9 mmol) of 4-bromo-1-(1-naphthyl)-2,3-dihydro-1H-inden-1-yl methyl ether in 200 ml of THF, 14.0 ml of 2.5 M ⁿBuLi (34.9 mmol) in hexanes was added with vigorous stirring for 1 hour at −78° C. Then, 20.0 ml (16.3 g, 86.7 mmol) of triisopropylborate was added at this temperature. The reaction mixture was warmed to ambient temperature, and 2.08 ml (2.18 g, 36.3 mmol) of glacial acetic acid was added. This mixture was stirred for 5 min at room temperature, then cooled to 0° C., and a mixture of 7.30 ml of 16% H₂O₂ was added. The resulting mixture was slowly warmed to ambient temperature and additionally stirred at this temperature for 30 min. Then, 300 ml of water was added, and the crude product was extracted with 3×150 ml of CH₂Cl₂. The combined extract was dried over Na₂SO₄ and evaporated to dryness. The analytically pure product was isolated by flash chromatography on Silica Gel 60 (40-63 μm, d 35 mm, 300 mm, eluant: hexanes-CH₂Cl₂=3:1). Yield, 3.98 g (44%).

Anal. calc. for C₁₉H₁₄O: C, 88.34; H, 5.46. Found: C, 88.27; H, 5.39.

¹H NMR (300 MHz, CDCl₃): δ 7.88-7.99 (m, 3H, 2,5,4-H in naphthyl), 7.49-7.60 (m, 3H, 6,7,8-H in naphthyl), 7.42 (m, 1H, 3-H in naphthyl), 7.16 (t, J=7.7 Hz, 1H, 5-H in indenyl), 6.78 (m, 1H, 4-H in indenyl), 6.75 (m, 1H, 6-H in indenyl), 6.68 (t, J=2.1 Hz, 1H, 2-H in indenyl), 5.13 (br.s, 1H, OH), 3.64 (d, J=2.1 Hz, 2H, 1-CH₂ in indenyl).

¹³C{¹H} NMR (75 MHz, CDCl₃): δ 151.2, 148.1, 144.3, 134.0, 133.7, 132.8, 131.8, 128.6, 128.2, 128.02, 127.98, 126.6, 126.2, 125.8, 125.7, 125.4, 114.3, 112.2, 37.3.

Bis[3-(1-naphthyl)-1H-inden-7-yl]ether

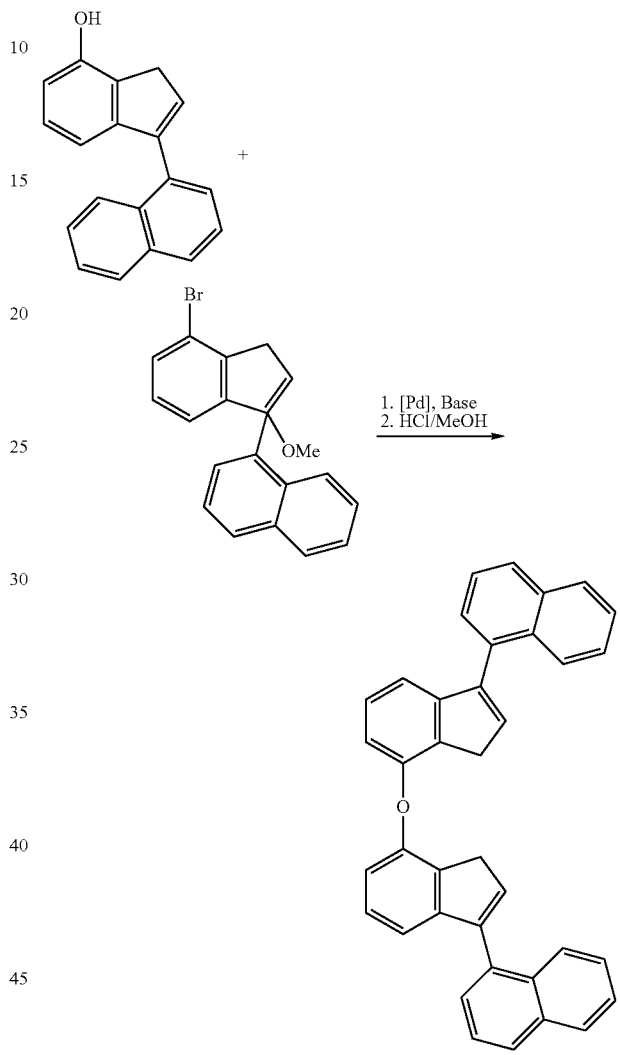

Under an argon atmosphere, to a mixture of 5.50 g (15.6 mmol) of 4-bromo-1-(1-naphthyl)-2,3-dihydro-1H-inden-1-yl methyl ether, 4.00 g (15.5 mmol) of 3-(1-naphthyl)-1H-inden-7-ol, 6.60 g (31.1 mmol) of K₃PO₄, and 150 ml of toluene, a mixture of 183 mg (0.32 mmol) of Pd(dba)₂ and 212 mg (0.62 mmol) of N-{2'-[di(tert-butyl)phosphino][1,1'-biphenyl]-2-yl}-N,N-dimethylamine was added. The resulting mixture was stirred for 8 hours at 100° C. Then, 300 ml of water was added, the organic layer was separated, and the aqueous layer was extracted with 3×75 ml of CH₂Cl₂. The combined extract was dried over Na₂SO₄ and evaporated to dryness. The crude 1-(1-methoxy-4-{[1-methoxy-1-(1-naphthyl)-2,3-dihydro-1H-inden-4-yl]oxy}-2,3-dihydro-1H-inden-1-yl)naphthalene was purified using a short column with Silica Gel 60 (40-63 μm, d 50 mm, l 70 mm, eluant: CH₂Cl₂). This product was demethoxylated in a mixture of 170 ml of 16 M HCl and 170 ml of methanol for 7 hours at reflux. The crude product was extracted with 3×150 ml of CH₂Cl₂. The combined extract was washed with 2×100 ml of water, dried over $K_2CO_3$, and evaporated to dryness. The analytically pure product was obtained by flash chromatography on Silica Gel 60 (40-63 μm, d 35 mm, l 300 mm, eluant:hexanes-$CH_2Cl_2$=5:1). Yield, 2.65 g (34%) of a white solid.

Anal. calc. for $C_{38}H_{26}O$: C, 91.54; H, 5.26. Found: C, 91.40; H, 5.06.

$^1$H NMR (300 MHz, $CDCl_3$): δ 7.98 (m, 2H, 2,2'-H in naphthyl), 7.87-7.96 (m, 4H, 4,4',8,8'-H in naphthyl), 7.39-7.59 (m, 8H, 3,3',5,5',6,6',7,7'-H in naphthyl), 7.21 (t, J=7.9 Hz, 2H, 5,5'-H in indenyl), 6.91 (m, 4H, 4,4',6,6'-H in indenyl), 6.68 (t, J=1.9 Hz, 2H, 2,2'-H in indenyl), 3.68 (d, J=1.9 Hz, 4H, 1,1'-$CH_2$ in indenyl).

$^{13}C\{^1H\}$ NMR (75 MHz, $CDCl_3$): δ 152.7, 148.4, 144.1, 134.0, 133.9, 133.4, 133.2, 132.0, 128.3, 128.1, 127.8, 126.7, 126.3, 125.9 (two resonances), 125.5, 116.5, 115.0, 36.2.

4,4'-oxadiyl-bis($\eta^5$-1-naphthylindenyl)zirconium dichloride (O4)

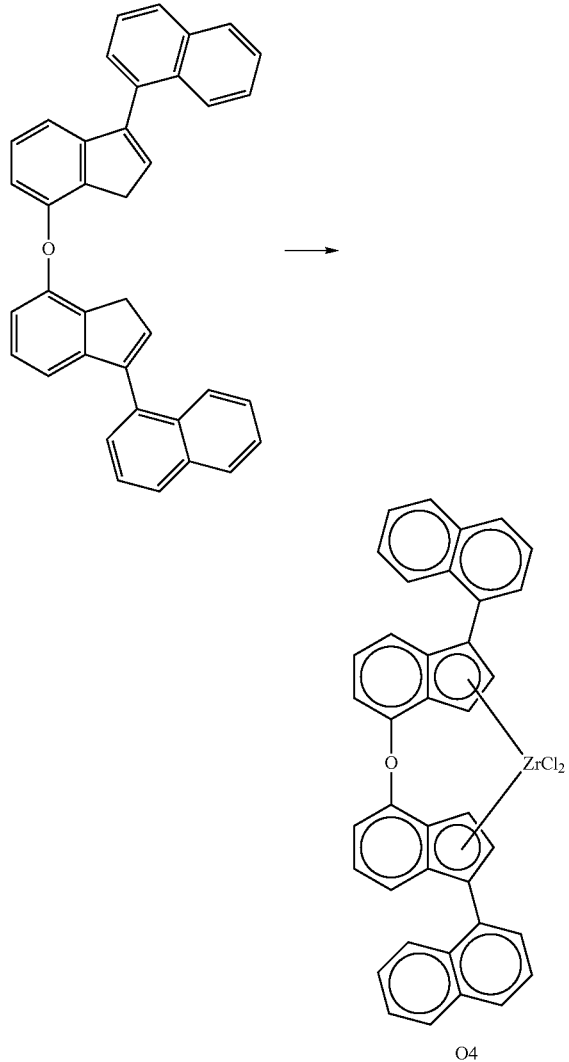

O4

Under an argon atmosphere, to a solution of 2.59 g (5.19 mmol) of bis[3-(1-naphthyl)-1H-inden-7-yl]ether in 150 ml toluene, 4.50 ml of 2.5 M (11.3 mmol) $^n$BuLi in hexanes was added with vigorous stirring at ambient temperature. This mixture was stirred for 5 hours; then, 3.00 g (12.4 mmol) of triethyltin chloride was added. The resulting mixture was stirred overnight and then filtered through Celite 503. The filtrate was evaporated to ca. 130 ml; then, 1.21 g (5.19 mmol) of $ZrCl_4$ was added. This mixture was stirred for 1 hour at room temperature and 7 hours at 100° C. Then, it was filtered through a glass frit at 100° C. Crystals precipitated from the filtrate and were collected, washed with cold toluene, and dried in vacuum. Yield, 1.31 g (38%) of a yellow crystalline product.

Anal. calc. for $C_{38}H_{24}Cl_2OZr$: C, 69.29; H, 3.67. Found: C, 69.44; H, 3.75.

$^1$H NMR (300 MHz, $CD_2Cl_2$): δ 7.88-7.94 (m, 6H, 5,5'-H in indenyl and 4,4',8,8'-H in naphthyl), 7.59 (dd, J=8.1 Hz, J=7.3 Hz, 2H, 6,6'-H in indenyl), 7.52 (ddd, J=7.3 Hz, J=0.9 Hz, J=0.3 Hz, 2H, 2,2'-H in naphthyl), 7.46 (m, 2H, 7,7'-H in naphthyl), 7.39-7.43 (m, 2H, 3,3'-H in naphthyl), 7.39 (dd, J=8.5 Hz, J=7.3 Hz, 2H, 7,7'-H in indenyl), 7.31 (ddd, J=8.0 Hz, J=6.6 Hz, J=1.4 Hz, 2H, 6,6'-H in naphthyl), 7.21 (dt, J=8.5 Hz, J=0.8 Hz, 2H, 5,5'-H in naphthyl), 6.89 (d, J=3.4 Hz, 2H, 2,2'-H in indenyl), 4.77 (dd, J=3.4 Hz, J=0.9 Hz, 2H, 3,3'-H in indenyl).

Example 10

Synthesis of 4,4'-sulfandiyl-bis($\eta^5$-1-napthylindenyl) zirconium dichloride (S4)

Bis[3-(1-naphthyl)-1H-inden-7-yl]sulfide

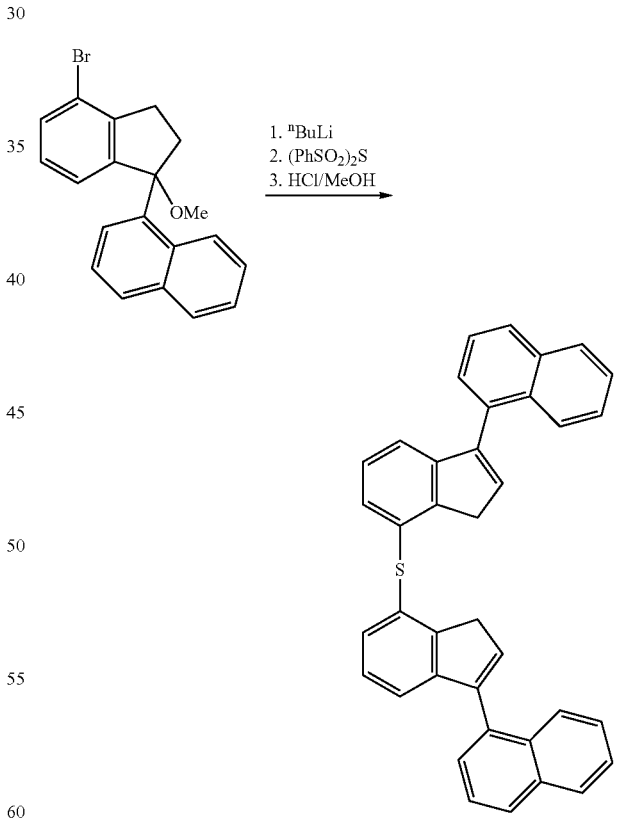

Under an argon atmosphere, following the procedure described for bis(2-methyl-1H-inden-7-yl)sulfide, 16.6 g (47.0 mmol) of 4-bromo-1-(1-naphthyl)-2,3-dihydro-1H-inden-1-yl methyl ether in 200 ml of THF, 19.0 ml 2.5 M $^n$BuLi (47.5 mmol) in hexanes, and 7.35 g (23.4 mmol) of $(PhSO_2)_2$S gave crude 1-(1-methoxy-4-{[1-methoxy-1-(1-naphthyl)-

2,3-dihydro-1H-inden-4-yl]sulfanyl}-2,3-dihydro-1H-inden-1-yl)naphthalene, which was demethoxylated in a mixture of 150 ml of 16 M HCl and 150 ml of methanol for 10 hours at reflux. The analytically pure product was isolated by flash chromatography on Silica Gel 60 (40-63 μm, d 35 mm, l 350 mm, eluant:hexanes-$CH_2Cl_2$=3:1). Yield, 5.31 g (44%).

Anal. calc. for $C_{38}H_{26}S$: C, 88.68; H, 5.09. Found: C, 88.60; H, 5.16.

$^1$H NMR (300 MHz, $CDCl_3$): δ 7.87-7.97 (m, 6H, 2,2',4,4',8,8'-H in naphthyl), 7.39-7.57 (m, 8H, 3,3',5,5',6,6',7,7'-H in naphthyl), 7.21 (d, J=3.1 Hz, 2H, 4,4'-H in indenyl), 7.20 (d, J=5.5 Hz, 2H, 6,6'-H in indenyl), 7.05 (dd, J=5.5 Hz, J=3.1 Hz, 2H, 5,5'-H in indenyl), 6.70 (t, J=2.0 Hz, 2H, 2,2'-H in indenyl), 3.68 (d, J=1.9 Hz, 4H, 1,1'-$CH_2$ in indenyl).

$^{13}C\{^1H\}$ NMR (75 MHz, $CDCl_3$): δ 146.4, 144.9, 144.0, 133.8, 133.7, 133.4, 131.8, 129.8, 128.3, 128.1, 127.6, 127.5, 126.7, 126.2, 125.9, 125.8, 125.5, 38.5.

4,4'-sulfandiyl-bis($\eta^5$-1-naphthylindenyl)zirconium dichloride (S4)

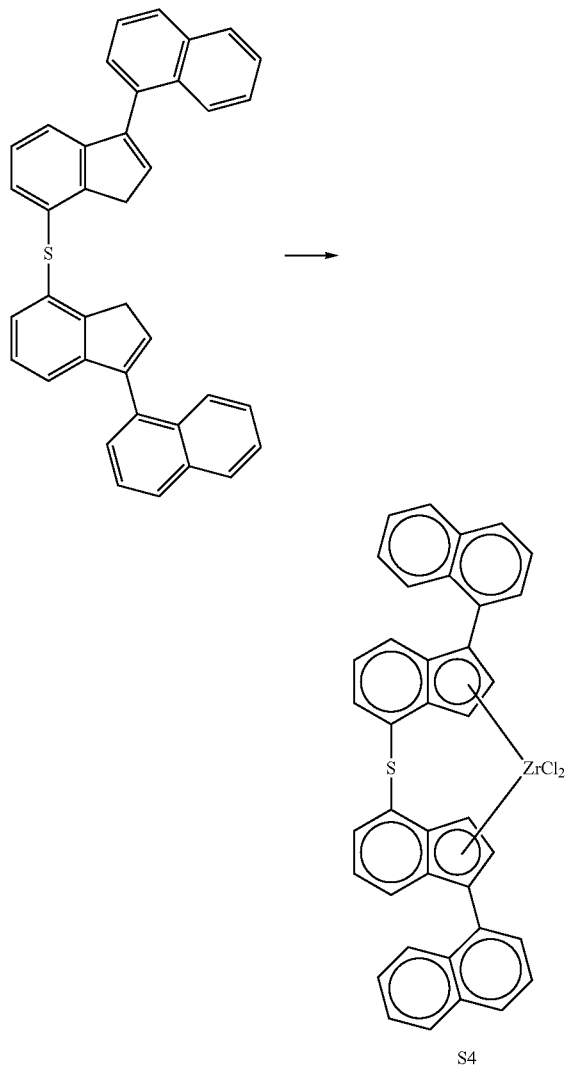

S4

Under an argon atmosphere, to a solution of 5.22 g (10.1 mmol) of bis[3-(1-naphthyl)-1H-inden-7-yl]ether in 200 ml of toluene, 8.20 ml of 2.5 M (20.5 mmol) of $^n$BuLi in hexanes was added. This mixture was stirred for 5 hours; then, 5.00 g (20.7 mmol) of triethyltin chloride was added. The resulting mixture was stirred overnight and then filtered through Celite 503. This mixture was evaporated to ca. 180 ml; and, then, 2.36 g (10.1 mmol) of $ZrCl_4$ was added. The resulting mixture was stirred for 1 hour at room temperature and 7 hours at 100° C. The obtained red solution was filtered through a glass flit (G4) at 100° C. Crystals precipitated at 5° C., and were separated, washed with cold toluene, and dried in vacuum. Yield, 4.77 g (70%) of a yellow crystalline solid.

Anal. calc. for $C_{38}H_{24}Cl_2SZr$: C, 67.64; H, 3.58. Found: C, 67.81; H, 3.50.

$^1$H NMR (300 MHz, $CD_2Cl_2$): δ 7.98 (dd, J=7.2 Hz, J=1.2 Hz, 2H, 5,5'-H in indenyl), 7.88-7.94 (m, 6H, 7,7'-H in indenyl and 2,2',8,8'-H in naphthyl), 7.59 (dd, J=8.2 Hz, J=7.2 Hz, 2H, 6,6'-H in indenyl), 7.44 (m, 2H, 3,3'-H in naphthyl), 7.18-7.34 (m, 8H, 4,4',5,5',6,6',7,7'-H in naphthyl), 6.91 (d, J=3.4 Hz, 2H, 2,2'-H in indenyl), 5.05 (d, J=3.4 Hz, 2H, 3,3'-H in indenyl).

Example 11

Synthesis of 4,4'-phenylphosphindiyl-bis($\eta^5$-1-naphthylindene)zirconium dichloride (P4)

Bis[3-(1-naphthyl)-1H-inden-7-yl](phenyl)phosphine

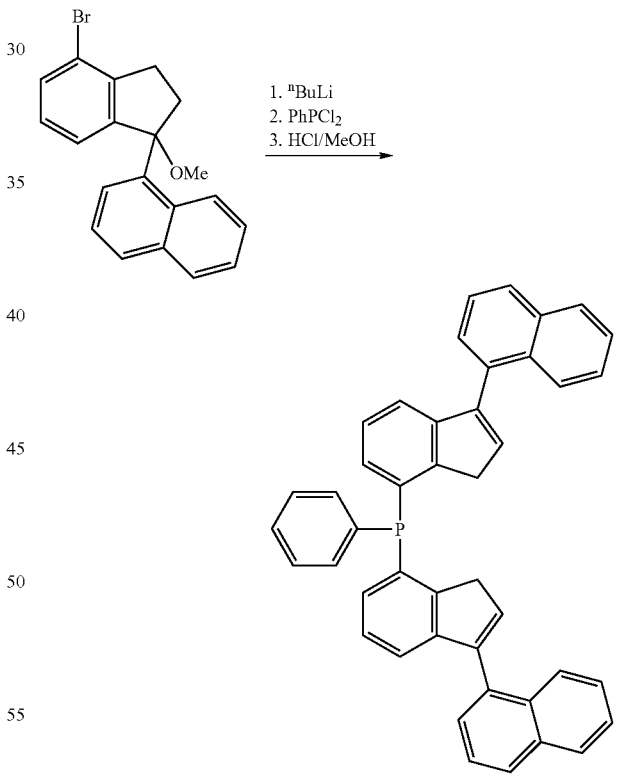

1. $^n$BuLi
2. $PhPCl_2$
3. HCl/MeOH

Under an argon atmosphere, following the procedure described for bis(1-methoxy-2-methyl-2,3-dihydro-1H-inden-4-yl)(phenyl)phosphine, 15.4 g (43.5 mmol) of 4-bromo-1-(1-naphthyl)-2,3-dihydro-1H-inden-1-yl methyl ether in 200 ml of THF, 17.3 ml of 2.5 M $^n$BuLi (43.3 mmol) in hexanes, and 2.93 ml (3.87 g, 21.6 mmol) of $PhPCl_2$ in 20 ml of THF gave crude bis(1-methoxy-1-naphthyl-2,3-dihydro-1H-inden-4-yl)(phenyl)phosphine, which was demethoxylated in a mixture of 170 ml of 16 M HCl and 170 ml of methanol for 2 hours at reflux. The analytically pure product was obtained by flash chromatography on Silica Gel 60 (40-63 μm, d 50 mm, l 350 mm, eluant:hexanes-$CH_2Cl_2$=2:1). Yield, 11.1 g (87%).

Anal. calc. for $C_{44}H_{31}P$: C, 89.47; H, 5.29. Found: C, 89.58; H, 5.33.

$^1$H NMR (300 MHz, $CDCl_3$): δ 7.87-8.04 (m, 6H, 2,2',4,4',8,8'-H in naphthyl), 7.41-7.63 (m, 14H, 5,5'-H in indenyl, 3,3',5,5',6,6',7,7'-H in naphthyl, and 2,3,5,6-H in Ph), 7.14-7.27 (m, 4H, 4,4',6,6'-H in indenyl), 6.95-7.01 (m, 1H, 4-H in Ph), 6.71 (m, 2H, 2,2'-H in indenyl), 3.70 (br.s, 4H, 1,1'-$CH_2$ in indenyl).

$^{13}C\{^1H\}$ NMR (75 MHz, $CDCl_3$): δ 148.9, 148.5, 145.5 (d, J=6.9 Hz), 134.9 (d, J=6.9 Hz), 134.3, 134.1, 133.9, 133.7, 133.4, 131.8, 130.9 (d, J=11.5 Hz), 129.0 (d, J=4.6 Hz), 128.6 (d, J=6.9 Hz), 128.2, 128.0, 126.8, 126.6, 126.2, 125.83, 125.77, 125.5, 121.5, 38.8 (d, J=11.5 Hz).

$^{31}P\{^1H\}$ NMR (121 MHz, $CDCl_3$): δ −21.7.

4,4'-phenylphosphindiyl-bis($\eta^5$-1-naphthylindene) zirconium dichloride (P4)

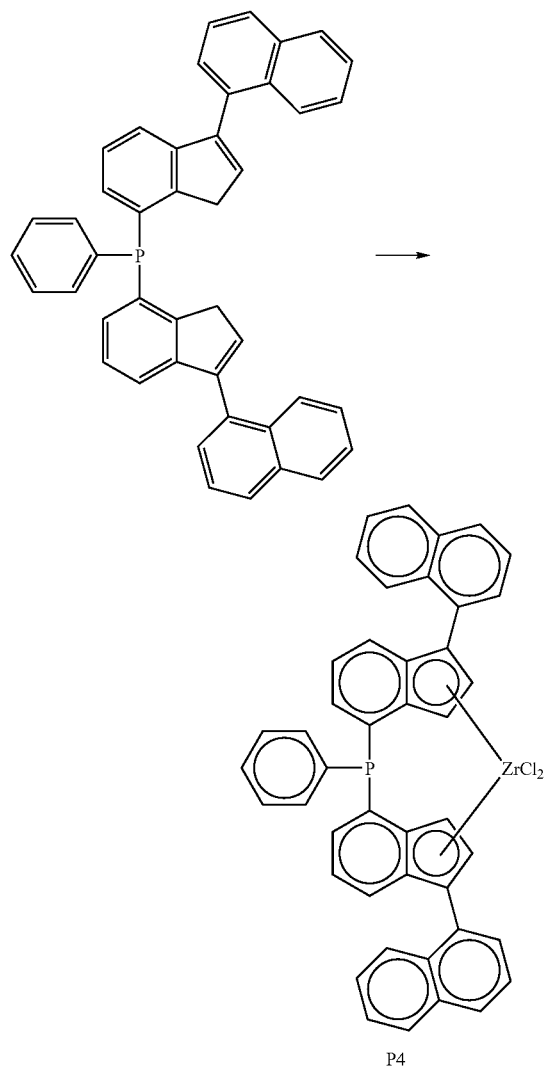

P4

Under an argon atmosphere, to a solution of 8.72 g (14.8 mmol) of bis[3-(1-naphthyl)-1H-inden-7-yl](phenyl)phosphine in 250 ml of toluene, 12.5 ml of 2.5 M (31.3 mmol) $^n$BuLi in hexanes was added with vigorous stirring at ambient temperature. This mixture was stirred for 5 hours; then, 8.00 g (33.1 mmol) of triethyltin chloride was added. The resulting mixture was stirred overnight and then filtered through Celite 503. The filtrate was evaporated to ca. 200 ml, and 3.44 g (14.8 mmol) of $ZrCl_4$ was added. The resulting mixture was stirred for 1 hour at room temperature and 7 hours at 100° C. The obtained orange solution was filtered through glass frit (G4) at 100° C. Crystals precipitated from the filtrate at room temperature, and were separated, washed with cold toluene, and dried in vacuum. An additional amount of the product was obtained from the toluene solution. It was evaporated to ca. 50 ml, and crystals that precipitated at 5° C. were collected, washed with cold toluene, and dried in vacuum. Yield, 3.42 g (31%) of a yellow crystalline solid.

Anal. calc. for $C_{44}H_{29}Cl_2PZr$: C, 70.39; H, 3.89. Found: C, 70.55; H, 3.99.

$^1$H NMR (300 MHz, $CD_2Cl_2$): δ 8.33 (ddd, $J_{PH}$=14.9 Hz, J=6.6 Hz, J=1.0 Hz, 1H, 4-H in Ph), 8.09 (dd, J=7.1 Hz, J=1.2 Hz, 1H, 5-H in indenyl), 8.00 (dd, J=7.2 Hz, J=1.2 Hz, 1H, 5'-H in indenyl), 7.88-7.95 (m, 4H, 2,2',8,8'-H in naphthyl), 7.74-7.81 and 7.25-7.56 (m, 15H, 3,3',4,4',5,5',6,6',7,7'-H in naphthyl and 2,3,5,6-H in Ph), 7.62 (dd, J=8.3 Hz, J=2.6 Hz, 1H, 6-H in indenyl), 7.59 (dd, J=8.3 Hz, J=2.6 Hz, 1H, 6'-H in indenyl), 6.88 (d, J=3.5 Hz, 1H, 2-H in indenyl), 6.85 (d, J=3.4 Hz, 1H, 2'-H in indenyl), 4.91 (dd, J=3.4 Hz, $J_{PH}$=0.9 Hz, 1H, 3-H in indenyl), 4.75 (m, 1H, 3'-H in indenyl).

$^{13}C\{^1H\}$ NMR (75 MHz, $CD_2Cl_2$): δ 140.6, 140.0, 138.5 (d, J=11.5 Hz), 135.7, 135.5, 135.2, 134.5 (d, J=13.8 Hz), 133.6 (d, J=6.9 Hz), 132.6, 132.0, 131.8 (d, J=71.3 Hz), 130.8 (d, J=6.9 Hz), 130.5, 130.3 (d, J=6.9 Hz), 130.2 (d, J=6.2 Hz), 129.7 (d, J=4.6 Hz), 129.4, 127.5 (d, J=6.5 Hz), 127.4, 127.2 (d, J=6.7 Hz), 127.0, 105.8, 104.5 (d, J=4.6 Hz).

$^{31}P\{^1H\}$ NMR (121 MHz, $CD_2Cl_2$): δ −8.0.

Example 12

Synthesis of 4,4'-sulfandiyl-bis($\eta^5$-2-methyl-1-phenylindenyl)zirconium dichloride (S5)/

Dioxalane-protected 4-bromo-2-methylindanone

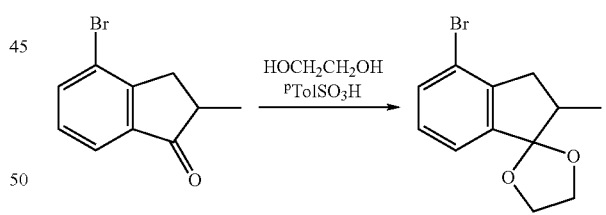

A mixture of 61.4 g (0.272 mol) of 4-bromo-2-methyl-1-indanone, 31.0 ml (34.5 g, 0.556 mol) of ethylene glycol, 5.2 g of para-toluenesulfonic acid, and 500 ml of toluene was refluxed for 10 hours in a round-bottom flask equipped with a Dean-Stark trap. The reaction mixture was washed with 200 ml of saturated aqueous $NaHCO_3$. The organic layer was separated, dried over $Na_2SO_4$, and evaporated to dryness. Fractional distillation gave the title product, b.p. 158° C./10 mm Hg. Yield, 22.9 g (31%) of a colorless oil.

Anal. calc. for $C_{12}H_{13}BrO_2$: C, 53.55; H, 4.87. Found: C, 66.68; H, 4.94.

$^1$H NMR (300 MHz, $CDCl_3$): δ 7.44 (d, J=7.9 Hz, 1H, 5-H), 7.25 (d, J=7.5 Hz, 1H, 6-H), 7.11 (m, 1H, 6-H), 4.02-4.25 (m, 4H, $OCH_2CH_2O$), 3.06 (m, 1H, CHMe), 2.50-2.59 (m, 2H, $CH_2$CHMe), 1.13 (d, J=6.6 Hz, 3H, Me).

$^{13}C\{^1H\}$ NMR (75 MHz, CDCl$_3$): δ 145.0, 142.5, 132.1, 128.6, 121.8, 120.5, 65.8, 65.2, 42.4, 37.9, 13.4.

2-Methyl-4-[(2-methyl-1-oxo-2,3-dihydro-1H-inden-4-yl)sulfanyl]-1-indanone

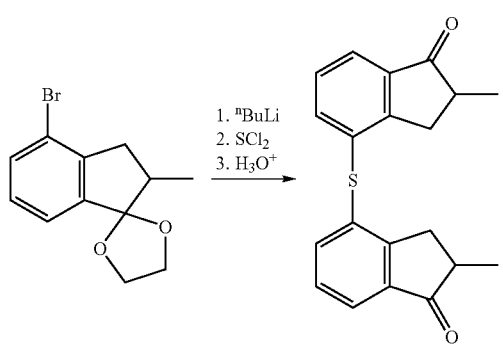

Under an argon atmosphere, following the procedure described for bis(2-methyl-1H-inden-7-yl)sulfide, 22.9 g (85.2 mmol) of the above-described dioxalane-protected 4-bromo-2-methylindanone in 150 ml of THF, 34.1 ml of 2.5 M (85.3 mmol) $^n$BuLi in hexanes, and 4.39 g (42.6 mmol) of SCl$_2$ in 35 ml of hexanes gave crude dioxalane-protected 2-methyl-4-[(2-methyl-1-oxo-2,3-dihydro-1H-inden-4-yl)sulfanyl]-1-indanone, which was deprotected in a mixture of 150 ml of 16 M HCl and 150 ml of methanol for 7 hours at reflux. The product was isolated by flash chromatography on Silica Gel 60 (40-63 μm, d 35 mm, l 400 mm, eluant: CH$_2$Cl$_2$) and then recrystallized from hexanes. Yield, 3.53 g (26%) of a white solid.

Anal. calc. for C$_{20}$H$_{18}$O$_2$S: C, 74.50; H, 5.63. Found: C, 74.35; H, 5.56.

$^1$H NMR (300 MHz, CDCl$_3$): δ 7.70 (d, J=7.2 Hz, 2H, 7-H), 7.32-7.41 (m, 4H, 5,6-H), 3.34 (dd, J=17.6 Hz, J=7.9 Hz, 2H, 3-H), 2.74 (m, 2H, 2-H), 2.63 (m, 2H, 3'-H), 1.32 (d, J=7.3 Hz, 6H, 2-Me).

Bis(2-methyl-3-phenyl-1H-inden-7-yl) sulfide

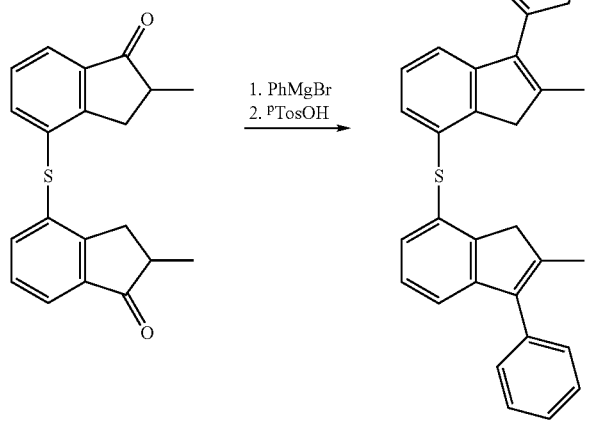

Under an argon atmosphere, to a solution of 3.20 g (9.93 mmol) of 2-methyl-4-[(2-methyl-1-oxo-2,3-dihydro-1H-inden-4-yl)sulfanyl]-1-indanone in 20 ml of ether, a solution of PhMgBr in ether [obtained from 0.73 g (30.0 mmol) of magnesium turnings, 4.77 g (30.4 mmol) of bromobenzene, and 30 ml of ether] was added dropwise with vigorous stirring at 0° C. This mixture was stirred overnight and then added to 50 ml of water. Then, to this mixture 12 M HCl (to pH 1) was added. The organic layer was separated; and the aqueous layer was extracted with 3×20 ml of dichloromethane. The combined extract was evaporated, and a mixture of the residue and 0.5 g para-toluenesulfonic acid in 150 ml benzene was refluxed for 1 hour. The resulting mixture was washed with 50 ml of saturated aqueous NaHCO$_3$. The organic layer was separated, dried over Na$_2$SO$_4$, and evaporated to dryness. The product was isolated by flash chromatography on Silica Gel 60 (40-63 μm, d 35 mm, l 300 mm, eluant: hexanes-CH$_2$Cl$_2$=1:2, vol.). Yield, 2.20 g (50%) of a yellowish solid.

Anal. calc. for C$_{32}$H$_{26}$S: C, 86.83; H, 5.92. Found: C, 86.70; H, 5.85.

$^1$H NMR (300 MHz, CDCl$_3$): δ 7.33-7.49 (m, 10H, 4,5-H in indenyl and 2,4,6-H in Ph), 7.13-7.19 (m, 4H, 3,5-H in Ph), 7.03 (dd, J=6.9 Hz, J=1.8 Hz, 2H, 6-H in indenyl), 3.43 (s, 4H, CH$_2$), 2.14 (s, 6H, Me).

$^{13}C\{^1H\}$ NMR (75 MHz, CDCl$_3$): δ 147.0, 143.3, 141.1, 138.5, 135.3, 129.2, 129.1, 128.4, 127.4, 127.1, 126.7, 118.4, 42.9, 14.9.

4,4'-sulfandiyl-bis(η$^5$-2-methyl-1-phenylindenyl) zirconium dichloride (S5)

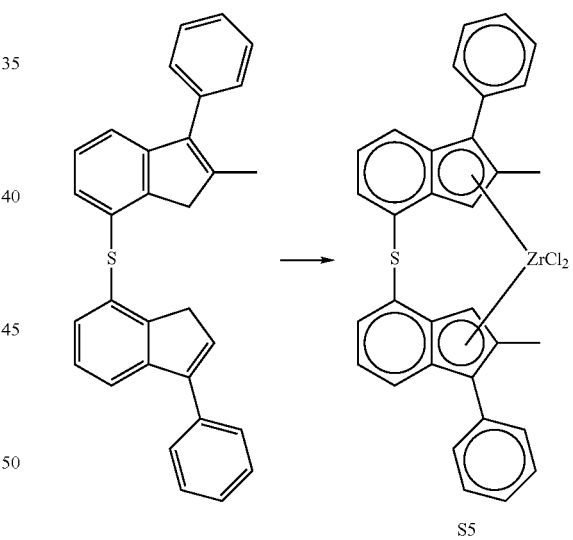

S5

Under an argon atmosphere, to a solution of 1.66 g (3.75 mmol) of bis(2-methyl-3-phenyl-1H-inden-7-yl) sulfide in 100 ml of toluene, 3.0 ml of 2.5 M (7.50 mmol) $^n$BuLi in hexanes was added with vigorous stirring. This mixture was stirred for 5 hours; then, 1.90 g (7.87 mmol) of triethyltin chloride was added. The resulting mixture was stirred overnight and then filtered through Celite 503. To the filtrate 0.87 g (3.75 mmol) of ZrCl$_4$ was added. This mixture was stirred for 1 hour at room temperature, then for 7 hours at 100° C. and filtered through glass frit (G4) at 80-90° C. Crystals precipitated from the filtrate at 5° C., and were separated, washed with cold toluene, and dried in vacuum. Yield, 0.62 g (27%) of an orange crystalline solid.

Anal. calc. for $C_{32}H_{24}Cl_2SZr$: C, 63.77; H, 4.01. Found: C, 63.91; H, 4.11.

$^1$H NMR (300 MHz, CDCl$_3$): δ 7.83 (s, 2H, 3,3'-H), 7.49-7.54 (m, 4H, 2,2',6,6'-H in Ph), 7.37-7.44 (m, 4H, 3,3',5,5'-H in Ph), 7.27-7.34 (m, 4H, 5,5'-H in indenyl and 4,4'-H in Ph), 7.25 (dd, J=6.9 Hz, J=0.8 Hz, 2H, 7,7'-H in indenyl), 6.97 (dd, J=6.9 Hz, J=8.6 Hz, 2H, 6,6'-H in indenyl), 2.34 (s, 6H, 2,2'-Me)

$^{13}$C{$^1$H} NMR (75 MHz, CDCl$_3$): δ 141.6, 136.5, 134.5, 133.9, 132.2, 132.1, 130.0, 129.7, 129.1, 126.8, 125.4, 103.6, 18.3.

Example 13

Synthesis of 4,4'-sulfandiyl-bis(η$^5$-4-bromo-6-methylindenyl)zirconium dichloride (10)

3,6-Dibromotoluene

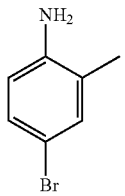 1. NaNO$_2$, HBr
2. CuBr, HBr
→ 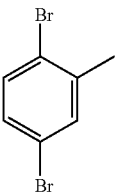

In a 2000 ml beaker containing 400 ml of 23% aqueous HBr, 46.5 g (0.25 mol) of melted 2-methyl-4-bromoaniline was slowly added. This mixture was stirred for 20 minutes using a mechanical stirrer, then cooled to −5° C. Then a solution of 22.4 g (0.33 mol) of NaNO$_2$ in 130 ml of water was added dropwise over 1 hour at this temperature. The diazonium reagent obtained was added in several portions to a solution of 35.9 g (0.25 mmol) of CuBr in 100 ml of 47% HBr at 0° C. The resulting mixture was warmed to 70° C., stirred for 30 minutes at this temperature, and, then, cooled to room temperature. The product was extracted with 3×200 ml of methyl-tert-butyl ether. The combined extract was dried over K$_2$CO$_3$ and evaporated to dryness. Firstly, the crude product was purified using short column with Silica Gel 60 (40-63 µm, d 60 mm, 1 40 mm; eluant:hexanes). Fractional distillation gave colorless oil, b.p. 100-102° C./10 mm Hg. Yield, 36.1 g (58%).

Anal. calc. for $C_7H_6Br_2$: C, 33.64; H, 2.42. Found: C, 33.79; H, 2.50.

$^1$H NMR (300 MHz, CDCl$_3$): δ 7.39 (m, 1H, 5-H), 7.37 (m, 1H, 3-H), 7.18 (m, 1H, 6-H), 2.38 (s, 3H, Me).

$^{13}$C NMR (75 MHz, CDCl$_3$): δ 139.9, 133.6, 133.5, 130.3, 123.5, 120.9, 22.7.

3,6-Dibromobenzylbromide

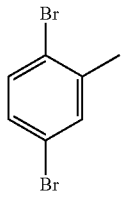 Br$_2$, hv → 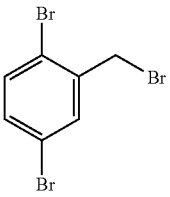

In a 250 ml three-necked round-bottom flask equipped with a reflux condenser, thermometer, a pressure-equalizing dropping funnel, a magnetic stirring bar, and 74.9 g (0.30 mol) of 3,6-dibromotoluene, 15.5 ml (47.9 g, 0.30 mmol) of bromine was added dropwise under exposure to 500 W lamp for 3 hours at 190° C. The resulting mixture was cooled to room temperature. Fractional distillation gave a colorless liquid, b.p. 132-135° C./3 mm Hg. Yield, 84.3 g (85%).

Anal. calc. for $C_7H_5Br_3$: C, 25.57; H, 1.53. Found: C, 25.81; H, 1.62.

$^1$H NMR (300 MHz, CDCl$_3$): δ 7.59 (m, 1H, 5-H), 7.43 (m, 1H, 3-H), 7.28 (m, 1H, 3-H), 4.52 (s, 2H, CH$_2$).

$^{13}$C NMR (75 MHz, CDCl$_3$): δ 138.9, 134.6, 134.0, 133.1, 123.0, 121.5, 32.2.

3-(2,5-Dibromophenyl)-2-methylpropionic acid, 3-(2,5-dibromophenyl)-2-methylpropionyl chloride, and 4,7-dibromo-2-methyl-1-indanone

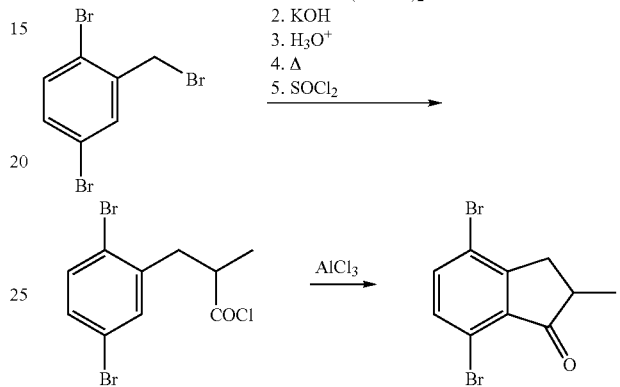

In a 1000 ml three-necked round-bottom flask equipped with a reflux condenser, a pressure-equalizing dropping funnel, and magnetic stirring bar, 6.10 g (0.27 mol) of sodium metal was dissolved in 150 ml of dry ethanol. To the resulting solution, 45.5 g (0.26 mol) of diethylmethylmalonate in 50 ml of dry ethanol was added dropwise within 10 min. This mixture was stirred for 15 min; then 84.3 g (0.26 mol) of 3,6-dibromobenzylbromide was added with vigorous stirring at such a rate, so that the reaction mixture was maintained at a gentle reflux. Additionally, this mixture was refluxed for 4 hours and, then, cooled to room temperature. A solution of 52.1 g of KOH in 140 ml of water was added. This mixture was refluxed for 3 hours to saponificate the ester formed. Ethanol and water were distilled off. To the residue, 200 ml of water and, then, 12 M HCl (to pH 1) were added. The substituted methylmalonic acid precipitated, and was separated, washed with 3×100 ml of cold water, and dried overnight on a watch glass. Crude 3-(2,5-dibromophenyl)-2-methylpropionic acid was obtained after decarboxylation of this substituted methylmalonic acid by heating it in a round bottom flask for 2 hours at 160° C. Crude 3-(2,5-dibromophenyl)-2-methylpropionic acid was used without further purification. A mixture of this acid, 70 ml of SOCl$_2$, and 100 ml of CH$_2$Cl$_2$ was stirred for 3 hours at reflux. Thionyl chloride and CH$_2$Cl$_2$ were distilled off. The residue was dried in vacuum and, then, dissolved in 95 ml of CH$_2$Cl$_2$. To a suspension of 47.0 g (0.35 mol) of AlCl$_3$ in 470 ml of CH$_2$Cl$_2$ the above-obtained solution of 3-(2,5-dibromophenyl)-2-methylpropionyl chloride was added dropwise with vigorous stirring for 1 hour at −20° C. This mixture was refluxed for 3 hours, cooled to ambient temperature, and, then, poured on 500 cm$^3$ of ice. The organic layer was separated. The aqueous layer was extracted with 3×200 ml of methyl-tert-butyl ether. The combined extract was dried over K$_2$CO$_3$ and evaporated to dryness. The crude 4,7-dibromo-2-methyl-1-indanone was purified by flash chromatography on Silica Gel 60 (40-63 µm, d 50 mm, h 250 mm; eluant:hexanes/methyl-tert-butyl ether (1:1, vol.)). Yield, 54.1 g (70%).

Anal. calc. for $C_{10}H_8Br_2O$: C, 39.51; H, 2.65. Found: C, 39.40; H, 2.58.

¹H NMR (300 MHz, CDCl₃): δ 7.52 (d, J=8.4 Hz, 1H, 6-H), 7.37 (d, J=8.4 Hz, 1H, 5-H), 3.27 (dd, J=17.7 Hz, J=8.0 Hz, 1H, 3-H), 3.73 (m, 1H, 2-H), 2.58 (dd, J=17.7 Hz, J=4.2 Hz, 1H, 3'-H), 1.31 (d, J=7.3 Hz, 3H, 2-Me).

¹³C NMR (75 MHz, CDCl₃): δ 205.5, 155.4, 137.6, 135.3, 133.9, 121.0, 118.6, 42.6, 35.3, 16.1.

4,7-Dibromo-2-methyl-1-indanol and a mixture of cis- and trans-4,7-dibromo-1-methoxy-2-methylindane

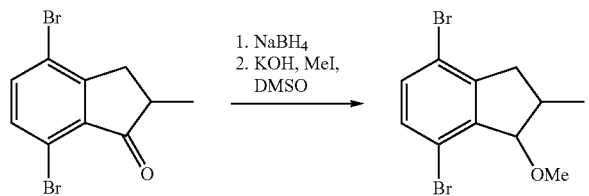

To a solution of 54.1 g (0.178 mol) of 4,7-dibromo-2-methyl-1-indanone in 240 ml of THF-methanol (2:1, vol.), 9.40 g (0.248 mol) of NaBH₄ was added in small portions at –5° C. The resulting mixture was stirred overnight at ambient temperature and, then, poured on 500 cm³ of ice. Then, 1 M HCl (to pH 4) was added. The organic layer was separated; and the aqueous layer was extracted with 3×200 ml of methyl-tert-butyl ether. The combined extract was dried over K₂CO₃ and evaporated to dryness. To a mixture of 40 g of KOH and 140 ml of DMSO, 22.3 ml (50.8 g, 0.358 mol) of MeI, followed immediately with the crude 4,7-dibromo-2-methyl-1-indanol dissolved in 70 ml of DMSO were added at ambient temperature. The resulting mixture was stirred for 3 hours and, then, poured on 2500 cm³ of cold water. The organic layer was separated. The aqueous layer was extracted with 3×200 ml of methyl-tert-butyl ether. The combined extract was washed twice with 500 ml of water, dried over K₂CO₃, and evaporated to dryness. Fractional distillation gave yellowish liquid, b.p. 121-125° C./2 mm Hg. Yield, 50.1 g (88%) of 1 to 1 mixture of two diastereomeric compounds.

Anal. calc. for C₁₁H₁₂Br₂O: C, 41.28; H, 3.78. Found: C, 41.10; H, 3.69.

¹H NMR (300 MHz, CDCl₃): δ 7.23 (m, 4H, 5,6-H in cis- and trans-products), 4.63 (d, J=5.6 Hz, 1H, 1-H in trans-product), 4.47 (d, J=1.5 Hz, 1H, 1-H in cis-product), 3.53 (s, 3H, MeO in trans- or cis-product), 3.45 (s, 3H, MeO in cis- or trans-product), 3.34 (dd, J=16.7 Hz, J=7.3 Hz, 1H, 3-H in trans- or cis-products), 2.98 (dd, J=16.4 Hz, J=7.6 Hz, 1H, 3-H in cis- or trans-product), 2.78 (dd, J=16.4 Hz, J=9.7 Hz, 1H, 3'-H in cis- or trans-product), 2.52 (m, 2H, 2-H in cis- and trans-products), 2.51 (dd, J=16.7 Hz, J=2.4 Hz, 1H, 3'-H in trans- or cis-product), 1.24 (d, J=7.0 Hz, 3H, 2-Me in trans- or cis-product), 1.06 (d, J=7.3 Hz, 3H, 2-Me in cis- or trans-product).

¹³C NMR (75 MHz, CDCl₃): δ 146.8, 146.0, 145.0, 142.8, 133.1, 132.7, 131.7, 131.4, 131.3, 131.1, 130.1, 129.7, 92.3, 86.8, 59.0, 57.0, 40.8 (two resonances), 38.5, 36.4, 19.5, 13.3.

Bis(4-bromo-2-methyl-1H-inden-7-yl) sulfide

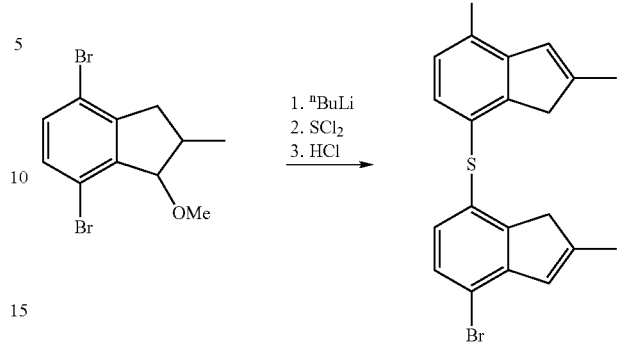

Under an argon atmosphere, in a 500 ml three-necked round-bottom flask equipped with a reflux condenser, a pressure-equalizing dropping funnel, a magnetic stirring bar, and containing a solution of 48.55 g (152 mmol) of 4,7-dibromo-1-methoxy-2-methylindane in 250 ml of THF, 60.7 ml of 2.50 M ⁿBuLi (152 mmol) in hexanes was added dropwise with vigorous stirring for 30 min at –78° C. Then a solution of 7.81 g (75.9 mmol) of freshly distilled SCl₂ in 50 ml of hexanes was added dropwise with vigorous stirring for 15 min at –94° C. The reaction mixture was warmed slowly for 1 hour to ambient temperature; then 10 ml of water was added dropwise with vigorous stirring. The methoxy-disulfide was extracted with 3×300 ml of diethyl ether. The combined extract was washed with 2×400 ml of cold water and evaporated to dryness. The residue was dissolved in a mixture of 250 ml of methanol and 250 ml of 12 M HCl. The resulting mixture was refluxed for 6 hours and, then, cooled to ambient temperature. The crude product was extracted with 2×250 ml of CH₂Cl₂. The combined extract was evaporated to dryness; and the residue was purified using flash chromatography on Silica Gel 60 (40-63 μm, d 50 mm, l 500 mm; eluant: hexanes-CH₂Cl₂ (4:1, vol.)). Yield, 7.65 g (23%) of a white solid.

Anal. calc. for C₂₀H₁₆Br₂S: C, 53.59; H, 3.60. Found: C, 53.87; H, 3.77.

¹H NMR (300 MHz, CDCl₃): δ 7.11 (d, J=8.2 Hz, 2H, 5,5'-H), 6.90 (d, J=8.2 Hz, 2H, 6,6'-H), 6.67 (m, 2H, 3,3'-H), 3.32 (m, 4H, 1,1'-CH₂), 2.16 (m, 6H, 2,2'-Me).

¹³C NMR (75 MHz, CDCl₃): δ 148.0, 143.7, 131.1, 128.6, 127.5, 126.0, 124.8, 117.3, 44.9, 16.9.

4,4'-sulfandiyl-bis(η⁵-7-bromo-2-methylindenyl) zirconium dichloride (10)

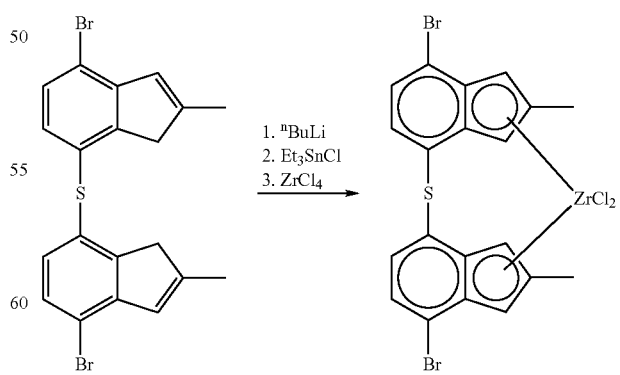

In an argon atmosphere Glove Box, to a solution of 7.65 g (17.1 mmol) of bis(4-bromo-2-methyl-1H-inden-7-yl) sulfide in a mixture of 250 ml of diethyl ether and 70 ml of DME, 14.0 ml of 2.50 M ⁿBuLi (35.0 mmol) in hexanes was added with vigorous stirring for 2 hours at ambient temperature. This mixture was stirred additionally for 1 hour; then 10.0 g (41.4 mmol) of Et$_3$SnCl was added in one portion. The resulting mixture was stirred overnight and, then, evaporated to dryness. The residue was dissolved in 250 ml of toluene. The suspension formed was filtered through a glass frit (G4). To the filtrate, 4.18 g of ZrCl$_4$ was added. The resulting mixture was stirred for 7 hours at 100° C. The hot suspension was filtered through a glass frit (G4). Red crystals precipitated from the filtrate at 0° C., and were separated, washed with 15 ml of cold toluene, and dried in vacuum. Yield, 2.50 g (24%).

Anal. calc. for C$_{20}$H$_{14}$Br$_2$Cl$_2$SZr: C, 39.49; H, 2.32. Found: C, 39.17; H, 2.22.

$^1$H NMR (300 MHz, CD$_2$Cl$_2$): δ 6.84 (d, J=7.5 Hz, 2H, 5,5'-H), 6.78 (d, J=7.5 Hz, 2H, 6,6'-H), 6.30 (d, J=2.4 Hz, 2H, 3,3'-H), 4.42 (d, J=2.4 Hz, 2H, 1,1'-H), 1.83 (s, 6H, 2,2'-Me).

Figure 3:
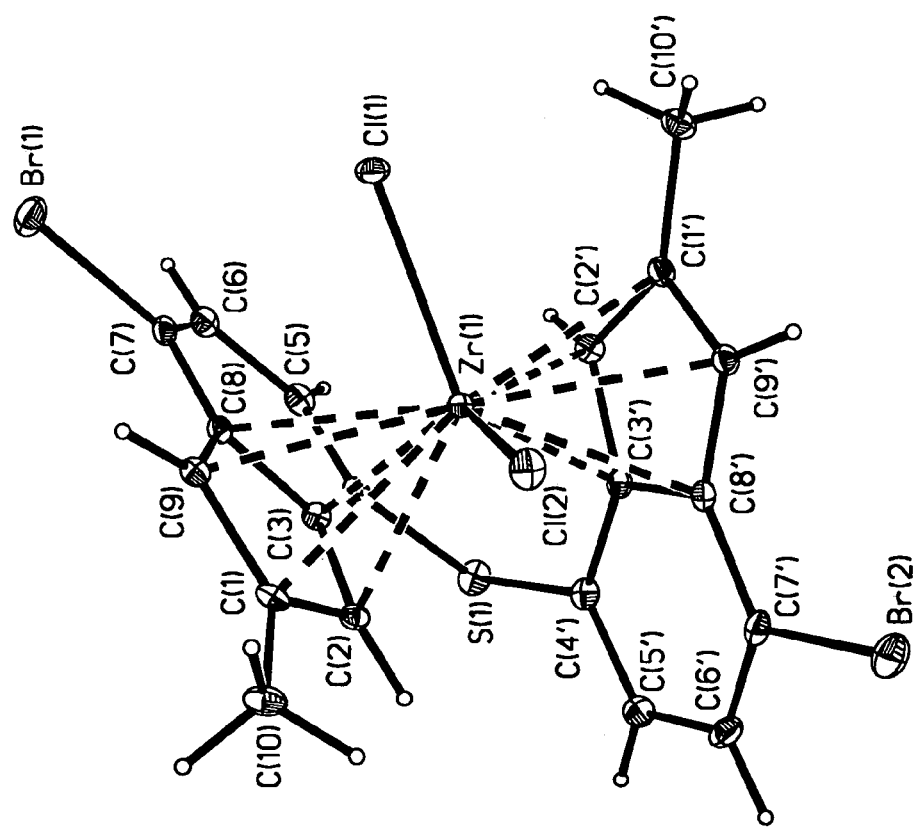
FIG. 3 is a drawing of 4,4'-sulfandiyl-bis($\eta^5$-7-bromo-2-methylindenyl)zirconium dichloride (10).

The X-ray crystal structure of this compound was determined, and its molecular structure is represented in FIG. 3.

Examples 14-27

Negishi coupling using 4,4'-sulfandiyl-bis(η$^5$-7-bromo-2-methylindenyl)zirconium dichloride (10)

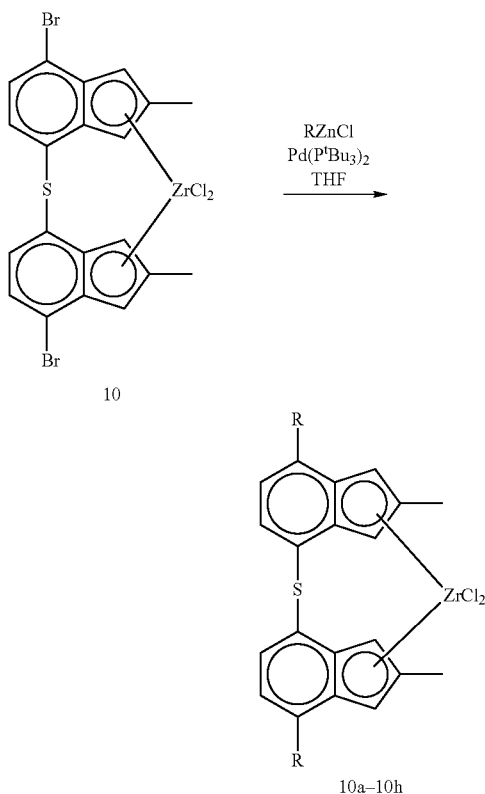

R=Me (10a), Ph (10b), 4-MeC$_6$H$_4$ (10c), 3-MeC$_6$H$_4$ (10d), 4-$^t$BuC$_6$H$_4$ (10e), 2,4,6Me$_3$C$_6$H$_2$ (10f), 5-Me-2-thienyl (10g), 5-Me-2-furyl (10h), 2-benzothiopheneyl (10i), 2-benzofuranyl (10k), 4-FC$_6$H$_4$ (10l), 3-CF$_3$C$_6$H$_4$ (10m), 2,5-dimethylphenyl (10n), 4-biphenyl (10o).

Example 14

4,4'-sulfandiyl-bis(η$^5$-2,7-dimethylindenyl)zirconium dichloride (10a)

Under a nitrogen atmosphere, in a 16 ml vial equipped with PTFE coated stir bar and a suspension of 286 mg (0.47 mmol) of 10 in 8.0 ml of THF, 0.61 ml of 2.0 M MeZnCl (1.22 mmol) in THF and 0.94 ml of 0.02 M (0.019 mmol) Pd(P$^t$Bu$_3$)$_2$ in THF were added by a dosing pipette. The reaction mixture was stirred for 2 hours at 70° C. and then evaporated to dryness. To the residue, a solution of 1.0 ml of MeSiCl3 in 10 ml of dry dichloromethane was added to eliminate an excess of the organozinc reagent. The resulting mixture was stirred at ambient temperature for 1 hour and then evaporated to dryness. In order to eliminate THF contamination, toluene (20 ml) was added and the mixture was vigorously stirred and brought to reflux; then the suspension was evaporated to dryness. This procedure was repeated a second time using 60 ml of toluene, and the resulting suspension was filtered through Celite 503. The resulting toluene filtrate was evaporated to dryness. The obtained solid was washed with 3×15 ml of hexanes and dried in vacuum. Yield, 210 mg (93%) of a yellow solid.

Anal. calc. for C22H20Cl2SZr: C, 55.21; H, 4.21. Found: C, 55.35; H, 4.16.

$^1$H NMR (300 MHz, CD$_2$Cl$_2$): δ 7.51 (d, J=7.1 Hz, 2H, 5,5'-H), 6.95 (m, 2H, 6,6'-H), 6.39 (d, J=2.3 Hz, 2H, 1,1'-H), 4.52 (d, J=2.3 Hz, 2H, 3,3'-H), 2.52 (s, 6H, 7,7'-Me), 2.06 (s, 6H, 2,2'-Me).

$^{13}$C{$^1$H} NMR (75 MHz, CD$_2$Cl$_2$): δ 143.6, 143.2, 132.8, 130.3, 127.0, 125.3, 110.9, 106.4, 105.1, 21.3, 18.6.

Figure 4:
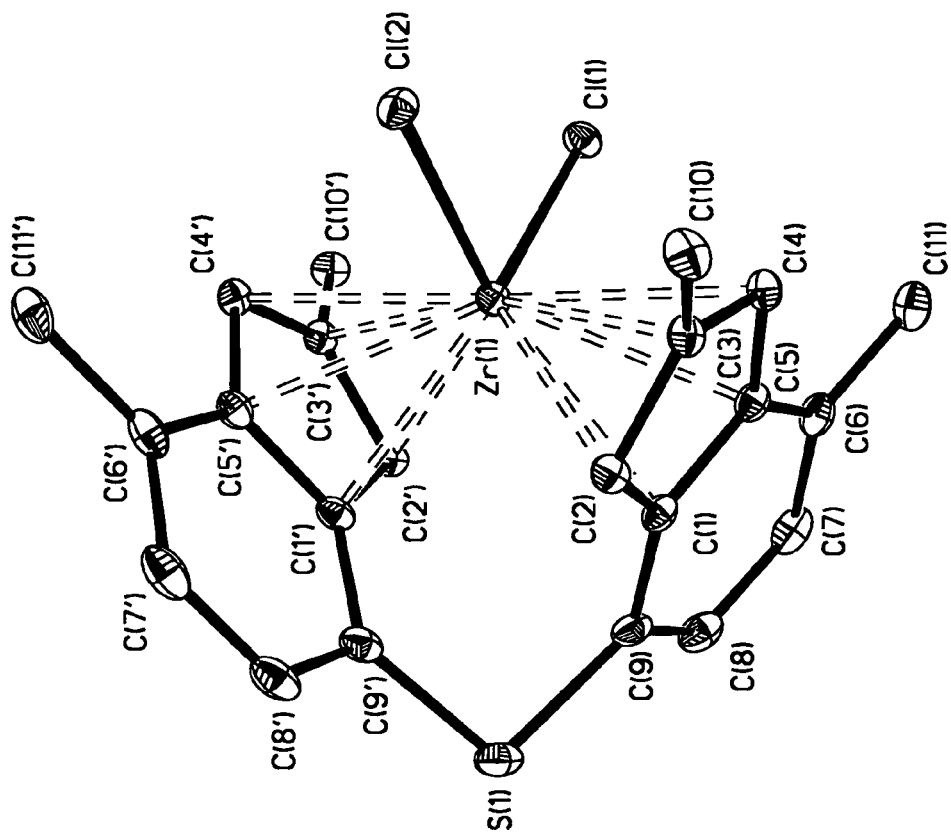
FIG. 4 is a drawing of 4,4'-sulfandiyl-bis($\eta^5$-2,7-dimethylindenyl)zirconium dichloride (10a).

The X-ray crystal structure of this compound was determined, and its molecular structure is represented in FIG. 4.

Example 15

4,4'-sulfandiyl-bis(η$^5$-7-phenyl-2-methylindenyl) zirconium dichloride (10b)

Under a nitrogen atmosphere, in a 16 ml vial equipped with PTFE coated stir bar, 0.57 ml of 1.0 M (0.57 mmol) phenylmagnesium bromide in THF was added by a dosing pipette to a mixture of 1.25 ml of 0.5 M (0.63 mmol) ZnCl$_2$ in THF and 5 ml of THF with vigorous stirring at ambient temperature. This organozinc reagent was additionally stirred for 1 hour and then added to a mixture of 133 mg (0.22 mmol) of 10, 0.44 ml of 0.02 M (0.009 mmol) Pd(P$^t$Bu$_3$)$_2$ in THF, and 2 ml of THF placed in a separate 16 ml vial equipped with PTFE coated stir bar. The reaction mixture was stirred for 2 hours at 70° C. and then evaporated to dryness. To the residue, a solution of 1.0 ml of MeSiCl$_3$ in 10 ml of dry dichloromethane was added to eliminate an excess of the organozinc reagent. The resulting mixture was stirred at ambient temperature for 1 hour and then evaporated to dryness. In order to eliminate THF contamination, toluene (20 ml) was added and the mixture was vigorously stirred and brought to reflux; then the suspension was evaporated to dryness. This procedure was repeated a second time using 60 ml of toluene, and the resulting suspension was filtered through Celite 503. The resulting toluene filtrate was evaporated to dryness. The obtained solid was washed with 3×15 ml of hexanes and dried in vacuum. Yield, 50 mg (38%) of a yellow solid.

Anal. calc. for C$_{32}$H$_{24}$Cl$_2$SZr: C, 63.77; H, 4.01. Found: C, 63.94; H, 3.92.

$^1$H NMR (300 MHz, CD$_2$Cl$_2$): δ 7.74 (d, J=7.2 Hz, 2H, 5,5'-H), 7.62-7.69 (m, 4H, 2,2',6,6'-H in Ph), 7.33-7.49 (m, 6H, 3,3',4,4',5,5'-H in Ph), 7.23 (d, J=7.2 Hz, 2H, 6,6'-H), 6.59 (d, J=2.2 Hz, 2H, 1,1'-H), 4.80 (d, J=2.2 Hz, 2H, 3,3'-H), 2.08 (s, 6H, 2,2'-Me).

$^{13}$C{$^1$H} NMR (75 MHz, CD$_2$Cl$_2$): δ 143.5, 139.3, 136.0, 134.3, 130.6, 130.0, 129.5, 127.4, 127.2, 122.9, 110.5, 106.1, 103.3, 18.5.

Example 16

4,4'-sulfandiyl-bis(η$^5$-2-methyl-7-p-tolyl-indenyl) zirconium dichloride (10c)

Under a nitrogen atmosphere, following the procedure described for 10b, 0.79 ml of 1.0 M (0.79 mmol) p-tolylmagnesium bromide in THF, 1.74 ml of 0.5 M (0.87 mmol) ZnCl$_2$ in THF, 185 mg (0.30 mmol) of 10, and 0.61 ml of 0.02 M (0.012 mmol) Pd(P$^t$Bu$_3$)$_2$ in THF gave a yellow solid for 2 hours at 70° C. Yield, 104 mg (54%).

Anal. calc. for C$_{34}$H$_{28}$Cl$_2$SZr: C, 64.74; H, 4.47. Found: C, 64.89; H, 4.40.

$^1$H NMR (300 MHz, CD$_2$Cl$_2$): δ 7.72 (d, J=7.4 Hz, 2H, 5,5'-H), 7.52-7.58 (m, 4H, 2,2',6,6'-H in p-tolyl), 7.23-7.29 (m, 4H, 3,3',5,5'-H in p-tolyl), 7.21 (d, J=7.4 Hz, 2H, 6,6'-H), 6.59 (d, J=2.5 Hz, 2H, 1,1'-H), 4.77 (d, J=2.5 Hz, 2H, 3,3'-H), 2.37 (s, 6H, 4,4'-Me in p-tolyl), 2.07 (s, 6H, 2,2'-Me).

$^{13}$C{$^1$H} NMR (75 MHz, CD$_2$Cl$_2$): δ 143.4, 139.6, 139.3, 137.9, 135.6, 130.7, 130.5, 130.0, 127.0, 122.9, 110.5, 106.1, 103.3, 22.5, 18.5.

Figure 5:
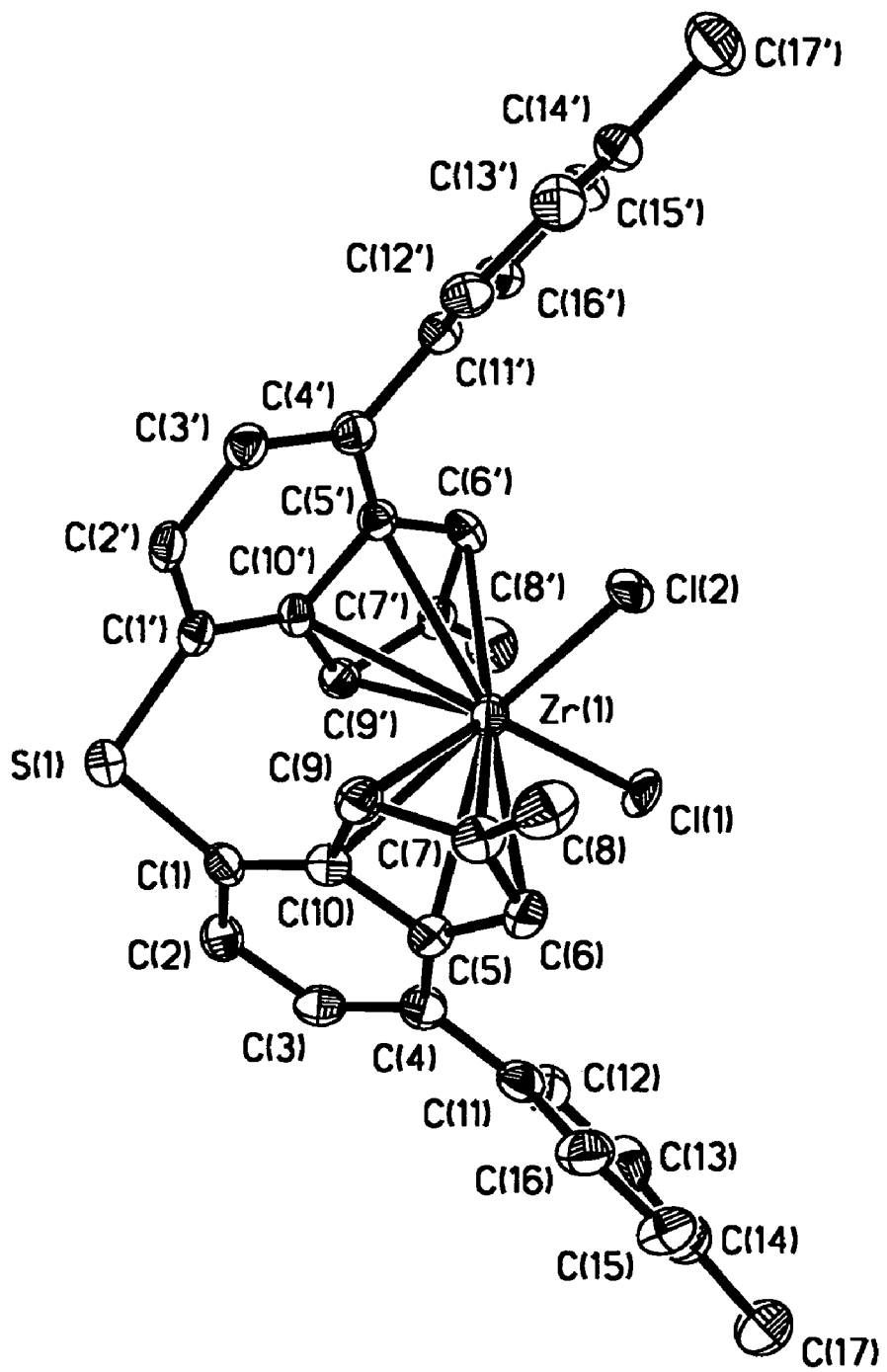
FIG. 5 is a drawing of 4,4'-sulfandiyl-bis($\eta^5$-2-methyl-7-p-tolyl-indenyl)zirconium dichloride (10c).

The X-ray crystal structure of this compound was determined, and its molecular structure is represented in FIG. 5.

Example 17

4,4'-sulfandiyl-bis(η$^5$-2-methyl-7-m-tolylindenyl) zirconium dichloride (10d)

Under a nitrogen atmosphere, following the procedure described for 10b, 0.53 ml of 1.0 M (0.53 mmol) m-tolylmagnesium chloride in THF, 1.16 ml of 0.5 M (0.58 mmol) ZnCl$_2$ in THF, 123 mg (0.20 mmol) of 10, and 0.40 ml of 0.02 M (0.008 mmol) Pd(P$^t$Bu$_3$)$_2$ in THF gave yellow solid for 2 hours at 70° C. Yield, 85 mg (67%).

Anal. calc. for C$_{34}$H$_{28}$Cl$_2$SZr: C, 64.74; H, 4.47. Found: C, 65.03; H, 4.55.

$^1$H NMR (300 MHz, CD$_2$Cl$_2$): δ 7.73 (d, J=7.3 Hz, 2H, 5,5'-H), 7.16-7.52 (m, 10H, 6,6'-H in indenyl and 2,2',4,4',5, 5',6,6'-H in m-tolyl), 6.60 (d, J=2.2 Hz, 2H, 1,1'-H), 4.79 (d, J=2.2 Hz, 2H, 3,3'-H), 2.39 (s, 6H, 4,4'-Me in p-tolyl), 2.09 (s, 6H, 2,2'-Me).

$^{13}$C{$^1$H} NMR (75 MHz, CD$_2$Cl$_2$): δ 143.5, 138.7, 138.6, 136.2, 135.9, 131.3, 130.3, 130.0 (two resonances), 127.8, 127.2, 124.6, 110.7, 106.1, 103.3, 22.8, 18.5.

Example 18

4,4'-sulfandiyl-bis[η$^1$-2-methyl-7-(4-tert-butylphenyl)indenyl]zirconium dichloride (10e)

Under a nitrogen atmosphere, in a 16 ml vial equipped with PTFE coated stir bar, 0.98 ml of 0.8 M (0.78 mmol) 4-tert-butylphenylmagnesium bromide in ether was added by a dosing pipette to a mixture of 0.87 ml of 0.5 M (0.44 mmol) ZnCl$_2$ in THF and 5 ml of THF with vigorous stirring at ambient temperature. This organozinc reagent was additionally stirred for 1 hour and then added to a mixture of 184 mg (0.30 mmol) of 10, 0.61 ml of 0.02 M (0.012 mmol) Pd(P$^t$Bu$_3$)$_2$ in THF, and 2 ml of THF placed in a separate 16 ml vial equipped with PTFE coated stir bar. The reaction mixture was stirred for 2 hours at 70° C. and then evaporated to dryness. The product was extracted with 3×30 ml of hexanes. The yellow solution was evaporated to dryness, and the residue was washed with 10 ml of cold hexanes and dried in vacuum. Yield, 176 mg (81%) of a yellow solid.

Anal. calc. for C$_{40}$H$_{40}$Cl$_2$SZr: C, 67.20; H, 5.64. Found: C, 67.48; H, 5.74.

$^1$H NMR (300 MHz, CD$_2$Cl$_2$): δ 7.72 (d, J=7.3 Hz, 2H, 5,5'-H), 7.59-7.67 (m, 4H, 2,2',6,6'-H in C$_6$H$_4$), 7.40-7.48 (m, 4H, 3,3',5,5'-H in C$_6$H$_4$), 7.23 (d, J=7.3 Hz, 2H, 6,6'-H), 6.62 (d, J=2.3 Hz, 2H, 1,1'-H), 4.80 (d, J=2.3 Hz, 2H, 3,3'-H), 2.08 (s, 6H, 2,2'-Me), 1.33 (s, 18H, $^t$Bu).

$^{13}$C{$^1$H} NMR (75 MHz, CD$_2$Cl$_2$): δ 143.5, 139.3, 138.6, 137.9, 135.6, 130.3, 130.0, 128.1, 127.0, 118.2, 110.7, 106.2, 104.6, 36.2, 32.7, 18.5.

Example 19

4,4'-sulfandiyl-bis(η$^5$-7-mesityl-2-methylindenyl) zirconium dichloride (10f)

Under a nitrogen atmosphere, following the procedure described for 10b, 0.97 ml of 0.88 M (0.85 mmol) mesitylmagnesium bromide in THF, 1.88 ml of 0.5 M (0.94 mmol) ZnCl$_2$ in THF, 200 mg (0.33 mmol) of 10, and 0.66 ml of 0.02 M (0.013 mmol) Pd(P$^t$Bu$_3$)$_2$ in THF gave yellow solid for 2 hours at 70° C. Yield, 214 mg (95%).

Anal. calc. for C$_{38}$H$_{36}$Cl$_2$SZr: C, 66.45; H, 5.28. Found: C, 66.11; H, 5.39.

$^1$H NMR (300 MHz, CD$_2$Cl$_2$): δ 7.71 (d, J=7.3 Hz, 2H, 5,5'-H of indenyl), 7.06 (d, J=7.3 Hz, 2H, 6,6'-H of indenyl), 6.96 (m, 2H, 3,3'-H of mesityl), 6.91 (m, 2H, 3,3'-H of mesityl), 6.04 (m, 2H, 1,1'-H of indenyl), 4.87 (m, 2H, 3,3'-H of indenyl), 2.29 (s, 6H, 2,2'-Me of mesityl), 2.19 (s, 6H, 4,4'-Me of mesityl), 2.08 (s, 6H, 6,6'-Me of mesityl), 1.84 (s, 6H, 2,2'-Me of indenyl).

$^{13}$C{$^1$H} NMR (75 MHz, CD$_2$Cl$_2$): δ 143.0, 138.9, 138.1, 137.8, 136.1, 135.6, 132.4, 130.3, 129.9, 129.5, 129.0, 123.1, 112.7, 111.2, 104.5, 23.3, 22.4, 21.9, 18.4.

Example 20

4,4'-sulfandiyl-bis[η$^5$-2-methyl-7-(5-methyl-thien-2-yl)indenyl]zirconium dichloride (10 g)

Under a nitrogen atmosphere, in a 16 ml vial equipped with PTFE coated stir bar to 1.68 ml of 0.51 M (0.86 mmol) of 2-methylthiophene in THF, 1.71 ml of 0.5 M (0.86 mmol) $^n$BuLi in hexanes was added by a dosing pipette with vigorous stirring at −80° C. This mixture was stirred and slowly warmed (for ca. 1 hour) to 0° C. Then, 1.88 ml of 0.5 M (0.94 mmol) ZnCl$_2$ in THF was added at −80° C., and the obtained mixture was stirred and slowly warmed to ambient temperature and then evaporated to dryness. In a separate 16 ml vial equipped with PTFE coated stir bar containing a mixture of 200 mg (0.33 mmol) of 10, 0.66 ml of 0.02 M (0.013 mmol) Pd(P$^t$Bu$_3$)$_2$ in THF, and 4 ml of THF, the above described organozinc reagent was added. This mixture was stirred for 4 hours at room temperature, and then evaporated to dryness. To the residue, a solution of 1.0 ml of MeSiCl$_3$ in 10 ml of dry dichloromethane was added to eliminate an excess of the organozinc reagent. The resulting mixture was stirred at ambient temperature for 1 hour and then evaporated to dryness. In order to eliminate THF contamination, toluene (20 ml) was added and the mixture was vigorously stirred and brought to reflux; then the suspension was evaporated to dryness. This procedure was repeated a second time using 60 ml of toluene, and the resulting suspension was filtered through Celite 503. The resulting toluene filtrate was evaporated to dryness. The obtained solid was washed with 3×15 ml of hexanes and dried in vacuum. Yield, 181 mg (86%) of a yellow solid.

Anal. calc. for $C_{30}H_{24}Cl_2S_3Zr$: C, 56.05; H, 3.76. Found: C, 55.88; H, 3.85.

$^1$H NMR (300 MHz, $CD_2Cl_2$): δ 7.63 (d, J=7.5 Hz, 2H, 5,5'-H of indenyl), 7.46 (d, J=3.6 Hz, 3,3'-H of thienyl), 7.35 (d, J=7.5 Hz, 2H, 6,6'-H of indenyl), 6.84 (d, J=2.4 Hz, 2H, 1,1'-H of indenyl), 6.80 (m, 2H, 4,4'-H of thienyl), 4.79 (d, J=2.4 Hz, 2H, 3,3'-H), 2.51 (s, 6H, 5,5'-Me of thienyl), 2.09 (s, 6H, 2,2'-Me of indenyl).

Example 21

4,4'-sulfandiyl-bis[η$^5$-2-methyl-7-(5-methyl-furan-2-yl)indenyl]zirconium dichloride (10h)

Under a nitrogen atmosphere, following the procedure described for 10 g, 1.41 ml of 0.61 M (0.85 mmol) of 2-methylfuran, 1.71 ml of 0.5 M $^n$BuLi (0.86 mmol), 1.88 ml of 0.5 M (0.94 mmol) $ZnCl_2$ in THF, 200 mg (0.33 mmol) of 10, and 0.66 ml of 0.02 M (0.013 mmol) $Pd(P^tBu_3)_2$ in THF gave a yellow solid. Yield, 162 mg (81%).

Anal. calc. for $C_{30}H_{24}Cl_2O_2SZr$: C, 59.00; H, 3.96. Found: C, 58.78; H, 4.10.

$^1$H NMR (300 MHz, $CD_2Cl_2$): δ 7.65 (d, J=7.6 Hz, 2H, 5,5'-H of indenyl), 7.52 (d, J=7.6 Hz, 2H, 6,6'-H of indenyl), 6.90 (d, J=3.3 Hz, 3,3'-H of furanyl), 6.87 (d, J=2.4 Hz, 2H, 1,1'-H of indenyl), 6.15 (m, 2H, 4,4'-H of furanyl), 4.73 (d, J=2.4 Hz, 2H, 3,3'-H), 2.39 (s, 6H, 5,5'-Me of furanyl), 2.08 (s, 6H, 2,2'-Me of indenyl).

Example 22

4,4'-sulfandiyl-bis[η$^5$-2-methyl-7-(2-benzothiopheneyl)indenyl]zirconium dichloride (10i)

Under a nitrogen atmosphere, to a solution of 115 mg (0.855 mmol) of benzothiophene in 4 ml of THF, 1.71 ml of 0.5 M (0.855 mmol) of $^n$BuLi in hexanes was added at −80° C. The resulted mixture was stirred for 3 hours at room temperature, then cooled to −80° C., and 0.954 ml (0.954 mmol) of 1.0 M $ZnCl_2$ in THF was added. This mixture was slowly warmed to ambient temperature and additionally stirred for 1 hour at this temperature. The solution of organozinc reagent was added to a mixture of 200 mg (0.329 mmol) of 10. Then, 0.825 ml of 0.02 M (0.0165 mmol) $Pd(P^tBu_3)_2$ in THF was added. The cross-coupling reaction was carried out by vigorous stirring for 2 hours at 65° C. Then, this mixture was evaporated to dryness, and 30 ml of toluene was added to the residue. This mixture was heated to 110° C., then evaporated to dryness. To the residue 30 ml of toluene was added, the mixture was heated to 110° C. and filtered through Celite 503. The Celite layer was additionally washed by 2×15 ml of hot toluene. The combined toluene extract was evaporated to dryness. The residue was washed by 2×10 ml of hexanes and dried in vacuum. Yield 175 mg (75%).

Anal. calc. for $C_{36}H_{24}Cl_2S_3Zr$: C, 60.48; H, 3.38. Found: C, 60.69; H, 3.47.

$^1$H NMR (300 MHz, $CD_2Cl_2$): δ 7.84 (d, J=7.6 Hz, 2H, 5,5'-H of indenyl), 7.76 (d, J=7.6 Hz, 2H, 6,6'-H of indenyl), 7.63 (m, 2H, 4/7,4'/7'-H in benzothienyl), 7.55 (m, 2H, 7/4,7'/4'-H in benzothienyl), 7.41 (m, 2H, 3,3'-H in benzothienyl), 7.32 (m, 2H, 5/6,5'/6'-H in benzothienyl), 7.24 (m, 2H, 6/5,6'/5'-H in benzothienyl), 7.05 (m, 2H, 1,1'-H of indenyl), 4.85 (m, 2H, 3,3'-H of indenyl), 2.11 (s, 6H, 2,2'-Me of indenyl).

Example 23

4,4'-sulfandiyl-bis [η$^5$-2-methyl-7-(2-benzofuranyl)indenyl]zirconium dichloride (10 k)

Under a nitrogen atmosphere, to a solution of 101 mg (0.855 mmol) of benzofuran in 4 ml of THF, 1.71 ml of 0.5 M (0.855 mmol) of $^n$BuLi in hexanes was added at −80° C. The resulted mixture was stirred for 3 hours at room temperature, then cooled to −80° C., and 0.954 ml (0.954 mmol) of 1.0 M $ZnCl_2$ in THF was added. This mixture was slowly warmed to ambient temperature and additionally stirred for 1 hour at this temperature. The solution of organozinc reagent was added to a mixture of 200 mg (0.329 mmol) of 10. Then, 0.825 ml of 0.02 M (0.0165 mmol) $Pd(P^tBu_3)_2$ in THF was added. The cross-coupling reaction was carried out by vigorous stirring for 2 hours at 65° C. Then, this mixture was evaporated to dryness, and 30 ml of toluene was added to the residue. This mixture was heated to 110° C., then evaporated to dryness. To the residue 30 ml of toluene was added, the mixture was heated to 110° C. and filtered through Celite 503. The Celite layer was additionally washed by 2×15 ml of hot toluene. The combined toluene extract was evaporated to dryness. The residue was washed by 2×10 ml of hexanes and dried in vacuum. Yield 162 mg (72%).

Anal. calc. for $C_{36}H_{24}Cl_2O_2SZr$: C, 63.33; H, 3.54. Found: C, 63.51; H, 3.66.

$^1$H NMR (300 MHz, $CD_2Cl_2$): δ 7.84 (d, J=7.6 Hz, 2H, 5,5'-H of indenyl), 7.77 (d, J=7.6 Hz, 2H, 6,6'-H of indenyl), 7.63 (m, 2H, 4/7,4'/7'-H in benzofuryl), 7.55 (m, 2H, 7/4,7'/4'-H in benzofuryl), 7.42 (m, 2H, 3,3'-H in benzofuryl), 7.32 (m, 2H, 5/6,5'/6'-H in benzofuryl), 7.24 (m, 2H, 6/5,6'/5'-H in benzofuryl), 7.05 (m, 2H, 1,1'-H of indenyl), 4.86 (m, 2H, 3,3'-H of indenyl), 2.12 (s, 6H, 2,2'-Me of indenyl).

Example 24

4,4'-sulfandiyl-bis[η5-2-methyl-7-(4-fluorophenyl)indenyl]zirconium dichloride (10l)

Under a nitrogen atmosphere, to a mixture of 0.954 ml (0.954 mmol) of 1.0 M $ZnCl_2$ in THF and 4 ml of THF 0.725 ml of 1.18 M (0.855 mmol), para-fluorophenylmagnesium bromide in THF was added. This mixture was stirred for 1 hour at room temperature. The resulted white suspension was added to 200 mg (0.329 mmol) of 10 in 3 ml of THF. Then, 0.825 ml of 0.02 M (0.0165 mmol) $Pd(P^tBu_3)_2$ in THF was added. The cross-coupling reaction was carried out by vigorous stirring for 2 hours at 70° C. Then, this mixture was evaporated to dryness, and 30 ml of toluene was added to the residue. This mixture was heated to 110° C., then evaporated to dryness. To the residue 30 ml of toluene was added, the mixture was heated to 110° C. and filtered through Celite 503. The Celite layer was additionally washed by 2×15 ml of hot toluene. The combined toluene extract was evaporated to dryness. The residue was washed by 2×10 ml of hexanes and dried in vacuum. Yield 175 mg (83%).

Anal. calc. for $C_{32}H_{22}Cl_2F_2SZr$: C, 60.17; H, 3.47. Found: C, 60.35; H, 3.56.

$^1$H NMR (300 MHz, $CD_2Cl_2$): δ 7.73 (d, J=7.3 Hz, 2H, 5,5'-H of indenyl), 7.64 (m, 4H, 2,2',6,6'-H of $C_6H_4F$), 7.20 (d, J=7.3 Hz, 2H, 6,6'-H of indenyl), 7.14 (m, 4H, 3,3',5,5'-H of $C_6H_4F$), 6.55 (d, J=2.5 Hz, 2H, 1,1'-H of indenyl), 4.80 (d, J=2.5 Hz, 2H, 3,3'-H of indenyl), 2.09 (s, 6H, 2,2'-Me of indenyl).

Example 25

4,4'-sulfandiyl-bis[$\eta^5$-2-methyl-7-(3-trifluoromethylphenyl)indenyl]zirconium dichloride (10m)

Under a nitrogen atmosphere, to a mixture of 0.954 ml (0.954 mmol) of 1.0 M ZnCl$_2$ in THF and 4 ml of THF 0.838 ml of 1.02 M (0.855 mmol), meta-trifluoromethylphenylmagnesium bromide in THF was added. This mixture was stirred for 1 h at room temperature. The resulted white suspension was added to 200 mg (0.329 mmol) of 10 in 3 ml of THF. Then, 0.825 ml of 0.02 M (0.0165 mmol) Pd(P$^t$Bu$_3$)$_2$ in THF was added. The cross-coupling reaction was carried out by vigorous stirring for 2 h at 70° C. Then, this mixture was evaporated to dryness, and 30 ml of toluene was added to the residue. This mixture was heated to 110° C., then evaporated to dryness. To the residue 30 ml of toluene was added, the mixture was heated to 110° C. and filtered through Celite 503. The Celite layer was additionally washed by 2×15 ml of hot toluene. The combined toluene extract was evaporated to dryness. The residue was washed by 2×10 ml of hexanes and dried in vacuum. Yield 160 mg (66%).

Anal. calc. for C$_{34}$H$_{22}$Cl$_2$F$_6$SZr: C, 55.28; H, 3.00. Found: C, 55.12; H, 3.09.

$^1$H NMR (300 MHz, CD$_2$Cl$_2$): δ 7.85-7.94 (m, 4H, 2,2',4,4'-H in C$_6$H$_4$CF$_3$), 7.77 (d, J=7.3 Hz, 2H, 5,5'-H of indenyl), 7.55-7.67 (m, 4H, 5,5',6,6'-H in C$_6$H$_4$CF$_3$), 7.26 (d, J=7.3 Hz, 2H, 6,6'-H of indenyl), 6.53 (m, 2H, 1,1'-H of indenyl), 4.84 (m, 2H, 3,3'-H of indenyl), 2.10 (s, 6H, 2,2'-Me of indenyl).

Example 26

4,4'-sulfandiyl-bis[$\eta^5$-2-methyl-7-(2,5-dimethylphenyl)indenyl]zirconium dichloride (10n)

Under a nitrogen atmosphere in a 16 ml vial equipped with PTFE coated stir bar and containing a suspension of 150 mg (0.25 mmol) of 10 in 4.0 ml of THF, 1.26 ml of 0.5 M (0.63 mmol) 2,5-dimethylphenylmagnesium bromide in THF and 0.50 ml of 0.02 M (0.010 mmol) Pd(P$^t$Bu$_3$)$_2$ in THF were added by a dosing pipette. The reaction mixture was stirred for 3 hours at 70° C. and then evaporated to dryness. To the residue, a solution of 1.0 ml of MeSiCl$_3$ in 10 ml of dry dichloromethane was added to eliminate an excess of the organozinc reagent. The resulted mixture was stirred at ambient temperature for 1 hour and then evaporated to dryness. In order to eliminate THF contamination, the residue was treated with hot toluene (20 ml), then, the suspension was evaporated to dryness. The residue was additionally treated with 60 ml of hot toluene, and the resulted suspension filtered through Celite 503. The toluene extract was evaporated to dryness. The obtained solid was washed with 3×15 ml of hexanes and dried in vacuum. Yield 130 mg (80%) of yellowish solid.

Anal. calc. for C$_{36}$H$_{32}$Cl$_2$SZr: C, 65.63; H, 4.90. Found: C, 65.81; H, 5.00.

$^1$H NMR (CD$_2$Cl$_2$): δ 7.72 (d, J=7.3 Hz, 2H, 5,5'-H in indenyl), 7.05-7.20 (m, 8H, 6,6'-H in indenyl and 3,3',4,4',6,6'-H in 2,5-Me$_2$C$_6$H$_3$), 6.25 (br.s, 2H, 1,1'-H in indenyl), 4.80 (d, J=2.4 Hz, 2H, 3,3'-H in indenyl), 2.31 (s, 6H, 5,5'-Me in 2,5-Me$_2$C$_6$H$_3$), 2.11 (s, 6H, 2,2'-Me in indenyl), 2.10 (br.s, 6H, 2,2'-Me in 2,5-Me$_2$C$_6$H$_3$).

Example 27

4,4'-sulfandiyl-bis[$\eta^5$-2-methyl-7-(4-biphenyl)indenyl]zirconium dichloride (10o)

Under a nitrogen atmosphere in a 16 ml vial equipped with PTFE coated stir bar and containing a suspension of 150 mg (0.25 mmol) of 10 in 4.0 ml of THF, 1.26 ml of 0.5 M (0.63 mmol) 4-biphenylmagnesium bromide in THF and 0.50 ml of 0.02 M (0.010 mmol) Pd(P$^t$Bu$_3$)$_2$ in THF were added by a dosing pipette. The reaction mixture was stirred for 3 hours at 70° C. and then evaporated to dryness. To the residue, a solution of 1.0 ml of MeSiCl$_3$ in 10 ml of dry dichloromethane was added to eliminate an excess of the organozinc reagent. The resulted mixture was stirred at ambient temperature for 1 hour and then evaporated to dryness. In order to eliminate THF contamination, the residue was treated with hot toluene (20 ml), then, the suspension was evaporated to dryness. The residue was additionally treated with 60 ml of hot toluene, and the resulted suspension filtered through Celite 503. The toluene extract was evaporated to dryness. The obtained solid was washed with 3×15 ml of hexanes and dried in vacuum. Yield 140 mg (75%) of yellowish solid.

Anal. calc. for C$_{44}$H$_{32}$Cl$_2$SZr: C, 70.00; H, 4.27. Found: C, 70.29; H, 4.36.

$^1$H NMR (CD$_2$Cl$_2$): δ 7.28-7.80 (m, 22H, 5,5',6,6'-H in indenyls and 4-biphenyls), 6.67 (d, J=2.4 Hz, 2H, 1,1'-H in indenyl), 4.85 (d, J=2.4 Hz, 2H, 3,3'-H in indenyl), 2.12 (s, 6H, 2,2'-Me in indenyl).

EXPERIMENTAL

Polymerizations

In the following experiments pressure is reported in atmospheres and pounds per square inch. The conversion factors to S. I. Units are; 1 psi equals 6.894757 kPa and 1 atm equals 101.325 kPa.

Transition metal compound (TMC) solutions were typically prepared using toluene (ExxonMobil Chemical—anhydrous, stored under N$_2$) (98%). Unless otherwise mentioned, TMC solutions are 0.2 mmol/L for C$_2$ and C$_2$/C$_8$ (co)polymerizations, and 0.6 mmol/L for C$_3$ and C$_3$/C$_2$ (co)polymerizations.

Solvents, polymerization grade toluene and hexanes were supplied by ExxonMobil Chemical Co. and thoroughly dried and degassed prior to use.

1-octene (98%) was purchased from Aldrich Chemical Company and dried by stirring over NaK overnight followed by filtration through basic alumina (Aldrich Chemical Company, Brockman Basic 1).

Polymerization grade ethylene was used and further purified by passing it through a series of columns: 500 cc Oxyclear cylinder from Labclear (Oakland, Calif.) followed by a 500 cc column packed with dried 3 Å mole sieves purchased from Aldrich Chemical Company, and a 500 cc column packed with dried 5 Å mole sieves purchased from Aldrich Chemical Company.

Polymerization grade propylene was used without further purification.

MAO (methylalumoxane, 10 wt % in toluene) was purchased from Albemarle Corporation and was used as a 1 wt % or 2 wt % in toluene solution. Micromoles of MAO reported in the experimental section is based on the micromoles of aluminum in MAO. The formula weight of MAO is 58.0 grams/mole.

Reactor Description and Preparation: Polymerizations were conducted in an inert atmosphere (N$_2$) drybox using autoclaves equipped with an external heater for temperature control, glass inserts (internal volume of reactor=23.5 mL for C2 and C2/C8 runs; 22.5 mL for C3 and C2/C3 runs), septum inlets, regulated supply of nitrogen, ethylene and propylene, and equipped with disposable PEEK mechanical stirrers (800

RPM). The autoclaves were prepared by purging with dry nitrogen at 110° C. or 115° C. for 5 hours and then at 25° C. for 5 hours.

Ethylene Polymerization or Ethylene/1-Octene Copolymerization: The reactor was prepared as described above, and then purged with ethylene. Toluene, 1-octene (100 µL), and MAO, were added via syringe at room temperature and atmospheric pressure. The reactor was then brought to process temperature (80° C.) and charged with ethylene to process pressure (75 psig=517.1 kPa) while stirring at 800 RPM. The TMC was added via syringe with the reactor at process conditions. Amounts of reagents not specified above are given in Tables 3 and 5. Ethylene was allowed to enter (through the use of computer controlled solenoid valves) the autoclaves during polymerization to maintain reactor gauge pressure (+/−2 psig). Reactor temperature was monitored and typically maintained within +/−1° C. Polymerizations were halted by addition of approximately 50 psid $O_2$/Ar (5 mole % $O_2$) gas mixture to the autoclaves for approximately 30 seconds. The polymerizations were quenched after a predetermined cumulative amount of ethylene had been added or for a maximum of 20 minutes polymerization time. The final conversion (in psi) of ethylene added/consumed is reported in the Tables 3 and 5, in addition to the quench time for each run. The reactors were cooled and vented. The polymer was isolated after the solvent was removed in-vacuo. Yields reported include total weight of polymer and residual catalyst. Catalyst activity is reported as grams of polymer per mmol transition metal compound per atmosphere ethylene per hour of reaction time (g/mmol·hr·atm).

Propylene Polymerization: The reactor was prepared as described above, then heated to 40° C. and then purged with propylene gas at atmospheric pressure. Hexanes, MAO, and liquid propylene (1.066 mL, unless indicated otherwise in Table 7) were added via syringe. The reactor was then heated to process temperature (70° C.) while stirring at 800 RPM. The TMC was added via syringe with the reactor at process conditions. Amounts of reagents not specified above are given in Table 7. Reactor temperature was monitored and typically maintained within +/−1° C. Polymerizations were halted by addition of approximately 50 psid $O_2$/Ar (5 mole % $O_2$) gas mixture to the autoclaves for approximately 30 seconds. The polymerizations were quenched based on a predetermined pressure loss of approximately 5 psid. The actual quench time is reported in Table 7 for each run. The reactors were cooled and vented. The polymer was isolated after the solvent was removed in-vacuo. Yields reported include total weight of polymer and residual catalyst. Catalyst activity is reported as grams of polymer per mmol transition metal compound per hour of reaction time (g/mmol·hr).

Ethylene/Propylene Copolymerization: The reactor was prepared as described above, and then purged with ethylene. Reactors were heated to 40° C. and ethylene was then added to the reactor to a target pressure of 10 psig (single addition), followed by the addition of hexanes, MAO, and then liquid propylene (1.066 mL). All additions were made via syringe. The reactor was then heated to process temperature (70° C.) while stirring at 800 RPM. The TMC was added via syringe with the reactor at process conditions. Amounts of reagents not specified above are given in Table 9. Reactor temperature was monitored and typically maintained within +/−1° C. Polymerizations were halted by addition of approximately 50 psid $O_2$/Ar (5 mole % $O_2$) gas mixture to the autoclaves for approximately 30 seconds. The polymerizations were quenched based on a predetermined pressure loss of approximately 5 psid. The actual quench time is reported in Table 9 for each run. The reactors were cooled and vented. The polymer was isolated after the solvent was removed in-vacuo. Yields reported include total weight of polymer and residual catalyst. Catalyst activity is reported as grams of polymer per mmol transition metal compound per hour of reaction time (g/mmol·hr).

Polymer Characterization:

Polymer characterization results for polyethylene samples are reported in Table 4, for ethylene-1-octene copolymers are reported in Table 6, for polypropylene samples are reported in Table 8, and for ethylene-propylene copolymers are reported in Table 10.

For analytical testing, polymer sample solutions were prepared by dissolving polymer in 1,2,4-trichlorobenzene (TCB, 99+% purity from Sigma-Aldrich) containing 2,6-di-tert-butyl-4-methylphenol (BHT, 99% from Aldrich) at 160° C. in a shaker oven for approximately 3 hours. The typical concentration of polymer in solution is between 0.4 to 0.9 mg/mL with a BHT concentration of 1.25 mg BHT/mL of TCB. Samples are cooled to 135° C. for testing.

Molecular weights (weight average molecular weight (Mw) and number average molecular weight (Mn)) and molecular weight distribution (MWD=Mw/Mn), which is also sometimes referred to as the polydispersity (PDI) of the polymer, were measured by Gel Permeation Chromatography using a Symyx Technology GPC equipped with evaporative light scattering detector and calibrated using polystyrene standards (Polymer Laboratories: Polystyrene Calibration Kit S-M-10: Mp (peak Mw) between 5000 and 3,390,000). Samples were run in TCB at (135° C. sample temperatures, 160° C. oven/columns) using three Polymer Laboratories: PLgel 10 µm Mixed-B 300×7.5 mm columns in series. No column spreading corrections were employed. Numerical analyses were performed using Epoch® software available from Symyx Technologies.

The sample preparation for SAMMS (Sensory Array Modular Measurement System) thermal analysis measurements involved depositing the stabilized polymer solution onto a silanized wafer (Part Number S10457, Symyx). The solvent was then evaporated off at ~145° C. By this method, approximately between 0.12 and 0.24 mg of polymer is deposited onto each corresponding wafer cell. Thermal analysis was measured on a Symyx Technologies SAMMS instrument that measures polymer melt temperatures via the 3 ω technique. The analysis first employs a rapid-scan protocol that heats each cell from 27° C. to 200° C. in ~35 seconds and then rapidly cools the sample to room temperature. This complete procedure takes approximately 60 seconds per cell and is used to minimize each sample's thermal history. The second step involves running a high-resolution scan protocol to measure the second melt of the sample. The protocol heats each cell from 27° C. to 200° C. in ~3 minutes and then rapidly cools the sample to room temperature. The high-resolution scan takes approximately three times the amount of time to complete as the rapid-scan protocol. If multiple melting peaks are present, Epoch® Software reports the largest amplitude peak. SAMMS data is reported under the heading of Tm (C) in Tables 4 and 6.

For propylene homopolymers, the thermal analysis was performed using a 1290 TA Instruments Differential Scanning Calorimeter (DSC) by first heating the sample from 25° C. to 220° C. at 10° C./min, holding the temperature at 220° C. for 5 minutes, then cooling at 10° C./min from 220° C. to 25° C., and finally again heating to 220° C. at 10° C./min. The second heat results have been reported under the heading of DSC (° C.) in Table 8. An entry of none indicates that the polymer had no melting point. Multiple numbers indicate a polymer with more than one melting point. The heat of fusion, delta H, is also recorded in Table 8.

Samples for infrared analysis were prepared by depositing the stabilized polymer solution onto a silanized wafer (Part number S10860, Symyx). By this method, approximately between 0.12 and 0.24 mg of polymer is deposited on the wafer cell. The samples were subsequently analyzed on a Brucker Equinox 55 FTIR spectrometer equipped with Pikes's MappIR specular reflectance sample accessory. Spectra, covering a spectral range of 5000 $cm^{-1}$ to 500 $cm^{-1}$, were collected at a 2 $cm^{-1}$ resolution with 32 scans.

For ethylene-1-octene copolymers, the wt. % copolymer is determined via measurement of the methyl deformation band at ~1375 $cm^{-1}$. The peak height of this band is normalized by the combination and overtone band at ~4321 $cm^{-1}$, which corrects for path length differences. The normalized peak height is correlated to individual calibration curves from $^1H$ NMR data to predict the wt. % copolymer content within a concentration range of ~2 to 35 wt. % for octene. Typically, $R^2$ correlations of 0.98 or greater are achieved. These numbers are reported in Table 6 under the heading, Octene wt %).

For ethylene-propylene copolymers, the wt. % ethylene is determined via measurement of the methylene rocking band (~770 $cm^{-1}$ to 700 $cm^{-1}$). The peak area of this band is normalized by sum of the band areas of the combination and overtone bands in the 4500 $cm^{-1}$ to 4000 $cm^{-1}$ range. The normalized band area is then correlated to a calibration curved from $^{13}C$ NMR data to predict the wt. % ethylene within a concentration range of ~5 to 40 wt. %. Typically, $R^2$ correlations of 0.98 or greater are achieved. These numbers are reported in Table 10 under the heading, Ethylene (wt %).

For propylene homo-polymers, an infrared spectroscopy-based partial least-squares (PLS) model was developed for predicting an IR tacticity index, reported as an estimated Tm, for isotactic polypropylene (iPP). The model was built using PLSplus/IQ add-on application to the Grams/AI (Version 7.00) software from ThermoGalactic. The model is based on a training set consisting of IR spectra of iPP samples with known Tm values spanning a range of ~100° C. to ~166° C. The iPPs were prepared in lab and commercial reactors using metallocene and Zieglar-Natta catalyst systems. Their average Mw ranged from 157 k to 436 k. Their IR spectra were collected from solution cast films supported on gold-coated silicon wafers via a Bruker Equinox 55 FTIR spectrometer with a Pike MappIR specular reflectance sample accessory. Each sample was prepared and cast in triplicate. Briefly, before model development, each spectra was baseline-corrected with a cubic function fit, mean-centered, and path length-corrected using the ~1165/1155 cm-1 band. Then the optimum number of PLS factors to include in the final model was determined using leave-one-out cross validation analysis and the selected spectral region of 1364 $cm^{-1}$ to 764 $cm^{-1}$. This resulted in a model with 7 factors and standard error of prediction of 3 C. These calculated Tm's are reported in Table 8 under the heading, FTIR Crystallinity Index (C). Values reported under 100° C., are outside the calibration range of the model.

TABLE 3

Ethylene Polymerization Runs - Part 1.

| Ex # | TMC | TMC (μmol) | MAO* (μmol) | Total Toluene (mL) | Final Conversion (psi) | Quench Time (sec) | Polymer Yield (g) | Activity (g/mmol · hr · atm) |
|---|---|---|---|---|---|---|---|---|
| PE-1 | 10a | 0.02 | 10.00 | 5.00 | 20.1 | 172.7 | 0.0824 | 16,832 |
| PE-2 | 10a | 0.02 | 10.00 | 5.00 | 20.1 | 273.1 | 0.0852 | 11,006 |
| PE-3 | 10a | 0.02 | 10.00 | 5.00 | 20.1 | 280.9 | 0.0879 | 11,039 |
| PE-4 | 10a | 0.02 | 10.00 | 5.00 | 20.1 | 289.9 | 0.0889 | 10,818 |
| PE-5 | 10c | 0.02 | 10.00 | 5.00 | 20.1 | 228.0 | 0.0880 | 13,616 |
| PE-6 | 10c | 0.02 | 10.00 | 5.00 | 20.1 | 241.5 | 0.0880 | 12,856 |
| PE-7 | 10c | 0.02 | 10.00 | 5.00 | 20.1 | 164.1 | 0.0882 | 18,965 |
| PE-8 | 10c | 0.02 | 10.00 | 5.00 | 20.1 | 229.2 | 0.0931 | 14,329 |
| PE-9 | 10d | 0.02 | 10.00 | 5.00 | 20.1 | 255.9 | 0.0657 | 9,056 |
| PE-10 | 10d | 0.02 | 10.00 | 5.00 | 20.1 | 245.7 | 0.0728 | 10,454 |
| PE-11 | 10d | 0.02 | 10.00 | 5.00 | 20.1 | 347.4 | 0.0754 | 7,657 |
| PE-12 | 10d | 0.02 | 10.00 | 5.00 | 20.1 | 254.7 | 0.0770 | 10,668 |
| PE-13 | S2 | 0.02 | 9.98 | 3.80 | 25.0 | 118.6 | 0.091 | 27,072 |
| PE-14 | S2 | 0.02 | 9.98 | 3.80 | 25.0 | 182.2 | 0.092 | 17,814 |
| PE-15 | S2 | 0.02 | 9.98 | 3.80 | 25.0 | 246.8 | 0.093 | 13,293 |
| PE-16 | S2 | 0.02 | 9.98 | 3.80 | 25.0 | 143.0 | 0.094 | 23,188 |
| PE-17 | S1 | 0.02 | 9.98 | 3.80 | 25.3 | 348.8 | 0.087 | 8,801 |
| PE-18 | S1 | 0.02 | 9.98 | 3.80 | 25.0 | 320.8 | 0.090 | 9,899 |
| PE-19 | S1 | 0.02 | 9.98 | 3.80 | 25.0 | 281.2 | 0.092 | 11,542 |
| PE-20 | S1 | 0.02 | 9.98 | 3.80 | 25.0 | 330.4 | 0.092 | 9,823 |
| PE-21 | 10 | 0.02 | 10.00 | 5.00 | 20.1 | 434.5 | 0.0653 | 5,302 |
| PE-22 | 10 | 0.02 | 10.00 | 5.00 | 20.1 | 388.6 | 0.0722 | 6,555 |
| PE-23 | 10 | 0.02 | 10.00 | 5.00 | 20.1 | 374.6 | 0.0765 | 7,205 |
| PE-24 | 10 | 0.02 | 10.00 | 5.00 | 20.1 | 375.5 | 0.0781 | 7,337 |
| PE-25 | P4 | 0.02 | 10.00 | 5.00 | 5.0 | 1200.9 | 0.0006 | 18 |
| PE-26 | P4 | 0.02 | 10.00 | 5.00 | 4.4 | 1200.8 | 0.0008 | 24 |
| PE-27 | P4 | 0.02 | 10.00 | 5.00 | 3.2 | 1200.4 | 0.0009 | 26 |
| PE-28 | P4 | 0.02 | 10.00 | 5.00 | 2.1 | 1201.2 | 0.0010 | 29 |
| PE-29 | P4 | 0.02 | 10.00 | 5.00 | 4.4 | 1200.3 | 0.0043 | 126 |
| PE-30 | P4 | 0.02 | 10.00 | 5.00 | 4.6 | 1201.1 | 0.0045 | 132 |
| PE-31 | P4 | 0.02 | 10.00 | 5.00 | 6.3 | 1201.5 | 0.0092 | 270 |
| PE-32 | P4 | 0.02 | 10.00 | 5.00 | 16.9 | 1200.3 | 0.0110 | 323 |
| PE-33 | P3 | 0.02 | 10.00 | 5.00 | 20.3 | 99.3 | 0.0452 | 16,067 |
| PE-34 | P3 | 0.02 | 10.00 | 5.00 | 20.3 | 94.5 | 0.0457 | 17,054 |
| PE-35 | P3 | 0.02 | 10.00 | 5.00 | 20.1 | 95.9 | 0.0467 | 17,175 |
| PE-36 | P3 | 0.02 | 10.00 | 5.00 | 20.3 | 86.6 | 0.0480 | 19,562 |

TABLE 3-continued

Ethylene Polymerization Runs - Part 1.

| Ex # | TMC | TMC (µmol) | MAO* (µmol) | Total Toluene (mL) | Final Conversion (psi) | Quench Time (sec) | Polymer Yield (g) | Activity (g/mmol · hr · atm) |
|---|---|---|---|---|---|---|---|---|
| PE-37 | 10f | 0.02 | 10.00 | 4.90 | 20.1 | 297.6 | 0.0406 | 4,814 |
| PE-38 | 10f | 0.02 | 10.00 | 4.90 | 20.1 | 282.5 | 0.0396 | 4,945 |
| PE-39 | 10f | 0.02 | 10.00 | 4.90 | 20.1 | 302.8 | 0.0334 | 3,891 |
| PE-40 | 10f | 0.02 | 10.00 | 4.90 | 20.1 | 501.1 | 0.0442 | 3,112 |
| PE-41 | 10h | 0.02 | 10.00 | 4.90 | 20.3 | 207.0 | 0.0821 | 13,993 |
| PE-42 | 10h | 0.02 | 10.00 | 4.90 | 20.5 | 281.8 | 0.0811 | 10,153 |
| PE-43 | 10h | 0.02 | 10.00 | 4.90 | 20.1 | 344.3 | 0.0806 | 8,258 |
| PE-44 | 10h | 0.02 | 10.00 | 4.90 | 20.1 | 230.6 | 0.0840 | 12,854 |
| PE-45 | N3 | 0.02 | 10.00 | 4.90 | 20.1 | 29.9 | 0.0637 | 75,137 |
| PE-46 | N3 | 0.02 | 10.00 | 4.90 | 20.6 | 36.0 | 0.0845 | 82,764 |
| PE-47 | N3 | 0.02 | 10.00 | 4.90 | 21.2 | 36.0 | 0.0828 | 81,167 |
| PE-48 | N3 | 0.02 | 10.00 | 4.90 | 20.8 | 34.3 | 0.0863 | 88,688 |
| PE-49 | O3 | 0.02 | 10.00 | 4.90 | 20.1 | 53.5 | 0.0608 | 40,116 |
| PE-50 | O3 | 0.02 | 10.00 | 4.90 | 20.5 | 65.2 | 0.0652 | 35,296 |
| PE-51 | O3 | 0.02 | 10.00 | 4.90 | 20.1 | 68.5 | 0.0669 | 34,466 |
| PE-52 | O3 | 0.02 | 10.00 | 4.90 | 20.1 | 104.0 | 0.0493 | 16,729 |
| PE-53 | O4 | 0.02 | 10.00 | 4.90 | 15.7 | 1200.1 | 0.0055 | 162 |
| PE-54 | O4 | 0.02 | 10.00 | 4.90 | 5.0 | 1200.7 | 0.0047 | 138 |
| PE-55 | O4 | 0.02 | 10.00 | 4.90 | 2.6 | 1201.0 | 0.0022 | 65 |
| PE-56 | O4 | 0.02 | 10.00 | 4.90 | 2.9 | 1200.4 | 0.0034 | 100 |
| PE-57 | S3 | 0.02 | 10.00 | 4.90 | 20.5 | 104.2 | 0.0592 | 20,038 |
| PE-58 | S3 | 0.02 | 10.00 | 4.90 | 20.1 | 66.6 | 0.0728 | 38,587 |
| PE-59 | S3 | 0.02 | 10.00 | 4.90 | 20.1 | 57.6 | 0.0712 | 43,610 |
| PE-60 | S3 | 0.02 | 10.00 | 4.90 | 20.6 | 65.3 | 0.0785 | 42,405 |
| PE-61 | S4 | 0.02 | 10.00 | 4.90 | 4.9 | 1201.1 | 0.0030 | 88 |
| PE-62 | S4 | 0.02 | 10.00 | 4.90 | 4.6 | 1201.1 | 0.0027 | 79 |
| PE-63 | S4 | 0.02 | 10.00 | 4.90 | 6.7 | 1200.2 | 0.0030 | 88 |
| PE-64 | S4 | 0.02 | 10.00 | 4.90 | 4.4 | 1201.3 | 0.0032 | 94 |
| PE-65 | S5 | 0.02 | 10.00 | 4.90 | 20.3 | 314.1 | 0.0691 | 7,761 |
| PE-66 | S5 | 0.02 | 10.00 | 4.90 | 20.3 | 328.9 | 0.0714 | 7,660 |
| PE-67 | S5 | 0.02 | 10.00 | 4.90 | 20.1 | 411.7 | 0.0451 | 3,865 |
| PE-68 | S5 | 0.02 | 10.00 | 4.90 | 20.1 | 452.3 | 0.0565 | 4,407 |
| PE-69 | 10i | 0.02 | 10.00 | 4.90 | 20.1 | 226.3 | 0.0761 | 11,866 |
| PE-70 | 10i | 0.02 | 10.00 | 4.90 | 20.1 | 235.1 | 0.0740 | 11,106 |
| PE-71 | 10i | 0.02 | 10.00 | 4.90 | 20.1 | 212.9 | 0.0764 | 12,658 |
| PE-72 | 10i | 0.02 | 10.00 | 4.90 | 20.3 | 223.3 | 0.0778 | 12,292 |
| PE-73 | 10l | 0.02 | 10.00 | 4.90 | 20.1 | 348.4 | 0.0716 | 7,251 |
| PE-74 | 10l | 0.02 | 10.00 | 4.90 | 20.1 | 364.7 | 0.0634 | 6,133 |
| PE-75 | 10l | 0.02 | 10.00 | 4.90 | 20.1 | 298.9 | 0.0669 | 7,897 |
| PE-76 | 10l | 0.02 | 10.00 | 4.90 | 20.1 | 340.8 | 0.0590 | 6,108 |

*Micromoles of Al in MAO.

TABLE 4

Ethylene Polymerization Runs - Part 2.

| Ex # | TMC | Mw | Mn | PDI | Octene (wt %) | Tm (° C.) |
|---|---|---|---|---|---|---|
| PE-1 | 10a | — | — | — | — | — |
| PE-2 | 10a | 1,503,445 | 745,634 | 2.0 | 1.5 | — |
| PE-3 | 10a | 1,597,972 | 809,117 | 2.0 | 1.1 | — |
| PE-4 | 10a | 1,476,887 | 733,458 | 2.0 | 1.0 | — |
| PE-5 | 10c | 897,886 | 435,584 | 2.1 | 1.6 | — |
| PE-6 | 10c | 883,041 | 439,963 | 2.0 | 1.2 | — |
| PE-7 | 10c | 868,039 | 421,203 | 2.1 | 1.1 | — |
| PE-8 | 10c | 885,542 | 413,962 | 2.1 | 1.0 | — |
| PE-9 | 10d | 1,035,416 | 544,016 | 1.9 | 1.2 | — |
| PE-10 | 10d | 1,121,787 | 571,158 | 2.0 | 1.2 | — |
| PE-11 | 10d | 987,849 | 507,307 | 1.9 | 1.5 | — |
| PE-12 | 10d | 1,109,300 | 569,078 | 1.9 | 1.4 | — |
| PE-13 | S2 | 2,587,864 | 1,341,613 | 1.9 | 0.0 | 138.2 |
| PE-14 | S2 | 2,414,917 | 1,027,728 | 2.3 | 0.0 | 141.0 |
| PE-15 | S2 | 2,448,758 | 1,153,318 | 2.1 | 0.0 | 141.7 |
| PE-16 | S2 | 2,856,607 | 1,347,645 | 2.1 | 0.0 | 136.4 |
| PE-17 | S1 | 667,865 | 354,155 | 1.9 | 0.0 | 142.1 |
| PE-18 | S1 | 706,377 | 315,565 | 2.2 | 0.0 | 141.6 |
| PE-19 | S1 | 672,879 | 359,074 | 1.9 | 0.0 | 142.7 |
| PE-20 | S1 | 754,702 | 395,615 | 1.9 | 0.0 | 141.4 |
| PE-21 | 10 | 1,002,301 | 535,137 | 1.9 | 1.4 | — |
| PE-22 | 10 | 1,016,772 | 537,999 | 1.9 | 1.4 | — |
| PE-23 | 10 | 998,474 | 520,443 | 1.9 | 1.3 | — |
| PE-24 | 10 | 1,008,148 | 514,269 | 2.0 | 1.4 | — |
| PE-25 | P4 | — | — | — | — | — |
| PE-26 | P4 | — | — | — | — | — |
| PE-27 | P4 | — | — | — | — | — |
| PE-28 | P4 | — | — | — | — | — |
| PE-29 | P4 | — | — | — | — | — |
| PE-30 | P4 | — | — | — | — | — |
| PE-31 | P4 | — | — | — | — | — |
| PE-32 | P4 | — | — | — | — | — |
| PE-33 | P3 | 746,554 | 477,988 | 1.6 | 1.4 | — |
| PE-34 | P3 | 688,711 | 425,653 | 1.6 | 1.4 | — |
| PE-35 | P3 | 722,777 | 463,555 | 1.6 | 1.4 | — |
| PE-36 | P3 | 700,816 | 432,384 | 1.6 | 1.2 | — |
| PE-37 | 10f | 369,189 | 220,852 | 1.7 | 1.6 | — |
| PE-38 | 10f | 338,273 | 209,756 | 1.6 | 1.7 | — |
| PE-39 | 10f | 364,019 | 226,037 | 1.6 | 1.2 | — |
| PE-40 | 10f | 360,570 | 216,986 | 1.7 | 1.5 | — |

TABLE 4-continued

Ethylene Polymerization Runs - Part 2.

| Ex # | TMC | Mw | Mn | PDI | Octene (wt %) | Tm (° C.) |
|---|---|---|---|---|---|---|
| PE-41 | 10h | 1,747,022 | 966,770 | 1.8 | 1.2 | — |
| PE-42 | 10h | 1,686,875 | 947,112 | 1.8 | 1.4 | — |
| PE-43 | 10h | 1,570,490 | 839,810 | 1.9 | 1.1 | — |
| PE-44 | 10h | 1,743,700 | 963,941 | 1.8 | 1.1 | — |
| PE-45 | N3 | 228,979 | 151,106 | 1.5 | 0.5 | — |
| PE-46 | N3 | 219,423 | 144,964 | 1.5 | 0.8 | — |
| PE-47 | N3 | 223,381 | 149,313 | 1.5 | 0.6 | — |
| PE-48 | N3 | 219,986 | 142,278 | 1.5 | 0.8 | — |
| PE-49 | O3 | 168,940 | 114,856 | 1.5 | 1.0 | — |
| PE-50 | O3 | 173,738 | 118,165 | 1.5 | 0.9 | — |
| PE-51 | O3 | 173,344 | 118,709 | 1.5 | 1.4 | — |
| PE-52 | O3 | 174,549 | 119,308 | 1.5 | 1.1 | — |
| PE-53 | O4 | — | — | — | — | — |
| PE-54 | O4 | — | — | — | — | — |
| PE-55 | O4 | — | — | — | — | — |
| PE-56 | O4 | — | — | — | — | — |
| PE-57 | S3 | 472,368 | 308,592 | 1.5 | 1.2 | — |
| PE-58 | S3 | 446,860 | 290,066 | 1.5 | 1.3 | — |
| PE-59 | S3 | 425,476 | 276,083 | 1.5 | 0.8 | — |
| PE-60 | S3 | 438,444 | 284,619 | 1.5 | 1.0 | — |
| PE-61 | S4 | — | — | — | — | — |
| PE-62 | S4 | — | — | — | — | — |
| PE-63 | S4 | — | — | — | — | — |
| PE-64 | S4 | — | — | — | — | — |
| PE-65 | S5 | 1,132,996 | 699,326 | 1.6 | 0.9 | — |
| PE-66 | S5 | 1,144,169 | 716,012 | 1.6 | 1.2 | — |
| PE-67 | S5 | 1,303,203 | 827,986 | 1.6 | 0.9 | — |
| PE-68 | S5 | 1,220,091 | 775,305 | 1.6 | 0.9 | — |
| PE-69 | 10i | 1,270,137 | 742,247 | 1.7 | 1.3 | — |
| PE-70 | 10i | 1,244,880 | 712,931 | 1.7 | 1.4 | — |
| PE-71 | 10i | 1,254,487 | 717,342 | 1.7 | 1.2 | — |
| PE-72 | 10i | 1,266,887 | 731,985 | 1.7 | 1.2 | — |
| PE-73 | 10l | 1,053,566 | 641,260 | 1.6 | 2.0 | — |
| PE-74 | 10l | 1,064,339 | 645,602 | 1.6 | 1.6 | — |
| PE-75 | 10l | 1,183,817 | 700,852 | 1.7 | 1.2 | — |
| PE-76 | 10l | 1,112,845 | 678,478 | 1.6 | 1.4 | — |

TABLE 5

Ethylene-1-Octene Polymerization Runs - Part 1.

| Ex # | TMC | TMC (μmol) | MAO* (μmol) | 1-Octene (μmol) | Total Toluene (mL) | Final Conversion (psi) | Quench Time (sec) | Polymer Yield (g) | Activity (g/mmol · hr · atm) |
|---|---|---|---|---|---|---|---|---|---|
| EO-1 | 10a | 0.02 | 10.00 | 637.14 | 4.90 | 20.1 | 401.8 | 0.0885 | 7,772 |
| EO-2 | 10a | 0.02 | 10.00 | 637.14 | 4.90 | 20.1 | 542.3 | 0.0932 | 6,063 |
| EO-3 | 10a | 0.02 | 10.00 | 637.14 | 4.90 | 20.1 | 565.4 | 0.0964 | 6,015 |
| EO-4 | 10a | 0.02 | 10.00 | 637.14 | 4.90 | 20.3 | 613.9 | 0.0977 | 5,614 |
| EO-5 | 10c | 0.02 | 10.00 | 637.14 | 4.90 | 20.1 | 131.4 | 0.0558 | 14,981 |
| EO-6 | 10c | 0.02 | 10.00 | 637.14 | 4.90 | 20.3 | 142.0 | 0.0583 | 14,486 |
| EO-7 | 10c | 0.02 | 10.00 | 637.14 | 4.90 | 20.1 | 130.0 | 0.0607 | 16,471 |
| EO-8 | 10c | 0.02 | 10.00 | 637.14 | 4.90 | 20.1 | 142.0 | 0.0621 | 15,424 |
| EO-9 | 10d | 0.02 | 10.00 | 637.14 | 4.90 | 20.1 | 542.4 | 0.0608 | 3,955 |
| EO-10 | 10d | 0.02 | 10.00 | 637.14 | 4.90 | 20.1 | 523.3 | 0.0624 | 4,207 |
| EO-11 | 10d | 0.02 | 10.00 | 637.14 | 4.90 | 20.1 | 468.6 | 0.0635 | 4,780 |
| EO-12 | 10d | 0.02 | 10.00 | 637.14 | 4.90 | 20.3 | 609.3 | 0.0723 | 4,186 |
| EO-13 | S2 | 0.02 | 9.98 | 638.1 | 3.80 | 25.0 | 729.5 | 0.092 | 4,450 |
| EO-14 | S2 | 0.02 | 9.98 | 638.1 | 3.80 | 25.0 | 700.0 | 0.100 | 5,040 |
| EO-15 | S2 | 0.02 | 9.98 | 638.1 | 3.80 | 25.0 | 555.0 | 0.102 | 6,484 |
| EO-16 | S2 | 0.02 | 9.98 | 638.1 | 3.80 | 25.2 | 579.7 | 0.103 | 6,268 |
| EO-17 | S1 | 0.02 | 9.98 | 638.1 | 3.80 | 25.0 | 332.7 | 0.097 | 10,286 |
| EO-18 | S1 | 0.02 | 9.98 | 638.1 | 3.80 | 25.0 | 409.3 | 0.098 | 8,447 |
| EO-19 | S1 | 0.02 | 9.98 | 638.1 | 3.80 | 25.0 | 369.7 | 0.101 | 9,638 |
| EO-20 | S1 | 0.02 | 9.98 | 638.1 | 3.80 | 25.0 | 565.5 | 0.101 | 6,301 |
| EO-21 | 10 | 0.02 | 10.00 | 637.14 | 4.90 | 20.1 | 167.1 | 0.0483 | 10,197 |
| EO-22 | 10 | 0.02 | 10.00 | 637.14 | 4.90 | 20.1 | 180.2 | 0.0483 | 9,455 |
| EO-23 | 10 | 0.02 | 10.00 | 637.14 | 4.90 | 20.1 | 181.7 | 0.0515 | 9,999 |
| EO-24 | 10 | 0.02 | 10.00 | 637.14 | 4.90 | 20.1 | 187.9 | 0.0520 | 9,766 |
| EO-25 | P4 | 0.02 | 10.00 | 637.14 | 4.90 | 5.6 | 1200.1 | 0.0004 | 12 |
| EO-26 | P4 | 0.02 | 10.00 | 637.14 | 4.90 | 2.7 | 1201.2 | 0.0004 | 12 |
| EO-27 | P4 | 0.02 | 10.00 | 637.14 | 4.90 | 4.1 | 1200.9 | 0.0006 | 18 |
| EO-28 | P4 | 0.02 | 10.00 | 637.14 | 4.90 | 2.3 | 1200.9 | 0.0008 | 24 |
| EO-29 | P4 | 0.02 | 10.00 | 637.14 | 4.90 | 4.9 | 1201.1 | 0.0011 | 32 |
| EO-30 | P4 | 0.02 | 10.00 | 637.14 | 4.90 | 2.6 | 1201.0 | 0.0017 | 50 |
| EO-31 | P4 | 0.02 | 10.00 | 637.14 | 4.90 | 7.2 | 1201.1 | 0.0052 | 153 |
| EO-32 | P4 | 0.02 | 10.00 | 637.14 | 4.90 | 5.6 | 1201.0 | 0.0067 | 197 |
| EO-33 | P3 | 0.02 | 10.00 | 637.14 | 4.90 | 20.1 | 115.7 | 0.0391 | 11,922 |
| EO-34 | P3 | 0.02 | 10.00 | 637.14 | 4.90 | 20.3 | 136.1 | 0.0397 | 10,288 |
| EO-35 | P3 | 0.02 | 10.00 | 637.14 | 4.90 | 20.3 | 103.3 | 0.0414 | 14,146 |
| EO-36 | P3 | 0.02 | 10.00 | 637.14 | 4.90 | 20.1 | 119.8 | 0.0417 | 12,279 |
| EO-37 | 10f | 0.02 | 10.00 | 637.14 | 4.90 | 20.1 | 1001.4 | 0.0373 | 1,314 |
| EO-38 | 10f | 0.02 | 10.00 | 637.14 | 4.90 | 20.1 | 1035.8 | 0.0393 | 1,339 |
| EO-39 | 10f | 0.02 | 10.00 | 637.14 | 4.90 | 20.1 | 950.4 | 0.0338 | 1,255 |
| EO-40 | 10f | 0.02 | 10.00 | 637.14 | 4.90 | 20.1 | 1040.2 | 0.0333 | 1,129 |
| EO-41 | 10h | 0.02 | 10.00 | 637.14 | 4.90 | 20.1 | 237.0 | 0.0750 | 11,165 |
| EO-42 | 10h | 0.02 | 10.00 | 637.14 | 4.90 | 20.1 | 180.5 | 0.0700 | 13,684 |
| EO-43 | 10h | 0.02 | 10.00 | 637.14 | 4.90 | 20.1 | 335.4 | 0.0872 | 9,171 |

TABLE 5-continued

Ethylene-1-Octene Polymerization Runs - Part 1.

| Ex # | TMC | TMC (μmol) | MAO* (μmol) | 1-Octene (μmol) | Total Toluene (mL) | Final Conversion (psi) | Quench Time (sec) | Polymer Yield (g) | Activity (g/mmol · hr · atm) |
|---|---|---|---|---|---|---|---|---|---|
| EO-44 | 10h | 0.02 | 10.00 | 637.14 | 4.90 | 20.1 | 207.2 | 0.0748 | 12,735 |
| EO-45 | N3 | 0.02 | 10.00 | 637.14 | 4.90 | 20.6 | 35.5 | 0.0832 | 82,638 |
| EO-46 | N3 | 0.02 | 10.00 | 637.14 | 4.90 | 20.6 | 43.2 | 0.0690 | 56,337 |
| EO-47 | N3 | 0.02 | 10.00 | 637.14 | 4.90 | 20.6 | 31.3 | 0.0888 | 100,123 |
| EO-48 | N3 | 0.02 | 10.00 | 637.14 | 4.90 | 20.5 | 34.5 | 0.0813 | 83,162 |
| EO-49 | O3 | 0.02 | 10.00 | 637.14 | 4.90 | 20.1 | 209.9 | 0.0346 | 5,817 |
| EO-50 | O3 | 0.02 | 10.00 | 637.14 | 4.90 | 20.8 | 71.5 | 0.0555 | 27,374 |
| EO-51 | O3 | 0.02 | 10.00 | 637.14 | 4.90 | 20.5 | 71.4 | 0.0560 | 27,659 |
| EO-52 | O3 | 0.02 | 10.00 | 637.14 | 4.90 | 20.1 | 90.5 | 0.0512 | 19,960 |
| EO-53 | O4 | 0.02 | 10.00 | 637.14 | 4.90 | 1.1 | 1201.4 | 0.0026 | 76 |
| EO-54 | O4 | 0.02 | 10.00 | 637.14 | 4.90 | 2.0 | 1201.6 | 0.0014 | 41 |
| EO-55 | O4 | 0.02 | 10.00 | 637.14 | 4.90 | 2.9 | 1200.7 | 0.0022 | 65 |
| EO-56 | O4 | 0.02 | 10.00 | 637.14 | 4.90 | 4.4 | 1200.8 | 0.0023 | 68 |
| EO-57 | S3 | 0.02 | 10.00 | 637.14 | 4.90 | 20.3 | 61.2 | 0.0667 | 38,457 |
| EO-58 | S3 | 0.02 | 10.00 | 637.14 | 4.90 | 20.1 | 59.4 | 0.0702 | 41,716 |
| EO-59 | S3 | 0.02 | 10.00 | 637.14 | 4.90 | 20.5 | 56.3 | 0.0770 | 48,269 |
| EO-60 | S3 | 0.02 | 10.00 | 637.14 | 4.90 | 20.3 | 65.5 | 0.0750 | 40,385 |
| EO-61 | S4 | 0.02 | 10.00 | 637.14 | 4.90 | 4.0 | 1200.4 | 0.0013 | 38 |
| EO-62 | S4 | 0.02 | 10.00 | 637.14 | 4.90 | 1.7 | 1200.8 | 0.0010 | 29 |
| EO-63 | S4 | 0.02 | 10.00 | 637.14 | 4.90 | 5.2 | 1200.4 | 0.0015 | 44 |
| EO-64 | S4 | 0.02 | 10.00 | 637.14 | 4.90 | 2.4 | 1201.4 | 0.0016 | 47 |
| EO-65 | S5 | 0.02 | 10.00 | 637.14 | 4.90 | 20.1 | 287.2 | 0.0458 | 5,626 |
| EO-66 | S5 | 0.02 | 10.00 | 637.14 | 4.90 | 20.3 | 254.5 | 0.0424 | 5,877 |
| EO-67 | S5 | 0.02 | 10.00 | 637.14 | 4.90 | 20.1 | 244.2 | 0.0489 | 7,065 |
| EO-68 | S5 | 0.02 | 10.00 | 637.14 | 4.90 | 20.1 | 281.4 | 0.0446 | 5,592 |
| EO-69 | 10i | 0.02 | 10.00 | 637.14 | 4.90 | 20.3 | 205.2 | 0.0448 | 7,702 |
| EO-70 | 10i | 0.02 | 10.00 | 637.14 | 4.90 | 20.1 | 199.8 | 0.0394 | 6,959 |
| EO-71 | 10i | 0.02 | 10.00 | 637.14 | 4.90 | 20.1 | 198.2 | 0.0421 | 7,495 |
| EO-72 | 10i | 0.02 | 10.00 | 637.14 | 4.90 | 20.1 | 233.4 | 0.0462 | 6,983 |
| EO-73 | 10l | 0.02 | 10.00 | 637.14 | 4.90 | 20.1 | 251.1 | 0.0368 | 5,171 |
| EO-74 | 10l | 0.02 | 10.00 | 637.14 | 4.90 | 20.1 | 276.9 | 0.0399 | 5,085 |
| EO-75 | 10l | 0.02 | 10.00 | 637.14 | 4.90 | 20.1 | 279.0 | 0.0414 | 5,236 |
| EO-76 | 10l | 0.02 | 10.00 | 637.14 | 4.90 | 20.1 | 306.3 | 0.0400 | 4,607 |

*Micromoles of Al in MAO.

TABLE 6

Ethylene-1-Octene Polymerization Runs - Part 2.

| Ex # | TMC | Mw | Mn | PDI | Octene (wt %) | Tm (° C.) |
|---|---|---|---|---|---|---|
| EO-1 | 10a | 1,277,225 | 645,928 | 2.0 | 7.0 | — |
| EO-2 | 10a | 1,262,217 | 611,220 | 2.1 | 7.7 | — |
| EO-3 | 10a | 1,251,099 | 586,370 | 2.1 | 7.3 | — |
| EO-4 | 10a | 1,218,474 | 557,821 | 2.2 | 7.4 | — |
| EO-5 | 10c | 868,385 | 498,841 | 1.7 | 11.2 | — |
| EO-6 | 10c | 865,442 | 501,104 | 1.7 | 11.5 | — |
| EO-7 | 10c | 814,718 | 470,094 | 1.7 | 10.8 | — |
| EO-8 | 10c | 872,038 | 501,300 | 1.7 | 12.0 | — |
| EO-9 | 10d | 928,925 | 533,605 | 1.7 | 12.9 | — |
| EO-10 | 10d | 939,313 | 512,396 | 1.8 | 11.9 | — |
| EO-11 | 10d | 908,742 | 499,591 | 1.8 | 11.1 | — |
| EO-12 | 10d | 980,527 | 537,104 | 1.8 | 11.7 | — |
| EO-13 | S2 | 972,084 | 405,997 | 2.4 | 4.1 | 120.7 |
| EO-14 | S2 | 1,668,639 | 645,233 | 2.6 | 7.3 | 117.0 |
| EO-15 | S2 | 2,037,255 | 881,126 | 2.3 | 8.5 | 118.2 |
| EO-16 | S2 | 1,594,432 | 522,875 | 3.0 | 8.4 | 118.0 |
| EO-17 | S1 | 514,344 | 241,180 | 2.1 | — | 126.3 |
| EO-18 | S1 | 555,840 | 220,474 | 2.5 | 5.6 | 125.3 |
| EO-19 | S1 | 654,904 | 375,866 | 1.7 | 5.2 | 137.9 |
| EO-20 | S1 | 593,994 | 220,791 | 2.7 | 5.3 | 125.0 |
| EO-21 | 10 | 814,165 | 518,678 | 1.6 | 9.9 | — |
| EO-22 | 10 | 1,002,231 | 599,846 | 1.7 | 10.5 | — |
| EO-23 | 10 | 1,001,190 | 605,667 | 1.7 | 9.2 | — |
| EO-24 | 10 | 877,607 | 548,944 | 1.6 | 9.1 | — |
| EO-25 | P4 | — | — | — | — | — |
| EO-26 | P4 | — | — | — | — | — |
| EO-27 | P4 | — | — | — | — | — |
| EO-28 | P4 | — | — | — | — | — |
| EO-29 | P4 | — | — | — | — | — |
| EO-30 | P4 | — | — | — | — | — |
| EO-31 | P4 | — | — | — | — | — |
| EO-32 | P4 | — | — | — | — | — |
| EO-33 | P3 | 735,340 | 469,712 | 1.6 | 2.9 | — |
| EO-34 | P3 | 696,501 | 443,167 | 1.6 | 2.7 | — |
| EO-35 | P3 | 702,484 | 446,626 | 1.6 | 2.9 | — |
| EO-36 | P3 | 687,796 | 436,033 | 1.6 | 3.2 | — |
| EO-37 | 10f | 283,023 | 169,829 | 1.7 | 19.2 | — |
| EO-38 | 10f | 285,259 | 175,716 | 1.6 | 19.7 | — |
| EO-39 | 10f | 346,064 | 188,594 | 1.8 | 15.9 | — |
| EO-40 | 10f | 300,375 | 178,109 | 1.7 | 19.8 | — |
| EO-41 | 10h | 1,351,068 | 874,463 | 1.5 | 9.7 | — |
| EO-42 | 10h | 1,311,510 | 823,148 | 1.6 | 9.6 | — |
| EO-43 | 10h | 1,142,379 | 702,456 | 1.6 | 12.0 | — |
| EO-44 | 10h | 1,297,679 | 839,149 | 1.5 | 10.7 | — |
| EO-45 | N3 | 203,471 | 133,092 | 1.5 | 4.9 | — |
| EO-46 | N3 | 221,287 | 152,903 | 1.4 | 4.0 | — |
| EO-47 | N3 | 198,052 | 129,340 | 1.5 | 5.1 | — |
| EO-48 | N3 | 193,630 | 126,829 | 1.5 | 5.4 | — |
| EO-49 | O3 | 164,917 | 109,205 | 1.5 | 2.6 | — |
| EO-50 | O3 | 170,490 | 115,925 | 1.5 | 3.5 | — |
| EO-51 | O3 | 168,436 | 114,274 | 1.5 | 3.5 | — |
| EO-52 | O3 | 167,618 | 115,500 | 1.5 | 3.6 | — |
| EO-53 | O4 | — | — | — | — | — |
| EO-54 | O4 | — | — | — | — | — |

TABLE 6-continued

Ethylene-1-Octene Polymerization Runs - Part 2.

| Ex # | TMC | Mw | Mn | PDI | Octene (wt %) | Tm (° C.) |
|---|---|---|---|---|---|---|
| EO-55 | O4 | — | — | — | — | — |
| EO-56 | O4 | — | — | — | — | — |
| EO-57 | S3 | 411,891 | 268,612 | 1.5 | 3.3 | — |
| EO-58 | S3 | 410,515 | 265,930 | 1.5 | 3.4 | — |
| EO-59 | S3 | 388,703 | 249,811 | 1.6 | 3.4 | — |
| EO-60 | S3 | 404,263 | 260,583 | 1.6 | 3.4 | — |
| EO-61 | S4 | — | — | — | — | — |
| EO-62 | S4 | — | — | — | — | — |
| EO-63 | S4 | — | — | — | — | — |
| EO-64 | S4 | — | — | — | — | — |
| EO-65 | S5 | 1,015,924 | 669,864 | 1.5 | 2.7 | — |
| EO-66 | S5 | 1,052,317 | 690,864 | 1.5 | 2.4 | — |
| EO-67 | S5 | 1,130,956 | 740,634 | 1.5 | 2.3 | — |
| EO-68 | S5 | 1,176,851 | 775,789 | 1.5 | 2.2 | — |
| EO-69 | 10i | 1,125,916 | 750,609 | 1.5 | 11.4 | — |
| EO-70 | 10i | 1,160,571 | 802,503 | 1.4 | 11.8 | — |
| EO-71 | 10i | 1,164,150 | 796,644 | 1.5 | 11.6 | — |
| EO-72 | 10i | 1,154,685 | 819,920 | 1.4 | 11.1 | — |
| EO-73 | 10l | 1,192,177 | 788,044 | 1.5 | 19.5 | — |
| EO-74 | 10l | 1,119,818 | 781,029 | 1.4 | 17.5 | — |
| EO-75 | 10l | 1,200,596 | 829,844 | 1.4 | 26.5 | — |
| EO-76 | 10l | 1,113,991 | 760,611 | 1.5 | 12.1 | — |

TABLE 7

Propylene polymerization Runs - Part 1.

| Ex # | TMC | TMC (μmol) | MAO* (μmol) | Toluene (μL) | Hexanes (μL) | Propene (μL) | Quench Time (sec) | Polymer Yield (g) | Activity (g/mmol · hr) |
|---|---|---|---|---|---|---|---|---|---|
| PP-1 | S1 | 0.10 | 50 | 499 | 3633 | 1066 | 417 | 0.0473 | 4088 |
| PP-2 | S1 | 0.10 | 50 | 499 | 3633 | 1066 | 466 | 0.0479 | 3699 |
| PP-3 | S1 | 0.08 | 40 | 399 | 3733 | 1066 | 575 | 0.0439 | 3434 |
| PP-4 | S1 | 0.08 | 40 | 399 | 3733 | 1066 | 627 | 0.0451 | 3238 |
| PP-5 | S2 | 0.10 | 50 | 499 | 3633 | 1066 | 510 | 0.0511 | 3605 |
| PP-6 | S2 | 0.10 | 50 | 499 | 3633 | 1066 | 572 | 0.0535 | 3366 |
| PP-7 | S2 | 0.08 | 40 | 399 | 3733 | 1066 | 661 | 0.0481 | 3274 |
| PP-8 | S2 | 0.08 | 40 | 399 | 3733 | 1066 | 677 | 0.0473 | 3146 |
| PP-9 | S3 | 0.10 | 50 | 331 | 3700 | 1066 | 341 | 0.0577 | 6093 |
| PP-10 | S3 | 0.10 | 50 | 331 | 3700 | 1066 | 367 | 0.0534 | 5233 |
| PP-11 | S3 | 0.08 | 40 | 265 | 3767 | 1066 | 459 | 0.0508 | 4979 |
| PP-12 | S3 | 0.08 | 40 | 265 | 3767 | 1066 | 469 | 0.0463 | 4443 |
| PP-13 | S4 | 0.08 | 40 | 265 | 3767 | 1066 | 901 | 0.0291 | 1454 |
| PP-14 | S4 | 0.10 | 50 | 331 | 3700 | 1066 | 901 | 0.0025 | 100 |
| PP-15 | S4 | 0.08 | 40 | 265 | 3767 | 1066 | 901 | 0.002 | 100 |
| PP-16 | S4 | 0.10 | 50 | 331 | 3700 | 1066 | 901 | 0.0025 | 100 |
| PP-17 | S4 | 0.10 | 50 | 331 | 3700 | 1066 | 901 | 0.0024 | 96 |
| PP-18 | S4 | 0.10 | 50 | 331 | 3700 | 1066 | 901 | 0.0024 | 96 |
| PP-19 | S4 | 0.08 | 40 | 265 | 3767 | 1066 | 901 | 0.0016 | 80 |
| PP-20 | S4 | 0.08 | 40 | 265 | 3767 | 1066 | 901 | 0.0016 | 80 |
| PP-21 | S5 | 0.10 | 50 | 331 | 3700 | 1066 | 901 | 0.0017 | 68 |
| PP-22 | S5 | 0.10 | 50 | 331 | 3700 | 1066 | 901 | 0.0007 | 28 |
| PP-23 | S5 | 0.08 | 40 | 265 | 3767 | 1066 | 901 | 0.0003 | 15 |
| PP-24 | S5 | 0.08 | 40 | 265 | 3767 | 1066 | 902 | 0 | 0 |
| PP-25 | O3 | 0.08 | 40 | 265 | 3767 | 1066 | 409 | 0.0524 | 5762 |
| PP-26 | O3 | 0.10 | 50 | 331 | 3700 | 1066 | 373 | 0.0531 | 5125 |
| PP-27 | O3 | 0.08 | 40 | 265 | 3767 | 1066 | 538 | 0.0549 | 4593 |
| PP-28 | O3 | 0.10 | 50 | 331 | 3700 | 1066 | 517 | 0.0559 | 3896 |
| PP-29 | O4 | 0.08 | 40 | 265 | 3767 | 1066 | 900 | 0.0046 | 230 |
| PP-30 | O4 | 0.08 | 40 | 265 | 3767 | 1066 | 900 | 0.0038 | 190 |
| PP-31 | O4 | 0.10 | 50 | 331 | 3700 | 1066 | 901 | 0.0037 | 148 |
| PP-32 | O4 | 0.10 | 50 | 331 | 3700 | 1066 | 900 | 0.0027 | 108 |
| PP-33 | N2 | 0.10 | 50 | 331 | 3700 | 1066 | 901 | 0.0338 | 1351 |
| PP-34 | N2 | 0.10 | 50 | 331 | 3700 | 1066 | 901 | 0.0327 | 1307 |
| PP-35 | N2 | 0.08 | 40 | 265 | 3767 | 1066 | 901 | 0.0241 | 1204 |
| PP-36 | N2 | 0.08 | 40 | 265 | 3767 | 1066 | 900 | 0.0234 | 1170 |
| PP-37 | N3 | 0.08 | 40 | 265 | 3767 | 1066 | 190 | 0.0636 | 15097 |
| PP-38 | N3 | 0.10 | 50 | 331 | 3700 | 1066 | 203 | 0.0725 | 12840 |
| PP-39 | N3 | 0.10 | 50 | 331 | 3700 | 1066 | 181 | 0.0644 | 12811 |
| PP-40 | N3 | 0.08 | 40 | 265 | 3767 | 1066 | 485 | 0.0552 | 5124 |
| PP-41 | P2 | 0.10 | 50 | 331 | 3700 | 1066 | 900 | 0.0143 | 572 |
| PP-42 | P2 | 0.10 | 50 | 331 | 3700 | 1066 | 901 | 0.0138 | 552 |
| PP-43 | P2 | 0.08 | 40 | 265 | 3767 | 1066 | 900 | 0.0098 | 490 |
| PP-44 | P2 | 0.08 | 40 | 265 | 3767 | 1066 | 901 | 0.0087 | 434 |
| PP-45 | P3 | 0.08 | 40 | 265 | 3767 | 1066 | 534 | 0.0448 | 3775 |
| PP-46 | P3 | 0.08 | 40 | 265 | 3767 | 1066 | 652 | 0.0491 | 3391 |
| PP-47 | P3 | 0.10 | 50 | 331 | 3700 | 1066 | 618 | 0.0512 | 2980 |
| PP-48 | P3 | 0.10 | 50 | 331 | 3700 | 1066 | 671 | 0.0496 | 2662 |
| PP-49 | P4 | 0.10 | 50 | 331 | 3700 | 1066 | 900 | 0.0028 | 112 |
| PP-50 | P4 | 0.10 | 50 | 331 | 3700 | 1066 | 901 | 0.0028 | 112 |

TABLE 7-continued

Propylene polymerization Runs - Part 1.

| Ex # | TMC | TMC (µmol) | MAO* (µmol) | Toluene (µL) | Hexanes (µL) | Propene (µL) | Quench Time (sec) | Polymer Yield (g) | Activity (g/mmol · hr) |
|---|---|---|---|---|---|---|---|---|---|
| PP-51 | P4 | 0.10 | 50 | 331 | 3700 | 1066 | 902 | 0.0028 | 112 |
| PP-52 | P4 | 0.08 | 40 | 265 | 3767 | 1066 | 901 | 0.0021 | 105 |
| PP-53 | P4 | 0.08 | 40 | 265 | 3767 | 1066 | 901 | 0.002 | 100 |
| PP-54 | P4 | 0.10 | 50 | 331 | 3700 | 1066 | 901 | 0.0024 | 96 |
| PP-55 | P4 | 0.08 | 40 | 265 | 3767 | 1066 | 901 | 0.0018 | 90 |
| PP-56 | P4 | 0.08 | 40 | 265 | 3767 | 1066 | 901 | 0.0017 | 85 |
| PP-57 | 10 | 0.10 | 50 | 331 | 3700 | 1066 | 901 | 0.0075 | 300 |
| PP-58 | 10 | 0.10 | 50 | 331 | 3700 | 1066 | 901 | 0.0065 | 260 |
| PP-59 | 10 | 0.08 | 40 | 265 | 3767 | 1066 | 901 | 0.0013 | 65 |
| PP-60 | 10 | 0.08 | 40 | 265 | 3767 | 1066 | 900 | 0.0009 | 45 |
| PP-61 | 10a | 0.10 | 50 | 331 | 3700 | 1066 | 729 | 0.0496 | 2448 |
| PP-62 | 10a | 0.10 | 50 | 331 | 3700 | 1066 | 731 | 0.0497 | 2446 |
| PP-63 | 10a | 0.08 | 40 | 265 | 3767 | 1066 | 824 | 0.0426 | 2326 |
| PP-64 | 10a | 0.08 | 40 | 265 | 3767 | 1066 | 760 | 0.0383 | 2267 |
| PP-65 | 10b | 0.10 | 50 | 331 | 3700 | 1066 | 324 | 0.0624 | 6932 |
| PP-66 | 10b | 0.10 | 50 | 331 | 3700 | 1066 | 305 | 0.058 | 6839 |
| PP-67 | 10b | 0.08 | 40 | 265 | 3767 | 1066 | 387 | 0.0575 | 6688 |
| PP-68 | 10b | 0.08 | 40 | 265 | 3767 | 1066 | 444 | 0.0508 | 5147 |
| PP-69 | 10d | 0.10 | 50 | 331 | 3700 | 1066 | 901 | 0.0059 | 236 |
| PP-70 | 10d | 0.08 | 40 | 265 | 3767 | 1066 | 900 | 0.0046 | 230 |
| PP-71 | 10d | 0.10 | 50 | 331 | 3700 | 1066 | 900 | 0.0048 | 192 |
| PP-72 | 10d | 0.08 | 40 | 265 | 3767 | 1066 | 901 | 0.0034 | 170 |
| PP-73 | 10e | 0.10 | 50 | 331 | 3700 | 1066 | 314 | 0.0559 | 6402 |
| PP-74 | 10e | 0.08 | 40 | 265 | 3767 | 1066 | 415 | 0.0572 | 6197 |
| PP-75 | 10e | 0.10 | 50 | 331 | 3700 | 1066 | 324 | 0.0549 | 6102 |
| PP-76 | 10e | 0.08 | 40 | 265 | 3767 | 1066 | 404 | 0.0538 | 5988 |
| PP-77 | 10f | 0.10 | 50 | 499 | 3633 | 1066 | 900 | 0.0069 | 276 |
| PP-78 | 10f | 0.10 | 50 | 499 | 3633 | 1066 | 902 | 0.0067 | 267 |
| PP-79 | 10f | 0.08 | 40 | 399 | 3733 | 1066 | 901 | 0.0053 | 265 |
| PP-80 | 10f | 0.08 | 40 | 399 | 3733 | 1066 | 900 | 0.0051 | 255 |
| PP-81 | 10g | 0.10 | 50 | 331 | 3700 | 1066 | 587 | 0.0487 | 2986 |
| PP-82 | 10g | 0.10 | 50 | 331 | 3700 | 1066 | 564 | 0.0429 | 2740 |
| PP-83 | 10g | 0.08 | 40 | 265 | 3767 | 1066 | 900 | 0.042 | 2099 |
| PP-84 | 10g | 0.08 | 40 | 265 | 3767 | 1066 | 901 | 0.0392 | 1958 |
| PP-85 | 10h | 0.10 | 50 | 331 | 3700 | 1066 | 486 | 0.0581 | 4305 |
| PP-86 | 10h | 0.08 | 40 | 265 | 3767 | 1066 | 547 | 0.0497 | 4092 |
| PP-87 | 10h | 0.10 | 50 | 331 | 3700 | 1066 | 480 | 0.0545 | 4090 |
| PP-88 | 10h | 0.08 | 40 | 265 | 3767 | 1066 | 558 | 0.0491 | 3957 |
| PP-89 | 10i | 0.10 | 50 | 499 | 3633 | 1066 | 519 | 0.0516 | 3578 |
| PP-90 | 10i | 0.10 | 50 | 499 | 3633 | 1066 | 565 | 0.053 | 3378 |
| PP-91 | 10i | 0.08 | 40 | 399 | 3733 | 1066 | 632 | 0.0451 | 3214 |
| PP-92 | 10i | 0.08 | 40 | 399 | 3733 | 1066 | 901 | 0.0335 | 1674 |
| PP-93 | 10k | 0.10 | 50 | 499 | 3633 | 1066 | 571 | 0.0557 | 3510 |
| PP-94 | 10k | 0.10 | 50 | 499 | 3633 | 1066 | 554 | 0.0532 | 3459 |
| PP-95 | 10k | 0.08 | 40 | 399 | 3733 | 1066 | 637 | 0.0489 | 3452 |
| PP-96 | 10k | 0.08 | 40 | 399 | 3733 | 1066 | 664 | 0.0463 | 3139 |
| PP-97 | 10l | 0.10 | 50 | 499 | 3633 | 1066 | 409 | 0.057 | 5012 |
| PP-98 | 10l | 0.10 | 50 | 499 | 3633 | 1066 | 468 | 0.0537 | 4135 |
| PP-99 | 10l | 0.08 | 40 | 399 | 3733 | 1066 | 669 | 0.0511 | 3435 |
| PP-100 | 10l | 0.08 | 40 | 399 | 3733 | 1066 | 901 | 0.0298 | 1489 |
| PP-101 | 10m | 0.10 | 50 | 499 | 3633 | 1066 | 547 | 0.0501 | 3297 |
| PP-102 | 10m | 0.08 | 40 | 399 | 3733 | 1066 | 631 | 0.0448 | 3197 |
| PP-103 | 10m | 0.10 | 50 | 499 | 3633 | 1066 | 555 | 0.0479 | 3110 |
| PP-104 | 10m | 0.08 | 40 | 399 | 3733 | 1066 | 672 | 0.0417 | 2792 |

*Micromoles of Al in MAO.

TABLE 8

Propylene Polymerization Runs - Part 2.

| Ex # | TMC | Mw | Mn | PDI | FTIR Crystallinity Index (° C.)* | DSC (° C.) | delta H (J/g) |
|---|---|---|---|---|---|---|---|
| PP-1 | S1 | 3,355 | 2,412 | 1.39 | 69.1 | — | — |
| PP-2 | S1 | 3,181 | 2,304 | 1.38 | 74.6 | none | — |
| PP-3 | S1 | 3,559 | 2,466 | 1.44 | — | — | — |
| PP-4 | S1 | 3,708 | 2,540 | 1.46 | — | — | — |
| PP-5 | S2 | 14,217 | 8,386 | 1.70 | 88.6 | — | — |
| PP-6 | S2 | 15,075 | 8,970 | 1.68 | 87.7 | none | — |

TABLE 8-continued

Propylene Polymerization Runs - Part 2.

| Ex # | TMC | Mw | Mn | PDI | FTIR Crystallinity Index (° C.)* | DSC (° C.) | delta H (J/g) |
|---|---|---|---|---|---|---|---|
| PP-7 | S2 | 14,366 | 8,496 | 1.69 | 91.5 | none | — |
| PP-8 | S2 | 14,313 | 8,497 | 1.68 | — | — | — |
| PP-9 | S3 | 8,148 | 5,188 | 1.57 | 132.0 | 131.0 | 101.2 |
| PP-10 | S3 | 7,772 | 4,959 | 1.57 | 127.1 | — | — |
| PP-11 | S3 | 7,689 | 4,887 | 1.57 | 139.9 | — | — |
| PP-12 | S3 | 6,970 | 4,527 | 1.54 | 136.8 | — | — |
| PP-13 | S4 | 234,731 | 103,777 | 2.26 | 157.2 | 154.0 | 117 |
| PP-14 | S4 | — | — | — | — | — | — |
| PP-15 | S4 | — | — | — | — | — | — |
| PP-16 | S4 | — | — | — | — | — | — |
| PP-17 | S4 | — | — | — | — | — | — |
| PP-18 | S4 | — | — | — | — | — | — |
| PP-19 | S4 | — | — | — | — | — | — |
| PP-20 | S4 | — | — | — | — | — | — |
| PP-21 | S5 | — | — | — | — | — | — |
| PP-22 | S5 | — | — | — | — | — | — |
| PP-23 | S5 | — | — | — | — | — | — |
| PP-24 | S5 | — | — | — | — | — | — |
| PP-25 | O3 | 9,631 | 6,012 | 1.60 | 139.8 | 129.0 | 85 |
| PP-26 | O3 | 8,143 | 5,221 | 1.56 | 137.5 | — | — |
| PP-27 | O3 | 8,492 | 5,376 | 1.58 | 139.5 | — | — |
| PP-28 | O3 | 7,704 | 4,918 | 1.57 | 137.9 | — | — |
| PP-29 | O4 | — | — | — | — | — | — |
| PP-30 | O4 | — | — | — | — | — | — |
| PP-31 | O4 | — | — | — | — | — | — |
| PP-32 | O4 | — | — | — | — | — | — |
| PP-33 | N2 | 10,789 | 6,170 | 1.75 | 101.0 | none | — |
| PP-34 | N2 | 10,104 | 5,758 | 1.75 | 100.9 | — | — |
| PP-35 | N2 | 10,398 | 6,093 | 1.71 | — | — | — |
| PP-36 | N2 | 10,575 | 6,205 | 1.70 | — | — | — |
| PP-37 | N3 | 11,612 | 7,087 | 1.64 | — | — | — |
| PP-38 | N3 | 11,025 | 6,717 | 1.64 | — | 129,138 | 56.7 |
| PP-39 | N3 | 10,806 | 6,653 | 1.62 | — | — | — |
| PP-40 | N3 | 8,592 | 5,292 | 1.62 | — | — | — |
| PP-41 | P2 | 13,108 | 7,106 | 1.84 | — | none | — |
| PP-42 | P2 | 13,483 | 7,588 | 1.78 | — | — | — |
| PP-43 | P2 | — | — | — | — | — | — |
| PP-44 | P2 | — | — | — | — | — | — |
| PP-45 | P3 | 10,919 | 6,514 | 1.68 | — | — | — |
| PP-46 | P3 | 11,185 | 6,722 | 1.66 | — | — | — |
| PP-47 | P3 | 9,950 | 6,012 | 1.66 | — | 126 | 56.7 |
| PP-48 | P3 | 9,211 | 5,651 | 1.63 | — | — | — |
| PP-49 | P4 | — | — | — | — | — | — |
| PP-50 | P4 | — | — | — | — | — | — |
| PP-51 | P4 | — | — | — | — | — | — |
| PP-52 | P4 | — | — | — | — | — | — |
| PP-53 | P4 | — | — | — | — | — | — |
| PP-54 | P4 | — | — | — | — | — | — |
| PP-55 | P4 | — | — | — | — | — | — |
| PP-56 | P4 | — | — | — | — | — | — |
| PP-57 | 10 | — | — | — | — | — | — |
| PP-58 | 10 | — | — | — | — | — | — |
| PP-59 | 10 | — | — | — | — | — | — |
| PP-60 | 10 | — | — | — | — | — | — |
| PP-61 | 10a | 15,574 | 9,303 | 1.67 | 79.3 | 0.0 | — |
| PP-62 | 10a | 14,530 | 8,780 | 1.65 | 81.6 | — | — |
| PP-63 | 10a | 15,223 | 9,202 | 1.65 | 77.0 | — | — |
| PP-64 | 10a | 15,124 | 9,033 | 1.67 | 76.6 | — | — |
| PP-65 | 10b | 145,076 | 92,497 | 1.57 | 104.2 | 96.0 | 15 |
| PP-66 | 10b | 145,401 | 93,723 | 1.55 | 105.7 | — | — |
| PP-67 | 10b | 151,074 | 97,313 | 1.55 | 106.4 | — | — |
| PP-68 | 10b | 128,894 | 83,361 | 1.55 | 104.9 | — | — |
| PP-69 | 10d | — | — | — | — | — | — |
| PP-70 | 10d | — | — | — | — | — | — |
| PP-71 | 10d | — | — | — | — | — | — |
| PP-72 | 10d | — | — | — | — | — | — |
| PP-73 | 10e | 154,659 | 85,721 | 1.80 | 114.0 | — | — |
| PP-74 | 10e | 157,340 | 90,116 | 1.75 | 114.3 | 111 | 33.1 |
| PP-75 | 10e | 158,271 | 89,187 | 1.77 | 112.7 | — | — |
| PP-76 | 10e | 156,374 | 92,740 | 1.69 | 115.1 | — | — |
| PP-77 | 10f | — | — | — | — | — | — |
| PP-78 | 10f | — | — | — | — | — | — |
| PP-79 | 10f | — | — | — | — | — | — |

TABLE 8-continued

Propylene Polymerization Runs - Part 2.

| Ex # | TMC | Mw | Mn | PDI | FTIR Crystallinity Index (° C.)* | DSC (° C.) | delta H (J/g) |
|---|---|---|---|---|---|---|---|
| PP-80 | 10f | — | — | — | — | — | — |
| PP-81 | 10g | 45,219 | 24,853 | 1.82 | 92.5 | 68 | — |
| PP-82 | 10g | 42,389 | 23,044 | 1.84 | 91.2 | — | — |
| PP-83 | 10g | 42,547 | 23,813 | 1.79 | 97.2 | — | — |
| PP-84 | 10g | 41,901 | 23,230 | 1.80 | 91.7 | — | — |
| PP-85 | 10h | 41,779 | 24,095 | 1.73 | 97.3 | none | — |
| PP-86 | 10h | 41,705 | 24,000 | 1.74 | 89.9 | — | — |
| PP-87 | 10h | 41,586 | 24,259 | 1.71 | 95.2 | — | — |
| PP-88 | 10h | 42,175 | 24,716 | 1.71 | 89.9 | — | — |
| PP-89 | 10i | 60,267 | 35,759 | 1.69 | 84.8 | — | — |
| PP-90 | 10i | 56,906 | 33,608 | 1.69 | 86.1 | none | — |
| PP-91 | 10i | 56,731 | 33,300 | 1.70 | — | none | — |
| PP-92 | 10i | 66,921 | 38,883 | 1.72 | 31.2 | — | — |
| PP-93 | 10k | 62,268 | 37,935 | 1.64 | 92.9 | none | — |
| PP-94 | 10k | 61,485 | 37,558 | 1.64 | 86.5 | — | — |
| PP-95 | 10k | 57,643 | 38,672 | 1.49 | 82.6 | none | — |
| PP-96 | 10k | 57,212 | 36,399 | 1.57 | 95.4 | — | — |
| PP-97 | 10l | 171,939 | 103,773 | 1.66 | 102.5 | 79 | — |
| PP-98 | 10l | 172,948 | 103,924 | 1.66 | 102.2 | — | — |
| PP-99 | 10l | 185,262 | 109,720 | 1.69 | 103.7 | 80 | — |
| PP-100 | 10l | 168,001 | 100,790 | 1.67 | 105.2 | — | — |
| PP-101 | 10m | 179,738 | 107,811 | 1.67 | 102.1 | 89 | — |
| PP-102 | 10m | 174,133 | 106,451 | 1.64 | 69.3 | none | — |
| PP-103 | 10m | 118,275 | 58,217 | 2.03 | 102.6 | — | — |
| PP-104 | 10m | 175,092 | 106,871 | 1.64 | 96.7 | — | — |

*Numbers below 100° C. are outside the calibration range of the calculation.

TABLE 9

Ethylene-Propylene Copolymerization Runs - Part 1.

| Ex # | TMC | TMC (μmol) | MAO# (μmol) | Hexanes (μL) | Toluene (μL) | Propene (μL) | Quench Time (sec) | Yield (g) | Activity (g/mmol · hr) |
|---|---|---|---|---|---|---|---|---|---|
| EP-1 | S1 | 0.08 | 40 | 3767 | 265 | 1066 | 111.5 | 0.0385 | 15541 |
| EP-2 | S1 | 0.08 | 40 | 3767 | 265 | 1066 | 78.6 | 0.0427 | 24431 |
| EP-3 | S1 | 0.10 | 50 | 3600 | 331 | 1066 | 77.2 | 0.0504 | 23493 |
| EP-4 | S1 | 0.10 | 50 | 3600 | 331 | 1066 | 87.3 | 0.0526 | 21688 |
| EP-5 | S2 | 0.08 | 40 | 3767 | 265 | 1066 | 90.5 | 0.0514 | 25555 |
| EP-6 | S2 | 0.08 | 40 | 3767 | 265 | 1066 | 114.2 | 0.0502 | 19776 |
| EP-7 | S2 | 0.10 | 50 | 3600 | 331 | 1066 | 114.4 | 0.0616 | 19383 |
| EP-8 | S2 | 0.10 | 50 | 3600 | 331 | 1066 | 110.3 | 0.06 | 19592 |
| EP-9 | S3 | 0.08 | 40 | 3724 | 265 | 1066 | 142.7 | 0.0348 | 10976 |
| EP-10 | S3 | 0.08 | 40 | 3724 | 265 | 1066 | 170.4 | 0.0335 | 8848 |
| EP-11 | S3 | 0.10 | 50 | 3657 | 331 | 1066 | 116.2 | 0.0425 | 13168 |
| EP-12 | S3 | 0.10 | 50 | 3657 | 331 | 1066 | 266.1 | 0.0807 | 10918 |
| EP-13 | S4 | 0.08 | 40 | 3724 | 265 | 1066 | 901.1 | 0.0019 | 95 |
| EP-14 | S4 | 0.08 | 40 | 3724 | 265 | 1066 | 901.5 | 0.0025 | 125 |
| EP-15 | S4 | 0.10 | 50 | 3657 | 331 | 1066 | 901.0 | 0.0033 | 132 |
| EP-16 | S4 | 0.10 | 50 | 3657 | 331 | 1066 | 900.0 | 0.0034 | 136 |
| EP-17 | S5 | 0.08 | 40 | 3724 | 265 | 1066 | 900.1 | 0 | 0 |
| EP-18 | S5 | 0.08 | 40 | 3724 | 265 | 1066 | 900.6 | 0.0072 | 360 |
| EP-19 | S5 | 0.10 | 50 | 3657 | 331 | 1066 | 900.2 | 0.0141 | 564 |
| EP-20 | S5 | 0.10 | 50 | 3657 | 331 | 1066 | 742.3 | 0.0224 | 1086 |
| EP-21 | O3 | 0.08 | 40 | 3724 | 265 | 1066 | 151.2 | 0.0486 | 14461 |
| EP-22 | O3 | 0.08 | 40 | 3724 | 265 | 1066 | 233.2 | 0.0443 | 8550 |
| EP-23 | O3 | 0.10 | 50 | 3657 | 331 | 1066 | 181.3 | 0.0487 | 9671 |
| EP-24 | O3 | 0.10 | 50 | 3657 | 331 | 1066 | 181.9 | 0.0425 | 8414 |
| EP-25 | O4 | 0.08 | 40 | 3724 | 265 | 1066 | 900.4 | 0.0058 | 290 |
| EP-26 | O4 | 0.08 | 40 | 3724 | 265 | 1066 | 901.2 | 0.0082 | 409 |
| EP-27 | O4 | 0.10 | 50 | 3657 | 331 | 1066 | 900.4 | 0.0073 | 292 |
| EP-28 | O4 | 0.10 | 50 | 3657 | 331 | 1066 | 900.7 | 0.0094 | 376 |
| EP-29 | N2 | 0.08 | 40 | 3724 | 265 | 1066 | 337.9 | 0.0264 | 3516 |
| EP-30 | N2 | 0.08 | 40 | 3724 | 265 | 1066 | 142.2 | 0.037 | 11706 |
| EP-31 | N2 | 0.10 | 50 | 3657 | 331 | 1066 | 108.7 | 0.0443 | 14673 |
| EP-32 | N2 | 0.10 | 50 | 3657 | 331 | 1066 | 114.0 | 0.0444 | 14022 |
| EP-33 | N3 | 0.10 | 50 | 3657 | 331 | 1066 | 99.0 | 0.0715 | 26011 |
| EP-34 | N3 | 0.10 | 50 | 3657 | 331 | 1066 | 93.5 | 0.0754 | 29022 |
| EP-35 | N3 | 0.08 | 40 | 3724 | 265 | 1066 | 127.1 | 0.0472 | 16714 |

TABLE 9-continued

Ethylene-Propylene Copolymerization Runs - Part 1.

| Ex # | TMC | TMC (μmol) | MAO# (μmol) | Hexanes (μL) | Toluene (μL) | Propene (μL) | Quench Time (sec) | Yield (g) | Activity (g/mmol · hr) |
|---|---|---|---|---|---|---|---|---|---|
| EP-36 | N3 | 0.08 | 40 | 3724 | 265 | 1066 | 113.1 | 0.0518 | 20616 |
| EP-37 | P2 | 0.08 | 40 | 3724 | 265 | 1066 | 791.9 | 0.0227 | 1290 |
| EP-38 | P2 | 0.08 | 40 | 3724 | 265 | 1066 | 818.0 | 0.0228 | 1254 |
| EP-39 | P2 | 0.10 | 50 | 3657 | 331 | 1066 | 901.7 | 0.01 | 399 |
| EP-40 | P2 | 0.10 | 50 | 3657 | 331 | 1066 | 493.1 | 0.0256 | 1869 |
| EP-41 | P3 | 0.10 | 50 | 3657 | 331 | 1066 | 900.1 | 0.0221 | 884 |
| EP-42 | P3 | 0.10 | 50 | 3657 | 331 | 1066 | 901.5 | 0.0238 | 950 |
| EP-43 | P3 | 0.08 | 40 | 3724 | 265 | 1066 | 888.8 | 0.0263 | 1332 |
| EP-44 | P3 | 0.08 | 40 | 3724 | 265 | 1066 | 901.8 | 0.0207 | 1033 |
| EP-45 | P4 | 0.08 | 40 | 3724 | 265 | 1066 | 900.7 | 0.0023 | 115 |
| EP-46 | P4 | 0.08 | 40 | 3724 | 265 | 1066 | 901.2 | 0.0024 | 120 |
| EP-47 | P4 | 0.10 | 50 | 3657 | 331 | 1066 | 900.2 | 0.0052 | 208 |
| EP-48 | P4 | 0.10 | 50 | 3657 | 331 | 1066 | 900.9 | 0.0064 | 256 |
| EP-49 | 10 | 0.08 | 40 | 3724 | 265 | 1066 | 901.0 | 0.0061 | 305 |
| EP-50 | 10 | 0.08 | 40 | 3724 | 265 | 1066 | 901.6 | 0.0047 | 235 |
| EP-51* | 10 | 0.10 | 50 | 3657 | 331 | 1066 | 901.3 | 0.0008 | 32 |
| EP-52 | 10 | 0.10 | 50 | 3657 | 331 | 1066 | 525.3 | 0.0298 | 2042 |
| EP-53 | 10a | 0.10 | 50 | 3657 | 331 | 1066 | 134.2 | 0.0417 | 11188 |
| EP-54 | 10a | 0.10 | 50 | 3657 | 331 | 1066 | 249.7 | 0.0582 | 8390 |
| EP-55 | 10a | 0.08 | 40 | 3724 | 265 | 1066 | 314.5 | 0.0355 | 5080 |
| EP-56 | 10a | 0.08 | 40 | 3724 | 265 | 1066 | 177.4 | 0.0392 | 9943 |
| EP-57 | 10b | 0.08 | 40 | 3724 | 265 | 1066 | 134.3 | 0.0604 | 20234 |
| EP-58 | 10b | 0.08 | 40 | 3724 | 265 | 1066 | 156.5 | 0.0543 | 15610 |
| EP-59 | 10b | 0.10 | 50 | 3657 | 331 | 1066 | 127.7 | 0.0616 | 17363 |
| EP-60 | 10b | 0.10 | 50 | 3657 | 331 | 1066 | 206.0 | 0.0981 | 17145 |
| EP-61 | 10c | 0.10 | 50 | 3657 | 331 | 1066 | 105.9 | 0.0751 | 25525 |
| EP-62 | 10c | 0.10 | 50 | 3657 | 331 | 1066 | 182.1 | 0.105 | 20753 |
| EP-63 | 10c | 0.08 | 40 | 3724 | 265 | 1066 | 98.1 | 0.0676 | 31012 |
| EP-64 | 10c | 0.08 | 40 | 3724 | 265 | 1066 | 107.1 | 0.0649 | 27269 |
| EP-65 | 10d | 0.08 | 40 | 3724 | 265 | 1066 | 900.7 | 0.0275 | 1374 |
| EP-66 | 10d | 0.08 | 40 | 3724 | 265 | 1066 | 729.8 | 0.0308 | 1899 |
| EP-67 | 10d | 0.10 | 50 | 3657 | 331 | 1066 | 402.8 | 0.044 | 3933 |
| EP-68 | 10d | 0.10 | 50 | 3657 | 331 | 1066 | 900.5 | 0.0284 | 1135 |
| EP-69 | 10e | 0.08 | 40 | 3724 | 265 | 1066 | 145.3 | 0.0594 | 18399 |
| EP-70 | 10e | 0.08 | 40 | 3724 | 265 | 1066 | 179.7 | 0.0501 | 12546 |
| EP-71 | 10e | 0.10 | 50 | 3657 | 331 | 1066 | 122.3 | 0.0613 | 18052 |
| EP-72 | 10e | 0.10 | 50 | 3657 | 331 | 1066 | 126.7 | 0.0622 | 17679 |
| EP-73 | 10f | 0.10 | 50 | 3700 | 331 | 1066 | 900.7 | 0.0295 | 1179 |
| EP-74 | 10f | 0.10 | 50 | 3700 | 331 | 1066 | 865.2 | 0.0315 | 1311 |
| EP-75 | 10f | 0.08 | 40 | 3767 | 265 | 1066 | 900.1 | 0.02 | 1000 |
| EP-76 | 10f | 0.08 | 40 | 3767 | 265 | 1066 | 900.4 | 0.0275 | 1374 |
| EP-77 | 10g | 0.10 | 50 | 3657 | 331 | 1066 | 179.0 | 0.0463 | 9314 |
| EP-78 | 10g | 0.10 | 50 | 3657 | 331 | 1066 | 184.0 | 0.0432 | 8450 |
| EP-79 | 10g | 0.08 | 40 | 3724 | 265 | 1066 | 204.7 | 0.0346 | 7605 |
| EP-80 | 10g | 0.08 | 40 | 3724 | 265 | 1066 | 252.8 | 0.0378 | 6728 |
| EP-81 | 10h | 0.10 | 50 | 3657 | 331 | 1066 | 97.1 | 0.062 | 22996 |
| EP-82 | 10h | 0.10 | 50 | 3657 | 331 | 1066 | 89.4 | 0.0683 | 27497 |
| EP-83 | 10h | 0.08 | 40 | 3724 | 265 | 1066 | 110.2 | 0.0845 | 34509 |
| EP-84 | 10h | 0.08 | 40 | 3724 | 265 | 1066 | 112.6 | 0.0534 | 21335 |
| EP-85 | 10i | 0.10 | 50 | 3700 | 331 | 1066 | 158.5 | 0.0567 | 12881 |
| EP-86 | 10i | 0.10 | 50 | 3700 | 331 | 1066 | 153.5 | 0.0562 | 13181 |
| EP-87 | 10i | 0.08 | 40 | 3767 | 265 | 1066 | 152.2 | 0.0348 | 10289 |
| EP-88 | 10i | 0.08 | 40 | 3767 | 265 | 1066 | 292.6 | 0.033 | 5074 |
| EP-89 | 10k | 0.10 | 50 | 3700 | 331 | 1066 | 159.9 | 0.0459 | 10334 |
| EP-90 | 10k | 0.10 | 50 | 3700 | 331 | 1066 | 156.4 | 0.0453 | 10425 |
| EP-91 | 10k | 0.08 | 40 | 3767 | 265 | 1066 | 174.4 | 0.0406 | 10476 |
| EP-92 | 10k | 0.08 | 40 | 3767 | 265 | 1066 | 182.3 | 0.0427 | 10540 |
| EP-93 | 10l | 0.08 | 40 | 3767 | 265 | 1066 | 251.0 | 0.0429 | 7691 |
| EP-94 | 10l | 0.08 | 40 | 3767 | 265 | 1066 | 246.8 | 0.0416 | 7586 |
| EP-95 | 10l | 0.10 | 50 | 3700 | 331 | 1066 | 181.4 | 0.0607 | 12049 |
| EP-96 | 10l | 0.10 | 50 | 3700 | 331 | 1066 | 184.6 | 0.0578 | 11275 |
| EP-97 | 10m | 0.08 | 40 | 3767 | 265 | 1066 | 170.2 | 0.0368 | 9730 |
| EP-98 | 10m | 0.08 | 40 | 3767 | 265 | 1066 | 190.6 | 0.0339 | 8003 |
| EP-99 | 10m | 0.10 | 50 | 3700 | 331 | 1066 | 150.5 | 0.0403 | 9641 |
| EP-100 | 10m | 0.10 | 50 | 3700 | 331 | 1066 | 144.0 | 0.0418 | 10448 |

*Problem Cell,
Micromoles of Al in MAO.

TABLE 10

Ethylene-Propylene Copolymerization Runs - Part 2.

| Ex # | TMC | Mw | Mn | PDI | Ethylene (wt %) |
|---|---|---|---|---|---|
| EP-1 | S1 | 26,040 | 11,730 | 2.2 | 48.3* |
| EP-2 | S1 | 78,276 | 15,790 | 5.0 | 48.4* |
| EP-3 | S1 | 25,382 | 13,238 | 1.9 | — |
| EP-4 | S1 | 23,785 | 11,426 | 2.1 | 56.9* |
| EP-5 | S2 | 136,087 | 72,516 | 1.9 | 42.4* |
| EP-6 | S2 | 111,732 | 59,376 | 1.9 | 42.0* |
| EP-7 | S2 | 65,752 | 28,086 | 2.3 | 38.3 |
| EP-8 | S2 | 74,797 | 31,092 | 2.4 | 38.8 |
| EP-9 | S3 | 23,175 | 12,536 | 1.8 | 22.3 |
| EP-10 | S3 | 20,259 | 12,348 | 1.6 | 28.0 |
| EP-11 | S3 | 24,029 | 13,357 | 1.8 | 16.3 |
| EP-12 | S3 | 19,926 | 10,262 | 1.9 | 3.2 |
| EP-13 | S4 | — | — | — | — |
| EP-14 | S4 | — | — | — | — |
| EP-15 | S4 | — | — | — | — |
| EP-16 | S4 | — | — | — | — |
| EP-17 | S5 | — | — | — | — |
| EP-18 | S5 | — | — | — | — |
| EP-19 | S5 | — | — | — | — |
| EP-20 | S5 | — | — | — | — |
| EP-21 | O3 | 27,005 | 15,544 | 1.7 | 28.3 |
| EP-22 | O3 | 20,212 | 11,380 | 1.8 | 24.3 |
| EP-23 | O3 | 20,033 | 11,346 | 1.8 | 24.7 |
| EP-24 | O3 | 20,322 | 11,368 | 1.8 | 25.3 |
| EP-25 | O4 | — | — | — | — |
| EP-26 | O4 | — | — | — | — |
| EP-27 | O4 | — | — | — | — |
| EP-28 | O4 | — | — | — | — |
| EP-29 | N2 | 156,503 | 89,892 | 1.7 | 45.3* |
| EP-30 | N2 | 125,691 | 66,235 | 1.9 | 44.6* |
| EP-31 | N2 | 141,474 | 75,195 | 1.9 | 43.5* |
| EP-32 | N2 | 136,054 | 72,192 | 1.9 | 41.6* |
| EP-33 | N3 | 24,782 | 13,959 | 1.8 | 23.8 |
| EP-34 | N3 | 27,094 | 14,275 | 1.9 | 20.1 |
| EP-35 | N3 | 20,587 | 11,933 | 1.7 | 28.8 |
| EP-36 | N3 | 24,713 | 14,072 | 1.8 | 25.5 |
| EP-37 | P2 | 139,069 | 78,783 | 1.8 | 46.3* |
| EP-38 | P2 | 158,137 | 89,796 | 1.8 | 40.5* |
| EP-39 | P2 | — | — | — | — |
| EP-40 | P2 | 151,178 | 82,253 | 1.8 | 40.3* |
| EP-41 | P3 | 29,669 | 17,525 | 1.7 | 28.1 |
| EP-42 | P3 | 35,674 | 18,464 | 1.9 | 30.5 |
| EP-43 | P3 | 23,030 | 13,219 | 1.7 | 18.5 |
| EP-44 | P3 | 35,800 | 20,394 | 1.8 | — |
| EP-45 | P4 | — | — | — | — |
| EP-46 | P4 | — | — | — | — |
| EP-47 | P4 | — | — | — | — |
| EP-48 | P4 | — | — | — | — |
| EP-49 | 10 | — | — | — | — |
| EP-50 | 10 | — | — | — | — |
| EP-51 | 10 | — | — | — | — |
| EP-52 | 10 | 53,966 | 29,105 | 1.9 | 28.0 |
| EP-53 | 10a | 92,503 | 55,432 | 1.7 | 35.9 |
| EP-54 | 10a | 71,232 | 35,791 | 2.0 | 30.5 |
| EP-55 | 10a | 41,728 | 22,993 | 1.8 | 25.0 |
| EP-56 | 10a | 96,435 | 52,601 | 1.8 | 30.5 |
| EP-57 | 10b | 167,275 | 99,785 | 1.7 | 23.4 |
| EP-58 | 10b | 161,430 | 96,226 | 1.7 | 21.0 |
| EP-59 | 10b | 152,791 | 86,618 | 1.8 | 18.7 |
| EP-60 | 10b | 135,789 | 79,606 | 1.7 | 21.5 |
| EP-61 | 10c | 150,338 | 87,012 | 1.7 | 20.4 |
| EP-62 | 10c | 128,583 | 71,785 | 1.8 | 19.3 |
| EP-63 | 10c | 160,233 | 96,920 | 1.7 | 24.4 |
| EP-64 | 10c | 166,938 | 96,667 | 1.7 | 21.7 |
| EP-65 | 10d | 245,783 | 129,894 | 1.9 | 27.4 |
| EP-66 | 10d | 265,550 | 145,750 | 1.8 | 15.3 |
| EP-67 | 10d | 248,086 | 137,237 | 1.8 | 13.4 |
| EP-68 | 10d | 233,468 | 116,849 | 2.0 | 24.1 |
| EP-69 | 10e | 167,171 | 102,897 | 1.6 | 30.4 |
| EP-70 | 10e | 146,180 | 89,061 | 1.6 | 28.3 |
| EP-71 | 10e | 166,462 | 101,838 | 1.6 | 28.3 |
| EP-72 | 10e | 166,421 | 101,623 | 1.6 | 29.6 |
| EP-73 | 10f | 38,351 | 18,365 | 2.1 | 29.5 |
| EP-74 | 10f | 34,493 | 16,812 | 2.1 | 29.8 |
| EP-75 | 10f | 102,647 | 28,681 | 3.6 | 32.9 |
| EP-76 | 10f | 155,577 | 38,961 | 4.0 | 32.0 |
| EP-77 | 10g | 116,069 | 64,526 | 1.8 | 30.8 |
| EP-78 | 10g | 117,467 | 64,808 | 1.8 | 31.3 |
| EP-79 | 10g | 120,927 | 68,239 | 1.8 | 30.7 |
| EP-80 | 10g | 122,662 | 72,577 | 1.7 | 33.3 |
| EP-81 | 10h | 121,471 | 74,298 | 1.6 | 36.4 |
| EP-82 | 10h | 116,565 | 71,451 | 1.6 | 30.3 |
| EP-83 | 10h | 104,377 | 40,264 | 2.6 | — |
| EP-84 | 10h | 144,029 | 88,986 | 1.6 | 36.3 |
| EP-85 | 10i | 103,303 | 54,405 | 1.9 | 42.6* |
| EP-86 | 10i | 98,212 | 49,013 | 2.0 | 41.8* |
| EP-87 | 10i | 133,737 | 78,523 | 1.7 | 39.2* |
| EP-88 | 10i | 133,438 | 75,598 | 1.8 | 40.1* |
| EP-89 | 10k | 130,038 | 78,262 | 1.7 | 35.9 |
| EP-90 | 10k | 132,943 | 79,326 | 1.7 | 33.6 |
| EP-91 | 10k | 134,557 | 80,204 | 1.7 | 37.6 |
| EP-92 | 10k | 138,380 | 83,567 | 1.7 | 35.6 |
| EP-93 | 10l | 209,496 | 128,180 | 1.6 | 29.7 |
| EP-94 | 10l | 220,137 | 127,869 | 1.7 | 29.3 |
| EP-95 | 10l | 152,017 | 70,633 | 2.2 | 34.2 |
| EP-96 | 10l | 147,835 | 65,455 | 2.3 | 34.5 |
| EP-97 | 10m | 178,450 | 103,865 | 1.7 | 31.1 |
| EP-98 | 10m | 173,346 | 102,022 | 1.7 | 29.6 |
| EP-99 | 10m | 171,117 | 98,578 | 1.7 | 31.0 |
| EP-100 | 10m | 176,799 | 104,293 | 1.7 | 33.7 |

*Outside FTIR calibration range of 5.14 to 38.79 wt % ethylene.

While certain representative embodiments and details have been shown to illustrate the invention, it will be apparent to skilled artisans that various process and product changes from those disclosed in this application may be made without departing from this invention's scope, which the appended claims define.

All cited patents, test procedures, priority documents, and other cited documents are fully incorporated by reference to the extent that this material is consistent with this specification and for all jurisdictions in which such incorporation is permitted.

Certain features of the present invention are described in terms of a set of numerical upper limits and a set of numerical lower limits. This specification discloses all ranges formed by any combination of these limits. All combinations of these limits are within the scope of the invention unless otherwise indicated.

The invention claimed is:

1. A transition metal compound represented by the formula:

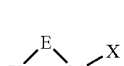

wherein

M is a group 3, 4, 5 or 6 transition metal atom, a lanthanide metal atom, or an actinide metal atom;

E is: 1) a substituted or unsubstituted indenyl ligand that is bonded to Y through the four, five, six or seven position of the indenyl ring, or 2) a substituted or unsubstituted heteroindenyl ligand that is bonded to Y through the four, five or six position of the heteroindenyl ring, provided that the bonding position is not the same as the position of the ring heteroatom, or 3) a substituted or unsubstituted fluorenyl ligand that is bonded to Y through the one, two, three, four, five, six, seven or eight position of the fluorenyl ring, or 4) a substituted or unsubstituted heterofluorenyl ligand that is bonded to Y through the one, two, three, four, five or six position of the heterofluorenyl ring, provided that the bonding position is not the same as the position of the ring heteroatom;

A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, a substituted or unsubstituted heterofluorenyl ligand, or other monoanionic ligand;

Y is a Group 15 or 16 bridging heteroatom substituent that is bonded via the heteroatom to E and A; and each X is, independently, univalent anionic ligands, or both X are joined and bound to the metal atom to form a metallocycle ring, or both X join to form a chelating ligand, a diene ligand, or an alkylidene ligand.

2. The compound of claim 1 wherein M is Ti, Hf or Zr.

3. The compound of claim 1 where:

M is Ti, Zr or Hf;

Y is S, O, NR', PR', O—O, S—S, R'N—NR', R'P—PR', O—S, O—NR', O—PR', S—NR', S—PR', or R'N—PR', where each R' is, independently, hydrogen, a hydrocarbyl, substituted hydrocarbyl, halocarbyl, substituted halocarbyl, silylcarbyl, substituted silylcarbyl, germylcarbyl, or substituted germylcarbyl substituent; and A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand.

4. A catalyst system comprising the compound of claim 1 and an activator.

5. A supported catalyst system comprising the catalyst system of claim 4 and a support.

6. A process to polymerize olefins comprising contacting the catalyst system of claim 4 with one or more olefins.

7. A process to polymerize olefins comprising contacting the catalyst system of claim 5 with one or more olefins.

8. The process of claim 6 wherein the olefins comprise ethylene and or propylene.

9. The process of claim 7 wherein the olefins comprise ethylene and or propylene.

10. The process of claim 6 wherein the olefins comprise ethylene and a comonomer selected from the group consisting of propylene, butene, pentene, hexene, heptene, octene, nonene, decene, undecene, dodecene, hexadecene, 4-methylpentene-1, 3-methylpentene-1, 3,5,5-trimethylhexene-1, 5-ethylnonene-1, and isomers thereof.

11. The process of claim 7 wherein the olefins comprise ethylene and a comonomer selected from the group consisting of propylene, butene, pentene, hexene, heptene, octene, nonene, decene, undecene, dodecene, hexadecene, 4-methylpentene-1, 3-methylpentene-1, 3,5,5-trimethylhexene-1, 5-ethylnonene-1, and isomers thereof.

12. The process of claim 6 wherein the olefins comprise propylene and a comonomer selected from the group consisting of ethylene, butene, pentene, hexene, heptene, octene, nonene, decene, undecene, dodecene, hexadecene, 4-methylpentene-1, 3-methylpentene-1, 3,5,5-trimethylhexene-1, 5-ethylnonene-1, and isomers thereof.

13. The process of claim 7 wherein the olefins comprise propylene and a comonomer selected from the group consisting of ethylene, butene, pentene, hexene, heptene, octene, nonene, decene, undecene, dodecene, hexadecene, 4-methylpentene-1, 3-methylpentene-1, 3,5,5-trimethylhexene-1, 5-ethylnonene-1, and isomers thereof.

14. The process of claim 7, where the polymerization occurs in the gas phase.

15. The process of claim 6, where the polymerization occurs in the slurry phase.

16. The process of claim 6, where the polymerization occurs in the solution phase.

17. A transition metal compound represented by formula:

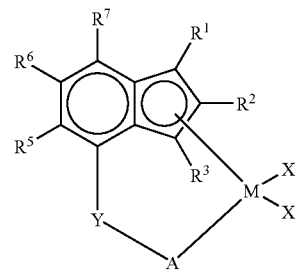

wherein

M is a group 3, 4, 5 or 6 transition metal atom, a lanthanide metal atom, or an actinide metal atom, $R^1$, $R^2$, $R^3$, $R^5$, $R^6$, and $R^7$ are, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent $R^1$, $R^2$, $R^3$, $R^5$, $R^6$, and $R^7$ may join together to form a substituted or unsubstituted, saturated, partially unsaturated, or aromatic cyclic or polycyclic substituent;

Y is a Group 15 or 16 bridging heteroatom substituent that is bonded via the heteroatom to the indicated ring system, and to A;

A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand where A is bonded to Y through any bondable ring position; or A is a mono-anionic ligand such as a substituted or unsubstituted pentadienyl ligand, a substituted or unsubstituted allyl ligand, or a substituted or unsubstituted boratabenzene; and each X is, independently, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from about 3 to about 20 carbon atoms; or both together can be an olefin, diolefin or aryne ligand; or both X may, independently, be a halogen, alkoxide, aryloxide, amide, phosphide or other univalent anionic ligand or both X can also be joined to form a anionic chelating ligand.

18. The compound of claim 17 where M is Ti, Zr or Hf.

19. The compound of claim 17 where:
$R^1$, $R^2$, $R^3$, $R^5$, $R^6$, and $R^7$ are, independently, hydrogen, a hydrocarbyl, substituted hydrocarbyl, halocarbyl, or substituted halocarbyl;
Y is S, O, NR', PR', O—O, S—S, R'N—NR', R'P—PR', O—S, O—NR', O—PR', S—NR', S—PR', or R'N—PR', where each R' is, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituent; and
A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand.

20. The compound of claim 18 where:
$R^1$, $R^2$, $R^3$, $R^5$, $R^6$, and $R^7$ are, independently, hydrogen, a hydrocarbyl, substituted hydrocarbyl, halocarbyl, or substituted halocarbyl;
Y is S, O, NR', PR', O—O, S—S, R'N—NR', R'P—PR', O—S, O—NR', O—PR', S—NR', S—PR', or R'N—PR', where each R' is, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituent; and
A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand.

21. The compound of claim 17 where $R^1$, $R^2$ and $R^3$ are each, independently hydrogen or a C1 to C6 hydrocarbyl group.

22. A catalyst system comprising the compound of claim 17 and an activator.

23. A supported catalyst system comprising the catalyst system of claim 22 and a support.

24. A process to polymerize olefins comprising contacting the catalyst system of claim 22 with one or more olefins.

25. A process to polymerize olefins comprising contacting the catalyst system of claim 23 with one or more olefins.

26. The process of claim 24 wherein the olefins comprise ethylene and or propylene.

27. The process of claim 25 wherein the olefins comprise ethylene and or propylene.

28. The process of claim 24 wherein the olefins comprise ethylene and a comonomer selected from the group consisting of propylene, butene, pentene, hexene, heptene, octene, nonene, decene, undecene, dodecene, hexadecene, 4-methylpentene-1, 3-methylpentene-1, 3,5,5-trimethylhexene-1, 5-ethylnonene-1, and isomers thereof.

29. The process of claim 24 wherein the olefins comprise propylene and a comonomer selected from the group consisting of ethylene, butene, pentene, hexene, heptene, octene, nonene, decene, undecene, dodecene, hexadecene, 4-methylpentene-1, 3-methylpentene-1, 3,5,5-trimethylhexene-1, 5-ethylnonene-1, and isomers thereof.

30. The process of claim 24 wherein the olefins comprise ethylene and/or propylene and one or more comonomers selected from the group consisting of butene, pentene, hexene, heptene, octene, nonene, decene, undecene, dodecene, hexadecene, 4-methylpentene-1, 3-methylpentene-1,3,5,5-trimethylhexene-1, 5-ethylnonene-1, butadiene, hexadiene, heptadiene, pentadiene, octadiene, nonadiene, decadiene, dodecadiene, styrene, 3,5,5-trimethylhexene-1, 3-methylpentene-1, 4-methylpentene-1, cyclopentadiene, cyclohexene, cyclooctene, hexadiene, cyclohexadiene, alpha-methylstyrene, vinyltoluene, vinylnaphthalene, ally benzene, indene, para-methylstyrene, 4-phenyl-1-butene, vinylcyclohexane, vinylcyclohexene, cyclopentadiene, cyclopentene, 4-methylcyclopentene, cyclohexene, 4-methylcyclohexene, cyclobutene, vinyladamantane, norbornene, 5-methylnorbornene, 5-ethylnorbornene, 5-propylnorbornene, 5-butylylnorbornene, 5-pentylnorbornene, 5-hexylnorbornene, 5-heptylnorbornene, 5-octylnorbornene, 5-nonylnorbornene, 5-decylnorbornene, 5-phenylnorbornene, vinylnorbornene, ethylidene norbornene, 5,6-dimethylnorbornene, 5,6-dibutylnorbornene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, vinylnorbornene, norbornadiene, ethylidene norbornene, divinylbenzene, dicyclopentadiene, and isomers thereof.

31. The process of claim 24, where the polymerization occurs in the gas phase.

32. The process of claim 24, where the polymerization occurs in the slurry phase.

33. The process of claim 24, where the polymerization occurs in the solution phase.

34. The process of claim 24 wherein the activator is selected from the group consisting of alumoxane, modified alumoxane, trispentafluorophenylborane, trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, trimethylammonium tetrakis-(2,3,4,6-tetrafluorophenyl) borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(tert-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(tert-butyl)ammonium tetrakis(perfluorobiphenyl)borate, N,N-dimethylanilinium tetrakis(perfluorobiphenyl)borate, N,N-diethylanilinium tetrakis (perfluorobiphenyl)borate, N,N-dimethyl-(2,4,6-trimethylanilinium) tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(tert-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, di-(iso-propyl)ammonium tetrakis(pentafluorophenyl)borate, and dicyclohexylammonium tetrakis(pentafluorophenyl)borate; and other salts such as tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, and benzene(diazonium) tetrakis(3,5-bis(trifluoromethyl)phenyl)borate.

35. A transition metal compound represented by formula:

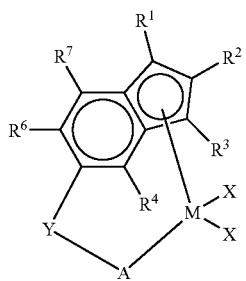

wherein

M is a group 3, 4, 5 or 6 transition metal atom, a lanthanide metal atom, or an actinide metal atom;

$R^1, R^2, R^3, R^4, R^6$, and $R^7$ are, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent $R^1, R^2, R^3, R^4, R^6$, and $R^7$, may join together to form a substituted or unsubstituted, saturated, partially unsaturated, or aromatic cyclic or polycyclic substituent;

Y is a Group 15 or 16 bridging heteroatom substituent that is bonded via the heteroatom to the indicated ring system, and to A;

A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand where A is bonded to Y through any bondable ring position; or A is a mono-anionic ligand such as a substituted or unsubstituted pentadienyl ligand, a substituted or unsubstituted allyl ligand, or a substituted or unsubstituted boratabenzene; and each X is, independently, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from about 3 to about 20 carbon atoms; or both together can be an olefin, diolefin or aryne ligand; or both X may, independently, be a halogen, alkoxide, aryloxide, amide, phosphide or other univalent anionic ligand or both X can also be joined to form a anionic chelating ligand.

36. The compound of claim 35 where M is Ti, Zr or Hf.

37. The compound of claim 35 where:

$R^1, R^2, R^3, R^4, R^6$, and $R^7$ are, independently, hydrogen, a hydrocarbyl, substituted hydrocarbyl, halocarbyl, or substituted halocarbyl;

Y is S, O, NR', PR', O—O, S—S, R'N—NR', R'P—PR', O—S, O—NR', O—PR', S—NR', S—PR', or R'N—PR', where each R' is, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituent; and A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand.

38. The compound of claim 35 where $R^1, R^2$ and $R^3$ are each, independently hydrogen or a C1 to C6 hydrocarbyl group.

39. A catalyst system comprising the compound of claim 35 and an activator.

40. A supported catalyst system comprising the catalyst system of claim 39 and a support.

41. A process to polymerize olefins comprising contacting the catalyst system of claim 39 with one or more olefins.

42. The process of claim 41 wherein the olefins comprise ethylene and or propylene.

43. The process of claim 41 wherein the olefins comprise ethylene and a comonomer selected from the group consisting of propylene, butene, pentene, hexene, heptene, octene, nonene, decene, undecene, dodecene, hexadecene, 4-methylpentene-1, 3-methylpentene-1, 3,5,5-trimethylhexene-1, 5-ethylnonene-1, and isomers thereof.

44. The process of claim 41 wherein the olefins comprise propylene and a comonomer selected from the group consisting of ethylene, butene, pentene, hexene, heptene, octene, nonene, decene, undecene, dodecene, hexadecene, 4-methylpentene-1, 3-methylpentene-1, 3,5,5-trimethylhexene-1, 5-ethylnonene-1, and isomers thereof.

45. The process of claim 41 wherein the olefins comprise ethylene and/or propylene and one or more comonomers selected from the group consisting of butene, pentene, hexene, heptene, octene, nonene, decene, undecene, dodecene, hexadecene, 4-methylpentene-1, 3-methylpentene-1,3,5,5-trimethylhexene-1, 5-ethylnonene-1, butadiene, hexadiene, heptadiene, pentadiene, octadiene, nonadiene, decadiene, dodecadiene, styrene, 3,5,5-trimethylhexene-1, 3-methylpentene-1, 4-methylpentene-1, cyclopentadiene, cyclohexene, cyclooctene, hexadiene, cyclohexadiene, alpha-methylstyrene, vinyltoluene, vinylnaphthalene, allyl benzene, indene, para-methylstyrene, 4-phenyl-1-butene, vinylcyclohexane, vinylcyclohexene, cyclopentadiene, cyclopentene, 4-methylcyclopentene, cyclohexene, 4-methylcyclohexene, cyclobutene, vinyladamantane, norbornene, 5-methylnorbornene, 5-ethylnorbornene, 5-propylnorbornene, 5-butylylnorbornene, 5-pentylnorbornene, 5-hexylnorbornene, 5-heptylnorbornene, 5-octylnorbornene, 5-nonylnorbornene, 5-decylnorbornene, 5-phenylnorbornene, vinylnorbornene, ethylidene norbornene, 5,6-dimethylnorbornene, 5,6-dibutylnorbornene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, vinylnorbornene, norbornadiene, ethylidene norbornene, divinylbenzene, dicyclopentadiene, and isomers thereof.

46. The process of claim 41, where the polymerization occurs in the gas phase.

47. The process of claim 41, where the polymerization occurs in the slurry phase.

48. The process of claim 41, where the polymerization occurs in the solution phase.

49. The process of claim 41 wherein the activator is selected from the group consisting of alumoxane, modified alumoxane, trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(tert-butyl)ammonium tetrakis (perfluoronaphthyl)borate, N,N-dimethylanilinium tetrakis (perfluoronaphthyl)borate, N,N-diethylanilinium tetrakis (perfluoronaphthyl)borate, N,N-dimethyl-(2,4,6-trimethylanilinium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(tert-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis (perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(tert-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis (trifluoromethyl)phenyl)borate, di-(iso-propyl)ammonium tetrakis(pentafluorophenyl)borate, and dicyclohexylammonium tetrakis(pentafluorophenyl)borate; and other salts such as tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis (pentafluorophenyl)borate, triethylsilylium tetrakis (pentafluorophenyl)borate, benzene(diazonium) tetrakis (pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, tropillium tetrakis (perfluoronaphthyl)borate, triphenylcarbenium tetrakis(perfluoronaphthyl)borate, triphenylphosphonium tetrakis(perfluoronaphthyl)borate, triethylsilylium tetrakis (perfluoronaphthyl)borate, benzene(diazonium) tetrakis (perfluoronaphthyl)borate, tropillium tetrakis (perfluorobiphenyl)borate, triphenylcarbenium tetrakis (perfluorobiphenyl)borate, triphenylphosphonium tetrakis (perfluorobiphenyl)borate, triethylsilylium tetrakis (perfluorobiphenyl)borate, benzene(diazonium) tetrakis (perfluorobiphenyl)borate, tropillium tetrakis(3,5-bis (trifluoromethyl)phenyl)borate, triphenylcarbenium tetrakis (3,5-bis(trifluoromethyl)phenyl)borate,
triphenylphosphonium tetrakis(3,5-bis(trifluoromethyl)phenyl)borate, triethylsilylium tetrakis(3,5-bis(trifluoromethyl) phenyl)borate, and benzene(diazonium) tetrakis(3,5-bis(trifluoromethyl)phenyl)borate.

50. A transition metal compound represented by formula:

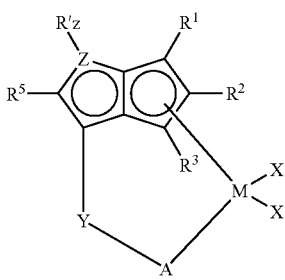

wherein
- M is a group 3, 4, 5 or 6 transition metal atom, or a lanthanide metal atom, or actinide metal atom;
- $R^1$, $R^2$, $R^3$, $R^5$, and R' are, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent $R^1$, $R^2$, $R^3$, $R^5$, and R' may join together to form a substituted or unsubstituted, saturated, partially unsaturated, or aromatic cyclic or polycyclic substituent;
- Z is a Group 16 atom or a Group 15 atom; when Z is a Group 15 atom, "z" is one, indicating the presence of R' bonded to Z, and when Z is a Group 16 atom, "z" is zero, indicating the absence of R';
- Y is a Group 15 or 16 bridging heteroatom substituent that is bonded via the heteroatom to the indicated ring system, and to A;
- A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand where A is bonded to Y through any bondable ring position; or A is a mono-anionic ligand such as a substituted or unsubstituted pentadienyl ligand, a substituted or unsubstituted allyl ligand, or a substituted or unsubstituted boratabenzene; and
- each X is, independently, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from about 3 to about 20 carbon atoms; or both together can be an olefin, diolefin or aryne ligand; or both X may, independently, be a halogen, alkoxide, aryloxide, amide, phosphide or other univalent anionic ligand or both X can also be joined to form a anionic chelating ligand.

51. The compound of claim 50 where M is Ti, Zr or Hf.

52. The compound of claim 50 where:
$R^1$, $R^2$, $R^3$, $R^5$, and R' are, independently, hydrogen, a hydrocarbyl, substituted hydrocarbyl, halocarbyl, or substituted halocarbyl;
Y is S, O, NR', PR', O—O, S—S, R'N—NR', R'P—PR', O—S, O—NR', O—PR', S—NR', S—PR', or R'N—PR', where each R' is, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituent; and A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand.

53. The compound of claim 50 where $R^1$, $R^2$ and $R^3$ are each, independently hydrogen or a C1 to C6 hydrocarbyl group.

54. A catalyst system comprising the compound of claim 50 and an activator.

55. A supported catalyst system comprising the catalyst system of claim 54 and a support.

56. A process to polymerize olefins comprising contacting the catalyst system of claim 54 with one or more olefins.

57. The process of claim 56 wherein the olefins comprise ethylene and or propylene.

58. The process of claim 56 wherein the olefins comprise ethylene and a comonomer selected from the group consisting of propylene, butene, pentene, hexene, heptene, octene, nonene, decene, undecene, dodecene, hexadecene, 4-methylpentene-1, 3-methylpentene-1, 3,5,5-trimethylhexene-1, 5-ethylnonene-1, and isomers thereof.

59. The process of claim 56 wherein the olefins comprise propylene and a comonomer selected from the group consisting of ethylene, butene, pentene, hexene, heptene, octene, nonene, decene, undecene, dodecene, hexadecene, 4-methylpentene-1, 3-methylpentene-1, 3,5,5-trimethylhexene-1, 5-ethylnonene-1, and isomers thereof.

60. The process of claim 56 wherein the olefins comprise ethylene and/or propylene and one or more comonomers selected from the group consisting of butene, pentene, hexene, heptene, octene, nonene, decene, undecene, dodecene, hexadecene, 4-methylpentene-1, 3-methylpentene-1,3,5,5-trimethylhexene-1, 5-ethylnonene-1, butadiene, hexadiene, heptadiene, pentadiene, octadiene, nonadiene, decadiene, dodecadiene, styrene, 3,5,5-trimethylhexene-1, 3-methylpentene-1, 4-methylpentene-1, cyclopentadiene, cyclohexene, cyclooctene, hexadiene, cyclohexadiene, alpha-methylstyrene, vinyltoluene, vinylnaphthalene, allyl benzene, indene, para-methylstyrene, 4-phenyl-1-butene, vinylcyclohexane, vinylcyclohexene, cyclopentadiene, cyclopentene, 4-methylcyclopentene, cyclohexene, 4-methylcyclohexene, cyclobutene, vinyladamantane, norbornene, 5-methylnorbornene, 5-ethylnorbornene, 5-propylnorbornene, 5-butylylnorbornene, 5-pentylnorbornene, 5-hexylnorbornene, 5-heptylnorbornene, 5-octylnorbornene, 5-nonylnorbornene, 5-decylnorbornene, 5-phenylnorbornene, vinylnorbornene, ethylidene norbornene, 5,6-dimethylnorbornene, 5,6-dibutylnorbornene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, vinylnorbornene, norbornadiene, ethylidene norbornene, divinylbenzene, dicyclopentadiene, and isomers thereof.

61. The process of claim 56, where the catalyst system is supported and where the polymerization occurs in the gas phase.

62. The process of claim 56, where the polymerization occurs in the slurry phase.

63. The process of claim 56, where the polymerization occurs in the solution phase.

64. The process of claim 56 wherein the activator is selected from the group consisting of alumoxane, modified alumoxane, trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(tert-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(tert-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(tert-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, di-(iso-propyl)ammonium tetrakis(pentafluorophenyl)borate, and dicyclohexylammonium tetrakis(pentafluorophenyl)borate; and other salts such as tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, and benzene(diazonium) tetrakis(3,5-bis(trifluoromethyl)phenyl)borate.

65. A transition metal compound represented by formula:

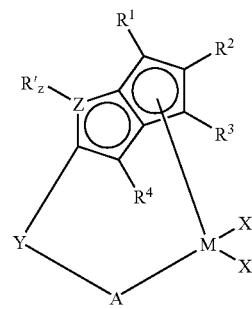

wherein
M is a group 3, 4, 5 or 6 transition metal atom, or a lanthanide metal atom, or actinide metal atom;
$R^1$, $R^2$, $R^3$, $R^4$, and R' are, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent $R^1$, $R^2$, $R^3$, $R^4$, and R' may join together to form a substituted or unsubstituted, saturated, partially unsaturated, or aromatic cyclic or polycyclic substituent;
Z is a Group 16 atom or a Group 15 atom; when Z is a Group 15 atom, "z" is one, indicating the presence of R' bonded to Z, and when Z is a Group 16 atom, "z" is zero, indicating the absence of R';
Y is a Group 15 or 16 bridging heteroatom substituent that is bonded via the heteroatom to the indicated ring system, and to A;
A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand where A is bonded to Y through any bondable ring position; or A is a mono-anionic ligand such as a substituted or unsubstituted pentadienyl ligand, a substituted or unsubstituted allyl ligand, or a substituted or unsubstituted boratabenzene; and
each X is, independently, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from about 3 to about 20 carbon atoms; or both together can be an olefin, diolefin or aryne ligand; or both X may, independently, be a halogen, alkoxide, aryloxide, amide, phosphide or other univalent anionic ligand or both X can also be joined to form a anionic chelating ligand.

66. The compound of claim 65 where M is Ti, Zr or Hf.

67. The compound of claim 65 where:

$R^1$, $R^2$, $R^3$, $R^4$, and R' are, independently, hydrogen, a hydrocarbyl, substituted hydrocarbyl, halocarbyl, or substituted halocarbyl;

Y is S, O, NR', PR', O—O, S—S, R'N—NR', R'P—PR', O—S, O—NR', O—PR', S—NR', S—PR', or R'N—PR', where each R' is, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituent; and A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand.

68. The compound of claim 65 where $R^1$, $R^2$ and $R^3$ are each, independently hydrogen or a C1 to C6 hydrocarbyl group.

69. A catalyst system comprising the compound of claim 65 and an activator.

70. A supported catalyst system comprising the catalyst system of claim 69 and a support.

71. A process to polymerize olefins comprising contacting the catalyst system of claim 69 with one or more olefins.

72. The process of claim 71 wherein the olefins comprise ethylene and or propylene.

73. The process of claim 71 wherein the olefins comprise ethylene and a comonomer selected from the group consisting of propylene, butene, pentene, hexene, heptene, octene, nonene, decene, undecene, dodecene, hexadecene, 4-methylpentene-1, 3-methylpentene-1, 3,5,5-trimethylhexene-1, 5-ethylnonene-1, and isomers thereof.

74. The process of claim 71 wherein the olefins comprise propylene and a comonomer selected from the group consisting of ethylene, butene, pentene, hexene, heptene, octene, nonene, decene, undecene, dodecene, hexadecene, 4-methylpentene-1, 3-methylpentene-1, 3,5,5-trimethylhexene-1, 5-ethylnonene-1, and isomers thereof.

75. The process of claim 71 wherein the olefins comprise ethylene and/or propylene and one or more comonomers selected from the group consisting of butene, pentene, hexene, heptene, octene, nonene, decene, undecene, dodecene, hexadecene, 4-methylpentene-1, 3-methylpentene-1,3,5,5-trimethylhexene-1, 5-ethylnonene-1, butadiene, hexadiene, heptadiene, pentadiene, octadiene, nonadiene, decadiene, dodecadiene, styrene, 3,5,5-trimethylhexene-1, 3-methylpentene-1, 4-methylpentene-1, cyclopentadiene, cyclohexene, cyclooctene, hexadiene, cyclohexadiene, alpha-methylstyrene, vinyltoluene, vinylnaphthalene, allyl benzene, indene, para-methylstyrene, 4-phenyl-1-butene, vinylcyclohexane, vinylcyclohexene, cyclopentadiene, cyclopentene, 4-methylcyclopentene, cyclohexene, 4-methylcyclohexene, cyclobutene, vinyladamantane, norbornene, 5-methylnorbornene, 5-ethylnorbornene, 5-propylnorbornene, 5-butylylnorbornene, 5-pentylnorbornene, 5-hexylnorbornene, 5-heptylnorbornene, 5-octylnorbornene, 5-nonylnorbornene, 5-decylnorbornene, 5-phenylnorbornene, vinylnorbornene, ethylidene norbornene, 5,6-dimethylnorbornene, 5,6-dibutylnorbornene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, vinylnorbornene, norbornadiene, ethylidene norbornene, divinylbenzene, dicyclopentadiene, and isomers thereof.

76. The process of claim 71, where the polymerization occurs in the gas phase.

77. The process of claim 71, where the polymerization occurs in the slurry phase.

78. The process of claim 71, where the polymerization occurs in the solution phase.

79. The process of claim 71 wherein the activator is selected from the group consisting of alumoxane, modified alumoxane, trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(tert-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(tert-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(tert-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, di-(iso-propyl)ammonium tetrakis(pentafluorophenyl)borate, and dicyclohexylammonium tetrakis(pentafluorophenyl)borate; and other salts such as tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, and benzene(diazonium) tetrakis(3,5-bis(trifluoromethyl)phenyl)borate.

80. A transition metal compound represented by formula:

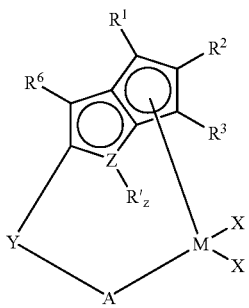

wherein

M is a group 3, 4, 5 or 6 transition metal atom, or a lanthanide metal atom, or actinide metal atom;

$R^1$, $R^2$, $R^3$, $R^6$, and R' are, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent $R^1$, $R^2$, $R^3$, $R^6$, and R' may join together to form a substituted or unsubstituted, saturated, partially unsaturated, or aromatic cyclic or polycyclic substituent;

Z is a Group 16 atom or a Group 15 atom; when Z is a Group 15 atom, "z" is one, indicating the presence of R' bonded to Z, and when Z is a Group 16 atom, "z" is zero, indicating the absence of R';

Y is a Group 15 or 16 bridging heteroatom substituent that is bonded via the heteroatom to the indicated ring system, and to A;

A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand where A is bonded to Y through any bondable ring position; or A is a mono-anionic ligand such as a substituted or unsubstituted pentadienyl ligand, a substituted or unsubstituted allyl ligand, or a substituted or unsubstituted boratabenzene; and each X is, independently, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from about 3 to about 20 carbon atoms; or both together can be an olefin, diolefin or aryne ligand; or both X may, independently, be a halogen, alkoxide, aryloxide, amide, phosphide or other univalent anionic ligand or both X can also be joined to form a anionic chelating ligand.

81. The compound of claim 80 where M is Ti, Zr or Hf.

82. The compound of claim 80 where:

$R^1$, $R^2$, $R^3$, $R^6$, and R' are, independently, hydrogen, a hydrocarbyl, substituted hydrocarbyl, halocarbyl, or substituted halocarbyl;

Y is S, O, NR', PR', O—O, S—S, R'N—NR', R'P—PR', O—S, O—NR', O—PR', S—NR', S—PR', or R'N—PR', where each R' is, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituent; and A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand.

83. The compound of claim 80 where $R^1$, $R^2$ and $R^3$ are each, independently hydrogen or a C1 to C6 hydrocarbyl group.

84. A catalyst system comprising the compound of claim 80 and an activator.

85. A supported catalyst system comprising the catalyst system of claim 84 and a support.

86. A process to polymerize olefins comprising contacting the catalyst system of claim 84 with one or more olefins.

87. The process of claim 86 wherein the olefins comprise ethylene and or propylene.

88. The process of claim 86 wherein the olefins comprise ethylene and a comonomer selected from the group consisting of propylene, butene, pentene, hexene, heptene, octene, nonene, decene, undecene, dodecene, hexadecene, 4-methylpentene-1, 3-methylpentene-1, 3,5,5-trimethylhexene-1, 5-ethylnonene-1, and isomers thereof.

89. The process of claim 86 wherein the olefins comprise propylene and a comonomer selected from the group consisting of ethylene, butene, pentene, hexene, heptene, octene, nonene, decene, undecene, dodecene, hexadecene, 4-methylpentene-1, 3-methylpentene-1, 3,5,5-trimethylhexene-1, 5-ethylnonene-1, and isomers thereof.

90. The process of claim 86 wherein the olefins comprise ethylene and/or propylene and one or more comonomers selected from the group consisting of butene, pentene, hexene, heptene, octene, nonene, decene, undecene, dodecene, hexadecene, 4-methylpentene-1, 3-methylpentene-1,3,5,5-trimethylhexene-1, 5-ethylnonene-1, butadiene, hexadiene, heptadiene, pentadiene, octadiene, nonadiene, decadiene, dodecadiene, styrene, 3,5,5-trimethylhexene-1, 3-methylpentene-1, 4-methylpentene-1, cyclopentadiene, cyclohexene, cyclooctene, hexadiene, cyclohexadiene, alpha-methylstyrene, vinyltoluene, vinylnaphthalene, allyl benzene, indene, para-methylstyrene, 4-phenyl-1-butene, vinylcyclohexane, vinylcyclohexene, cyclopentadiene, cyclopentene, 4-methylcyclopentene, cyclohexene, 4-methylcyclohexene, cyclobutene, vinyladamantane, norbornene, 5-methylnorbornene, 5-ethylnorbornene, 5-propylnorbornene, 5-butylylnorbornene, 5-pentylnorbornene, 5-hexylnorbornene, 5-heptylnorbornene, 5-octylnorbornene, 5-nonylnorbornene, 5-decylnorbornene, 5-phenylnorbornene, vinylnorbornene, ethylidene norbornene, 5,6-dimethylnorbornene, 5,6-dibutylnorbornene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, vinylnorbornene, norbornadiene, ethylidene norbornene, divinylbenzene, dicyclopentadiene, and isomers thereof.

91. The process of claim 86, where the polymerization occurs in the gas phase.

92. The process of claim 86, where the polymerization occurs in the slurry phase.

93. The process of claim 86, where the polymerization occurs in the solution phase.

94. The process of claim 86 wherein the activator is selected from the group consisting of alumoxane, modified alumoxane, trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(tert-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(tert-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(tert-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, di-(iso-propyl)ammonium tetrakis(pentafluorophenyl)borate, and dicyclohexylammonium tetrakis(pentafluorophenyl)borate; and other salts such as tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, tropillium tetrakis (perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, tropillium tetrakis(3,5-bis(trifluoromethyl)phenyl)borate, triphenylcarbenium tetrakis (3,5-bis(trifluoromethyl)phenyl)borate,
triphenylphosphonium tetrakis(3,5-bis(trifluoromethyl)phenyl)borate, triethylsilylium tetrakis(3,5-bis(trifluoromethyl)phenyl)borate, and benzene(diazonium) tetrakis(3,5-bis(trifluoromethyl)phenyl)borate.

95. A transition metal compound represented by formula:

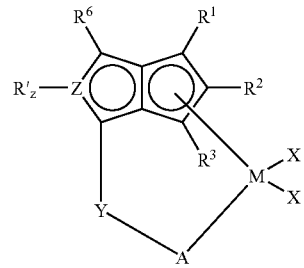

wherein

M is a group 3, 4, 5 or 6 transition metal atom, a lanthanide metal atom, or an actinide metal atom;

R$^1$, R$^2$, R$^3$, R$^6$, and R' are, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent R$^1$, R$^2$, R$^3$, R$^6$, and R' may join together to form a substituted or unsubstituted, saturated, partially unsaturated, or aromatic cyclic or polycyclic substituent;

Z is a Group 16 atom or a Group 15 atom; when Z is a Group 15 atom, "z" is one, indicating the presence of R' bonded to Z, and when Z is a Group 16 atom, "z" is zero, indicating the absence of R';

Y is a Group 15 or 16 bridging heteroatom substituent that is bonded via the heteroatom to the indicated ring system, and to A;

A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand where A is bonded to Y through any bondable ring position; or A is a mono-anionic ligand such as a substituted or unsubstituted pentadienyl ligand, a substituted or unsubstituted allyl ligand, or a substituted or unsubstituted boratabenzene; and each X is, independently, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from about 3 to about 20 carbon atoms; or both together can be an olefin, diolefin or aryne ligand; or both X may, independently, be a halogen, alkoxide, aryloxide, amide, phosphide or other univalent anionic ligand or both X can also be joined to form a anionic chelating ligand.

96. The compound of claim 95 where M is Ti, Zr or Hf.

97. The compound of claim 95 where:

R$^1$, R$^2$, R$^3$, R$^6$, and R' are, independently, hydrogen, a hydrocarbyl, substituted hydrocarbyl, halocarbyl, or substituted halocarbyl;

Y is S, O, NR', PR', O—O, S—S, R'N—NR', R'P—PR', O—S, O—NR', O—PR', S—NR', S—PR', or R'N—PR', where each R' is, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituent; and A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand.

98. The compound of claim 95 where R$^1$, R$^2$ and R$^3$ are each, independently hydrogen or a C1 to C6 hydrocarbyl group.

99. A catalyst system comprising the compound of claim 95 and an activator.

100. A supported catalyst system comprising the catalyst system of claim 99 and a support.

101. A process to polymerize olefins comprising contacting the catalyst system of claim 99 with one or more olefins.

102. The process of claim 101 wherein the olefins comprise ethylene and or propylene.

103. The process of claim 101 wherein the olefins comprise ethylene and a comonomer selected from the group consisting of propylene, butene, pentene, hexene, heptene, octene, nonene, decene, undecene, dodecene, hexadecene, 4-methylpentene-1, 3-methylpentene-1, 3,5,5-trimethylhexene-1, 5-ethylnonene-1, and isomers thereof.

104. The process of claim 101 wherein the olefins comprise propylene and a comonomer selected from the group consisting of ethylene, butene, pentene, hexene, heptene, octene, nonene, decene, undecene, dodecene, hexadecene, 4-methylpentene-1, 3-methylpentene-1, 3,5,5-trimethylhexene-1, 5-ethylnonene-1, and isomers thereof.

105. The process of claim 101 wherein the olefins comprise ethylene and/or propylene and one or more comonomers selected from the group consisting of butene, pentene, hexene, heptene, octene, nonene, decene, undecene, dodecene, hexadecene, 4-methylpentene-1, 3-methylpentene-1,3,5,5-trimethylhexene-1, 5-ethylnonene-1, butadiene, hexadiene, heptadiene, pentadiene, octadiene, nonadiene, decadiene, dodecadiene, styrene, 3,5,5-trimethylhexene-1, 3-methylpentene-1, 4-methylpentene-1, cyclopentadiene, cyclohexene, cyclooctene, hexadiene, cyclohexadiene, alpha-methylstyrene, vinyltoluene, vinylnaphthalene, allyl benzene, indene, para-methylstyrene, 4-phenyl-1-butene, vinylcyclohexane, vinylcyclohexene, cyclopentadiene, cyclopentene, 4-methylcyclopentene, cyclohexene, 4-methylcyclohexene, cyclobutene, vinyladamantane, norbornene, 5-methylnorbornene, 5-ethylnorbornene, 5-propylnorbornene, 5-butylylnorbornene, 5-pentylnorbornene, 5-hexylnorbornene, 5-heptylnorbornene, 5-octylnorbornene, 5-nonylnorbornene, 5-decylnorbornene, 5-phenylnorbornene, vinylnorbornene, ethylidene norbornene, 5,6-dimethylnorbornene, 5,6-dibutylnorbornene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, vinylnorbornene, norbornadiene, ethylidene norbornene, divinylbenzene, dicyclopentadiene, and isomers thereof.

106. The process of claim 101, where the polymerization occurs in the gas phase.

107. The process of claim 101, where the polymerization occurs in the slurry phase.

108. The process of claim 101, where the polymerization occurs in the solution phase.

109. The process of claim 101 wherein the activator is selected from the group consisting of alumoxane, modified alumoxane, trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis (pentafluorophenyl)borate, tri(sec-butyl)ammonium tetrakis (pentafluorophenyl)borate, N,N-dimethylanilinium tetrakis (pentafluorophenyl)borate, N,N-diethylanilinium tetrakis (pentafluorophenyl)borate, N,N-dimethyl-(2,4,6-trimethylanilinium) tetrakis(pentafluorophenyl)borate, trimethylammonium tetrakis-(2,3,4,6-tetrafluorophenyl) borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(tert-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(tert-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(tert-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, di-(iso-propyl)ammonium tetrakis(pentafluorophenyl)borate, and dicyclohexylammonium tetrakis(pentafluorophenyl)borate; and other salts such as tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, and benzene(diazonium) tetrakis(3,5-bis(trifluoromethyl)phenyl)borate.

110. A transition metal compound represented by formula:

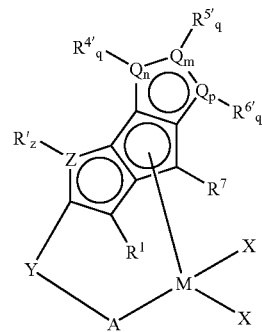

wherein
M is a group 3, 4, 5 or 6 transition metal atom, a lanthanide metal atom, or an actinide metal atom;
$R^1$, $R^7$, R', R", $R^{4'}$, $R^{5'}$, and $R^{6'}$ are, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent $R^1$, $R^7$, R', R", $R^{4'}$, $R^{5'}$, and $R^{6'}$ may join together to form a substituted or unsubstituted, saturated, partially unsaturated, or aromatic cyclic or polycyclic substituent;
Z is a Group 16 atom or a Group 15 atom; when Z is a Group 15 atom, "z" is one, indicating the presence of R' bonded to Z, and when Z is a Group 16 atom, "z" is zero, indicating the absence of R';
each Q, if present, is, independently, a Group 16 atom or a Group 15 atom; when a Q is a Group 15 atom, "q" is one, indicating the presence of $R^{4'}$, $R^{5'}$, or $R^{6'}$ bonded to Q, and when a Q is a Group 16 atom, "q" is zero, indicating the absence of $R^{4'}$, $R^{5'}$, or $R^{6'}$; m, n, and p are independently zero or one, and m+n+p=1; when m or n or p is one, Q is present in the ring as a Group 16 or a Group 15 atom; when m or n or p is zero, Q is absent and is replaced by a ring carbon atom having a substituent R";
Y is a Group 15 or 16 bridging heteroatom substituent that is bonded via the heteroatom to the indicated ring system, and to A;
A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand where A is bonded to Y through any bondable ring position; or A is a mono-anionic ligand such as a substituted or unsubstituted pentadienyl ligand, a substituted or unsubstituted allyl ligand, or a substituted or unsubstituted boratabenzene; and
each X is, independently, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from about 3 to about 20 carbon atoms; or both together can be an olefin, diolefin or aryne ligand; or both X may, independently, be a halogen, alkoxide, aryloxide, amide, phosphide or other univalent anionic ligand or both X can also be joined to form a anionic chelating ligand.

111. The compound of claim 110 where M is Ti, Zr or Hf.

112. The compound of claim 110 where:

$R^1$, $R^7$, R', R", $R^{4'}$, $R^{5'}$, and $R^{6'}$ are, independently, hydrogen, a hydrocarbyl, substituted hydrocarbyl, halocarbyl, or substituted halocarbyl;

Y is S, O, NR', PR', O—O, S—S, R'N—NR', R'P—PR', O—S, O—NR', O—PR', S—NR', S—PR', or R'N—PR', where each R' is, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituent; and A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand.

113. The compound of claim 110 where $R^{4'}$, $R^{5'}$ and $R^{6'}$ are each, independently hydrogen or a C1 to C6 hydrocarbyl group.

114. A catalyst system comprising the compound of claim 110 and an activator.

115. A supported catalyst system comprising the catalyst system of claim 114 and a support.

116. A process to polymerize olefins comprising contacting the catalyst system of claim 114 with one or more olefins.

117. The process of claim 116 wherein the olefins comprise ethylene and or propylene.

118. The process of claim 116 wherein the olefins comprise ethylene and a comonomer selected from the group consisting of propylene, butene, pentene, hexene, heptene, octene, nonene, decene, undecene, dodecene, hexadecene, 4-methylpentene-1, 3-methylpentene-1, 3,5,5-trimethylhexene-1, 5-ethylnonene-1, and isomers thereof.

119. The process of claim 116 wherein the olefins comprise propylene and a comonomer selected from the group consisting of ethylene, butene, pentene, hexene, heptene, octene, nonene, decene, undecene, dodecene, hexadecene, 4-methylpentene-1, 3-methylpentene-1, 3,5,5-trimethylhexene-1, 5-ethylnonene-1, and isomers thereof.

120. The process of claim 116 wherein the olefins comprise ethylene and/or propylene and one or more comonomers selected from the group consisting of butene, pentene, hexene, heptene, octene, nonene, decene, undecene, dodecene, hexadecene, 4-methylpentene-1, 3-methylpentene-1,3,5,5-trimethylhexene-1, 5-ethylnonene-1, butadiene, hexadiene, heptadiene, pentadiene, octadiene, nonadiene, decadiene, dodecadiene, styrene, 3,5,5-trimethylhexene-1, 3-methylpentene-1, 4-methylpentene-1, cyclopentadiene, cyclohexene, cyclooctene, hexadiene, cyclohexadiene, alpha-methylstyrene, vinyltoluene, vinylnaphthalene, allyl benzene, indene, para-methylstyrene, 4-phenyl-1-butene, vinylcyclohexane, vinylcyclohexene, cyclopentadiene, cyclopentene, 4-methylcyclopentene, cyclohexene, 4-methylcyclohexene, cyclobutene, vinyladamantane, norbornene, 5-methylnorbornene, 5-ethylnorbornene, 5-propylnorbornene, 5-butylylnorbornene, 5-pentylnorbornene, 5-hexylnorbornene, 5-heptylnorbornene, 5-octylnorbornene, 5-nonylnorbornene, 5-decylnorbornene, 5-phenylnorbornene, vinylnorbornene, ethylidene norbornene, 5,6-dimethylnorbornene, 5,6-dibutylnorbornene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, vinylnorbornene, norbornadiene, ethylidene norbornene, divinylbenzene, dicyclopentadiene, and isomers thereof.

121. The process of claim 116, where the polymerization occurs in the gas phase.

122. The process of claim 116, where the polymerization occurs in the slurry phase.

123. The process of claim 116, where the polymerization occurs in the solution phase.

124. The process of claim 116 wherein the activator is selected from the group consisting of alumoxane, modified alumoxane, trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, trimethylammonium tetrakis-(2,3,4,6-tetrafluorophenyl) borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(tert-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(tert-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(tert-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, di-(iso-propyl)ammonium tetrakis(pentafluorophenyl)borate, and dicyclohexylammonium tetrakis(pentafluorophenyl)borate; and other salts such as tri(o-tolyl)phosphonium tetrakis(pentafluorophenyl)borate, tri(2,6-dimethylphenyl)phosphonium tetrakis(pentafluoronaphthyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, and benzene(diazonium) tetrakis(3,5-bis(trifluoromethyl)phenyl)borate.

125. A transition metal compound represented by formula:

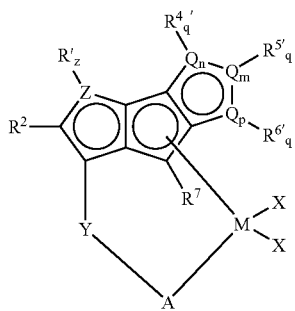

wherein
M is a group 3, 4, 5 or 6 transition metal atom, a lanthanide metal atom, or an actinide metal atom;
$R^2$, $R^7$, R', R'', $R^{4'}$, $R^{5'}$, and $R^{6'}$ are, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent $R^2$, $R^2$, R', R'', $R^{4'}$, $R^{5'}$, and $R^{6'}$ may join together to form a substituted or unsubstituted, saturated, partially unsaturated, or aromatic cyclic or polycyclic substituent;
Z is a Group 16 atom or a Group 15 atom; when Z is a Group 15 atom, "z" is one, indicating the presence of R' bonded to Z, and when Z is a Group 16 atom, "z" is zero, indicating the absence of R';
each Q, if present, is, independently, a Group 16 atom or a Group 15 atom; when a Q is a Group 15 atom, "q" is one, indicating the presence of $R^{4'}$, $R^{5'}$, or $R^{6'}$ bonded to Q, and when a Q is a Group 16 atom, "q" is zero, indicating the absence of $R^{4'}$, $R^{5'}$, or $R^{6'}$; m, n, and p are independently zero or one, and m+n+p=1; when m or n or p is one, Q is present in the ring as a Group 16 or a Group 15 atom; when m or n or p is zero, Q is absent and is replaced by a ring carbon atom having a substituent R'';

Y is a Group 15 or 16 bridging heteroatom substituent that is bonded via the heteroatom to the indicated ring system, and to A;
A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand where A is bonded to Y through any bondable ring position; or A is a mono-anionic ligand such as a substituted or unsubstituted pentadienyl ligand, a substituted or unsubstituted allyl ligand, or a substituted or unsubstituted boratabenzene; and
each X is, independently, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from about 3 to about 20 carbon atoms; or both together can be an olefin, diolefin or aryne ligand; or both X may, independently, be a halogen, alkoxide, aryloxide, amide, phosphide or other univalent anionic ligand or both X can also be joined to form a anionic chelating ligand.

126. The compound of claim 125 where M is Ti, Zr or Hf.
127. The compound of claim 125 where:
$R^2$, $R^2$, R', R'', $R^{4'}$, $R^{5'}$, and $R^{6'}$ are, independently, hydrogen, a hydrocarbyl, substituted hydrocarbyl, halocarbyl, or substituted halocarbyl;
Y is S, O, NR', PR', O—O, S—S, R'N—NR', R'P—PR', O—S, O—NR', O—PR', S—NR', S—PR', or R'N—PR', where each R' is, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituent; and
A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand.

128. The compound of claim 125 where $R^{4'}$, $R^{5'}$ and $R^{6'}$ are each, independently hydrogen or a C1 to C6 hydrocarbyl group.

129. A catalyst system comprising the compound of claim 125 and an activator.

130. A supported catalyst system comprising the catalyst system of claim 129 and a support.

131. A process to polymerize olefins comprising contacting the catalyst system of claim 129 with one or more olefins.

132. The process of claim 131 wherein the olefins comprise ethylene and or propylene.

133. The process of claim 131 wherein the olefins comprise ethylene and a comonomer selected from the group consisting of propylene, butene, pentene, hexene, heptene, octene, nonene, decene, undecene, dodecene, hexadecene, 4-methylpentene-1, 3-methylpentene-1, 3,5,5-trimethylhexene-1, 5-ethylnonene-1, and isomers thereof.

134. The process of claim 131 wherein the olefins comprise propylene and a comonomer selected from the group consisting of ethylene, butene, pentene, hexene, heptene, octene, nonene, decene, undecene, dodecene, hexadecene, 4-methylpentene-1, 3-methylpentene-1, 3,5,5-trimethylhexene-1, 5-ethylnonene-1, and isomers thereof.

135. The process of claim 131 wherein the olefins comprise ethylene and/or propylene and one or more comonomers selected from the group consisting of butene, pentene, hexene, heptene, octene, nonene, decene, undecene, dodecene, hexadecene, 4-methylpentene-1, 3-methylpentene-1,3,5,5-trimethylhexene-1, 5-ethylnonene-1, butadiene, hexadiene, heptadiene, pentadiene, octadiene, nonadiene, decadiene, dodecadiene, styrene, 3,5,5-trimethylhexene-1, 3-methylpentene-1, 4-methylpentene-1, cyclopentadiene, cyclohexene, cyclooctene, hexadiene, cyclohexadiene, alpha-methylstyrene, vinyltoluene, vinylnaphthalene, allyl benzene, indene, para-methylstyrene, 4-phenyl-1-butene, vinylcyclohexane, vinylcyclohexene, cyclopentadiene, cyclopentene, 4-methylcyclopentene, cyclohexene, 4-methylcyclohexene, cyclobutene, vinyladamantane, norbornene, 5-methylnorbornene, 5-ethylnorbornene, 5-propylnorbornene, 5-butylylnorbornene, 5-pentylnorbornene, 5-hexylnorbornene, 5-heptylnorbornene, 5-octylnorbornene, 5-nonylnorbornene, 5-decylnorbornene, 5-phenylnorbornene, vinylnorbornene, ethylidene norbornene, 5,6-dimethylnorbornene, 5,6-dibutylnorbornene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, vinylnorbornene, norbornadiene, ethylidene norbornene, divinylbenzene, dicyclopentadiene, and isomers thereof.

136. The process of claim 131, where the polymerization occurs in the gas phase.

137. The process of claim 131, where the polymerization occurs in the slurry phase.

138. The process of claim 131, where the polymerization occurs in the solution phase.

139. The process of claim 131 wherein the activator is selected from the group consisting of alumoxane, modified alumoxane, trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(tert-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(tert-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(tert-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, di-(iso-propyl)ammonium tetrakis(pentafluorophenyl)borate, and dicyclohexylammonium tetrakis(pentafluorophenyl)borate; and other salts such as tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, tropillium tetrakis (perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, tropillium tetrakis (perfluorobiphenyl)borate, triphenylcarbenium tetrakis (perfluorobiphenyl)borate, triphenylphosphonium tetrakis (perfluorobiphenyl)borate, triethylsilylium tetrakis (perfluorobiphenyl)borate, benzene(diazonium) tetrakis (perfluorobiphenyl)borate, tropillium tetrakis(3,5-bis(trifluoromethyl)phenyl)borate, triphenylcarbenium tetrakis (3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl) phenyl)borate, and benzene(diazonium) tetrakis(3,5-bis(trifluoromethyl)phenyl)borate.

140. A transition metal compound represented by formula:

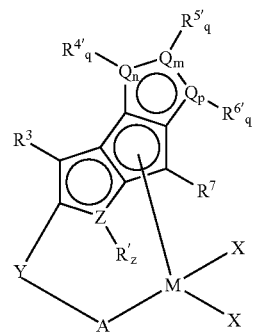

wherein

M is a group 3, 4, 5 or 6 transition metal atom, a lanthanide metal atom, or an actinide metal atom;

$R^3$, $R^7$, R', R", $R^{4'}$, $R^{5'}$, and $R^{6'}$ are, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent $R^3$, $R^7$, R', R", $R^{4'}$, $R^{5'}$, and $R^{6'}$ may join together to form a substituted or unsubstituted, saturated, partially unsaturated, or aromatic cyclic or polycyclic substituent;

Z is a Group 16 atom or a Group 15 atom; when Z is a Group 15 atom, "z" is one, indicating the presence of R' bonded to Z, and when Z is a Group 16 atom, "z" is zero, indicating the absence of R';

each Q, if present, is, independently, a Group 16 atom or a Group 15 atom; when a Q is a Group 15 atom, "q" is one, indicating the presence of $R^{4'}$, $R^{5'}$, or $R^{6'}$ bonded to Q, and when a Q is a Group 16 atom, "q" is zero, indicating the absence of $R^{4'}$, $R^{5'}$, or $R^{6'}$; m, n, and p are independently zero or one, and m+n+p=1; when m or n or p is one, Q is present in the ring as a Group 16 or a Group 15 atom; when m or n or p is zero, Q is absent and is replaced by a ring carbon atom having a substituent R";

Y is a Group 15 or 16 bridging heteroatom substituent that is bonded via the heteroatom to the indicated ring system, and to A;

A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand where A is bonded to Y through any bondable ring position; or A is a mono-anionic ligand such as a substituted or unsubstituted pentadienyl ligand, a substituted or unsubstituted allyl ligand, or a substituted or unsubstituted boratabenzene; and each X is, independently, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from about 3 to about 20 carbon atoms; or both together can be an olefin, diolefin or aryne ligand; or both X may, independently, be a halogen, alkoxide, aryloxide, amide, phosphide or other univalent anionic ligand or both X can also be joined to form a anionic chelating ligand.

141. The compound of claim 140 where M is Ti, Zr or Hf.

142. The compound of claim 140 where:

$R^3$, $R^7$, R', R", $R^{4'}$, $R^{5'}$, and $R^{6'}$ are, independently, hydrogen, a hydrocarbyl, substituted hydrocarbyl, halocarbyl, or substituted halocarbyl;

Y is S, O, NR', PR', O—O, S—S, R'N—NR', R'P—PR', O—S, O—NR', O—PR', S—NR', S—PR', or R'N—PR', where each R' is, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituent; and A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand.

143. The compound of claim 140 where $R^{4'}$, $R^{5'}$ and $R^{6'}$ are each, independently hydrogen or a C1 to C6 hydrocarbyl group.

144. A catalyst system comprising the compound of claim 140 and an activator.

145. A supported catalyst system comprising the catalyst system of claim 144 and a support.

146. A process to polymerize olefins comprising contacting the catalyst system of claim 144 with one or more olefins.

147. The process of claim 146 wherein the olefins comprise ethylene and or propylene.

148. The process of claim 146 wherein the olefins comprise ethylene and a comonomer selected from the group consisting of propylene, butene, pentene, hexene, heptene, octene, nonene, decene, undecene, dodecene, hexadecene, 4-methylpentene-1, 3-methylpentene-1, 3,5,5-trimethylhexene-1, 5-ethylnonene-1, and isomers thereof.

149. The process of claim 146 wherein the olefins comprise propylene and a comonomer selected from the group consisting of ethylene, butene, pentene, hexene, heptene, octene, nonene, decene, undecene, dodecene, hexadecene, 4-methylpentene-1, 3-methylpentene-1, 3,5,5-trimethylhexene-1, 5-ethylnonene-1, and isomers thereof.

150. The process of claim 146 wherein the olefins comprise ethylene and/or propylene and one or more comonomers selected from the group consisting of butene, pentene, hexene, heptene, octene, nonene, decene, undecene, dodecene, hexadecene, 4-methylpentene-1, 3-methylpentene-1,3,5,5-trimethylhexene-1, 5-ethylnonene-1, butadiene, hexadiene, heptadiene, pentadiene, octadiene, nonadiene, decadiene, dodecadiene, styrene, 3,5,5-trimethylhexene-1, 3-methylpentene-1, 4-methylpentene-1, cyclopentadiene, cyclohexene, cyclooctene, hexadiene, cyclohexadiene, alpha-methylstyrene, vinyltoluene, vinylnaphthalene, allyl benzene, indene, para-methylstyrene, 4-phenyl-1-butene, vinylcyclohexane, vinylcyclohexene, cyclopentadiene, cyclopentene, 4-methylcyclopentene, cyclohexene, 4-methylcyclohexene, cyclobutene, vinyladamantane, norbornene, 5-methylnorbornene, 5-ethylnorbornene, 5-propylnorbornene, 5-butylylnorbornene, 5-pentylnorbornene, 5-hexylnorbornene, 5-heptylnorbornene, 5-octylnorbornene, 5-nonylnorbornene, 5-decylnorbornene, 5-phenylnorbornene, vinylnorbornene, ethylidene norbornene, 5,6-dimethylnorbornene, 5,6-dibutylnorbornene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, vinylnorbornene, norbornadiene, ethylidene norbornene, divinylbenzene, dicyclopentadiene, and isomers thereof.

151. The process of claim 146, where the polymerization occurs in the gas phase.

152. The process of claim 146, where the polymerization occurs in the slurry phase.

153. The process of claim 146, where the polymerization occurs in the solution phase.

154. The process of claim 146 wherein the activator is selected from the group consisting of alumoxane, modified alumoxane, trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(tert-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(tert-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri (n-butyl)ammonium tetrakis(3,5-bis(trifluoromethyl)phenyl)borate, tri(tert-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, di-(iso-propyl)ammonium tetrakis(pentafluorophenyl)borate, and dicyclohexylammonium tetrakis(pentafluorophenyl)borate; and other salts such as tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, and benzene(diazonium) tetrakis(3,5-bis(trifluoromethyl)phenyl)borate.

155. A transition metal compound represented by formula:

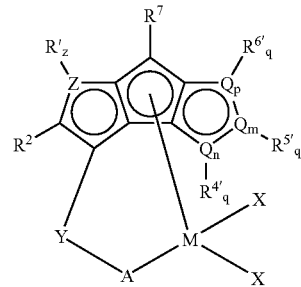

wherein

M is a group 3, 4, 5 or 6 transition metal atom, a lanthanide metal atom, or an actinide metal atom;

$R^2$, $R^7$, $R'$, $R''$, $R^{4'}$, $R^{5'}$, and $R^{6'}$ are, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent $R^2$, $R^7$, $R'$, $R''$, $R^{4'}$, $R^{5'}$, and $R^{6'}$ may join together to form a substituted or unsubstituted, saturated, partially unsaturated, or aromatic cyclic or polycyclic substituent;

Z is a Group 16 atom or a Group 15 atom; when Z is a Group 15 atom, "z" is one, indicating the presence of $R'$ bonded to Z, and when Z is a Group 16 atom, "z" is zero, indicating the absence of $R'$;

each Q, if present, is, independently, a Group 16 atom or a Group 15 atom; when a Q is a Group 15 atom, "q" is one, indicating the presence of $R^{4'}$, $R^{5'}$, or $R^{6'}$ bonded to Q, and when a Q is a Group 16 atom, "q" is zero, indicating the absence of $R^{4'}$, $R^{5'}$, or $R^{6'}$; m, n, and p are independently zero or one, and m+n+p=1; when m or n or p is one, Q is present in the ring as a Group 16 or a Group 15 atom; when m or n or p is zero, Q is absent and is replaced by a ring carbon atom having a substituent $R''$;

Y is a Group 15 or 16 bridging heteroatom substituent that is bonded via the heteroatom to the indicated ring system, and to A;

A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand where A is bonded to Y through any bondable ring position; or A is a mono-anionic ligand such as a substituted or unsubstituted pentadienyl ligand, a substituted or unsubstituted allyl ligand, or a substituted or unsubstituted boratabenzene; and each X is, independently, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from about 3 to about 20 carbon atoms; or both together can be an olefin, diolefin or aryne ligand; or both X may, independently, be a halogen, alkoxide, aryloxide, amide, phosphide or other univalent anionic ligand or both X can also be joined to form a anionic chelating ligand.

156. The compound of claim 155 where M is Ti, Zr or Hf.

157. The compound of claim 155 where:
$R^2$, $R^2$, R', R'', $R^{4'}$, $R^{5'}$, and $R^{6'}$ are, independently, hydrogen, a hydrocarbyl, substituted hydrocarbyl, halocarbyl, or substituted halocarbyl;
Y is S, O, NR', PR', O—O, S—S, R'N—NR', R'P—PR', O—S, O—NR', O—PR', S—NR', S—PR', or R'N—PR', where each R' is, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituent; and
A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand.

158. The compound of claim 155 where $R^{4'}$, $R^{5'}$ and $R^{6'}$ are each, independently hydrogen or a C1 to C6 hydrocarbyl group.

159. A catalyst system comprising the compound of claim 155 and an activator.

160. A supported catalyst system comprising the catalyst system of claim 159 and a support.

161. A process to polymerize olefins comprising contacting the catalyst system of claim 159 with one or more olefins.

162. The process of claim 161 wherein the olefins comprise ethylene and or propylene.

163. The process of claim 161 wherein the olefins comprise ethylene and a comonomer selected from the group consisting of propylene, butene, pentene, hexene, heptene, octene, nonene, decene, undecene, dodecene, hexadecene, 4-methylpentene-1, 3-methylpentene-1,3,5,5-trimethylhexene-1, 5-ethylnonene-1, and isomers thereof.

164. The process of claim 161 wherein the olefins comprise propylene and a comonomer selected from the group consisting of ethylene, butene, pentene, hexene, heptene, octene, nonene, decene, undecene, dodecene, hexadecene, 4-methylpentene-1, 3-methylpentene-1,3,5,5-trimethylhexene-1, 5-ethylnonene-1, and isomers thereof.

165. The process of claim 161 wherein the olefins comprise ethylene and/or propylene and one or more comonomers selected from the group consisting of butene, pentene, hexene, heptene, octene, nonene, decene, undecene, dodecene, hexadecene, 4-methylpentene-1, 3-methylpentene-1,3,5,5-trimethylhexene-1, 5-ethylnonene-1, butadiene, hexadiene, heptadiene, pentadiene, octadiene, nonadiene, decadiene, dodecadiene, styrene, 3,5,5-trimethylhexene-1, 3-methylpentene-1, 4-methylpentene-1, cyclopentadiene, cyclohexene, cyclooctene, hexadiene, cyclohexadiene, alpha-methylstyrene, vinyltoluene, vinylnaphthalene, allyl benzene, indene, para-methylstyrene, 4-phenyl-1-butene, vinylcyclohexane, vinylcyclohexene, cyclopentadiene, cyclopentene, 4-methylcyclopentene, cyclohexene, 4-methylcyclohexene, cyclobutene, vinyladamantane, norbornene, 5-methylnorbornene, 5-ethylnorbornene, 5-propylnorbornene, 5-butylylnorbornene, 5-pentylnorbornene, 5-hexylnorbornene, 5-heptylnorbornene, 5-octylnorbornene, 5-nonylnorbornene, 5-decylnorbornene, 5-phenylnorbornene, vinylnorbornene, ethylidene norbornene, 5,6-dimethylnorbornene, 5,6-dibutylnorbornene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, vinylnorbornene, norbornadiene, ethylidene norbornene, divinylbenzene, dicyclopentadiene, and isomers thereof.

166. The process of claim 161, where the polymerization occurs in the gas phase.

167. The process of claim 161, where the polymerization occurs in the slurry phase.

168. The process of claim 161, where the polymerization occurs in the solution phase.

169. The process of claim 161 wherein the activator is selected from the group consisting of alumoxane, modified alumoxane, trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis (perfluoronaphthyl)borate, tri(n-butyl)ammonium tetrakis (perfluoronaphthyl)borate, tri(tert-butyl)ammonium tetrakis (perfluoronaphthyl)borate, N,N-dimethylanilinium tetrakis (perfluoronaphthyl)borate, N,N-diethylanilinium tetrakis (perfluoronaphthyl)borate, N,N-dimethyl-(2,4,6-trimethylanilinium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl) ammonium tetrakis(perfluorobiphenyl)borate, tri(tert-butyl) ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis (perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri (n-butyl)ammonium tetrakis(3,5-bis(trifluoromethyl)phenyl)borate, tri(tert-butyl)ammonium tetrakis(3,5-bis (trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, di-(iso-propyl)ammonium tetrakis(pentafluorophenyl)borate, and dicyclohexylammonium tetrakis(pentafluorophenyl)borate; and other salts such as tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, and benzene(diazonium) tetrakis(3,5-bis(trifluoromethyl)phenyl)borate.

170. A transition metal compound represented by formula:

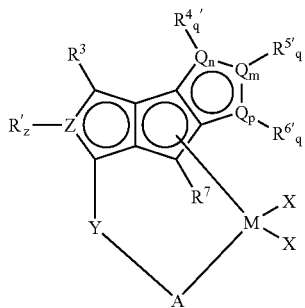

wherein
- M is a group 3, 4, 5 or 6 transition metal atom, a lanthanide metal atom, or an actinide metal atom;
- $R^3$, $R^7$, R', R", $R^{4'}$, $R^{5'}$, and $R^{6'}$ are, independently, hydrogen, hydrocarbyl, substituted hydrocarbyl, halocarbyl, substituted halocarbyl, silylcarbyl, substituted silylcarbyl, germylcarbyl, or substituted germylcarbyl substituents, and optionally, adjacent $R^3$, $R^7$, R', R", $R^{4'}$, $R^{5'}$, and $R^{6'}$ may join together to form a substituted or unsubstituted, saturated, partially unsaturated, or aromatic cyclic or polycyclic substituent;
- Z is a Group 16 atom or a Group 15 atom; when Z is a Group 15 atom, "z" is one, indicating the presence of R' bonded to Z, and when Z is a Group 16 atom, "z" is zero, indicating the absence of R';
- each Q, if present, is, independently, a Group 16 atom or a Group 15 atom; when a Q is a Group 15 atom, "q" is one, indicating the presence of $R^{4'}$, $R^{5'}$, or $R^{6'}$ bonded to Q, and when a Q is a Group 16 atom, "q" is zero, indicating the absence of $R^{4'}$, $R^{5'}$, or $R^{6'}$; m, n, and p are independently zero or one, and m+n+p=1; when m or n or p is one, Q is present in the ring as a Group 16 or a Group 15 atom; when m or n or p is zero, Q is absent and is replaced by a ring carbon atom having a substituent R";
- Y is a Group 15 or 16 bridging heteroatom substituent that is bonded via the heteroatom to the indicated ring system, and to A;
- A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand where A is bonded to Y through any bondable ring position; or A is a mono-anionic ligand such as a substituted or unsubstituted pentadienyl ligand, a substituted or unsubstituted allyl ligand, or a substituted or unsubstituted boratabenzene; and
- each X is, independently, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from about 3 to about 20 carbon atoms; or both together can be an olefin, diolefin or aryne ligand; or both X may, independently, be a halogen, alkoxide, aryloxide, amide, phosphide or other univalent anionic ligand or both X can also be joined to form a anionic chelating ligand.

171. The compound of claim 170 where M is Ti, Zr or Hf.

172. The compound of claim 170 where:
- $R^3$, $R^7$, R', R", $R^{4'}$, $R^{5'}$, and $R^{6'}$ are, independently, hydrogen, a hydrocarbyl, substituted hydrocarbyl, halocarbyl, or substituted halocarbyl;
- Y is S, O, NR', PR', O—O, S—S, R'N—NR', R'P—PR', O—S, O—NR', O—PR', S—NR', S—PR', or R'N—PR', where each R' is, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituent; and
- A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand.

173. The compound of claim 170 where $R^{4'}$, $R^{5'}$ and $R^{6'}$ are each, independently hydrogen or a C1 to C6 hydrocarbyl group.

174. A catalyst system comprising the compound of claim 170 and an activator.

175. A supported catalyst system comprising the catalyst system of claim 174 and a support.

176. A process to polymerize olefins comprising contacting the catalyst system of claim 174 with one or more olefins.

177. The process of claim 176 wherein the olefins comprise ethylene and or propylene.

178. The process of claim 176 wherein the olefins comprise ethylene and a comonomer selected from the group consisting of propylene, butene, pentene, hexene, heptene, octene, nonene, decene, undecene, dodecene, hexadecene, 4-methylpentene-1, 3-methylpentene-1,3,5,5-trimethylhexene-1, 5-ethylnonene-1, and isomers thereof.

179. The process of claim 176 wherein the olefins comprise propylene and a comonomer selected from the group consisting of ethylene, butene, pentene, hexene, heptene, octene, nonene, decene, undecene, dodecene, hexadecene, 4-methylpentene-1, 3-methylpentene-1,3,5,5-trimethylhexene-1, 5-ethylnonene-1, and isomers thereof.

180. The process of claim 176 wherein the olefins comprise ethylene and/or propylene and one or more comonomers selected from the group consisting of butene, pentene, hexene, heptene, octene, nonene, decene, undecene, dodecene, hexadecene, 4-methylpentene-1, 3-methylpentene-1,3,5,5-trimethylhexene-1, 5-ethylnonene-1, butadiene, hexadiene, heptadiene, pentadiene, octadiene, nonadiene, decadiene, dodecadiene, styrene, 3,5,5-trimethylhexene-1, 3-methylpentene-1, 4-methylpentene-1, cyclopentadiene, cyclohexene, cyclooctene, hexadiene, cyclohexadiene, alpha-methylstyrene, vinyltoluene, vinylnaphthalene, allyl benzene, indene, para-methylstyrene, 4-phenyl-1-butene, vinylcyclohexane, vinylcyclohexene, cyclopentadiene, cyclopentene, 4-methylcyclopentene, cyclohexene, 4-methylcyclohexene, cyclobutene, vinyladamantane, norbornene, 5-methylnorbornene, 5-ethylnorbornene, 5-propylnorbornene, 5-butylylnorbornene, 5-pentylnorbornene, 5-hexylnorbornene, 5-heptylnorbornene, 5-octylnorbornene, 5-nonylnorbornene, 5-decylnorbornene, 5-phenylnorbornene, vinylnorbornene, ethylidene norbornene, 5,6-dimethylnorbornene, 5,6-dibutylnorbornene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, vinylnorbornene, norbornadiene, ethylidene norbornene, divinylbenzene, dicyclopentadiene, and isomers thereof.

181. The process of claim 176, where the polymerization occurs in the gas phase.

182. The process of claim 176, where the polymerization occurs in the slurry phase.

183. The process of claim 176, where the polymerization occurs in the solution phase.

184. The process of claim 176 wherein the activator is selected from the group consisting of alumoxane, modified alumoxane, trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(tert-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(tert-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(tert-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, di-(iso-propyl)ammonium tetrakis(pentafluorophenyl)borate, and dicyclohexylammonium tetrakis(pentafluorophenyl)borate; and other salts such as tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, tropillium tetrakis (perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, tropillium tetrakis(3,5-bis(trifluoromethyl)phenyl)borate, triphenylcarbenium tetrakis(3,5-bis(trifluoromethyl)phenyl)borate,
triphenylphosphonium tetrakis(3,5-bis(trifluoromethyl)phenyl)borate, triethylsilylium tetrakis(3,5-bis(trifluoromethyl)phenyl)borate, and benzene(diazonium) tetrakis(3,5-bis(trifluoromethyl)phenyl)borate.

185. A transition metal compound represented by formula:

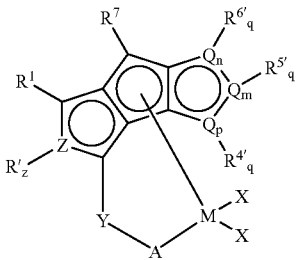

wherein

M is a group 3, 4, 5 or 6 transition metal atom, a lanthanide metal atom, or an actinide metal atom;

$R^1$, $R^7$, R', R", $R^{4'}$, $R^{5'}$, and $R^{6'}$ are, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent $R^1$, $R^7$, R', R", $R^{4'}$, $R^{5'}$, and $R^{6'}$ may join together to form a substituted or unsubstituted, saturated, partially unsaturated, or aromatic cyclic or polycyclic substituent;

Z is a Group 16 atom or a Group 15 atom; when Z is a Group 15 atom, "z" is one, indicating the presence of R' bonded to Z, and when Z is a Group 16 atom, "z" is zero, indicating the absence of R';

each Q, if present, is, independently, a Group 16 atom or a Group 15 atom; when a Q is a Group 15 atom, "q" is one, indicating the presence of $R^{4'}$, $R^{5'}$, or $R^{6'}$ bonded to Q, and when a Q is a Group 16 atom, "q" is zero, indicating the absence of $R^{4'}$, $R^{5'}$, or $R^{6'}$; m, n, and p are independently zero or one, and m+n+p=1; when m or n or p is one, Q is present in the ring as a Group 16 or a Group 15 atom; when m or n or p is zero, Q is absent and is replaced by a ring carbon atom having a substituent R";

Y is a Group 15 or 16 bridging heteroatom substituent that is bonded via the heteroatom to the indicated ring system, and to A;

A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand where A is bonded to Y through any bondable ring position; or A is a mono-anionic ligand such as a substituted or unsubstituted pentadienyl ligand, a substituted or unsubstituted allyl ligand, or a substituted or unsubstituted boratabenzene; and each X is, independently, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from about 3 to about 20 carbon atoms; or both together can be an olefin, diolefin or aryne ligand; or both X may, independently, be a halogen, alkoxide, aryloxide, amide, phosphide or other univalent anionic ligand or both X can also be joined to form a anionic chelating ligand.

186. The compound of claim 185 where M is Ti, Zr or Hf.

187. The compound of claim 185 where:

$R^1$, $R^7$, R', R", $R^{4'}$, $R^{5'}$, and $R^{6'}$ are, independently, hydrogen, a hydrocarbyl, substituted hydrocarbyl, halocarbyl, or substituted halocarbyl;

Y is S, O, NR', PR', O—O, S—S, R'N—NR', R'P—PR', O—S, O—NR', O—PR', S—NR', S—PR', or R'N—PR', where each R' is, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituent; and A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand.

188. The compound of claim 185 where $R^{4'}$, $R^{5'}$ and $R^{6'}$ are each, independently hydrogen or a C1 to C6 hydrocarbyl group.

189. A catalyst system comprising the compound of claim 185 and an activator.

190. A supported catalyst system comprising the catalyst system of claim 189 and a support.

191. A process to polymerize olefins comprising contacting the catalyst system of claim 189 with one or more olefins.

192. The process of claim 191 wherein the olefins comprise ethylene and or propylene.

193. The process of claim 191 wherein the olefins comprise ethylene and a comonomer selected from the group consisting of propylene, butene, pentene, hexene, heptene, octene, nonene, decene, undecene, dodecene, hexadecene, 4-methylpentene-1, 3-methylpentene-1,3,5,5-trimethylhexene-1, 5-ethylnonene-1, and isomers thereof.

194. The process of claim 191 wherein the olefins comprise propylene and a comonomer selected from the group consisting of ethylene, butene, pentene, hexene, heptene, octene, nonene, decene, undecene, dodecene, hexadecene, 4-methylpentene-1, 3-methylpentene-1,3,5,5-trimethylhexene-1, 5-ethylnonene-1, and isomers thereof.

195. The process of claim 191 wherein the olefins comprise ethylene and/or propylene and one or more comonomers selected from the group consisting of butene, pentene, hexene, heptene, octene, nonene, decene, undecene, dodecene, hexadecene, 4-methylpentene-1, 3-methylpentene-1,3,5,5-trimethylhexene-1, 5-ethylnonene-1, butadiene, hexadiene, heptadiene, pentadiene, octadiene, nonadiene, decadiene, dodecadiene, styrene, 3,5,5-trimethylhexene-1, 3-methylpentene-1, 4-methylpentene-1, cyclopentadiene, cyclohexene, cyclooctene, hexadiene, cyclohexadiene, alpha-methylstyrene, vinyltoluene, vinylnaphthalene, allyl benzene, indene, para-methylstyrene, 4-phenyl-1-butene, vinylcyclohexane, vinylcyclohexene, cyclopentadiene, cyclopentene, 4-methylcyclopentene, cyclohexene, 4-methylcyclohexene, cyclobutene, vinyladamantane, norbornene, 5-methylnorbornene, 5-ethylnorbornene, 5-propylnorbornene, 5-butylylnorbornene, 5-pentylnorbornene, 5-hexylnorbornene, 5-heptylnorbornene, 5-octylnorbornene, 5-nonylnorbornene, 5-decylnorbornene, 5-phenylnorbornene, vinylnorbornene, ethylidene norbornene, 5,6-dimethylnorbornene, 5,6-dibutylnorbornene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, vinylnorbornene, norbornadiene, ethylidene norbornene, divinylbenzene, dicyclopentadiene, and isomers thereof.

196. The process of claim 191, where the polymerization occurs in the gas phase.

197. The process of claim 191, where the polymerization occurs in the slurry phase.

198. The process of claim 191, where the polymerization occurs in the solution phase.

199. The process of claim 191, wherein the activator is selected from the group consisting of alumoxane, modified alumoxane, trimethylammonium tetraphenylborate, triethylammonium tetraphenylborate, tripropylammonium tetraphenylborate, tri(n-butyl)ammonium tetraphenylborate, tri (tert-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis (pentafluorophenyl)borate, tri(sec-butyl)ammonium tetrakis (pentafluorophenyl)borate, N,N-dimethylanilinium tetrakis (pentafluorophenyl)borate, N,N-diethylanilinium tetrakis (pentafluorophenyl)borate, N,N-dimethyl-(2,4,6-trimethylanilinium) tetrakis(pentafluorophenyl)borate, trimethylammonium tetrakis-(2,3,4,6-tetrafluorophenyl) borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis (perfluoronaphthyl)borate, tri(n-butyl)ammonium tetrakis (perfluoronaphthyl)borate, tri(tert-butyl)ammonium tetrakis (perfluoronaphthyl)borate, N,N-dimethylanilinium tetrakis (perfluoronaphthyl)borate, N,N-diethylanilinium tetrakis (perfluoronaphthyl)borate, N,N-dimethyl-(2,4,6-trimethylanilinium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl) ammonium tetrakis(perfluorobiphenyl)borate, tri(tert-butyl) ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis (perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri (n-butyl)ammonium tetrakis(3,5-bis(trifluoromethyl)phenyl)borate, tri(tert-butyl)ammonium tetrakis(3,5-bis (trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis (trifluoromethyl)phenyl)borate, di-(iso-propyl)ammonium tetrakis(pentafluorophenyl)borate, and dicyclohexylammonium tetrakis(pentafluorophenyl)borate; and other salts such as tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis (pentafluorophenyl)borate, triethylsilylium tetrakis (pentafluorophenyl)borate, benzene(diazonium) tetrakis (pentafluorophenyl)borate, tropillium tetrakis-(2,3,4,6-tetrafluorophenyl)borate, triphenylcarbenium tetrakis-(2,3,4, 6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, tropillium tetrakis (perfluoronaphthyl)borate, triphenylcarbenium tetrakis(perfluoronaphthyl)borate, triphenylphosphonium tetrakis(perfluoronaphthyl)borate, triethylsilylium tetrakis (perfluoronaphthyl)borate, benzene(diazonium) tetrakis (perfluoronaphthyl)borate, tropillium tetrakis (perfluorobiphenyl)borate, triphenylcarbenium tetrakis (perfluorobiphenyl)borate, triphenylphosphonium tetrakis (perfluorobiphenyl)borate, triethylsilylium tetrakis (perfluorobiphenyl)borate, benzene(diazonium) tetrakis (perfluorobiphenyl)borate, tropillium tetrakis(3,5-bis (trifluoromethyl)phenyl)borate, triphenylcarbenium tetrakis (3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl) phenyl)borate, and benzene(diazonium) tetrakis(3,5-bis(trifluoromethyl)phenyl)borate.

200. A transition metal compound represented by formula:

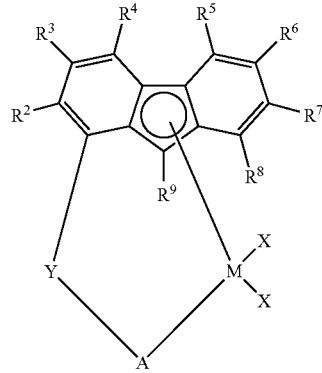

wherein
M is a group 3, 4, 5 or 6 transition metal atom, a lanthanide metal atom, or an actinide metal atom;

$R^2$, $R^3$, $R^4$, $R^5$, $R^6$, $R^7$, $R^8$, and $R^9$ are, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent $R^2$, $R^3$, $R^4$, $R^5$, $R^6$, $R^7$, $R^8$, and $R^9$ may join together to form a substituted or unsubstituted, saturated, partially unsaturated, or aromatic cyclic or polycyclic substituent;

Y is a Group 15 or 16 bridging heteroatom substituent that is bonded via the heteroatom to the indicated ring system, and to A;

A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand where A is bonded to Y through any bondable ring position; or A is a mono-anionic ligand such as a substituted or unsubstituted pentadienyl ligand, a substituted or unsubstituted allyl ligand, or a substituted or unsubstituted boratabenzene; and each X is, independently, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from about 3 to about 20 carbon atoms; or both together can be an olefin, diolefin or aryne ligand; or both X may, independently, be a halogen, alkoxide, aryloxide, amide, phosphide or other univalent anionic ligand or both X can also be joined to form a anionic chelating ligand.

201. The compound of claim 200 where M is Ti, Zr or Hf.

202. The compound of claim 200 where:

$R^2$, $R^3$, $R^4$, $R^5$, $R^6$, $R^2$, $R^8$, and $R^9$ are, independently, hydrogen, a hydrocarbyl, substituted hydrocarbyl, halocarbyl, or substituted halocarbyl;

Y is S, O, NR', PR', O—O, S—S, R'N—NR', R'P—PR', O—S, O—NR', O—PR', S—NR', S—PR', or R'N—PR', where each R' is, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituent; and A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand.

203. The compound of claim 200 where $R^2$, $R^3$, $R^4$, $R^5$, $R^6$, $R^7$, $R^8$, and $R^9$ are each, independently hydrogen or a C1 to C6 hydrocarbyl group.

204. A catalyst system comprising the compound of claim 200 and an activator.

205. A supported catalyst system comprising the catalyst system of claim 204 and a support.

206. A process to polymerize olefins comprising contacting the catalyst system of claim 204 with one or more olefins.

207. The process of claim 206 wherein the olefins comprise ethylene and or propylene.

208. The process of claim 206 wherein the olefins comprise ethylene and a comonomer selected from the group consisting of propylene, butene, pentene, hexene, heptene, octene, nonene, decene, undecene, dodecene, hexadecene, 4-methylpentene-1, 3-methylpentene-1,3,5,5-trimethylhexene-1, 5-ethylnonene-1, and isomers thereof.

209. The process of claim 206 wherein the olefins comprise propylene and a comonomer selected from the group consisting of ethylene, butene, pentene, hexene, heptene, octene, nonene, decene, undecene, dodecene, hexadecene, 4-methylpentene-1, 3-methylpentene-1,3,5,5-trimethylhexene-1, 5-ethylnonene-1, and isomers thereof.

210. The process of claim 206 wherein the olefins comprise ethylene and/or propylene and one or more comonomers selected from the group consisting of butene, pentene, hexene, heptene, octene, nonene, decene, undecene, dodecene, hexadecene, 4-methylpentene-1, 3-methylpentene-1,3,5,5-trimethylhexene-1, 5-ethylnonene-1, butadiene, hexadiene, heptadiene, pentadiene, octadiene, nonadiene, decadiene, dodecadiene, styrene, 3,5,5-trimethylhexene-1, 3-methylpentene-1, 4-methylpentene-1, cyclopentadiene, cyclohexene, cyclooctene, hexadiene, cyclohexadiene, alpha-methylstyrene, vinyltoluene, vinylnaphthalene, allyl benzene, indene, para-methylstyrene, 4-phenyl-1-butene, vinylcyclohexane, vinylcyclohexene, cyclopentadiene, cyclopentene, 4-methylcyclopentene, cyclohexene, 4-methylcyclohexene, cyclobutene, vinyladamantane, norbornene, 5-methylnorbornene, 5-ethylnorbornene, 5-propylnorbornene, 5-butylylnorbornene, 5-pentylnorbornene, 5-hexylnorbornene, 5-heptylnorbornene, 5-octylnorbornene, 5-nonylnorbornene, 5-decylnorbornene, 5-phenylnorbornene, vinylnorbornene, ethylidene norbornene, 5,6-dimethylnorbornene, 5,6-dibutylnorbornene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, vinylnorbornene, norbornadiene, ethylidene norbornene, divinylbenzene, dicyclopentadiene, and isomers thereof.

211. The process of claim 206, where the polymerization occurs in the gas phase.

212. The process of claim 206, where the polymerization occurs in the slurry phase.

213. The process of claim 206, where the polymerization occurs in the solution phase.

214. The process of claim 206 wherein the activator is selected from the group consisting of alumoxane, modified alumoxane, trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(tert-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(tert-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, trimethylammonium tetrakis(3,5- bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(tert-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, di-(iso-propyl)ammonium tetrakis(pentafluorophenyl)borate, and dicyclohexylammonium tetrakis(pentafluorophenyl)borate; and other salts such as tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, tropillium tetrakis (perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-b is (trifluoromethyl) phenyl)borate, and benzene(diazonium) tetrakis(3,5-bis(trifluoromethyl)phenyl)$_b$ orate.

215. A transition metal compound represented by formula:

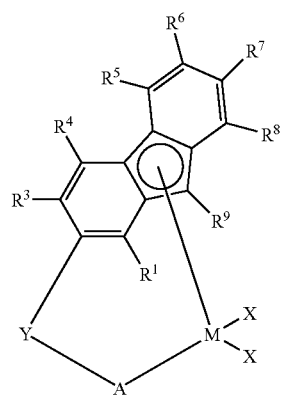

wherein

M is a group 3, 4, 5 or 6 transition metal atom, er-a lanthanide metal atom, or an actinide metal atom;

$R^1$, $R^2$, $R^3$, $R^4$, $R^5$, $R^6$, $R^7$, $R^8$, and $R^9$ are, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent $R^1$, $R^2$, $R^3$, $R^4$, $R^5$, $R^6$, $R^7$, $R^8$, and $R^9$ may join together to form a substituted or unsubstituted, saturated, partially unsaturated, or aromatic cyclic or polycyclic substituent;

Y is a Group 15 or 16 bridging heteroatom substituent that is bonded via the heteroatom to the indicated ring system, and to A;

A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand where A is bonded to Y through any bondable ring position; or A is a mono-anionic ligand such as a substituted or unsubstituted pentadienyl ligand, a substituted or unsubstituted allyl ligand, or a substituted or unsubstituted boratabenzene; and each X is, independently, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from about 3 to about 20 carbon atoms; or both together can be an olefin, diolefin or aryne ligand; or both X may, independently, be a halogen, alkoxide, aryloxide, amide, phosphide or other univalent anionic ligand or both X can also be joined to form a anionic chelating ligand.

216. The compound of claim 215 where M is Ti, Zr or Hf.
217. The compound of claim 215 where:

$R^1$, $R^2$, $R^3$, $R^4$, $R^5$, $R^6$, $R^7$, $R^8$, and $R^9$ are, independently, hydrogen, a hydrocarbyl, substituted hydrocarbyl, halocarbyl, or substituted halocarbyl;

Y is S, O, NR', PR', O—O, S—S, R'N—NR', R'P—PR', O—S, O—NR', O—PR', S—NR', S—PR', or R'N—PR', where each R' is, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituent; and A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand.

218. The compound of claim 215 where $R^1$, $R^3$, $R^4$, $R^5$, $R^6$, $R^7$, $R^8$, and $R^9$ are each, independently hydrogen or a C1 to C6 hydrocarbyl group.

219. A catalyst system comprising the compound of claim 215 and an activator.

220. A supported catalyst system comprising the catalyst system of claim 219 and a support.

221. A process to polymerize olefins comprising contacting the catalyst system of claim 219 with one or more olefins.

222. The process of claim 221 wherein the olefins comprise ethylene and or propylene.

223. The process of claim 221 wherein the olefins comprise ethylene and a comonomer selected from the group consisting of propylene, butene, pentene, hexene, heptene, octene, nonene, decene, undecene, dodecene, hexadecene, 4-methylpentene-1, 3-methylpentene-1,3,5,5-trimethylhexene-1, 5-ethylnonene-1, and isomers thereof.

224. The process of claim 221 wherein the olefins comprise propylene and a comonomer selected from the group consisting of ethylene, butene, pentene, hexene, heptene, octene, nonene, decene, undecene, dodecene, hexadecene, 4-methylpentene-1, 3-methylpentene-1,3,5,5-trimethylhexene-1, 5-ethylnonene-1, and isomers thereof.

225. The process of claim 221 wherein the olefins comprise ethylene and/or propylene and one or more comonomers selected from the group consisting of butene, pentene, hexene, heptene, octene, nonene, decene, undecene, dodecene, hexadecene, 4-methylpentene-1, 3-methylpentene-1,3,5,5-trimethylhexene-1, 5-ethylnonene-1, butadiene, hexadiene, heptadiene, pentadiene, octadiene, nonadiene, decadiene, dodecadiene, styrene, 3,5,5-trimethylhexene-1, 3-methylpentene-1, 4-methylpentene-1, cyclopentadiene, cyclohexene, cyclooctene, hexadiene, cyclohexadiene, alpha-methylstyrene, vinyltoluene, vinylnaphthalene, allyl benzene, indene, para-methylstyrene, 4-phenyl-1-butene, vinylcyclohexane, vinylcyclohexene, cyclopentadiene, cyclopentene, 4-methylcyclopentene, cyclohexene, 4-methylcyclohexene, cyclobutene, vinyladamantane, norbornene, 5-methylnorbornene, 5-ethylnorbornene, 5-propylnorbornene, 5-butylylnorbornene, 5-pentylnorbornene, 5-hexylnorbornene, 5-heptylnorbornene, 5-octylnorbornene, 5-nonylnorbornene, 5-decylnorbornene, 5-phenylnorbornene, vinylnorbornene, ethylidene norbornene, 5,6-dimethylnorbornene, 5,6-dibutylnorbornene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, vinylnorbornene, norbornadiene, ethylidene norbornene, divinylbenzene, dicyclopentadiene, and isomers thereof.

226. The process of claim 221, where the polymerization occurs in the gas phase.

227. The process of claim 221, where the polymerization occurs in the slurry phase.

228. The process of claim 221, where the polymerization occurs in the solution phase.

229. The process of claim 221 wherein the activator is selected from the group consisting of alumoxane, modified alumoxane, trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(tert-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(tert-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(tert-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, di-(iso-propyl)ammonium tetrakis(pentafluorophenyl)borate, and dicyclohexylammonium tetrakis(pentafluorophenyl)borate; and other salts such as tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, tropillium tetrakis (perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, and benzene(diazonium) tetrakis(3,5-bis(trifluoromethyl)phenyl)borate.

230. A transition metal compound represented by formula:

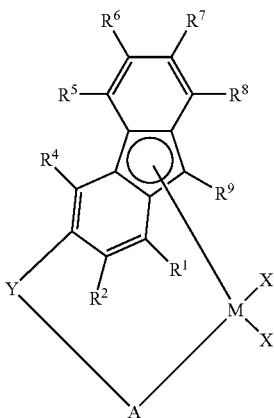

wherein
M is a group 3, 4, 5 or 6 transition metal atom, a lanthanide metal atom, or an actinide metal atom;

$R^1$, $R^2$, $R^4$, $R^5$, $R^6$, $R^7$, $R^8$, and $R^9$ are, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent $R^1$, $R^2$, $R^4$, $R^5$, $R^6$, $R^7$, $R^8$, and $R^9$ may join together to form a substituted or unsubstituted, saturated, partially unsaturated, or aromatic cyclic or polycyclic substituent;

Y is a Group 15 or 16 bridging heteroatom substituent that is bonded via the heteroatom to the indicated ring system, and to A;

A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand where A is bonded to Y through any bondable ring position; or A is a mono-anionic ligand such as a substituted or unsubstituted pentadienyl ligand, a substituted or unsubstituted allyl ligand, or a substituted or unsubstituted boratabenzene; and each X is, independently, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from about 3 to about 20 carbon atoms; or both together can be an olefin, diolefin or aryne ligand; or both X may, independently, be a halogen, alkoxide, aryloxide, amide, phosphide or other univalent anionic ligand or both X can also be joined to form a anionic chelating ligand.

231. The compound of claim 230 where M is Ti, Zr or Hf.

232. The compound of claim 230 where:
$R^1$, $R^2$, $R^4$, $R^5$, $R^6$, $R^7$, $R^8$, and $R^9$ are, independently, hydrogen, a hydrocarbyl, substituted hydrocarbyl, halocarbyl, or substituted halocarbyl;
Y is S, O, NR', PR', O—O, S—S, R'N—NR', R'P—PR', O—S, O—NR', O—PR', S—NR', S—PR', or R'N—PR', where each R' is, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituent; and A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand.

233. The compound of claim 230 where $R^1$, $R^2$, $R^4$, $R^5$, $R^6$, $R^7$, $R^8$, and $R^9$ are each, independently hydrogen or a C1 to C6 hydrocarbyl group.

234. A catalyst system comprising the compound of claim 230 and an activator.

235. A supported catalyst system comprising the catalyst system of claim 234 and a support.

236. A process to polymerize olefins comprising contacting the catalyst system of claim 234 with one or more olefins.

237. The process of claim 236 wherein the olefins comprise ethylene and or propylene.

238. The process of claim 236 wherein the olefins comprise ethylene and a comonomer selected from the group consisting of propylene, butene, pentene, hexene, heptene, octene, nonene, decene, undecene, dodecene, hexadecene, 4-methylpentene-1, 3-methylpentene-1,3,5,5-trimethylhexene-1, 5-ethylnonene-1, and isomers thereof.

239. The process of claim 236 wherein the olefins comprise propylene and a comonomer selected from the group consisting of ethylene, butene, pentene, hexene, heptene, octene, nonene, decene, undecene, dodecene, hexadecene, 4-methylpentene-1, 3-methylpentene-1,3,5,5-trimethylhexene-1, 5-ethylnonene-1, and isomers thereof.

240. The process of claim 236 wherein the olefins comprise ethylene and/or propylene and one or more comonomers selected from the group consisting of butene, pentene, hexene, heptene, octene, nonene, decene, undecene, dodecene, hexadecene, 4-methylpentene-1, 3-methylpentene-1,3,5,5-trimethylhexene-1, 5-ethylnonene-1, butadiene, hexadiene, heptadiene, pentadiene, octadiene, nonadiene, decadiene, dodecadiene, styrene, 3,5,5-trimethylhexene-1, 3-methylpentene-1, 4-methylpentene-1, cyclopentadiene, cyclohexene, cyclooctene, hexadiene, cyclohexadiene, alpha-methylstyrene, vinyltoluene, vinylnaphthalene, allyl benzene, indene, para-methylstyrene, 4-phenyl-1-butene, vinylcyclohexane, vinylcyclohexene, cyclopentadiene, cyclopentene, 4-methylcyclopentene, cyclohexene, 4-methylcyclohexene, cyclobutene, vinyladamantane, norbornene, 5-methylnorbornene, 5-ethylnorbornene, 5-propylnorbornene, 5-butylylnorbornene, 5-pentylnorbornene, 5-hexylnorbornene, 5-heptylnorbornene, 5-octylnorbornene, 5-nonylnorbornene, 5-decylnorbornene, 5-phenylnorbornene, vinylnorbornene, ethylidene norbornene, 5,6-dimethylnorbornene, 5,6-dibutylnorbornene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, vinylnorbornene, norbornadiene, ethylidene norbornene, divinylbenzene, dicyclopentadiene, and isomers thereof.

241. The process of claim 236, where the polymerization occurs in the gas phase.

242. The process of claim 236, where the polymerization occurs in the slurry phase.

243. The process of claim 236, where the polymerization occurs in the solution phase.

244. The process of claim 236 wherein the activator is selected from the group consisting of alumoxane, modified alumoxane, trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(tert-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(tert-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(tert-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, di-(iso-propyl)ammonium tetrakis(pentafluorophenyl)borate, and dicyclohexylammonium tetrakis(pentafluorophenyl)borate; and other salts such as tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, and benzene(diazonium) tetrakis(3,5-bis(trifluoromethyl)phenyl)borate.

245. A transition metal compound represented by formula:

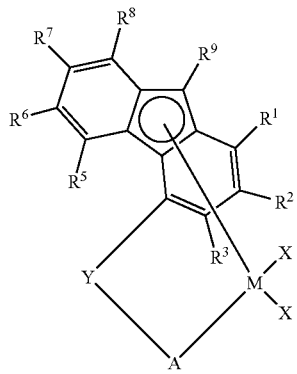

wherein
  M is a group 3, 4, 5 or 6 transition metal atom, a lanthanide metal atom, or an actinide metal atom;
  $R^1$, $R^2$, $R^3$, $R^5$, $R^6$, $R^7$, $R^8$, and $R^9$ are, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituents, and optionally, adjacent $R^1$, $R^2$, $R^3$, $R^5$, $R^6$, $R^7$, $R^8$, and
  $R^9$ may join together to form a substituted or unsubstituted, saturated, partially unsaturated, or aromatic cyclic or polycyclic substituent;
  Y is a Group 15 or 16 bridging heteroatom substituent that is bonded via the heteroatom to the indicated ring system, and to A;
  A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand where A is bonded to Y through any bondable ring position; or A is a mono-anionic ligand such as a substituted or unsubstituted pentadienyl ligand, a substituted or unsubstituted allyl ligand, or a substituted or unsubstituted boratabenzene; and
  each X is, independently, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from about 3 to about 20 carbon atoms; or both together can be an olefin, diolefin or aryne ligand; or both X may, independently, be a halogen, alkoxide, aryloxide, amide, phosphide or other univalent anionic ligand or both X can also be joined to form a anionic chelating ligand.

246. The compound of claim 245 where M is Ti, Zr or Hf.

247. The compound of claim 245 where:

$R^1$, $R^2$, $R^3$, $R^5$, $R^6$, $R^7$, $R^8$, and $R^9$ are, independently, hydrogen, a hydrocarbyl, substituted hydrocarbyl, halocarbyl, or substituted halocarbyl;

Y is S, O, NR', PR', O—O, S—S, R'N—NR', R'P—PR', O—S, O—NR', O—PR', S—NR', S—PR', or R'N—PR', where each R' is, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituent; and A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand.

248. The compound of claim 245 where $R^1$, $R^2$, $R^4$, $R^5$, $R^6$, $R^7$, $R^8$, and $R^9$ are each, independently hydrogen or a C1 to C6 hydrocarbyl group.

249. A catalyst system comprising the compound of claim 245 and an activator.

250. A supported catalyst system comprising the catalyst system of claim 249 and a support.

251. A process to polymerize olefins comprising contacting the catalyst system of claim 249 with one or more olefins.

252. The process of claim 251 wherein the olefins comprise ethylene and or propylene.

253. The process of claim 251 wherein the olefins comprise ethylene and a comonomer selected from the group consisting of propylene, butene, pentene, hexene, heptene, octene, nonene, decene, undecene, dodecene, hexadecene, 4-methylpentene-1, 3-methylpentene-1,3,5,5-trimethylhexene-1, 5-ethylnonene-1, and isomers thereof.

254. The process of claim 251 wherein the olefins comprise propylene and a comonomer selected from the group consisting of ethylene, butene, pentene, hexene, heptene, octene, nonene, decene, undecene, dodecene, hexadecene, 4-methylpentene-1, 3-methylpentene-1,3,5,5-trimethylhexene-1, 5-ethylnonene-1, and isomers thereof.

255. The process of claim 251 wherein the olefins comprise ethylene and/or propylene and one or more comonomers selected from the group consisting of butene, pentene, hexene, heptene, octene, nonene, decene, undecene, dodecene, hexadecene, 4-methylpentene-1, 3-methylpentene-1,3,5,5-trimethylhexene-1, 5-ethylnonene-1, butadiene, hexadiene, heptadiene, pentadiene, octadiene, nonadiene, decadiene, dodecadiene, styrene, 3,5,5-trimethylhexene-1, 3-methylpentene-1, 4-methylpentene-1, cyclopentadiene, cyclohexene, cyclooctene, hexadiene, cyclohexadiene, alpha-methylstyrene, vinyltoluene, vinylnaphthalene, allyl benzene, indene, para-methylstyrene, 4-phenyl-1-butene, vinylcyclohexane, vinylcyclohexene, cyclopentadiene, cyclopentene, 4-methylcyclopentene, cyclohexene, 4-methylcyclohexene, cyclobutene, vinyladamantane, norbornene, 5-methylnorbornene, 5-ethylnorbornene, 5-propylnorbornene, 5-butylylnorbornene, 5-pentylnorbornene, 5-hexylnorbornene, 5-heptylnorbornene, 5-octylnorbornene, 5-nonylnorbornene, 5-decylnorbornene, 5-phenylnorbornene, vinylnorbornene, ethylidene norbornene, 5,6-dimethylnorbornene, 5,6-dibutylnorbornene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, vinylnorbornene, norbornadiene, ethylidene norbornene, divinylbenzene, dicyclopentadiene, and isomers thereof.

256. The process of claim 251, where the polymerization occurs in the gas phase.

257. The process of claim 251, where the polymerization occurs in the slurry phase.

258. The process of claim 251, where the polymerization occurs in the solution phase.

259. The process of claim 251 wherein the activator is selected from the group consisting of alumoxane, modified alumoxane, trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(tert-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(tert-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(tert-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis (trifluoromethyl)phenyl)borate, di-(iso-propyl)ammonium tetrakis(pentafluorophenyl)borate, and dicyclohexylammonium tetrakis(pentafluorophenyl)borate; and other salts such as tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis (pentafluorophenyl)borate, triethylsilylium tetrakis (pentafluorophenyl)borate, benzene(diazonium) tetrakis (pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, tropillium tetrakis (perfluoronaphthyl)borate, triphenylcarbenium tetrakis(perfluoronaphthyl)borate, triphenylphosphonium tetrakis(perfluoronaphthyl)borate, triethylsilylium tetrakis (perfluoronaphthyl)borate, benzene(diazonium) tetrakis (perfluoronaphthyl)borate, tropillium tetrakis (perfluorobiphenyl)borate, triphenylcarbenium tetrakis (perfluorobiphenyl)borate, triphenylphosphonium tetrakis (perfluorobiphenyl)borate, triethylsilylium tetrakis (perfluorobiphenyl)borate, benzene(diazonium) tetrakis (perfluorobiphenyl)borate, tropillium tetrakis(3,5-bis (trifluoromethyl)phenyl)borate, triphenylcarbenium tetrakis (3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl) phenyl)borate, and benzene(diazonium) tetrakis(3,5-bis(trifluoromethyl)phenyl)borate.

260. A compound represented by the formula HE-Y-AH, where

H is hydrogen;

E is: 1) a substituted or unsubstituted indenyl ligand that is bonded to Y through the four, five, six or seven position of the indenyl ring, or 2) a substituted or unsubstituted heteroindenyl ligand that is bonded to Y through the four, five or six position of the heteroindenyl ring, provided that the bonding position is not the same as the position of the ring heteroatom, or 3) a substituted or unsubstituted fluorenyl ligand that is bonded to Y through the one, two, three, four, five, six, seven or eight position of the fluorenyl ring, or 4) a substituted or unsubstituted heterofluorenyl ligand that is bonded to Y through the one, two, three, four, five or six position of the heteroindenyl ring, provided that the bonding position is not the same as the position of the ring heteroatom;

A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, a substituted or unsubstituted heterofluorenyl ligand, or other monoanionic ligand; and Y is a Group 15 or 16 bridging heteroatom substituent that is bonded via the heteroatom to E and A.

261. A compound represented by the formula $R_3SnE-Y-ASnR_3$, where each R is, independently, a hydrocarbyl group;

Sn is tin;

E is: 1) a substituted or unsubstituted indenyl ligand that is bonded to Y through the four, five, six or seven position of the indenyl ring, or 2) a substituted or unsubstituted heteroindenyl ligand that is bonded to Y through the four, five or six position of the heteroindenyl ring, provided that the bonding position is not the same as the position of the ring heteroatom, or 3) a substituted or unsubstituted fluorenyl ligand that is bonded to Y through the one, two, three, four, five, six, seven or eight position of the fluorenyl ring, or 4) a substituted or unsubstituted heterofluorenyl ligand that is bonded to Y through the one, two, three, four, five or six position of the heteroindenyl ring, provided that the bonding position is not the same as the position of the ring heteroatom;

A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, a substituted or unsubstituted heterofluorenyl ligand, or other monoanionic ligand; and Y is a Group 15 or 16 bridging heteroatom substituent that is bonded via the heteroatom to E and A.

262. The compound of claim 261 where each R is, independently, methyl, ethyl, propyl or butyl.

263. A compound represented by the formula $R_3SiE-Y-ASiR_3$, where each R is, independently, a hydrocarbyl group;

Si is silicon;

E is: 1) a substituted or unsubstituted indenyl ligand that is bonded to Y through the four, five, six or seven position of the indenyl ring, or 2) a substituted or unsubstituted heteroindenyl ligand that is bonded to Y through the four, five or six position of the heteroindenyl ring, provided that the bonding position is not the same as the position of the ring heteroatom, or 3) a substituted or unsubstituted fluorenyl ligand that is bonded to Y through the one, two, three, four, five, six, seven or eight position of the fluorenyl ring, or 4) a substituted or unsubstituted heterofluorenyl ligand that is bonded to Y through the one, two, three, four, five or six position of the heteroindenyl ring, provided that the bonding position is not the same as the position of the ring heteroatom;

A is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, a substituted or unsubstituted heterofluorenyl ligand, or other monoanionic ligand; and Y is a Group 15 or 16 bridging heteroatom substituent that is bonded via the heteroatom to E and A.

264. The compound of claim 261 where each R is, independently, methyl, ethyl, propyl or butyl.

265. A process to oligomerize olefins comprising contacting the catalyst system of claim 4 with one or more olefins.

266. The process of claim 265 wherein the olefins comprise ethylene and or propylene.

267. The process of claim 265 where the oligomerization occurs in the presence of hydrogen.

268. The process of claim 6 where hydrogen or a chain termination agent is added to the polymerization.

269. The process of claim 268 where the chain termination agent is phenyl silane.

270. A transition metal compound comprising a transition metal bound to: 1) at least one substituted or unsubstituted indenyl ligand that is bridged by a heteroatom substituent in the four, five, six or seven position of the indenyl ligand, and 2) a monoanionic ligand.

271. A transition metal compound comprising a transition metal bound to: 1) at least one substituted or unsubstituted heteroindenyl ligand that is bridged by a heteroatom substituent in the four, five, or six position of the heteroindenyl ligand, provided that the bridging position is not the same as the position of the ring heteroatom, and 2) a monoanionic ligand.

272. A transition metal compound comprising a transition metal bound to: 1) at least one substituted or unsubstituted fluorenyl ligand that is bridged by a heteroatom substituent in the one, two, three, four, five, six, seven or eight position of the fluorenyl ligand, and 2) a monoanionic ligand.

273. A transition metal compound comprising a transition metal bound to: 1) at least one substituted or unsubstituted heterofluorenyl ligand that is bridged by a heteroatom substituent in the one, two, three, four, five, or six position of the heterofluorenyl ligand, provided that the bridging position is not the same as the position of the ring heteroatom, and 2) a monoanionic ligand.

274. The compound of claim 270 wherein the monoanionic ligand is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand.

275. The compound of claim 271 wherein the monoanionic ligand is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand.

276. The compound of claim 272 wherein the monoanionic ligand is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand.

277. The compound of claim 273 wherein the monoanionic ligand is a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, or a substituted or unsubstituted heterofluorenyl ligand.

278. The compound of claim 270 where the metal is Ti, Hf or Zr.

279. The compound of claim 271 where the metal is Ti, Hf or Zr.

280. The compound of claim 272 where the metal is Ti, Hf or Zr.

281. The compound of claim 273 where the metal is Ti, Hf or Zr.

282. The compound of claim 274 where the metal is Ti, Hf or Zr.

283. The compound of claim 275 where the metal is Ti, Hf or Zr.

284. The compound of claim 276 where the metal is Ti, Hf or Zr.

285. The compound of claim 277 where the metal is Ti, Hf or Zr.

286. A compound selected from the group consisting of:
4,4'-sulfandiyl-bis($\eta^5$-2,7-dimethylindenyl)zirconium dichloride,
4,4'-sulfandiyl-bis($\eta^5$-7-phenyl-2-methylindenyl)zirconium dichloride,
4,4'-sulfandiyl-bis($\eta^5$-7-(p-tolyl)-2-methylindenyl)zirconium dichloride,
4,4'-sulfandiyl-bis($\eta^5$-7-(m-tolyl)-2-methylindenyl)zirconium dichloride,
4,4'-sulfandiyl-bis($\eta^5$-7-(4-t-butylphenyl)-2-methylindenyl)zirconium dichloride,
4,4'-sulfandiyl-bis($\eta^5$-7-mesityl-2-methylindenyl)zirconium dichloride,
4,4'-sulfandiyl-bis($\eta^5$-7-(5-methyl-2-thienyl)-2-methylindenyl)zirconium dichloride,
4,4'-sulfandiyl-bis($\eta^5$-7-(5-methyl-2-furyl)-2-methylindenyl)zirconium dichloride,
4,4'-sulfandiyl-bis($\eta^5$-7-(2-benzothienyl)-2-methylindenyl)zirconium dichloride,
4,4'-sulfandiyl-bis($\eta^5$-7-(2-benzofuryl)-2-methylindenyl)zirconium dichloride,
4,4'-sulfandiyl-bis($\eta^5$-7-(4-fluorophenyl)-2-methylindenyl)zirconium dichloride,
4,4'-sulfandiyl-bis($\eta^5$-7-(3-trifluoromethylphenyl)-2-methylindenyl)zirconium dichloride,
4,4'-sulfandiyl-bis($\eta^5$-7-(2,5-dimethylphenyl)-2-methylindenyl)zirconium dichloride,
4,4'-sulfandiyl-bis($\eta^5$-7-(4-biphenyl)-2-methylindenyl)zirconium dichloride,
4,4'-sulfandiyl-bis($\eta^5$-2,7-dimethylindenyl)zirconium dichloride,
4,4'-sulfandiyl-bis($\eta^5$-7-phenyl-2-methylindenyl)hafnium dichloride,
4,4'-sulfandiyl-bis($\eta^5$-7-(p-tolyl)-2-methylindenyl)hafnium dichloride,
4,4'-sulfandiyl-bis($\eta^5$-7-(m-tolyl)-2-methylindenyl)hafnium dichloride,
4,4'-sulfandiyl-bis($\eta^5$-7-(4-t-butylphenyl)-2-methylindenyl)hafnium dichloride,
4,4'-sulfandiyl-bis($\eta^5$-7-mesityl-2-methylindenyl)hafnium dichloride,
4,4'-sulfandiyl-bis($\eta^5$-7-(5-methyl-2-thienyl)-2-methylindenyl)hafnium dichloride,
4,4'-sulfandiyl-bis($\eta^5$-7-(5-methyl-2-furyl)-2-methylindenyl)hafnium dichloride,
4,4'-sulfandiyl-bis($\eta^5$-7-(2-benzothienyl)-2-methylindenyl)hafnium dichloride,
4,4'-sulfandiyl-bis($\eta^5$-7-(2-benzofuryl)-2-methylindenyl)hafnium dichloride,
4,4'-sulfandiyl-bis($\eta^5$-7-(4-fluorophenyl)-2-methylindenyl)hafnium dichloride,
4,4'-sulfandiyl-bis($\eta^5$-7-(3-trifluoromethylphenyl)-2-methylindenyl)hafnium dichloride,
4,4'-sulfandiyl-bis($\eta^5$-7-(2,5-dimethylphenyl)-2-methylindenyl)hafnium dichloride,
4,4'-sulfandiyl-bis($\eta^5$-7-(4-biphenyl)-2-methylindenyl)hafnium dichloride,
4,4'-tolylazandiyl-bis($\eta^5$-2,7-dimethylindenyl)zirconium dichloride,
4,4'-tolylazandiyl-bis($\eta^5$-7-(p-tolyl)-2-methylindenyl)zirconium dichloride,
4,4'-tolylazandiyl-bis($\eta^5$-2,7-dimethylindenyl)hafnium dichloride,
4,4'-tolylazandiyl-bis($\eta^5$-7-(p-tolyl)-2-methylindenyl)hafnium dichloride,
4,4'-oxadiyl-bis($\eta^5$-2,7-dimethylindenyl)zirconium dichloride, 4,4'-oxadiyl-bis($\eta^5$-7-(p-tolyl)-2-methylindenyl)zirconium dichloride,
4,4'-oxadiyl-bis($\eta^5$-7-(4-dimethylaminophenyl)-2-methylindenyl)zirconium dichloride,
4,4'-oxadiyl-bis($\eta^5$-7-(2-benzofuryl)-2-methylindenyl)zirconium dichloride,
4,4'-oxadiyl-bis($\eta^5$-7-(2-benzothienyl)-2-methylindenyl)zirconium dichloride,
4,4'-oxadiyl-bis($\eta^5$-2,7-dimethylindenyl)hafnium dichloride,
4,4'-oxadiyl-bis($\eta^5$-7-(p-tolyl)-2-methylindenyl)hafnium dichloride,
4,4'-oxadiyl-bis($\eta^5$-7-(4-dimethylaminophenyl)-2-methylindenyl)hafnium dichloride,
4,4'-oxadiyl-bis($\eta^5$-7-(2-benzofuryl)-2-methylindenyl)hafnium dichloride, and
4,4'-oxadiyl-bis($\eta^5$-7-(2-benzothienyl)-2-methylindenyl)hafnium dichloride.

287. The compound of claim 1 wherein Y is S, O, O—O, S—S, R'N—NR', R'P—PR', O—S, 0-NR', O—PR', S—NR', S—PR', or R'N—PR', where each R' is, independently, hydrogen, a hydrocarbyl, substituted hydrocarbyl, halocarbyl, substituted halocarbyl, silylcarbyl, substituted silylcarbyl, germylcarbyl, or substituted germylcarbyl substituent.

288. The compound of claim 1 wherein E is: 1) a substituted or unsubstituted indenyl ligand that is bonded to Y through the five, six or seven position of the indenyl ring, or 2) a substituted or unsubstituted heteroindenyl ligand that is bonded to Y through the four, five or six position of the heteroindenyl ring, provided that the bonding position is not the same as the position of the ring heteroatom, or 3) a substituted or unsubstituted fluorenyl ligand that is bonded to Y through the one, two, three, four, five, six, seven or eight position of the fluorenyl ring, or 4) a substituted or unsubstituted heterofluorenyl ligand that is bonded to Y through the one, two, three, four, five or six position of the heterofluorenyl ring, provided that the bonding position is not the same as the position of the ring heteroatom.

289. The compound of claim 17 wherein Y is S, O, O—O, S—S, R'N—NR', R'P—PR', O—S, O—NR', O—PR', S—NR', S—PR', or R'N—PR', where each R' is, independently, hydrogen, or a hydrocarbyl, substituted hydrocarbyl, halocarbyl, substituted halocarbyl, silylcarbyl, substituted silylcarbyl, germylcarbyl, or substituted germylcarbyl substituent.

290. The compound of claim 3 wherein Y is not Nr' or Pr' when E is: 1) a substituted or unsubstituted indenyl ligand that is bonded to Y through the 4 position of the indenyl ring.

* * * * *